US007317092B2

(12) United States Patent
Ashkenazi et al.

(10) Patent No.: US 7,317,092 B2
(45) Date of Patent: Jan. 8, 2008

(54) SECRETED AND TRANSMEMBRANE POLYPEPTIDES AND NUCLEIC ACIDS ENCODING THE SAME

(75) Inventors: Avi J. Ashkenazi, San Mateo, CA (US); Kevin P. Baker, Darnestown, MD (US); David A. Botstein, Belmont, CA (US); Luc Desnoyers, San Francisco, CA (US); Dan L. Eaton, San Rafael, CA (US); Napoleone Ferrara, San Francisco, CA (US); Sherman Fong, Alameda, CA (US); Wei-Qiang Gao, Palo Alto, CA (US); Hanspeter Gerber, San Francisco, CA (US); Mary E. Gerritsen, San Mateo, CA (US); Audrey Goddard, San Francisco, CA (US); Paul J. Godowski, Hillsborough, CA (US); Austin L. Gurney, Belmont, CA (US); Ivar J. Kljavin, Layfayette, CA (US); Jennie P. Mather, Millbrae, CA (US); Mary A. Napier, Hillsborough, CA (US); James Pan, Belmont, CA (US); Nicholas F. Paoni, Belmont, CA (US); Margaret Ann Roy, San Francisco, CA (US); Timothy A. Stewart, San Francisco, CA (US); Daniel Tumas, Orinda, CA (US); Colin K. Watanabe, Moraga, CA (US); P. Mickey Williams, Half Moon Bay, CA (US); William I. Wood, Hillsborough, CA (US); Zemin Zhang, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 791 days.

(21) Appl. No.: 10/066,273

(22) Filed: Feb. 1, 2002

(65) Prior Publication Data
US 2003/0032062 A1 Feb. 13, 2003

Related U.S. Application Data

(63) Continuation of application No. 10/002,796, filed on Nov. 15, 2001, now abandoned.

(51) Int. Cl.
*C07K 16/00* (2006.01)
*C07K 17/00* (2006.01)
(52) U.S. Cl. ............... 530/387.9; 530/350; 530/388.1; 530/388.15; 530/391.3
(58) Field of Classification Search ............ 530/387.1, 530/388.1, 388.15, 391.1, 350; 424/130.1, 424/133.1, 178.1
See application file for complete search history.

(56) References Cited

U.S. PATENT DOCUMENTS 5,536,637 A 7/1996 Jacobs ..................... 435/6

OTHER PUBLICATIONS

Kovacs, 1998, Neurochem. Int., vol. 33, pp. 287-297.*
Herrera et al., 1996, Progress in Neurobiology, vol. 50, pp. 83-107.*
Janknecht et al., 1995, Carcinogenesis, vol. 16, No. 3, pp. 443-450.*
Coulon et al., 1999, J. Biol. Chem., vol. 274, No. 43, pp. 30439-30446.*
Sakurai et al., 2002, Invest. Ophthalmology and Visual Sci., vol. 43, No. 8, pp. 2774-2781.*
Otani et al., 2000, Invest. Ophthalmology and Visual Sci., vol. 41, No. 5, pp. 1192-1199.*
Ozerdem et al., 2003, Angiogenesis, 6, pp. 241-249.*
Diaz-Florez et al., 1994, Histol. Histopath., vol. 9, pp. 807-843.*
Orlandi et al., 1996, Proc. Natl. Acad. Sci. USA, vol. 93, pp. 11675-11680.*
Klein, Robert, et al., "Selection for genes encoding secreted proteins and receptors", Proc. Natl. Acad. Sci. USA vol. 93, pp. 7108-7113 (1996).
Database search, locus list: hum (349, 801 seqs, 66, 964, 548 aa) Mon. Jan. 7 16:12:28 2002 [BLASTP 2.2.1 [Jul. 12, 2001], NCBI].
Database search, locus list hum-est (1,803,435 seqs, 6,559,376, 613 bp) Tue Jan. 8 09:13:48 2002 [BLASTN 2.2.1 [Jul. 12, 2001], [NCBI].
Alon, et al. "Vascular endothelial growth factor acts as a survival factor for newly formed retinal vessels and has implications for retinopathy of prematurity." *Nature Medicine*. 1(10): 1024-1028 (1995).
Benjamin, et al. "Conditional switching of vascular endothelial growth factor (VEGF) expression in tumors: Induction of endothelial cell shedding and regression of hemangioblastoma-like vessels by VEGF withdrawal." *Proc. Natl. Acad. Sci.* 94: 8761-8766 (1997).
Ellis, et al. "Synopsis of Angiogenesis Inhibitors in Oncology." *Oncology*. 16(5), Supplement: 14-22 (2002).
Ferrara, Napoleone. "The role of vascular endothelial growth factor in pathological angiogenesis." *Breast Cancer Research and Treatment*. 36: 127-137 (1995).
Fidler, et al. "Critical Determinants of Neoplastic Angiogenesis." *The Cancer Journal*. 6(Suppl. 3): S225-S236 (2000).
Janknecht, et al. "Signal integration at the *c-fos* promoter." *Carcinogenesis*. 16(3): 443-450 (1995).
Kirkpatrick, Peter. "Bevacizumab." *Nature*. Nature Reviews/Drug Discover. Nature Publishing Group. S8-S9 (May 2005).
Kolch, et al. "Regulation of the expression of the VEGF/VPS and its receptors: role in tumor angiogenesis." *Breast Cancer Research and Treatment*. 36: 139-155 (1995).

(Continued)

*Primary Examiner*—Olga N. Chernyshev
(74) *Attorney, Agent, or Firm*—Elizabeth M. Barnes; Mark T. Kresnak; Knobbe Martens Olson & Bear LLP

(57) ABSTRACT

The present invention is directed to novel polypeptides and to nucleic acid molecules encoding those polypeptides. Also provided herein are vectors and host cells comprising those nucleic acid sequences, chimeric polypeptide molecules comprising the polypeptides of the present invention fused to heterologous polypeptide sequences, antibodies which bind to the polypeptides of the present invention and to methods for producing the polypeptides of the present invention.

5 Claims, 75 Drawing Sheets

OTHER PUBLICATIONS

Nehls, et al. "Pericyte involvement in capillary sprouting during angiogenesis in situ." *Cell Tissue Res.* 270: 469-474 (1992).

Rhodin, et al. "Capillary growth in the mesentery of normal young rats. Intravital video and electron microscope analyses." *J. Submicrosc. Cythol. Pathol.* 21(1): 1-34 (1989).

Shima, et al. "The Mouse Gene for Vascular Endothelial Growth Factor." *The Journal of Biological Chemistry.* 271(7): 3877-3883 (1996).

Tischer, et al. "The Human Gene for Vascular Endothelial Growth Factor." *The Journal of Biological Chemistry.* 266(18): 11947-11954 (1991).

Willett, et al. "Direct evidence that the VEGF-specific antibody bevacizumab has antivascular effects in human rectal cancer." *Nature Medicine.* 10(2): 145-147 (2004).

Klein, Robert, et al., "Selection for genes encoding secreted proteins and receptors", Proc. Natl. Acad. Sci. USA vol. 93, pp. 7108-7113 (1996).

Database search, locus list: hum (349, 801 seqs, 66, 964, 548 aa) Mon. Jan. 7 16:12:28 2002 [BLASTP 2.2.1 [Jul. 12, 2001], NCBI].

Database search, locus list hum-est (1,803,435 seqs, 6,559,376,613 bp) Tue Jan. 8 09:13:48 2002 [BLASTN 2.2.1 [Jul. 12, 2001], [NCBI].

\* cited by examiner

FIGURE 1

GGCTGAGGGGAGGCCCGGAGCCTTTCTGGGGCCTGGGGGATCCTCTTGCACTGGTGGGTGGA
GAGAAGCGCCTGCAGCCAACCAGGGTCAGGCTGTGCTCACAGTTTCCTCTGGCGGCATGTAA
AGGCTCCACAAAGGAGTTGGGAGTTCAAATGAGGCTGCTGCGGACGGCCTGAGGATGGACCC
CAAGCCCTGGACCTGCCGAGCGTGGCACTGAGGCAGCGGCTGACGCTACTGTGAGGGAAAGA
AGGTTGTGAGCAGCCCCGCAGGACCCCTGGCCAGCCCTGGCCCCAGCCTCTGCCGGAGCCCT
CTGTGGAGGCAGAGCCAGTGGAGCCCAGTGAGGCAGGGCTGCTTGGCAGCCACCGGCCTGCA
ACTCAGGAACCCCTCCAGAGGCCATGGACAGGCTGCCCCGCTGACGGCCAGGGTGAAGCATG
TGAGGAGCCGCCCCGGAGCCAAGCAGGAGGGAAGAGGCTTTCATAGATTCTATTCACAAAGA
ATAACCACCATTTTGCAAGGACCATGAGGCCACTGTGCGTGACATGCTGGTGGCTCGGACTG
CTGGCTGCCATGGGAGCTGTTGCAGGCCAGGAGGACGGTTTTGAGGGCACTGAGGAGGGCTC
GCCAAGAGAGTTCATTTACCTAAACAGGTACAAGCGGGCGGGCGAGTCCCAGGACAAGTGCA
CCTACACCTTCATTGTGCCCCAGCAGCGGGTCACGGGTGCCATCTGCGTCAACTCCAAGGAG
CCTGAGGTGCTTCTGGAGAACCGAGTGCATAAGCAGGAGCTAGAGCTGCTCAACAATGAGCT
GCTCAAGCAGAAGCGGCAGATCGAGACGCTGCAGCAGCTGGTGGAGGTGGACGGCGGCATTG
TGAGCGAGGTGAAGCTGCTGCGCAAGGAGAGCCGCAACATGAACTCGCGGGTCACGCAGCTC
TACATGCAGCTCCTGCACGAGATCATCCGCAAGCGGGACAACGCGTTGGAGCTCTCCCAGCT
GGAGAACAGGATCCTGAACCAGACAGCCGACATGCTGCAGCTGGCCAGCAAGTACAAGGACC
TGGAGCACAAGTACCAGCACCTGGCCACACTGGCCCACAACCAATCAGAGATCATCGCGCAG
CTTGAGGAGCACTGCCAGAGGGTGCCCTCGGCCAGGCCCGTCCCCAGCCACCCCCGCTGC
CCCGCCCCGGGTCTACCAACCACCCACCTACAACCGCATCATCAACCAGATCTCTACCAACG
AGATCCAGAGTGACCAGAACCTGAAGGTGCTGCCACCCCCTCTGCCCACTATGCCCACTCTC
ACCAGCCTCCCATCTTCCACCGACAAGCCGTCGGGCCCATGGAGAGACTGCCTGCAGGCCCT
GGAGGATGGCCACGACACCAGCTCCATCTACCTGGTGAAGCCGGAGAACACCAACCGCCTCA
TGCAGGTGTGGTGCGACCAGAGACACGACCCCGGGGGCTGGACCGTCATCCAGAGACGCCTG
GATGGCTCTGTTAACTTCTTCAGGAACTGGGAGACGTACAAGCAAGGGTTTGGGAACATTGA
CGGCGAATACTGGCTGGGCCTGGAGAACATTTACTGGCTGACGAACCAAGGCAACTACAAAC
TCCTGGTGACCATGGAGGACTGGTCCGGCCGCAAAGTCTTTGCAGAATACGCCAGTTTCCGC
CTGGAACCTGAGAGCGAGTATTATAAGCTGCGGCTGGGGCGCTACCATGGCAATGCGGGTGA
CTCCTTTACATGGCACAACGGCAAGCAGTTCACCACCCTGGACAGAGATCATGATGTCTACA
CAGGAAACTGTGCCCACTACCAGAAGGGAGGCTGGTGGTATAACGCCTGTGCCCACTCCAAC
CTCAACGGGGTCTGGTACCGCGGGGGCCATTACCGGAGCCGCTACCAGGACGGAGTCTACTG
GGCTGAGTTCCGAGGAGGCTCTTACTCACTCAAGAAAGTGGTGATGATGATCCGACCGAACC
CCAACACCTTCCACTAAGCCAGCTCCCCTCCTGACCTCTCGTGGCCATTGCCAGGAGCCCA
CCCTGGTCACGCTGGCCACAGCACAAGAACAACTCCTCACCAGTTCATCCTGAGGCTGGGA
GGACCGGGATGCTGGATTCTGTTTTCCGAAGTCACTGCAGCGGATGATGGAACTGAATCGAT
ACGGTGTTTTCTGTCCCTCCTACTTTCCTTCACACCAGACAGCCCTCATGTCTCCAGGACA
GGACAGGACTACAGACAACTCTTTCTTTAAATAAATTAAGTCTCTACAATAAAAAAA

FIGURE 2

```
></usr/seqdb2/sst/DNA/Dnaseqs.min/ss.DNA22779
><subunit 1 of 1, 493 aa, 1 stop
><MW: 57104, pI: 7.67, NX(S/T): 2
MRPLCVTCWWLGLLAAMGAVAGQEDGFEGTEEGSPREFIYLNRYKRAGESQDKCTYTFIVPQ
QRVTGAICVNSKEPEVLLENRVHKQELELLNNELLKQKRQIETLQQLVEVDGGIVSEVKLLR
KESRNMNSRVTQLYMQLLHEIIRKRDNALELSQLENRILNQTADMLQLASKYKDLEHKYQHL
ATLAHNQSEIIAQLEEHCQRVPSARPVPQPPPAAPPRVYQPPTYNRIINQISTNEIQSDQNL
KVLPPPLPTMPTLTSLPSSTDKPSGPWRDCLQALEDGHDTSSIYLVKPENTNRLMQVWCDQR
HDPGGWTVIQRRLDGSVNFFRNWETYKQGFGNIDGEYWLGLENIYWLTNQGNYKLLVTMEDW
SGRKVFAEYASFRLEPESEYYKLRLGRYHGNAGDSFTWHNGKQFTTLDRDHDVYTGNCAHYQ
KGGWWYNACAHSNLNGVWYRGGHYRSRYQDGVYWAEFRGGSYSLKKVVMMIRPNPNTFH
```

Important features of the protein:

Signal peptide:

amino acids 1-22

N-glycosylation sites.

amino acids 164-168, 192-196 cAMP- and cGMP-dependent protein kinase phosphorylation site.

amino acids 124-128

Tyrosine kinase phosphorylation sites.

amino acids 177-184, 385-393, 385-394, 461-468

N-myristoylation sites.

amino acids 12-18, 18-24, 22-28, 29-35, 114-120, 341-347, 465-471, 473-479

Amidation site.

amino acids 373-377

Fibrinogen beta and gamma chains C-terminal domain signature.

amino acids 438-451

Fibrinogen beta and gamma chains C-terminal domain proteins.

amino acids 305-343, 365-402, 411-424, 428-458

Trehalase proteins.

amino acids 275-292

FIGURE 3

CCCACGCGTCCGGCGCCGTGGCCTCGCGTCCATCTTTGCCGTTCTCTCGGACCTGTCACAAA
GGAGTCGCGCCGCCGCCGCCGCCCCTCCCTCCGGTGGGCCCGGGAGGTAGAGAAAGTCAGT
GCCACAGCCCGACCGCGCTGCTCTGAGCCCTGGGCACGCGGAACGGGAGGGAGTCTGAGGGT
TGGGGACGTCTGTGAGGGAGGGGAACAGCCGCTCGAGCCTGGGGCGGGCGGACCGGACTGGG
GCCGGGGTAGGCTCTGGAAAGGGCCCGGGAGAGAGGTGGCGTTGGTCAGAACCTGAGAAACA
GCCGAGAGGTTTTCCACCGAGGCCCGCGCTTGAGGGATCTGAAGAGGTTCCTAGAAGAGGGT
GTTCCCTCTTTCGGGGGTCCTCACCAGAAGAGGTTCTTGGGGGTCGCCCTTCTGAGGAGGCT
GCGGCTAACAGGGCCCAGAACTGCCATTGGATGTCCAGAATCCCCTGTAGTTGATAATGTTG
GGAATAAGCTCTGCAACTTTCTTTGGCATTCAGTTGTTAAAAACAAATAGGATGCAAATTCC
TCAACTCCAGGTTATGAAAACAGTACTTGGAAAACTGAAAACTACCTAAATGATCGTCTTTG
GTTGGGCCGTGTTCTTAGCGAGCAGAAGCCTTGGCCAGGGTCTGTTGTTGACTCTCGAAGAG
CACATAGCCCACTTCCTAGGGACTGGAGGTGCCGCTACTACCATGGGTAATTCCTGTATCTG
CCGAGATGACAGTGGAACAGATGACAGTGTTGACACCCAACAGCAACAGGCCGAGAACAGTG
CAGTACCCACTGCTGACACAAGGAGCCAACCACGGGACCCTGTTCGGCCACCAAGGAGGGGC
CGAGGACCTCATGAGCCAAGGAGAAAGAAACAAAATGTGGATGGGCTAGTGTTGGACACACT
GGCAGTAATACGGACTCTTGTAGATAAGTAAGTATCGACTCACGGTCACCTCCAGTGGAAT
GAAAAGTGTTCTGCCCGGAACCATGACTTTAGGACTCCTTCAGTTCCTTTAGGACATACTCG
CCAAGCCTTGTGCTCACAGGGCAAGGAGAATATTTTAATGCTCCGCTGATGGCAGAGTAAA
TGATAAGATTTGATGTTTTGCTTGCTGTCATCTACTTTGTCTGGAAATGTCTAAATGTTTC
TGTAGCAGAAAACACGATAAAGCTATGATCTTTATTAGAG

FIGURE 4

</usr/seqdb2/sst/DNA/Dnaseqs.min/ss.DNA26846
<subunit 1 of 1, 117 aa, 1 stop
<MW: 12692, pI: 7.50, NX(S/T): 0
MIVFGWAVFLASRSLGQGLLLTLEEHIAHFLGTGGAATTMGNSCICRDDSGTDDSVDTQQQQ
AENSAVPTADTRSQPRDPVRPPRRGRGPHEPRRKKQNVDGLVLDTLAVIRTLVDK

Important features:

Signal peptide:

amino acids 1-16

N-myristoylation sites.

amino acids 18-24, 32-38, 34-40, 35-41, 51-57

FIGURE 5

CCCACGCGTCCGCGCAGTCGCGCAGTTCTGCCTCCGCCTGCCAGTCTCGCCCGCGATCCCGG
CCCGGGGCTGTGGCGTCGACTCCGACCCAGGCAGCCAGCAGCCCGCGCGGGAGCCGGACCGC
CGCCGGAGGAGCTCGGACGGCATGCTGAGCCCCCTCCTTTGCTGAAGCCCGAGTGCGGAGAA
GCCCGGGCAAACGCAGGCTAAGGAGACCAAAGCGGCGAAGTCGCGAGACAGCGGACAAGCAG
CGGAGGAGAAGGAGGAGGAGGCGAACCCAGAGAGGGGCAGCAAAAGAAGCGGTGGTGGTGGG
CGTCGTGGCCATGGCGGCGGCTATCGCCAGCTCGCTCATCCGTCAGAAGAGGCAAGCCCGCG
AGCGCGAGAAATCCAACGCCTGCAAGTGTGTCAGCAGCCCCAGCAAAGGCAAGACCAGCTGC
GACAAAAACAAGTTAAATGTCTTTTCCCGGGTCAAACTCTTCGGCTCCAAGAAGAGGCGCAG
AAGAAGACCAGAGCCTCAGCTTAAGGGTATAGTTACCAAGCTATACAGCCGACAAGGCTACC
ACTTGCAGCTGCAGGCGGATGGAACCATTGATGGCACCAAAGATGAGGACAGCACTTACACT
CTGTTTAACCTCATCCCTGTGGGTCTGCGAGTGGTGGCTATCCAAGGAGTTCAAACCAAGCT
GTACTTGGCAATGAACAGTGAGGGATACTTGTACACCTCGGAACTTTTCACACCTGAGTGCA
AATTCAAAGAATCAGTGTTTGAAAATTATTATGTGACATATTCATCAATGATATACCGTCAG
CAGCAGTCAGGCCGAGGGTGGTATCTGGGTCTGAACAAAGAAGGAGAGATCATGAAAGGCAA
CCATGTGAAGAAGAACAAGCCTGCAGCTCATTTCTGCCTAAACCACTGAAAGTGGCCATGT
ACAAGGAGCCATCACTGCACGATCTCACGGAGTTCTCCCGATCTGGAAGCGGGACCCCAACC
AAGAGCAGAAGTGTCTCTGGCGTGCTGAACGGAGGCAAATCCATGAGCCACAATGAATCAAC
GTAGCCAGTGAGGGCAAAAGAAGGGCTCTGTAACAGAACCTTACCTCCAGGTGCTGTTGAAT
TCTTCTAGCAGTCCTTCACCCAAAAGTTCAAATTTGTCAGTGACATTTACCAAACAAACAGG
CAGAGTTCACTATTCTATCTGCCATTAGACCTTCTTATCATCCATACTAAAGC

FIGURE 6

```
></usr/seqdb2/sst/DNA/Dnaseqs.full/ss.DNA28498
><subunit 1 of 1, 245 aa, 1 stop
><MW: 27564, pI: 10.18, NX(S/T): 1
MAAAIASSLIRQKRQAREREKSNACKCVSSPSKGKTSCDKNKLNVFSRVKLFGSKKRRRRRP
EPQLKGIVTKLYSRQGYHLQLQADGTIDGTKDEDSTYTLFNLIPVGLRVVAIQGVQTKLYLA
MNSEGYLYTSELFTPECKFKESVFENYYVTYSSMIYRQQQSGRGWYLGLNKEGEIMKGNHVK
KNKPAAHFLPKPLKVAMYKEPSLHDLTEFSRSGSGTPTKSRSVSGVLNGGKSMSHNEST
```

N-glycosylation site.

amino acids 242-246

Glycosaminoglycan attachment site.

amino acids 165-169, 218-222

Tyrosine kinase phosphorylation site.

amino acids 93-100

N-myristoylation site.

amino acids 87-93, 231-237

ATP/GTP-binding site motif A (P-loop).

amino acids 231-239

HBGF/FGF family proteins amino acids 78-94, 102-153

FIGURE 7

ATGGCCGCGGCCATCGCTAGCGGCTTGATCCGCCAGAAGCGGCAGGCGCGGGAGCAGCACTG
GGACCGGCCGTCTGCCAGCAGGAGGCGGAGCAGCCCCAGCAAGAACCGCGGGCTCTGCAACG
GCAACCTGGTGGATATCTTCTCCAAAGTGCGCATCTTCGGCCTCAAGAAGCGCAGGTTGCGG
CGCCAAGATCCCCAGCTCAAGGGTATAGTGACCAGGTTATATTGCAGGCAAGGCTACTACTT
GCAAATGCACCCCGATGGAGCTCTCGATGGAACCAAGGATGACAGCACTAATTCTACACTCT
TCAACCTCATACCAGTGGGACTACGTGTTGTTGCCATCCAGGGAGTGAAAACAGGGTTGTAT
ATAGCCATGAATGGAGAAGGTTACCTCTACCCATCAGAACTTTTTACCCCTGAATGCAAGTT
TAAAGAATCTGTTTTTGAAAATTATTATGTAATCTACTCATCCATGTTGTACAGACAACAGG
AATCTGGTAGAGCCTGGTTTTTGGGATTAAATAAGGAAGGGCAAGCTATGAAAGGGAACAGA
GTAAAGAAAACCAAACCAGCAGCTCATTTTCTACCCAAGCCATTGGAAGTTGCCATGTACCG
AGAACCATCTTTGCATGATGTTGGGGAAACGGTCCCGAAGCCTGGGGTGACGCCAAGTAAAA
GCACAAGTGCGTCTGCAATAATGAATGGAGGCAAACCAGTCAACAAGAGTAAGACAACATAG

FIGURE 8

```
></usr/seqdb2/sst/DNA/Dnaseqs.min/ss.DNA28503
><subunit 1 of 1, 247 aa, 1 stop
><MW: 27702, pI: 10.36, NX(S/T): 2
MAAAIASGLIRQKRQAREQHWDRPSASRRRSSPSKNRGLCNGNLVDIFSKVRIFGLKKRRLR
RQDPQLKGIVTRLYCRQGYYLQMHPDGALDGTKDDSTNSTLFNLIPVGLRVVAIQGVKTGLY
IAMNGEGYLYPSELFTPECKFKESVFENYYVIYSSMLYRQQESGRAWFLGLNKEGQAMKGNR
VKKTKPAAHFLPKPLEVAMYREPSLHDVGETVPKPGVTPSKSTSASAIMNGGKPVNKSKTT
```

N-glycosylation site.

amino acids 100-104, 242-246 cAMP- and cGMP-dependent protein kinase phosphorylation site.

amino acids 28-32, 29-33

Tyrosine kinase phosphorylation site.

amino acids 199-207

N-myristoylation site.

amino acids 38-44, 89-95, 118-124, 122-128, 222-228

HBGF/FGF family proteins.

amino acids 104-155, 171-198

FIGURE 9

```
CTCGCAGCCGAGCGCGGCCGGGGAAGGGCTCTCCTTCCAGCGCCGAGCACTGGGCCCTGGCA
GACGCCCCAAGATTGTTGTGAGGAGTCTAGCCAGTTGGTGAGCGCTGTAATCTGAACCAGCT
GTGTCCAGACTGAGGCCCCATTTGCATTGTTTAACATACTTAGAAAATGAAGTGTTCATTTT
TAACATTCCTCCTCCAATTGGTTTAATGCTGAATTACTGAAGAGGGCTAAGCAAAACCAGGT
GCTTGCGCTGAGGGCTCTGCAGTGGCTGGGAGGACCCCGGCGCTCTCCCCGTGTCCTCTCCA
CGACTCGCTCGGCCCCTCTGGAATAAAACACCCGCGAGCCCCGAGGGCCCAGAGGAGGCCGA
CGTGCCCGAGCTCCTCCGGGGGTCCCGCCCGCGAGCTTTCTTCTCGCCTTCGCATCTCCTCC
TCGCGCGTCTTGGACATGCCAGGAATAAAAAGGATACTCACTGTTACCATTCTGGCTCTCTG
TCTTCCAAGCCCTGGGAATGCACAGGCACAGTGCACGAATGGCTTTGACCTGGATCGCCAGT
CAGGACAGTGTTTAGATATTGATGAATGCCGAACCATCCCCGAGGCCTGCCGAGGAGACATG
ATGTGTGTTAACCAAAATGGCGGGTATTTATGCATTCCCCGGACAAACCCTGTGTATCGAGG
GCCCTACTCGAACCCCTACTCGACCCCCTACTCAGGTCCGTACCCAGCAGCTGCCCCACCAC
TCTCAGCTCCAAACTATCCCACGATCTCCAGGCCTCTTATATGCCGCTTTGGATACCAGATG
GATGAAAGCAACCAATGTGTGGATGTGGACGAGTGTGCAACAGATTCCCACCAGTGCAACCC
CACCCAGATCTGCATCAATACTGAAGGCGGGTACACCTGCTCCTGCACCGACGGATATTGGC
TTCTGGAAGGCCAGTGCTTAGACATTGATGAATGTCGCTATGGTTACTGCCAGCAGCTCTGT
GCGAATGTTCCTGGATCCTATTCTTGTACATGCAACCCTGGTTTTACCCTCAATGAGGATGG
AAGGTCTTGCCAAGATGTGAACGAGTGTGCCACCGAGAACCCCTGCGTGCAAACCTGCGTCA
ACACCTACGGCTCTCTCATCTGCCGCTGTGACCCAGGATATGAACTTGAGGAAGATGGCGTT
CATTGCAGTGATATGGACGAGTGCAGCTTCTCTGAGTTCCTCTGCCAACATGAGTGTGTGAA
CCAGCCCGGCACATACTTCTGCTCCTGCCCTCCAGGCTACATCCTGCTGGATGACAACCGAA
GCTGCCAAGACATCAACGAATGTGAGCACAGGAACCACACGTGCAACCTGCAGCAGACGTGC
TACAATTTACAAGGGGGCTTCAAATGCATCGACCCCATCCGCTGTGAGGAGCCTTATCTGAG
GATCAGTGATAACCGCTGTATGTGTCCTGCTGAGAACCCTGGCTGCAGAGACCAGCCCTTTA
CCATCTTGTACCGGGACATGGACGTGGTGTCAGGACGCTCCGTTCCCGCTGACATCTTCCAA
ATGCAAGCCACGACCCGCTACCCTGGGGCCTATTACATTTTCCAGATCAAATCTGGGAATGA
GGGCAGAGAATTTTACATGCGGCAAACGGGCCCCATCAGTGCCACCCTGGTGATGACACGCC
CCATCAAAGGGCCCCGGGAAATCCAGCTGGACTTGGAAATGATCACTGTCAACACTGTCATC
AACTTCAGAGGCAGCTCCGTGATCCGACTGCGGATATATGTGTCGCAGTACCCATTCTGAGC
CTCGGGCTGGAGCCTCCGACGCTGCCTCTCATTGGCACCAAGGGACAGGAGAAGAGAGGAAA
TAACAGAGAGAATGAGAGCGACACAGACGTTAGGCATTTCCTGCTGAACGTTTCCCCGAAGA
GTCAGCCCCGACTTCCTGACTCTCACCTGTACTATTGCAGACCTGTCACCCTGCAGGACTTG
CCACCCCAGTTCCTATGACACAGTTATCAAAAGTATTATCATTGCTCCCCTGATAGAAGA
TTGTTGGTGAATTTTCAAGGCCTTCAGTTTATTTCCACTATTTTCAAAGAAAATAGATTAGG
TTTGCGGGGTCTGAGTCTATGTTCAAAGACTGTGAACAGCTTGCTGTCACTTCTTCACCTC
TTCCACTCCTTCTCTCACTGTGTTACTGCTTTGCAAAGACCCGGGAGCTGGCGGGGAACCCT
GGGAGTAGCTAGTTTGCTTTTTGCGTACACAGAGAAGGCTATGTAAACAAACCACAGCAGGA
TCGAAGGGTTTTTAGAGAATGTGTTTCAAAACCATGCCTGGTATTTTCAACCATAAAAGAAG
TTTCAGTTGTCCTTAAATTTGTATAACGGTTTAATTCTGTCTTGTTCATTTTGAGTATTTTT
AAAAAATATGTCGTAGAATTCCTTCGAAAGGCCTTCAGACACATGCTATGTTCTGTCTTCCC
AAACCCAGTCTCCTCTCCATTTTAGCCCAGTGTTTTCTTTGAGGACCCCTTAATCTTGCTTT
CTTTAGAATTTTTACCCAATTGGATTGGAATGCAGAGGTCTCCAAACTGATTAAATATTTGA
AGAGA
```

FIGURE 10

MPGIKRILTVTILALCLPSPGNAQAQCTNGFDLDRQSGQCLDIDECRTIPEACRGDMMCVNQ
NGGYLCIPRTNPVYRGPYSNPYSTPYSGPYPAAAPPLSAPNYPTISRPLICRFGYQMDESNQ
CVDVDECATDSHQCNPTQICINTEGGYTCSCTDGYWLLEGQCLDIDECRYGYCQQLCANVPG
SYSCTCNPGFTLNEDGRSCQDVNECATENPCVQTCVNTYGSLICRCDPGYELEEDGVHCSDM
DECSFSEFLCQHECVNQPGTYFCSCPPGYILLDDNRSCQDINECEHRNHTCNLQQTCYNLQG
GFKCIDPIRCEEPYLRISDNRCMCPAENPGCRDQPFTILYRDMDVVSGRSVPADIFQMQATT
RYPGAYYIFQIKSGNEGREFYMRQTGPISATLVMTRPIKGPREIQLDLEMITVNTVINFRGS
SVIRLRIYVSQYPF

Important features of the protein:

Signal peptide:

amino acids 1-25

N-glycosylation sites.

amino acids 283-287, 296-300

N-myristoylation sites.

amino acids 21-27, 64-70, 149-155, 186-192, 226-232, 242-248, 267-273, 310-316

Aspartic acid and asparagine hydroxylation sites.

amino acids 144-156, 181-193, 262-274

Cell attachment sequence.

amino acids 54-57

Calcium-binding EGF-like.

amino acids 131-166, 172-205, 211-245, 251-286

FIGURE 11

CAGGTCCAACTGCACCTCGGTTCTATCGATTGAATTCCCCGGGGATCCTCTAGAGATCCCTC
GACCTCGACCCACGCGTCCGAACACAGGTCCTTGTTGCTGCAGAGAAGCAGTTGTTTTGCTG
GAAGGAGGGAGTGCGCGGGCTGCCCCGGGCTCCTCCCTGCCGCCTCCTCTCAGTGGATGGTT
CCAGGCACCCTGTCTGGGGCAGGGAGGGCACAGGCCTGCACATCGAAGGTGGGGTGGGACCA
GGCTGCCCCTCGCCCCAGCATCCAAGTCCTCCCTTGGGCGCCCGTGGCCCTGCAGACTCTCA
GGGCTAAGGTCCTCTGTTGCTTTTGGTTCCACCTTAGAAGAGGCTCCGCTTGACTAAGAGT
AGCTTGAAGGAGGCACCATGCAGGAGCTGCATCTGCTCTGGTGGGCGCTTCTCCTGGGCCTG
GCTCAGGCCTGCCCTGAGCCCTGCGACTGTGGGGAAAAGTATGGCTTCCAGATCGCCGACTG
TGCCTACCGCGACCTAGAATCCGTGCCGCCTGGCTTCCCGGCCAATGTGACTACACTGAGCC
TGTCAGCCAACCGGCTGCCAGGCTTGCCGGAGGGTGCCTTCAGGGAGGTGCCCCTGCTGCAG
TCGCTGTGGCTGGCACACAATGAGATCCGCACGGTGGCCGCCGGAGCCCTGGCCTCTCTGAG
CCATCTCAAGAGCCTGGACCTCAGCCACAATCTCATCTCTGACTTTGCCTGGAGCGACCTGC
ACAACCTCAGTGCCCTCCAATTGCTCAAGATGGACAGCAACGAGCTGACCTTCATCCCCCGC
GACGCCTTCCGCAGCCTCCGTGCTCTGCGCTCGCTGCAACTCAACCACAACCGCTTGCACAC
ATTGGCCGAGGGCACCTTCACCCCGCTCACCGCGCTGTCCCACCTGCAGATCAACGAGAACC
CCTTCGACTGCACCTGCGGCATCGTGTGGCTCAAGACATGGGCCCTGACCACGGCCGTGTCC
ATCCCGGAGCAGGACAACATCGCCTGCACCTCACCCCATGTGCTCAAGGGTACACCGCTGAG
CCGCCTGCCGCCACTGCCATGCTCGGCGCCCTCAGTGCAGCTCAGCTACCAACCCAGCCAGG
ATGGTGCCGAGCTGCGGCCTGGTTTTGTGCTGGCACTGCACTGTGATGTGGACGGGCAGCCG
GCCCCTCAGCTTCACTGGCACATCCAGATACCCAGTGGCATTGTGGAGATCACCAGCCCCAA
CGTGGGCACTGATGGGCGTGCCCTGCCTGGCACCCCTGTGGCCAGCTCCCAGCCGCGCTTCC
AGGCCTTTGCCAATGGCAGCCTGCTTATCCCCGACTTTGGCAAGCTGGAGGAAGGCACCTAC
AGCTGCCTGGCCACCAATGAGCTGGGCAGTGCTGAGAGCTCAGTGGACGTGGCACTGGCCAC
GCCCGGTGAGGGTGGTGAGGACACACTGGGGCGCAGGTTCCATGGCAAAGCGGTTGAGGGAA
AGGGCTGCTATACGGTTGACAACGAGGTGCAGCCATCAGGGCCGGAGGACAATGTGGTCATC
ATCTACCTCAGCCGTGCTGGGAACCCTGAGGCTGCAGTCGCAGAAGGGGTCCCTGGGCAGCT
GCCCCCAGGCCTGCTCCTGCTGGGCCAAAGCCTCCTCCTCTTCTTCTTCCTCACCTCCTTCT
AGCCCCACCCAGGGCTTCCCTAACTCCTCCCCTTGCCCCTACCAATGCCCCTTTAAGTGCTG
CAGGGGTCTGGGGTTGGCAACTCCTGAGGCCTGCATGGGTGACTTCACATTTTCCTACCTCT
CCTTCTAATCTCTTCTAGAGCACCTGCTATCCCCAACTTCTAGACCTGCTCCAAACTAGTGA
CTAGGATAGAATTTGATCCCCTAACTCACTGTCTGCGGTGCTCATTGCTGCTAACAGCATTG
CCTGTGCTCTCCTCTCAGGGGCAGCATGCTAACGGGGCGACGTCCTAATCCAACTGGGAGAA
GCCTCAGTGGTGGAATTCCAGGCACTGTGACTGTCAAGCTGGCAAGGGCCAGGATTGGGGGA
ATGGAGCTGGGGCTTAGCTGGAGGTGGTCTGAAGCAGACAGGGAATGGGAGAGGAGGATGG
GAAGTAGACAGTGGCTGGTATGGCTCTGAGGCTCCCTGGGGCCTGCTCAAGCTCCTCCTGCT
CCTTGCTGTTTTCTGATGATTTGGGGGCTTGGGAGTCCCTTTGTCCTCATCTGAGACTGAAA
TGTGGGGATCCAGGATGGCCTTCCTTCCTCTTACCCTTCCTCCCTCAGCCTGCAACCTCTAT
CCTGGAACCTGTCCTCCCTTTCTCCCCAACTATGCATCTGTTGTCTGCTCCTCTGCAAGGC
CAGCCAGCTTGGGAGCAGCAGAGAAATAAACAGCATTTCTGATGCCAAAAAAAAAAAAAAA
AAGGGCGGCCGCGACTCTAGAGTCGACCT

FIGURE 12

```
MQELHLLWWALLLGLAQACPEPCDCGEKYGFQIADCAYRDLESVPPGFPANVTTLSLSANRL
PGLPEGAFREVPLLQSLWLAHNEIRTVAAGALASLSHLKSLDLSHNLISDFAWSDLHNLSAL
QLLKMDSNELTFIPRDAFRSLRALRSLQLNHNRLHTLAEGTFTPLTALSHLQINENPFDCTC
GIVWLKTWALTTAVSIPEQDNIACTSPHVLKGTPLSRLPPLPCSAPSVQLSYQPSQDGAELR
PGFVLALHCDVDGQPAPQLHWHIQIPSGIVEITSPNVGTDGRALPGTPVASSQPRFQAFANG
SLLIPDFGKLEEGTYSCLATNELGSAESSVDVALATPGEGGEDTLGRRFHGKAVEGKGCYTV
DNEVQPSGPEDNVVIIYLSRAGNPEAAVAEGVPGQLPPGLLLLGQSLLLFFFLTSF
```

Important features of the protein:

Signal peptide:

amino acids 1-18

Transmembrane domain:

amino acids 403-418

N-glycosylation sites.

amino acids 51-55, 120-124, 309-313

Tyrosine kinase phosphorylation site.

amino acids 319-326

N-myristoylation sites.

amino acids 14-20, 64-70, 92-98, 218-224, 294-300, 323-329, 334-340, 350-356, 394-400

Amidation site.

amino acids 355-359

Leucine rich repeats.

amino acids 51-74, 75-98, 99-122, 123-146, 147-170

Leucine rich repeat C-terminal domain.

amino acids 180-230

FIGURE 13

CCAGGCCGGGAGGCGACGCGCCCAGCCGTCTAAACGGGAACAGCCCTGGCTGAGGGAGCTGC
AGCGCAGCAGAGTATCTGACGGCGCCAGGTTGCGTAGGTGCGGCACGAGGAGTTTTCCCGGC
AGCGAGGAGGTCCTGAGCAGCATGGCCCGGAGGAGCGCCTTCCCTGCCGCCGCGCTCTGGCT
CTGGAGCATCCTCCTGTGCCTGCTGGCACTGCGGGCGGAGGCCGGGCCGCCGCAGGAGGAGA
GCCTGTACCTATGGATCGATGCTCACCAGGCAAGAGTACTCATAGGATTTGAAGAAGATATC
CTGATTGTTTCAGAGGGGAAAATGGCACCTTTTACACATGATTTCAGAAAAGCGCAACAGAG
AATGCCAGCTATTCCTGTCAATATCCATTCCATGAATTTTACCTGGCAAGCTGCAGGGCAGG
CAGAATACTTCTATGAATTCCTGTCCTTGCGCTCCCTGGATAAAGGCATCATGGCAGATCCA
ACCGTCAATGTCCCTCTGCTGGGAACAGTGCCTCACAAGGCATCAGTTGTTCAAGTTGGTTT
CCCATGTCTTGGAAAACAGGATGGGGTGGCAGCATTTGAAGTGGATGTGATTGTTATGAATT
CTGAAGGCAACACCATTCTCCAAACACCTCAAAATGCTATCTTCTTTAAAACATGTCAACAA
GCTGAGTGCCCAGGCGGGTGCCGAAATGGAGGCTTTTGTAATGAAAGACGCATCTGCGAGTG
TCCTGATGGGTTCCACGGACCTCACTGTGAGAAAGCCCTTTGTACCCCACGATGTATGAATG
GTGGACTTTGTGTGACTCCTGGTTTCTGCATCTGCCCACCTGGATTCTATGGAGTGAACTGT
GACAAAGCAAACTGCTCAACCACCTGCTTTAATGGAGGGACCTGTTTCTACCCTGGAAAATG
TATTTGCCCTCCAGGACTAGAGGGAGAGCAGTGTGAAATCAGCAAATGCCCACAACCCTGTC
GAAATGGAGGTAAATGCATTGGTAAAAGCAAATGTAAGTGTTCCAAAGGTTACCAGGGAGAC
CTCTGTTCAAAGCCTGTCTGCGAGCCTGGCTGTGGTGCACATGGAACCTGCCATGAACCCAA
CAAATGCCAATGTCAAGAAGGTTGGCATGGAAGACACTGCAATAAAAGGTACGAAGCCAGCC
TCATACATGCCCTGAGGCCAGCAGGCGCCCAGCTCAGGCAGCACACGCCTTCACTTAAAAAG
GCCGAGGAGCGGCGGGATCCACCTGAATCCAATTACATCTGGTGAACTCCGACATCTGAAAC
GTTTTAAGTTACACCAAGTTCATAGCCTTTGTTAACCTTTCATGTGTTGAATGTTCAAATAA
TGTTCATTACACTTAAGAATACTGGCCTGAATTTTATTAGCTTCATTATAAATCACTGAGCT
GATATTTACTCTTCCTTTTAAGTTTTCTAAGTACGTCTGTAGCATGATGGTATAGATTTTCT
TGTTTCAGTGCTTTGGGACAGATTTTATATTATGTCAATTGATCAGGTTAAAATTTTCAGTG
TGTAGTTGGCAGATATTTTCAAAATTACAATGCATTTATGGTGTCTGGGGGCAGGGGAACAT
CAGAAAGGTTAAATTGGGCAAAATGCGTAAGTCACAAGAATTTGGATGGTGCAGTTAATGT
TGAAGTTACAGCATTTCAGATTTTATTGTCAGATATTTAGATGTTTGTTACATTTTTAAAAA
TTGCTCTTAATTTTTAAACTCTCAATACAATATATTTTGACCTTACCATTATTCCAGAGATT
CAGTATTAAAAAAAAAAAATTACACTGTGGTAGTGGCATTTAAACAATATAATATATTCTA
AACACAATGAAATAGGGAATATAATGTATGAACTTTTTGCATTGGCTTGAAGCAATATAATA
TATTGTAAACAAAACACAGCTCTTACCTAATAAACATTTTATACTGTTTGTATGTATAAAAT
AAAGGTGCTGCTTTAGTTTTTTGGAAAAAAAAAAAAAAAAAAAAAAAA

FIGURE 14

```
MARRSAFPAAALWLWSILLCLLALRAEAGPPQEESLYLWIDAHQARVLIGFEEDILIVSEGK
MAPFTHDFRKAQQRMPAIPVNIHSMNFTWQAAGQAEYFYEFLSLRSLDKGIMADPTVNVPLL
GTVPHKASVVQVGFPCLGKQDGVAAFEVDVIVMNSEGNTILQTPQNAIFFKTCQQAECPGGC
RNGGFCNERRICECPDGFHGPHCEKALCTPRCMNGGLCVTPGFCICPPGFYGVNCDKANCST
TCFNGGTCFYPGKCICPPGLEGEQCEISKCPQPCRNGGKCIGKSKCKCSKGYQGDLCSKPVC
EPGCGAHGTCHEPNKCQCQEGWHGRHCNKRYEASLIHALRPAGAQLRQHTPSLKKAEERRDP
PESNYIW
```

Signal sequence.

amino acids 1-28

N-glycosylation sites.

amino acids 88-92, 245-249

Tyrosine kinase phosphorylation site.

amino acids 370-378

N-myristoylation sites.

amino acids 184-190, 185-191, 189-195, 315-321

ATP/GTP-binding site motif A (P-loop).

amino acids 285-293

EGF-like domain cysteine pattern signature.

amino acids 198-210, 230-242, 262-274, 294-306, 326-338

FIGURE 15

AGAACCTCAGAAATGTGAGTTATTTGGGAATGGCTGTTTGTAAATGTCCTTACGTAAGCCAA
GAGGAGGTCTTGACTTGGGGTCCCAGGGGTACCGCAGATCCCAGGGACTGGAGCAGCACTAG
CAAGCTCTGGAGGATGAGCCAGGAGTCTGGAATTGAGGCTGAGCCAAAGACCCCAGGGCCGT
CTCAGTCTCATAAAAGGGGATCAGGCAGGAGGAGTTTGGGAGAAACCTGAGAAGGGCCTGAT
TGCAGCATCATGATGGCCTCTCCTTGGCCTCTGCTGTGCTCCTGGCCTCCCTCCTGAGTC
TCCACCTTGGAACTGCCACACGTGGGAGTGACATATCCAAGACCTGCTGCTTCCAATACAGC
CACAAGCCCCTTCCCTGGACCTGGGTGCGAAGCTATGAATTCACCAGTAACAGCTGCTCCCA
GCGGGCTGTGATATTCACTACCAAAAGAGGCAAGAAAGTCTGTACCCATCCAAGGAAAAAT
GGGTGCAAAAATACATTTCTTTACTGAAAACTCCGAAACAATTGTGACTCAGCTGAATTTTC
ATCCGAGGACGCTTGGACCCCGCTCTTGGCTCTGCAGCCCTCTGGGGAGCCTGCGGAATCTT
TTCTGAAGGCTACATGGACCCGCTGGGGAGGAGAGGGTGTTTCCTCCCAGAGTTACTTTAAT
AAAGGTTGTTCATAGAGTTGAAAAAAAAAAAAAAAAAAAAAAAAAAAAAAAAAAAAAAAAAA
AAAAAAAAAAAAAAAAAAAAAAAAAAAAAAAAAAAAA

FIGURE 16

MMGLSLASAVLLASLLSLHLGTATRGSDISKTCCFQYSHKPLPWTWVRSYEFTSNSCSQRAV
IFTTKRGKKVCTHPRKKWVQKYISLLKTPKQL

Important features of the protein:

Signal peptide:

amino acids 1-23

N-myristoylation sites.

amino acids 3-9, 26-32

Amidation site.

amino acids 68-72

Small cytokines (intecrine/chemokine).

amino acids 23-88

FIGURE 17

```
GCGAGAACCTTTGCACGCGCACAAACTACGGGGACGATTTCTGATTGATTTTTGGCGCTTTCGATCCACCCTCC
TCCCTTCTCATGGGACTTTGGGGACAAAGCGTCCCGACCGCCTCGAGCGCTCGAGCAGGGCGCTATCCAGGAGC
CAGGACAGCGTCGGGAACCAGACCATGGCTCCTGGACCCCAAGATCCTTAAGTTCGTCGTCTTCATCGTCGCGG
TTCTGCTGCCGGTCCGGGTTGACTCTGCCACCATCCCCGGCAGGACGAAGTTCCCCAGCAGACAGTGGCCCCA
CAGCAACAGAGGCGCAGCCTCAAGGAGGAGGAGTGTCCAGCAGGATCTCATAGATCAGAATATACTGGAGCCTG
TAACCCGTGCACAGAGGGTGTGGATTACACCATTGCTTCCAACAATTTGCCTTCTTGCCTGCTATGTACAGTTT
GTAAATCAGGTCAAACAAATAAAGTTCCTGTACCACGACCAGAGACACCGTGTGTCAGTGTGAAAAAGGAAGC
TTCCAGGATAAAAACTCCCCTGAGATGTGCCGGACGTGTAGAACAGGGTGTCCCAGAGGGATGGTCAAGGTCAG
TAATTGTACGCCCCGGAGTGACATCAAGTGCAAAAATGAATCAGCTGCCAGTTCCACTGGGAAAACCCCAGCAG
CGGAGGAGACAGTGACCACCATCCTGGGGATGCTTGCCTCTCCCTATCACTACCTTATCATCATAGTGGTTTTA
GTCATCATTTTAGCTGTGGTTGTGGTTGGCTTTTCATGTCGGAAGAAATTCATTTCTTACCTCAAAGGCATCTG
CTCAGGTGGTGGAGGAGGTCCCGAACGTGTGCACAGAGTCCTTTTCCGGCGGCGTTCATGTCCTTCACGAGTTC
CTGGGGCGGAGGACAATGCCCGCAACGAGACCCTGAGTAACAGATACTTGCAGCCCACCCAGGTCTCTGAGCAG
GAAATCCAAGGTCAGGAGCTGGCAGAGCTAACAGGTGTGACTGTAGAGTCGCCAGAGGAGCCACAGCGTCTGCT
GGAACAGGCAGAAGCTGAAGGGTGTCAGAGGAGGAGGCTGCTGGTTCCAGTGAATGACGCTGACTCCGCTGACA
TCAGCACCTTGCTGGATGCCTCGGCAACACTGGAAGAAGGACATGCAAAGGAAACAATTCAGGACCAACTGGTG
GGCTCCGAAAAGCTCTTTTATGAAGAAGATGAGGCAGGCTCTGCTACGTCCTGCCTGTGAAAGAATCTCTTCAG
GAAACCAGAGCTTCCCTCATTTACCTTTTCTCCTACAAAGGGAAGCAGCCTGGAAGAAACAGTCCAGTACTTGA
CCCATGCCCCAACAAACTCTACTATCCAATATGGGGCAGCTTACCAATGGTCCTAGAACTTTGTTAACGCACTT
GGAGTAATTTTTATGAAATACTGCGTGTGATAAGCAAACGGGAGAAATTTATATCAGATTCTTGGCTGCATAGT
TATACGATTGTGTATTAAGGGTCGTTTTAGGCCACATGCGGTGGCTCATGCCTGTAATCCCAGCACTTTGATAG
GCTGAGGCAGGTGGATTGCTTGAGCTCGGGAGTTTGAGACCAGCCTCATCAACACAGTGAAACTCCATCTCAAT
TTAAAAAGAAAAAAAGTGGTTTTAGGATGTCATTCTTTGCAGTTCTTCATCATGAGACAAGTCTTTTTTTCTGC
TTCTTATATTGCAAGCTCCATCTCTACTGGTGTGTGCATTTAATGACATCTAACTACAGATGCCGCACAGCCAC
AATGCTTTGCCTTATAGTTTTTTAACTTTAGAACGGGATTATCTTGTTATTACCTGTATTTTCAGTTTCGGATA
TTTTTGACTTAATGATGAGATTATCAAGACGTAGCCCTATGCTAAGTCATGAGCATATGGACTTACGAGGGTTC
GACTTAGAGTTTTGAGCTTTAAGATAGGATTATTGGGGCTTACCCCCACCTTAATTAGAGAAACATTTATATTG
CTTACTACTGTAGGCTGTACATCTCTTTTCCGATTTTTGTATAATGATGTAAACATGGAAAAACTTTAGGAAAT
GCACTTATTAGGCTGTTTACATGGGTTGCCTGGATACAAATCAGCAGTCAAAAATGACTAAAAATATAACTAGT
GACGGAGGGAGAAATCCTCCCTCTGTGGGAGGCACTTACTGCATTCCAGTTCTCCCTCCTGCGCCCTGAGACTG
GACCAGGGTTTGATGGCTGGCAGCTTCTCAAGGGGCAGCTTGTCTTACTTGTTAATTTTAGAGGTATATAGCCA
TATTTATTTATAAATAAATATTTATTTATTTATTTATAAGTAGATGTTTACATATGCCCAGGATTTTGAAGAGC
CTGGTATCTTTGGGAAGCCATGTGTCTGGTTTGTCGTGCTGGGACAGTCATGGGACTGCATCTTCCGACTTGTC
CACAGCAGATGAGGACAGTGAGAATTAAGTTAGATCCGAGACTGCGAAGAGCTTCTCTTTCAAGCGCCATTACA
GTTGAACGTTAGTGAATCTTGAGCCTCATTTGGGCTCAGGGCAGAGCAGGTGTTTATCTGCCCCGGCATCTGCC
ATGGCATCAAGAGGGAAGAGTGGACGGTGCTTGGGAATGGTGTGAAATGGTTGCCGACTCAGGCATGGATGGGC
CCCTCTCGCTTCTGGTGGTCTGTGAACTGAGTCCCTGGGATGCCTTTTAGGGCAGAGATTCCTGAGCTGCGTTT
TAGGGTACAGATTCCCTGTTTGAGGAGCTTGGCCCCTCTGTAAGCATCTGACTCATCTCAGAGATATCAATTCT
TAAACACTGTGACAACGGGATCTAAAATGGCTGACACATTTGTCCTTGTGTCACGTTCCATTATTTTATTTAAA
AACCTCAGTAATCGTTTTAGCTTCTTTCCAGCAAACTCTTCTCCACAGTAGCCCAGTCGTGGTAGGATAAATTA
CGGATATAGTCATTCTAGGGGTTTCAGTCTTTTCCATCTCAAGGCATTGTGTGTTTTGTTCCGGGACTGGTTTG
GCTGGGACAAAGTTAGAACTGCCTGAAGTTCGCACATTCAGATTGTTGTGTCCATGGAGTTTTAGGAGGGGATG
GCCTTTCCGGTCTTCGCACTTCCATCCTCTCCCACTTCCATCTGGCGTCCCACACCTTGTCCCCTGCACTTCTG
GATGACACAGGGTGCTGCTGCCTCCTAGTCTTTGCCTTTGCTGGGCCTTCTGTGCAGGAGACTTGGTCTCAAAG
CTCAGAGAGAGCCAGTCCGGTCCCAGCTCCTTTGTCCCTTCCTCAGAGGCCTTCCTTGAAGATGCATCTAGACT
ACCAGCCTTATCAGTGTTTAAGCTTATTCCTTTAACATAAGCTTCCTGACAACATGAAATTGTTGGGGTTTTTT
GGCGTTGGTTGATTTGTTTAGGTTTTGCTTTATACCCGGGCCAAATAGCACATAACACCTGGTTATATATGAAA
TACTCATATGTTTATGACCAAAATAAATATGAAACCTCATRTTAAAAAAAAAAAAAAAAAAAAAAAAAAAAAAA
```

FIGURE 18

```
MGLWGQSVPTASSARAGRYPGARTASGTRPWLLDPKILKFVVFIVAVLLPVRVDSATIPRQD
EVPQQTVAPQQQRRSLKEEECPAGSHRSEYTGACNPCTEGVDYTIASNNLPSCLLCTVCKSG
QTNKSSCTTTRDTVCQCEKGSFQDKNSPEMCRTCRTGCPRGMVKVSNCTPRSDIKCKNESAA
SSTGKTPAAEETVTTILGMLASPYHYLIIIVVLVIILAVVVVGFSCRKKFISYLKGICSGGG
GGPERVHRVLFRRRSCPSRVPGAEDNARNETLSNRYLQPTQVSEQEIQGQELAELTGVTVES
PEEPQRLLEQAEAEGCQRRRLLVPVNDADSADISTLLDASATLEEGHAKETIQDQLVGSEKL
FYEEDEAGSATSCL
```

Important features of the protein:

Transmembrane domains:

amino acids 35-52, 208-230

N-glycosylation sites.

amino acids 127-131, 182-186, 277-281

Glycosaminoglycan attachment site.

amino acids 245-249 cAMP- and cGMP-dependent protein kinase phosphorylation site.

amino acids 260-264

N-myristoylation sites.

amino acids 21-27, 86-92, 102-108, 161-167, 242-248, 270-276, 297-303, 380-386

ATP/GTP-binding site motif A (P-loop).

amino acids 185-193

TNFR/NGFR cysteine-rich region.

amino acids 99-139

FIGURE 19

GCGGCACCTGGAAGATGCGCCCATTGGCTGGTGGCCTGCTCAAGGTGGTGTTCGTGGTCTTC
GCCTCCTTGTGTGCCTGGTATTCGGGGTACCTGCTCGCAGAGCTCATTCCAGATGCACCCT
GTCCAGTGCTGCCTATAGCATCCGCAGCATCGGGGAGAGGCCTGTCCTCAAAGCTCCAGTCC
CCAAAAGGCAAAAATGTGACCACTGGACTCCCTGCCCATCTGACACCTATGCCTACAGGTTA
CTCAGCGGAGGTGGCAGAAGCAAGTACGCCAAAATCTGCTTTGAGGATAACCTACTTATGGG
AGAACAGCTGGGAAATGTTGCCAGAGGAATAAACATTGCCATTGTCAACTATGTAACTGGGA
ATGTGACAGCAACACGATGTTTTGATATGTATGAAGGCGATAACTCTGGACCGATGACAAAG
TTTATTCAGAGTGCTGCTCCAAAATCCCTGCTCTTCATGGTGACCTATGACGACGGAAGCAC
AAGACTGAATAACGATGCCAAGAATGCCATAGAAGCACTTGGAAGTAAAGAAATCAGGAACA
TGAAATTCAGGTCTAGCTGGGTATTTATTGCAGCAAAAGGCTTGGAACTCCCTTCCGAAATT
CAGAGAGAAAAGATCAACCACTCTGATGCTAAGAACAACAGATATTCTGGCTGGCCTGCAGA
GATCCAGATAGAAGGCTGCATACCCAAAGAACGAAGCTGACACTGCAGGGTCCTGAGTAAAT
GTGTTCTGTATAAACAAATGCAGCTGGAATCGCTCAAGAATCTTATTTTTCTAAATCCAACA
GCCCATATTTGATGAGTATTTTGGGTTTGTTGTAAACCAATGAACATTTGCTAGTTGTATCA
AATCTTGGTACGCAGTATTTTTATACCAGTATTTTATGTAGTGAAGATGTCAATTAGCAGGA
AACTAAAATGAATGGAAATTCTTAAAAAAAAAA

FIGURE 20

MRPLAGGLLKVVFVVFASLCAWYSGYLLAELIPDAPLSSAAYSIRSIGERPVLKAPVPKRQK
CDHWTPCPSDTYAYRLLSGGGRSKYAKICFEDNLLMGEQLGNVARGINIAIVNYVTGNVTAT
RCFDMYEGDNSGPMTKFIQSAAPKSLLFMVTYDDGSTRLNNDAKNAIEALGSKEIRNMKFRS
SWVFIAAKGLELPSEIQREKINHSDAKNNRYSGWPAEIQIEGCIPKERS

Important features of the protein:

Signal peptide:

amino acids 1-20

N-glycosylation sites.

amino acids 120-124, 208-212

Glycosaminoglycan attachment site.

amino acids 80-84

N-myristoylation sites.

amino acids 81-87, 108-114, 119-125

FIGURE 21

CCGGGGAGGGGAGGGCCCGTCCCGCCCCTCCCCGTCTCTCCCCGCCCCTCCCCGTCCCTCCC
GCCGAAGCTCCGTCCCGCCCGCGGGCCGGCTCCGCCCTCACCTCCCGGCCGCGGCTGCCCTC
TGCCCGGGTTGTCCAAGATGGAGGGCGCTCCACCGGGGTCGCTCGCCCTCCGGCTCCTGCTG
TTCGTGGCGCTACCCGCCTCCGGCTGGCTGACGACGGGCGCCCCCGAGCCGCCGCCGCTGTC
CGGAGCCCCACAGGACGGCATCAGAATTAATGTAACTACACTGAAAGATGATGGGGACATAT
CTAAACAGCAGGTTGTTCTTAACATAACCTATGAGAGTGGACAGGTGTATGTAAATGACTTA
CCTGTAAATAGTGGTGTAACCCGAATAAGCTGTCAGACTTTGATAGTGAAGAATGAAATCT
TGAAAATTTGGAGGAAAAGAATATTTTGGAATTGTCAGTGTAAGGATTTTAGTTCATGAGT
GGCCTATGACATCTGGTTCCAGTTTGCAACTAATTGTCATTCAAGAAGAGGTAGTAGAGATT
GATGGAAAACAAGTTCAGCAAAGGATGTCACTGAAATTGATATTTTAGTTAAGAACCGGGG
AGTACTCAGACATTCAAACTATACCCTCCCTTTGGAAGAAAGCATGCTCTACTCTATTTCTC
GAGACAGTGACATTTTATTTACCCTTCCTAACCTCTCCAAAAAAGAAAGTGTTAGTTCACTG
CAAACCACTAGCCAGTATCTTATCAGGAATGTGGAAACCACTGTAGATGAAGATGTTTTACC
TGGCAAGTTACCTGAAACTCCTCTCAGAGCAGAGCCGCCATCTTCATATAAGGTAATGTGTC
AGTGGATGGAAAAGTTTAGAAAAGATCTGTGTAGGTTCTGGAGCAACGTTTTCCCAGTATTC
TTTCAGTTTTTGAACATCATGGTGGTTGGAATTACAGGAGCAGCTGTGGTAATAACCATCTT
AAAGGTGTTTTTCCCAGTTTCTGAATACAAAGGAATTCTTCAGTTGGATAAAGTGGACGTCA
TACCTGTGACAGCTATCAACTTATATCCAGATGGTCCAGAGAAAAGAGCTGAAAACCTTGAA
GATAAAACATGTATTTAAAACGCCATCTCATATCATGGACTCCGAAGTAGCCTGTTGCCTCC
AAATTTGCCACTTGAATATAATTTTCTTTAAATCGTT

FIGURE 22

```
></usr/seqdb2/sst/DNA/Dnaseqs.min/ss.DNA60783
><subunit 1 of 1, 330 aa, 1 stop
><MW: 36840, pI: 4.84, NX(S/T): 4
MEGAPPGSLALRLLLFVALPASGWLTTGAPEPPPLSGAPQDGIRINVTTLKDDGDISKQQVV
LNITYESGQVYVNDLPVNSGVTRISCQTLIVKNENLENLEEKEYFGIVSVRILVHEWPMTSG
SSLQLIVIQEEVVEIDGKQVQQKDVTEIDILVKNRGVLRHSNYTLPLEESMLYSISRDSDIL
FTLPNLSKKESVSSLQTTSQYLIRNVETTVDEDVLPGKLPETPLRAEPPSSYKVMCQWMEKF
RKDLCRFWSNVFPVFFQFLNIMVVGITGAAVVITILKVFFPVSEYKGILQLDKVDVIPVTAI
NLYPDGPEKRAENLEDKTCI
```

Important features of the protein:

Signal peptide:

amino acids 1-23

Transmembrane domain:

amino acids 266-284

Leucine zipper pattern.

amino acids 155-176

N-glycosylation sites.

amino acids 46-49, 64-67, 166-169, 191-194

FIGURE 23

CGTCTCTGCGTTCGCCATGCGTCCCGGGGCGCCAGGGCCACTCTGGCCTCTGCCCTGGGGGG
GCCTGGCTTGGGCCGTGGGCTTCGTGAGCTCCATGGGCTCGGGGAACCCCGCGCCCGGTGGT
GTTTGCTGGCTCCAGCAGGGCCAGGAGGCCACCTGCAGCCTGGTGCTCCAGACTGATGTCAC
CCGGGCCGAGTGCTGTGCCTCCGGCAACATTGACACCGCCTGGTCCAACCTCACCCACCCGG
GGAACAAGATCAACCTCCTCGGCTTCTTGGGCCTTGTCCACTGCCTTCCCTGCAAAGATTCG
TGCGACGGCGTGGAGTGCGGCCCGGGCAAGGCGTGCCGCATGCTGGGGGGCCGCCCGCGCTG
CGAGTGCGCGCCCGACTGCTCGGGGCTCCCGGCGCGGCTGCAGGTCTGCGGCTCAGACGGCG
CCACCTACCGCGACGAGTGCGAGCTGCGCGCCGCGCGCTGCCGCGGCCACCCGGACCTGAGC
GTCATGTACCGGGGCCGCTGCCGCAAGTCCTGTGAGCACGTGGTGTGCCCGCGGCCACAGTC
GTGCGTCGTGGACCAGACGGGCAGCGCCCACTGCGTGGTGTGTCGAGCGGCGCCCTGCCCTG
TGCCCTCCAGCCCCGGCCAGGAGCTTTGCGGCAACAACAACGTCACCTACATCTCCTCGTGC
CACATGCGCCAGGCCACCTGCTTCCTGGGCCGCTCCATCGGCGTGCGCCACGCGGGCAGCTG
CGCAGGCACCCTGAGGAGCCGCCAGGTGGTGAGTCTGCAGAAGAGGAAGAGAACTTCGTG**T
GA**GCCTGCAGGACAGGCCTGGGCCTGGTGCCCGAGGCCCCCCATCATCCCCTGTTATTTATT
GCCACAGCAGAGTCTAATTTATATGCCACGGACACTCCTTAGAGCCCGGATTCGGACCACTT
GGGGATCCCAGAACCTCCCTGACGATATCCTGGAAGGACTGAGGAAGGGAGGCCTGGGGGCC
GGCTGGTGGGTGGGATAGACCTGCGTTCCGGACACTGAGCGCCTGATTTAGGGCCCTTCTCT
AGGATGCCCCAGCCCCTACCCTAAGACCTATTGCCGGGGAGGATTCCACACTTCCGCTCCTT
TGGGGATAAACCTATTAATTATTGCTACTATCAAGAGGGCTGGGCATTCTCTGCTGGTAATT
CCTGAAGAGGCATGACTGCTTTTCTCAGCCCCAAGCCTCTAGTCTGGGTGTGTACGGAGGGT
CTAGCCTGGGTGTGTACGGAGGGTCTAGCCTGGGTGAGTACGGAGGGTCTAGCCTGGGTGAG
TACGGAGGGTCTAGCCTGGGTGAGTACGGAGGGTCTAGCCTGGGTGTGTATGGAGGATCTAG
CCTGGGTGAGTATGGAGGGTCTAGCCTGGGTGAGTATGGAGGGTCTAGCCTGGGTGTGTATG
GAGGGTCTAGCCTGGGTGAGTATGGAGGGTCTAGCCTGGGTGTGTATGGAGGGTCTAGCCTG
GGTGAGTATGGAGGGTCTAGCCTGGGTGTGTACGGAGGGTCTAGTCTGAGTGCGTGTGGGGA
CCTCAGAACACTGTGACCTTAGCCCAGCAAGCCAGGCCTTCATGAAGGCCAAGAAGGCTGC
CACCATTCCCTGCCAGCCCAAGAACTCCAGCTTCCCCACTGCCTCTGTGTGCCCCTTTGCGT
CCTGTGAAGGCCATTGAGAAATGCCCAGTGTGCCCCTGGGAAAGGGCACGGCCTGTGCTCC
TGACACGGGCTGTGCTTGGCCACAGAACCACCCAGCGTCTCCCCTGCTGCTGTCCACGTCAG
TTCATGAGGCAACGTCGCGTGGTCTCAGACGTGGAGCAGCCAGCGGCAGCTCAGAGCAGGGC
ACTGTGTCCGGCGGAGCCAAGTCCACTCTGGGGGAGCTCTGGCGGGACCACGGGCCACTGC
TCACCCACTGGCCCCGAGGGGGTGTAGACGCCAAGACTCACGCATGTGTGACATCCGGAGT
CCTGGAGCCGGGTGTCCCAGTGGCACCACTAGGTGCCTGCTGCCTCCACAGTGGGGTTCACA
CCCAGGGCTCCTTGGTCCCCCACAACCTGCCCCGGCCAGGCCTGCAGACCCAGACTCCAGCC
AGACCTGCCTCACCCACCAATGCAGCCGGGGCTGGCGACACCAGCCAGGTGCTGGTCTTGGG
CCAGTTCTCCCACGACGGCTCACCCTCCCTCCATCTGCGTTGATGCTCAGAATCGCCTACC
TGTGCCTGCGTGTAAACCACAGCCTCAGACCAGCTATGGGGAGAGGACAACACGGAGGATAT
CCAGCTTCCCCGGTCTGGGGTGAGGAATGTGGGGAGCTTGGGCATCCTCCTCCAGCCTCCTC
CAGCCCCCAGGCAGTGCCTTACCTGTGGTGCCCAGAAAAGTGCCCCTAGGTTGGTGGGTCTA
CAGGAGCCTCAGCCAGGCAGCCCACCCCACCCTGGGGCCCTGCCTCACCAAGGAAATAAAGA
CTCAAGCCATAAAAAAAA

FIGURE 24

</usr/seqdb2/sst/DNA/Dnaseqs.min/ss.DNA62306
<subunit 1 of 1, 263 aa, 1 stop
<MW: 27663, pI: 6.77, NX(S/T): 2
MRPGAPGPLWPLPWGALAWAVGFVSSMGSGNPAPGGVCWLQQGQEATCSLVLQTDVTRAECC
ASGNIDTAWSNLTHPGNKINLLGFLGLVHCLPCKDSCDGVECGPGKACRMLGGRPRCECAPD
CSGLPARLQVCGSDGATYRDECELRAARCRGHPDLSVMYRGRCRKSCEHVVCPRPQSCVVDQ
TGSAHCVVCRAAPCPVPSSPGQELCGNNNVTYISSCHMRQATCFLGRSIGVRHAGSCAGTPE
EPPGGESAEEEENFV

Important features:
Signal peptide:
amino acids 1-20

N-glycosylation sites.
amino acids 73-77, 215-219

Osteonectin domain proteins.
amino acids 97-130, 169-202

FIGURE 25

```
TGCAGAGCTTGTGGAGGCCATGGGGCGCGTCGTCGCGGAGCTCGTCTCCTCGCTGCTGGGGT
TGTGGCTGTTGCTGTGCAGCTGCGGATGCCCCGAGGGCGCCGAGCTGCGTGCTCCGCCAGAT
AAAATCGCGATTATTGGAGCCGGAATTGGTGGCACTTCAGCAGCCTATTACCTGCGGCAGAA
ATTTGGGAAAGATGTGAAGATAGACCTGTTTGAAAGAGAAGAGGTCGGGGGCCGCCTGGCTA
CCATGATGGTGCAGGGGCAAGAATACGAGGCAGGAGGTTCTGTCATCCATCCTTTAAATCTG
CACATGAAACGTTTTGTCAAAGACCTGGGTCTCTCTGCTGTTCAGGCCTCTGGTGGCCTACT
GGGGATATATAATGGAGAGACTCTGGTATTTGAGGAGAGCAACTGGTTCATAATTAACGTGA
TTAAATTAGTTTGGCGCTATGGATTTCAATCCCTCCGTATGCACATGTGGGTAGAGGACGTG
TTAGACAAGTTCATGAGGATCTACCGCTACCAGTCTCATGACTATGCCTTCAGTAGTGTCGA
AAAATTACTTCATGCTCTAGGAGGAGATGACTTCCTTGGAATGCTTAATCGAACACTTCTTG
AAACCTTGCAAAAGGCCGGCTTTTCTGAGAAGTTCCTCAATGAAATGATTGCTCCTGTTATG
AGGGTCAATTATGGCCAAAGCACGGACATCAATGCCTTTGTGGGGCGGTGTCACTGTCCTG
TTCTGATTCTGGCCTTTGGGCAGTAGAAGGTGGCAATAAACTTGTTTGCTCAGGGCTTCTGC
AGGCATCCAAAAGCAATCTTATATCTGGCTCAGTAATGTACATCGAGGAGAAAACAAAGACC
AAGTACACAGGAAATCCAACAAAGATGTATGAAGTGGTCTACCAAATTGGAACTGAGACTCG
TTCAGACTTCTATGACATCGTCTTGGTGGCCACTCCGTTGAATCGAAAAATGTCGAATATTA
CTTTTCTCAACTTTGATCCTCCAATTGAGGAATTCCATCAATATTATCAACATATAGTGACA
ACTTTAGTTAAGGGGGAATTGAATACATCTATCTTTAGCTCTAGACCCATAGATAAATTTGG
CCTTAATACAGTTTTAACCACTGATAATTCAGATTTGTTCATTAACAGTATTGGGATTGTGC
CCTCTGTGAGAGAAAAGGAAGATCCTGAGCCATCAACAGATGGAACATATGTTTGGAAGATC
TTTTCCCAAGAAACTCTTACTAAAGCACAAATTTTAAAGCTCTTTCTGTCCTATGATTATGC
TGTGAAGAAGCCATGGCTTGCATATCCTCACTATAAGCCCCGGAGAAATGCCCCTCTATCA
TTCTCCATGATCGACTTTATTACCTCAATGGCATAGAGTGTGCAGCAAGTGCCATGGAGATG
AGTGCCATTGCAGCCCACAACGCTGCACTCCTTGCCTATCACCGCTGGAACGGGCACACAGA
CATGATTGATCAGGATGGCTTATATGAGAAACTTAAAACTGAACTATGAAGTGACACACTCC
TTTTTCCCCTCCTAGTTCCAAATGACTATCAGTGGCAAAAAGAACAAAATCTGAGCAGAGA
TGATTTTGAACCAGATATTTTGCCATTATCATTGTTTAATAAAAGTAATCCCTGCTGGTCAT
AGGAAAAAAAAAAAAA
```

FIGURE 26

```
</usr/seqdb2/sst/DNA/Dnaseqs.min/ss.DNA62880
<subunit 1 of 1, 505 aa, 1 stop
<MW: 56640, pI: 6.10, NX(S/T): 4
MGRVVAELVSSLLGLWLLLCSCGCPEGAELRAPPDKIAIIGAGIGGTSAAYYLRQKFGKDVK
IDLFEREEVGGRLATMMVQGQEYEAGGSVIHPLNLHMKRFVKDLGLSAVQASGGLLGIYNGE
TLVFEESNWFIINVIKLVWRYGFQSLRMHMWVEDVLDKFMRIYRYQSHDYAFSSVEKLLHAL
GGDDFLGMLNRTLLETLQKAGFSEKFLNEMIAPVMRVNYGQSTDINAFVGAVSLSCSDSGLW
AVEGGNKLVCSGLLQASKSNLISGSVMYIEEKTKTKYTGNPTKMYEVVYQIGTETRSDFYDI
VLVATPLNRKMSNITFLNFDPPIEEFHQYYQHIVTTLVKGELNTSIFSSRPIDKFGLNTVLT
TDNSDLFINSIGIVPSVREKEDPEPSTDGTYVWKIFSQETLTKAQILKLFLSYDYAVKKPWL
AYPHYKPPEKCPSIILHDRLYYLNGIECAASAMEMSAIAAHNAALLAYHRWNGHTDMIDQDG
LYEKLKTEL
```

Important features:

Signal peptide:

amino acids 1-23

N-glycosylation sites.

amino acids 196-200, 323-327, 353-357

Tyrosine kinase phosphorylation site.

amino acids 291-298

N-myristoylation sites.

amino acids 23-29, 41-47, 43-49, 45-51, 46-52, 72-78, 115-121, 119-125, 260-266, 384-390, 459-465

Prokaryotic membrane lipoprotein lipid attachment site.

amino acids 12-23, 232-243

FIGURE 27

CATTTCCAACAAGAGCACTGGCCAAGTCAGCTTCTTCTGAGAGAGTCTCTAGAAGACATGAT
GCTACACTCAGCTTTGGGTCTCTGCCTCTTACTCGTCACAGTTTCTTCCAACCTTGCCATTG
CAATAAAAAGGAAAAGAGGCCTCCTCAGACACTCTCAAGAGGATGGGGAGATGACATCACT
TGGGTACAAACTTATGAAGAAGGTCTCTTTTATGCTCAAAAAAGTAAGAAGCCATTAATGGT
TATTCATCACCTGGAGGATTGTCAATACTCTCAAGCACTAAAGAAAGTATTTGCCCAAAATG
AAGAAATACAAGAAATGGCTCAGAATAAGTTCATCATGCTAAACCTTATGCATGAAACCACT
GATAAGAATTTATCACCTGATGGGCAATATGTGCCTAGAATCATGTTTGTAGACCCTTCTTT
AACAGTTAGAGCTGACATAGCTGGAAGATACTCTAACAGATTGTACACATATGAGCCTCGGG
ATTTACCCCTATTGATAGAAAACATGAAGAAAGCATTAAGACTTATTCAGTCAGAGCTATAA
GAGATGATGGAAAAAGCCTTCACTTCAAAGAAGTCAAATTTCATGAAGAAACCTCTGGCA
CATTGACAAATACTAAATGTGCAAGTATATAGATTTTGTAATATTACTATTTAGTTTTTTA
ATGTGTTTGCAATAGTCTTATTAAAATAAATGTTTTTAAATCTGA

FIGURE 28

</usr/seqdb2/sst/DNA/Dnaseqs.min/ss.DNA64896
<subunit 1 of 1, 166 aa, 1 stop
<MW: 19171, pI: 8.26, NX(S/T): 1
MMLHSALGLCLLLVTVSSNLAIAIKKEKRPPQTLSRGWGDDITWVQTYEEGLFYAQKSKKPL
MVIHHLEDCQYSQALKKVFAQNEEIQEMAQNKFIMLNLMHETTDKNLSPDGQYVPRIMFVDP
SLTVRADIAGRYSNRLYTYEPRDLPLLIENMKKALRLIQSEL

Important features:

Signal peptide:

amino acids 1-23

N-myristoylation site.

amino acids 51-57

FIGURE 29

TAAAACAGCTACAATATTCCAGGGCCAGTCACTTGCCATTTCTCATAACAGCGTCAGAGAGA
AAGAACTGACTGAAACGTTTGAGATGAAGAAAGTTCTCCTCCTGATCACAGCCATCTTGGCA
GTGGCTGTTGGTTTCCCAGTCTCTCAAGACCAGGAACGAGAAAAAAGAAGTATCAGTGACAG
CGATGAATTAGCTTCAGGGTTTTTTGTGTTCCCTTACCCATATCCATTTCGCCCACTTCCAC
CAATTCCATTTCCAAGATTTCCATGGTTTAGACGTAATTTTCCTATTCCAATACCTGAATCT
GCCCCTACAACTCCCCTTCCTAGCGAAAAGTAAACAAGAAGGATAAGTCACGATAAACCTGG
TCACCTGAAATTGAAATTGAGCCACTTCCTTGAAGAATCAAAATTCCTGTTAATAAAGAAA
AACAAATGTAATTGAAATAGCACACAGCATTCTCTAGTCAATATCTTTAGTGATCTTCTTTA
ATAAACATGAAAGCAAAGATTTTGGTTTCTTAATTTCCACA

FIGURE 30

></usr/seqdb2/sst/DNA/Dnaseqs.min/ss.DNA71290
><subunit 1 of 1, 85 aa, 1 stop
><MW: 9700, pI: 9.55, NX(S/T): 0
MKKVLLLITAILAVAVGFPVSQDQEREKRSISDSDELASGFFVFPYPYPFRPLPPIPFPRFP
WFRRNFPIPIPESAPTTPLPSEK

Important features of the protein:
Signal peptide:
amino acids 1-17

Homologous region to B3-hordein:
amino acids 47-85

FIGURE 31

```
CGGACGCGTGGGCGGGCGCGCCGGGAGGGACCGGCGGCGGCATGGGCCGGGGGCCCTGGGAT
GCGGGCCCGTCTCGCCGCCTGCTGCCGCTGTTGCTGCTGCTCGGCCTGGCCCGCGGCGCCGC
GGGAGCGCCGGGCCCCGACGGTTTAGACGTCTGTGCCACTTGCCATGAACATGCCACATGCC
AGCAAAGAGAAGGGAAGAAGATCTGTATTTGCAACTATGGATTTGTAGGGAACGGGAGGACT
CAGTGTGTTGATAAAAATGAGTGCCAGTTTGGAGCCACTCTTGTCTGTGGGAACCACACATC
TTGCCACAACACCCCGGGGGCTTCTATTGCATTTGCCTGGAAGGATATCGAGCCACAAACA
ACAACAAGACATTCATTCCCAACGATGGCACCTTTTGTACAGACATAGATGAGTGTGAAGTT
TCTGGCCTGTGCAGGCATGGAGGGCGATGCGTGAACACTCATGGAGCTTTGAATGCTACTG
TATGGATGGATACTTGCCAAGGAATGGACCTGAACCTTTCCACCCGACCACCGATGCCACAT
CATGCACAGAAATAGACTGTGGTACCCCTCCTGAGGTTCCAGATGGCTATATCATAGGAAAT
TATACGTCTAGTCTGGGCAGCCAGGTTCGTTATGCTTGCAGAGAAGGATTCTTCAGTGTTCC
AGAAGATACAGTTTCAAGCTGCACAGGCCTGGGCACATGGGAGTCCCCAAAATTACATTGCC
AAGAGATCAACTGTGGCAACCCTCCAGAAATGCGGCACGCCATCTTGGTAGGAAATCACAGC
TCCAGGCTGGGCGGTGTGGCTCGCTATGTCTGTCAAGAGGGCTTTGAGAGCCCTGGAGGAAA
GATCACTTCTGTTTGCACAGAGAAAGGCACCTGGAGAGAAGTACTTTAACATGCACAGAAA
TTCTGACAAAGATTAATGATGTATCACTGTTTAATGATACCTGTGTGAGATGGCAAATAAAC
TCAAGAAGAATAAACCCCAAGATCTCATATGTGATATCCATAAAAGGACAACGGTTGGACCC
TATGGAATCAGTTCGTGAGGAGACAGTCAACTTGACCACAGACAGCAGGACCCCAGAAGTGT
GCCTAGCCCTGTACCCAGGCACCAACTACACCGTGAACATCTCCACAGCACCTCCCAGGCGC
TCGATGCCAGCCGTCATCGGTTTCCAGACAGCTGAAGTTGATCTCTTAGAAGATGATGGAAG
TTTCAATATTTCAATATTTAATGAAACTTGTTTGAAATTGAACAGGCGTTCTAGGAAAGTTG
GATCAGAACACATGTACCAATTTACCGTTCTGGGTCAGAGGTGGTATCTGGCTAACTTTTCT
CATGCAACATCGTTTAACTTCACAACGAGGGAACAAGTGCCTGTAGTGTGTTTGGATCTGTA
CCCTACGACTGATTATACGGTGAATGTGACCCTGCTGAGATCTCCTAAGCGGCACTCAGTGC
AAATAACAATAGCAACTCCCCCAGCAGTAAAACAGACCATCAGTAACATTTCAGGATTTAAT
GAAACCTGCTTGAGATGGAGAAGCATCAAGACAGCTGATATGGAGGAGATGTATTTATTCCA
CATTTGGGGCCAGAGATGGTATCAGAAGGAATTTGCCCAGGAAATGACCTTTAATATCAGTA
GCAGCAGCCGAGATCCCGAGGTGTGCTTGGACCTACGTCCGGGTACCAACTACAATGTCAGT
CTCCGGGCTCTGTCTTCGGAACTTCCTGTGGTCATCTCCCTGACAACCCAGATAACAGAGCC
TCCCCTCCCGGAAGTAGAATTTTTTACGGTGCACAGAGGACCTCTACCACGCCTCAGACTGA
GGAAAGCCAAGGAGAAAAATGGACCAATCAGTTCATATCAGGTGTTAGTGCTTCCCCTGGCC
CTCCAAAGCACATTTTCTTGTGATTCTGAAGGCGCTTCCTCCTTCTTTAGCAACGCCTCTGA
TGCTGATGGATACGTGGCTGCAGAACTACTGGCCAAAGATGTTCCAGATGATGCCATGGAGA
TACCTATAGGAGACAGGCTGTACTATGGGAATATTATAATGCACCCTTGAAAAGAGGGAGT
GATTACTGCATTATATTACGAATCACAAGTGAATGGAATAAGGTGAGAAGACACTCCTGTGC
AGTTTGGGCTCAGGTGAAAGATTCGTCACTCATGCTGCTGCAGATGGCGGGTGTTGGACTGG
GTTCCCTGGCTGTTGTGATCATTCTCACATTCCTCTCCTTCTCAGCGGTGTGATGGCAGATG
GACACTGAGTGGGGAGGATGCACTGCTGCTGGGCAGGTGTTCTGGCAGCTTCTCAGGTGCCC
GCACAGAGGCTCCGTGTGACTTCCGTCCAGGGAGCATGTGGGCCTGCAACTTTCTCCATTCC
CAGCTGGGCCCCATTCCTGGATTTAAGATGGTGGCTATCCCTGAGGAGTCACCATAAGGAGA
AAACTCAGGAATTCTGAGTCTTCCCTGCTACAGGACCAGTTCTGTGCAATGAACTTGAGACT
CCTGATGTACACTGTGATATTGACCGAAGGCTACATACAGATCTGTGAATCTTGGCTGGGAC
TTCCTCTGAGTGATGCCTGAGGGTCAGCTCCTCTAGACATTGACTGCAAGAGAATCTCTGCA
ACCTCCTATATAAAAGCATTTCTGTTAATTCATTCAGAATCCATTCTTTACAATATGCAGTG
AGATGGGCTTAAGTTTGGGCTAGAGTTTGACTTTATGAAGGAGGTCATTGAAAAGAGAACA
GTGACGTAGGCAAATGTTTCAAGCACTTTAGAAACAGTACTTTTCCTATAATTAGTTGATAT
ACTAATGAGAAAATATACTAGCCTGGCCATGCCAATAAGTTTCCTGCTGTGTCTGTTAGGCA
GCATTGCTTTGATGCAATTTCTATTGTCCTATATATTCAAAAGTAATGTCTACATTCCAGTA
AAATATCCCGTAATTAAAAA
```

FIGURE 32

```
></usr/seqdb2/sst/DNA/Dnaseqs.min/ss.DNA96031
><subunit 1 of 1, 747 aa, 1 stop
><MW: 82710, pI: 6.36, NX(S/T): 18
MGRGPWDAGPSRRLLPLLLLLGLARGAAGAPGPDGLDVCATCHEHATCQQREGKKICICNYG
FVGNGRTQCVDKNECQFGATLVCGNHTSCHNTPGGFYCICLEGYRATNNNKTFIPNDGTFCT
DIDECEVSGLCRHGGRCVNTHGSFECYCMDGYLPRNGPEPFHPTTDATSCTEIDCGTPPEVP
DGYIIGNYTSSLGSQVRYACREGFFSVPEDTVSSCTGLGTWESPKLHCQEINCGNPPEMRHA
ILVGNHSSRLGGVARYVCQEGFESPGGKITSVCTEKGTWRESTLTCTEILTKINDVSLFNDT
CVRWQINSRRINPKISYVISIKGQRLDPMESVREETVNLTTDSRTPEVCLALYPGTNYTVNI
STAPPRRSMPAVIGFQTAEVDLLEDDGSFNISIFNETCLKLNRRSRKVGSEHMYQFTVLGQR
WYLANFSHATSFNFTTREQVPVVCLDLYPTTDYTVNVTLLRSPKRHSVQITIATPPAVKQTI
SNISGFNETCLRWRSIKTADMEEMYLFHIWGQRWYQKEFAQEMTFNISSSSRDPEVCLDLRP
GTNYNVSLRALSSELPVVISLTTQITEPPLPEVEFFTVHRGPLPRLRLRKAKEKNGPISSYQ
VLVLPLALQSTFSCDSEGASSFFSNASDADGYVAAELLAKDVPDDAMEIPIGDRLYYGEYYN
APLKRGSDYCIILRITSEWNKVRRHSCAVWAQVKDSSLMLLQMAGVGLGSLAVVIILTFLSF
SAV
```

Important features of the protein:
Signal peptide:
amino acids 1-29
Transmembrane domain:
amino acids 718-740
N-glycosylation sites.
amino acids 87-91, 112-116, 193-197, 253-257, 308-312, 348-352, 367-371, 371-375, 402-406, 407-411, 439-443, 447-451, 470-474, 498-502, 503-507, 542-546, 563-567, 645-649
cAMP- and cGMP-dependent protein kinase phosphorylation sites.
amino acids 478-482, 686-690, 705-709
Tyrosine kinase phosphorylation site.
amino acids 419-427
N-myristoylation sites.
amino acids 22-28, 35-41, 65-71, 86-92, 96-102, 120-126, 146-152, 192-198, 252-258, 274-280, 365-371, 559-565, 688-694, 727-733.
Amidation site.
amino acids 52-56
Aspartic acid and asparagine hydroxylation sites.
amino acids 91-103, 141-153.
Prokaryotic membrane lipoprotein lipid attachment site.
amino acids 624-635
Cytochrome c family heme-binding site signature.
amino acids 39-45
Calcium-binding EGF-like domain proteins pattern proteins.
amino acids 85-106, 135-156
Receptor tyrosine kinase class V proteins:
amino acids 389-422

FIGURE 33

GGAAAAGGTACCCGCGAGAGACAGCCAGCAGTTCTGTGGAGCAGCGGTGGCCGGCTAGGATG
GGCTGTCTCTGGGGTCTGGCTCTGCCCCTTTTCTTCTTCTGCTGGGAGGTTGGGGTCTCTGG
GAGCTCTGCAGGCCCCAGCACCCGCAGAGCAGACACTGCGATGACAACGGACGACACAGAAG
TGCCCGCTATGACTCTAGCACCGGGCCACGCCGCTCTGGAAACTCAAACGCTGAGCGCTGAG
ACCTCTTCTAGGGCCTCAACCCCAGCCGGCCCCATTCCAGAAGCAGAGACCAGGGGAGCCAA
GAGAATTTCCCCTGCAAGAGAGACCAGGAGTTTCACAAAAACATCTCCCAACTTCATGGTGC
TGATCGCCACCTCCGTGGAGACATCAGCCGCCAGTGGCAGCCCCGAGGGAGCTGGAATGACC
ACAGTTCAGACCATCACAGGCAGTGATCCCGAGGAAGCCATCTTTGACACCCTTTGCACCGA
TGACAGCTCTGAAGAGGCAAAGACACTCACAATGGACATATTGACATTGGCTCACACCTCCA
CAGAAGCTAAGGGCCTGTCCTCAGAGAGCAGTGCCTCTTCCGACGGCCCCCATCCAGTCATC
ACCCCGTCACGGGCCTCAGAGAGCAGCGCCTCTTCCGACGGCCCCCATCCAGTCATCACCCC
GTCACGGGCCTCAGAGAGCAGCGCCTCTTCCGACGGCCCCCATCCAGTCATCACCCCGTCAT
GGTCCCCGGGATCTGATGTCACTCTCCTCGCTGAAGCCCTGGTGACTGTCACAAACATCGAG
GTTATTAATTGCAGCATCACAGAAATAGAAACAACAACTTCCAGCATCCCTGGGGCCTCAGA
CATAGATCTCATCCCCACGGAAGGGGTGAAGGCCTCGTCCACCTCCGATCCACCAGCTCTGC
CTGACTCCACTGAAGCAAAACCACACATCACTGAGGTCACAGCCTCTGCCGAGACCCTGTCC
ACAGCCGGCACCACAGAGTCAGCTGCACCTCATGCCACGGTTGGGACCCCACTCCCCACTAA
CAGCGCCACAGAAAGAGAAGTGACAGCACCCGGGGCCACGACCCTCAGTGGAGCTCTGGTCA
CAGTTAGCAGGAATCCCCTGGAAGAAACCTCAGCCCTCTCTGTTGAGACACCAAGTTACGTC
AAAGTCTCAGGAGCAGCTCCGGTCTCCATAGAGGCTGGGTCAGCAGTGGGCAAAACAACTTC
CTTTGCTGGGAGCTCTGCTTCCTCCTACAGCCCCTCGGAAGCCGCCCTCAAGAACTTCACCC
CTTCAGAGACACCGACCATGGACATCGCAACCAAGGGGCCCTTCCCCACCAGCAGGGACCCT
CTTCCTTCTGTCCCTCCGACTACAACCAACAGCAGCCGAGGGACGAACAGCACCTTAGCCAA
GATCACAACCTCAGCGAAGACCACGATGAAGCCCCAACAGCCACGCCCACGACTGCCCGGAC
GAGGCCGACCACAGACGTGAGTGCAGGTGAAAATGGAGGTTTCCTCCTCCTGCGGCTGAGTG
TGGCTTCCCCGGAAGACCTCACTGACCCCAGAGTGGCAGAAAGGCTGATGCAGCAGCTCCAC
CGGGAACTCCACGCCCACGCGCCTCACTTCCAGGTCTCCTTACTGCGTGTCAGGAGAGGCTA
ACGGACATCAGCTGCAGCCAGGCATGTCCCGTATGCCAAAAGAGGGTGCTGCCCCTAGCCTG
GGCCCCCACCGACAGACTGCAGCTGCGTTACTGTGCTGAGAGGTACCCAGAAGGTTCCCATG
AAGGGCAGCATGTCCAAGCCCCTAACCCCAGATGTGGCAACAGGACCCTCGCTCACATCCAC
CGGAGTGTATGTATGGGGAGGGGCTTCACCTGTTCCCAGAGGTGTCCTTGGACTCACCTTGG
CACATGTTCTGTGTTTCAGTAAAGAGAGACCTGATCACCCATCTGTGTGCTTCCATCCTGCA
TTAAAATTCACTCAGTGTGGCCCAAAAAAA

FIGURE 34

```
></usr/seqdb2/sst/DNA/Dnaseqs.min/ss.DNA108722
><subunit 1 of 1, 482 aa, 1 stop
><MW: 49060, pI: 4.74, NX(S/T): 4
MGCLWGLALPLFFFCWEVGVSGSSAGPSTRRADTAMTTDDTEVPAMTLAPGHAALETQTLSA
ETSSRASTPAGPIPEAETRGAKRISPARETRSFTKTSPNFMVLIATSVETSAASGSPEGAGM
TTVQTITGSDPEEAIFDTLCTDDSSEEAKTLTMDILTLAHTSTEAKGLSSESSASSDGPHPV
ITPSRASESSASSDGPHPVITPSRASESSASSDGPHPVITPSWSPGSDVTLLAEALVTVTNI
EVINCSITEIETTTSSIPGASDIDLIPTEGVKASSTSDPPALPDSTEAKPHITEVTASAETL
STAGTTESAAPHATVGTPLPTNSATEREVTAPGATTLSGALVTVSRNPLEETSALSVETPSY
VKVSGAAPVSIEAGSAVGKTTSFAGSSASSYSPSEAALKNFTPSETPTMDIATKGPFPTSRD
PLPSVPPTTTNSSRGTNSTLAKITTSAKTTMKPQQPRPRLPGRGRPQT
```

Important features of the protein:

Signal peptide:

amino acids 1-25

N-glycosylation sites.

amino acids 252-256, 445-449, 451-455 cAMP- and cGMP-dependent protein kinase phosphorylation site.

amino acids 84-88

N-myristoylation sites.

amino acids 2-8, 19-25, 117-123, 121-127, 232-238, 278-284, 314-320, 349-355, 386-392, 397-403, 449-455

ATP/GTP-binding site motif A (P-loop).

amino acids 385-393

FIGURE 35

```
GCCTCTGAATTGTTGGGCAGTCTGGCAGTGGAGCTCTCCCCGGTCTGACAGCCACTCCAGAG
GCCATGCTTCGTTTCTTGCCAGATTTGGCTTTCAGCTTCCTGTTAATTCTGGCTTTGGGCCA
GGCAGTCCAATTTCAAGAATATGTCTTTCTCCAATTTCTGGGCTTAGATAAGGCGCCTTCAC
CCCAGAAGTTCCAACCTGTGCCTTATATCTTGAAGAAAATTTTCCAGGATCGCGAGGCAGCA
GCGACCACTGGGGTCTCCCGAGACTTATGCTACGTAAAGGAGCTGGGCGTCCGCGGGAATGT
ACTTCGCTTTCTCCAGACCAAGGTTTCTTTCTTTACCCAAAGAAAATTTCCCAAGCTTCCT
CCTGCCTGCAGAAGCTCCTCTACTTTAACCTGTCTGCCATCAAAGAAAGGGAACAGTTGACA
TTGGCCCAGCTGGGCCTGGACTTGGGGCCCAATTCTTACTATAACCTGGGACCAGAGCTGGA
ACTGGCTCTGTTCCTGGTTCAGGAGCCTCATGTGTGGGCCAGACCACCCCTAAGCCAGGTA
AAATGTTTGTGTTGCGGTCAGTCCCATGGCCACAAGGTGCTGTTCACTTCAACCTGCTGGAT
GTAGCTAAGGATTGGAATGACAACCCCGGAAAAATTTCGGGTTATTCCTGGAGATACTGGT
CAAAGAAGATAGAGACTCAGGGGTGAATTTTCAGCCTGAAGACACCTGTGCCAGACTAAGAT
GCTCCCTTCATGCTTCCCTGCTGGTGGTGACTCTCAACCCTGATCAGTGCCACCCTTCTCGG
AAAAGGAGAGCAGCCATCCCTGTCCCCAAGCTTTCTTGTAAGAACCTCTGCCACCGTCACCA
GCTATTCATTAACTTCCGGGACCTGGGTTGGCACAAGTGGATCATTGCCCCCAAGGGGTTCA
TGGCAAATTACTGCCATGGAGAGTGTCCCTTCTCACTGACCATCTCTCTCAACAGCTCCAAT
TATGCTTTCATGCAAGCCCTGATGCATGCCGTTGACCCAGAGATCCCCCAGGCTGTGTGTAT
CCCCACCAAGCTGTCTCCCATTTCCATGCTCTACCAGGACAATAATGACAATGTCATTCTAC
GACATTATGAAGACATGGTAGTCGATGAATGTGGGTGTGGGTAGGATGTCAGAAATGGGAAT
AGAAGGAGTGTTCTTAGGGTAAATCTTTTAATAAAACTACCTATCTGGTTTATGACCACTTA
GATCGAAATGTC
```

FIGURE 36

MLRFLPDLAFSFLLILALGQAVQFQEYVFLQFLGLDKAPSPQKFQPVPYILKKIFQDREAAA
TTGVSRDLCYVKELGVRGNVLRFLPDQGFFLYPKKISQASSCLQKLLYFNLSAIKEREQLTL
AQLGLDLGPNSYYNLGPELELALFLVQEPHVWGQTTPKPGKMFVLRSVPWPQGAVHFNLLDV
AKDWNDNPRKNFGLFLEILVKEDRDSGVNFQPEDTCARLRCSLHASLLVVTLNPDQCHPSRK
RRAAIPVPKLSCKNLCHRHQLFINFRDLGWHKWIIAPKGFMANYCHGECPFSLTISLNSSNY
AFMQALMHAVDPEIPQAVCIPTKLSPISMLYQDNNDNVILRHYEDMVVDECGCG

Important features of the protein:
Signal peptide:
amino acids 1-21

N-glycosylation sites.
amino acids 112-116, 306-310 cAMP- and cGMP-dependent protein kinase phosphorylation site.
amino acids 96-100

N-myristoylation site.
amino acids 77-83

TGF-beta family proteins.
amino acids 264-299, 327-341, 345-364

FIGURE 37

```
CACTTTCTCCCTCTCTTCCTTTACTTTCGAGAAACCGCGCTTCCGCTTCTGGTCGCAGAGAC
CTCGGAGACCGCGCCGGGGAGACGGAGGTGCTGTGGGTGGGGGGGACCTGTGGCTGCTCGTA
CCGCCCCCCACCCTCCTCTTCTGCACTGCCGTCCTCCGGAAGACCTTTTCCCCTGCTCTGTT
TCCTTCACCGAGTCTGTGCATCGCCCCGGACCTGGCCGGGAGGAGGCTTGGCCGGCGGGAGA
TGCTCTAGGGGCGGCGCGGGAGGAGCGGCCGGCGGGACGGAGGGCCCGGCAGGAAGATGGGC
TCCCGTGGACAGGGACTCTTGCTGGCGTACTGCCTGCTCCTTGCCTTTGCCTCTGGCCTGGT
CCTGAGTCGTGTGCCCCATGTCCAGGGGAACAGCAGGAGTGGGAGGGGACTGAGGAGCTGC
CGTCGCCTCCGGACCATGCCGAGAGGGCTGAAGAACAACATGAAAAATACAGGCCCAGTCAG
GACCAGGGGCTCCCTGCTTCCCGGTGCTTGCGCTGCTGTGACCCCGGTACCTCCATGTACCC
GGCGACCGCCGTGCCCCAGATCAACATCACTATCTTGAAAGGGGAGAAGGGTGACCGCGGAG
ATCGAGGCCTCCAAGGGAAATATGGCAAAACAGGCTCAGCAGGGGCCAGGGGCCACACTGGA
CCCAAAGGGCAGAAGGGCTCCATGGGGGCCCCTGGGGAGCGGTGCAAGAGCCACTACGCCGC
CTTTTCGGTGGGCCGGAAGAAGCCCATGCACAGCAACCACTACTACCAGACGGTGATCTTCG
ACACGGAGTTCGTGAACCTCTACGACCACTTCAACATGTTCACCGGCAAGTTCTACTGCTAC
GTGCCCGGCCTCTACTTCTTCAGCCTCAACGTGCACACCTGGAACCAGAAGGAGACCTACCT
GCACATCATGAAGAACGAGGAGGAGGTGGTGATCTTGTTCGCGCAGGTGGGCGACCGCAGCA
TCATGCAAAGCCAGAGCCTGATGCTGGAGCTGCGAGAGCAGGACCAGGTGTGGGTACGCCTC
TACAAGGGCGAACGTGAGAACGCCATCTTCAGCGAGGAGCTGGACACCTACATCACCTTCAG
TGGCTACCTGGTCAAGCACGCCACCGAGCCCTAGCTGGCCGGCCACCTCCTTTCCTCTCGCC
ACCTTCCACCCCTGCGCTGTGCTGACCCCACCGCCTCTTCCCCGATCCCTGGACTCCGACTC
CCTGGCTTTGGCATTCAGTGAGACGCCCTGCACACACAGAAAGCCAAAGCGATCGGTGCTCC
CAGATCCCGCAGCCTCTGGAGAGAGCTGACGGCAGATGAAATCACCAGGGCGGGGCACCCGC
GAGAACCCTCTGGGACCTTCCGCGGCCCTCTCTGCACACATCCTCAAGTGACCCCGCACGGC
GAGACGCGGGTGGCGGCAGGGCGTCCCAGGGTGCGGCACCGCGGCTCCAGTCCTTGGAAATA
ATTAGGCAAATTCTAAAGGTCTCAAAAGGAGCAAAGTAAACCGTGGAGGACAAAGAAAAGGG
TTGTTATTTTTGTCTTTCCAGCCAGCCTGCTGGCTCCCAAGAGAGAGGCCTTTTCAGTTGAG
ACTCTGCTTAAGAGAAGATCCAAAGTTAAAGCTCTGGGGTCAGGGGAGGGGCCGGGGGCAGG
AAACTACCTCTGGCTTAATTCTTTTAAGCCACGTAGGAACTTTCTTGAGGGATAGGTGGACC
CTGACATCCCTGTGGCCTTGCCCAAGGGCTCTGCTGGTCTTTCTGAGTCACAGCTGCGAGGT
GATGGGGGCTGGGGCCCCAGGCGTCAGCCTCCCAGAGGGACAGCTGAGCCCCCTGCCTTGGC
TCCAGGTTGGTAGAAGCAGCCGAAGGGCTCCTGACAGTGGCCAGGGACCCCTGGGTCCCCCA
GGCCTGCAGATGTTTCTATGAGGGGCAGAGCTCCTTGGTACATCCATGTGTGGCTCTGCTCC
ACCCCTGTGCCACCCCAGAGCCCTGGGGGGTGGTCTCCATGCCTGCCACCCTGGCATCGGCT
TTCTGTGCCGCCTCCCACACAAATCAGCCCCAGAAGGCCCCGGGGCCTTGGCTTCTGTTTTT
TATAAAACACCTCAAGCAGCACTGCAGTCTCCCATCTCCTCGTGGGCTAAGCATCACCGCTT
CCACGTGTGTTGTGTTGGTTGGCAGCAAGGCTGATCCAGACCCCTTCTGCCCCCACTGCCCT
CATCCAGGCCTCTGACCAGTAGCCTGAGAGGGCTTTTTCTAGGCTTCAGAGCAGGGGAGAG
CTGGAAGGGGCTAGAAAGCTCCCGCTTGTCTGTTTCTCAGGCTCCTGTGAGCCTCAGTCCTG
AGACCAGAGTCAAGAGGAAGTACACGTCCCAATCACCCGTGTCAGGATTCACTCTCAGGAGC
TGGGTGGCAGGAGAGGCAATAGCCCCTGTGGCAATTGCAGGACCAGCTGGAGCAGGGTTGCG
GTGTCTCCACGGTGCTCTCGCCCTGCCCATGGCCACCCCAGACTCTGATCTCCAGGAACCCC
ATAGCCCCTCTCCACCTCACCCCATGTTGATGCCCAGGGTCACTCTTGCTACCCGCTGGGCC
CCCAAACCCCGCTGCCTCTCTTCCTTCCCCCATCCCCCACCTGGTTTTGACTAATCCTGC
TTCCCTCTCTGGGCCTGGCTGCCGGGATCTGGGGTCCCTAAGTCCCTCTCTTTAAAGAACTT
CTGCGGGTCAGACTCTGAAGCCGAGTTGCTGTGGGCGTGCCCGGAAGCAGAGCGCCACACTC
GCTGCTTAAGCTCCCCCAGCTCTTTCCAGAAAACATTAAACTCAGAATTGTGTTTTCAA
```

FIGURE 38

></usr/seqdb2/sst/DNA/Dnaseqs.min/ss.DNA41234
><subunit 1 of 1, 281 aa, 1 stop
><MW: 31743, pI: 6.83, NX(S/T): 1
MGSRGQGLLLAYCLLLAFASGLVLSRVPHVQGEQQEWEGTEELPSPPDHAERAEEQHEKYRP
SQDQGLPASRCLRCCDPGTSMYPATAVPQINITILKGEKGDRGDRGLQGKYGKTGSAGARGH
TGPKGQKGSMGAPGERCKSHYAAFSVGRKKPMHSNHYYQTVIFDTEFVNLYDHFNMFTGKFY
CYVPGLYFFSLNVHTWNQKETYLHIMKNEEEVVILFAQVGDRSIMQSQSLMLELREQDQVWV
RLYKGERENAIFSEELDTYITFSGYLVKHATEP

Signal sequence.

amino acids 1-25

N-glycosylation site.

amino acids 93-97

N-myristoylation sites.

amino acids 7-13, 21-27, 67-73, 117-123, 129-135

Amidation site.

amino acids 150-154

Cell attachment sequence.

amino acids 104-107

FIGURE 39

GAATTCGGCACGAGGGAAGAAGAGAAAGAAAATCTCCGGGGCTGCTGGGAGCATATAAAGAA
GCCCTGTGGCCTTGCTGGTTTTACCATCCAGACCAGAGTCAGGCCACAGACGGACATGGCTG
CTCAAGGCTGGTCCATGCTCCTGCTGGCTGTCCTTAACCTAGGCATCTTCGTCCGTCCCTGT
GACACTCAAGAGCTACGATGTCTGTGTATTCAGGAACACTCTGAATTCATTCCTCTCAAACT
CATTAAAAATATAATGGTGATATTCGAGACCATTTACTGCAACAGAAAGGAAGTGATAGCAG
TCCCAAAAAATGGGAGTATGATTTGTTTGGATCCTGATGCTCCATGGGTGAAGGCTACTGTT
GGCCCAATTACTAACAGGTTCCTACCTGAGGACCTCAAACAAAGGAATTTCCACCGGCAAT
GAAGCTTCTGTATAGTGTTGAGCATGAAAAGCCTCTATATCTTTCATTTGGGAGACCTGAGA
ACAAGAGAATATTTCCCTTTCCAATTCGGGAGACCTCTAGACACTTTGCTGATTTAGCTCAC
AACAGTGATAGGAATTTTCTACGGGACTCCAGTGAAGTCAGCTTGACAGGCAGTGATGCCTA
AAAGCCACTCATGAGGCAAAGAGTTTCAAGGAAGCTCTCCTCCTGGAGTTTTGGCGTTCTCA
TTCTTATACTCTATTCCCGCGTTAGTCTGGTGTATGGATCTATGAGCTCTCTTTTAATATTT
TATTATAAATGTTTTATTTACTTAACTTCCTAGTGAATGTTCACAGGTGACTGCTCCCCAT
CCCCATTTCTTGATATTACATATAATGGCATCATATACCCCTTTATTGACTGACAAACTACT
CAGATTGCTTAACATTTTGTGCTTCAAAGTCTTATCCCACTCCACTATGGGCTGTTACAGAG
TGCATCTCGGTGTAGAGCAAGGCTCCTTGTCTTCAGTGCCCCAGGGTGAAATACTTCTTTGA
AAAATTTTCATTCATCAGAAATCTGAAATAAAAATATGTCTTAATTGAG

FIGURE 40

></usr/seqdb2/sst/DNA/Dnaseqs.min/ss.DNA73838
><subunit 1 of 1, 167 aa, 1 stop
><MW: 19091, pI: 7.48, NX(S/T): 1
MAAQGWSMLLLAVLNLGIFVRPCDTQELRCLCIQEHSEFIPLKLIKNIMVIFETIYCNRKEV
IAVPKNGSMICLDPDAPWVKATVGPITNRFLPEDLKQKEFPPAMKLLYSVEHEKPLYLSFGR
PENKRIFPFPIRETSRHFADLAHNSDRNFLRDSSEVSLTGSDA Important features of the protein:
Signal peptide:
amino acids 1-25

N-glycosylation site.
amino acids 68-72

N-myristoylation site.
amino acids 69-75

Small cytokines (intercrine/chemokine) C-x-C subfamily signature
amino acids 40-85

FIGURE 41

CAGACATGGCTCAGTCACTGGCTCTGAGCCTCCTTATCCTGGTTCTGGCCTTTGGCATCCCC
AGGACCCAAGGCAGTGATGGAGGGGCTCAGGACTGTTGCCTCAAGTACAGCCAAAGGAAGAT
TCCCGCCAAGGTTGTCCGCAGCTACCGGAAGCAGGAACCAAGCTTAGGCTGCTCCATCCCAG
CTATCCTGTTCTTGCCCCGCAAGCGCTCTCAGGCAGAGCTATGTGCAGACCCAAAGGAGCTC
TGGGTGCAGCAGCTGATGCAGCATCTGGACAAGACACCATCCCCACAGAAACCAGCCCAGGG
CTGCAGGAAGGACAGGGGGGCCTCCAAGACTGGCAAGAAAGGAAAGGGCTCCAAAGGCTGCA
AGAGGACTGAGCGGTCACAGACCCCTAAAGGCCATAGCCCAGTGAGCAGCCTGGAGCCCTG
GAGACCCCACCAGCCTCACCAGCGCTTGAAGCCTGAACCCAAGATGCAAGAAGGAGGCTATG
CTCAGGGGCCCTGGAGCAGCCACCCCATGCTGGCCTTGCCACACTCTTTCTCCTGCTTTAAC
CACCCCATCTGCATTCCCAGCTCTACCCTGCATGGCTGAGCTGCCCACAGCAGGCCAGGTCC
AGAGAGACCGAGGAGGGAGAGTCTCCCAGGGAGCATGAGAGGAGGCAGCAGGACTGTCCCCT
TGAAGGAGAATCATCAGGACCCTGGACCTGATACGGCTCCCCAGTACACCCCACCTCTTCCT
TGTAAATATGATTTATACCTAACTGAATAAAAGCTGTTCTGTCTTCCCNCCCA

FIGURE 42

>\<MW: 14646, pI: 10.45, NX(S/T): 0
MAQSLALSLLILVLAFGIPRTQGSDGGAQDCCLKYSQRKIPAKVVRSYRKQEPSLGCSIPAI
LFLPRKRSQAELCADPKELWVQQLMQHLDKTPSPQKPAQGCRKDRGASKTGKKGKGSKGCKR
TERSQTPKGP

Important features of the protein:

Signal peptide:

amino acids 1-17 cAMP- and cGMP-dependent protein kinase phosphorylation site.

amino acids 67-71

N-myristoylation sites.

amino acids 17-23, 23-29, 27-33, 108-114, 118-124, 121-127

Amidation site.

amino acids 112-116

Small cytokines.

amino acids 51-91

FIGURE 43

AAGGAGCAGCCCGCAAGCACCAAGTGAGAGGCATGAAGTTACAGTGTGTTTCCCTTTGGCTC
CTGGGTACAATACTGATATTGTGCTCAGTAGACAACCACGGTCTCAGGAGATGTCTGATTTC
CACAGACATGCACCATATAGAAGAGAGTTTCCAAGAAATCAAAAGAGCCATCCAAGCTAAGG
ACACCTTCCCAAATGTCACTATCCTGTCCACATTGGAGACTCTGCAGATCATTAAGCCCTTA
GATGTGTGCTGCGTGACCAAGAACCTCCTGGCGTTCTACGTGGACAGGGTGTTCAAGGATCA
TCAGGAGCCAAACCCCAAAATCTTGAGAAAAATCAGCAGCATTGCCAACTCTTTCCTCTACA
TGCAGAAAACTCTGCGGCAATGTCAGGAACAGAGGCAGTGTCACTGCAGGCAGGAAGCCACC
AATGCCACCAGAGTCATCCATGACAACTATGATCAGCTGGAGGTCCACGCTGCTGCCATTAA
ATCCCTGGGAGAGCTCGACGTCTTTCTAGCCTGGATTAATAAGAATCATGAAGTAATGTTCT
CAGCTTGATGACAAGGAACCTGTATAGTGATCCAGGGATGAACACCCCTGTGCGGTTTACT
GTGGGAGACAGCCCACCTTGAAGGGGAAGGAGATGGGGAAGGCCCCTTGCAGCTGAAAGTCC
CACTGGCTGGCCTCAGGCTGTCTTATTCCGCTTGAAAATAGGCAAAAAGTCTACTGTGGTAT
TTGTAATAAACTCTATCTGCTGAAAGGGCCTGCAGGCCATCCTGGGAGTAAAGGGCTGCCTT
CCCATCTAATTTATTGTAAAGTCATATAGTCCATGTCTGTGATGTGAGCCAAGTGATATCCT
GTAGTACACATTGTACTGAGTGGTTTTTCTGAATAAATTCCATATTTTACCTATGA

FIGURE 44

></usr/seqdb2/sst/DNA/Dnaseqs.full/ss.DNA92282
><subunit 1 of 1, 177 aa, 1 stop
><MW: 20452, pI: 8.00, NX(S/T): 2
MKLQCVSLWLLGTILILCSVDNHGLRRCLISTDMHHIEESFQEIKRAIQAKDTFPNVTILST
LETLQIIKPLDVCCVTKNLLAFYVDRVFKDHQEPNPKILRKISSIANSFLYMQKTLRQCQEQ
RQCHCRQEATNATRVIHDNYDQLEVHAAAIKSLGELDVFLAWINKNHEVMFSA

Signal sequence:
amino acids 1-18

N-glycosylation sites.
amino acids 56-60, 135-139 cAMP- and cGMP-dependent protein kinase phosphorylation site.
amino acids 102-106

N-myristoylation site.
amino acids 24-30

Actinin-type actin-binding domain signature 1.
amino acids 159-169

FIGURE 45

GCTCCCAGCCAAGAACCTCGGGGCCGCTGCGCGGTGGGGAGGAGTTCCCCGAAACCCGGCCG
CTAAGCGAGGCCTCCTCCTCCCGCAGATCCGAACGGCCTGGGCGGGGTCACCCCGGCTGGGA
CAAGAAGCCGCCGCCTGCCTGCCCGGGCCCGGGGAGGGGGCTGGGGCTGGGGCCGGAGGCGG
GGTGTGAGTGGGTGTGTGCGGGGGGCGGAGGCTTGATGCAATCCCGATAAGAAATGCTCGGG
TGTCTTGGGCACCTACCCGTGGGGCCCGTAAGGCGCTACTATATAAGGCTGCCGGCCCGGAG
CCGCCGCGCCGTCAGAGCAGGAGCGCTGCGTCCAGGATCTAGGGCCACGACCATCCCAACCC
GGCACTCACAGCCCCGCAGCGCATCCCGGTCGCCGCCCAGCCTCCCGCACCCCATCGCCGG
AGCTGCGCCGAGAGCCCCAGGGAGGTGCCATGCGGAGCGGGTGTGTGGTGGTCCACGTATGG
ATCCTGGCCGGCCTCTGGCTGGCCGTGGCCGGGCGCCCCTCGCCTTCTCGGACGCGGGGCC
CCACGTGCACTACGGCTGGGGCGACCCCATCCGCCTGCGGCACCTGTACACCTCCGGCCCCC
ACGGGCTCTCCAGCTGCTTCCTGCGCATCCGTGCCGACGGCGTCGTGGACTGCGCGCGGGGC
CAGAGCGCGCACAGTTTGCTGGAGATCAAGGCAGTCGCTCTGCGGACCGTGGCCATCAAGGG
CGTGCACAGCGTGCGGTACCTCTGCATGGGCGCCGACGGCAAGATGCAGGGGCTGCTTCAGT
ACTCGGAGGAAGACTGTGCTTTCGAGGAGGAGATCCGCCCAGATGGCTACAATGTGTACCGA
TCCGAGAAGCACCGCCTCCCGGTCTCCCTGAGCAGTGCCAAACAGCGGCAGCTGTACAAGAA
CAGAGGCTTTCTTCCACTCTCTCATTTCCTGCCCATGCTGCCCATGGTCCCAGAGGAGCCTG
AGGACCTCAGGGGCCACTTGGAATCTGACATGTTCTCTTCGCCCCTGGAGACCGACAGCATG
GACCCATTTGGGCTTGTCACCGGACTGGAGGCCGTGAGGAGTCCCAGCTTTGAGAAGTAACT
GAGACCATGCCCGGGCCTCTTCACTGCTGCCAGGGGCTGTGGTACCTGCAGCGTGGGGGACG
TGCTTCTACAAGAACAGTCCTGAGTCCACGTTCTGTTTAGCTTTAGGAAGAAACATCTAGAA
GTTGTACATATTCAGAGTTTTCCATTGGCAGTGCCAGTTTCTAGCCAATAGACTTGTCTGAT
CATAACATTGTAAGCCTGTAGCTTGCCCAGCTGCTGCCTGGGCCCCATTCTGCTCCCTCGA
GGTTGCTGGACAAGCTGCTGCACTGTCTCAGTTCTGCTTGAATACCTCCATCGATGGGGAAC
TCACTTCCTTTGGAAAAATTCTTATGTCAAGCTGAAATTCTCTAATTTTTCTCATCACTTC
CCCAGGAGCAGCCAGAAGACAGGCAGTAGTTTTAATTTCAGGAACAGGTGATCCACTCTGTA
AAACAGCAGGTAAATTTCACTCAACCCCATGTGGGAATTGATCTATATCTCTACTTCCAGGG
ACCATTTGCCCTTCCCAAATCCCTCCAGGCCAGAACTGACTGGAGCAGGCATGGCCCACCAG
GCTTCAGGAGTAGGGGAAGCCTGGAGCCCCACTCCAGCCCTGGGACAACTTGAGAATTCCCC
CTGAGGCCAGTTCTGTCATGGATGCTGTCCTGAGAATAACTTGCTGTCCCGGTGTCACCTGC
TTCCATCTCCCAGCCCACCAGCCCTCTGCCCACCTCACATGCCTCCCATGGATTGGGGCCT
CCCAGGCCCCCACCTTATGTCAACCTGCACTTCTTGTTCAAAAATCAGGAAAAGAAAAGAT
TTGAAGACCCCAAGTCTTGTCAATAACTTGCTGTGTGGAAGCAGCGGGGGAAGACCTAGAAC
CCTTTCCCCAGCACTTGGTTTTCCAACATGATATTTATGAGTAATTTATTTTGATATGTACA
TCTCTTATTTTCTTACATTATTTATGCCCCAAATTATATTTATGTATGTAAGTGAGGTTTG
TTTTGTATATTAAAATGGAGTTTGTTTGT

FIGURE 46

MRSGCVVVHVWILAGLWLAVAGRPLAFSDAGPHVHYGWGDPIRLRHLYTSGPHGLSSCFLRI
RADGVVDCARGQSAHSLLEIKAVALRTVAIKGVHSVRYLCMGADGKMQGLLQYSEEDCAFEE
EIRPDGYNVYRSEKHRLPVSLSSAKQRQLYKNRGFLPLSHFLPMLPMVPEEPEDLRGHLESD
MFSSPLETDSMDPFGLVTGLEAVRSPSFEK

Signal peptide:

amino acids 1-22

Casein kinase II phosphorylation site.

amino acids 78-82, 116-120, 190-194, 204-208

N-myristoylation site.

amino acids 15-21, 54-60, 66-72, 201-207

Prokaryotic membrane lipoprotein lipid attachment site.

amino acids 48-59

FIGURE 47

GTCTGTTCCCAGGAGTCCTTCGGCGGCTGTTGTGTCAGTGGCCTGATCGCGATGGGGACAAA
GGCGCAAGTCGAGAGGAAACTGTTGTGCCTCTTCATATTGGCGATCCTGTTGTGCTCCCTGG
CATTGGGCAGTGTTACAGTGCACTCTTCTGAACCTGAAGTCAGAATTCCTGAGAATAATCCT
GTGAAGTTGTCCTGTGCCTACTCGGGCTTTTCTTCTCCCCGTGTGGAGTGGAAGTTTGACCA
AGGAGACACCACCAGACTCGTTTGCTATAATAACAAGATCACAGCTTCCTATGAGGACCGGG
TGACCTTCTTGCCAACTGGTATCACCTTCAAGTCCGTGACACGGGAAGACACTGGGACATAC
ACTTGTATGGTCTCTGAGGAAGGCGGCAACAGCTATGGGGAGGTCAAGGTCAAGCTCATCGT
GCTTGTGCCTCCATCCAAGCCTACAGTTAACATCCCCTCCTCTGCCACCATTGGGAACCGGG
CAGTGCTGACATGCTCAGAACAAGATGGTTCCCCACCTTCTGAATACACCTGGTTCAAAGAT
GGGATAGTGATGCCTACGAATCCCAAAAGCACCCGTGCCTTCAGCAACTCTTCCTATGTCCT
GAATCCCACAACAGGAGAGCTGGTCTTTGATCCCCTGTCAGCCTCTGATACTGGAGAATACA
GCTGTGAGGCACGGAATGGGTATGGGACACCCATGACTTCAAATGCTGTGCGCATGGAAGCT
GTGGAGCGGAATGTGGGGGTCATCGTGGCAGCCGTCCTTGTAACCCTGATTCTCCTGGGAAT
CTTGGTTTTTGGCATCTGGTTTGCCTATAGCCGAGGCCACTTTGACAGAACAAAGAAAGGGA
CTTCGAGTAAGAAGGTGATTTACAGCCAGCCTAGTGCCCGAAGTGAAGGAGAATTCAAACAG
ACCTCGTCATTCCTGGTGTGAGCCTGGTCGGCTCACCGCCTATCATCTGCATTTGCCTTACT
CAGGTGCTACCGGACTCTGGCCCCTGATGTCTGTAGTTTCACAGGATGCCTTATTTGTCTTC
TACACCCCACAGGGCCCCCTACTTCTTCGGATGTGTTTTTAATAATGTCAGCTATGTGCCCC
ATCCTCCTTCATGCCCTCCCTCCCTTTCCTACCACTGCTGAGTGGCCTGGAACTTGTTTAAA
GTGTTTATTCCCCATTTCTTTGAGGGATCAGGAAGGAATCCTGGGTATGCCATTGACTTCCC
TTCTAAGTAGACAGCAAAAATGGCGGGGGTCGCAGGAATCTGCACTCAACTGCCCACCTGGC
TGGCAGGGATCTTTGAATAGGTATCTTGAGCTTGGTTCTGGGCTCTTTCCTTGTGTACTGAC
GACCAGGGCCAGCTGTTCTAGAGCGGGAATTAGAGGCTAGAGCGGCTGAAATGGTTGTTTGG
TGATGACACTGGGGTCCTTCCATCTCTGGGGCCCACTCTCTTCTGTCTTCCCATGGGAAGTG
CCACTGGGATCCCTCTGCCCTGTCCTCCTGAATACAAGCTGACTGACATTGACTGTGTCTGT
GGAAAATGGGAGCTCTTGTTGTGGAGAGCATAGTAAATTTTCAGAGAACTTGAAGCCAAAAG
GATTTAAAACCGCTGCTCTAAAGAAAAGAAACTGGAGGCTGGGCGCAGTGGCTCACGCCTG
TAATCCCAGAGGCTGAGGCAGGCGGATCACCTGAGGTCGGGAGTTCGGGATCAGCCTGACCA
ACATGGAGAAACCCTACTGGAAATACAAAGTTAGCCAGGCATGGTGGTGCATGCCTGTAGTC
CCAGCTGCTCAGGAGCCTGGCAACAAGAGCAAAACTCCAGCTCAAAAAAAAAAAAAAA

FIGURE 48

MGTKAQVERKLLCLFILAILLCSLALGSVTVHSSEPEVRIPENNPVKLSCAYSGFSSPRVEW
KFDQGDTTRLVCYNNKITASYEDRVTFLPTGITFKSVTREDTGTYTCMVSEEGGNSYGEVKV
KLIVLVPPSKPTVNIPSSATIGNRAVLTCSEQDGSPPSEYTWFKDGIVMPTNPKSTRAFSNS
SYVLNPTTGELVFDPLSASDTGEYSCEARNGYGTPMTSNAVRMEAVERNVGVIVAAVLVTLI
LLGILVFGIWFAYSRGHFDRTKKGTSSKKVIYSQPSARSEGEFKQTSSFLV

Signal sequence:

amino acids 1-27

Transmembrane domain:

amino acids 238-255

N-glycosylation site.

amino acids 185-189 cAMP- and cGMP-dependent protein kinase phosphorylation site.

amino acids 270-274

Casein kinase II phosphorylation site.

amino acids 34-38, 82-86, 100-104, 118-122, 152-156, 154-158, 193-197, 203-207, 287-291

N-myristoylation site.

amino acids 105-111, 116-122, 158-164, 219-225, 237-243, 256-262

FIGURE 49

CCCACGCGTCCGAACCTCTCCAGCGATGGGAGCCGCCCGCCTGCTGCCCAACCTCACTCTGT
GCTTACAGCTGCTGATTCTCTGCTGTCAAACTCAGTACGTGAGGGACCAGGGCGCCATGACC
GACCAGCTGAGCAGGCGGCAGATCCGCGAGTACCAACTCTACAGCAGGACCAGTGGCAAGCA
CGTGCAGGTCACCGGGCGTCGCATCTCCGCCACCGCCGAGGACGGCAACAAGTTTGCCAAGC
TCATAGTGGAGACGGACACGTTTGGCAGCCGGGTTCGCATCAAAGGGGCTGAGAGTGAGAAG
TACATCTGTATGAACAAGAGGGGCAAGCTCATCGGGAAGCCCAGCGGGAAGAGCAAAGACTG
CGTGTTCACGGAGATCGTGCTGGAGAACAACTATACGGCCTTCCAGAACGCCCGGCACGAGG
GCTGGTTCATGGCCTTCACGCGGCAGGGCGGCCCCGCCAGGCTTCCCGCAGCCGCCAGAAC
CAGCGCGAGGCCCACTTCATCAAGCGCCTCTACCAAGGCCAGCTGCCCTTCCCCAACCACGC
CGAGAAGCAGAAGCAGTTCGAGTTTGTGGGCTCCGCCCCCACCCGCCGGACCAAGCGCACAC
GGCGGCCCCAGCCCCTCACGTAGTCTGGGAGGCAGGGGGCAGCAGCCCCTGGGCCGCCTCCC
CACCCCTTTCCCTTCTTAATCCAAGGACTGGGCTGGGGTGGCGGGAGGGGAGCCAGATCCCC
GAGGGAGGACCCTGAGGGCCGCGAAGCATCCGAGCCCCCAGCTGGGAAGGGGCAGGCCGGTG
CCCCAGGGGCGGCTGGCACAGTGCCCCCTTCCCGGACGGGTGGCAGGCCCTGGAGAGGAACT
GAGTGTCACCCTGATCTCAGGCCACCAGCCTCTGCCGGCCTCCCAGCCGGGCTCCTGAAGCC
CGCTGAAAGGTCAGCGACTGAAGGCCTTGCAGACAACCGTCTGGAGGTGGCTGTCCTCAAAA
TCTGCTTCTCGGATCTCCCTCAGTCTGCCCCCAGCCCCCAAACTCCTCCTGGCTAGACTGTA
GGAAGGGACTTTTGTTTGTTTGTTTCAGGAAAAAGAAAGGGAGAGAGAGGAAAATAG
AGGGTTGTCCACTCCTCACATTCCACGACCCAGGCCTGCACCCCACCCCCAACTCCCAGCCC
CGGAATAAACCATTTTCCTGC

FIGURE 50

MGAARLLPNLTLCLQLLILCCQTQYVRDQGAMTDQLSRRQIREYQLYSRTSGKHVQVTGRRI
SATAEDGNKFAKLIVETDTFGSRVRIKGAESEKYICMNKRGKLIGKPSGKSKDCVFTEIVLE
NNYTAFQNARHEGWFMAFTRQGRPRQASRSRQNQREAHFIKRLYQGQLPFPNHAEKQKQFEF
VGSAPTRRTKRTRRPQPLT

Signal peptide:

amino acids 1-22

N-glycosylation site.

amino acids 9-13, 126-130 cAMP- and cGMP-dependent protein kinase phosphorylation site.

amino acids 60-64

Casein kinase II phosphorylation site.

amino acids 65-69

Tyrosine kinase phosphorylation site.

amino acids 39-48, 89-97

N-myristoylation site.

amino acids 69-75, 188-194

Amidation site.

amino acids 58-62

HBGF/FGF family signature.

amino acids 103-128

FIGURE 51

GTTGTGTCCTTCAGCAAAACAGTGGATTTAAATCTCCTTGCACAAGCTTGAGAGCAACACAA
TCTATCAGGAAAGAAAGAAAGAAAAAAACCGAACCTGACAAAAAGAAGAAAAGAAGAAGA
AAAAAAATCATGAAAACCATCCAGCCAAAAATGCACAATTCTATCTCTTGGGCAATCTTCAC
GGGGCTGGCTGCTCTGTGTCTCTTCCAAGGAGTGCCCGTGCGCAGCGGAGATGCCACCTTCC
CCAAAGCTATGGACAACGTGACGGTCCGGCAGGGGAGAGCGCCACCCTCAGGTGCACTATT
GACAACCGGGTCACCCGGGTGGCCTGGCTAAACCGCAGCACCATCCTCTATGCTGGGAATGA
CAAGTGGTGCCTGGATCCTCGCGTGGTCCTTCTGAGCAACACCCAAACGCAGTACAGCATCG
AGATCCAGAACGTGGATGTGTATGACGAGGGCCCTTACACCTGCTCGGTGCAGACAGACAAC
CACCCAAAGACCTCTAGGGTCCACCTCATTGTGCAAGTATCTCCCAAAATTGTAGAGATTTC
TTCAGATATCTCCATTAATGAAGGGAACAATATTAGCCTCACCTGCATAGCAACTGGTAGAC
CAGAGCCTACGGTTACTTGGAGACACATCTCTCCCAAAGCGGTTGGCTTTGTGAGTGAAGAC
GAATACTTGGAAATTCAGGGCATCACCCGGGAGCAGTCAGGGGACTACGAGTGCAGTGCCTC
CAATGACGTGGCCGCGCCCGTGGTACGGAGAGTAAAGGTCACCGTGAACTATCCACCATACA
TTTCAGAAGCCAAGGGTACAGGTGTCCCCGTGGGACAAAAGGGGACACTGCAGTGTGAAGCC
TCAGCAGTCCCCTCAGCAGAATTCCAGTGGTACAAGGATGACAAAAGACTGATTGAAGGAAA
GAAAGGGGTGAAAGTGGAAAACAGACCTTTCCTCTCAAAACTCATCTTCTTCAATGTCTCTG
AACATGACTATGGGAACTACACTTGCGTGGCCTCCAACAAGCTGGGCCACACCAATGCCAGC
ATCATGCTATTTGGTCCAGGCGCCGTCAGCGAGGTGAGCAACGGCACGTCGAGGAGGGCAGG
CTGCGTCTGGCTGCTGCCTCTTCTGGTCTTGCACCTGCTTCTCAAATTTTGATGTGAGTGCC
ACTTCCCCACCCGGGAAAGGCTGCCGCCACCACCACCACCAACACAACAGCAATGGCAACAC
CGACAGCAACCAATCAGATATATACAAATGAAATTAGAAGAAACACAGCCTCATGGGACAGA
AATTTGAGGGAGGGGAACAAAGAATACTTTGGGGGGAAAAGAGTTTTAAAAAAGAAATTGAA
AATTGCCTTGCAGATATTTAGGTACAATGGAGTTTTCTTTTCCCAAACGGGAAGAACACAGC
ACACCCGGCTTGGACCCACTGCAAGCTGCATCGTGCAACCTCTTTGGTGCCAGTGTGGGCAA
GGGCTCAGCCTCTCTGCCCACAGAGTGCCCCACGTGGAACATTCTGGAGCTGGCCATCCCA
AATTCAATCAGTCCATAGAGACGAACAGAATGAGACCTTCCGGCCCAAGCGTGGCGCTGCGG
GCACTTTGGTAGACTGTGCCACCACGGCGTGTGTTGTGAAACGTGAAATAAAAGAGCAAAA
AAAAA

FIGURE 52

MKTIQPKMHNSISWAIFTGLAALCLFQGVPVRSGDATFPKAMDNVTVRQGESATLRCTIDNR
VTRVAWLNRSTILYAGNDKWCLDPRVVLLSNTQTQYSIEIQNVDVYDEGPYTCSVQTDNHPK
TSRVHLIVQVSPKIVEISSDISINEGNNISLTCIATGRPEPTVTWRHISPKAVGFVSEDEYL
EIQGITREQSGDYECSASNDVAAPVVRRVKVTVNYPPYISEAKGTGVPVGQKGTLQCEASAV
PSAEFQWYKDDKRLIEGKKGVKVENRPFLSKLIFFNVSEHDYGNYTCVASNKLGHTNASIML
FGPGAVSEVSNGTSRRAGCVWLLPLLVLHLLLKF

Signal peptide:
amino acids 1-28

FIGURE 53

GTGGACTCTGAGAAGCCCAGGCAGTTGAGGACAGGAGAGAGAAGGCTGCAGACCCAGAGGGA
GGGAGGACAGGGAGTCGGAAGGAGGAGGACAGAGGAGGGCACAGAGACGCAGAGCAAGGGCG
GCAAGGAGGAGACCCTGGTGGGAGGAAGACACTCTGGAGAGAGAGGGGGCTGGGCAGAGATG
AAGTTCCAGGGGCCCCTGGCCTGCCTCCTGCTGGCCCTCTGCCTGGGCAGTGGGGAGGCTGG
CCCCCTGCAGAGCGGAGAGGAAAGCACTGGGACAAATATTGGGGAGGCCCTTGGACATGGCC
TGGGAGACGCCCTGAGCGAAGGGGTGGGAAAGGCCATTGGCAAAGAGGCCGGAGGGGCAGCT
GGCTCTAAAGTCAGTGAGGCCCTTGGCCAAGGGACCAGAGAAGCAGTTGGCACTGGAGTCAG
GCAGGTTCCAGGCTTTGGCGCAGCAGATGCTTTGGGCAACAGGGTCGGGGAAGCAGCCCATG
CTCTGGGAAACACTGGGCACGAGATTGGCAGACAGGCAGAAGATGTCATTCGACACGGAGCA
GATGCTGTCCGCGGCTCCTGGCAGGGGTGCCTGGCCACAGTGGTGCTTGGGAAACTTCTGG
AGGCCATGGCATCTTTGGCTCTCAAGGTGGCCTTGGAGGCCAGGCCAGGGCAATCCTGGAG
GTCTGGGGACTCCGTGGGTCCACGGATACCCCGGAAACTCAGCAGGCAGCTTTGGAATGAAT
CCTCAGGGAGCTCCCTGGGGTCAAGGAGGCAATGGAGGGCCACCAAACTTTGGGACCAACAC
TCAGGGAGCTGTGGCCCAGCCTGGCTATGGTTCAGTGAGAGCCAGCAACCAGAATGAAGGGT
GCACGAATCCCCCACCATCTGGCTCAGGTGGAGGCTCCAGCAACTCTGGGGGAGGCAGCGGC
TCACAGTCGGGCAGCAGTGGCAGTGGCAGCAATGGTGACAACAACAATGGCAGCAGCAGTGG
TGGCAGCAGCAGTGGCAGCAGCAGTGGCAGCAGCAGTGGCGGCAGCAGTGGCGGCAGCAGTG
GTGGCAGCAGTGGCAACAGTGGTGGCAGCAGAGGTGACAGCGGCAGTGAGTCCTCCTGGGGA
TCCAGCACCGGCTCCTCCTCCGGCAACCACGGTGGGAGCGGCGGAGGAAATGGACATAAACC
CGGGTGTGAAAAGCCAGGGAATGAAGCCCGCGGGAGCGGGGAATCTGGGATTCAGGGCTTCA
GAGGACAGGGAGTTTCCAGCAACATGAGGGAAATAAGCAAAGAGGGCAATCGCCTCCTTGGA
GGCTCTGGAGACAATTATCGGGGGCAAGGGTCGAGCTGGGGCAGTGGAGGAGGTGACGCTGT
TGGTGGAGTCAATACTGTGAACTCTGAGACGTCTCCTGGGATGTTTAACTTTGACACTTTCT
GGAAGAATTTTAAATCCAAGCTGGGTTTCATCAACTGGGATGCCATAAACAAGGACCAGAGA
AGCTCTCGCATCCCGTGACCTCCAGACAAGGAGCCACCAGATTGGATGGGAGCCCCCACACT
CCCTCCTTAAAACACCACCCTCTCATCACTAATCTCAGCCCTTGCCCTTGAAATAAACCTTA
GCTGCCCCACAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAAAAAAAAAAAA

FIGURE 54

></usr/seqdb2/sst/DNA/Dnaseqs.min/ss.DNA59212
><subunit 1 of 1, 440 aa, 1 stop
><MW: 42208, pI: 6.36, NX(S/T): 1

MKFQGPLACLLLALCLGSGEAGPLQSGEESTGTNIGEALGHGLGDALSEGVGKAIGKEAGGA
AGSKVSEALGQGTREAVGTGVRQVPGFGAADALGNRVGEAAHALGNTGHEIGRQAEDVIRHG
ADAVRGSWQGVPGHSGAWETSGGHGIFGSQGGLGGQGQGNPGGLGTPWVHGYPGNSAGSFGM
NPQGAPWGQGGNGGPPNFGTNTQGAVAQPGYGSVRASNQNEGCTNPPPSGSGGGSSNSGGGS
GSQSGSSGSGSNGDNNNGSSSGGSSSGSSSGSSSGGSSGGSSGGSSGNSGGSRGDSGSESSW
GSSTGSSSGNHGGSGGGNGHKPGCEKPGNEARGSGESGIQGFRGQGVSSNMREISKEGNRLL
GGSGDNYRGQGSSWGSGGGDAVGGVNTVNSETSPGMFNFDTFWKNFKSKLGFINWDAINKDQ
RSSRIP

Signal peptide:

amino acids 1-21

N-glycosylation site.

amino acids 265-269

Glycosaminoglycan attachment site.

amino acids 235-239, 237-241, 244-248, 255-259, 324-328, 388-392

Casein kinase II phosphorylation site.

amino acids 26-30, 109-113, 259-263, 300-304, 304-308

N-myristoylation site.

amino acids 17-23, 32-38, 42-48, 50-56, 60-66, 61-67, 64-70, 74-80, 90-96, 96-102, 130-136, 140-146, 149-155, 152-158, 155-161, 159-165, 163-169, 178-184, 190-196, 194-200, 199-205, 218-224, 236-242, 238-244, 239-245, 240-246, 245-251, 246-252, 249-252, 253-259, 256-262, 266-272, 270-276, 271-277, 275-281, 279-285, 283-289, 284-290, 287-293, 288-294, 291-297, 292-298, 295-301, 298-304, 305-311, 311-317, 315-321, 319-325, 322-328, 323-329, 325-331, 343-349, 354-360, 356-362, 374-380, 381-387, 383-389, 387-393, 389-395, 395-401

Cell attachment sequence.

amino acids 301-304

FIGURE 55

AGCCAGGCAGCACATCACAGCGGGAGGAGCTGTCCCAGGTGGCCCAGCTCAGCAATGGCAAT
GGGGGTCCCCAGAGTCATTCTGCTCTGCCTCTTTGGGGCTGCGCTCTGCCTGACAGGGTCCC
AAGCCCTGCAGTGCTACAGCTTTGAGCACACCTACTTTGGCCCCTTTGACCTCAGGGCCATG
AAGCTGCCCAGCATCTCCTGTCCTCATGAGTGCTTTGAGGCTATCCTGTCTCTGGACACCGG
GTATCGCGCCGGTGACCCTGGTGCGGAAGGGCTGCTGGACCGGGCCTCCTGCGGGCCAGA
CGCAATCGAACCCGGACGCGCTGCCGCCAGACTACTCGGTGGTGCGCGGCTGCACAACTGAC
AAATGCAACGCCCACCTCATGACTCATGACGCCCTCCCCAACCTGAGCCAAGCACCCGACCC
GCCGACGCTCAGCGGCGCCGAGTGCTACGCCTGTATCGGGGTCCACCAGGATGACTGCGCTA
TCGGCAGGTCCCGACGAGTCCAGTGTCACCAGGACCAGACCGCCTGCTTCCAGGGCAGTGGC
AGAATGACAGTTGGCAATTTCTCAGTCCCTGTGTACATCAGAACCTGCCACCGGCCCTCCTG
CACCACCGAGGGCACCACCAGCCCCTGGACAGCCATCGACCTCCAGGGCTCCTGCTGTGAGG
GGTACCTCTGCAACAGGAAATCCATGACCCAGCCCTTCACCAGTGCTTCAGCCACCACCCCT
CCCCGAGCACTACAGGTCCTGGCCCTGCTCCTCCCAGTCCTCCTGCTGGTGGGGCTCTCAGC
ATAGACCGCCCCTCCAGGATGCTGGGGACAGGGCTCACACACCTCATTCTTGCTGCTTCAGC
CCCTATCACATAGCTCACTGGAAAATGATGTTAAAGTAAGAATTGCAAAA

FIGURE 56

></usr/seqdb2/sst/DNA/Dnaseqs.min/ss.DNA86576
><subunit 1 of 1, 251 aa, 1 stop
><MW: 26935, pI: 7.42, NX(S/T): 2

MAMGVPRVILLCLFGAALCLTGSQALQCYSFEHTYFGPFDLRAMKLPSISCPHECFEAILSL
DTGYRAPVTLVRKGCWTGPPAGQTQSNPDALPPDYSVVRGCTTDKCNAHLMTHDALPNLSQA
PDPPTLSGAECYACIGVHQDDCAIGRSRRVQCHQDQTACFQGSGRMTVGNFSVPVYIRTCHR
PSCTTEGTTSPWTAIDLQGSCCEGYLCNRKSMTQPFTSASATTPPRALQVLALLLPVLLLVG
LSA

Important features of the protein:

Signal peptide:

amino acids 1-19

Transmembrane domain:

amino acids 233-251

N-glycosylation sites.

amino acids 120-124, 174-178

N-myristoylation sites.

amino acids 15-21, 84-90

FIGURE 57

GGAGCCGCCCTGGGTGTCAGCGGCTCGGCTCCCGCGCACGCTCCGGCCGTCGCGCAGCCTCG
GCACCTGCAGGTCCGTGCGTCCCGCGGCTGGCGCCCTGACTCCGTCCCGGCCAGGGAGGGC
CATGATTTCCCTCCCGGGGCCCCTGGTGACCAACTTGCTGCGGTTTTGTTCCTGGGGCTGA
GTGCCCTCGCGCCCCCTCGCGGGCCCAGCTGCAACTGCACTTGCCCGCCAACCGGTTGCAG
GCGGTGGAGGGAGGGGAAGTGGTGCTTCCAGCGTGGTACACCTTGCACGGGGAGGTGTCTTC
ATCCCAGCCATGGGAGGTGCCCTTTGTGATGTGGTTCTTCAAACAGAAAGAAAAGGAGGATC
AGGTGTTGTCCTACATCAATGGGGTCACAACAAGCAAACCTGGAGTATCCTTGGTCTACTCC
ATGCCCTCCCGGAACCTGTCCCTGCGGCTGGAGGGTCTCCAGGAGAAAGACTCTGGCCCCTA
CAGCTGCTCCGTGAATGTGCAAGACAAACAAGGCAAATCTAGGGGCCACAGCATCAAAACCT
TAGAACTCAATGTACTGGTTCCTCCAGCTCCTCCATCCTGCCGTCTCCAGGGTGTGCCCCAT
GTGGGGGCAAACGTGACCCTGAGCTGCCAGTCTCCAAGGAGTAAGCCCGCTGTCCAATACCA
GTGGGATCGGCAGCTTCCATCCTTCCAGACTTTCTTTGCACCAGCATTAGATGTCATCCGTG
GGTCTTTAAGCCTCACCAACCTTTCGTCTTCCATGGCTGGAGTCTATGTCTGCAAGGCCCAC
AATGAGGTGGGCACTGCCCAATGTAATGTGACGCTGGAAGTGAGCACAGGGCCTGGAGCTGC
AGTGGTTGCTGGAGCTGTTGTGGGTACCCTGGTTGGACTGGGGTTGCTGGCTGGGCTGGTCC
TCTTGTACCACCGCCGGGGCAAGGCCCTGGAGGAGCCAGCCAATGATATCAAGGAGGATGCC
ATTGCTCCCCGGACCCTGCCCTGGCCCAAGAGCTCAGACACAATCTCCAAGAATGGGACCCT
TTCCTCTGTCACCTCCGCACGAGCCCTCCGGCCACCCCATGGCCCTCCCAGGCCTGGTGCAT
TGACCCCCACGCCCAGTCTCTCCAGCCAGGCCCTGCCCTCACCAAGACTGCCCACGACAGAT
GGGGCCCACCCTCAACCAATATCCCCCATCCCTGGTGGGGTTTCTTCCTCTGGCTTGAGCCG
CATGGGTGCTGTGCCTGTGATGGTGCCTGCCCAGAGTCAAGCTGGCTCTCTGGTATGATGAC
CCCACCACTCATTGGCTAAAGGATTTGGGGTCTCTCCTTCCTATAAGGGTCACCTCTAGCAC
AGAGGCCTGAGTCATGGGAAAGAGTCACACTCCTGACCCTTAGTACTCTGCCCCCACCTCTC
TTTACTGTGGGAAAACCATCTCAGTAAGACCTAAGTGTCCAGGAGACAGAAGGAGAAGAGGA
AGTGGATCTGGAATTGGGAGGAGCCTCCACCCACCCCTGACTCCTCCTTATGAAGCCAGCTG
CTGAAATTAGCTACTCACCAAGAGTGAGGGCAGAGACTTCCAGTCACTGAGTCTCCCAGGC
CCCCTTGATCTGTACCCCACCCCTATCTAACACCACCCTTGGCTCCCACTCCAGCTCCCTGT
ATTGATATAACCTGTCAGGCTGGCTTGGTTAGGTTTTACTGGGGCAGAGGATAGGGAATCTC
TTATTAAAACTAACATGAAATATGTGTTGTTTTCATTTGCAAATTTAAATAAAGATACATAA
TGTTTGTATGAAAAA

FIGURE 58

MISLPGPLVTNLLRFLFLGLSALAPPSRAQLQLHLPANRLQAVEGGEVVLPAWYTLHGEVSS
SQPWEVPFVMWFFKQKEKEDQVLSYINGVTTSKPGVSLVYSMPSRNLSLRLEGLQEKDSGPY
SCSVNVQDKQGKSRGHSIKTLELNVLVPPAPPSCRLQGVPHVGANVTLSCQSPRSKPAVQYQ
WDRQLPSFQTFFAPALDVIRGSLSLTNLSSSMAGVYVCKAHNEVGTAQCNVTLEVSTGPAA
VVAGAVVGTLVGLGLLAGLVLLYHRRGKALEEPANDIKEDAIAPRTLPWPKSSDTISKNGTL
SSVTSARALRPPHGPPRPGALTPTPSLSSQALPSPRLPTTDGAHPQPISPIPGGVSSSGLSR
MGAVPVMVPAQSQAGSLV

Signal peptide:

amino acids 1-29

Transmembrane domain:

amino acids 245-267

N-glycosylation site.

amino acids 108-112, 169-173, 213-217, 236-240, 307-311

N-myristoylation site.

amino acids 90-96, 167-173, 220-226, 231-237, 252-258, 256-262, 262-268, 308-314, 363-369, 364-370

Prokaryotic membrane lipoprotein lipid attachment site.

amino acids 164-175

FIGURE 59

ACTTGCCATCACCTGTTGCCAGTGTGGAAAAATTCTCCCTGTTGAATTTTTTGCACATGGAG
GACAGCAGCAAAGAGGGCAACACAGGCTGATAAGACCAGAGACAGCAGGGAGATTATTTTAC
CATACGCCCTCAGGACGTTCCCTCTAGCTGGAGTTCTGGACTTCAACAGAACCCCATCCAGT
CATTTTGATTTTGCTGTTTATTTTTTTTTCTTTTTCTTTTTCCCACCACATTGTATTTTAT
TTCCGTACTTCAGAAATGGGCCTACAGACCACAAAGTGGCCCAGCCATGGGCTTTTTTCCT
GAAGTCTTGGCTTATCATTTCCCTGGGGCTCTACTCACAGGTGTCCAAACTCCTGGCCTGCC
CTAGTGTGTGCCGCTGCGACAGGAACTTTGTCTACTGTAATGAGCGAAGCTTGACCTCAGTG
CCTCTTGGGATCCCGGAGGGCGTAACCGTACTCTACCTCCACAACAACCAAATTAATAATGC
TGGATTTCCTGCAGAACTGCACAATGTACAGTCGGTGCACACGGTCTACCTGTATGGCAACC
AACTGGACGAATTCCCCATGAACCTTCCCAAGAATGTCAGAGTTCTCCATTTGCAGGAAAAC
AATATTCAGACCATTTCACGGGCTGCTCTTGCCCAGCTCTTGAAGCTTGAAGAGCTGCACCT
GGATGACAACTCCATATCCACAGTGGGGGTGGAAGACGGGGCCTTCCGGGAGGCTATTAGCC
TCAAATTGTTGTTTTTGTCTAAGAATCACCTGAGCAGTGTGCCTGTTGGGCTTCCTGTGGAC
TTGCAAGAGCTGAGAGTGGATGAAAATCGAATTGCTGTCATATCCGACATGGCCTTCCAGAA
TCTCACGAGCTTGGAGCGTCTTATTGTGGACGGGAACCTCCTGACCAACAAGGGTATCGCCG
AGGGCACCTTCAGCCATCTCACCAAGCTCAAGGAATTTTCAATTGTACGTAATTCGCTGTCC
CACCCTCCTCCCGATCTCCCAGGTACGCATCTGATCAGGCTCTATTTGCAGGACAACCAGAT
AAACCACATTCCTTTGACAGCCTTCTCAAATCTGCGTAAGCTGGAACGGCTGGATATATCCA
ACAACCAACTGCGGATGCTGACTCAAGGGGTTTTTGATAATCTCTCCAACCTGAAGCAGCTC
ACTGCTCGGAATAACCCTTGGTTTTGTGACTGCAGTATTAAATGGGTCACAGAATGGCTCAA
ATATATCCCTTCATCTCTCAACGTGCGGGGTTTCATGTGCCAAGGTCCTGAACAAGTCCGGG
GGATGGCCGTCAGGGAATTAAATATGAATCTTTTGTCCTGTCCCACCACGACCCCCGGCCTG
CCTCTCTTCACCCCAGCCCCAAGTACAGCTTCTCCGACCACTCAGCCTCCCACCCTCTCTAT
TCCAAACCCTAGCAGAAGCTACACGCCTCCAACTCCTACCACATCGAAACTTCCCACGATTC
CTGACTGGGATGGCAGAGAAAGAGTGACCCCACCTATTTCTGAACGGATCCAGCTCTCTATC
CATTTTGTGAATGATACTTCCATTCAAGTCAGCTGGCTCTCTCTCTTCACCGTGATGGCATA
CAAACTCACATGGGTGAAAATGGGCCACAGTTTAGTAGGGGCATCGTTCAGGAGCGCATAG
TCAGCGGTGAGAAGCAACACCTGAGCCTGGTTAACTTAGAGCCCCGATCCACCTATCGGATT
TGTTTAGTGCCACTGGATGCTTTTAACTACCGCGCGGTAGAAGACACCATTTGTTCAGAGGC
CACCACCCATGCCTCCTATCTGAACAACGGCAGCAACACAGCGTCCAGCCATGAGCAGACGA
CGTCCCACAGCATGGGCTCCCCCTTTCTGCTGGCGGGCTTGATCGGGGCGCGGTGATATTT
GTGCTGGTGGTCTTGCTCAGCGTCTTTTGCTGGCATATGCACAAAAAGGGGCGCTACACCTC
CCAGAAGTGGAAATACAACCGGGGCCGGCGGAAGATGATTATTGCGAGGCAGGCACCAAGA
AGGACAACTCCATCCTGGAGATGACAGAAACCAGTTTTCAGATCGTCTCCTTAAATAACGAT
CAACTCCTTAAAGGAGATTTCAGACTGCAGCCCATTTACACCCCAAATGGGGCATTAATTA
CACAGACTGCCATATCCCCAACAACATGCGATACTGCAACAGCAGCGTGCCAGACCTGGAGC
ACTGCCATACGTGACAGCCAGAGGCCCAGCGTTATCAAGGCGGACAATTAGACTCTTGAGAA
CACACTCGTGTGTGCACATAAAGACACGCAGATTACATTTGATAAATGTTACACAGATGCAT
TTGTGCATTTGAATACTCTGTAATTTATACGGTGTACTATATAATGGGATTTAAAAAAGTG
CTATCTTTTCTATTTCAAGTTAATTACAAACAGTTTTGTAACTCTTTGCTTTTTAAATCTT

FIGURE 60

MGLQTTKWPSHGAFFLKSWLIISLGLYSQVSKLLACPSVCRCDRNFVYCNERSLTSVPLGIP
EGVTVLYLHNNQINNAGFPAELHNVQSVHTVYLYGNQLDEFPMNLPKNVRVLHLQENNIQTI
SRAALAQLLKLEELHLDDNSISTVGVEDGAFREAISLKLLFLSKNHLSSVPVGLPVDLQELR
VDENRIAVISDMAFQNLTSLERLIVDGNLLTNKGIAEGTFSHLTKLKEFSIVRNSLSHPPPD
LPGTHLIRLYLQDNQINHIPLTAFSNLRKLERLDISNNQLRMLTQGVFDNLSNLKQLTARNN
PWFCDCSIKWVTEWLKYIPSSLNVRGFMCQGPEQVRGMAVRELNMNLLSCPTTTPGLPLFTP
APSTASPTTQPPTLSIPNPSRSYTPPTPTTSKLPTIPDWDGRERVTPPISERIQLSIHFVND
TSIQVSWLSLFTVMAYKLTWVKMGHSLVGGIVQERIVSGEKQHLSLVNLEPRSTYRICLVPL
DAFNYRAVEDTICSEATTHASYLNNGSNTASSHEQTTSHSMGSPFLLAGLIGGAVIFVLVVL
LSVFCWHMHKKGRYTSQKWKYNRGRRKDDYCEAGTKKDNSILEMTETSFQIVSLNNDQLLKG
DFRLQPIYTPNGGINYTDCHIPNNMRYCNSSVPDLEHCHT

Signal peptide:

amino acids 1-42

Transmembrane domain:

amino acids 542-561

N-glycosylation site.

amino acids 202-206, 298-302, 433-437, 521-525, 635-639, 649-653

Casein kinase II phosphorylation site.

amino acids 204-208, 407-411, 527-531, 593-597, 598-602, 651-655

Tyrosine kinase phosphorylation site.

amino acids 319-328

N-myristoylation site.

amino acids 2-8, 60-66, 149-155, 213-219, 220-226, 294-300, 522-528, 545-551, 633-639

Amidation site.

amino acids 581-585

Leucine zipper pattern.

amino acids 164-186

Phospholipase A2 aspartic acid active site.

amino acids 39-50

FIGURE 61

TGAAGAGTAATAGTTGGAATCAAAAGAGTCAACGCAATGAACTGTTATTTACTGCTGCGTTT
TATGTTGGGAATTCCTCTCCTATGGCCTTGTCTTGGAGCAACAGAAAACTCTCAAACAAAGA
AAGTCAAGCAGCCAGTGCGATCTCATTTGAGAGTGAAGCGTGGCTGGGTGTGGAACCAATTT
TTTGTACCAGAGGAAATGAATACGACTAGTCATCACATCGGCCAGCTAAGATCTGATTTAGA
CAATGGAAACAATTCTTTCCAGTACAAGCTTTTGGGAGCTGGAGCTGGAAGTACTTTTATCA
TTGATGAAAGAACAGGTGACATATATGCCATACAGAAGCTTGATAGAGAGGAGCGATCCCTC
TACATCTTAAGAGCCCAGGTAATAGACATCGCTACTGGAAGGGCTGTGGAACCTGAGTCTGA
GTTTGTCATCAAAGTTTCGGATATCAATGACAATGAACCAAAATTCCTAGATGAACCTTATG
AGGCCATTGTACCAGAGATGTCTCCAGAAGGAACATTAGTTATCCAGGTGACAGCAAGTGAT
GCTGACGATCCCTCAAGTGGTAATAATGCTCGTCTCCTCTACAGCTTACTTCAAGGCCAGCC
ATATTTTCTGTTGAACCAACAACAGGAGTCATAAGAATATCTTCTAAAATGGATAGAGAAC
TGCAAGATGAGTATTGGGTAATCATTCAAGCCAAGGACATGATTGGTCAGCCAGGAGCGTTG
TCTGGAACAACAAGTGTATTAATTAAACTTTCAGATGTTAATGACAATAAGCCTATATTTAA
AGAAAGTTTATACCGCTTGACTGTCTCTGAATCTGCACCCACTGGGACTTCTATAGGAACAA
TCATGGCATATGATAATGACATAGGAGAGAATGCAGAAATGGATTACAGCATTGAAGAGGAT
GATTCGCAAACATTTGACATTATTACTAATCATGAAACTCAAGAAGGAATAGTTATATTAAA
AAAGAAAGTGGATTTTGAGCACCAGAACCACTACGGTATTAGAGCAAAAGTTAAAAACCATC
ATGTTCCTGAGCAGCTCATGAAGTACCACACTGAGGCTTCCACCACTTTCATTAAGATCCAG
GTGGAAGATGTTGATGAGCCTCCTCTTTTCCTCCTTCCATATTATGTATTTGAAGTTTTTGA
AGAAACCCCACAGGGATCATTTGTAGGCGTGGTGTCTGCCACAGACCCAGACAATAGGAAAT
CTCCTATCAGGTATTCTATTACTAGGAGCAAAGTGTTCAATATCAATGATAATGGTACAATC
ACTACAAGTAACTCACTGGATCGTGAAATCAGTGCTTGGTACAACCTAAGTATTACAGCCAC
AGAAAAATACAATATAGAACAGATCTCTTCGATCCCACTGTATGTGCAAGTTCTTAACATCA
ATGATCATGCTCCTGAGTTCTCTCAATACTATGAGACTTATGTTTGTGAAAATGCAGGCTCT
GGTCAGGTAATTCAGACTATCAGTGCAGTGGATAGAGATGAATCCATAGAAGAGCACCATTT
TTACTTTAATCTATCTGTAGAAGACACTAACAATTCAAGTTTTACAATCATAGATAATCAAG
ATAACACAGCTGTCATTTTGACTAATAGAACTGGTTTTAACCTTCAAGAAGAACCTGTCTTC
TACATCTCCATCTTAATTGCCGACAATGGAATCCCGTCACTTACAAGTACAAACACCCTTAC
CATCCATGTCTGTGACTGTGGTGACAGTGGGAGCACACAGACCTGCCAGTACCAGGAGCTTG
TGCTTTCCATGGGATTCAAGACAGAAGTTATCATTGCTATTCTCATTTGCATTATGATCATA
TTTGGGTTTATTTTTTTGACTTTGGGTTTAAAACAACGGAGAAAACAGATTCTATTTCCTGA
GAAAAGTGAAGATTTCAGAGAGAATATATTCCAATATGATGATGAAGGGGGTGGAGAAGAAG
ATACAGAGGCCTTTGATATAGCAGAGCTGAGGAGTAGTACCATAATGCGGGAACGCAAGACT
CGGAAAACCACAAGCGCTGAGATCAGGAGCCTATACAGGCAGTCTTTGCAAGTTGGCCCCGA
CAGTGCCATATTCAGGAAATTCATTCTGGAAAAGCTCGAAGAAGCTAATACTGATCCGTGTG
CCCCTCCTTTTGATTCCCTCCAGACCTACGCTTTTGAGGGAACAGGGTCATTAGCTGGATCC
CTGAGCTCCTTAGAATCAGCAGTCTCTGATCAGGATGAAAGCTATGATTACCTTAATGAGTT
GGGACCTCGCTTTAAAAGATTAGCATGCATGTTTGGTTCTGCAGTGCAGTCAAATAATTAGG
GCTTTTTACCATCAAAATTTTTAAAAGTGCTAATGTGTATTCGAACCCAATGGTAGTCTTAA
AGAGTTTTGTGCCCTGGCTCTATGGCGGGGAAAGCCCTAGTCTATGGAGTTTTCTGATTTCC
CTGGAGTAAATACTCCATGGTTATTTTAAGCTACCTACATGCTGTCATTGAACAGAGATGTG
GGGAGAAATGTAAACAATCAGCTCACAGGCATCAATACAACCAGATTTGAAGTAAAATAATG
TAGGAAGATATTAAAAGTAGATGAGAGGACACAAGATGTAGTCGATCCTTATGCGATTATAT
CATTATTTACTTAGGAAAGAGTAAAAATACCAAACGAGAAATTTAAAGGAGCAAAAATTTG
CAAGTCAAATAGAAATGTACAAATCGAGATAACATTTACATTTCTATCATATTGACATGAAA
ATTGAAAATGTATAGTCAGAGAAATTTTCATGAATTATTCCATGAAGTATTGTTTCCTTTAT
TTAAA

FIGURE 62

```
></usr/seqdb2/sst/DNA/Dnaseqs.min/ss.DNA53906
><subunit 1 of 1, 772 aa, 1 stop
><MW: 87002, pI: 4.64, NX(S/T): 8
MNCYLLLRFMLGIPLLWPCLGATENSQTKKVKQPVRSHLRVKRGWVWNQFFVPEEMNTTSHH
IGQLRSDLDNGNNSFQYKLLGAGAGSTFIIDERTGDIYAIQKLDREERSLYILRAQVIDIAT
GRAVEPESEFVIKVSDINDNEPKFLDEPYEAIVPEMSPEGTLVIQVTASDADDPSSGNNARL
LYSLLQGQPYFSVEPTTGVIRISSKMDRELQDEYWVIIQAKDMIGQPGALSGTTSVLIKLSD
VNDNKPIFKESLYRLTVSESAPTGTSIGTIMAYDNDIGENAEMDYSIEEDDSQTFDIITNHE
TQEGIVILKKKVDFEHQNHYGIRAKVKNHHVPEQLMKYHTEASTTFIKIQVEDVDEPPLFLL
PYYVFEVFEETPQGSFVGVVSATDPDNRKSPIRYSITRSKVFNINDNGTITTSNSLDREISA
WYNLSITATEKYNIEQISSIPLYVQVLNINDHAPEFSQYYETYVCENAGSGQVIQTISAVDR
DESIEEHHFYFNLSVEDTNNSSFTIIDNQDNTAVILTNRTGFNLQEEPVFYISILIADNGIP
SLTSTNTLTIHVCDCGDSGSTQTCQYQELVLSMGFKTEVIIAILICIMIIFGFIFLTLGLKQ
RRKQILFPEKSEDFRENIFQYDDEGGGEEDTEAFDIAELRSSTIMRERKTRKTTSAEIRSLY
RQSLQVGPDSAIFRKFILEKLEEANTDPCAPPFDSLQTYAFEGTGSLAGSLSSLESAVSDQD
ESYDYLNELGPRFKRLACMFGSAVQSNN Important features:
Signal peptide:
amino acids 1-21

Transmembrane domain:
amino acids 597-617

N-glycosylation sites.
amino acids 57-60, 74-77, 419-423, 437-440, 508-511, 515-518,
516-519 and 534-537

Cadherins extracellular repeated domain signature.
amino acids 136-146 and 244-254
```

FIGURE 63

CTTCAGAACAGGTTCTCCTTCCCCAGTCACCAGTTGCTCGAGTTAGAATTGTCTGCAATGGC
CGCCCTGCAGAAATCTGTGAGCTCTTTCCTTATGGGGACCCTGGCCACCAGCTGCCTCCTTC
TCTTGGCCCTCTTGGTACAGGGAGGAGCAGCTGCGCCCATCAGCTCCCACTGCAGGCTTGAC
AAGTCCAACTTCCAGCAGCCCTATATCACCAACCGCACCTTCATGCTGGCTAAGGAGGCTAG
CTTGGCTGATAACAACACAGACGTTCGTCTCATTGGGGAGAAACTGTTCCACGGAGTCAGTA
TGAGTGAGCGCTGCTATCTGATGAAGCAGGTGCTGAACTTCACCCTTGAAGAAGTGCTGTTC
CCTCAATCTGATAGGTTCCAGCCTTATATGCAGGAGGTGGTGCCCTTCCTGGCCAGGCTCAG
CAACAGGCTAAGCACATGTCATATTGAAGGTGATGACCTGCATATCCAGAGGAATGTGCAAA
AGCTGAAGGACACAGTGAAAAAGCTTGGAGAGAGTGGAGAGATCAAAGCAATTGGAGAACTG
GATTTGCTGTTTATGTCTCTGAGAAATGCCTGCATTTGACCAGAGCAAAGCTGAAAAATGAA
TAACTAACCCCCTTTCCCTGCTAGAAATAACAATTAGATGCCCCAAAGCGATTTTTTTAAC
CAAAAGGAAGATGGGAAGCCAAACTCCATCATGATGGGTGGATTCCAAATGAACCCCTGCGT
TAGTTACAAAGGAAACCAATGCCACTTTTGTTTATAAGACCAGAAGGTAGACTTTCTAAGCA
TAGATATTTATTGATAACATTTCATTGTAACTGGTGTTCTATACACAGAAAACAATTTATTT
TTTAAATAATTGTCTTTTTCCATAAAAAAGATTACTTTCCATTCCTTTAGGGGAAAAACCC
CTAAATAGCTTCATGTTTCCATAATCAGTACTTTATATTTATAAATGTATTTATTATTATTA
TAAGACTGCATTTTATTTATATCATTTTATTAATATGGATTTATTTATAGAAACATCATTCG
ATATTGCTACTTGAGTGTAAGGCTAATATTGATATTTATGACAATAATTATAGAGCTATAAC
ATGTTTATTTGACCTCAATAAACACTTGGATATCCC

FIGURE 64

```
></usr/seqdb2/sst/DNA/Dnaseqs.min/ss.DNA125185
><subunit 1 of 1, 179 aa, 1 stop
><MW: 20011, pI: 8.10, NX(S/T): 3
MAALQKSVSSFLMGTLATSCLLLLALLVQGGAAAPISSHCRLDKSNFQQPYITNRTFMLAKE
ASLADNNTDVRLIGEKLFHGVSMSERCYLMKQVLNFTLEEVLFPQSDRFQPYMQEVVPFLAR
LSNRLSTCHIEGDDLHIQRNVQKLKDTVKKLGESGEIKAIGELDLLFMSLRNACI
```

Important features of the protein:

Signal peptide:

amino acids 1-33

N-glycosylation sites.

amino acids 54-58, 68-72, 97-101

N-myristoylation sites.

amino acids 14-20, 82-88

Prokaryotic membrane lipoprotein lipid attachment site.

amino acids 10-21

FIGURE 65

GCCCTAACCTTCCCAGGGCTCAGCTCTTTGGAGCTGCCCATTCCTCCGGCTGCGAGAAAGGA
CGCGCGCCCTGCGTCGGGCGAAGAAAAGAAGCAAAACTTGTCGGGAGGGTTTCGTCATCAAC
CTCCTTCCCGCAAACCTAAACCTCCTGCCGGGGCCATCCCTAGACAGAGGAAAGTTCCTGCA
GAGCCGACCAGCCCTAGTGGATCTGGGGCAGGCAGCGGCGCTGGCTGTGGAATTAGATCTGT
TTTGAACCCAGTGGAGCGCATCGCTGGGGCTCGGAAGTCACCGTCCGCGGGCACCGGGTTGG
CGCTGCCCGAGTGGAACCGACAGTTTGCGAGCCTCGGCTGCAAGTGGCCTCTCCTCCCCGCG
GTTGTTGTTCAGTGTCGGTGAGGGCTGCGAGTGTGGCAAGTTGCAAAGAGAGCCTCAGAGG
TCCGAAGAGCGCTGCGCTCCTACTCGCGTTCGCTTCTTCCTCTTCTCGGTTCCCTACTGTGA
AATCGCAGCGACATTTACAAAGGCCTCCGGGTCCTACCGAGACCGATCCGCAGCGTTTGGCC
CGGTCGTGCCTATTGCATCGGGAGCCCCGAGCACCGGCGAAATGGCGAGGTTCCCGAAGGC
CGACCTGGCCGCTGCAGGAGTTATGTTACTTTGCCACTTCTTCACGGACCAGTTTCAGTTCG
CCGATGGGAAACCCGGAGACCAAATCCTTGATTGGCAGTATGGAGTTACTCAGGCCTTCCCT
CACACAGAGGAGGAGGTGGAAGTTGATTCACACGCGTACAGCCACAGGTGGAAAAGAAACTT
GGACTTTCTCAAGGCGGTAGACACGAACCGAGCAAGCGTCGGCCAAGACTCTCCTGAGCCCA
GAAGCTTCACAGACCTGCTGCTGGATGATGGGCAGGACAATAACACTCAGATCGAGGAGGAT
ACAGACCACAATTACTATATATCTCGAATATATGGTCCATCTGATTCTGCCAGCCGGGATTT
ATGGGTGAACATAGACCAAATGGAAAAGATAAAGTGAAGATTCATGGAATATTGTCCAATA
CTCATCGGCAAGCTGCAAGAGTGAATCTGTCCTTCGATTTTCCATTTTATGGCCACTTCCTA
CGTGAAATCACTGTGGCAACCGGGGGTTTCATATACACTGGAGAAGTCGTACATCGAATGCT
AACAGCCACACAGTACATAGCACCTTTAATGGCAAATTTCGATCCCAGTGTATCCAGAAATT
CAACTGTCAGATATTTTGATAATGGCACAGCACTTGTGGTCCAGTGGGACCATGTACATCTC
CAGGATAATTATAACCTGGGAAGCTTCACATTCCAGGCAACCCTGCTCATGGATGGACGAAT
CATCTTTGGATACAAAGAAATTCCTGTCTTGGTCACACAGATAAGTTCAACCAATCATCCAG
TGAAAGTCGGACTGTCCGATGCATTTGTCGTTGTCCACAGGATCCAACAAATTCCCAATGTT
CGAAGAAGAACAATTTATGAATACCACCGAGTAGAGCTACAAATGTCAAAAATTACCAACAT
TTCGGCTGTGGAGATGACCCCATTACCCACATGCCTCCAGTTTAACAGATGTGGCCCCTGTG
TATCTTCTCAGATTGGCTTCAACTGCAGTTGGTGTAGTAAACTTCAAAGATGTTCCAGTGGA
TTTGATCGTCATCGGCAGGACTGGGTGGACAGTGGATGCCCTGAAGAGTCAAAAGAGAAGAT
GTGTGAGAATACAGAACCAGTGGAAACTTCTTCTCGAACCACCACAACCGTAGGAGCGACAA
CCACCCAGTTCAGGGTCCTAACTACCACCAGAAGAGCAGTGACTTCTCAGTTTCCCACCAGC
CTCCCTACAGAAGATGATACCAAGATAGCACTACATCTAAAAGATAATGGAGCTTCTACAGA
TGACAGTGCAGCTGAGAAGAAAGGGGGAACCCTCCACGCTGGCCTCATCATTGGAATCCTCA
TCCTGGTCCTCATTGTAGCCACAGCCATTCTTGTGACAGTCTATATGTATCACCACCCAACA
TCAGCAGCCAGCATCTTCTTTATTGAGAGACGCCCAAGCAGATGGCCTGCGATGAAGTTTAG
AAGAGGCTCTGGACATCCTGCCTATGCTGAAGTTGAACCAGTTGGAGAGAAAGAAGGCTTTA
TTGTATCAGAGCAGTGCTAAAATTTCTAGGACAGAACAACACCAGTACTGGTTTACAGGTGT
TAAGACTAAAATTTTGCCTATACCTTTAAGACAAACAAACAAACACACACAAACAAGCTC
TAAGCTGCTGTAGCCTGAAGAAGACAAGATTTCTGGACAAGCTCAGCCCAGGAAACAAAGGG
TAAACAAAAACTAAAACTTATACAAGATACCATTTACACTGAACATAGAATTCCCTAGTGG
AATGTCATCTATAGTTCACTCGGAACATCTCCCGTGGACTTATCTGAAGTATGACAAGATTA
TAATGCTTTTGGCTTAGGTGCAGGGTTGCAAAGGGATCAGAAAAAAAAATCATAATAAAGC
TTTAGTTCATGAGGG

FIGURE 66

MAREFPKADLAAAGVMLLCHFFTDQFQFADGKPGDQILDWQYGVTQAFPHTEEEVEVDSHAYS
HRWKRNLDFLKAVDTNRASVGQDSPEPRSFTDLLLDDGQDNNTQIEEDTDHNYYISRIYGPS
DSASRDLWVNIDQMEKDKVKIHGILSNTHRQAARVNLSFDFPFYGHFLREITVATGGFIYTG
EVVHRMLTATQYIAPLMANFDPSVSRNSTVRYFDNGTALVVQWDHVHLQDNYNLGSFTFQAT
LLMDGRIIFGYKEIPVLVTQISSTNHPVKVGLSDAFVVVHRIQQIPNVRRRTIYEYHRVELQ
MSKITNISAVEMTPLPTCLQFNRCGPCVSSQIGFNCSWCSKLQRCSSGFDRHRQDWVDSGCP
EESKEKMCENTEPVETSSRTTTTVGATTTQFRVLTTTRRAVTSQFPTSLPTEDDTKIALHLK
DNGASTDDSAAEKKGGTLHAGLIIGILILVLIVATAILVTVYMYHHPTSAASIFFIERRPSR
WPAMKFRRGSGHPAYAEVEPVGEKEGFIVSEQC

Important features of the protein:
Transmembrane domain:
amino acids 454-478

N-glycosylation sites.
amino acids 103-107, 160-164, 213-217, 221-225, 316-320, 345-349 cAMP- and cGMP-dependent protein kinase phosphorylation sites.
amino acids 297-301, 492-496, 503-507

N-myristoylation sites.
amino acids 42-48, 100-106, 147-153, 279-285, 397-403, 450-456, 455-461

FIGURE 67A

GCAGCCCTAGCAGGGATGGACATGATGCTGTTGGTGCAGGGTGCTTGTTGCTCGAACCAGTG
GCTGGCGGCGGTGCTCCTCAGCCTGTGCTGCCTGCTACCCTCCTGCCTCCCGGCTGGACAGA
GTGTGGACTTCCCCTGGGCGGCCGTGGACAACATGATGGTCAGAAAAGGGGACACGGCGGTG
CTTAGGTGTTATTTGGAAGATGGAGCTTCAAAGGGTGCCTGGCTGAACCGGTCAAGTATTAT
TTTTGCGGGAGGTGATAAGTGGTCAGTGGATCCTCGAGTTTCAATTTCAACATTGAATAAAA
GGGACTACAGCCTCCAGATACAGAATGTAGATGTGACAGATGATGGCCCATACACGTGTTCT
GTTCAGACTCAACATACACCCAGAACAATGCAGGTGCATCTAACTGTGCAAGTTCCTCCTAA
GATATATGACATCTCAAATGATATGACCGTCAATGAAGGAACCAACGTCACTCTTACTTGTT
TGGCCACTGGGAAACCAGAGCCTTCCATTTCTTGGCGACACATCTCCCCATCAGCAAAACCA
TTTGAAAATGGACAATATTTGGACATTTATGGAATTACAAGGGACCAGGCTGGGGAATATGA
ATGCAGTGCGGAAAATGATGTGTCATTCCCAGATGTGAGGAAAGTAAAAGTTGTTGTCAACT
TGCTCCTACTATTCAGGAATTAAATCTGGCACCGTGACCCCCGGACGCAGTGGCCTGATA
AGATGTGAAGGTGCAGGTGTGCCGCCTCCAGCCTTTGAATGGTACAAAGGAGAGAAGAAGCT
CTTCAATGGCCAACAAGGAATTATTATTCAAAATTTTAGCACAAGATCCATTCTCACTGTTA
CCAACGTGACACAGGAGCACTTCGGCAATTATACTTGTGTGGCTGCCAACAAGCTAGGCACA
ACCAATGCGAGCCTGCCTCTTAACCCTCCAAGTACAGCCCAGTATGGAATTACCGGGAGCGC
TGATGTTCTTTTCTCCTGCTGGTACCTTGTGTTGACACTGTCCTCTTTCACCAGCATATTCT
ACCTGAAGAATGCCATTCTACAATAAATTCAAAGACCCATAAAAGGCTTTTAAGGATTCTCT
GAAAGTGCTGATGGCTGGATCCAATCTGGTACAGTTTGTTAAAAGCAGCGTGGGATATAATC
AGCAGTGCTTACATGGGGATGATCGCCTTCTGTAGAATTGCTCATTATGTAAATACTTTAAT
TCTACTCTTTTTTGATTAGCTACATTACCTTGTGAAGCAGTACACATTGTCCTTTTTTTAAG
ACGTGAAAGCTCTGAAATTACTTTTAGAGGATATTAATTGTGATTTCATGTTTGTAATCTAC
AACTTTTCAAAAGCATTCAGTCATGGTCTGCTAGGTTGCAGGCTGTAGTTTACAAAAACGAA
TATTGCAGTGAATATGTGATTCTTTAAGGCTGCAATACAAGCATTCAGTTCCTGTTTCAAT
AAGAGTCAATCCACATTTACAAAGATGCATTTTTTCTTTTTGATAAAAAAGCAAATAATA
TTGCCTTCAGATTATTTCTTCAAAATATAACACATATCTAGATTTTTCTGCTCGCATGATAT
TCAGGTTTCAGGAATGAGCCTTGTAATATAACTGGCTGTGCAGCTCTGCTTCTCTTTCCTGT
AAGTTCAGCATGGGTGTGCCTTCATACAATAATATTTTTCTCTTTGTCTCCAACTAATATAA
AATGTTTTGCTAAATCTTACAATTTGAAAGTAAAAATAAACCAGAGTGATCAAGTTAAACCA
TACACTATCTCTAAGTAACGAAGGAGCTATTGGACTGTAAAAATCTCTTCCTGCACTGACAA
TGGGGTTTGAGAATTTTGCCCCACACTAACTCAGTTCTTGTGATGAGAGACAATTTAATAAC
AGTATAGTAAATATACCATATGATTTCTTTAGTTGTAGCTAAATGTTAGATCCACCGTGGGA
AATCATTCCCTTTAAAATGACAGCACAGTCCACTCAAAGGATTGCCTAGCAATACAGCATCT
TTTCCTTTCACTAGTCCAAGCCAAAAATTTTAAGATGATTTGTCAGAAAGGGCACAAAGTCC
TATCACCTAATATTACAAGAGTTGGTAAGCGCTCATCATTAATTTTATTTTGTGGCAGCTAA
GTTAGTATGACAGAGGCAGTGCTCCTGTGGACAGGAGCATTTTGCATATTTTCCATCTGAAA
GTATCACTCAGTTGATAGTCTGGAATGCATGTTATATATTTAAAACTTCCAAAATATATTA
TAACAAACATTCTATATCGGTATGTAGCAGACCAATCTCTAAAATAGCTAATTCTTCAATAA
AATCTTTCTATATAGCCATTTCAGTGCAAACAAGTAAAATCAAAAAGACCATCCTTTATTT
TTCCTTACATGATATATGTAAGATGCGATCAAATAAAGACAAAACACCAGTGATGAGAATAT
CTTAAGATAAGTAATTATCAAATTATTGTGAATGTTAAATTATTTCTACTATAAAGAAGCAA
AACTACATTTTTGAAGGAAAATGCTGTTACTCTAACATTAATTTACAGGAATAGTTTGATGG
TTTCACTCTTTACTAAAGAAAGGCCATCACCTTGAAAGCCATTTTACAGGTTTGATGAAGTT
ACCAATTTCAGTACACCTAAATTTCTACAAATAGTCCCCTTTTACAAGTTGTAACAACAAAG
ACCCTATAATAAAATTAGATACAAGAAATTTTGCAGTGGTTATACATATTTGAGATATCTAG
TATGTTGCCCTAGCAGGGATGGCTTAAAAACTGTGATTTTTTTCTTCAAGTAAAACTTAGT
CCCAAAGTACATCATAAATCAATTTTAATTAGAAAAATGAATCTTAAATGAGGGGACATAAG
TATACTCTTTCCACAAAATGGCAATAATAAGGCATAAAGCTAGTAAATCTACTAACTGTAAT
AAATGTATGACATTATTTTGATTGATACATTAAAAAGAGTTTTTAGAACAAATATGGCATT
TAACTTTATTATTTATTTGCTTTTAAGAAATATTCTTTGTGGAATTGTTGAATAAACTATAA
AATATTATTTTGTATTGCAGCTTTAAAGTGGCACACTCCATAATAATCTACTTACTAGAAAT

FIGURE 67B

```
AGTGGTGCTACCACAAAAAATGTTAACCATCAGTACCATTGTTTGGGAGAAAGAAACAGATC
AAGAATGCATATTATTCAGTGACCGCTTTCCTAGAGTTAAAATACCTCCTCTTTGTAAGGTT
TGTAGGTAAATTGAGGTATAAACTATGGATGAACCAAATAATTAGTTCAAAGTGTTGTCATG
ATTCCAAATTTGTGGAGTCTGGTGTTTTTACCATAGAATGTGACAGAAGTACAGTCATAGCT
CAGTAGCTATATGTATTTGCCTTTATGTTAGAAGAGACTTTCTTGAGTGACATTTTTAAATA
GAGGAGGTATTCACTATGTTTTTCTGTATCACAGCAGCATTCCTAGTCCTTAGGCCCTCGGA
CAGAGTGAAATCATGAGTATTTATGAGTTCAATATTGTCAAATAAGGCTACAGTATTTGCTT
TTTTGTGTGAATGTATTGCATATAATGTTCAAGTAGATGATTTTACATTTATGGACATATAA
AATGTCTGATTACCCCATTTTATCAGTCCTGACTGTACAAGATTGTTGCAATTTCAGAATAG
CAGTTTTATAAATTGATTTATCTTTTAATCTATAACAATTTGTGTTAGCTGTTCATTTCAGG
ANTATATTTTCTACAAGTTCCACTTGTGGGACTCCTTTTGTTGCCCTATTTTTTTTAAAG
AAGGAAGAAGAAAATAAGTAGCAGTTTAAAAATGAGAATGGAGAGAAAAGAAAAGAATG
AAAAGGAAAGGCAGTAAAGAGGGAAAAAAAGGAAGGATGGAAGGAATGAAGGAAGGAAGGG
AGGAAGGGGAGAAGGTAGGAAGAAAGAAAGGATGAGAGGGAAGGAAGAATCAGAGTATTAGG
GTAGTTAACTTACACATTTGCATTCTTAGTTTAACTGCAAGTGGTGTAACTATGTTTTTCAA
TGATCGCATTTGAAACATAAGTCCTATTATACCATTAAGTTCCTATTATGCAGCAATTATAT
AATAAAAAGTACTGCCCAAGTTATAGTAATGTGGGTGTTTTGAGACACTAAAAGATTTGAG
AGGGAGAATTTCAAACTTAAAGCCACTTTTGGGGGGTTTATAACTTAACTGAAAAATTAATG
CTTCATCATAACATTTAAGCTATATCTAGAAAGTAGACTGGAGAACTGAGAAAATTACCCAG
GTAATTCAGGGAAAAAAAAAATATATATATATATAAATACCCCTACATTTGAAGTCAGAAA
ACTCTGAAAAACTGAATTATCAAAGTCAATCATCTATAATGATCAAATTTACTGAACAATTG
TTAATTTATCCATTGTGCTTAGCTTTGTGACACAGCCAAAAGTTACCTATTTAATCTTTTCA
ATAAAAATTGTTTTTTGAAATCCAGAAATGATTTAAAAAGAGGTCAGGTTTTTAACTATTTA
TTGAAGTATGTGGATGTACAGTATTTCAATAGATATGAATATGAATAAATGGTATGCCTTAA
GATTCTTTGAATATGTATTTACTTTAAAGACTGGAAAAGCTCTTCCTGTCTTTAGTAAAA
CATCCATATTTCATAACCTGATGTAAAATATGTTGTACTGTTTCCAATAGGTGAATATAAAC
TCAGTTTATCAATTAAAAAAAAAAAAAAAAAAAAAAAAAAAAAAAAAAAAAAAAAAAAAAA
```

FIGURE 68

```
></usr/seqdb2/sst/DNA/Dnaseqs.full/ss.DNA92259
><subunit 1 of 1, 354 aa, 1 stop
><MW: 38719, pI: 6.12, NX(S/T): 6
MDMMLLVQGACCSNQWLAAVLLSLCCLLPSCLPAGQSVDFPWAAVDNMMVRKGDTAVLRCYL
EDGASKGAWLNRSSIIFAGGDKWSVDPRVSISTLNKRDYSLQIQNVDVTDDGPYTCSVQTQH
TPRTMQVHLTVQVPPKIYDISNDMTVNEGTNVTLTCLATGKPEPSISWRHISPSAKPFENGQ
YLDIYGITRDQAGEYECSAENDVSFPDVRKVKVVVNFAPTIQEIKSGTVTPGRSGLIRCEGA
GVPPPAFEWYKGEKKLFNGQQGIIIQNFSTRSILTVTNVTQEHFGNYTCVAANKLGTTNASL
PLNPPSTAQYGITGSADVLFSCWYLVLTLSSFTSIFYLKNAILQ
```

Important features of the protein:

Signal peptide:

amino acids 1-33

Transmembrane domain:

amino acids 322-343

N-glycosylation sites.

amino acids 73-77, 155-159, 275-279, 286-290, 294-298, 307-311

Tyrosine kinase phosphorylation site.

amino acids 180-188

N-myristoylation sites.

amino acids 9-15, 65-71, 69-75, 153-159, 241-247, 293-299, 304-310, 321-327

Myelin P0 protein.

amino acids 94-123

FIGURE 69

ATAGTAGAAGAATGTCTCTGAAATTACTGGATGAGTTTCAGTCATACTTTCACATGGGCACA
ATTTCACATTCAAGCTCCTTATCCTAGGCTAATTTTATATTATGTTAAATCACTTGTTTTTG
TTCTCACGGCTTCCTGCCTGCTATAGGCATAATTACGAGGAAGCAGAACTTCTCCAGAAGCA
AGCGCACATGCGTTCCAAAATAAGAGCAAATTCGCTCTAAACACAGGAAAAGACCTGAAGCT
TTAATTAAGGGGTTACATCCAACCCCAGAGCGCTTTTGTGGGCACTGATTGCTCCAGCTTCT
GCGTCACTGCGCGAGGGAAGAGGGAAGAGGATCCAGGCGTTAGAATGTATAGACACAAAAA
CAGCTGGAGATTGGGCTTAAAATACCCACCAAGCTCCAAAGAAGAGACCCAAGTCCCCAAAA
CATTGATTTCAGGGCTGCCAGGAAGGAAGAGCAGCAGCAGGGTGGGAGAGAAGCTCCAGTCA
GCCCACAAGATGCCATTGTCCCCGGCCTCCTGCTGCTGCTGCTCTCCGGGGCCACGGCCAC
CGCTGCCCTGCCCCTGGAGGGTGGCCCCACCGGCCGAGACAGCGAGCATATGCAGGAAGCGG
CAGGAATAAGGAAAAGCAGCCTCCTGACTTTCCTCGCTTGGTGGTTTGAGTGGACCTCCCAG
GCCAGTGCCGGGCCCCTCATAGGAGAGGAAGCTCGGGAGGTGGCCAGGCGGCAGGAAGGCGC
ACCCCCCAGCAATCCGCGCGCCGGGACAGAATGCCCTGCAGGAACTTCTTCTGGAAGACCT
TCTCCTCCTGCAAATAG

FIGURE 70

></usr/seqdb2/sst/DNA/Dnaseqs.full/ss.DNA44175
><subunit 1 of 1, 155 aa, 1 stop
><MW: 17194, pI: 10.44, NX(S/T): 0
MYRHKNSWRLGLKYPPSSKEETQVPKTLISGLPGRKSSSRVGEKLQSAHKMPLSPGLLLLLL
SGATATAALPLEGGPTGRDSEHMQEAAGIRKSSLLTFLAWWFEWTSQASAGPLIGEEAREVA
RRQEGAPPQQSARRDRMPCRNFFWKTFSSCK

Important features of the protein:

Transmembrane domain:

amino acids 51-69 cAMP- and cGMP-dependent protein kinase phosphorylation sites.

amino acids 35-39, 92-96

N-myristoylation sites.

amino acids 64-70, 75-81, 90-96

Amidation site.

amino acids 33-37

FIGURE 71

GTCGTGTGCTTGGAGGAAGCCGCGGAACCCCCAGCGTCCGTCCATGGCGTGGAGCCTTGGGA
GCTGGCTGGGTGGCTGCCTGCTGGTGTCAGCATTGGGAATGGTACCACCTCCCGAAAATGTC
AGAATGAATTCTGTTAATTTCAAGAACATTCTACAGTGGGAGTCACCTGCTTTTGCCAAAGG
GAACCTGACTTTCACAGCTCAGTACCTAAGTTATAGGATATTCCAAGATAAATGCATGAATA
CTACCTTGACGGAATGTGATTTCTCAAGTCTTTCCAAGTATGGTGACCACACCTTGAGAGTC
AGGGCTGAATTTGCAGATGAGCATTCAGACTGGGTAAACATCACCTTCTGTCCTGTGGATGA
CACCATTATTGGACCCCTGGAATGCAAGTAGAAGTACTTGCTGATTCTTTACATATGCGTT
TCTTAGCCCCTAAAATTGAGAATGAATACGAAACTTGGACTATGAAGAATGTGTATAACTCA
TGGACTTATAATGTGCAATACTGGAAAAACGGTACTGATGAAAGTTTCAAATTACTCCCCA
GTATGACTTTGAGGTCCTCAGAAACCTGGAGCCATGGACAACTTATTGTGTTCAAGTTCGAG
GGTTTCTTCCTGATCGGAACAAAGCTGGGGAATGGAGTGAGCCTGTCTGTGAGCAAACAACC
CATGACGAAACGGTCCCCTCCTGGATGGTGGCCGTCATCCTCATGGCCTCGGTCTTCATGGT
CTGCCTGGCACTCCTCGGCTGCTTCTCCTTGCTGTGGTGCGTTTACAAGAAGACAAAGTACG
CCTTCTCCCCTAGGAATTCTCTTCCACAGCACCTGAAAGAGTTTTTGGGCCATCCTCATCAT
AACACACTTCTGTTTTTCTCCTTTCCATTGTCGGATGAGAATGATGTTTTTGACAAGCTAAG
TGTCATTGCAGAAGACTCTGAGAGCGGCAAGCAGAATCCTGGTGACAGCTGCAGCCTCGGGA
CCCCGCCTGGGCAGGGGCCCCAAAGCTAGGCTCTGAGAAGGAAACACACTCGGCTGGGCACA
GTGACGTACTCCATCTCACATCTGCCTCAGTGAGGGATCAGGGCAGCAAACAAGGGCCAAGA
CCATCTGAGCCAGCCCCACATCTAGAACTCCAGACCTGGACTTAGCCACCAGAGAGCTACAT
TTTAAAGGCTGTCTTGGCAAAATACTCCATTTGGGAACTCACTGCCTTATAAAGGCTTTCA
TGATGTTTTCAGAAGTTGGCCACTGAGAGTGTAATTTTCAGCCTTTTATATCACTAAAATAA
GATCATGTTTTAATTGTGAGAAACAGGGCCGAGCACAGTGGCTCACGCCTGTAATACCAGCA
CCTTAGAGGTCGAGGCAGGCGGATCACTTGAGGTCAGGAGTTCAAGACCAGCCTGGCCAATA
TGGTGAAACCCAGTCTCTACTAAAAATACAAAAATTAGCTAGGCATGATGGCGCATGCCTAT
AATCCCAGCTACTCGAGTGCCTGAGGCAGGAGAATTGCATGAACCCGGGAGGAGGAGGAGGA
GGTTGCAGTGAGCCGAGATAGCGGCACTGCACTCCAGCCTGGGTGACAAAGTGAGACTCCAT
CTCAAAAAAAAAAAAAAAAAAATTGTGAGAAACAGAAATACTTAAAATGAGGAATAAGAATGG
AGATGTTACATCTGGTAGATGTAACATTCTACCAGATTATGGATGGACTGATCTGAAAATCG
ACCTCAACTCAAGGGTGGTCAGCTCAATGCTACACAGAGCACGGACTTTTGGATTCTTTGCA
GTACTTTGAATTTATTTTTCTACCTATATATGTTTTATATGCTGCTGGTGCTCCATTAAAGT
TTTACTCTGTGTTGC

FIGURE 72

></usr/seqdb2/sst/DNA/Dnaseqs.min/ss.DNA83551
><subunit 1 of 1, 325 aa, 1 stop
><MW: 37011, pI: 5.09, NX(S/T): 4
MAWSLGSWLGGCLLVSALGMVPPPENVRMNSVNFKNILQWESPAFAKGNLTFTAQYLSYRIF
QDKCMNTTLTECDFSSLSKYGDHTLRVRAEFADEHSDWVNITFCPVDDTIIGPPGMQVEVLA
DSLHMRFLAPKIENEYETWTMKNVYNSWTYNVQYWKNGTDEKFQITPQYDFEVLRNLEPWTT
YCVQVRGFLPDRNKAGEWSEPVCEQTTHDETVPSWMVAVILMASVFMVCLALLGCFSLLWCV
YKKTKYAFSPRNSLPQHLKEFLGHPHHNTLLFFSFPLSDENDVFDKLSVIAEDSESGKQNPG
DSCSLGTPPGQGPQS

Important features of the protein:

Signal peptide:

amino acids 1-19

Transmembrane domain:

amino acids 222-245

N-glycosylation sites.

amino acids 49-53, 68-72, 102-106, 161-165

N-myristoylation sites.

amino acids 6-12, 316-322

FIGURE 73

CGAGCGCCAACCCGCTAGCGCCTGAATCCGGCGTGCTGCCCGCTCGCCGCCCGCCATGGCCC
GCGCAGCCCCGCTGCTCGCCGCGTTGACCGCGCTCCTCGCCGCCGCCGCTGCTGGCGGAGAT
GCCCCGCCGGGCAAAATCGCGGTGGTTGGGGCTGGGATTGGGGGCTCTGCTGTGGCCCATTT
TCTCCAGCAGCACTTTGGACCTCGGGTGCAGATCGACGTGTACGAGAAGGGAACCGTGGGTG
GCCGCTTGGCCACCATCTCAGTCAACAAGCAGCACTATGAGAGCGGGGCTGCCTCCTTCCAC
TCCCTGAGCCTGCACATGCAGGACTTCGTCAAGCTGCTGGGGCTGAGGCACCGGCGCGAGGT
GGTGGGCAGGAGCGCCATCTTCGGCGGGGAGCACTTCATGCTGGAGGAGACTGACTGGTACC
TGCTGAACCTCTTCCGCCTCTGGTGGCACTATGGCATCAGCTTCCTGAGGCTGCAGATGTGG
GTGGAGGAGGTCATGGAGAAGTTCATGAGGATCTATAAGTACCAGGCCCACGGCTATGCCTT
CTCGGGTGTGGAGGAGCTGCTCTACTCACTGGGGGAGTCCACCTTTGTTAACATGACCCAGC
ACTCTGTGGCTGAGTCCCTGCTGCAGGTGGGCGTCACGCAGCGCTTTATTGATGATGTCGTT
TCTGCTGTCCTGCGGGCCAGCTATGGCCAGTCAGCAGCGATGCCCGCCTTTGCAGGAGCCAT
GTCACTAGCCGGGGCCCAAGGCAGCCTGTGGTCTGTGGAAGGAGGCAATAAGCTGGTTTGTT
CCGGTTTGCTGAAGCTCACCAAGGCAATGTGATCCATGCCACAGTGACCTCTGTGACCCTG
CACAGCACAGAGGGGAAAGCCCTGTACCAGGTGGCGTATGAGAATGAGGTAGGCAACAGCTC
TGACTTCTATGACATCGTGGTCATCGCCACCCCCTGCACCTGGACAACAGCAGCAGCAACT
TAACCTTTGCAGGCTTCCACCCGCCCATTGATGACGTGCAGGGCTCTTTCCAGCCCACCGTC
GTCTCCTTGGTCCACGGCTACCTCAACTCGTCCTACTTCGGTTTCCCAGACCCTAAGCTTTT
CCCCTTTGCCAACATCCTTACCACAGATTTCCCCAGCTTCTTCTGCACTCTGGACAACATCT
GCCCTGTCAACATCTCTGCCAGCTTCCGGCGAAAGCAGCCCCAGGAGGCAGCTGTTTGGCGA
GTCCAGTCCCCCAAGCCCCTCTTTCGGACCCAGCTAAAGACCCTGTTCCGTTCCTATTACTC
AGTGCAGACAGCTGAGTGGCAGGCCCATCCCCTCTATGGCTCCCGCCCCACGCTCCCGAGGT
TTGCACTCCATGACCAGCTCTTCTACCTCAATGCCCTGGAGTGGGCGGCCAGCTCCGTGGAG
GTGATGGCCGTGGCTGCCAAGAATGTGGCCTTGCTGGCTTACAACCGCTGGTACCAGGACCT
AGACAAGATTGATCAAAAGATTTGATGCACAAGGTCAAGACTGAACTGTGAGGGCTCTAGG
GAGAGCCTGGGAACTTTCATCCCCCACTGAAGATGGATCATCCCACAGCAGCCCAGGACTGA
ATAAGCCATGCTCGCCCACCAGGCTTCTTTCTGACCCCTCATGTATCAAGCATCTCCAGGTG
ACCTACTGTCTGCCTATATTAAGGGTCCACACGGCGGCTGCTGCTTTTTTTTAAGGGGGAAA
GTAAGAAAAGAGAAGGAAATCCAAGCCAGTATATTTGTTTATTTATTTTTTTAAGAAGAA
AAAAGTTCATCTTCACAAGGTGCTTCAGACTTGGTTTCTTAGCTAGAAACCAGAAGACTACG
GGAGGGAATATAAGGCAGAGAACTATGAGTCTTATTTTATTACTGTTTTCACTACCTACTC
CCACAATGGACAATCAATTGAGGCAACCTACAAGAAAACATTTACAACCAGATGGTTACAAA
TAAAGTAGAAGGGAAGATCAGAAAACCTAAGAAATGATCATAGCTCCTGGTTACTGTGGACT
TGATGGATTTGAAGTACCTAGTTCAGAACTCCCTAGTCACCATCTCCAAGCCTGTCAACATC
ACTGCATATTGGAGGAGATGACTGTGGTAGGACCCAAGGAAGAGATGTGTGCCTGAATAGTC
GTCACCATATCTCCAAGCTTCCTGGCAACCAGTGGGAAAAGAAACATGCGAGGCTGTAGGAA
GAGGGAAGCTCTTCCTTGGCACCTAGAGGAATTAGCCATTCTCTTCCTTATGCAAAGATTGA
GGAATGCAACAATATAAAGAAGAGAAGTCCCAGATGGTAGAGAGCAGTCATATCTTACCCC
TAGATGTTCATCCCAGCAGAAGAAAGAAGAAGGTGTTGGGGTAGGATTCTTCAGAGGTTAGC
CTGGTACTTTCTCATCAGACACTAGCTTGAAGTAAGAGGAGAATTATGCTTTTCTTTGCTTT
TTCTACAAACCCTTAAAAATCACTTGTTTTAAAAAGAAAGTAAAAGCCCTTTTCATTCAAAA
AAAAAAAAAAAAAAAAAAAAAAAAA

FIGURE 74

></usr/seqdb2/sst/DNA/Dnaseqs.full/ss.DNA116510
><subunit 1 of 1, 494 aa, 1 stop
><MW: 54646, pI: 7.27, NX(S/T): 6
MARAAPLLAALTALLAAAAAGGDAPPGKIAVVGAGIGGSAVAHFLQQHFGPRVQIDVYEKGT
VGGRLATISVNKQHYESGAASFHSLSLHMQDFVKLLGLRHRREVVGRSAIFGGEHFMLEETD
WYLLNLFRLWWHYGISFLRLQMWVEEVMEKFMRIYKYQAHGYAFSGVEELLYSLGESTFVNM
TQHSVAESLLQVGVTQRFIDDVVSAVLRASYGQSAAMPAFAGAMSLAGAQGSLWSVEGGNKL
VCSGLLKLTKANVIHATVTSVTLHSTEGKALYQVAYENEVGNSSDFYDIVVIATPLHLDNSS
SNLTFAGFHPPIDDVQGSFQPTVVSLVHGYLNSSYFGFPDPKLFPFANILTTDFPSFFCTLD
NICPVNISASFRRKQPQEAAVWRVQSPKPLFRTQLKTLFRSYYSVQTAEWQAHPLYGSRPTL
PRFALHDQLFYLNALEWAASSVEVMAVAAKNVALLAYNRWYQDLDKIDQKDLMHKVKTEL Important features of the protein:
Signal peptide:
amino acids 1-19

N-glycosylation sites.
amino acids 185-189, 290-294, 308-312, 312-316, 342-346, 378-382

N-myristoylation sites.
amino acids 33-39, 35-41, 38-44, 61-67, 64-70, 218-224, 234-240, 237-243, 429-435

SEQUENCE LISTING

<160> NUMBER OF SEQ ID NOS: 151

<210> SEQ ID NO 1
<211> LENGTH: 43
<212> TYPE: DNA

<210> SEQ ID NO 1
<211> LENGTH: 43
<212> TYPE: DNA
<213> ORGANISM: Artificial Sequence
<220> FEATURE:
<223> OTHER INFORMATION: Synthetic oligonucleotide probe

<400> SEQUENCE: 1
tgtaaaacga cggccagtta aatagacctg caattattaa tct         43

<210> SEQ ID NO 2
<211> LENGTH: 41
<212> TYPE: DNA
<213> ORGANISM: Artificial Sequence
<220> FEATURE:
<223> OTHER INFORMATION: Synthetic oligonucleotide probe

<400> SEQUENCE: 2
caggaaacag ctatgaccac ctgcacacct gcaaatccat t           41

<210> SEQ ID NO 3
<211> LENGTH: 2290
<212> TYPE: DNA
<213> ORGANISM: Homo Sapien

<400> SEQUENCE: 3

| | |
|---|---|
| ggctgagggg aggcccggag cctttctggg gcctggggga tcctcttgca | 50 |
| ctggtgggtg gagagaagcg cctgcagcca accagggtca ggctgtgctc | 100 |
| acagtttcct ctggcggcat gtaaaggctc acaaaggag ttgggagttc | 150 |
| aaatgaggct gctgcggacg gcctgaggat ggaccccaag ccctggacct | 200 |
| gccgagcgtg gcactgaggc agcggctgac gctactgtga gggaaagaag | 250 |
| gttgtgagca gccccgcagg acccctggcc agccctggcc ccagcctctg | 300 |
| ccggagccct ctgtggaggc agagccagtg gagcccagtg aggcagggct | 350 |
| gcttggcagc caccggcctg caactcagga acccctccag aggccatgga | 400 |
| caggctgccc cgctgacggc cagggtgaag catgtgagga gccgccccgg | 450 |
| agccaagcag gagggaagag gctttcatag attctattca caaagaataa | 500 |
| ccaccatttt gcaaggacca tgaggccact gtgcgtgaca tgctggtggc | 550 |
| tcggactgct ggctgccatg ggagctgttg caggccagga ggacggtttt | 600 |
| gagggcactg aggagggctc gccaagagag ttcatttacc taaacaggta | 650 |
| caagcgggcg ggcgagtccc aggacaagtg cacctacacc ttcattgtgc | 700 |
| cccagcagcg ggtcacgggt gccatctgcg tcaactccaa ggagcctgag | 750 |
| gtgcttctgg agaaccgagt gcataagcag gagctagagc tgctcaacaa | 800 |
| tgagctgctc aagcagaagc ggcagatcga cacgctgcag cagctggtgg | 850 |
| aggtggacgg cggcattgtg agcgaggtga agctgctgcg caaggagagc | 900 |
| cgcaacatga actcgcgggt cacgcagctc tacatgcagc tcctgcacga | 950 |
| gatcatccgc aagcgggaca acgcgttgga gctctcccag ctggagaaca | 1000 |
| ggatcctgaa ccagacagcc gacatgctgc agctggccag caagtacaag | 1050 |
| gacctggagc acaagtacca gcacctggcc acactggccc acaaccaatc | 1100 |
| agagatcatc gcgcagcttg aggagcactg ccagagggtg ccctcggcca | 1150 |
| ggcccgtccc ccagccaccc cccgctgccc cgcccgggt ctaccaacca | 1200 |
| cccacctaca accgcatcat caaccagatc tctaccaacg agatccagag | 1250 |
| tgaccagaac ctgaaggtgc tgccacccc tctgcccact atgcccactc | 1300 |

-continued

```
tcaccagcct cccatcttcc accgacaagc cgtcgggccc atggagagac      1350
tgcctgcagg ccctggagga tggccacgac accagctcca tctacctggt      1400
gaagccggag aacaccaacc gcctcatgca ggtgtggtgc gaccagagac      1450
acgacccggg gggctggacc gtcatccaga gacgcctgga tggctctgtt      1500
aacttcttca ggaactggga gacgtacaag caagggtttg gaacattga       1550 cggcgaatac tggctgggcc tggagaacat ttactggctg acgaaccaag      1600
gcaactacaa actcctggtg accatggagg actggtccgg ccgcaaagtc      1650
tttgcagaat acgccagttt ccgcctggaa cctgagagcg agtattataa      1700
gctgcggctg gggcgctacc atggcaatgc gggtgactcc tttacatggc      1750
acaacggcaa gcagttcacc accctggaca gagatcatga tgtctacaca      1800
ggaaactgtg cccactacca gaagggaggc tggtggtata cgcctgtgc       1850 ccactccaac ctcaacgggg tctggtaccg cgggggccat taccggagcc      1900
gctaccagga cggagtctac tgggctgagt tccgaggagg ctcttactca      1950
ctcaagaaag tggtgatgat gatccgaccg aaccccaaca ccttccacta      2000
agccagctcc ccctcctgac ctctcgtggc cattgccagg agcccaccct      2050
ggtcacgctg gccacagcac aaagaacaac tcctcaccag ttcatcctga      2100
ggctgggagg accgggatgc tggattctgt tttccgaagt cactgcagcg      2150
gatgatggaa ctgaatcgat acggtgtttt ctgtccctcc tactttcctt      2200
cacaccagac agcccctcat gtctccagga caggacagga ctacagacaa      2250
ctctttcttt aaataaatta agtctctaca ataaaaaaaa                 2290
```

<210> SEQ ID NO 4
<211> LENGTH: 493
<212> TYPE: PRT
<213> ORGANISM: Homo Sapien

<400> SEQUENCE: 4

```
Met Arg Pro Leu Cys Val Thr Cys Trp Trp Leu Gly Leu Leu Ala
 1               5                  10                  15

Ala Met Gly Ala Val Ala Gly Gln Glu Asp Gly Phe Glu Gly Thr
                20                  25                  30

Glu Glu Gly Ser Pro Arg Glu Phe Ile Tyr Leu Asn Arg Tyr Lys
                35                  40                  45

Arg Ala Gly Glu Ser Gln Asp Lys Cys Thr Tyr Thr Phe Ile Val
                50                  55                  60

Pro Gln Gln Arg Val Thr Gly Ala Ile Cys Val Asn Ser Lys Glu
                65                  70                  75

Pro Glu Val Leu Leu Glu Asn Arg Val His Lys Gln Glu Leu Glu
                80                  85                  90

Leu Leu Asn Asn Glu Leu Leu Lys Gln Lys Arg Gln Ile Glu Thr
                95                 100                 105

Leu Gln Gln Leu Val Glu Val Asp Gly Gly Ile Val Ser Glu Val
               110                 115                 120

Lys Leu Leu Arg Lys Glu Ser Arg Asn Met Asn Ser Arg Val Thr
               125                 130                 135

Gln Leu Tyr Met Gln Leu Leu His Glu Ile Ile Arg Lys Arg Asp
               140                 145                 150
```

-continued

```
Asn Ala Leu Glu Leu Ser Gln Leu Glu Asn Arg Ile Leu Asn Gln
            155                 160                 165

Thr Ala Asp Met Leu Gln Leu Ala Ser Lys Tyr Lys Asp Leu Glu
        170                 175                 180

His Lys Tyr Gln His Leu Ala Thr Leu Ala His Asn Gln Ser Glu
    185                 190                 195

Ile Ile Ala Gln Leu Glu Glu His Cys Gln Arg Val Pro Ser Ala
200                 205                 210

Arg Pro Val Pro Gln Pro Pro Ala Ala Pro Pro Arg Val Tyr
                215                 220                 225

Gln Pro Pro Thr Tyr Asn Arg Ile Ile Asn Gln Ile Ser Thr Asn
            230                 235                 240

Glu Ile Gln Ser Asp Gln Asn Leu Lys Val Leu Pro Pro Pro Leu
        245                 250                 255

Pro Thr Met Pro Thr Leu Thr Ser Leu Pro Ser Ser Thr Asp Lys
    260                 265                 270

Pro Ser Gly Pro Trp Arg Asp Cys Leu Gln Ala Leu Glu Asp Gly
275                 280                 285

His Asp Thr Ser Ser Ile Tyr Leu Val Lys Pro Glu Asn Thr Asn
                290                 295                 300

Arg Leu Met Gln Val Trp Cys Asp Gln Arg His Asp Pro Gly Gly
            305                 310                 315

Trp Thr Val Ile Gln Arg Arg Leu Asp Gly Ser Val Asn Phe Phe
        320                 325                 330

Arg Asn Trp Glu Thr Tyr Lys Gln Gly Phe Gly Asn Ile Asp Gly
    335                 340                 345

Glu Tyr Trp Leu Gly Leu Glu Asn Ile Tyr Trp Leu Thr Asn Gln
350                 355                 360

Gly Asn Tyr Lys Leu Leu Val Thr Met Glu Asp Trp Ser Gly Arg
                365                 370                 375

Lys Val Phe Ala Glu Tyr Ala Ser Phe Arg Leu Glu Pro Glu Ser
            380                 385                 390

Glu Tyr Tyr Lys Leu Arg Leu Gly Arg Tyr His Gly Asn Ala Gly
        395                 400                 405

Asp Ser Phe Thr Trp His Asn Gly Lys Gln Phe Thr Thr Leu Asp
    410                 415                 420

Arg Asp His Asp Val Tyr Thr Gly Asn Cys Ala His Tyr Gln Lys
425                 430                 435

Gly Gly Trp Trp Tyr Asn Ala Cys Ala His Ser Asn Leu Asn Gly
                440                 445                 450

Val Trp Tyr Arg Gly Gly His Tyr Arg Ser Arg Tyr Gln Asp Gly
            455                 460                 465

Val Tyr Trp Ala Glu Phe Arg Gly Gly Ser Tyr Ser Leu Lys Lys
        470                 475                 480

Val Val Met Met Ile Arg Pro Asn Pro Asn Thr Phe His
    485                 490
```

<210> SEQ ID NO 5
<211> LENGTH: 33
<212> TYPE: DNA
<213> ORGANISM: Artificial Sequence
<220> FEATURE:
<223> OTHER INFORMATION: Synthetic oligonucleotide probe

<400> SEQUENCE: 5

```
                                           -continued gctgacgaac caaggcaact acaaactcct ggt                                33

<210> SEQ ID NO 6
<211> LENGTH: 41
<212> TYPE: DNA
<213> ORGANISM: Artificial Sequence
<220> FEATURE:
<223> OTHER INFORMATION: Synthetic oligonucleotide probe

<400> SEQUENCE: 6
tgcggccgga ccagtcctcc atggtcacca ggagtttgta g                       41

<210> SEQ ID NO 7
<211> LENGTH: 33
<212> TYPE: DNA
<213> ORGANISM: Artificial Sequence
<220> FEATURE:
<223> OTHER INFORMATION: Synthetic oligonucleotide probe

<400> SEQUENCE: 7
ggtggtgaac tgcttgccgt tgtgccatgt aaa                                33

<210> SEQ ID NO 8
<211> LENGTH: 1218
<212> TYPE: DNA
<213> ORGANISM: Homo Sapien

<400> SEQUENCE: 8
cccacgcgtc cggcgccgtg gcctcgcgtc catctttgcc gttctctcgg              50
acctgtcaca aaggagtcgc gccgccgccg ccgcccccctc cctccggtgg            100 gcccgggagg tagagaaagt cagtgccaca gcccgaccgc gctgctctga             150
gccctgggca cgcggaacgg gagggagtct gagggttggg gacgtctgtg             200
agggagggga acagccgctc gagcctgggg cgggcggacc ggactggggc              250
cggggtaggc tctggaaagg gcccgggaga gaggtggcgt tggtcagaac              300
ctgagaaaca gccgagaggt tttccaccga ggcccgcgct tgagggatct             350
gaagaggttc ctagaagagg gtgttccctc tttcgggggt cctcaccaga              400
agaggttctt gggggtcgcc cttctgagga ggctgcggct aacagggccc              450
agaactgcca ttggatgtcc agaatcccct gtagttgata atgttgggaa              500
taagctctgc aactttcttt ggcattcagt tgttaaaaac aaataggatg              550
caaattcctc aactccaggt tatgaaaaca gtacttggaa aactgaaaac              600
tacctaaatg atcgtctttg gttgggccgt gttcttagcg agcagaagcc              650
ttggccaggg tctgttgttg actctcgaag agcacatagc ccacttccta              700
gggactggag gtgccgctac taccatgggt aattcctgta tctgccgaga              750
tgacagtgga acagatgaca gtgttgacac ccaacagcaa caggccgaga              800
acagtgcagt acccactgct gacacaagga gccaaccacg ggaccctgtt              850
cggccaccaa ggaggggccg aggacctcat gagccaagga gaaagaaaca              900
aaatgtggat gggctagtgt tggacacact ggcagtaata cggactcttg              950
tagataagta agtatctgac tcacggtcac ctccagtgga atgaaaagtg             1000
ttctgcccgg aaccatgact ttaggactcc ttcagttcct ttaggacata             1050
ctcgccaagc cttgtgctca cagggcaaag gagaatattt taatgctccg             1100
ctgatggcag agtaaatgat aagatttgat gttttttgctt gctgtcatct             1150
```

| actttgtctg gaaatgtcta aatgtttctg tagcagaaaa cacgataaag | 1200 |
| ctatgatctt tattagag | 1218 |

<210> SEQ ID NO 9
<211> LENGTH: 117
<212> TYPE: PRT
<213> ORGANISM: Homo Sapien

<400> SEQUENCE: 9

```
Met Ile Val Phe Gly Trp Ala Val Phe Leu Ala Ser Arg Ser Leu
  1               5                  10                  15

Gly Gln Gly Leu Leu Leu Thr Leu Glu Glu His Ile Ala His Phe
                 20                  25                  30

Leu Gly Thr Gly Gly Ala Ala Thr Thr Met Gly Asn Ser Cys Ile
                 35                  40                  45

Cys Arg Asp Asp Ser Gly Thr Asp Asp Ser Val Asp Thr Gln Gln
                 50                  55                  60

Gln Gln Ala Glu Asn Ser Ala Val Pro Thr Ala Asp Thr Arg Ser
                 65                  70                  75

Gln Pro Arg Asp Pro Val Arg Pro Pro Arg Arg Gly Arg Gly Pro
                 80                  85                  90

His Glu Pro Arg Arg Lys Lys Gln Asn Val Asp Gly Leu Val Leu
                 95                 100                 105

Asp Thr Leu Ala Val Ile Arg Thr Leu Val Asp Lys
                110                 115
```

<210> SEQ ID NO 10
<211> LENGTH: 1231
<212> TYPE: DNA
<213> ORGANISM: Homo Sapien

<400> SEQUENCE: 10

| cccacgcgtc cgcgcagtcg cgcagttctg cctccgcctg ccagtctcgc | 50 |
| ccgcgatccc ggcccggggc tgtggcgtcg actccgaccc aggcagccag | 100 |
| cagcccgcgc gggagccgga ccgccgccgg aggagctcgg acggcatgct | 150 |
| gagccccctc ctttgctgaa gcccgagtgc ggagaagccc gggcaaacgc | 200 |
| aggctaagga gaccaaagcg gcgaagtcgc gagacagcgg acaagcagcg | 250 |
| gaggagaagg aggaggaggc gaacccagag aggggcagca aagaagcggc | 300 |
| tggtggtggg cgtcgtggcc atggcggcgg ctatcgccag ctcgctcatc | 350 |
| cgtcagaaga ggcaagcccg cgagcgcgag aaatccaacg cctgcaagtg | 400 |
| tgtcagcagc cccagcaaag gcaagaccag ctgcgacaaa aacaagttaa | 450 |
| atgtcttttc ccgggtcaaa ctcttcggct ccaagaagag cgcgcagaag a | 500 |
| agaccagagc ctcagcttaa gggtatagtt accaagctat acagccgaca | 550 |
| aggctaccac ttgcagctgc aggcggatgg aaccattgat ggcaccaaag | 600 |
| atgaggacag cacttacact ctgtttaacc tcatccctgt gggtctgcga | 650 |
| gtggtggcta tccaaggagt tcaaaccaag ctgtacttgg caatgaacag | 700 |
| tgagggatac ttgtacacct cggaactttt cacacctgag tgcaaattca | 750 |
| aagaatcagt gtttgaaaat tattatgtga catattcatc aatgatatac | 800 |
| cgtcagcagc agtcaggccg aggtggtat ctgggtctga caaagaagg | 850 |

-continued

```
agagatcatg aaaggcaacc atgtgaagaa gaacaagcct gcagctcatt        900
ttctgcctaa accactgaaa gtggccatgt acaaggagcc atcactgcac        950
gatctcacgg agttctcccg atctggaagc gggaccccaa ccaagagcag       1000
aagtgtctct ggcgtgctga acggaggcaa atccatgagc acaatgaat        1050 caacgtagcc agtgagggca aaagaagggc tctgtaacag aaccttacct       1100
ccaggtgctg ttgaattctt ctagcagtcc ttcacccaaa agttcaaatt       1150
tgtcagtgac atttaccaaa caaacaggca gagttcacta ttctatctgc       1200
cattagacct tcttatcatc catactaaag c                           1231
```

<210> SEQ ID NO 11
<211> LENGTH: 245
<212> TYPE: PRT
<213> ORGANISM: Homo Sapien

<400> SEQUENCE: 11

```
Met Ala Ala Ala Ile Ala Ser Ser Leu Ile Arg Gln Lys Arg Gln
  1               5                  10                  15

Ala Arg Glu Arg Glu Lys Ser Asn Ala Cys Lys Cys Val Ser Ser
                 20                  25                  30

Pro Ser Lys Gly Lys Thr Ser Cys Asp Lys Asn Lys Leu Asn Val
                 35                  40                  45

Phe Ser Arg Val Lys Leu Phe Gly Ser Lys Arg Arg Arg
                 50                  55                  60

Arg Pro Glu Pro Gln Leu Lys Gly Ile Val Thr Lys Leu Tyr Ser
                 65                  70                  75

Arg Gln Gly Tyr His Leu Gln Leu Gln Ala Asp Gly Thr Ile Asp
                 80                  85                  90

Gly Thr Lys Asp Glu Asp Ser Thr Tyr Thr Leu Phe Asn Leu Ile
                 95                 100                 105

Pro Val Gly Leu Arg Val Val Ala Ile Gln Gly Val Gln Thr Lys
                110                 115                 120

Leu Tyr Leu Ala Met Asn Ser Glu Gly Tyr Leu Tyr Thr Ser Glu
                125                 130                 135

Leu Phe Thr Pro Glu Cys Lys Phe Lys Glu Ser Val Phe Glu Asn
                140                 145                 150

Tyr Tyr Val Thr Tyr Ser Ser Met Ile Tyr Arg Gln Gln Gln Ser
                155                 160                 165

Gly Arg Gly Trp Tyr Leu Gly Leu Asn Lys Glu Gly Glu Ile Met
                170                 175                 180

Lys Gly Asn His Val Lys Lys Asn Lys Pro Ala Ala His Phe Leu
                185                 190                 195

Pro Lys Pro Leu Lys Val Ala Met Tyr Lys Glu Pro Ser Leu His
                200                 205                 210

Asp Leu Thr Glu Phe Ser Arg Ser Gly Ser Gly Thr Pro Thr Lys
                215                 220                 225

Ser Arg Ser Val Ser Gly Val Leu Asn Gly Gly Lys Ser Met Ser
                230                 235                 240

His Asn Glu Ser Thr
                245
```

<210> SEQ ID NO 12
<211> LENGTH: 744
<212> TYPE: DNA

-continued

<213> ORGANISM: Homo Sapien

<400> SEQUENCE: 12

```
atggccgcgg ccatcgctag cggcttgatc cgccagaagc ggcaggcgcg        50
ggagcagcac tgggaccggc cgtctgccag caggaggcgg agcagcccca       100
gcaagaaccg cgggctctgc aacggcaacc tggtggatat cttctccaaa       150
gtgcgcatct tcggcctcaa gaagcgcagg ttgcggcgcc aagatcccca       200
gctcaagggt atagtgacca ggttatattg caggcaaggc tactacttgc       250
aaatgcaccc cgatggagct ctcgatggaa ccaaggatga cagcactaat       300
tctacactct tcaacctcat accagtggga ctacgtgttg ttgccatcca       350
gggagtgaaa acagggttgt atatagccat gaatggagaa ggttacctct       400
acccatcaga acttttacc cctgaatgca gtttaaaga atctgttttt         450
gaaaattatt atgtaatcta ctcatccatg ttgtacagac aacaggaatc       500
tggtagagcc tggttttgg gattaaataa ggaagggcaa gctatgaaag        550
ggaacagagt aaagaaaacc aaaccagcag ctcattttct acccaagcca       600
ttggaagttg ccatgtaccg agaaccatct ttgcatgatg ttggggaaac       650
ggtcccgaag cctggggtga cgccaagtaa aagcacaagt gcgtctgcaa       700
taatgaatgg aggcaaacca gtcaacaaga gtaagacaac atag             744
```

<210> SEQ ID NO 13
<211> LENGTH: 247
<212> TYPE: PRT
<213> ORGANISM: Homo Sapien

<400> SEQUENCE: 13

```
Met Ala Ala Ala Ile Ala Ser Gly Leu Ile Arg Gln Lys Arg Gln
  1               5                  10                  15

Ala Arg Glu Gln His Trp Asp Arg Pro Ser Ala Ser Arg Arg Arg
                 20                  25                  30

Ser Ser Pro Ser Lys Asn Arg Gly Leu Cys Asn Gly Asn Leu Val
                 35                  40                  45

Asp Ile Phe Ser Lys Val Arg Ile Phe Gly Leu Lys Lys Arg Arg
                 50                  55                  60

Leu Arg Arg Gln Asp Pro Gln Leu Lys Gly Ile Val Thr Arg Leu
                 65                  70                  75

Tyr Cys Arg Gln Gly Tyr Tyr Leu Gln Met His Pro Asp Gly Ala
                 80                  85                  90

Leu Asp Gly Thr Lys Asp Asp Ser Thr Asn Ser Thr Leu Phe Asn
                 95                 100                 105

Leu Ile Pro Val Gly Leu Arg Val Val Ala Ile Gln Gly Val Lys
                110                 115                 120

Thr Gly Leu Tyr Ile Ala Met Asn Gly Glu Gly Tyr Leu Tyr Pro
                125                 130                 135

Ser Glu Leu Phe Thr Pro Glu Cys Lys Phe Lys Glu Ser Val Phe
                140                 145                 150

Glu Asn Tyr Tyr Val Ile Tyr Ser Ser Met Leu Tyr Arg Gln Gln
                155                 160                 165

Glu Ser Gly Arg Ala Trp Phe Leu Gly Leu Asn Lys Glu Gly Gln
                170                 175                 180

Ala Met Lys Gly Asn Arg Val Lys Lys Thr Lys Pro Ala Ala His
```

-continued

```
            185                 190                 195
Phe Leu Pro Lys Pro Leu Glu Val Ala Met Tyr Arg Glu Pro Ser
        200                 205                 210
Leu His Asp Val Gly Glu Thr Val Pro Lys Pro Gly Val Thr Pro
        215                 220                 225
Ser Lys Ser Thr Ser Ala Ser Ala Ile Met Asn Gly Gly Lys Pro
        230                 235                 240
Val Asn Lys Ser Lys Thr Thr
        245

<210> SEQ ID NO 14
<211> LENGTH: 2609
<212> TYPE: DNA
<213> ORGANISM: Homo Sapien

<400> SEQUENCE: 14
ctcgcagccg agcgcggccg gggaagggct ctccttccag cgccgagcac         50
tgggccctgg cagacgcccc aagattgttg tgaggagtct agccagttgg        100
tgagcgctgt aatctgaacc agctgtgtcc agactgaggc cccatttgca        150
ttgtttaaca tacttagaaa atgaagtgtt cattttttaac attcctcctc       200 caattggttt aatgctgaat tactgaagag ggctaagcaa aaccaggtgc        250
ttgcgctgag ggctctgcag tggctgggag gaccccggcg ctctccccgt        300
gtcctctcca cgactcgctc ggcccctctg aataaaaaca cccgcgagcc        350
ccgagggccc agaggaggcc gacgtgcccg agctcctccg ggggtcccgc        400
ccgcgagctt tcttctcgcc ttcgcatctc tccctcgcgc gtcttggaca        450
tgccaggaat aaaaaggata ctcactgtta ccattctggc tctctgtctt        500
ccaagccctg ggaatgcaca ggcacagtgc acgaatggct ttgacctgga        550
tcgccagtca ggacagtgtt tagatattga tgaatgccga accatccccg        600
aggcctgccg aggagacatg atgtgtgtta accaaaatgg cgggtattta        650
tgcattcccc ggacaaaccc tgtgtatcga gggccctact cgaaccccta        700
ctcgaccccc tactcaggtc cgtacccagc agctgcccca ccactctcag        750
ctccaaacta tcccacgatc tccaggcctc ttatatgccg ctttggatac        800
cagatggatg aaagcaacca atgtgtggat gtggacgagt gtgcaacaga        850
ttcccaccag tgcaaccccca cccagatctg catcaatact gaaggcgggt        900
acacctgctc ctgcaccgac ggatattggc ttctggaagg ccagtgctta        950
gacattgatg aatgtcgcta tggttactgc cagcagctct gtgcgaatgt       1000
tcctggatcc tattcttgta catgcaaccc tggttttacc ctcaatgagg       1050
atggaaggtc ttgccaagat gtgaacgagt gtgccaccga aacccctgc        1100 gtgcaaacct gcgtcaacac ctacggctct ctcatctgcc gctgtgaccc       1150
aggatatgaa cttgaggaag atggcgttca ttgcagtgat atggacgagt       1200
gcagcttctc tgagttcctc tgccaacatg agtgtgtgaa ccagcccggc       1250
acatacttct gctcctgccc tccaggctac atcctgctgg atgacaaccg       1300
aagctgccaa gacatcaacg aatgtgagca caggaaccac acgtgcaacc       1350
tgcagcagac gtgctacaat ttacaagggg gcttcaaatg catcgacccc       1400
atccgctgtg aggagcctta tctgaggatc agtgataacc gctgtatgtg       1450
```

```
-continued tcctgctgag aaccctggct gcagagacca gcccttttacc atcttgtacc          1500 gggacatgga cgtggtgtca ggacgctccg ttcccgctga catcttccaa          1550
atgcaagcca cgacccgcta ccctggggcc tattacattt tccagatcaa          1600
atctgggaat gagggcagag aattttacat gcggcaaacg ggccccatca          1650
gtgccaccct ggtgatgaca cgccccatca aagggccccg ggaaatccag          1700
ctggacttgg aaatgatcac tgtcaacact gtcatcaact tcagaggcag          1750
ctccgtgatc cgactgcgga tatatgtgtc gcagtaccca ttctgagcct          1800
cgggctggag cctccgacgc tgcctctcat ggcaccaag ggacaggaga           1850 agagaggaaa taacagagag aatgagagcg acacagacgt taggcatttc          1900
ctgctgaacg tttccccgaa gagtcagccc cgacttcctg actctcacct          1950
gtactattgc agacctgtca ccctgcagga cttgccaccc ccagttccta          2000
tgacacagtt atcaaaaagt attatcattg ctcccctgat agaagattgt          2050
tggtgaattt tcaaggcctt cagtttattt ccactatttt caaagaaaat          2100
agattaggtt tgcgggggtc tgagtctatg ttcaaagact gtgaacagct          2150
tgctgtcact tcttcacctc ttccactcct tctctcactg tgttactgct          2200
ttgcaaagac ccgggagctg gcggggaacc ctggagtag ctagtttgct           2250 ttttgcgtac acagagaagg ctatgtaaac aaaccacagc aggatcgaag          2300 ggttttttaga gaatgtgttt caaaaccatg cctggtattt tcaaccataa         2350
aagaagtttc agttgtcctt aaatttgtat aacggtttaa ttctgtcttg          2400
ttcattttga gtattttttaa aaaatatgtc gtagaattcc ttcgaaaggc         2450
cttcagacac atgctatgtt ctgtcttccc aaacccagtc tcctctccat          2500
tttagcccag tgtttctttt gaggacccct taatcttgct ttctttagaa          2550
tttttaccca attggattgg aatgcagagg tctccaaact gattaaatat          2600
ttgaagaga                                                       2609

<210> SEQ ID NO 15
<211> LENGTH: 448
<212> TYPE: PRT
<213> ORGANISM: Homo Sapien

<400> SEQUENCE: 15

Met Pro Gly Ile Lys Arg Ile Leu Thr Val Thr Ile Leu Ala Leu
  1               5                  10                  15

Cys Leu Pro Ser Pro Gly Asn Ala Gln Ala Gln Cys Thr Asn Gly
                 20                  25                  30

Phe Asp Leu Asp Arg Gln Ser Gly Gln Cys Leu Asp Ile Asp Glu
                 35                  40                  45

Cys Arg Thr Ile Pro Glu Ala Cys Arg Gly Asp Met Met Cys Val
                 50                  55                  60

Asn Gln Asn Gly Gly Tyr Leu Cys Ile Pro Arg Thr Asn Pro Val
                 65                  70                  75

Tyr Arg Gly Pro Tyr Ser Asn Pro Tyr Ser Thr Pro Tyr Ser Gly
                 80                  85                  90

Pro Tyr Pro Ala Ala Ala Pro Pro Leu Ser Ala Pro Asn Tyr Pro
                 95                 100                 105

Thr Ile Ser Arg Pro Leu Ile Cys Arg Phe Gly Tyr Gln Met Asp
```

```
                              110                 115                 120
Glu Ser Asn Gln Cys Val Asp Val Asp Glu Cys Ala Thr Asp Ser
            125                 130                 135
His Gln Cys Asn Pro Thr Gln Ile Cys Ile Asn Thr Glu Gly Gly
            140                 145                 150
Tyr Thr Cys Ser Cys Thr Asp Gly Tyr Trp Leu Leu Glu Gly Gln
            155                 160                 165
Cys Leu Asp Ile Asp Glu Cys Arg Tyr Gly Tyr Cys Gln Gln Leu
            170                 175                 180
Cys Ala Asn Val Pro Gly Ser Tyr Ser Cys Thr Cys Asn Pro Gly
            185                 190                 195
Phe Thr Leu Asn Glu Asp Gly Arg Ser Cys Gln Asp Val Asn Glu
            200                 205                 210
Cys Ala Thr Glu Asn Pro Cys Val Gln Thr Cys Val Asn Thr Tyr
            215                 220                 225
Gly Ser Leu Ile Cys Arg Cys Asp Pro Gly Tyr Glu Leu Glu Glu
            230                 235                 240
Asp Gly Val His Cys Ser Asp Met Asp Glu Cys Ser Phe Ser Glu
            245                 250                 255
Phe Leu Cys Gln His Glu Cys Val Asn Gln Pro Gly Thr Tyr Phe
            260                 265                 270
Cys Ser Cys Pro Pro Gly Tyr Ile Leu Leu Asp Asp Asn Arg Ser
            275                 280                 285
Cys Gln Asp Ile Asn Glu Cys Glu His Arg Asn His Thr Cys Asn
            290                 295                 300
Leu Gln Gln Thr Cys Tyr Asn Leu Gln Gly Gly Phe Lys Cys Ile
            305                 310                 315
Asp Pro Ile Arg Cys Glu Glu Pro Tyr Leu Arg Ile Ser Asp Asn
            320                 325                 330
Arg Cys Met Cys Pro Ala Glu Asn Pro Gly Cys Arg Asp Gln Pro
            335                 340                 345
Phe Thr Ile Leu Tyr Arg Asp Met Asp Val Val Ser Gly Arg Ser
            350                 355                 360
Val Pro Ala Asp Ile Phe Gln Met Gln Ala Thr Thr Arg Tyr Pro
            365                 370                 375
Gly Ala Tyr Tyr Ile Phe Gln Ile Lys Ser Gly Asn Glu Gly Arg
            380                 385                 390
Glu Phe Tyr Met Arg Gln Thr Gly Pro Ile Ser Ala Thr Leu Val
            395                 400                 405
Met Thr Arg Pro Ile Lys Gly Pro Arg Glu Ile Gln Leu Asp Leu
            410                 415                 420
Glu Met Ile Thr Val Asn Thr Val Ile Asn Phe Arg Gly Ser Ser
            425                 430                 435
Val Ile Arg Leu Arg Ile Tyr Val Ser Gln Tyr Pro Phe
            440                 445

<210> SEQ ID NO 16
<211> LENGTH: 2447
<212> TYPE: DNA
<213> ORGANISM: Homo Sapien

<400> SEQUENCE: 16
caggtccaac tgcacctcgg ttctatcgat tgaattcccc ggggatcctc          50
tagagatccc tcgacctcga cccacgcgtc cgaacacagg tccttgttgc         100
```

| | |
|---|---|
| tgcagagaag cagttgtttt gctggaagga gggagtgcgc gggctgcccc | 150 |
| gggctcctcc ctgccgcctc ctctcagtgg atggttccag gcaccctgtc | 200 |
| tggggcaggg agggcacagg cctgcacatc gaaggtgggg tgggaccagg | 250 |
| ctgcccctcg ccccagcatc caagtcctcc cttgggcgcc cgtggccctg | 300 |
| cagactctca gggctaaggt cctctgttgc ttttggttc caccttagaa | 350 |
| gaggctccgc ttgactaaga gtagcttgaa ggaggcacca tgcaggagct | 400 |
| gcatctgctc tggtgggcgc ttctcctggg cctggctcag gcctgccctg | 450 |
| agccctgcga ctgtggggaa agtatggct tccagatcgc cgactgtgcc | 500 |
| taccgcgacc tagaatccgt gccgcctggc ttcccggcca atgtgactac | 550 |
| actgagcctg tcagccaacc ggctgccagg cttgccggag ggtgccttca | 600 |
| ggaggtgcc cctgctgcag tcgctgtggc tggcacacaa tgagatccgc | 650 |
| acggtggccg ccggagccct ggcctctctg agccatctca agagcctgga | 700 |
| cctcagccac aatctcatct ctgactttgc ctggagcgac ctgcacaacc | 750 |
| tcagtgccct ccaattgctc aagatggaca gcaacgagct gaccttcatc | 800 |
| ccccgcgacg ccttccgcag cctccgtgct ctgcgctcgc tgcaactcaa | 850 |
| ccacaaccgc ttgcacacat tggccgaggg caccttcacc ccgctcaccg | 900 |
| cgctgtccca cctgcagatc aacgagaacc ccttcgactg cacctgcggc | 950 |
| atcgtgtggc tcaagacatg ggccctgacc acggccgtgt ccatcccgga | 1000 |
| gcaggacaac atcgcctgca cctcacccca tgtgctcaag ggtacaccgc | 1050 |
| tgagccgcct gccgccactg ccatgctcgg cgccctcagt gcagctcagc | 1100 |
| taccaaccca gccaggatgg tgccgagctg cggcctggtt ttgtgctggc | 1150 |
| actgcactgt gatgtggacg ggcagccggc ccctcagctt cactggcaca | 1200 |
| tccagatacc cagtggcatt gtggagatca ccagccccaa cgtgggcact | 1250 |
| gatgggcgtg ccctgcctgg caccctgtg gccagctccc agccgcgctt | 1300 |
| ccaggccttt gccaatggca gcctgcttat ccccgacttt ggcaagctgg | 1350 |
| aggaaggcac ctacagctgc ctggccacca atgagctggg cagtgctgag | 1400 |
| agctcagtgg acgtggcact ggccacgccc ggtgagggtg gtgaggacac | 1450 |
| actggggcgc aggttccatg gcaaagcggt tgagggaaag ggctgctata | 1500 |
| cggttgacaa cgaggtgcag ccatcagggc cggaggacaa tgtggtcatc | 1550 |
| atctacctca gccgtgctgg gaaccctgag gctgcagtcg cagaagggt | 1600 |
| ccctgggcag ctgcccccag gcctgctcct gctgggccaa agcctcctcc | 1650 |
| tcttcttctt cctcacctcc ttctagcccc acccagggct ccctaactc | 1700 |
| ctccccttgc ccctaccaat gcccctttaa gtgctgcagg ggtctgggt | 1750 |
| tggcaactcc tgaggcctgc atgggtgact tcacattttc ctacctctcc | 1800 |
| ttctaatctc ttctagagca cctgctatcc ccaacttcta gacctgctcc | 1850 |
| aaactagtga ctaggataga atttgatccc ctaactcact gtctgcggtg | 1900 |
| ctcattgctg ctaacagcat tgcctgtgct ctcctctcag gggcagcatg | 1950 |
| ctaacgggc gacgtcctaa tccaactggg agaagcctca gtggtggaat | 2000 |
| tccaggcact gtgactgtca agctggcaag ggccaggatt gggggaatgg | 2050 |

| agctggggct tagctgggag gtggtctgaa gcagacaggg aatgggagag | 2100 |
| ctgctcaagc tcctcctgct ccttgctgtt ttctgatgat ttgggggctt | 2200 |
| gggagtccct ttgtcctcat ctgagactga aatgtgggga tccaggatgg | 2250 |
| ccttccttcc tcttacccctt cctccctcag cctgcaacct ctatcctgga | 2300 |
| acctgtcctc cctttctccc caactatgca tctgttgtct gctcctctgc | 2350 |
| aaaggccagc cagcttggga gcagcagaga aataaacagc atttctgatg | 2400 |
| ccaaaaaaaa aaaaaaaaaa gggcggccgc gactctagag tcgacct | 2447 |

<210> SEQ ID NO 17
<211> LENGTH: 428
<212> TYPE: PRT
<213> ORGANISM: Homo Sapien

<400> SEQUENCE: 17

Met Gln Glu Leu His Leu Leu Trp Trp Ala Leu Leu Leu Gly Leu
 1               5                  10                  15

Ala Gln Ala Cys Pro Glu Pro Cys Asp Cys Gly Glu Lys Tyr Gly
             20                  25                  30

Phe Gln Ile Ala Asp Cys Ala Tyr Arg Asp Leu Glu Ser Val Pro
             35                  40                  45

Pro Gly Phe Pro Ala Asn Val Thr Thr Leu Ser Leu Ser Ala Asn
             50                  55                  60

Arg Leu Pro Gly Leu Pro Glu Gly Ala Phe Arg Glu Val Pro Leu
             65                  70                  75

Leu Gln Ser Leu Trp Leu Ala His Asn Glu Ile Arg Thr Val Ala
             80                  85                  90

Ala Gly Ala Leu Ala Ser Leu Ser His Leu Lys Ser Leu Asp Leu
             95                 100                 105

Ser His Asn Leu Ile Ser Asp Phe Ala Trp Ser Asp Leu His Asn
            110                 115                 120

Leu Ser Ala Leu Gln Leu Leu Lys Met Asp Ser Asn Glu Leu Thr
            125                 130                 135

Phe Ile Pro Arg Asp Ala Phe Arg Ser Leu Arg Ala Leu Arg Ser
            140                 145                 150

Leu Gln Leu Asn His Asn Arg Leu His Thr Leu Ala Glu Gly Thr
            155                 160                 165

Phe Thr Pro Leu Thr Ala Leu Ser His Leu Gln Ile Asn Glu Asn
            170                 175                 180

Pro Phe Asp Cys Thr Cys Gly Ile Val Trp Leu Lys Thr Trp Ala
            185                 190                 195

Leu Thr Thr Ala Val Ser Ile Pro Glu Gln Asp Asn Ile Ala Cys
            200                 205                 210

Thr Ser Pro His Val Leu Lys Gly Thr Pro Leu Ser Arg Leu Pro
            215                 220                 225

Pro Leu Pro Cys Ser Ala Pro Ser Val Gln Leu Ser Tyr Gln Pro
            230                 235                 240

Ser Gln Asp Gly Ala Glu Leu Arg Pro Gly Phe Val Leu Ala Leu
            245                 250                 255

His Cys Asp Val Asp Gly Gln Pro Ala Pro Gln Leu His Trp His
            260                 265                 270

Ile Gln Ile Pro Ser Gly Ile Val Glu Ile Thr Ser Pro Asn Val

```
                275                 280                 285

Gly Thr Asp Gly Arg Ala Leu Pro Gly Thr Pro Val Ala Ser Ser
            290                 295                 300

Gln Pro Arg Phe Gln Ala Phe Ala Asn Gly Ser Leu Leu Ile Pro
            305                 310                 315

Asp Phe Gly Lys Leu Glu Glu Gly Thr Tyr Ser Cys Leu Ala Thr
            320                 325                 330

Asn Glu Leu Gly Ser Ala Glu Ser Ser Val Asp Val Ala Leu Ala
            335                 340                 345

Thr Pro Gly Glu Gly Glu Asp Thr Leu Gly Arg Arg Phe His
            350                 355                 360

Gly Lys Ala Val Glu Gly Lys Gly Cys Tyr Thr Val Asp Asn Glu
            365                 370                 375

Val Gln Pro Ser Gly Pro Glu Asp Asn Val Val Ile Ile Tyr Leu
            380                 385                 390

Ser Arg Ala Gly Asn Pro Glu Ala Ala Val Ala Glu Gly Val Pro
            395                 400                 405

Gly Gln Leu Pro Pro Gly Leu Leu Leu Gly Gln Ser Leu Leu
            410                 415                 420

Leu Phe Phe Phe Leu Thr Ser Phe
            425

<210> SEQ ID NO 18
<211> LENGTH: 22
<212> TYPE: DNA
<213> ORGANISM: Artificial Sequence
<220> FEATURE:
<223> OTHER INFORMATION: Synthetic oligonucleotide probe

<400> SEQUENCE: 18
gtggctggca cacaatgaga tc                                              22

<210> SEQ ID NO 19
<211> LENGTH: 22
<212> TYPE: DNA
<213> ORGANISM: Artificial Sequence
<220> FEATURE:
<223> OTHER INFORMATION: Synthetic oligonucleotide probe

<400> SEQUENCE: 19
ccaatgtgtg caagcggttg tg                                              22

<210> SEQ ID NO 20
<211> LENGTH: 50
<212> TYPE: DNA
<213> ORGANISM: Artificial Sequence
<220> FEATURE:
<223> OTHER INFORMATION: Synthetic oligonucleotide probe

<400> SEQUENCE: 20
tcaagagcct ggacctcagc cacaatctca tctctgactt tgcctggagc                50

<210> SEQ ID NO 21
<211> LENGTH: 2033
<212> TYPE: DNA
<213> ORGANISM: Homo Sapien

<400> SEQUENCE: 21
ccaggccggg aggcgacgcg cccagccgtc taaacgggaa cagccctggc                50
tgagggagct gcagcgcagc agagtatctg acggcgccag gttgcgtagg               100
```

-continued

| | |
|---|---|
| tgcggcacga ggagtttttcc cggcagcgag gaggtcctga gcagcatggc | 150 |
| ccggaggagc gccttccctg ccgccgcgct ctggctctgg agcatcctcc | 200 |
| tgtgcctgct ggcactgcgg gcggaggccg gccgccgca ggaggagagc | 250 |
| ctgtacctat ggatcgatgc tcaccaggca agagtactca taggatttga | 300 |
| agaagatatc ctgattgttt cagaggggaa aatggcacct tttacacatg | 350 |
| atttcagaaa agcgcaacag agaatgccag ctattcctgt caatatccat | 400 |
| tccatgaatt ttacctggca agctgcaggg caggcagaat acttctatga | 450 |
| attcctgtcc ttgcgctccc tggataaagg catcatggca gatccaaccg | 500 |
| tcaatgtccc tctgctggga acagtgcctc acaaggcatc agttgttcaa | 550 |
| gttggtttcc catgtcttgg aaaacaggat ggggtggcag catttgaagt | 600 |
| ggatgtgatt gttatgaatt ctgaaggcaa caccattctc caaacacctc | 650 |
| aaaatgctat cttctttaaa acatgtcaac aagctgagtg cccaggcggg | 700 |
| tgccgaaatg gaggcttttg taatgaaaga cgcatctgcg agtgtcctga | 750 |
| tgggttccac ggacctcact gtgagaaagc cctttgtacc ccacgatgta | 800 |
| tgaatggtgg actttgtgtg actcctggtt tctgcatctg cccacctgga | 850 |
| ttctatggag tgaactgtga caaagcaaac tgctcaacca cctgctttaa | 900 |
| tggagggacc tgtttctacc ctggaaaatg tatttgccct ccaggactag | 950 |
| agggagagca gtgtgaaatc agcaaatgcc acaacccctg tcgaaatgga | 1000 |
| ggtaaatgca ttggtaaaag caaatgtaag tgttccaaag gttaccaggg | 1050 |
| agacctctgt tcaaagcctg tctgcgagcc tggctgtgt gcacatgaaa | 1100 |
| cctgccatga acccaacaaa tgccaatgtc aagaaggttg gcatggaaga | 1150 |
| cactgcaata aaaggtacga agccagcctc atacatgccc tgaggccagc | 1200 |
| aggcgcccag ctcaggcagc acacgccttc acttaaaaag gccgaggagc | 1250 |
| ggcgggatcc acctgaatcc aattacatct ggtgaactcc gacatctgaa | 1300 |
| acgttttaag ttacaccaag ttcatagcct ttgttaacct ttcatgtgtt | 1350 |
| gaatgttcaa ataatgttca ttacacttaa gaatactggc ctgaattta | 1400 |
| ttagcttcat tataaatcac tgagctgata tttactcttc cttttaagtt | 1450 |
| ttctaagtac gtctgtagca tgatggtata gattttcttg tttcagtgct | 1500 |
| ttgggacaga ttttatatta tgtcaattga tcaggttaaa attttcagtg | 1550 |
| tgtagttggc agatattttc aaaattacaa tgcatttatg gtgtctgggg | 1600 |
| gcagggaac atcagaaagg ttaaattggg caaaaatgcg taagtcacaa | 1650 |
| gaatttggat ggtgcagtta atgttgaagt tacagcattt cagattttat | 1700 |
| tgtcagatat ttagatgttt gttacatttt taaaaattgc tcttaatttt | 1750 |
| taaactctca atacaatata ttttgacctt accattattc cagagattca | 1800 |
| gtattaaaaa aaaaaaaatt acactgtggt agtggcattt aaacaatata | 1850 |
| atatattcta aacacaatga aatagggaat ataatgtatg aacttttgc | 1900 |
| attggcttga agcaatataa tatattgtaa acaaaacaca gctcttacct | 1950 |
| aataaacatt ttatactgtt tgtatgtata aaataaaggt gctgctttag | 2000 |
| tttttttggaa aaaaaaaaa aaaaaaaaa aaa | 2033 |

```
<210> SEQ ID NO 22
<211> LENGTH: 379
<212> TYPE: PRT
<213> ORGANISM: Homo Sapien

<400> SEQUENCE: 22

Met Ala Arg Arg Ser Ala Phe Pro Ala Ala Leu Trp Leu Trp
  1               5                  10                  15

Ser Ile Leu Leu Cys Leu Leu Ala Leu Arg Ala Glu Ala Gly Pro
                 20                  25                  30

Pro Gln Glu Glu Ser Leu Tyr Leu Trp Ile Asp Ala His Gln Ala
                 35                  40                  45

Arg Val Leu Ile Gly Phe Glu Glu Asp Ile Leu Ile Val Ser Glu
                 50                  55                  60

Gly Lys Met Ala Pro Phe Thr His Asp Phe Arg Lys Ala Gln Gln
                 65                  70                  75

Arg Met Pro Ala Ile Pro Val Asn Ile His Ser Met Asn Phe Thr
                 80                  85                  90

Trp Gln Ala Ala Gly Gln Ala Glu Tyr Phe Tyr Glu Phe Leu Ser
                 95                 100                 105

Leu Arg Ser Leu Asp Lys Gly Ile Met Ala Asp Pro Thr Val Asn
                110                 115                 120

Val Pro Leu Leu Gly Thr Val Pro His Lys Ala Ser Val Val Gln
                125                 130                 135

Val Gly Phe Pro Cys Leu Gly Lys Gln Asp Gly Val Ala Ala Phe
                140                 145                 150

Glu Val Asp Val Ile Val Met Asn Ser Glu Gly Asn Thr Ile Leu
                155                 160                 165

Gln Thr Pro Gln Asn Ala Ile Phe Phe Lys Thr Cys Gln Gln Ala
                170                 175                 180

Glu Cys Pro Gly Gly Cys Arg Asn Gly Gly Phe Cys Asn Glu Arg
                185                 190                 195

Arg Ile Cys Glu Cys Pro Asp Gly Phe His Gly Pro His Cys Glu
                200                 205                 210

Lys Ala Leu Cys Thr Pro Arg Cys Met Asn Gly Gly Leu Cys Val
                215                 220                 225

Thr Pro Gly Phe Cys Ile Cys Pro Pro Gly Phe Tyr Gly Val Asn
                230                 235                 240

Cys Asp Lys Ala Asn Cys Ser Thr Thr Cys Phe Asn Gly Gly Thr
                245                 250                 255

Cys Phe Tyr Pro Gly Lys Cys Ile Cys Pro Pro Gly Leu Glu Gly
                260                 265                 270

Glu Gln Cys Glu Ile Ser Lys Cys Pro Gln Pro Cys Arg Asn Gly
                275                 280                 285

Gly Lys Cys Ile Gly Lys Ser Lys Cys Ser Lys Gly Tyr
                290                 295                 300

Gln Gly Asp Leu Cys Ser Lys Pro Val Cys Glu Pro Gly Cys Gly
                305                 310                 315

Ala His Gly Thr Cys His Glu Pro Asn Lys Cys Gln Cys Gln Glu
                320                 325                 330

Gly Trp His Gly Arg His Cys Asn Lys Arg Tyr Glu Ala Ser Leu
                335                 340                 345

Ile His Ala Leu Arg Pro Ala Gly Ala Gln Leu Arg Gln His Thr
                350                 355                 360
```

```
Pro Ser Leu Lys Lys Ala Glu Glu Arg Arg Asp Pro Pro Glu Ser
            365                 370                 375

Asn Tyr Ile Trp

<210> SEQ ID NO 23
<211> LENGTH: 783
<212> TYPE: DNA
<213> ORGANISM: Homo Sapien

<400> SEQUENCE: 23
agaacctcag aaatgtgagt tatttgggaa tggctgtttg taaatgtcct          50
tacgtaagcc aagaggaggt cttgacttgg ggtcccaggg gtaccgcaga         100
tcccagggac tggagcagca ctagcaagct ctggaggatg agccaggagt         150
ctggaattga ggctgagcca agaccccag ggccgtctca gtctcataaa          200 agggatcag gcaggaggag tttgggagaa acctgagaag ggcctgattt          250
gcagcatcat gatgggcctc tccttggcct ctgctgtgct cctggcctcc         300
ctcctgagtc tccaccttgg aactgccaca cgtgggagtg acatatccaa         350
gacctgctgc ttccaataca gccacaagcc ccttccctgg acctgggtgc         400
gaagctatga attcaccagt aacagctgct cccagcgggc tgtgatattc         450
actaccaaaa gaggcaagaa agtctgtacc atccaagga aaaaatgggt          500 gcaaaaatac atttctttac tgaaaactcc gaaacaattg tgactcagct         550
gaattttcat ccgaggacgc ttggaccccg ctcttggctc tgcagccctc         600
tggggagcct gcggaatctt ttctgaaggc tacatggacc cgctggggag         650
gagagggtgt ttcctcccag agttacttta ataaaggttg ttcatagagt         700
tgaaaaaaaa aaaaaaaaaa aaaaaaaaaa aaaaaaaaaa aaaaaaaaaa         750
aaaaaaaaaa aaaaaaaaaa aaaaaaaaaa aaa                           783

<210> SEQ ID NO 24
<211> LENGTH: 94
<212> TYPE: PRT
<213> ORGANISM: Homo Sapien

<400> SEQUENCE: 24

Met Met Gly Leu Ser Leu Ala Ser Ala Val Leu Leu Ala Ser Leu
  1               5                  10                  15

Leu Ser Leu His Leu Gly Thr Ala Thr Arg Gly Ser Asp Ile Ser
                 20                  25                  30

Lys Thr Cys Cys Phe Gln Tyr Ser His Lys Pro Leu Pro Trp Thr
                 35                  40                  45

Trp Val Arg Ser Tyr Glu Phe Thr Ser Asn Ser Cys Ser Gln Arg
             50                  55                  60

Ala Val Ile Phe Thr Thr Lys Arg Gly Lys Lys Val Cys Thr His
             65                  70                  75

Pro Arg Lys Lys Trp Val Gln Lys Tyr Ile Ser Leu Leu Lys Thr
             80                  85                  90

Pro Lys Gln Leu

<210> SEQ ID NO 25
<211> LENGTH: 23
<212> TYPE: DNA
<213> ORGANISM: Artificial Sequence
```

```
<220> FEATURE:
<223> OTHER INFORMATION: Synthetic oligonucleotide probe

<400> SEQUENCE: 25
ggatcaggca ggaggagttt ggg                                            23

<210> SEQ ID NO 26
<211> LENGTH: 23
<212> TYPE: DNA
<213> ORGANISM: Artificial Sequence
<220> FEATURE:
<223> OTHER INFORMATION: Synthetic oligonucleotide probe

<400> SEQUENCE: 26
ggatgggtac agactttctt gcc                                            23

<210> SEQ ID NO 27
<211> LENGTH: 50
<212> TYPE: DNA
<213> ORGANISM: Artificial Sequence
<220> FEATURE:
<223> OTHER INFORMATION: Synthetic oligonucleotide probe

<400> SEQUENCE: 27
atgatgggcc tctccttggc ctctgctgtg ctcctggcct ccctcctgag               50

<210> SEQ ID NO 28
<211> LENGTH: 3552
<212> TYPE: DNA
<213> ORGANISM: Homo Sapien

<400> SEQUENCE: 28
gcgagaacct ttgcacgcgc acaaactacg gggacgattt ctgattgatt               50
tttggcgctt tcgatccacc ctcctccctt tcatgggac tttggggaca               100 aagcgtcccg accgcctcga gcgctcgagc agggcgctat ccaggagcca              150
ggacagcgtc gggaaccaga ccatggctcc tgaccccaa gatccttaag               200 ttcgtcgtct tcatcgtcgc ggttctgctg ccggtccggg ttgactctgc               250
caccatcccc cggcaggacg aagttcccca gcagacagtg gccccacagc               300
aacagaggcg cagcctcaag gaggaggagt gtccagcagg atctcataga               350
tcagaatata ctggagcctg taacccgtgc acagagggtg tggattacac              400
cattgcttcc aacaatttgc cttcttgcct gctatgtaca gtttgtaaat               450
caggtcaaac aaataaaagt tcctgtacca cgaccagaga caccgtgtgt               500
cagtgtgaaa aaggaagctt ccaggataaa aactcccctg agatgtgccg               550
gacgtgtaga acagggtgtc ccagagggat ggtcaaggtc agtaattgta              600
cgccccggag tgacatcaag tgcaaaaatg aatcagctgc cagttccact               650
gggaaaaccc cagcagcgga ggagacagtg accaccatcc tggggatgct               700
tgcctctccc tatcactacc ttatcatcat agtggtttta gtcatcattt               750
tagctgtggt tgtggttggc ttttcatgtc ggaagaaatt catttcttac               800
ctcaaaggca tctgctcagg tggtggagga ggtcccgaac gtgtgcacag               850
agtccttttc cggcggcgtt catgtccttc acgagttcct ggggcggagg              900
acaatgcccg caacgagacc ctgagtaaca gatacttgca gccccaccag               950
gtctctgagc aggaaatcca aggtcaggag ctggcagagc taacaggtgt              1000
```

-continued

| | |
|---|---|
| gactgtagag tcgccagagg agccacagcg tctgctggaa caggcagaag | 1050 |
| ctgaaggtg tcagaggagg aggctgctgg ttccagtgaa tgacgctgac | 1100 |
| tccgctgaca tcagcacctt gctggatgcc tcggcaacac tggaagaagg | 1150 |
| acatgcaaag gaaacaattc aggaccaact ggtgggctcc gaaaagctct | 1200 |
| tttatgaaga agatgaggca ggctctgcta cgtcctgcct gtgaaagaat | 1250 |
| ctcttcagga aaccagagct tccctcattt acctttctc ctacaaaggg | 1300 |
| aagcagcctg gaagaaacag tccagtactt gacccatgcc ccaacaaact | 1350 |
| ctactatcca atatgggca gcttaccaat ggtcctagaa ctttgttaac | 1400 |
| gcacttggag taattttat gaaatactgc gtgtgataag caaacgggag | 1450 |
| aaatttatat cagattcttg gctgcatagt tatacgattg tgtattaagg | 1500 |
| gtcgttttag gccacatgcg gtggctcatg cctgtaatcc cagcactttg | 1550 |
| ataggctgag gcaggtggat tgcttgagct cgggagttgg agaccagcct | 1600 |
| catcaacaca gtgaaactcc atctcaattt aaaagaaaa aaagtggttt | 1650 |
| taggatgtca ttcttgcag ttcttcatca tgagacaagt cttttttct | 1700 |
| gcttcttata ttgcaagctc catctctact ggtgtgtgca tttaatgaca | 1750 |
| tctaactaca gatgccgcac agccacaatg ctttgcctta tagttttta | 1800 |
| actttagaac gggattatct tgttattacc tgtatttca gtttcggata | 1850 |
| tttttgactt aatgatgaga ttatcaagac gtagccctat gctaagtcat | 1900 |
| gagcatatgg acttacgagg gttcgactta gagttttgag ctttaagata | 1950 |
| ggattattgg ggcttacccc caccttaatt agagaaacat ttatattgct | 2000 |
| tactactgta ggctgtacat ctcttttccg attttgtat aatgatgtaa | 2050 |
| acatggaaaa actttaggaa atgcacttat taggctgttt acatgggttg | 2100 |
| cctggataca aatcagcagt caaaaatgac taaaaatata actagtgacg | 2150 |
| gagggagaaa tcctccctct gtgggaggca cttactgcat tccagttctc | 2200 |
| cctcctgcgc cctgagactg gaccagggtt tgatggctgg cagcttctca | 2250 |
| aggggcagct tgtcttactt gttaatttta gaggtatata gccatattta | 2300 |
| tttataaata aatatttatt tatttattta taagtagatg tttacatatg | 2350 |
| cccaggattt tgaagagcct ggtatctttg ggaagccatg tgtctggttt | 2400 |
| gtcgtgctgg gacagtcatg ggactgcatc ttccgacttg tccacagcag | 2450 |
| atgaggacag tgagaattaa gttagatccg agactgcgaa gagcttctct | 2500 |
| ttcaagcgcc attacagttg aacgttagtg aatcttgagc ctcatttggg | 2550 |
| ctcagggcag agcaggtgtt tatctgcccc ggcatctgcc atggcatcaa | 2600 |
| gagggaagag tggacggtgc ttgggaatgg tgtgaaatgg ttgccgactc | 2650 |
| aggcatggat gggcccctct cgcttctggt ggtctgtgaa ctgagtccct | 2700 |
| gggatgcctt ttagggcaga gattcctgag ctgcgtttta gggtacagat | 2750 |
| tccctgtttg aggagcttgg cccctctgta agcatctgac tcatctcaga | 2800 |
| gatatcaatt cttaaacact gtgacaacg gatctaaaat ggctgacaca | 2850 |
| tttgtccttg tgtcacgttc cattatttta tttaaaaacc tcagtaatcg | 2900 |
| ttttagcttc tttccagcaa actcttctcc acagtagccc agtcgtggta | 2950 |
| ggataaaatta cggatatagt cattctaggg gtttcagtct tttccatctc | 3000 |

-continued

```
aaggcattgt gtgttttgtt ccgggactgg tttggctggg acaaagttag          3050
aactgcctga agttcgcaca ttcagattgt tgtgtccatg gagttttagg          3100
aggggatggc ctttccggtc ttcgcacttc catcctctcc cacttccatc          3150
tggcgtccca caccttgtcc cctgcacttc tggatgacac agggtgctgc          3200
tgcctcctag tctttgcctt tgctgggcct tctgtgcagg agacttggtc          3250
tcaaagctca gagagagcca gtccggtccc agctcctttg tcccttcctc          3300
agaggccttc cttgaagatg catctagact accagcctta tcagtgttta          3350
agcttattcc tttaacataa gcttcctgac aacatgaaat tgttggggtt          3400
ttttggcgtt ggttgatttg tttaggtttt gctttatacc cgggccaaat          3450
agcacataac acctggttat atgaaaata ctcatatgtt tatgaccaaa           3500
ataaatatga aacctcatrt taaaaaaaaa aaaaaaaaaa aaaaaaaaaa          3550
aa                                                              3552
```

<210> SEQ ID NO 29
<211> LENGTH: 386
<212> TYPE: PRT
<213> ORGANISM: Homo Sapien

<400> SEQUENCE: 29

```
Met Gly Leu Trp Gly Gln Ser Val Pro Thr Ala Ser Ser Ala Arg
  1               5                  10                  15

Ala Gly Arg Tyr Pro Gly Ala Arg Thr Ala Ser Gly Thr Arg Pro
                 20                  25                  30

Trp Leu Leu Asp Pro Lys Ile Leu Lys Phe Val Val Phe Ile Val
                 35                  40                  45

Ala Val Leu Leu Pro Val Arg Val Asp Ser Ala Thr Ile Pro Arg
                 50                  55                  60

Gln Asp Glu Val Pro Gln Gln Thr Val Ala Pro Gln Gln Arg
                 65                  70                  75

Arg Ser Leu Lys Glu Glu Cys Pro Ala Gly Ser His Arg Ser
                 80                  85                  90

Glu Tyr Thr Gly Ala Cys Asn Pro Cys Thr Glu Gly Val Asp Tyr
                 95                 100                 105

Thr Ile Ala Ser Asn Asn Leu Pro Ser Cys Leu Leu Cys Thr Val
                110                 115                 120

Cys Lys Ser Gly Gln Thr Asn Lys Ser Ser Cys Thr Thr Thr Arg
                125                 130                 135

Asp Thr Val Cys Gln Cys Glu Lys Gly Ser Phe Gln Asp Lys Asn
                140                 145                 150

Ser Pro Glu Met Cys Arg Thr Cys Arg Thr Gly Cys Pro Arg Gly
                155                 160                 165

Met Val Lys Val Ser Asn Cys Thr Pro Arg Ser Asp Ile Lys Cys
                170                 175                 180

Lys Asn Glu Ser Ala Ala Ser Ser Thr Gly Lys Thr Pro Ala Ala
                185                 190                 195

Glu Glu Thr Val Thr Thr Ile Leu Gly Met Leu Ala Ser Pro Tyr
                200                 205                 210

His Tyr Leu Ile Ile Ile Val Leu Val Ile Ile Leu Ala Val
                215                 220                 225

Val Val Val Gly Phe Ser Cys Arg Lys Lys Phe Ile Ser Tyr Leu
```

```
                230             235             240
Lys Gly Ile Cys Ser Gly Gly Gly Gly Pro Glu Arg Val His
                    245             250             255
Arg Val Leu Phe Arg Arg Arg Ser Cys Pro Ser Arg Val Pro Gly
                    260             265             270
Ala Glu Asp Asn Ala Arg Asn Glu Thr Leu Ser Asn Arg Tyr Leu
                    275             280             285
Gln Pro Thr Gln Val Ser Glu Gln Glu Ile Gln Gly Gln Glu Leu
                    290             295             300
Ala Glu Leu Thr Gly Val Thr Val Glu Ser Pro Glu Glu Pro Gln
                    305             310             315
Arg Leu Leu Glu Gln Ala Glu Ala Glu Gly Cys Gln Arg Arg Arg
                    320             325             330
Leu Leu Val Pro Val Asn Asp Ala Asp Ser Ala Asp Ile Ser Thr
                    335             340             345
Leu Leu Asp Ala Ser Ala Thr Leu Glu Glu Gly His Ala Lys Glu
                    350             355             360
Thr Ile Gln Asp Gln Leu Val Gly Ser Glu Lys Leu Phe Tyr Glu
                    365             370             375
Glu Asp Glu Ala Gly Ser Ala Thr Ser Cys Leu
                    380             385

<210> SEQ ID NO 30
<211> LENGTH: 50
<212> TYPE: DNA
<213> ORGANISM: Artificial Sequence
<220> FEATURE:
<223> OTHER INFORMATION: Synthetic oligonucleotide probe

<400> SEQUENCE: 30
cataaaagtt cctgcaccat gaccagagac acagtgtgtc agtgtaaaga                50

<210> SEQ ID NO 31
<211> LENGTH: 963
<212> TYPE: DNA
<213> ORGANISM: Homo Sapien

<400> SEQUENCE: 31
gcggcacctg gaagatgcgc ccattggctg gtggcctgct caaggtggtg                50
ttcgtggtct cgcctccttt gtgtgcctgg tattcggggt acctgctcgc               100
agagctcatt ccagatgcac ccctgtccag tgctgcctat agcatccgca               150
gcatcgggga gaggcctgtc ctcaaagctc cagtccccaa aggcaaaaa                200 tgtgaccact ggactccctg cccatctgac acctatgcct acaggttact               250
cagcggaggt ggcagaagca agtacgccaa aatctgcttt gaggataacc               300
tacttatggg agaacagctg ggaaatgttg ccagaggaat aaacattgcc               350
attgtcaact atgtaactgg gaatgtgaca gcaacacgat gttttgatat               400
gtatgaaggc gataactctg gaccgatgac aaagtttatt cagagtgctg               450
ctccaaaatc cctgctcttc atggtgacct atgacgacgg aagcacaaga               500
ctgaataacg atgccaagaa tgccatagaa gcacttggag taaagaaat                550 caggaacatg aaaattcagg tctagctggg atttattgca gcaaaaggct               600
tggaactccc ttccgaaatt cagagagaaa agatcaacca ctctgatgct               650
aagaacaaca gatattctgg ctggcctgca gagatccaga tagaaggctg               700
```

```
cataccaaa gaacgaagct gacactgcag ggtcctgagt aaatgtgttc        750
tgtataaaca aatgcagctg gaatcgctca agaatcttat ttttctaaat       800
ccaacagccc atatttgatg agtatttttgg gtttgttgta aaccaatgaa      850
catttgctag ttgtatcaaa tcttggtacg cagtattttt ataccagtat       900
tttatgtagt gaagatgtca attagcagga aactaaaatg aatggaaatt       950
cttaaaaaaa aaa                                               963
```

<210> SEQ ID NO 32
<211> LENGTH: 235
<212> TYPE: PRT
<213> ORGANISM: Homo Sapien

<400> SEQUENCE: 32

```
Met Arg Pro Leu Ala Gly Gly Leu Leu Lys Val Val Phe Val Val
 1               5                  10                  15

Phe Ala Ser Leu Cys Ala Trp Tyr Ser Gly Tyr Leu Leu Ala Glu
                20                  25                  30

Leu Ile Pro Asp Ala Pro Leu Ser Ser Ala Ala Tyr Ser Ile Arg
                35                  40                  45

Ser Ile Gly Glu Arg Pro Val Leu Lys Ala Pro Val Pro Lys Arg
            50                  55                  60

Gln Lys Cys Asp His Trp Thr Pro Cys Pro Ser Asp Thr Tyr Ala
        65                  70                  75

Tyr Arg Leu Leu Ser Gly Gly Arg Ser Lys Tyr Ala Lys Ile
                80                  85                  90

Cys Phe Glu Asp Asn Leu Leu Met Gly Glu Gln Leu Gly Asn Val
                95                  100                 105

Ala Arg Gly Ile Asn Ile Ala Ile Val Asn Tyr Val Thr Gly Asn
                110                 115                 120

Val Thr Ala Thr Arg Cys Phe Asp Met Tyr Glu Gly Asp Asn Ser
                125                 130                 135

Gly Pro Met Thr Lys Phe Ile Gln Ser Ala Ala Pro Lys Ser Leu
                140                 145                 150

Leu Phe Met Val Thr Tyr Asp Asp Gly Ser Thr Arg Leu Asn Asn
                155                 160                 165

Asp Ala Lys Asn Ala Ile Glu Ala Leu Gly Ser Lys Glu Ile Arg
                170                 175                 180

Asn Met Lys Phe Arg Ser Ser Trp Val Phe Ile Ala Ala Lys Gly
                185                 190                 195

Leu Glu Leu Pro Ser Glu Ile Gln Arg Glu Lys Ile Asn His Ser
                200                 205                 210

Asp Ala Lys Asn Asn Arg Tyr Ser Gly Trp Pro Ala Glu Ile Gln
                215                 220                 225

Ile Glu Gly Cys Ile Pro Lys Glu Arg Ser
                230                 235
```

<210> SEQ ID NO 33
<211> LENGTH: 18
<212> TYPE: DNA
<213> ORGANISM: Artificial Sequence
<220> FEATURE:
<223> OTHER INFORMATION: Synthetic oligonucleotide probe

<400> SEQUENCE: 33

| | |
|---|---|
| ggctggcctg cagagatc | 18 |

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide probe

<400> SEQUENCE: 34

| | |
|---|---|
| aatgtgacca ctggactccc | 20 |

<210> SEQ ID NO 35
<211> LENGTH: 18
<212> TYPE: DNA
<213> ORGANISM: Artificial Sequence
<220> FEATURE:
<223> OTHER INFORMATION: Synthetic oligonucleotide probe

<400> SEQUENCE: 35

| | |
|---|---|
| aggcttggaa ctcccttc | 18 |

<210> SEQ ID NO 36
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 36

| | |
|---|---|
| aagattcttg agcgattcca gctg | 24 |

<210> SEQ ID NO 37
<211> LENGTH: 47
<212> TYPE: DNA
<213> ORGANISM: Artificial Sequence
<220> FEATURE:
<223> OTHER INFORMATION: Synthetic oligonucleotide probe

<400> SEQUENCE: 37

| | |
|---|---|
| aatccctgct cttcatggtg acctatgacg acggaagcac aagactg | 47 |

<210> SEQ ID NO 38
<211> LENGTH: 1215
<212> TYPE: DNA
<213> ORGANISM: Homo Sapien

<400> SEQUENCE: 38

| | |
|---|---|
| ccggggaggg gagggcccgt cccgcccctc ccgtctctc cccgcccctc | 50 |
| cccgtccctc ccgccgaagc tccgtcccgc ccgcgggccg gctccgccct | 100 |
| cacctcccgg ccgcggctgc cctctgcccg ggttgtccaa gatggagggc | 150 |
| gctccaccgg ggtcgctcgc cctccggctc ctgctgttcg tggcgctacc | 200 |
| cgcctccggc tggctgacga cgggcgcccc cgagccgccg ccgctgtccg | 250 |
| gagccccaca ggacggcatc agaattaatg taactacact gaaagatgat | 300 |
| ggggacatat ctaaacagca ggttgttctt aacataacct atgagagtgg | 350 |
| acaggtgtat gtaaatgact tacctgtaaa tagtggtgta acccgaataa | 400 |
| gctgtcagac tttgatagtg aagaatgaaa atcttgaaaa tttggaggaa | 450 |
| aaagaatatt ttgaattgt cagtgtaagg attttagttc atgagtggcc | 500 |
| tatgacatct ggttccagtt tgcaactaat tgtcattcaa gaagaggtag | 550 |

-continued

```
tagagattga tggaaaacaa gttcagcaaa aggatgtcac tgaaattgat      600
attttagtta agaaccgggg agtactcaga cattcaaact ataccctccc      650
tttggaagaa agcatgctct actctatttc tcgagacagt gacattttat      700
ttacccttcc taacctctcc aaaaaagaaa gtgttagttc actgcaaacc      750
actagccagt atcttatcag gaatgtggaa accactgtag atgaagatgt      800
tttacctggc aagttacctg aaactcctct cagagcagag ccgccatctt      850
catataaggt aatgtgtcag tggatggaaa agtttagaaa agatctgtgt      900
aggttctgga gcaacgtttt cccagtattc tttcagtttt tgaacatcat      950
ggtggttgga attacaggag cagctgtggt aataaccatc ttaaaggtgt     1000
ttttcccagt ttctgaatac aaaggaattc ttcagttgga taaagtggac     1050
gtcatacctg tgacagctat caacttatat ccagatggtc cagagaaaag     1100
agctgaaaac cttgaagata aacatgtat ttaaaacgcc atctcatatc     1150
atggactccg aagtagcctg ttgcctccaa atttgccact tgaatataat     1200
tttcttttaaa tcgtt                                          1215
```

<210> SEQ ID NO 39
<211> LENGTH: 330
<212> TYPE: PRT
<213> ORGANISM: Homo Sapien

<400> SEQUENCE: 39

```
Met Glu Gly Ala Pro Pro Gly Ser Leu Ala Leu Arg Leu Leu Leu
  1               5                  10                  15

Phe Val Ala Leu Pro Ala Ser Gly Trp Leu Thr Thr Gly Ala Pro
                 20                  25                  30

Glu Pro Pro Pro Leu Ser Gly Ala Pro Gln Asp Gly Ile Arg Ile
                 35                  40                  45

Asn Val Thr Thr Leu Lys Asp Asp Gly Asp Ile Ser Lys Gln Gln
                 50                  55                  60

Val Val Leu Asn Ile Thr Tyr Glu Ser Gly Gln Val Tyr Val Asn
             65                  70                  75

Asp Leu Pro Val Asn Ser Gly Val Thr Arg Ile Ser Cys Gln Thr
                 80                  85                  90

Leu Ile Val Lys Asn Glu Asn Leu Glu Asn Leu Glu Glu Lys Glu
                 95                 100                 105

Tyr Phe Gly Ile Val Ser Val Arg Ile Leu Val His Glu Trp Pro
                110                 115                 120

Met Thr Ser Gly Ser Ser Leu Gln Leu Ile Val Ile Gln Glu Glu
                125                 130                 135

Val Val Glu Ile Asp Gly Lys Gln Val Gln Gln Lys Asp Val Thr
                140                 145                 150

Glu Ile Asp Ile Leu Val Lys Asn Arg Gly Val Leu Arg His Ser
                155                 160                 165

Asn Tyr Thr Leu Pro Leu Glu Glu Ser Met Leu Tyr Ser Ile Ser
                170                 175                 180

Arg Asp Ser Asp Ile Leu Phe Thr Leu Pro Asn Leu Ser Lys Lys
                185                 190                 195

Glu Ser Val Ser Ser Leu Gln Thr Thr Ser Gln Tyr Leu Ile Arg
                200                 205                 210
```

```
Asn Val Glu Thr Thr Val Asp Glu Asp Val Leu Pro Gly Lys Leu
                215                 220                 225

Pro Glu Thr Pro Leu Arg Ala Glu Pro Ser Ser Tyr Lys Val
                230                 235                 240

Met Cys Gln Trp Met Glu Lys Phe Arg Lys Asp Leu Cys Arg Phe
                245                 250                 255

Trp Ser Asn Val Phe Pro Val Phe Phe Gln Phe Leu Asn Ile Met
                260                 265                 270

Val Val Gly Ile Thr Gly Ala Ala Val Val Ile Thr Ile Leu Lys
                275                 280                 285

Val Phe Phe Pro Val Ser Glu Tyr Lys Gly Ile Leu Gln Leu Asp
                290                 295                 300

Lys Val Asp Val Ile Pro Val Thr Ala Ile Asn Leu Tyr Pro Asp
                305                 310                 315

Gly Pro Glu Lys Arg Ala Glu Asn Leu Glu Asp Lys Thr Cys Ile
                320                 325                 330

<210> SEQ ID NO 40
<211> LENGTH: 2498
<212> TYPE: DNA
<213> ORGANISM: Homo Sapien

<400> SEQUENCE: 40
```

| | | |
|---|---|---|
| cgtctctgcg ttcgccatgc gtcccggggc gccagggcca ctctggcctc | 50 |
| tgccctgggg ggccctggct tgggccgtgg gcttcgtgag ctccatgggc | 100 |
| tcggggaacc ccgcgcccgg tggtgtttgc tggctccagc agggccagga | 150 |
| ggccacctgc agcctggtgc tccagactga tgtcacccgg gccgagtgct | 200 |
| gtgcctccgg caacattgac accgcctggt ccaacctcac ccacccgggg | 250 |
| aacaagatca acctcctcgg cttcttgggc cttgtccact gccttccctg | 300 |
| caaagattcg tgcgacggcg tggagtgcgg cccgggcaag gcgtgccgca | 350 |
| tgctgggggg ccgcccgcgc tgcgagtgcg cgcccgactg ctcggggctc | 400 |
| ccggcgcggc tgcaggtctg cggctcagac ggcgccacct accgcgacga | 450 |
| gtgcgagctg cgcgccgcgc gctgccgcgc ccacccggac ctgagcgtca | 500 |
| tgtaccgggg ccgctgccgc aagtcctgtg agcacgtggt gtgcccgcgg | 550 |
| ccacagtcgt gcgtcgtgga ccagacgggc agcgcccact gcgtggtgtg | 600 |
| tcgagcggcc cctgccctg tgccctccag ccccggccag gagctttgcg | 650 |
| gcaacaacaa cgtcacctac atctcctcgt gccacatgcg ccaggccacc | 700 |
| tgcttcctgg gccgctccat cggcgtgcgc acgcgggca gctgcgcagg | 750 |
| cacccctgag gagccgccag gtggtgagtc tgcagaagag gaagagaact | 800 |
| tcgtgtgagc ctgcaggaca ggcctgggcc tggtgcccga ggcccccat | 850 |
| catcccctgt tatttattgc cacagcagag tctaatttat atgccacgga | 900 |
| cactccttag agcccggatt cggaccactt ggggatccca gaacctccct | 950 |
| gacgatatcc tggaaggact gaggaaggga ggcctggggg ccggctggtg | 1000 |
| ggtgggatag acctgcgttc cggacactga gcgcctgatt tagggccctt | 1050 |
| ctctaggatg ccccagcccc taccctaaga cctattgccg gggaggattc | 1100 |
| cacacttccg ctcctttggg gataaaccta ttaattattg ctactatcaa | 1150 |
| gagggctggg cattctctgc tggtaattcc tgaagaggca tgactgcttt | 1200 |

-continued

```
tctcagcccc aagcctctag tctgggtgtg tacggagggt ctagcctggg        1250
tgtgtacgga gggtctagcc tgggtgagta cggagggtct agcctgggtg        1300
agtacggagg gtctagcctg ggtgagtacg gagggtctag cctgggtgtg        1350
tatggaggat ctagcctggg tgagtatgga gggtctagcc tgggtgagta        1400
tggagggtct agcctgggtg tgtatggagg gtctagcctg ggtgagtatg        1450
gagggtctag cctgggtgtg tatggagggt ctagcctggg tgagtatgga        1500
gggtctagcc tgggtgtgta cggagggtct agtctgagtg cgtgtgggga        1550
cctcagaaca ctgtgacctt agcccagcaa gccaggccct tcatgaaggc        1600
caagaaggct gccaccattc cctgccagcc caagaactcc agcttcccca        1650
ctgcctctgt gtgcccctttt gcgtcctgtg aaggccattg agaaatgccc        1700
agtgtgcccc ctgggaaagg gcacggcctg tgctcctgac acgggctgtg        1750
cttggccaca gaaccaccca gcgtctcccc tgctgctgtc cacgtcagtt        1800
catgaggcaa cgtcgcgtgg tctcagacgt ggagcagcca gcggcagctc        1850
agagcagggc actgtgtccg gcggagccaa gtccactctg ggggagctct        1900
ggcggggacc acgggccact gctcacccac tggccccgag gggggtgtag        1950
acgccaagac tcacgcatgt gtgacatccg gagtcctgga gccgggtgtc        2000
ccagtggcac cactaggtgc ctgctgcctc cacagtgggg ttcacaccca        2050
gggctccttg gtcccccaca acctgccccg gccaggcctg cagacccaga        2100
ctccagccag acctgcctca cccaccaatg cagccggggc tggcgacacc        2150
agccaggtgc tggtcttggg ccagttctcc cacgacggct caccctcccc        2200
tccatctgcg ttgatgctca gaatcgccta cctgtgcctg cgtgtaaacc        2250
acagcctcag accagctatg gggagaggac aacacggagg atatccagct        2300
tccccggtct ggggtgagga atgtgggagg cttgggcatc ctcctccagc        2350
ctcctccagc ccccaggcag tgccttacct gtggtgccca gaaagtgcc         2400 cctaggttgg tgggtctaca ggagcctcag ccaggcagcc caccccaccc        2450
tggggccctg cctcaccaag gaaataaaga ctcaagccat aaaaaaaa         2498
```

<210> SEQ ID NO 41
<211> LENGTH: 263
<212> TYPE: PRT
<213> ORGANISM: Homo Sapien

<400> SEQUENCE: 41

```
Met Arg Pro Gly Ala Pro Gly Pro Leu Trp Pro Leu Pro Trp Gly
  1               5                  10                  15

Ala Leu Ala Trp Ala Val Gly Phe Val Ser Met Gly Ser Gly
                 20                  25                  30

Asn Pro Ala Pro Gly Gly Val Cys Trp Leu Gln Gln Gly Gln Glu
                 35                  40                  45

Ala Thr Cys Ser Leu Val Leu Gln Thr Asp Val Thr Arg Ala Glu
                 50                  55                  60

Cys Cys Ala Ser Gly Asn Ile Asp Thr Ala Trp Ser Asn Leu Thr
                 65                  70                  75

His Pro Gly Asn Lys Ile Asn Leu Leu Gly Phe Leu Gly Leu Val
                 80                  85                  90
```

```
His Cys Leu Pro Cys Lys Asp Ser Cys Asp Gly Val Glu Cys
                95                 100                 105

Pro Gly Lys Ala Cys Arg Met Leu Gly Gly Arg Pro Arg Cys Glu
                110                 115                 120

Cys Ala Pro Asp Cys Ser Gly Leu Pro Ala Arg Leu Gln Val Cys
                125                 130                 135

Gly Ser Asp Gly Ala Thr Tyr Arg Asp Glu Cys Glu Leu Arg Ala
                140                 145                 150

Ala Arg Cys Arg Gly His Pro Asp Leu Ser Val Met Tyr Arg Gly
                155                 160                 165

Arg Cys Arg Lys Ser Cys Glu His Val Val Cys Pro Arg Pro Gln
                170                 175                 180

Ser Cys Val Val Asp Gln Thr Gly Ser Ala His Cys Val Val Cys
                185                 190                 195

Arg Ala Ala Pro Cys Pro Val Pro Ser Ser Pro Gly Gln Glu Leu
                200                 205                 210

Cys Gly Asn Asn Asn Val Thr Tyr Ile Ser Ser Cys His Met Arg
                215                 220                 225

Gln Ala Thr Cys Phe Leu Gly Arg Ser Ile Gly Val Arg His Ala
                230                 235                 240

Gly Ser Cys Ala Gly Thr Pro Glu Pro Pro Gly Gly Glu Ser
                245                 250                 255

Ala Glu Glu Glu Glu Asn Phe Val
                260
```

<210> SEQ ID NO 42
<211> LENGTH: 20
<212> TYPE: DNA
<213> ORGANISM: Artificial Sequence
<220> FEATURE:
<223> OTHER INFORMATION: Synthetic oligonucleotide probe

<400> SEQUENCE: 42
tcctgtgagc acgtggtgtg                                               20

<210> SEQ ID NO 43
<211> LENGTH: 18
<212> TYPE: DNA
<213> ORGANISM: Artificial Sequence
<220> FEATURE:
<223> OTHER INFORMATION: Synthetic oligonucleotide probe

<400> SEQUENCE: 43
gggtgggata gacctgcg                                                 18

<210> SEQ ID NO 44
<211> LENGTH: 18
<212> TYPE: DNA
<213> ORGANISM: Artificial Sequence
<220> FEATURE:
<223> OTHER INFORMATION: Synthetic oligonucleotide probe

<400> SEQUENCE: 44
aaggccaaga aggctgcc                                                 18

<210> SEQ ID NO 45
<211> LENGTH: 18
<212> TYPE: DNA
<213> ORGANISM: Artificial Sequence
<220> FEATURE:
<223> OTHER INFORMATION: Synthetic oligonucleotide probe

```
<400> SEQUENCE: 45
ccaggcctgc agacccag                                                   18

<210> SEQ ID NO 46
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 46
cttcctcagt ccttccagga tatc                                            24

<210> SEQ ID NO 47
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 47
aagctggata tcctccgtgt tgtc                                            24

<210> SEQ ID NO 48
<211> LENGTH: 27
<212> TYPE: DNA
<213> ORGANISM: Artificial Sequence
<220> FEATURE:
<223> OTHER INFORMATION: Synthetic oligonucleotide probe

<400> SEQUENCE: 48
cctgaagagg catgactgct tttctca                                         27

<210> SEQ ID NO 49
<211> LENGTH: 27
<212> TYPE: DNA
<213> ORGANISM: Artificial Sequence
<220> FEATURE:
<223> OTHER INFORMATION: Synthetic oligonucleotide probe

<400> SEQUENCE: 49
ggggataaac ctattaatta ttgctac                                         27

<210> SEQ ID NO 50
<211> LENGTH: 44
<212> TYPE: DNA
<213> ORGANISM: Artificial Sequence
<220> FEATURE:
<223> OTHER INFORMATION: Synthetic oligonucleotide probe

<400> SEQUENCE: 50
aacgtcacct acatctcctc gtgccacatg cgccaggcca cctg                      44

<210> SEQ ID NO 51
<211> LENGTH: 1690
<212> TYPE: DNA
<213> ORGANISM: Homo Sapien

<400> SEQUENCE: 51
tgcagagctt gtggaggcca tggggcgcgt cgtcgcggag ctcgtctcct                50
cgctgctggg gttgtggctg ttgctgtgca gctgcggatg ccccgagggc               100
gccgagctgc gtgctccgcc agataaaatc gcgattattg gagccggaat               150
```

-continued

| | |
|---|---|
| tggtggcact tcagcagcct attacctgcg gcagaaattt gggaaagatg | 200 |
| tgaagataga cctgtttgaa agagaagagg tcggggccg cctggctacc | 250 |
| atgatggtgc aggggcaaga atacgaggca ggaggttctg tcatccatcc | 300 |
| tttaaatctg cacatgaaac gttttgtcaa agacctgggt ctctctgctg | 350 |
| ttcaggcctc tggtggccta ctggggatat ataatggaga gactctggta | 400 |
| tttgaggaga gcaactggtt cataattaac gtgattaaat tagtttggcg | 450 |
| ctatggattt caatccctcc gtatgcacat gtgggtagag gacgtgttag | 500 |
| acaagttcat gaggatctac cgctaccagt ctcatgacta tgccttcagt | 550 |
| agtgtcgaaa aattacttca tgctctagga ggagatgact tccttggaat | 600 |
| gcttaatcga acacttcttg aaaccttgca aaaggccggc ttttctgaga | 650 |
| agttcctcaa tgaaatgatt gctcctgtta tgagggtcaa ttatggccaa | 700 |
| agcacggaca tcaatgcctt tgtgggggcg tgtcactgt cctgttctga | 750 |
| ttctggcctt tgggcagtag aaggtggcaa taaacttgtt tgctcagggc | 800 |
| ttctgcaggc atccaaaagc aatcttatat ctggctcagt aatgtacatc | 850 |
| gaggagaaaa caaagaccaa gtacacagga atccaacaa agatgtatga | 900 |
| agtggtctac caaattggaa ctgagactcg ttcagacttc tatgacatcg | 950 |
| tcttggtggc cactccgttg aatcgaaaaa tgtcgaatat tactttctc | 1000 |
| aactttgatc ctccaattga ggaattccat caatattatc aacatatagt | 1050 |
| gacaacttta gttaaggggg aattgaatac atctatcttt agctctagac | 1100 |
| ccatagataa atttggcctt aatacagttt taaccactga taattcagat | 1150 |
| ttgttcatta acagtattgg gattgtgccc tctgtgagag aaaaggaaga | 1200 |
| tcctgagcca tcaacagatg gaacatatgt ttggaagatc ttttcccaag | 1250 |
| aaactcttac taaagcacaa attttaaagc tctttctgtc ctatgattat | 1300 |
| gctgtgaaga agccatggct tgcatatcct cactataagc ccccggagaa | 1350 |
| atgcccctct atcattctcc atgatcgact ttattacctc aatggcatag | 1400 |
| agtgtgcagc aagtgccatg gagatgagtg ccattgcagc ccacaacgct | 1450 |
| gcactccttg cctatcaccg ctggaacggg cacacagaca tgattgatca | 1500 |
| ggatggctta tatgagaaac ttaaaactga actatgaagt gacacactcc | 1550 |
| tttttcccct cctagttcca aatgactatc agtggcaaaa aagaacaaaa | 1600 |
| tctgagcaga gatgattttg aaccagatat tttgccatta tcattgttta | 1650 |
| ataaaagtaa tccctgctgg tcataggaaa aaaaaaaaa | 1690 |

<210> SEQ ID NO 52
<211> LENGTH: 505
<212> TYPE: PRT
<213> ORGANISM: Homo Sapien

<400> SEQUENCE: 52

Met Gly Arg Val Val Ala Glu Leu Val Ser Ser Leu Leu Gly Leu
1               5                   10                  15

Trp Leu Leu Leu Cys Ser Cys Gly Cys Pro Glu Gly Ala Glu Leu
            20                  25                  30

Arg Ala Pro Pro Asp Lys Ile Ala Ile Ile Gly Ala Gly Ile Gly
        35                  40                  45

-continued

```
Gly Thr Ser Ala Ala Tyr Tyr Leu Arg Gln Lys Phe Gly Lys Asp
             50                  55                  60

Val Lys Ile Asp Leu Phe Glu Arg Glu Val Gly Gly Arg Leu
             65                  70                  75

Ala Thr Met Met Val Gln Gly Gln Glu Tyr Glu Ala Gly Gly Ser
             80                  85                  90

Val Ile His Pro Leu Asn Leu His Met Lys Arg Phe Val Lys Asp
             95                 100                 105

Leu Gly Leu Ser Ala Val Gln Ala Ser Gly Gly Leu Leu Gly Ile
            110                 115                 120

Tyr Asn Gly Glu Thr Leu Val Phe Glu Glu Ser Asn Trp Phe Ile
            125                 130                 135

Ile Asn Val Ile Lys Leu Val Trp Arg Tyr Gly Phe Gln Ser Leu
            140                 145                 150

Arg Met His Met Trp Val Glu Asp Val Leu Asp Lys Phe Met Arg
            155                 160                 165

Ile Tyr Arg Tyr Gln Ser His Asp Tyr Ala Phe Ser Ser Val Glu
            170                 175                 180

Lys Leu Leu His Ala Leu Gly Gly Asp Asp Phe Leu Gly Met Leu
            185                 190                 195

Asn Arg Thr Leu Leu Glu Thr Leu Gln Lys Ala Gly Phe Ser Glu
            200                 205                 210

Lys Phe Leu Asn Glu Met Ile Ala Pro Val Met Arg Val Asn Tyr
            215                 220                 225

Gly Gln Ser Thr Asp Ile Asn Ala Phe Val Gly Ala Val Ser Leu
            230                 235                 240

Ser Cys Ser Asp Ser Gly Leu Trp Ala Val Glu Gly Gly Asn Lys
            245                 250                 255

Leu Val Cys Ser Gly Leu Leu Gln Ala Ser Lys Ser Asn Leu Ile
            260                 265                 270

Ser Gly Ser Val Met Tyr Ile Glu Glu Lys Thr Lys Thr Lys Tyr
            275                 280                 285

Thr Gly Asn Pro Thr Lys Met Tyr Glu Val Val Tyr Gln Ile Gly
            290                 295                 300

Thr Glu Thr Arg Ser Asp Phe Tyr Asp Ile Val Leu Val Ala Thr
            305                 310                 315

Pro Leu Asn Arg Lys Met Ser Asn Ile Thr Phe Leu Asn Phe Asp
            320                 325                 330

Pro Pro Ile Glu Glu Phe His Gln Tyr Tyr Gln His Ile Val Thr
            335                 340                 345

Thr Leu Val Lys Gly Glu Leu Asn Thr Ser Ile Phe Ser Ser Arg
            350                 355                 360

Pro Ile Asp Lys Phe Gly Leu Asn Thr Val Leu Thr Thr Asp Asn
            365                 370                 375

Ser Asp Leu Phe Ile Asn Ser Ile Gly Ile Val Pro Ser Val Arg
            380                 385                 390

Glu Lys Glu Asp Pro Glu Pro Ser Thr Asp Gly Thr Tyr Val Trp
            395                 400                 405

Lys Ile Phe Ser Gln Glu Thr Leu Thr Lys Ala Gln Ile Leu Lys
            410                 415                 420

Leu Phe Leu Ser Tyr Asp Tyr Ala Val Lys Lys Pro Trp Leu Ala
            425                 430                 435

Tyr Pro His Tyr Lys Pro Pro Glu Lys Cys Pro Ser Ile Ile Leu
```

```
                440           445           450
His Asp Arg Leu Tyr Tyr Leu Asn Gly Ile Glu Cys Ala Ala Ser
            455           460           465

Ala Met Glu Met Ser Ala Ile Ala Ala His Asn Ala Ala Leu Leu
            470           475           480

Ala Tyr His Arg Trp Asn Gly His Thr Asp Met Ile Asp Gln Asp
            485           490           495

Gly Leu Tyr Glu Lys Leu Lys Thr Glu Leu
            500           505

<210> SEQ ID NO 53
<211> LENGTH: 728
<212> TYPE: DNA
<213> ORGANISM: Homo Sapien

<400> SEQUENCE: 53
catttccaac aagagcactg gccaagtcag cttcttctga gagagtctct            50
agaagacatg atgctacact cagctttggg tctctgcctc ttactcgtca           100
cagtttcttc caaccttgcc attgcaataa aaaaggaaaa gaggcctcct           150
cagacactct caagaggatg gggagatgac atcacttggg tacaaactta           200
tgaagaaggt ctcttttatg ctcaaaaaag taagaagcca ttaatggtta           250
ttcatcacct ggaggattgt caatactctc aagcactaaa gaaagtattt           300
gcccaaaatg aagaaataca agaaatggct cagaataagt tcatcatgct           350
aaaccttatg catgaaacca ctgataagaa tttatcacct gatgggcaat           400
atgtgcctag aatcatgttt gtagacccct ctttaacagt tagagctgac           450
atagctggaa gatactctaa cagattgtac acatatgagc ctcgggattt           500 accccctattg atagaaaaca tgaagaaagc attaagactt attcagtcag           550
agctataaga gatgatggaa aaaagccttc acttcaaaga agtcaaattt           600
catgaagaaa acctctggca cattgacaaa tactaaatgt gcaagtatat           650
agattttgta atattactat ttagttttttt taatgtgttt gcaatagtct           700
tattaaaata aatgtttttt aaatctga                                    728

<210> SEQ ID NO 54
<211> LENGTH: 166
<212> TYPE: PRT
<213> ORGANISM: Homo Sapien

<400> SEQUENCE: 54

Met Met Leu His Ser Ala Leu Gly Leu Cys Leu Leu Leu Val Thr
  1               5                  10                  15

Val Ser Ser Asn Leu Ala Ile Ala Ile Lys Lys Glu Lys Arg Pro
             20                  25                  30

Pro Gln Thr Leu Ser Arg Gly Trp Gly Asp Asp Ile Thr Trp Val
             35                  40                  45

Gln Thr Tyr Glu Glu Gly Leu Phe Tyr Ala Gln Lys Ser Lys Lys
             50                  55                  60

Pro Leu Met Val Ile His His Leu Glu Asp Cys Gln Tyr Ser Gln
             65                  70                  75

Ala Leu Lys Lys Val Phe Ala Gln Asn Glu Glu Ile Gln Glu Met
             80                  85                  90

Ala Gln Asn Lys Phe Ile Met Leu Asn Leu Met His Glu Thr Thr
```

```
                    95                 100                  105

Asp Lys Asn Leu Ser Pro Asp Gly Gln Tyr Val Pro Arg Ile Met
            110                  115                 120

Phe Val Asp Pro Ser Leu Thr Val Arg Ala Asp Ile Ala Gly Arg
            125                  130                 135

Tyr Ser Asn Arg Leu Tyr Thr Tyr Glu Pro Arg Asp Leu Pro Leu
            140                  145                 150

Leu Ile Glu Asn Met Lys Lys Ala Leu Arg Leu Ile Gln Ser Glu
            155                  160                 165

Leu

<210> SEQ ID NO 55
<211> LENGTH: 537
<212> TYPE: DNA
<213> ORGANISM: Homo Sapien

<400> SEQUENCE: 55
taaaacagct acaatattcc agggccagtc acttgccatt tctcataaca        50
gcgtcagaga gaaagaactg actgaaacgt ttgagatgaa gaaagttctc       100
ctcctgatca cagccatctt ggcagtggct gttggtttcc cagtctctca       150
agaccaggaa cgagaaaaaa gaagtatcag tgacagcgat gaattagctt       200
cagggttttt tgtgttccct tacccatatc catttcgccc acttccacca       250
attccatttc caagatttcc atggtttaga cgtaattttc ctattccaat       300
acctgaatct gccctacaa ctcccttcc tagcgaaaag taaacaagaa        350
ggataagtca cgataaacct ggtcacctga aattgaaatt gagccacttc       400
cttgaagaat caaaattcct gttaataaaa gaaaaacaaa tgtaattgaa       450
atagcacaca gcattctcta gtcaatatct ttagtgatct tctttaataa       500
acatgaaagc aaagattttg gtttcttaat ttccaca                     537

<210> SEQ ID NO 56
<211> LENGTH: 85
<212> TYPE: PRT
<213> ORGANISM: Homo Sapien

<400> SEQUENCE: 56

Met Lys Lys Val Leu Leu Ile Thr Ala Ile Leu Ala Val Ala
  1               5                  10                  15

Val Gly Phe Pro Val Ser Gln Asp Gln Glu Arg Glu Lys Arg Ser
                20                  25                  30

Ile Ser Asp Ser Asp Glu Leu Ala Ser Gly Phe Phe Val Phe Pro
            35                  40                  45

Tyr Pro Tyr Pro Phe Arg Pro Leu Pro Ile Pro Phe Pro Arg
            50                  55                  60

Phe Pro Trp Phe Arg Arg Asn Phe Pro Ile Pro Glu Ser
            65                  70                  75

Ala Pro Thr Thr Pro Leu Pro Ser Glu Lys
            80                  85

<210> SEQ ID NO 57
<211> LENGTH: 2997
<212> TYPE: DNA
<213> ORGANISM: Homo Sapien

<400> SEQUENCE: 57
```

-continued

```
cggacgcgtg ggcgggcgcg ccgggaggga ccggcggcgg catgggccgg      50
gggccctggg atgcgggccc gtctcgccgc ctgctgccgc tgttgctgct     100
gctcggcctg gcccgcggcg ccgcgggagc gccgggcccc gacggtttag     150
acgtctgtgc cacttgccat gaacatgcca catgccagca agagaagggg     200
aagaagatct gtatttgcaa ctatggattt gtagggaacg ggaggactca     250
gtgtgttgat aaaaatgagt gccagtttgg agccactctt gtctgtggga     300
accacacatc ttgccacaac accccgggg gcttctattg catttgcctg      350
gaaggatatc gagccacaaa caacaacaag acattcattc ccaacgatgg     400
cacctttgt acagacatag atgagtgtga agtttctggc ctgtgcaggc      450
atggagggcg atgcgtgaac actcatggga gctttgaatg ctactgtatg     500
gatggatact tgccaaggaa tggacctgaa ccttcccacc cgaccaccga     550
tgccacatca tgcacagaaa tagactgtgg taccctcct gaggttccag      600
atggctatat cataggaaat tatacgtcta gtctgggcag ccaggttcgt     650
tatgcttgca gagaaggatt cttcagtgtt ccagaagata cagtttcaag     700
ctgcacaggc ctgggcacat gggagtcccc aaaattacat tgccaagaga     750
tcaactgtgg caaccctcca gaaatgcggc acgccatctt ggtaggaaat     800
cacagctcca ggctgggcgg tgtggctcgc tatgtctgtc aagagggctt     850
tgagagccct ggaggaaaga tcacttctgt ttgcacagaa aaaggcacct     900
ggagagaaag tactttaaca tgcacagaaa ttctgacaaa gattaatgat     950
gtatcactgt ttaatgatac ctgtgtgaga tggcaaataa actcaagaag    1000
aataaacccc aagatctcat atgtgatatc cataaaagga caacggttgg    1050
accctatgga atcagttcgt gaggagacag tcaacttgac cacagacagc    1100
aggaccccag aagtgtgcct agccctgtac ccaggcacca actacaccgt    1150
gaacatctcc acagcaccct ccaggcgctc gatgccagcc gtcatcggtt    1200
tccagacagc tgaagttgat ctcttagaag atgatggaag tttcaatatt    1250
tcaatattta tgaaacttg tttgaaattg aacaggcgtt ctaggaaagt     1300
tggatcagaa cacatgtacc aatttaccgt tctgggtcag aggtggtatc    1350
tggctaactt ttctcatgca acatcgttta acttcacaac gagggaacaa    1400
gtgcctgtag tgtgtttgga tctgtaccct acgactgatt atacggtgaa    1450
tgtgaccctg ctgagatctc ctaagcggca ctcagtgcaa ataacaatag    1500
caactccccc agcagtaaaa cagaccatca gtaacatttc aggatttaat    1550
gaaacctgct tgagatggag aagcatcaag acagctgata tggaggagat    1600
gtatttattc cacatttggg gccagagatg gtatcagaag gaatttgccc    1650
aggaaatgac ctttaatatc agtagcagca gccgagatcc cgaggtgtgc    1700
ttggacctac gtccgggtac caactacaat gtcagtctcc gggctctgtc    1750
ttcggaactt cctgtggtca tctccctgac aacccagata acagagcctc    1800
ccctcccgga agtagaattt tttacggtgc acagaggacc tctaccacgc    1850
ctcagactga ggaaagccaa ggagaaaaat ggaccaatca gttcatatca    1900
ggtgttagtg cttcccctgg ccctccaaag cacatttcct tgtgattctg    1950
```

-continued

| | |
|---|---|
| aaggcgcttc ctccttcttt agcaacgcct ctgatgctga tggatacgtg | 2000 |
| gctgcagaac tactggccaa agatgttcca gatgatgcca tggagatacc | 2050 |
| tataggagac aggctgtact atggggaata ttataatgca cccttgaaaa | 2100 |
| gagggagtga ttactgcatt atattacgaa tcacaagtga atggaataag | 2150 |
| gtgagaagac actcctgtgc agtttgggct caggtgaaag attcgtcact | 2200 |
| catgctgctg cagatggcgg tgttggact gggttccctg ctgttgtga | 2250 |
| tcattctcac attcctctcc ttctcagcgg tgtgatggca gatggacact | 2300 |
| gagtggggag gatgcactgc tgctgggcag gtgttctggc agcttctcag | 2350 |
| gtgcccgcac agaggctccg tgtgacttcc gtccagggag catgtgggcc | 2400 |
| tgcaactttc tccattccca gctgggcccc attcctggat ttaagatggt | 2450 |
| ggctatccct gaggagtcac cataaggaga aaactcagga attctgagtc | 2500 |
| ttccctgcta caggaccagt tctgtgcaat gaacttgaga ctcctgatgt | 2550 |
| acactgtgat attgaccgaa ggctacatac agatctgtga atcttggctg | 2600 |
| ggacttcctc tgagtgatgc ctgagggtca gctcctctag acattgactg | 2650 |
| caagagaatc tctgcaacct cctatataaa agcatttctg ttaattcatt | 2700 |
| cagaatccat tctttacaat atgcagtgag atgggcttaa gtttgggcta | 2750 |
| gagtttgact ttatgaagga ggtcattgaa aaagagaaca gtgacgtagg | 2800 |
| caaatgtttc aagcacttta gaaacagtac ttttcctata attagttgat | 2850 |
| atactaatga gaaatatac tagcctggcc atgccaataa gtttcctgct | 2900 |
| gtgtctgtta ggcagcattg ctttgatgca atttctattg tcctatatat | 2950 |
| tcaaaagtaa tgtctacatt ccagtaaaaa tatcccgtaa ttaaaaa | 2997 |

<210> SEQ ID NO 58
<211> LENGTH: 747
<212> TYPE: PRT
<213> ORGANISM: Homo Sapien

<400> SEQUENCE: 58

```
Met Gly Arg Gly Pro Trp Asp Ala Gly Pro Ser Arg Arg Leu Leu
 1               5                  10                  15

Pro Leu Leu Leu Leu Gly Leu Ala Arg Gly Ala Ala Gly Ala
                20                  25                  30

Pro Gly Pro Asp Gly Leu Asp Val Cys Ala Thr Cys His Glu His
                35                  40                  45

Ala Thr Cys Gln Gln Arg Glu Gly Lys Lys Ile Cys Ile Cys Asn
                50                  55                  60

Tyr Gly Phe Val Gly Asn Gly Arg Thr Gln Cys Val Asp Lys Asn
 65                  70                  75

Glu Cys Gln Phe Gly Ala Thr Leu Val Cys Gly Asn His Thr Ser
                80                  85                  90

Cys His Asn Thr Pro Gly Gly Phe Tyr Cys Ile Cys Leu Glu Gly
                95                 100                 105

Tyr Arg Ala Thr Asn Asn Asn Lys Thr Phe Ile Pro Asn Asp Gly
                110                115                 120

Thr Phe Cys Thr Asp Ile Asp Glu Cys Glu Val Ser Gly Leu Cys
                125                130                 135

Arg His Gly Gly Arg Cys Val Asn Thr His Gly Ser Phe Glu Cys
                140                145                 150
```

-continued

```
Tyr Cys Met Asp Gly Tyr Leu Pro Arg Asn Gly Pro Glu Pro Phe
            155                 160                 165
His Pro Thr Thr Asp Ala Thr Ser Cys Thr Glu Ile Asp Cys Gly
            170                 175                 180
Thr Pro Pro Glu Val Pro Asp Gly Tyr Ile Ile Gly Asn Tyr Thr
            185                 190                 195
Ser Ser Leu Gly Ser Gln Val Arg Tyr Ala Cys Arg Glu Gly Phe
            200                 205                 210
Phe Ser Val Pro Glu Asp Thr Val Ser Cys Thr Gly Leu Gly
            215                 220                 225
Thr Trp Glu Ser Pro Lys Leu His Cys Gln Glu Ile Asn Cys Gly
            230                 235                 240
Asn Pro Pro Glu Met Arg His Ala Ile Leu Val Gly Asn His Ser
            245                 250                 255
Ser Arg Leu Gly Gly Val Ala Arg Tyr Val Cys Gln Glu Gly Phe
            260                 265                 270
Glu Ser Pro Gly Gly Lys Ile Thr Ser Val Cys Thr Glu Lys Gly
            275                 280                 285
Thr Trp Arg Glu Ser Thr Leu Thr Cys Thr Glu Ile Leu Thr Lys
            290                 295                 300
Ile Asn Asp Val Ser Leu Phe Asn Asp Thr Cys Val Arg Trp Gln
            305                 310                 315
Ile Asn Ser Arg Arg Ile Asn Pro Lys Ile Ser Tyr Val Ile Ser
            320                 325                 330
Ile Lys Gly Gln Arg Leu Asp Pro Met Glu Ser Val Arg Glu Glu
            335                 340                 345
Thr Val Asn Leu Thr Thr Asp Ser Arg Thr Pro Glu Val Cys Leu
            350                 355                 360
Ala Leu Tyr Pro Gly Thr Asn Tyr Thr Val Asn Ile Ser Thr Ala
            365                 370                 375
Pro Pro Arg Arg Ser Met Pro Ala Val Ile Gly Phe Gln Thr Ala
            380                 385                 390
Glu Val Asp Leu Leu Glu Asp Asp Gly Ser Phe Asn Ile Ser Ile
            395                 400                 405
Phe Asn Glu Thr Cys Leu Lys Leu Asn Arg Arg Ser Arg Lys Val
            410                 415                 420
Gly Ser Glu His Met Tyr Gln Phe Thr Val Leu Gly Gln Arg Trp
            425                 430                 435
Tyr Leu Ala Asn Phe Ser His Ala Thr Ser Phe Asn Phe Thr Thr
            440                 445                 450
Arg Glu Gln Val Pro Val Cys Leu Asp Leu Tyr Pro Thr Thr
            455                 460                 465
Asp Tyr Thr Val Asn Val Thr Leu Leu Arg Ser Pro Lys Arg His
            470                 475                 480
Ser Val Gln Ile Thr Ile Ala Thr Pro Pro Ala Val Lys Gln Thr
            485                 490                 495
Ile Ser Asn Ile Ser Gly Phe Asn Glu Thr Cys Leu Arg Trp Arg
            500                 505                 510
Ser Ile Lys Thr Ala Asp Met Glu Glu Met Tyr Leu Phe His Ile
            515                 520                 525
Trp Gly Gln Arg Trp Tyr Gln Lys Glu Phe Ala Gln Glu Met Thr
            530                 535                 540
```

-continued

```
Phe Asn Ile Ser Ser Ser Arg Asp Pro Glu Val Cys Leu Asp
            545                 550                 555

Leu Arg Pro Gly Thr Asn Tyr Asn Val Ser Leu Arg Ala Leu Ser
            560                 565                 570

Ser Glu Leu Pro Val Val Ile Ser Leu Thr Thr Gln Ile Thr Glu
            575                 580                 585

Pro Pro Leu Pro Glu Val Glu Phe Phe Thr Val His Arg Gly Pro
            590                 595                 600

Leu Pro Arg Leu Arg Leu Arg Lys Ala Lys Glu Lys Asn Gly Pro
            605                 610                 615

Ile Ser Ser Tyr Gln Val Leu Val Leu Pro Leu Ala Leu Gln Ser
            620                 625                 630

Thr Phe Ser Cys Asp Ser Glu Gly Ala Ser Ser Phe Phe Ser Asn
            635                 640                 645

Ala Ser Asp Ala Asp Gly Tyr Val Ala Ala Glu Leu Leu Ala Lys
            650                 655                 660

Asp Val Pro Asp Ala Met Glu Ile Pro Ile Gly Asp Arg Leu
            665                 670                 675

Tyr Tyr Gly Glu Tyr Tyr Asn Ala Pro Leu Lys Arg Gly Ser Asp
            680                 685                 690

Tyr Cys Ile Ile Leu Arg Ile Thr Ser Glu Trp Asn Lys Val Arg
            695                 700                 705

Arg His Ser Cys Ala Val Trp Ala Gln Val Lys Asp Ser Ser Leu
            710                 715                 720

Met Leu Leu Gln Met Ala Gly Val Gly Leu Gly Ser Leu Ala Val
            725                 730                 735

Val Ile Ile Leu Thr Phe Leu Ser Phe Ser Ala Val
            740                 745

<210> SEQ ID NO 59
<211> LENGTH: 22
<212> TYPE: DNA
<213> ORGANISM: Artificial Sequence
<220> FEATURE:
<223> OTHER INFORMATION: Synthetic oligonucleotide probe

<400> SEQUENCE: 59
ccacttgcca tgaacatgcc ac                                             22

<210> SEQ ID NO 60
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 60
cctcttgaca gacatagcga gccac                                          25

<210> SEQ ID NO 61
<211> LENGTH: 43
<212> TYPE: DNA
<213> ORGANISM: Artificial Sequence
<220> FEATURE:
<223> OTHER INFORMATION: Synthetic oligonucleotide probe

<400> SEQUENCE: 61
cactcttgtc tgtgggaacc acacatcttg ccacaactgt ggc                      43
```

<210> SEQ ID NO 62
<211> LENGTH: 2015
<212> TYPE: DNA
<213> ORGANISM: Homo Sapien

<400> SEQUENCE: 62

| | | | | | |
|---|---|---|---|---|---|
| ggaaaaggta | cccgcgagag | acagccagca | gttctgtgga | gcagcggtgg | 50 |
| ccggctagga | tgggctgtct | ctgggtctg | gctctgcccc | ttttcttctt | 100 |
| ctgctgggag | gttggggtct | ctgggagctc | tgcaggcccc | agcacccgca | 150 |
| gagcagacac | tgcgatgaca | acggacgaca | cagaagtgcc | cgctatgact | 200 |
| ctagcaccgg | gccacgccgc | tctggaaact | caaacgctga | gcgctgagac | 250 |
| ctcttctagg | gcctcaaccc | cagccggccc | cattccagaa | gcagagacca | 300 |
| ggggagccaa | gagaatttcc | cctgcaagag | agaccaggag | tttcacaaaa | 350 |
| acatctccca | acttcatggt | gctgatcgcc | acctccgtgg | agacatcagc | 400 |
| cgccagtggc | agccccgagg | gagctggaat | gaccacagtt | cagaccatca | 450 |
| caggcagtga | tcccgaggaa | gccatctttg | cacccctttg | caccgatgac | 500 |
| agctctgaag | aggcaaagac | actcacaatg | gacatattga | cattggctca | 550 |
| cacctccaca | gaagctaagg | gcctgtcctc | agagagcagt | gcctcttccg | 600 |
| acggccccca | tccagtcatc | accccgtcac | gggcctcaga | gagcagcgcc | 650 |
| tcttccgacg | gccccatcc | agtcatcacc | ccgtcacggg | cctcagagag | 700 |
| cagcgcctct | tccgacggcc | cccatccagt | catcaccccg | tcatggtccc | 750 |
| cgggatctga | tgtcactctc | ctcgctgaag | ccctggtgac | tgtcacaaac | 800 |
| atcgaggtta | ttaattgcag | catcacagaa | atagaaacaa | caacttccag | 850 |
| catccctggg | gcctcagaca | tagatctcat | ccccacggaa | ggggtgaagg | 900 |
| cctcgtccac | ctccgatcca | ccagctctgc | ctgactccac | tgaagcaaaa | 950 |
| ccacacatca | ctgaggtcac | agcctctgcc | gagaccctgt | ccacagccgg | 1000 |
| caccacagag | tcagctgcac | ctcatgccac | ggttgggacc | ccactcccca | 1050 |
| ctaacagcgc | cacagaaaga | gaagtgacag | cacccggggc | cacgaccctc | 1100 |
| agtggagctc | tggtcacagt | tagcaggaat | cccctggaag | aaacctcagc | 1150 |
| cctctctgtt | gagacaccaa | gttacgtcaa | agtctcagga | gcagctccgg | 1200 |
| tctccataga | ggctgggtca | gcagtgggca | aaacaacttc | ctttgctggg | 1250 |
| agctctgctt | cctcctacag | cccctcggaa | gccgccctca | agaacttcac | 1300 |
| cccttcagag | acaccgacca | tggacatcgc | aaccaagggg | cccttcccca | 1350 |
| ccagcaggga | ccctcttcct | tctgtccctc | cgactacaac | caacagcagc | 1400 |
| cgagggacga | acagcaccctt | agccaagatc | acaacctcag | cgaagaccac | 1450 |
| gatgaagccc | caacagccac | gcccacgact | gcccggacga | ggccgaccac | 1500 |
| agacgtgagt | gcaggtgaaa | atggaggttt | cctcctcctg | cggctgagtg | 1550 |
| tggcttcccc | ggaagaccttc | actgacccca | gagtggcaga | aaggctgatg | 1600 |
| cagcagctcc | accgggaact | ccacgcccac | gcgcctcact | tccaggtctc | 1650 |
| cttactgcgt | gtcaggagag | gctaacggac | atcagctgca | gccaggcatg | 1700 |
| tcccgtatgc | caaaagaggg | tgctgccctt | agcctgggcc | cccaccgaca | 1750 |
| gactgcagct | gcgttactgt | gctgagaggt | acccagaagg | ttcccatgaa | 1800 |

```
gggcagcatg tccaagcccc taacccaga tgtggcaaca ggaccctcgc              1850
tcacatccac cggagtgtat gtatggggag gggcttcacc tgttcccaga              1900
ggtgtccttg gactcacctt ggcacatgtt ctgtgtttca gtaaagagag              1950
acctgatcac ccatctgtgt gcttccatcc tgcattaaaa ttcactcagt              2000
gtggcccaaa aaaaa                                                     2015
```

<210> SEQ ID NO 63
<211> LENGTH: 482
<212> TYPE: PRT
<213> ORGANISM: Homo Sapien

<400> SEQUENCE: 63

```
Met Gly Cys Leu Trp Gly Leu Ala Leu Pro Leu Phe Phe Phe Cys
 1               5                  10                  15

Trp Glu Val Gly Val Ser Gly Ser Ser Ala Gly Pro Ser Thr Arg
                20                  25                  30

Arg Ala Asp Thr Ala Met Thr Thr Asp Asp Thr Glu Val Pro Ala
                35                  40                  45

Met Thr Leu Ala Pro Gly His Ala Ala Leu Glu Thr Gln Thr Leu
                50                  55                  60

Ser Ala Glu Thr Ser Arg Ala Ser Thr Pro Ala Gly Pro Ile
                65                  70                  75

Pro Glu Ala Glu Thr Arg Gly Ala Lys Arg Ile Ser Pro Ala Arg
                80                  85                  90

Glu Thr Arg Ser Phe Thr Lys Thr Ser Pro Asn Phe Met Val Leu
                95                 100                 105

Ile Ala Thr Ser Val Glu Thr Ser Ala Ala Ser Gly Ser Pro Glu
               110                 115                 120

Gly Ala Gly Met Thr Thr Val Gln Thr Ile Thr Gly Ser Asp Pro
               125                 130                 135

Glu Glu Ala Ile Phe Asp Thr Leu Cys Thr Asp Ser Ser Glu
               140                 145                 150

Glu Ala Lys Thr Leu Thr Met Asp Ile Leu Thr Leu Ala His Thr
               155                 160                 165

Ser Thr Glu Ala Lys Gly Leu Ser Ser Glu Ser Ser Ala Ser Ser
               170                 175                 180

Asp Gly Pro His Pro Val Ile Thr Pro Ser Arg Ala Ser Glu Ser
               185                 190                 195

Ser Ala Ser Ser Asp Gly Pro His Pro Val Ile Thr Pro Ser Arg
               200                 205                 210

Ala Ser Glu Ser Ser Ala Ser Ser Asp Gly Pro His Pro Val Ile
               215                 220                 225

Thr Pro Ser Trp Ser Pro Gly Ser Asp Val Thr Leu Leu Ala Glu
               230                 235                 240

Ala Leu Val Thr Val Thr Asn Ile Glu Val Ile Asn Cys Ser Ile
               245                 250                 255

Thr Glu Ile Glu Thr Thr Thr Ser Ser Ile Pro Gly Ala Ser Asp
               260                 265                 270

Ile Asp Leu Ile Pro Thr Glu Gly Val Lys Ala Ser Ser Thr Ser
               275                 280                 285

Asp Pro Pro Ala Leu Pro Asp Ser Thr Glu Ala Lys Pro His Ile
               290                 295                 300

Thr Glu Val Thr Ala Ser Ala Glu Thr Leu Ser Thr Ala Gly Thr
```

-continued

```
                305                 310                 315
Thr Glu Ser Ala Ala Pro His Ala Thr Val Gly Thr Pro Leu Pro
            320                 325                 330
Thr Asn Ser Ala Thr Glu Arg Glu Val Thr Ala Pro Gly Ala Thr
            335                 340                 345
Thr Leu Ser Gly Ala Leu Val Thr Val Ser Arg Asn Pro Leu Glu
            350                 355                 360
Glu Thr Ser Ala Leu Ser Val Glu Thr Pro Ser Tyr Val Lys Val
            365                 370                 375
Ser Gly Ala Ala Pro Val Ser Ile Glu Ala Gly Ser Ala Val Gly
            380                 385                 390
Lys Thr Thr Ser Phe Ala Gly Ser Ser Ala Ser Ser Tyr Ser Pro
            395                 400                 405
Ser Glu Ala Ala Leu Lys Asn Phe Thr Pro Ser Glu Thr Pro Thr
            410                 415                 420
Met Asp Ile Ala Thr Lys Gly Pro Phe Pro Thr Ser Arg Asp Pro
            425                 430                 435
Leu Pro Ser Val Pro Pro Thr Thr Thr Asn Ser Ser Arg Gly Thr
            440                 445                 450
Asn Ser Thr Leu Ala Lys Ile Thr Thr Ser Ala Lys Thr Thr Met
            455                 460                 465
Lys Pro Gln Gln Pro Arg Pro Arg Leu Pro Gly Arg Gly Arg Pro
            470                 475                 480
Gln Thr
```

<210> SEQ ID NO 64
<211> LENGTH: 1252
<212> TYPE: DNA
<213> ORGANISM: Homo Sapien

<400> SEQUENCE: 64

| | | |
|---|---|---|
| gcctctgaat tgttgggcag tctggcagtg gagctctccc cggtctgaca | 50 |
| gccactccag aggccatgct tcgtttcttg ccagatttgg ctttcagctt | 100 |
| cctgttaatt ctggctttgg gccaggcagt ccaatttcaa gaatatgtct | 150 |
| ttctccaatt tctgggctta gataaggcgc cttcacccca gaagttccaa | 200 |
| cctgtgcctt atatcttgaa gaaaattttc caggatcgcg aggcagcagc | 250 |
| gaccactggg gtctcccgag acttatgcta cgtaaaggag ctgggcgtcc | 300 |
| gcgggaatgt acttcgcttt ctcccagacc aaggtttctt tctttaccca | 350 |
| aagaaaattt cccaagcttc ctcctgcctg cagaagctcc tctactttaa | 400 |
| cctgtctgcc atcaaagaaa gggaacagtt gacattggcc cagctgggcc | 450 |
| tggacttggg gcccaattct tactataacc tgggaccaga gctggaactg | 500 |
| gctctgttcc tggttcagga gcctcatgtg tggggccaga ccaccccctaa | 550 |
| gccaggtaaa atgtttgtgt tgcggtcagt cccatggcca caaggtgctg | 600 |
| ttcacttcaa cctgctggat gtagctaagg attggaatga caaccccccgg | 650 |
| aaaaatttcg ggttattcct ggagatactg gtcaaagaag atagagactc | 700 |
| aggggtgaat tttcagcctg aagacacctg tgccagacta agatgctccc | 750 |
| ttcatgcttc cctgctggtg gtgactctca accctgatca gtgccaccct | 800 |
| tctcggaaaa ggagagcagc catccctgtc cccaagcttt cttgtaagaa | 850 |

```
cctctgccac cgtcaccagc tattcattaa cttccgggac ctgggttggc        900
acaagtggat cattgccccc aagggggttca tggcaaatta ctgccatgga       950
gagtgtccct tctcactgac catctctctc aacagctcca attatgcttt       1000
catgcaagcc ctgatgcatg ccgttgaccc agagatcccc caggctgtgt       1050
gtatccccac caagctgtct cccatttcca tgctctacca ggacaataat       1100
gacaatgtca ttctacgaca ttatgaagac atggtagtcg atgaatgtgg       1150
gtgtgggtag gatgtcagaa atgggaatag aaggagtgtt cttagggtaa       1200
atcttttaat aaaactacct atctggttta tgaccactta gatcgaaatg       1250
tc                                                          1252
```

<210> SEQ ID NO 65
<211> LENGTH: 364
<212> TYPE: PRT
<213> ORGANISM: Homo Sapien

<400> SEQUENCE: 65

```
Met Leu Arg Phe Leu Pro Asp Leu Ala Phe Ser Phe Leu Leu Ile
 1               5                  10                  15

Leu Ala Leu Gly Gln Ala Val Gln Phe Gln Glu Tyr Val Phe Leu
                20                  25                  30

Gln Phe Leu Gly Leu Asp Lys Ala Pro Ser Pro Gln Lys Phe Gln
                35                  40                  45

Pro Val Pro Tyr Ile Leu Lys Lys Ile Phe Gln Asp Arg Glu Ala
                50                  55                  60

Ala Ala Thr Thr Gly Val Ser Arg Asp Leu Cys Tyr Val Lys Glu
                65                  70                  75

Leu Gly Val Arg Gly Asn Val Leu Arg Phe Leu Pro Asp Gln Gly
                80                  85                  90

Phe Phe Leu Tyr Pro Lys Lys Ile Ser Gln Ala Ser Ser Cys Leu
                95                 100                 105

Gln Lys Leu Leu Tyr Phe Asn Leu Ser Ala Ile Lys Glu Arg Glu
               110                 115                 120

Gln Leu Thr Leu Ala Gln Leu Gly Leu Asp Leu Gly Pro Asn Ser
               125                 130                 135

Tyr Tyr Asn Leu Gly Pro Glu Leu Glu Leu Ala Leu Phe Leu Val
               140                 145                 150

Gln Glu Pro His Val Trp Gly Gln Thr Thr Pro Lys Pro Gly Lys
               155                 160                 165

Met Phe Val Leu Arg Ser Val Pro Trp Pro Gln Gly Ala Val His
               170                 175                 180

Phe Asn Leu Leu Asp Val Ala Lys Asp Trp Asn Asp Asn Pro Arg
               185                 190                 195

Lys Asn Phe Gly Leu Phe Leu Glu Ile Leu Val Lys Glu Asp Arg
               200                 205                 210

Asp Ser Gly Val Asn Phe Gln Pro Glu Asp Thr Cys Ala Arg Leu
               215                 220                 225

Arg Cys Ser Leu His Ala Ser Leu Leu Val Thr Leu Asn Pro
               230                 235                 240

Asp Gln Cys His Pro Ser Arg Lys Arg Arg Ala Ala Ile Pro Val
               245                 250                 255

Pro Lys Leu Ser Cys Lys Asn Leu Cys His Arg His Gln Leu Phe
               260                 265                 270
```

```
Ile Asn Phe Arg Asp Leu Gly Trp His Lys Trp Ile Ile Ala Pro
            275                 280                 285

Lys Gly Phe Met Ala Asn Tyr Cys His Gly Glu Cys Pro Phe Ser
            290                 295                 300

Leu Thr Ile Ser Leu Asn Ser Ser Asn Tyr Ala Phe Met Gln Ala
            305                 310                 315

Leu Met His Ala Val Asp Pro Glu Ile Pro Gln Ala Val Cys Ile
            320                 325                 330

Pro Thr Lys Leu Ser Pro Ile Ser Met Leu Tyr Gln Asp Asn Asn
            335                 340                 345

Asp Asn Val Ile Leu Arg His Tyr Glu Asp Met Val Val Asp Glu
            350                 355                 360

Cys Gly Cys Gly

<210> SEQ ID NO 66
<211> LENGTH: 20
<212> TYPE: DNA
<213> ORGANISM: Artificial Sequence
<220> FEATURE:
<223> OTHER INFORMATION: Synthetic oligonucleotide probe

<400> SEQUENCE: 66
gtctgacagc cactccagag                                              20

<210> SEQ ID NO 67
<211> LENGTH: 47
<212> TYPE: DNA
<213> ORGANISM: Artificial Sequence
<220> FEATURE:
<223> OTHER INFORMATION: Synthetic oligonucleotide probe

<400> SEQUENCE: 67
tctccaattt ctgggcttag ataaggcgcc ttcaccccag aagttcc                 47

<210> SEQ ID NO 68
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 68
gtcccaggtt atagtaagaa ttgg                                         24

<210> SEQ ID NO 69
<211> LENGTH: 20
<212> TYPE: DNA
<213> ORGANISM: Artificial Sequence
<220> FEATURE:
<223> OTHER INFORMATION: Synthetic oligonucleotide probe

<400> SEQUENCE: 69
gtgttgcggt cagtcccatg                                              20

<210> SEQ ID NO 70
<211> LENGTH: 20
<212> TYPE: DNA
<213> ORGANISM: Artificial Sequence
<220> FEATURE:
<223> OTHER INFORMATION: Synthetic oligonucleotide probe

<400> SEQUENCE: 70
```

| | |
|---|---|
| gctgtctccc atttccatgc | 20 |

<210> SEQ ID NO 71
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 71

| | |
|---|---|
| cgactaccat gtcttcataa tgtc | 24 |

<210> SEQ ID NO 72
<211> LENGTH: 2849
<212> TYPE: DNA
<213> ORGANISM: Homo Sapien

<400> SEQUENCE: 72

| | |
|---|---|
| cactttctcc ctctcttcct ttactttcga gaaaccgcgc ttccgcttct | 50 |
| ggtcgcagag acctcggaga ccgcgccggg gagacggagg tgctgtgggt | 100 |
| gggggggacc tgtggctgct cgtaccgccc cccaccctcc tcttctgcac | 150 |
| tgccgtcctc cggaagacct tttccctgc tctgtttcct tcaccgagtc | 200 |
| tgtgcatcgc cccggacctg gccgggagga ggcttggccg gcgggagatg | 250 |
| ctctagggc ggcgcgggag gagcggccgg cgggacggag ggcccggcag | 300 |
| gaagatgggc tcccgtggac agggactctt gctggcgtac tgcctgctcc | 350 |
| ttgcctttgc ctctggcctg gtcctgagtc gtgtgcccca tgtccagggg | 400 |
| gaacagcagg agtgggaggg gactgaggag ctgccgtcgc ctccggacca | 450 |
| tgccgagagg gctgaagaac aacatgaaaa atacaggccc agtcaggacc | 500 |
| aggggctccc tgcttcccgg tgcttgcgct gctgtgaccc cggtacctcc | 550 |
| atgtacccgg cgaccgccgt gccccagatc aacatcacta tcttgaaagg | 600 |
| ggagaagggt gaccgcggag atcgaggcct ccaagggaaa tatggcaaaa | 650 |
| caggctcagc aggggccagg ggccacactg gacccaaagg gcagaagggc | 700 |
| tccatggggg cccctgggga gcggtgcaag agccactacg ccgccttttc | 750 |
| ggtgggccgg aagaagccca tgcacagcaa ccactactac cagacggtga | 800 |
| tcttcgacac ggagttcgtg aacctctacg accacttcaa catgttcacc | 850 |
| ggcaagttct actgctacgt gcccggcctc tacttcttca gcctcaacgt | 900 |
| gcacacctgg aaccagaagg agacctacct gcacatcatg aagaacgagg | 950 |
| aggaggtggt gatcttgttc gcgcaggtgg gcgaccgcag catcatgcaa | 1000 |
| agccagagcc tgatgctgga gctgcgagag caggaccagg tgtgggtacg | 1050 |
| cctctacaag ggcgaacgtg agaacgccat cttcagcgag gagctggaca | 1100 |
| cctacatcac cttcagtggc tacctggtca agcacgccac cgagccctag | 1150 |
| ctggccggcc acctcctttc ctctcgccac cttccacccc tgcgctgtgc | 1200 |
| tgacccccacc gcctcttccc cgatccctgg actccgactc cctggctttg | 1250 |
| gcattcagtg agacgccctg cacacacaga aagccaaagc gatcggtgct | 1300 |
| cccagatccc gcagcctctg gagagagctg acggcagatg aaatcaccag | 1350 |
| ggcggggcac ccgcgagaac cctctgggac cttccgcggc cctctctgca | 1400 |
| cacatcctca agtgaccccg cacggcgaga cgcgggtggc ggcagggcgt | 1450 |

-continued

```
cccagggtgc ggcaccgcgg ctccagtcct tggaaataat taggcaaatt      1500
ctaaaggtct caaaaggagc aaagtaaacc gtggaggaca agaaaaggg        1550 ttgttatttt tgtctttcca gccagcctgc tggctcccaa gagagaggcc      1600
ttttcagttg agactctgct taagagaaga tccaaagtta aagctctggg      1650
gtcaggggag gggccggggg caggaaacta cctctggctt aattctttta      1700
agccacgtag gaactttctt gagggatagg tggaccctga catccctgtg      1750
gccttgccca agggctctgc tggtctttct gagtcacagc tgcgaggtga      1800
tgggggctgg ggccccaggc gtcagcctcc cagagggaca gctgagcccc      1850
ctgccttggc tccaggttgg tagaagcagc cgaagggctc ctgacagtgg      1900
ccagggaccc ctgggtcccc caggcctgca gatgtttcta tgaggggcag      1950
agctccttgg tacatccatg tgtggctctg ctccacccct gtgccacccc      2000
agagccctgg ggggtggtct ccatgcctgc caccctggca tcggctttct      2050
gtgccgcctc ccacacaaat cagccccaga aggccccggg gccttggctt      2100
ctgtttttta taaaacacct caagcagcac tgcagtctcc catctcctcg      2150
tgggctaagc atcaccgctt ccacgtgtgt tgtgttggtt ggcagcaagg      2200
ctgatccaga ccccttctgc ccccactgcc ctcatccagg cctctgacca      2250
gtagcctgag agggcttttt tctaggcttc agagcagggg agagctggaa      2300
ggggctagaa agctcccgct tgtctgtttc tcaggctcct gtgagcctca      2350
gtcctgagac cagagtcaag aggaagtaca cgtcccaatc acccgtgtca      2400
ggattcactc tcaggagctg ggtggcagga gaggcaatag ccctgtggc       2450 aattgcagga ccagctggag cagggttgcg gtgtctccac ggtgctctcg      2500
ccctgcccat ggccacccca gactctgatc tccaggaacc ccatagcccc      2550
tctccacctc accccatgtt gatgcccagg gtcactcttg ctacccgctg      2600 ggccccaaa ccccgctgc ctctcttcct tcccccatc cccacctgg          2650 ttttgactaa tcctgcttcc ctctctgggc ctggctgccg ggatctgggg      2700
tccctaagtc cctctctta aagaacttct gcgggtcaga ctctgaagcc       2750
gagttgctgt gggcgtgccc ggaagcagag cgccacactc gctgcttaag      2800
ctcccccagc tctttccaga aaacattaaa ctcagaattg tgttttcaa       2849
```

<210> SEQ ID NO 73
<211> LENGTH: 281
<212> TYPE: PRT
<213> ORGANISM: Homo Sapien

<400> SEQUENCE: 73

```
Met Gly Ser Arg Gly Gln Gly Leu Leu Leu Ala Tyr Cys Leu Leu
 1               5                  10                  15

Leu Ala Phe Ala Ser Gly Leu Val Leu Ser Arg Val Pro His Val
                20                  25                  30

Gln Gly Glu Gln Gln Glu Trp Glu Gly Thr Glu Glu Leu Pro Ser
                35                  40                  45

Pro Pro Asp His Ala Glu Arg Ala Glu Glu Gln His Glu Lys Tyr
                50                  55                  60

Arg Pro Ser Gln Asp Gln Gly Leu Pro Ala Ser Arg Cys Leu Arg
                65                  70                  75
```

-continued

```
Cys Cys Asp Pro Gly Thr Ser Met Tyr Pro Ala Thr Ala Val Pro
            80                  85                  90

Gln Ile Asn Ile Thr Ile Leu Lys Gly Glu Lys Gly Asp Arg Gly
            95                 100                 105

Asp Arg Gly Leu Gln Gly Lys Tyr Gly Lys Thr Gly Ser Ala Gly
           110                 115                 120

Ala Arg Gly His Thr Gly Pro Lys Gly Gln Lys Gly Ser Met Gly
           125                 130                 135

Ala Pro Gly Glu Arg Cys Lys Ser His Tyr Ala Ala Phe Ser Val
           140                 145                 150

Gly Arg Lys Lys Pro Met His Ser Asn His Tyr Tyr Gln Thr Val
           155                 160                 165

Ile Phe Asp Thr Glu Phe Val Asn Leu Tyr Asp His Phe Asn Met
           170                 175                 180

Phe Thr Gly Lys Phe Tyr Cys Tyr Val Pro Gly Leu Tyr Phe Phe
           185                 190                 195

Ser Leu Asn Val His Thr Trp Asn Gln Lys Glu Thr Tyr Leu His
           200                 205                 210

Ile Met Lys Asn Glu Glu Val Val Ile Leu Phe Ala Gln Val
           215                 220                 225

Gly Asp Arg Ser Ile Met Gln Ser Gln Ser Leu Met Leu Glu Leu
           230                 235                 240

Arg Glu Gln Asp Gln Val Trp Val Arg Leu Tyr Lys Gly Glu Arg
           245                 250                 255

Glu Asn Ala Ile Phe Ser Glu Glu Leu Asp Thr Tyr Ile Thr Phe
           260                 265                 270

Ser Gly Tyr Leu Val Lys His Ala Thr Glu Pro
           275                 280
```

<210> SEQ ID NO 74
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 74
tacaggccca gtcaggacca gggg                                              24

<210> SEQ ID NO 75
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 75
ctgaagaagt agaggccggg cacg                                              24

<210> SEQ ID NO 76
<211> LENGTH: 45
<212> TYPE: DNA
<213> ORGANISM: Artificial Sequence
<220> FEATURE:
<223> OTHER INFORMATION: Synthetic oligonucleotide probe

<400> SEQUENCE: 76
cccggtgctt gcgctgctgt gaccccggta cctccatgta cccgg                       45

<210> SEQ ID NO 77
<211> LENGTH: 1042
<212> TYPE: DNA
<213> ORGANISM: Homo Sapien

<400> SEQUENCE: 77

| | | | | | |
|---|---|---|---|---|---|
| gaattcggca | cgagggaaga | agagaaagaa | aatctccggg | gctgctggga | 50 |
| gcatataaag | aagccctgtg | gccttgctgg | ttttaccatc | cagaccagag | 100 |
| tcaggccaca | gacggacatg | gctgctcaag | gctggtccat | gctcctgctg | 150 |
| gctgtcctta | acctaggcat | cttcgtccgt | ccctgtgaca | ctcaagagct | 200 |
| acgatgtctg | tgtattcagg | aacactctga | attcattcct | ctcaaactca | 250 |
| ttaaaaatat | aatggtgata | ttcgagacca | tttactgcaa | cagaaaggaa | 300 |
| gtgatagcag | tcccaaaaaa | tgggagtatg | atttgtttgg | atcctgatgc | 350 |
| tccatgggtg | aaggctactg | ttggcccaat | tactaacagg | ttcctacctg | 400 |
| aggacctcaa | acaaaaggaa | tttccaccgg | caatgaagct | tctgtatagt | 450 |
| gttgagcatg | aaaagcctct | atatctttca | tttgggagac | ctgagaacaa | 500 |
| gagaatattt | ccctttccaa | ttcgggagac | ctctagacac | tttgctgatt | 550 |
| tagctcacaa | cagtgatagg | aattttctac | gggactccag | tgaagtcagc | 600 |
| ttgacaggca | gtgatgccta | aaagccactc | atgaggcaaa | gagtttcaag | 650 |
| gaagctctcc | tcctggagtt | ttggcgttct | cattcttata | ctctattccc | 700 |
| gcgttagtct | ggtgtatgga | tctatgagct | ctcttttaat | attttattat | 750 |
| aaatgtttta | tttacttaac | ttcctagtga | atgttcacag | gtgactgctc | 800 |
| ccccatcccc | atttcttgat | attacatata | atggcatcat | atacccttt | 850 |
| attgactgac | aaactactca | gattgcttaa | cattttgtgc | ttcaaagtct | 900 |
| tatcccactc | cactatgggc | tgttacagag | tgcatctcgg | tgtagagcaa | 950 |
| ggctccttgt | cttcagtgcc | ccagggtgaa | atacttcttt | gaaaaatttt | 1000 |
| cattcatcag | aaaatctgaa | ataaaaatat | gtcttaattg | ag | 1042 |

<210> SEQ ID NO 78
<211> LENGTH: 167
<212> TYPE: PRT
<213> ORGANISM: Homo Sapien

<400> SEQUENCE: 78

Met Ala Ala Gln Gly Trp Ser Met Leu Leu Leu Ala Val Leu Asn
1               5                   10                  15

Leu Gly Ile Phe Val Arg Pro Cys Asp Thr Gln Glu Leu Arg Cys
                20                  25                  30

Leu Cys Ile Gln Glu His Ser Glu Phe Ile Pro Leu Lys Leu Ile
                35                  40                  45

Lys Asn Ile Met Val Ile Phe Glu Thr Ile Tyr Cys Asn Arg Lys
                50                  55                  60

Glu Val Ile Ala Val Pro Lys Asn Gly Ser Met Ile Cys Leu Asp
                65                  70                  75

Pro Asp Ala Pro Trp Val Lys Ala Thr Val Gly Pro Ile Thr Asn
                80                  85                  90

Arg Phe Leu Pro Glu Asp Leu Lys Gln Lys Glu Phe Pro Pro Ala
                95                  100                 105

```
Met Lys Leu Leu Tyr Ser Val Glu His Glu Lys Pro Leu Tyr Leu
                110                 115                 120

Ser Phe Gly Arg Pro Glu Asn Lys Arg Ile Phe Pro Phe Pro Ile
                125                 130                 135

Arg Glu Thr Ser Arg His Phe Ala Asp Leu Ala His Asn Ser Asp
                140                 145                 150

Arg Asn Phe Leu Arg Asp Ser Ser Glu Val Ser Leu Thr Gly Ser
                155                 160                 165

Asp Ala

<210> SEQ ID NO 79
<211> LENGTH: 798
<212> TYPE: DNA
<213> ORGANISM: Homo Sapien
<220> FEATURE:
<221> NAME/KEY: unsure
<222> LOCATION: 794
<223> OTHER INFORMATION: unknown base

<400> SEQUENCE: 79
cagacatggc tcagtcactg gctctgagcc tccttatcct ggttctggcc         50
tttggcatcc ccaggaccca aggcagtgat ggagggctc aggactgttg         100
cctcaagtac agccaaagga agattcccgc caaggttgtc cgcagctacc        150
ggaagcagga accaagctta ggctgctcca tcccagctat cctgttcttg        200
ccccgcaagc gctctcaggc agagctatgt gcagacccaa aggagctctg        250
ggtgcagcag ctgatgcagc atctggacaa gacaccatcc ccacagaaac        300
cagcccaggg ctgcaggaag gacaggggg cctccaagac tggcaagaaa         350
ggaaagggct ccaaaggctg caagaggact gagcggtcac agacccctaa        400
agggccatag cccagtgagc agcctggagc cctggagacc ccaccagcct        450
caccagcgct tgaagcctga acccaagatg caagaaggag gctatgctca        500
ggggccctgg agcagccacc ccatgctggc cttgccacac tctttctcct        550
gctttaacca ccccatctgc attcccagct ctaccctgca tggctgagct        600
gcccacagca ggccaggtcc agagagaccg aggagggaga gtctcccagg        650
gagcatgaga ggaggcagca ggactgtccc cttgaaggag aatcatcagg        700
accctggacc tgatacggct ccccagtaca ccccacctct tccttgtaaa        750
tatgatttat acctaactga ataaaaagct gttctgtctt cccncccca         798

<210> SEQ ID NO 80
<211> LENGTH: 134
<212> TYPE: PRT
<213> ORGANISM: Homo Sapien

<400> SEQUENCE: 80

Met Ala Gln Ser Leu Ala Leu Ser Leu Leu Ile Leu Val Leu Ala
 1               5                  10                  15

Phe Gly Ile Pro Arg Thr Gln Gly Ser Asp Gly Gly Ala Gln Asp
                20                  25                  30

Cys Cys Leu Lys Tyr Ser Gln Arg Lys Ile Pro Ala Lys Val Val
                35                  40                  45

Arg Ser Tyr Arg Lys Gln Glu Pro Ser Leu Gly Cys Ser Ile Pro
                50                  55                  60

Ala Ile Leu Phe Leu Pro Arg Lys Arg Ser Gln Ala Glu Leu Cys
```

```
                    65                  70                  75
Ala Asp Pro Lys Glu Leu Trp Val Gln Gln Leu Met Gln His Leu
                80                  85                  90
Asp Lys Thr Pro Ser Pro Gln Lys Pro Ala Gln Gly Cys Arg Lys
                95                 100                 105
Asp Arg Gly Ala Ser Lys Thr Gly Lys Lys Gly Lys Gly Ser Lys
               110                 115                 120
Gly Cys Lys Arg Thr Glu Arg Ser Gln Thr Pro Lys Gly Pro
               125                 130

<210> SEQ ID NO 81
<211> LENGTH: 20
<212> TYPE: DNA
<213> ORGANISM: Artificial Sequence
<220> FEATURE:
<223> OTHER INFORMATION: Synthetic oligonucleotide probe

<400> SEQUENCE: 81
agacatggct cagtcactgg                                                  20

<210> SEQ ID NO 82
<211> LENGTH: 19
<212> TYPE: DNA
<213> ORGANISM: Artificial Sequence
<220> FEATURE:
<223> OTHER INFORMATION: Synthetic oligonucleotide probe

<400> SEQUENCE: 82
gacccctaaa gggccatag                                                   19

<210> SEQ ID NO 83
<211> LENGTH: 924
<212> TYPE: DNA
<213> ORGANISM: Homo Sapien

<400> SEQUENCE: 83
aaggagcagc ccgcaagcac caagtgagag gcatgaagtt acagtgtgtt                 50 tcccttggc tcctgggtac aatactgata ttgtgctcag tagacaacca                 100
cggtctcagg agatgtctga tttccacaga catgcaccat atagaagaga                150
gtttccaaga aatcaaaaga gccatccaag ctaaggacac cttcccaaat                200
gtcactatcc tgtccacatt ggagactctg cagatcatta gcccttaga                 250 tgtgtgctgc gtgaccaaga acctcctggc gttctacgtg dacagggtgt                300
tcaaggatca tcaggagcca aaccccaaaa tcttgagaaa aatcagcagc                350
attgccaact ctttcctcta catgcagaaa actctgcggc aatgtcagga                400
acagaggcag tgtcactgca ggcaggaagc caccaatgcc accagagtca                450
tccatgacaa ctatgatcag ctggaggtcc acgctgctgc cattaaatcc                500
ctgggagagc tcgacgtctt tctagcctgg attaataaga atcatgaagt                550
aatgttctca gcttgatgac aaggaacctg tatagtgatc cagggatgaa                600
caccccctgt gcggtttact gtgggagaca gcccaccttg aaggggaagg                650
agatggggaa ggcccccttgc agctgaaagt cccactggct ggcctcaggc                700
tgtcttattc cgcttgaaaa taggcaaaaa gtctactgtg gtatttgtaa                750
taaactctat ctgctgaaag ggcctgcagg ccatcctggg agtaaagggc                800
tgccttccca tctaatttat tgtaaagtca tatagtccat gtctgtgatg                850
```

```
tgagccaagt gatatcctgt agtacacatt gtactgagtg gttttttctga        900 ataaattcca tattttacct atga                                    924
```

<210> SEQ ID NO 84
<211> LENGTH: 177
<212> TYPE: PRT
<213> ORGANISM: Homo Sapien

<400> SEQUENCE: 84

```
Met Lys Leu Gln Cys Val Ser Leu Trp Leu Leu Gly Thr Ile Leu
  1               5                  10                  15

Ile Leu Cys Ser Val Asp Asn His Gly Leu Arg Arg Cys Leu Ile
                 20                  25                  30

Ser Thr Asp Met His His Ile Glu Glu Ser Phe Gln Glu Ile Lys
                 35                  40                  45

Arg Ala Ile Gln Ala Lys Asp Thr Phe Pro Asn Val Thr Ile Leu
                 50                  55                  60

Ser Thr Leu Glu Thr Leu Gln Ile Ile Lys Pro Leu Asp Val Cys
                 65                  70                  75

Cys Val Thr Lys Asn Leu Leu Ala Phe Tyr Val Asp Arg Val Phe
                 80                  85                  90

Lys Asp His Gln Glu Pro Asn Pro Lys Ile Leu Arg Lys Ile Ser
                 95                 100                 105

Ser Ile Ala Asn Ser Phe Leu Tyr Met Gln Lys Thr Leu Arg Gln
                110                 115                 120

Cys Gln Glu Gln Arg Gln Cys His Cys Arg Gln Glu Ala Thr Asn
                125                 130                 135

Ala Thr Arg Val Ile His Asp Asn Tyr Asp Gln Leu Glu Val His
                140                 145                 150

Ala Ala Ala Ile Lys Ser Leu Gly Glu Leu Asp Val Phe Leu Ala
                155                 160                 165

Trp Ile Asn Lys Asn His Glu Val Met Phe Ser Ala
                170                 175
```

<210> SEQ ID NO 85
<211> LENGTH: 2137
<212> TYPE: DNA
<213> ORGANISM: Homo Sapien

<400> SEQUENCE: 85

```
gctcccagcc aagaacctcg gggccgctgc gcggtgggga ggagttcccc         50
gaaacccggc cgctaagcga ggcctcctcc tcccgcagat ccgaacggcc        100
tgggcggggt caccccggct gggacaagaa gccgccgcct gcctgcccgg        150
gcccggggag ggggctgggg ctggggccgg aggcggggtg tgagtgggtg        200
tgtgcggggg gcggaggctt gatgcaatcc cgataagaaa tgctcgggtg        250
tcttgggcac ctacccgtgg ggcccgtaag gcgctactat ataaggctgc        300
cggcccggag ccgccgcgcc gtcagagcag gagcgctgcg tccaggatct        350
agggccacga ccatcccaac ccggcactca cagccccgca gcgcatcccg        400
gtcgccgccc agcctcccgc acccccatcg ccggagctgc gccgagagcc        450
ccagggaggt gccatgcgga gcgggtgtgt ggtggtccac gtatggatcc        500
tggccggcct ctggctggcc gtggccgggc gccccctcgc cttctcggac        550
```

-continued

```
gcggggcccc acgtgcacta cggctggggc gacccccatcc gcctgcggca        600
cctgtacacc tccggccccc acgggctctc cagctgcttc ctgcgcatcc        650
gtgccgacgg cgtcgtggac tgcgcgcggg gccagagcgc gcacagtttg        700
ctggagatca aggcagtcgc tctgcggacc gtggccatca agggcgtgca        750
cagcgtgcgg tacctctgca tgggcgccga cggcaagatg caggggctgc        800
ttcagtactc ggaggaagac tgtgctttcg aggaggagat ccgcccagat        850
ggctacaatg tgtaccgatc cgagaagcac cgcctcccgg tctccctgag        900
cagtgccaaa cagcggcagc tgtacaagaa cagaggcttt cttccactct        950
ctcatttcct gcccatgctg cccatggtcc cagaggagcc tgaggacctc       1000
agggccact tggaatctga catgttctct tcgcccctgg agaccgacag        1050
catggaccca tttgggcttg tcaccggact ggaggccgtg aggagtccca       1100
gctttgagaa gtaactgaga ccatgcccgg gcctcttcac tgctgccagg       1150
ggctgtggta cctgcagcgt gggggacgtg cttctacaag aacagtcctg       1200
agtccacgtt ctgtttagct ttaggaagaa acatctagaa gttgtacata       1250
ttcagagttt tccattggca gtgccagttt ctagccaata gacttgtctg       1300
atcataacat tgtaagcctg tagcttgccc agctgctgcc tgggccccca       1350
ttctgctccc tcgaggttgc tggacaagct gctgcactgt ctcagttctg       1400
cttgaatacc tccatcgatg gggaactcac ttcctttgga aaaattctta       1450
tgtcaagctg aaattctcta attttttctc atcacttccc caggagcagc       1500
cagaagacag gcagtagttt taatttcagg aacaggtgat ccactctgta       1550
aaacagcagg taaatttcac tcaacccccat gtgggaattg atctatatct      1600
ctacttccag ggaccatttg cccttcccaa atccctccag gccagaactg       1650
actggagcag gcatggccca ccaggcttca ggagtagggg aagcctggag       1700
ccccactcca gccctgggac aacttgagaa ttccccctga ggccagttct       1750
gtcatggatg ctgtcctgag aataacttgc tgtcccggtg tcacctgctt       1800
ccatctccca gcccaccagc cctctgccca cctcacatgc ctccccatgg       1850
attgggcct cccaggcccc ccaccttatg tcaacctgca cttcttgttc        1900
aaaaatcagg aaaagaaaag atttgaagac cccaagtctt gtcaataact       1950
tgctgtgtgg aagcagcggg ggaagaccta gaacccttc cccagcactt        2000
ggttttccaa catgatattt atgagtaatt tattttgata tgtacatctc       2050
ttattttctt acattattta tgcccccaaa ttatatttat gtatgtaagt       2100
gaggtttgtt ttgtatatta aaatggagtt tgtttgt                     2137
```

<210> SEQ ID NO 86
<211> LENGTH: 216
<212> TYPE: PRT
<213> ORGANISM: Homo Sapien

<400> SEQUENCE: 86

```
Met Arg Ser Gly Cys Val Val His Val Trp Ile Leu Ala Gly
  1               5                  10                  15

Leu Trp Leu Ala Val Ala Gly Arg Pro Leu Ala Phe Ser Asp Ala
                 20                  25                  30

Gly Pro His Val His Tyr Gly Trp Gly Asp Pro Ile Arg Leu Arg
```

```
                 35                  40                  45

His Leu Tyr Thr Ser Gly Pro His Gly Leu Ser Ser Cys Phe Leu
             50                  55                  60

Arg Ile Arg Ala Asp Gly Val Val Asp Cys Ala Arg Gly Gln Ser
         65                  70                  75

Ala His Ser Leu Leu Glu Ile Lys Ala Val Ala Leu Arg Thr Val
     80                  85                  90

Ala Ile Lys Gly Val His Ser Val Arg Tyr Leu Cys Met Gly Ala
             95                 100                 105

Asp Gly Lys Met Gln Gly Leu Leu Gln Tyr Ser Glu Glu Asp Cys
        110                 115                 120

Ala Phe Glu Glu Glu Ile Arg Pro Asp Gly Tyr Asn Val Tyr Arg
    125                 130                 135

Ser Glu Lys His Arg Leu Pro Val Ser Leu Ser Ser Ala Lys Gln
        140                 145                 150

Arg Gln Leu Tyr Lys Asn Arg Gly Phe Leu Pro Leu Ser His Phe
            155                 160                 165

Leu Pro Met Leu Pro Met Val Pro Glu Glu Pro Glu Asp Leu Arg
        170                 175                 180

Gly His Leu Glu Ser Asp Met Phe Ser Ser Pro Leu Glu Thr Asp
        185                 190                 195

Ser Met Asp Pro Phe Gly Leu Val Thr Gly Leu Glu Ala Val Arg
        200                 205                 210

Ser Pro Ser Phe Glu Lys
        215

<210> SEQ ID NO 87
<211> LENGTH: 26
<212> TYPE: DNA
<213> ORGANISM: Artificial Sequence
<220> FEATURE:
<223> OTHER INFORMATION: Synthetic oligonucleotide probe

<400> SEQUENCE: 87
atccgcccag atggctacaa tgtgta                                          26

<210> SEQ ID NO 88
<211> LENGTH: 42
<212> TYPE: DNA
<213> ORGANISM: Artificial Sequence
<220> FEATURE:
<223> OTHER INFORMATION: Synthetic oligonucleotide probe

<400> SEQUENCE: 88
gcctcccggt ctccctgagc agtgccaaac agcggcagtg ta                        42

<210> SEQ ID NO 89
<211> LENGTH: 22
<212> TYPE: DNA
<213> ORGANISM: Artificial Sequence
<220> FEATURE:
<223> OTHER INFORMATION: Synthetic oligonucleotide probe

<400> SEQUENCE: 89
ccagtccggt gacaagccca aa                                              22

<210> SEQ ID NO 90
<211> LENGTH: 1857
<212> TYPE: DNA
<213> ORGANISM: Homo Sapien
```

<400> SEQUENCE: 90

```
gtctgttccc aggagtcctt cggcggctgt tgtgtcagtg gcctgatcgc        50
gatgggaca aaggcgcaag tcgagaggaa actgttgtgc ctcttcatat        100
tggcgatcct gttgtgctcc ctggcattgg gcagtgttac agtgcactct       150
tctgaacctg aagtcagaat tcctgagaat aatcctgtga agttgtcctg       200
tgcctactcg ggcttttctt ctccccgtgt ggagtggaag tttgaccaag       250
gagacaccac cagactcgtt tgctataata caagatcac agcttcctat       300
gaggaccggg tgaccttctt gccaactggt atcaccttca agtccgtgac       350
acgggaagac actgggacat acacttgtat ggtctctgag gaaggcggca       400
acagctatgg ggaggtcaag gtcaagctca tcgtgcttgt gcctccatcc       450
aagcctacag ttaacatccc ctcctctgcc accattggga accgggcagt       500
gctgacatgc tcagaacaag atggttcccc accttctgaa tacacctggt       550
tcaaagatgg gatagtgatg cctacgaatc ccaaaagcac ccgtgccttc       600
agcaactctt cctatgtcct gaatcccaca acaggagagc tggtctttga       650
tcccctgtca gcctctgata ctggagaata cagctgtgag gcacggaatg       700
ggtatgggac acccatgact tcaaatgctg tgcgcatgga agctgtggag       750
cggaatgtgg gggtcatcgt ggcagccgtc cttgtaaccc tgattctcct       800
gggaatcttg gttttggca tctggtttgc ctatagccga ggccactttg       850
acagaacaaa gaaagggact tcgagtaaga aggtgattta cagccagcct       900
agtgcccgaa gtgaaggaga attcaaacag acctcgtcat tcctggtgtg       950
agcctggtcg gctcaccgcc tatcatctgc atttgcctta ctcaggtgct      1000
accggactct ggcccctgat gtctgtagtt tcacaggatg ccttatttgt      1050
cttctacacc ccacagggcc ccctacttct tcggatgtgt ttttaataat      1100
gtcagctatg tgccccatcc tccttcatgc cctccctccc tttcctacca      1150
ctgctgagtg gcctggaact tgtttaaagt gtttattccc catttctttg      1200
agggatcagg aaggaatcct gggtatgcca ttgacttccc ttctaagtag      1250
acagcaaaaa tggcgggggt cgcaggaatc tgcactcaac tgcccacctg      1300
gctggcaggg atctttgaat aggtatcttg agcttggttc tgggctcttt      1350
ccttgtgtac tgacgaccag ggccagctgt tctagagcgg gaattagagg      1400
ctagagcggc tgaaatggtt gtttggtgat gacactgggg tccttccatc      1450
tctggggccc actctcttct gtcttcccat gggaagtgcc actgggatcc      1500
ctctgccctg tcctcctgaa tacaagctga ctgacattga ctgtgtctgt      1550
ggaaaatggg agctcttgtt gtggagagca tagtaaattt tcagagaact      1600
tgaagccaaa aggatttaaa accgctgctc taaagaaaag aaaactggag      1650
gctgggcgca gtggctcacg cctgtaatcc cagaggctga ggcaggcgga      1700
tcacctgagg tcgggagttc gggatcagcc tgaccaacat ggagaaaccc      1750
tactggaaat acaaagttag ccaggcatgg tggtgcatgc ctgtagtccc      1800
agctgctcag gagcctggca acaagagcaa aactccagct caaaaaaaaa      1850
aaaaaaa                                                    1857
```

<210> SEQ ID NO 91
<211> LENGTH: 299
<212> TYPE: PRT
<213> ORGANISM: Homo Sapien

<400> SEQUENCE: 91

```
Met Gly Thr Lys Ala Gln Val Glu Arg Lys Leu Leu Cys Leu Phe
 1               5                  10                  15

Ile Leu Ala Ile Leu Leu Cys Ser Leu Ala Leu Gly Ser Val Thr
                20                  25                  30

Val His Ser Ser Glu Pro Glu Val Arg Ile Pro Glu Asn Asn Pro
                35                  40                  45

Val Lys Leu Ser Cys Ala Tyr Ser Gly Phe Ser Ser Pro Arg Val
                50                  55                  60

Glu Trp Lys Phe Asp Gln Gly Asp Thr Thr Arg Leu Val Cys Tyr
                65                  70                  75

Asn Asn Lys Ile Thr Ala Ser Tyr Glu Asp Arg Val Thr Phe Leu
                80                  85                  90

Pro Thr Gly Ile Thr Phe Lys Ser Val Thr Arg Glu Asp Thr Gly
                95                 100                 105

Thr Tyr Thr Cys Met Val Ser Glu Glu Gly Gly Asn Ser Tyr Gly
                110                115                 120

Glu Val Lys Val Lys Leu Ile Val Leu Val Pro Ser Lys Pro
                125                130                 135

Thr Val Asn Ile Pro Ser Ser Ala Thr Ile Gly Asn Arg Ala Val
                140                145                 150

Leu Thr Cys Ser Glu Gln Asp Gly Ser Pro Pro Ser Glu Tyr Thr
                155                160                 165

Trp Phe Lys Asp Gly Ile Val Met Pro Thr Asn Pro Lys Ser Thr
                170                175                 180

Arg Ala Phe Ser Asn Ser Ser Tyr Val Leu Asn Pro Thr Thr Gly
                185                190                 195

Glu Leu Val Phe Asp Pro Leu Ser Ala Ser Asp Thr Gly Glu Tyr
                200                205                 210

Ser Cys Glu Ala Arg Asn Gly Tyr Gly Thr Pro Met Thr Ser Asn
                215                220                 225

Ala Val Arg Met Glu Ala Val Glu Arg Asn Val Gly Val Ile Val
                230                235                 240

Ala Ala Val Leu Val Thr Leu Ile Leu Leu Gly Ile Leu Val Phe
                245                250                 255

Gly Ile Trp Phe Ala Tyr Ser Arg Gly His Phe Asp Arg Thr Lys
                260                265                 270

Lys Gly Thr Ser Ser Lys Lys Val Ile Tyr Ser Gln Pro Ser Ala
                275                280                 285

Arg Ser Glu Gly Glu Phe Lys Gln Thr Ser Ser Phe Leu Val
                290                295
```

<210> SEQ ID NO 92
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 92
tcgcggagct gtgttctgtt tccc                                              24

```
<210> SEQ ID NO 93
<211> LENGTH: 50
<212> TYPE: DNA
<213> ORGANISM: Artificial Sequence
<220> FEATURE:
<223> OTHER INFORMATION: Synthetic oligonucleotide probe

<400> SEQUENCE: 93
tgatcgcgat ggggacaaag gcgcaagctc gagaggaaac tgttgtgcct            50

<210> SEQ ID NO 94
<211> LENGTH: 20
<212> TYPE: DNA
<213> ORGANISM: Artificial Sequence
<220> FEATURE:
<223> OTHER INFORMATION: Synthetic oligonucleotide probe

<400> SEQUENCE: 94
acacctggtt caaagatggg                                             20

<210> SEQ ID NO 95
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 95
taggaagagt tgctgaaggc acgg                                        24

<210> SEQ ID NO 96
<211> LENGTH: 20
<212> TYPE: DNA
<213> ORGANISM: Artificial Sequence
<220> FEATURE:
<223> OTHER INFORMATION: Synthetic oligonucleotide probe

<400> SEQUENCE: 96
ttgccttact caggtgctac                                             20

<210> SEQ ID NO 97
<211> LENGTH: 20
<212> TYPE: DNA
<213> ORGANISM: Artificial Sequence
<220> FEATURE:
<223> OTHER INFORMATION: Synthetic oligonucleotide probe

<400> SEQUENCE: 97
actcagcagt ggtaggaaag                                             20

<210> SEQ ID NO 98
<211> LENGTH: 1200
<212> TYPE: DNA
<213> ORGANISM: Homo Sapien

<400> SEQUENCE: 98
cccacgcgtc cgaacctctc cagcgatggg agccgcccgc ctgctgccca            50
acctcactct gtgcttacag ctgctgattc tctgctgtca aactcagtac           100
gtgagggacc agggcgccat gaccgaccag ctgagcaggg ggcagatccg           150
cgagtaccaa ctctacagca ggaccagtgg caagcacgtg caggtcaccg           200
ggcgtcgcat ctccgccacc gccgaggacg gcaacaagtt tgccaagctc           250
```

-continued

```
atagtggaga cggacacgtt tggcagccgg gttcgcatca aaggggctga         300
gagtgagaag tacatctgta tgaacaagag gggcaagctc atcgggaagc         350
ccagcgggaa gagcaaagac tgcgtgttca cggagatcgt gctggagaac         400
aactatacgg ccttccagaa cgcccggcac gagggctggt tcatggcctt         450
cacgcggcag gggcggcccc gccaggcttc ccgcagccgc cagaaccagc         500
gcgaggccca cttcatcaag cgcctctacc aaggccagct gcccttcccc         550
aaccacgccg agaagcagaa gcagttcgag tttgtgggct ccgccccac          600 ccgccggacc aagcgcacac ggcggcccca gcccctcacg tagtctggga         650 ggcaggggc agcagcccct gggccgcctc ccacccctt tcccttctta           700 atccaaggac tgggctgggg tggcgggagg ggagccagat ccccgaggga         750
ggaccctgag ggccgcgaag catccgagcc ccagctgggg aaggggcagg         800
ccggtgcccc aggggcggct ggcacagtgc ccccttcccg gacgggtggc         850
aggccctgga gaggaactga gtgtcaccct gatctcaggc caccagcctc         900
tgccggcctc ccagccgggc tcctgaagcc cgctgaaagg tcagcgactg         950
aaggccttgc agacaaccgt ctggaggtgg ctgtcctcaa aatctgcttc        1000
tcggatctcc ctcagtctgc ccccagcccc caaactcctc ctggctagac        1050
tgtaggaagg gacttttgtt tgtttgtttg tttcaggaaa aaagaaaggg        1100
agagagagga aaatagaggg ttgtccactc ctcacattcc acgacccagg        1150
cctgcacccc acccccaact cccagccccg aataaaaacc attttcctgc        1200
```

<210> SEQ ID NO 99
<211> LENGTH: 205
<212> TYPE: PRT
<213> ORGANISM: Homo Sapien

<400> SEQUENCE: 99

```
Met Gly Ala Ala Arg Leu Leu Pro Asn Leu Thr Leu Cys Leu Gln
 1               5                  10                  15

Leu Leu Ile Leu Cys Cys Gln Thr Gln Tyr Val Arg Asp Gln Gly
                20                  25                  30

Ala Met Thr Asp Gln Leu Ser Arg Arg Gln Ile Arg Glu Tyr Gln
                35                  40                  45

Leu Tyr Ser Arg Thr Ser Gly Lys His Val Gln Val Thr Gly Arg
                50                  55                  60

Arg Ile Ser Ala Thr Ala Glu Asp Gly Asn Lys Phe Ala Lys Leu
                65                  70                  75

Ile Val Glu Thr Asp Thr Phe Gly Ser Arg Val Arg Ile Lys Gly
                80                  85                  90

Ala Glu Ser Glu Lys Tyr Ile Cys Met Asn Lys Arg Gly Lys Leu
                95                  100                 105

Ile Gly Lys Pro Ser Gly Lys Ser Lys Asp Cys Val Phe Thr Glu
                110                 115                 120

Ile Val Leu Glu Asn Asn Tyr Thr Ala Phe Gln Asn Ala Arg His
                125                 130                 135

Glu Gly Trp Phe Met Ala Phe Thr Arg Gln Gly Arg Pro Arg Gln
                140                 145                 150

Ala Ser Arg Ser Arg Gln Asn Gln Arg Glu Ala His Phe Ile Lys
                155                 160                 165
```

```
Arg Leu Tyr Gln Gly Gln Leu Pro Phe Pro Asn His Ala Glu Lys
            170                 175                 180

Gln Lys Gln Phe Glu Phe Val Gly Ser Ala Pro Thr Arg Arg Thr
            185                 190                 195

Lys Arg Thr Arg Arg Pro Gln Pro Leu Thr
            200                 205

<210> SEQ ID NO 100
<211> LENGTH: 28
<212> TYPE: DNA
<213> ORGANISM: Artificial Sequence
<220> FEATURE:
<223> OTHER INFORMATION: Synthetic oligonucleotide probe

<400> SEQUENCE: 100
cagtacgtga gggaccaggg cgccatga                                   28

<210> SEQ ID NO 101
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 101
ccggtgacct gcacgtgctt gcca                                       24

<210> SEQ ID NO 102
<211> LENGTH: 41
<212> TYPE: DNA
<213> ORGANISM: Artificial Sequence
<220> FEATURE:
<223> OTHER INFORMATION: Synthetic oligonucleotide probe
<221> NAME/KEY: unsure
<222> LOCATION: 21
<223> OTHER INFORMATION: unknown base

<400> SEQUENCE: 102
gcggatctgc cgcctgctca nctggtcggt catggcgccc t                    41

<210> SEQ ID NO 103
<211> LENGTH: 1679
<212> TYPE: DNA
<213> ORGANISM: Homo Sapien

<400> SEQUENCE: 103
gttgtgtcct tcagcaaaac agtggattta aatctccttg cacaagcttg           50
agagcaacac aatctatcag gaaagaaaga aagaaaaaaa ccgaacctga          100
caaaaaagaa gaaaaagaag aagaaaaaaa atcatgaaaa ccatccagcc          150
aaaaatgcac aattctatct cttgggcaat cttcacgggg ctggctgctc          200
tgtgtctctt ccaaggagtg cccgtgcgca gcggagatgc caccttcccc          250
aaagctatgg acaacgtgac ggtccggcag ggggagagcg ccaccctcag          300
gtgcactatt gacaaccggg tcacccgggt ggcctggcta aaccgcagca          350
ccatcctcta tgctgggaat gacaagtggt gcctggatcc tcgcgtggtc          400
cttctgagca acaccaaaac gcagtacagc atcgagatcc agaacgtgga          450
tgtgtatgac gagggccctt acacctgctc ggtgcagaca gacaaccacc          500
caaagacctc tagggtccac ctcattgtgc aagtatctcc caaaattgta          550
gagatttctt cagatatctc cattaatgaa gggaacaata ttagcctcac          600
```

-continued

```
ctgcatagca actggtagac cagagcctac ggttacttgg agacacatct           650
ctcccaaagc ggttggcttt gtgagtgaag acgaatactt ggaaattcag           700
ggcatcaccc gggagcagtc aggggactac gagtgcagtg cctccaatga           750
cgtggccgcg cccgtggtac ggagagtaaa ggtcaccgtg aactatccac           800
catacatttc agaagccaag ggtacaggtg tccccgtggg acaaaagggg           850
acactgcagt gtgaagcctc agcagtcccc tcagcagaat tccagtggta           900
caaggatgac aaaagactga ttgaaggaaa gaaaggggtg aaagtggaaa           950
acagaccttt cctctcaaaa ctcatcttct tcaatgtctc tgaacatgac          1000
tatgggaact acacttgcgt ggcctccaac aagctgggcc acaccaatgc          1050
cagcatcatg ctatttggtc caggcgccgt cagcgaggtg agcaacggca          1100
cgtcgaggag ggcaggctgc gtctggctgc tgcctcttct ggtcttgcac          1150
ctgcttctca aattttgatg tgagtgccac ttccccaccc gggaaaggct          1200
gccgccacca ccaccaccaa cacaacagca atggcaacac cgacagcaac          1250
caatcagata tatacaaatg aaattagaag aaacacagcc tcatgggaca          1300
gaaatttgag ggaggggaac aaagaatact ttggggggaa aagagtttta          1350
aaaaagaaat tgaaaattgc cttgcagata tttaggtaca atggagtttt          1400
cttttcccaa acgggaagaa cacagcacac ccggcttgga cccactgcaa          1450
gctgcatcgt gcaacctctt tggtgccagt gtgggcaagg gctcagcctc          1500
tctgcccaca gagtgccccc acgtggaaca ttctggagct ggccatccca          1550
aattcaatca gtccatagag acgaaacagaa tgagaccttc cggcccaagc          1600
gtggcgctgc gggcactttg gtagactgtg ccaccacggc gtgtgttgtg          1650
aaacgtgaaa taaaaagagc aaaaaaaaa                                 1679
```

<210> SEQ ID NO 104
<211> LENGTH: 344
<212> TYPE: PRT
<213> ORGANISM: Homo Sapien

<400> SEQUENCE: 104

```
Met Lys Thr Ile Gln Pro Lys Met His Asn Ser Ile Ser Trp Ala
  1               5                  10                  15

Ile Phe Thr Gly Leu Ala Ala Leu Cys Leu Phe Gln Gly Val Pro
                 20                  25                  30

Val Arg Ser Gly Asp Ala Thr Phe Pro Lys Ala Met Asp Asn Val
                 35                  40                  45

Thr Val Arg Gln Gly Glu Ser Ala Thr Leu Arg Cys Thr Ile Asp
                 50                  55                  60

Asn Arg Val Thr Arg Val Ala Trp Leu Asn Arg Ser Thr Ile Leu
                 65                  70                  75

Tyr Ala Gly Asn Asp Lys Trp Cys Leu Asp Pro Arg Val Val Leu
                 80                  85                  90

Leu Ser Asn Thr Gln Thr Gln Tyr Ser Ile Glu Ile Gln Asn Val
                 95                 100                 105

Asp Val Tyr Asp Glu Gly Pro Tyr Thr Cys Ser Val Gln Thr Asp
                110                 115                 120

Asn His Pro Lys Thr Ser Arg Val His Leu Ile Val Gln Val Ser
                125                 130                 135
```

-continued

```
Pro Lys Ile Val Glu Ile Ser Ser Asp Ile Ser Ile Asn Glu Gly
            140                 145                 150
Asn Asn Ile Ser Leu Thr Cys Ile Ala Thr Gly Arg Pro Glu Pro
            155                 160                 165
Thr Val Thr Trp Arg His Ile Ser Pro Lys Ala Val Gly Phe Val
            170                 175                 180
Ser Glu Asp Glu Tyr Leu Glu Ile Gln Gly Ile Thr Arg Glu Gln
            185                 190                 195
Ser Gly Asp Tyr Glu Cys Ser Ala Ser Asn Asp Val Ala Ala Pro
            200                 205                 210
Val Val Arg Arg Val Lys Val Thr Val Asn Tyr Pro Pro Tyr Ile
            215                 220                 225
Ser Glu Ala Lys Gly Thr Gly Val Pro Val Gly Gln Lys Gly Thr
            230                 235                 240
Leu Gln Cys Glu Ala Ser Ala Val Pro Ser Ala Glu Phe Gln Trp
            245                 250                 255
Tyr Lys Asp Asp Lys Arg Leu Ile Glu Gly Lys Lys Gly Val Lys
            260                 265                 270
Val Glu Asn Arg Pro Phe Leu Ser Lys Leu Ile Phe Phe Asn Val
            275                 280                 285
Ser Glu His Asp Tyr Gly Asn Tyr Thr Cys Val Ala Ser Asn Lys
            290                 295                 300
Leu Gly His Thr Asn Ala Ser Ile Met Leu Phe Gly Pro Gly Ala
            305                 310                 315
Val Ser Glu Val Ser Asn Gly Thr Ser Arg Arg Ala Gly Cys Val
            320                 325                 330
Trp Leu Leu Pro Leu Leu Val Leu His Leu Leu Lys Phe
            335                 340

<210> SEQ ID NO 105
<211> LENGTH: 1734
<212> TYPE: DNA
<213> ORGANISM: Homo Sapien

<400> SEQUENCE: 105
gtggactctg agaagcccag gcagttgagg acaggagaga gaaggctgca          50
gacccagagg gagggaggac agggagtcgg aaggaggagg acagaggagg         100
gcacagagac gcagagcaag ggcggcaagg aggagaccct ggtgggagga         150
agacactctg gagagagagg gggctgggca gagatgaagt tccagggcc          200 cctggcctgc ctcctgctgg ccctctgcct gggcagtggg gaggctggcc         250
ccctgcagag cggagaggaa agcactggga caaatattgg ggaggccctt         300
ggacatggcc tgggagacgc cctgagcgaa ggggtgggaa aggccattgg         350
caaagaggcc ggaggggcag ctggctctaa agtcagtgag gcccttggcc         400
aagggaccag agaagcagtt ggcactggag tcaggcaggt tccaggcttt         450
ggcgcagcag atgctttggg caacagggtc ggggaagcag cccatgctct         500
gggaaacact gggcacgaga ttggcagaca ggcagaagat gtcattcgac         550
acggagcaga tgctgtccgc ggctcctggc aggggtgcc  tggccacagt         600 ggtgcttggg aaacttctgg aggccatggc atctttggct ctcaaggtgg         650
ccttggaggc cagggccagg gcaatcctgg aggtctgggg actccgtggg         700
```

-continued

| | |
|---|---|
| tccacggata ccccggaaac tcagcaggca gctttggaat gaatcctcag | 750 |
| ggagctccct ggggtcaagg aggcaatgga gggccaccaa actttgggac | 800 |
| caacactcag ggagctgtgg cccagcctgg ctatggttca gtgagagcca | 850 |
| gcaaccagaa tgaagggtgc acgaatcccc caccatctgg ctcaggtgga | 900 |
| ggctccagca actctggggg aggcagcggc tcacagtcgg gcagcagtgg | 950 |
| cagtggcagc aatggtgaca caacaatgg cagcagcagt ggtggcagca | 1000 |
| gcagtggcag cagcagtggc agcagcagtg gcggcagcag tggcggcagc | 1050 |
| agtggtggca gcagtggcaa cagtggtggc agcagaggtg acagcggcag | 1100 |
| tgagtcctcc tggggatcca gcaccggctc ctcctccggc aaccacggtg | 1150 |
| ggagcggcg aggaaatgga cataaacccg ggtgtgaaaa gccagggaat | 1200 |
| gaagcccgcg ggagcgggga atctgggatt cagggcttca gaggacaggg | 1250 |
| agtttccagc aacatgaggg aaataagcaa agagggcaat cgcctccttg | 1300 |
| gaggctctgg agacaattat cggggcaag gtcgagctg gggcagtgga | 1350 |
| ggaggtgacg ctgttggtgg agtcaatact gtgaactctg agacgtctcc | 1400 |
| tgggatgttt aactttgaca cttcctggaa gaattttaaa tccaagctgg | 1450 |
| gtttcatcaa ctgggatgcc ataaacaagg accagaaag ctctcgcatc | 1500 |
| ccgtgacctc cagacaagga gccaccagat tggatgggag cccccacact | 1550 |
| ccctccttaa aacaccaccc tctcatcact aatctcagcc cttgcccttg | 1600 |
| aaataaacct tagctgcccc acaaaaaaaa aaaaaaaaaa aaaaaaaaa | 1650 |
| aaaaaaaaaa aaaaaaaaaa aaaaaaaaa aaaaaaaaa aaaaaaaaaa | 1700 |
| aaaaaaaaaa aaaaaaaaaa aaaaaaaaaa aaaa | 1734 |

<210> SEQ ID NO 106
<211> LENGTH: 440
<212> TYPE: PRT
<213> ORGANISM: Homo Sapien

<400> SEQUENCE: 106

```
Met Lys Phe Gln Gly Pro Leu Ala Cys Leu Leu Ala Leu Cys
1               5                  10                  15

Leu Gly Ser Gly Glu Ala Gly Pro Leu Gln Ser Gly Glu Glu Ser
            20                  25                  30

Thr Gly Thr Asn Ile Gly Glu Ala Leu Gly His Gly Leu Gly Asp
            35                  40                  45

Ala Leu Ser Glu Gly Val Gly Lys Ala Ile Gly Lys Glu Ala Gly
            50                  55                  60

Gly Ala Ala Gly Ser Lys Val Ser Glu Ala Leu Gly Gln Gly Thr
            65                  70                  75

Arg Glu Ala Val Gly Thr Gly Val Arg Gln Val Pro Gly Phe Gly
            80                  85                  90

Ala Ala Asp Ala Leu Gly Asn Arg Val Gly Glu Ala Ala His Ala
            95                  100                 105

Leu Gly Asn Thr Gly His Glu Ile Gly Arg Gln Ala Glu Asp Val
            110                 115                 120

Ile Arg His Gly Ala Asp Ala Val Arg Gly Ser Trp Gln Val
            125                 130                 135

Pro Gly His Ser Gly Ala Trp Glu Thr Ser Gly Gly His Gly Ile
            140                 145                 150
```

-continued

Phe Gly Ser Gln Gly Gly Leu Gly Gly Gln Gly Gln Gly Asn Pro
              155                 160                 165
Gly Gly Leu Gly Thr Pro Trp Val His Gly Tyr Pro Gly Asn Ser
          170                 175                 180
Ala Gly Ser Phe Gly Met Asn Pro Gln Gly Ala Pro Trp Gly Gln
          185                 190                 195
Gly Gly Asn Gly Gly Pro Pro Asn Phe Gly Thr Asn Thr Gln Gly
          200                 205                 210
Ala Val Ala Gln Pro Gly Tyr Gly Ser Val Arg Ala Ser Asn Gln
          215                 220                 225
Asn Glu Gly Cys Thr Asn Pro Pro Ser Gly Ser Gly Gly Gly
          230                 235                 240
Ser Ser Asn Ser Gly Gly Gly Ser Gly Ser Gln Ser Gly Ser Ser
          245                 250                 255
Gly Ser Gly Ser Asn Gly Asp Asn Asn Asn Gly Ser Ser Ser Gly
          260                 265                 270
Gly Ser Ser Ser Gly Ser Ser Ser Gly Ser Ser Ser Gly Gly Ser
          275                 280                 285
Ser Gly Gly Ser Ser Gly Gly Ser Ser Gly Asn Ser Gly Gly Ser
          290                 295                 300
Arg Gly Asp Ser Gly Ser Glu Ser Ser Trp Gly Ser Ser Thr Gly
          305                 310                 315
Ser Ser Ser Gly Asn His Gly Gly Ser Gly Gly Gly Asn Gly His
          320                 325                 330
Lys Pro Gly Cys Glu Lys Pro Gly Asn Glu Ala Arg Gly Ser Gly
          335                 340                 345
Glu Ser Gly Ile Gln Gly Phe Arg Gly Gln Gly Val Ser Ser Asn
          350                 355                 360
Met Arg Glu Ile Ser Lys Glu Gly Asn Arg Leu Leu Gly Gly Ser
          365                 370                 375
Gly Asp Asn Tyr Arg Gly Gln Gly Ser Ser Trp Gly Ser Gly Gly
          380                 385                 390
Gly Asp Ala Val Gly Gly Val Asn Thr Val Asn Ser Glu Thr Ser
          395                 400                 405
Pro Gly Met Phe Asn Phe Asp Thr Phe Trp Lys Asn Phe Lys Ser
          410                 415                 420
Lys Leu Gly Phe Ile Asn Trp Asp Ala Ile Asn Lys Asp Gln Arg
          425                 430                 435
Ser Ser Arg Ile Pro
          440

<210> SEQ ID NO 107
<211> LENGTH: 918
<212> TYPE: DNA
<213> ORGANISM: Homo Sapien

<400> SEQUENCE: 107
agccaggcag cacatcacag cgggaggagc tgtcccaggt ggcccagctc         50
agcaatggca atgggggtcc ccagagtcat tctgctctgc ctctttgggg        100
ctgcgctctg cctgacaggg tcccaagccc tgcagtgcta cagctttgag        150
cacacctact ttggcccctt tgacctcagg gccatgaagc tgcccagcat        200
ctcctgtcct catgagtgct ttgaggctat cctgtctctg gacaccgggt        250

-continued

| | |
|---|---|
| atcgcgcgcc ggtgaccctg gtgcggaagg gctgctggac cgggcctcct | 300 |
| gcgggccaga cgcaatcgaa cccggacgcg ctgccgccag actactcggt | 350 |
| ggtgcgcggc tgcacaactg acaaatgcaa cgcccacctc atgactcatg | 400 |
| acgccctccc caacctgagc caagcacccg acccgccgac gctcagcggc | 450 |
| gccgagtgct acgcctgtat cggggtccac caggatgact gcgctatcgg | 500 |
| caggtcccga cgagtccagt gtcaccagga ccagaccgcc tgcttccagg | 550 |
| gcagtggcag aatgacagtt ggcaatttct cagtccctgt gtacatcaga | 600 |
| acctgccacc ggccctcctg caccaccgag gcaccacca gccctggac | 650 |
| agccatcgac ctccagggct cctgctgtga ggggtacctc tgcaacagga | 700 |
| aatccatgac ccagcccttc accagtgctt cagccaccac ccctcccga | 750 |
| gcactacagg tcctggcccct gctcctccca gtcctcctgc tggtggggct | 800 |
| ctcagcatag accgccctc caggatgctg gggacagggc tcacacacct | 850 |
| cattcttgct gcttcagccc ctatcacata gctcactgga aaatgatgtt | 900 |
| aaagtaagaa ttgcaaaa | 918 |

<210> SEQ ID NO 108
<211> LENGTH: 251
<212> TYPE: PRT
<213> ORGANISM: Homo Sapien

<400> SEQUENCE: 108

```
Met Ala Met Gly Val Pro Arg Val Ile Leu Leu Cys Leu Phe Gly
 1               5                  10                  15

Ala Ala Leu Cys Leu Thr Gly Ser Gln Ala Leu Gln Cys Tyr Ser
                20                  25                  30

Phe Glu His Thr Tyr Phe Gly Pro Phe Asp Leu Arg Ala Met Lys
                35                  40                  45

Leu Pro Ser Ile Ser Cys Pro His Glu Cys Phe Glu Ala Ile Leu
                50                  55                  60

Ser Leu Asp Thr Gly Tyr Arg Ala Pro Val Thr Leu Val Arg Lys
                65                  70                  75

Gly Cys Trp Thr Gly Pro Pro Ala Gly Gln Thr Gln Ser Asn Pro
                80                  85                  90

Asp Ala Leu Pro Pro Asp Tyr Ser Val Val Arg Gly Cys Thr Thr
                95                  100                 105

Asp Lys Cys Asn Ala His Leu Met Thr His Asp Ala Leu Pro Asn
                110                 115                 120

Leu Ser Gln Ala Pro Asp Pro Pro Thr Leu Ser Gly Ala Glu Cys
                125                 130                 135

Tyr Ala Cys Ile Gly Val His Gln Asp Asp Cys Ala Ile Gly Arg
                140                 145                 150

Ser Arg Arg Val Gln Cys His Gln Asp Gln Thr Ala Cys Phe Gln
                155                 160                 165

Gly Ser Gly Arg Met Thr Val Gly Asn Phe Ser Val Pro Val Tyr
                170                 175                 180

Ile Arg Thr Cys His Arg Pro Ser Cys Thr Thr Glu Gly Thr Thr
                185                 190                 195

Ser Pro Trp Thr Ala Ile Asp Leu Gln Gly Ser Cys Cys Glu Gly
                200                 205                 210

Tyr Leu Cys Asn Arg Lys Ser Met Thr Gln Pro Phe Thr Ser Ala
```

```
                    215                 220                 225
Ser Ala Thr Thr Pro Pro Arg Ala Leu Gln Val Leu Ala Leu Leu
            230                 235                 240

Leu Pro Val Leu Leu Leu Val Gly Leu Ser Ala
            245                 250

<210> SEQ ID NO 109
<211> LENGTH: 1813
<212> TYPE: DNA
<213> ORGANISM: Homo Sapien

<400> SEQUENCE: 109
ggagccgccc tgggtgtcag cggctcggct cccgcgcacg ctccggccgt        50
cgcgcagcct cggcacctgc aggtccgtgc gtcccgcggc tggcgcccct       100
gactccgtcc cggccaggga gggccatgat ttccctcccg ggcccctgg        150 tgaccaactt gctgcggttt ttgttcctgg ggctgagtgc cctcgcgccc       200
ccctcgcggg cccagctgca actgcacttg ccgccaacc ggttgcaggc        250 ggtggaggga gggaagtgg tgcttccagc gtggtacacc ttgcacgggg        300
aggtgtcttc atcccagcca tgggaggtgc cctttgtgat gtggttcttc       350
aaacagaaag aaaaggagga tcaggtgttg tcctacatca tgggggtcac       400
aacaagcaaa cctggagtat ccttggtcta ctccatgccc tcccggaacc       450
tgtccctgcg gctggagggt ctccaggaga aagactctgg cccctacagc       500
tgctccgtga atgtgcaaga caaacaaggc aaatctaggg gccacagcat       550
caaaacctta gaactcaatg tactggttcc tccagctcct ccatcctgcc       600
gtctccaggg tgtgccccat gtggggggcaa acgtgaccct gagctgccag       650
tctccaagga gtaagcccgc tgtccaatac cagtgggatc ggcagcttcc       700
atccttccag actttctttg caccagcatt agatgtcatc cgtgggtctt       750
taagcctcac caacctttcg tcttccatgg ctggagtcta tgtctgcaag       800
gcccacaatg aggtgggcac tgcccaatgt aatgtgacgc tggaagtgag       850
cacagggcct ggagctgcag tggttgctgg agctgttgtg ggtaccctgg       900
ttggactggg gttgctggct gggctggtcc tcttgtacca ccgccggggc       950
aaggccctgg aggagccagc caatgatatc aaggaggatg ccattgctcc      1000
ccggaccctg ccctggccca gagctcaga cacaatctcc aagaatggga       1050 cccttcctc tgtcacctcc gcacgagccc tccggccacc ccatggccct       1100
cccaggcctg gtgcattgac ccccacgccc agtctctcca gccaggccct      1150
gccctcacca agactgccca cgacagatgg ggcccaccct caaccaatat      1200
cccccatccc tggtggggtt tcttcctctg gcttgagccg catgggtgct      1250
gtgcctgtga tggtgcctgc ccagagtcaa gctggctctc tggtatgatg      1300
accccaccac tcattggcta aaggatttgg ggtctctcct tcctataagg      1350
gtcacctcta gcacagaggc ctgagtcatg ggaaagagtc acactcctga      1400
cccttagtac tctgccccca cctctcttta ctgtgggaaa accatctcag      1450
taagacctaa gtgtccagga gacagaagga gaagaggaag tggatctgga      1500
attgggagga gcctccaccc accccctgact cctccttatg aagccagctg      1550
ctgaaattag ctactcacca agagtgaggg gcagagactt ccagtcactg      1600
```

```
agtctcccag gccccttga tctgtacccc acccctatct aacaccaccc         1650
ttggctccca ctccagctcc ctgtattgat ataacctgtc aggctggctt         1700
ggttaggttt tactggggca gaggataggg aatctcttat taaaactaac         1750
atgaaatatg tgttgttttc atttgcaaat ttaaataaag atacataatg         1800
tttgtatgaa aaa                                                 1813
```

<210> SEQ ID NO 110
<211> LENGTH: 390
<212> TYPE: PRT
<213> ORGANISM: Homo Sapien

<400> SEQUENCE: 110

```
Met Ile Ser Leu Pro Gly Pro Leu Val Thr Asn Leu Leu Arg Phe
 1               5                  10                  15

Leu Phe Leu Gly Leu Ser Ala Leu Ala Pro Pro Ser Arg Ala Gln
                20                  25                  30

Leu Gln Leu His Leu Pro Ala Asn Arg Leu Gln Ala Val Glu Gly
            35                  40                  45

Gly Glu Val Val Leu Pro Ala Trp Tyr Thr Leu His Gly Glu Val
        50                  55                  60

Ser Ser Ser Gln Pro Trp Glu Val Pro Phe Val Met Trp Phe Phe
    65                  70                  75

Lys Gln Lys Glu Lys Glu Asp Gln Val Leu Ser Tyr Ile Asn Gly
                80                  85                  90

Val Thr Thr Ser Lys Pro Gly Val Ser Leu Val Tyr Ser Met Pro
                95                 100                 105

Ser Arg Asn Leu Ser Leu Arg Leu Glu Gly Leu Gln Glu Lys Asp
               110                 115                 120

Ser Gly Pro Tyr Ser Cys Ser Val Asn Val Gln Asp Lys Gln Gly
               125                 130                 135

Lys Ser Arg Gly His Ser Ile Lys Thr Leu Glu Leu Asn Val Leu
               140                 145                 150

Val Pro Pro Ala Pro Pro Ser Cys Arg Leu Gln Gly Val Pro His
               155                 160                 165

Val Gly Ala Asn Val Thr Leu Ser Cys Gln Ser Pro Arg Ser Lys
               170                 175                 180

Pro Ala Val Gln Tyr Gln Trp Asp Arg Gln Leu Pro Ser Phe Gln
               185                 190                 195

Thr Phe Phe Ala Pro Ala Leu Asp Val Ile Arg Gly Ser Leu Ser
               200                 205                 210

Leu Thr Asn Leu Ser Ser Ser Met Ala Gly Val Tyr Val Cys Lys
               215                 220                 225

Ala His Asn Glu Val Gly Thr Ala Gln Cys Asn Val Thr Leu Glu
               230                 235                 240

Val Ser Thr Gly Pro Gly Ala Ala Val Ala Gly Ala Val Val
               245                 250                 255

Gly Thr Leu Val Gly Leu Gly Leu Leu Ala Gly Leu Val Leu Leu
               260                 265                 270

Tyr His Arg Arg Gly Lys Ala Leu Glu Glu Pro Ala Asn Asp Ile
               275                 280                 285

Lys Glu Asp Ala Ile Ala Pro Arg Thr Leu Pro Trp Pro Lys Ser
               290                 295                 300
```

-continued

```
Ser Asp Thr Ile Ser Lys Asn Gly Thr Leu Ser Ser Val Thr Ser
            305                 310                 315

Ala Arg Ala Leu Arg Pro Pro His Gly Pro Pro Arg Pro Gly Ala
            320                 325                 330

Leu Thr Pro Thr Pro Ser Leu Ser Ser Gln Ala Leu Pro Ser Pro
            335                 340                 345

Arg Leu Pro Thr Thr Asp Gly Ala His Pro Gln Pro Ile Ser Pro
            350                 355                 360

Ile Pro Gly Gly Val Ser Ser Gly Leu Ser Arg Met Gly Ala
            365                 370                 375

Val Pro Val Met Val Pro Ala Gln Ser Gln Ala Gly Ser Leu Val
            380                 385                 390
```

<210> SEQ ID NO 111
<211> LENGTH: 22
<212> TYPE: DNA
<213> ORGANISM: Artificial Sequence
<220> FEATURE:
<223> OTHER INFORMATION: Synthetic oligonucleotide probe

<400> SEQUENCE: 111
agggtctcca ggagaaagac tc                                          22

<210> SEQ ID NO 112
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 112
attgtgggcc ttgcagacat agac                                        24

<210> SEQ ID NO 113
<211> LENGTH: 50
<212> TYPE: DNA
<213> ORGANISM: Artificial Sequence
<220> FEATURE:
<223> OTHER INFORMATION: Synthetic oligonucleotide probe

<400> SEQUENCE: 113
ggccacagca tcaaaacctt agaactcaat gtactggttc ctccagctcc            50

<210> SEQ ID NO 114
<211> LENGTH: 2479
<212> TYPE: DNA
<213> ORGANISM: Homo Sapien

<400> SEQUENCE: 114
acttgccatc acctgttgcc agtgtggaaa aattctccct gttgaatttt            50
ttgcacatgg aggacagcag caaagagggc aacacaggct gataagacca           100
gagacagcag ggagattatt ttaccatacg ccctcaggac gttccctcta           150
gctggagttc tggacttcaa cagaaccccca tccagtcatt ttgattttgc          200
tgtttatttt ttttttcttt ttcttttttcc caccacattg tatttattt            250 ccgtacttca gaaatgggcc tacagaccac aaagtggccc agccatgggg           300
cttttttcct gaagtcttgg cttatcattt ccctggggct ctactcacag           350
gtgtccaaac tcctggcctg ccctagtgtg tgccgctgcg acaggaactt           400
tgtctactgt aatgagcgaa gcttgacctc agtgcctctt gggatcccgg           450
```

-continued

| | |
|---|---|
| agggcgtaac cgtactctac ctccacaaca accaaattaa taatgctgga | 500 |
| tttcctgcag aactgcacaa tgtacagtcg gtgcacacgg tctacctgta | 550 |
| tggcaaccaa ctggacgaat tccccatgaa ccttcccaag aatgtcagag | 600 |
| ttctccattt gcaggaaaac aatattcaga ccatttcacg ggctgctctt | 650 |
| gcccagctct tgaagcttga agagctgcac ctggatgaca actccatatc | 700 |
| cacagtgggg gtggaagacg gggccttccg ggaggctatt agcctcaaat | 750 |
| tgttgttttt gtctaagaat cacctgagca gtgtgcctgt tgggcttcct | 800 |
| gtggacttgc aagagctgag agtggatgaa atcgaattg ctgtcatatc | 850 |
| cgacatggcc ttccagaatc tcacgagctt ggagcgtctt attgtggacg | 900 |
| ggaacctcct gaccaacaag ggtatcgccg agggcacctt cagccatctc | 950 |
| accaagctca aggaattttc aattgtacgt aattcgctgt cccaccctcc | 1000 |
| tcccgatctc ccaggtacgc atctgatcag gctctatttg caggacaacc | 1050 |
| agataaacca cattcctttg acagccttct caaatctgcg taagctggaa | 1100 |
| cggctggata tatccaacaa ccaactgcgg atgctgactc aaggggtttt | 1150 |
| tgataatctc tccaacctga agcagctcac tgctcggaat aacccttggt | 1200 |
| tttgtgactg cagtattaaa tgggtcacag aatggctcaa atatatccct | 1250 |
| tcatctctca acgtgcgggg tttcatgtgc caaggtcctg aacaagtccg | 1300 |
| ggggatggcc gtcagggaat taaatatgaa tcttttgtcc tgtcccacca | 1350 |
| cgaccccgg cctgcctctc ttcaccccag ccccaagtac agcttctccg | 1400 |
| accactcagc ctcccaccct ctctattcca accctagca gaagctacac | 1450 |
| gcctccaact cctaccacat cgaaacttcc cacgattcct gactgggatg | 1500 |
| gcagagaaag agtgaccca cctatttctg aacggatcca gctctctatc | 1550 |
| cattttgtga atgatacttc cattcaagtc agctggctct ctctcttcac | 1600 |
| cgtgatggca tacaaactca catgggtgaa aatgggccac agtttagtag | 1650 |
| ggggcatcgt tcaggagcgc atagtcagcg gtgagaagca acacctgagc | 1700 |
| ctggttaact tagagccccg atccacctat cggatttgtt tagtgccact | 1750 |
| ggatgctttt aactaccgcg cggtagaaga caccatttgt tcagaggcca | 1800 |
| ccacccatgc ctcctatctg aacaacggca gcaacacagc gtccagccat | 1850 |
| gagcagacga cgtcccacag catgggctcc ccctttctgc tggcgggctt | 1900 |
| gatcgggggc gcggtgatat ttgtgctggt ggtcttgctc agcgtctttt | 1950 |
| gctggcatat gcacaaaaag gggcgctaca cctcccagaa gtggaaatac | 2000 |
| aaccggggcc ggcggaaaga tgattattgc gaggcaggca ccaagaagga | 2050 |
| caactccatc ctggagatga cagaaaccag ttttcagatc gtctccttaa | 2100 |
| ataacgatca actccttaaa ggagatttca gactgcagcc catttacacc | 2150 |
| ccaaatgggg gcattaatta cacagactgc catatcccca caacatgcg | 2200 |
| atactgcaac agcagcgtgc cagacctgga gcactgccat acgtgacagc | 2250 |
| cagaggccca gcgttatcaa ggcggacaat tagactcttg agaacacact | 2300 |
| cgtgtgtgca cataaagaca cgcagattac atttgataaa tgttacacag | 2350 |
| atgcatttgt gcatttgaat actctgtaat ttatacggtg tactatataa | 2400 |

-continued

```
tgggatttaa aaaaagtgct atcttttcta tttcaagtta attacaaaca         2450
gttttgtaac tctttgcttt ttaaatctt                                2479
```

<210> SEQ ID NO 115
<211> LENGTH: 660
<212> TYPE: PRT
<213> ORGANISM: Homo Sapien

<400> SEQUENCE: 115

```
Met Gly Leu Gln Thr Thr Lys Trp Pro Ser His Gly Ala Phe Phe
 1               5                  10                  15

Leu Lys Ser Trp Leu Ile Ile Ser Leu Gly Leu Tyr Ser Gln Val
                20                  25                  30

Ser Lys Leu Leu Ala Cys Pro Ser Val Cys Arg Cys Asp Arg Asn
                35                  40                  45

Phe Val Tyr Cys Asn Glu Arg Ser Leu Thr Ser Val Pro Leu Gly
                50                  55                  60

Ile Pro Glu Gly Val Thr Val Leu Tyr Leu His Asn Asn Gln Ile
                65                  70                  75

Asn Asn Ala Gly Phe Pro Ala Glu Leu His Asn Val Gln Ser Val
                80                  85                  90

His Thr Val Tyr Leu Tyr Gly Asn Gln Leu Asp Glu Phe Pro Met
                95                 100                 105

Asn Leu Pro Lys Asn Val Arg Val Leu His Leu Gln Glu Asn Asn
               110                 115                 120

Ile Gln Thr Ile Ser Arg Ala Ala Leu Ala Gln Leu Leu Lys Leu
               125                 130                 135

Glu Glu Leu His Leu Asp Asp Asn Ser Ile Ser Thr Val Gly Val
               140                 145                 150

Glu Asp Gly Ala Phe Arg Glu Ala Ile Ser Leu Lys Leu Leu Phe
               155                 160                 165

Leu Ser Lys Asn His Leu Ser Ser Val Pro Val Gly Leu Pro Val
               170                 175                 180

Asp Leu Gln Glu Leu Arg Val Asp Glu Asn Arg Ile Ala Val Ile
               185                 190                 195

Ser Asp Met Ala Phe Gln Asn Leu Thr Ser Leu Glu Arg Leu Ile
               200                 205                 210

Val Asp Gly Asn Leu Leu Thr Asn Lys Gly Ile Ala Glu Gly Thr
               215                 220                 225

Phe Ser His Leu Thr Lys Leu Lys Glu Phe Ser Ile Val Arg Asn
               230                 235                 240

Ser Leu Ser His Pro Pro Asp Leu Pro Gly Thr His Leu Ile
               245                 250                 255

Arg Leu Tyr Leu Gln Asp Asn Gln Ile Asn His Ile Pro Leu Thr
               260                 265                 270

Ala Phe Ser Asn Leu Arg Lys Leu Glu Arg Leu Asp Ile Ser Asn
               275                 280                 285

Asn Gln Leu Arg Met Leu Thr Gln Gly Val Phe Asp Asn Leu Ser
               290                 295                 300

Asn Leu Lys Gln Leu Thr Ala Arg Asn Asn Pro Trp Phe Cys Asp
               305                 310                 315

Cys Ser Ile Lys Trp Val Thr Glu Trp Leu Lys Tyr Ile Pro Ser
               320                 325                 330

Ser Leu Asn Val Arg Gly Phe Met Cys Gln Gly Pro Glu Gln Val
```

```
                    335                 340                 345
Arg Gly Met Ala Val Arg Glu Leu Asn Met Asn Leu Leu Ser Cys
                350                 355                 360
Pro Thr Thr Thr Pro Gly Leu Pro Leu Phe Thr Pro Ala Pro Ser
                365                 370                 375
Thr Ala Ser Pro Thr Thr Gln Pro Pro Thr Leu Ser Ile Pro Asn
                380                 385                 390
Pro Ser Arg Ser Tyr Thr Pro Pro Thr Pro Thr Thr Ser Lys Leu
                395                 400                 405
Pro Thr Ile Pro Asp Trp Asp Gly Arg Glu Arg Val Thr Pro Pro
                410                 415                 420
Ile Ser Glu Arg Ile Gln Leu Ser Ile His Phe Val Asn Asp Thr
                425                 430                 435
Ser Ile Gln Val Ser Trp Leu Ser Leu Phe Thr Val Met Ala Tyr
                440                 445                 450
Lys Leu Thr Trp Val Lys Met Gly His Ser Leu Val Gly Gly Ile
                455                 460                 465
Val Gln Glu Arg Ile Val Ser Gly Glu Lys Gln His Leu Ser Leu
                470                 475                 480
Val Asn Leu Glu Pro Arg Ser Thr Tyr Arg Ile Cys Leu Val Pro
                485                 490                 495
Leu Asp Ala Phe Asn Tyr Arg Ala Val Glu Asp Thr Ile Cys Ser
                500                 505                 510
Glu Ala Thr Thr His Ala Ser Tyr Leu Asn Asn Gly Ser Asn Thr
                515                 520                 525
Ala Ser Ser His Glu Gln Thr Thr Ser His Ser Met Gly Ser Pro
                530                 535                 540
Phe Leu Leu Ala Gly Leu Ile Gly Gly Ala Val Ile Phe Val Leu
                545                 550                 555
Val Val Leu Leu Ser Val Phe Cys Trp His Met His Lys Lys Gly
                560                 565                 570
Arg Tyr Thr Ser Gln Lys Trp Lys Tyr Asn Arg Gly Arg Arg Lys
                575                 580                 585
Asp Asp Tyr Cys Glu Ala Gly Thr Lys Lys Asp Asn Ser Ile Leu
                590                 595                 600
Glu Met Thr Glu Thr Ser Phe Gln Ile Val Ser Leu Asn Asn Asp
                605                 610                 615
Gln Leu Leu Lys Gly Asp Phe Arg Leu Gln Pro Ile Tyr Thr Pro
                620                 625                 630
Asn Gly Gly Ile Asn Tyr Thr Asp Cys His Ile Pro Asn Asn Met
                635                 640                 645
Arg Tyr Cys Asn Ser Ser Val Pro Asp Leu Glu His Cys His Thr
                650                 655                 660
```

<210> SEQ ID NO 116
<211> LENGTH: 21
<212> TYPE: DNA
<213> ORGANISM: Artificial Sequence
<220> FEATURE:
<223> OTHER INFORMATION: Synthetic oligonucleotide probe

<400> SEQUENCE: 116
cggtctacct gtatggcaac c     21

<210> SEQ ID NO 117

-continued

```
<211> LENGTH: 22
<212> TYPE: DNA
<213> ORGANISM: Artificial Sequence
<220> FEATURE:
<223> OTHER INFORMATION: Synthetic oligonucleotide probe

<400> SEQUENCE: 117
gcaggacaac cagataaacc ac                                              22

<210> SEQ ID NO 118
<211> LENGTH: 22
<212> TYPE: DNA
<213> ORGANISM: Artificial Sequence
<220> FEATURE:
<223> OTHER INFORMATION: Synthetic oligonucleotide probe

<400> SEQUENCE: 118
acgcagattt gagaaggctg tc                                              22

<210> SEQ ID NO 119
<211> LENGTH: 46
<212> TYPE: DNA
<213> ORGANISM: Artificial Sequence
<220> FEATURE:
<223> OTHER INFORMATION: Synthetic oligonucleotide probe

<400> SEQUENCE: 119
ttcacgggct gctcttgccc agctcttgaa gcttgaagag ctgcac                    46

<210> SEQ ID NO 120
<211> LENGTH: 2857
<212> TYPE: DNA
<213> ORGANISM: Homo Sapien

<400> SEQUENCE: 120
tgaagagtaa tagttggaat caaaagagtc aacgcaatga actgttattt                50
actgctgcgt tttatgttgg gaattcctct cctatggcct tgtcttggag               100
caacagaaaa ctctcaaaca agaaagtca agcagccagt gcgatctcat                150
ttgagagtga agcgtggctg ggtgtggaac caatttttg taccagagga                200
aatgaatacg actagtcatc acatcggcca gctaagatct gatttagaca               250
atggaaacaa ttcttccag tacaagcttt tgggagctgg agctggaagt                300
actttatca ttgatgaaag aacaggtgac atatatgcca tacagaagct                350
tgatagagag gagcgatccc tctacatctt aagagcccag gtaatagaca               400
tcgctactgg aagggctgtg gaacctgagt ctgagtttgt catcaaagtt               450
tcggatatca atgacaatga accaaaattc ctagatgaac cttatgaggc               500
cattgtacca gagatgtctc cagaaggaac attagttatc caggtgacag               550
caagtgatgc tgacgatccc tcaagtggta ataatgctcg tctcctctac               600
agcttacttc aaggccagcc atattttct gttgaaccaa caacaggagt                650
cataagaata tcttctaaaa tggatagaga actgcaagat gagtattggg                700
taatcattca agccaaggac atgattggtc agccaggagc gttgtctgga                750
acaacaagtg tattaattaa actttcgat gttaatgaca ataagcctat                800
atttaaagaa agtttatacc gcttgactgt ctctgaatct gcacccactg                850
ggacttctat aggaacaatc atggcatatg ataatgacat aggagagaat                900
gcagaaatgg attacagcat tgaagaggat gattcgcaaa catttgacat                950
```

-continued

| | |
|---|---|
| tattactaat catgaaactc aagaaggaat agttatatta aaaaagaaag | 1000 |
| tggattttga gcaccagaac cactacggta ttagagcaaa agttaaaaac | 1050 |
| catcatgttc ctgagcagct catgaagtac cacactgagg cttccaccac | 1100 |
| tttcattaag atccaggtgg aagatgttga tgagcctcct cttttcctcc | 1150 |
| ttccatatta tgtatttgaa gtttttgaag aaaccccaca gggatcattt | 1200 |
| gtaggcgtgg tgtctgccac agacccagac aataggaaat ctcctatcag | 1250 |
| gtattctatt actaggagca aagtgttcaa tatcaatgat aatggtacaa | 1300 |
| tcactacaag taactcactg gatcgtgaaa tcagtgcttg gtacaaccta | 1350 |
| agtattacag ccacagaaaa atacaatata gaacagatct cttcgatccc | 1400 |
| actgtatgtg caagttctta acatcaatga tcatgctcct gagttctctc | 1450 |
| aatactatga gacttatgtt tgtgaaaatg caggctctgg tcaggtaatt | 1500 |
| cagactatca gtgcagtgga tagagatgaa tccatagaag agcaccattt | 1550 |
| ttactttaat ctatctgtag aagacactaa caattcaagt tttacaatca | 1600 |
| tagataatca agataacaca gctgtcattt tgactaatag aactggtttt | 1650 |
| aaccttcaag aagaacctgt cttctacatc tccatcttaa ttgccgacaa | 1700 |
| tggaatcccg tcacttacaa gtacaaacac ccttaccatc catgtctgtg | 1750 |
| actgtggtga cagtgggagc acacagacct gccagtacca ggagcttgtg | 1800 |
| cttttccatgg gattcaagac agaagttatc attgctattc tcatttgcat | 1850 |
| tatgatcata tttgggttta ttttttttgac tttgggttta aaacaacgga | 1900 |
| gaaaacagat tctatttcct gagaaaagtg aagatttcag agagaatata | 1950 |
| ttccaatatg atgatgaagg gggtggagaa gaagatacag aggcctttga | 2000 |
| tatagcagag ctgaggagta gtaccataat gcgggaacgc aagactcgga | 2050 |
| aaaccacaag cgctgagatc aggagcctat acaggcagtc tttgcaagtt | 2100 |
| ggcccccgaca gtgccatatt caggaaattc attctggaaa agctcgaaga | 2150 |
| agctaatact gatccgtgtg cccctccttt tgattccctc cagacctacg | 2200 |
| cttttgaggg aacagggtca ttagctggat ccctgagctc cttagaatca | 2250 |
| gcagtctctg atcaggatga aagctatgat taccttaatg agttgggacc | 2300 |
| tcgctttaaa agattagcat gcatgtttgg ttctgcagtg cagtcaaata | 2350 |
| attagggctt tttaccatca aaattttttaa aagtgctaat gtgtattcga | 2400 |
| acccaatggt agtcttaaag agttttgtgc cctggctcta tggcggggaa | 2450 |
| agccctagtc tatggagttt tctgatttcc ctggagtaaa tactccatgg | 2500 |
| ttatttttaag ctacctacat gctgtcattg aacagagatg tggggagaaa | 2550 |
| tgtaaacaat cagctcacag gcatcaatac aaccagattt gaagtaaaat | 2600 |
| aatgtaggaa gatattaaaa gtagatgaga ggacacaaga tgtagtcgat | 2650 |
| ccttatgcga ttatatcatt atttacttag gaaagagtaa aaataccaaa | 2700 |
| cgagaaaatt taaggagca aaaatttgca agtcaaatag aaatgtacaa | 2750 |
| atcgagataa catttacatt tctatcatat tgacatgaaa attgaaaatg | 2800 |
| tatagtcaga gaaattttca tgaattattc catgaagtat tgtttccttt | 2850 |
| atttaaa | 2857 |

<210> SEQ ID NO 121
<211> LENGTH: 772
<212> TYPE: PRT
<213> ORGANISM: Homo Sapien

<400> SEQUENCE: 121

```
Met Asn Cys Tyr Leu Leu Arg Phe Met Leu Gly Ile Pro Leu
  1               5                  10                  15

Leu Trp Pro Cys Leu Gly Ala Thr Glu Asn Ser Gln Thr Lys Lys
                 20                  25                  30

Val Lys Gln Pro Val Arg Ser His Leu Arg Val Lys Arg Gly Trp
             35                  40                  45

Val Trp Asn Gln Phe Phe Val Pro Glu Glu Met Asn Thr Thr Ser
             50                  55                  60

His His Ile Gly Gln Leu Arg Ser Asp Leu Asp Asn Gly Asn Asn
             65                  70                  75

Ser Phe Gln Tyr Lys Leu Leu Gly Ala Gly Ala Gly Ser Thr Phe
                 80                  85                  90

Ile Ile Asp Glu Arg Thr Gly Asp Ile Tyr Ala Ile Gln Lys Leu
                 95                 100                 105

Asp Arg Glu Glu Arg Ser Leu Tyr Ile Leu Arg Ala Gln Val Ile
                110                 115                 120

Asp Ile Ala Thr Gly Arg Ala Val Glu Pro Glu Ser Glu Phe Val
                125                 130                 135

Ile Lys Val Ser Asp Ile Asn Asp Asn Glu Pro Lys Phe Leu Asp
                140                 145                 150

Glu Pro Tyr Glu Ala Ile Val Pro Glu Met Ser Pro Glu Gly Thr
                155                 160                 165

Leu Val Ile Gln Val Thr Ala Ser Asp Ala Asp Asp Pro Ser Ser
                170                 175                 180

Gly Asn Asn Ala Arg Leu Leu Tyr Ser Leu Leu Gln Gly Gln Pro
                185                 190                 195

Tyr Phe Ser Val Glu Pro Thr Thr Gly Val Ile Arg Ile Ser Ser
                200                 205                 210

Lys Met Asp Arg Glu Leu Gln Asp Glu Tyr Trp Val Ile Ile Gln
                215                 220                 225

Ala Lys Asp Met Ile Gly Gln Pro Gly Ala Leu Ser Gly Thr Thr
                230                 235                 240

Ser Val Leu Ile Lys Leu Ser Asp Val Asn Asp Asn Lys Pro Ile
                245                 250                 255

Phe Lys Glu Ser Leu Tyr Arg Leu Thr Val Ser Glu Ser Ala Pro
                260                 265                 270

Thr Gly Thr Ser Ile Gly Thr Ile Met Ala Tyr Asp Asn Asp Ile
                275                 280                 285

Gly Glu Asn Ala Glu Met Asp Tyr Ser Ile Glu Glu Asp Asp Ser
                290                 295                 300

Gln Thr Phe Asp Ile Ile Thr Asn His Glu Thr Gln Glu Gly Ile
                305                 310                 315

Val Ile Leu Lys Lys Lys Val Asp Phe Glu His Gln Asn His Tyr
                320                 325                 330

Gly Ile Arg Ala Lys Val Lys Asn His Val Pro Glu Gln Leu
                335                 340                 345

Met Lys Tyr His Thr Glu Ala Ser Thr Thr Phe Ile Lys Ile Gln
                350                 355                 360
```

-continued

```
Val Glu Asp Val Asp Glu Pro Pro Leu Phe Leu Leu Pro Tyr Tyr
            365                 370                 375

Val Phe Glu Val Phe Glu Thr Pro Gln Gly Ser Phe Val Gly
            380                 385                 390

Val Val Ser Ala Thr Asp Pro Asp Asn Arg Lys Ser Pro Ile Arg
            395                 400                 405

Tyr Ser Ile Thr Arg Ser Lys Val Phe Asn Ile Asn Asp Asn Gly
            410                 415                 420

Thr Ile Thr Thr Ser Asn Ser Leu Asp Arg Glu Ile Ser Ala Trp
            425                 430                 435

Tyr Asn Leu Ser Ile Thr Ala Thr Glu Lys Tyr Asn Ile Glu Gln
            440                 445                 450

Ile Ser Ser Ile Pro Leu Tyr Val Gln Val Leu Asn Ile Asn Asp
            455                 460                 465

His Ala Pro Glu Phe Ser Gln Tyr Tyr Glu Thr Tyr Val Cys Glu
            470                 475                 480

Asn Ala Gly Ser Gly Gln Val Ile Gln Thr Ile Ser Ala Val Asp
            485                 490                 495

Arg Asp Glu Ser Ile Glu Glu His His Phe Tyr Phe Asn Leu Ser
            500                 505                 510

Val Glu Asp Thr Asn Asn Ser Ser Phe Thr Ile Ile Asp Asn Gln
            515                 520                 525

Asp Asn Thr Ala Val Ile Leu Thr Asn Arg Thr Gly Phe Asn Leu
            530                 535                 540

Gln Glu Glu Pro Val Phe Tyr Ile Ser Ile Leu Ile Ala Asp Asn
            545                 550                 555

Gly Ile Pro Ser Leu Thr Ser Thr Asn Thr Leu Thr Ile His Val
            560                 565                 570

Cys Asp Cys Gly Asp Ser Gly Ser Thr Gln Thr Cys Gln Tyr Gln
            575                 580                 585

Glu Leu Val Leu Ser Met Gly Phe Lys Thr Glu Val Ile Ile Ala
            590                 595                 600

Ile Leu Ile Cys Ile Met Ile Ile Phe Gly Phe Ile Phe Leu Thr
            605                 610                 615

Leu Gly Leu Lys Gln Arg Arg Lys Gln Ile Leu Phe Pro Glu Lys
            620                 625                 630

Ser Glu Asp Phe Arg Glu Asn Ile Phe Gln Tyr Asp Asp Glu Gly
            635                 640                 645

Gly Gly Glu Glu Asp Thr Glu Ala Phe Asp Ile Ala Glu Leu Arg
            650                 655                 660

Ser Ser Thr Ile Met Arg Glu Arg Lys Thr Arg Lys Thr Thr Ser
            665                 670                 675

Ala Glu Ile Arg Ser Leu Tyr Arg Gln Ser Leu Gln Val Gly Pro
            680                 685                 690

Asp Ser Ala Ile Phe Arg Lys Phe Ile Leu Glu Lys Leu Glu Glu
            695                 700                 705

Ala Asn Thr Asp Pro Cys Ala Pro Pro Phe Asp Ser Leu Gln Thr
            710                 715                 720

Tyr Ala Phe Glu Gly Thr Gly Ser Leu Ala Gly Ser Leu Ser Ser
            725                 730                 735

Leu Glu Ser Ala Val Ser Asp Gln Asp Glu Ser Tyr Asp Tyr Leu
            740                 745                 750
```

```
Asn Glu Leu Gly Pro Arg Phe Lys Arg Leu Ala Cys Met Phe Gly
        755                 760                 765
Ser Ala Val Gln Ser Asn Asn
        770

<210> SEQ ID NO 122
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 122
cttgactgtc tctgaatctg caccc                                           25

<210> SEQ ID NO 123
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 123
aagtggtgga agcctccagt gtgg                                            24

<210> SEQ ID NO 124
<211> LENGTH: 52
<212> TYPE: DNA
<213> ORGANISM: Artificial Sequence
<220> FEATURE:
<223> OTHER INFORMATION: Synthetic oligonucleotide probe

<400> SEQUENCE: 124
ccactacggt attagagcaa aagttaaaaa ccatcatggt tcctggagca                50
    gc 52

<210> SEQ ID NO 125
<211> LENGTH: 1152
<212> TYPE: DNA
<213> ORGANISM: Homo Sapien

<400> SEQUENCE: 125
cttcagaaca ggttctcctt ccccagtcac cagttgctcg agttagaatt                50
gtctgcaatg gccgccctgc agaaatctgt gagctctttc cttatgggga              100
ccctggccac cagctgcctc cttctcttgg ccctcttggt acaggagga               150 gcagctgcgc ccatcagctc ccactgcagg cttgacaagt ccaacttcca              200
gcagccctat atcaccaacc gcaccttcat gctggctaag gaggctagct              250
tggctgataa caacacagac gttcgtctca ttggggagaa actgttccac              300
ggagtcagta tgagtgagcg ctgctatctg atgaagcagg tgctgaactt              350 caccccttgaa gaagtgctgt tccctcaatc tgataggttc cagccttata              400
tgcaggaggt ggtgcccttc ctggccaggc tcagcaacag gctaagcaca              450
tgtcatattg aaggtgatga cctgcatatc cagaggaatg tgcaaaagct              500
gaaggacaca gtgaaaaagc ttggagagag tggagagatc aaagcaattg              550
gagaactgga tttgctgttt atgtctctga gaaatgcctg catttgacca              600
gagcaaagct gaaaaatgaa taactaaccc cctttccctg ctagaaataa              650
caattagatg ccccaaagcg atttttttta accaaaagga agatgggaag              700
```

| | |
|---|---|
| ccaaactcca tcatgatggg tggattccaa atgaacccct gcgttagtta | 750 |
| caaaggaaac caatgccact tttgtttata agaccagaag gtagactttc | 800 |
| taagcataga tatttattga taacatttca ttgtaactgg tgttctatac | 850 |
| acagaaaaca atttatttt taaataattg tcttttcca taaaaagat | 900 |
| tactttccat tcctttaggg gaaaaaaccc ctaaatagct tcatgttcc | 950 |
| ataatcagta ctttatattt ataaatgtat ttattattat tataagactg | 1000 |
| cattttattt atatcatttt attaatatgg atttatttat agaaacatca | 1050 |
| ttcgatattg ctacttgagt gtaaggctaa tattgatatt tatgacaata | 1100 |
| attatagagc tataacatgt ttatttgacc tcaataaaca cttggatatc | 1150 |
| cc | 1152 |

<210> SEQ ID NO 126
<211> LENGTH: 179
<212> TYPE: PRT
<213> ORGANISM: Homo Sapien

<400> SEQUENCE: 126

```
Met Ala Ala Leu Gln Lys Ser Val Ser Ser Phe Leu Met Gly Thr
 1               5                  10                  15
Leu Ala Thr Ser Cys Leu Leu Leu Ala Leu Leu Val Gln Gly
                20                  25                  30
Gly Ala Ala Ala Pro Ile Ser Ser His Cys Arg Leu Asp Lys Ser
                35                  40                  45
Asn Phe Gln Gln Pro Tyr Ile Thr Asn Arg Thr Phe Met Leu Ala
                50                  55                  60
Lys Glu Ala Ser Leu Ala Asp Asn Asn Thr Asp Val Arg Leu Ile
                65                  70                  75
Gly Glu Lys Leu Phe His Gly Val Ser Met Ser Glu Arg Cys Tyr
                80                  85                  90
Leu Met Lys Gln Val Leu Asn Phe Thr Leu Glu Glu Val Leu Phe
                95                 100                 105
Pro Gln Ser Asp Arg Phe Gln Pro Tyr Met Gln Glu Val Val Pro
               110                 115                 120
Phe Leu Ala Arg Leu Ser Asn Arg Leu Ser Thr Cys His Ile Glu
               125                 130                 135
Gly Asp Asp Leu His Ile Gln Arg Asn Val Gln Lys Leu Lys Asp
               140                 145                 150
Thr Val Lys Lys Leu Gly Glu Ser Gly Glu Ile Lys Ala Ile Gly
               155                 160                 165
Glu Leu Asp Leu Leu Phe Met Ser Leu Arg Asn Ala Cys Ile
               170                 175
```

<210> SEQ ID NO 127
<211> LENGTH: 2557
<212> TYPE: DNA
<213> ORGANISM: Homo Sapien

<400> SEQUENCE: 127

| | |
|---|---|
| gccctaacct tcccagggct cagctctttg gagctgccca ttcctccggc | 50 |
| tgcgagaaag gacgcgcgcc ctgcgtcggg cgaagaaaag aagcaaaact | 100 |
| tgtcgggagg gtttcgtcat caacctcctt cccgcaaacc taaacctcct | 150 |
| gccggggcca tccctagaca gaggaaagtt cctgcagagc cgaccagccc | 200 |

-continued

```
tagtggatct ggggcaggca gcggcgctgg ctgtggaatt agatctgttt      250
tgaacccagt ggagcgcatc gctggggctc ggaagtcacc gtccgcgggc      300
accgggttgg cgctgcccga gtggaaccga cagtttgcga gcctcggctg      350
caagtggcct ctcctccccg cggttgttgt tcagtgtcgg gtgagggctg      400
cgagtgtggc aagttgcaaa gagagcctca gaggtccgaa gagcgctgcg      450
ctcctactcg cgttcgcttc ttcctcttct cggttcccta ctgtgaaatc      500
gcagcgacat ttacaaaggc ctccgggtcc taccgagacc gatccgcagc      550
gtttggcccg gtcgtgccta ttgcatcggg agcccccgag caccggcgaa      600
atggcgaggt tcccgaaggc cgacctggcc gctgcaggag ttatgttact      650
ttgccacttc ttcacggacc agtttcagtt cgccgatggg aaacccggag      700
accaaatcct tgattggcag tatggagtta ctcaggcctt ccctcacaca      750
gaggaggagg tggaagttga ttcacacgcg tacagccaca ggtggaaaag      800
aaacttggac tttctcaagg cggtagacac gaaccgagca agcgtcggcc      850
aagactctcc tgagcccaga agcttcacag acctgctgct ggatgatggg      900
caggacaata acactcagat cgaggaggat acagaccaca attactatat      950
atctcgaata tatggtccat ctgattctgc cagccgggat ttatgggtga     1000
acatagacca aatggaaaaa gataaagtga agattcatgg aatattgtcc     1050
aatactcatc ggcaagctgc aagagtgaat ctgtccttcg attttccatt     1100
ttatggccac ttcctacgtg aaatcactgt ggcaaccggg ggtttcatat     1150
acactggaga agtcgtacat cgaatgctaa cagccacaca gtacatagca     1200
cctttaatgg caaatttcga tcccagtgta tccagaaatt caactgtcag     1250
atattttgat aatggcacag cacttgtggt ccagtgggac catgtacatc     1300
tccaggataa ttataacctg ggaagcttca cattccaggc aaccctgctc     1350
atggatggac gaatcatctt tggatacaaa gaaattcctg tcttggtcac     1400
acagataagt tcaaccaatc atccagtgaa agtcggactg tccgatgcat     1450
ttgtcgttgt ccacaggatc caacaaattc ccaatgttcg aagaagaaca     1500
atttatgaat accaccgagt agagctacaa atgtcaaaaa ttaccaacat     1550
ttcggctgtg gagatgaccc cattacccac atgcctccag tttaacagat     1600
gtggcccctg tgtatcttct cagattggct tcaactgcag ttggtgtagt     1650
aaacttcaaa gatgttccag tggatttgat cgtcatcggc aggactgggt     1700
ggacagtgga tgccctgaag agtcaaaaga gaagatgtgt gagaatacag     1750
aaccagtgga aacttcttct cgaaccacca caaccgtagg agcgacaacc     1800
acccagttca gggtcctaac taccaccaga agagcagtga cttctcagtt     1850
tcccaccagc ctccctacag aagatgatac caagatagcc ctacatctaa     1900
aagataatgg agcttctaca gatgacagtg cagctgagaa gaaaggggga     1950
accctccacg ctggcctcat cattggaatc ctcatcctgg tcctcattgt     2000
agccacagcc attcttgtga cagtctatat gtatcaccac ccaacatcag     2050
cagccagcat cttctttatt gagagacgcc caagcagatg gcctgcgatg     2100
aagtttagaa gaggctctgg acatcctgcc tatgctgaag ttgaaccagt     2150
```

| | |
|---|---|
| tggagagaaa gaaggcttta ttgtatcaga gcagtgctaa aatttctagg | 2200 |
| acagaacaac accagtactg gtttacaggt gttaagacta aaattttgcc | 2250 |
| tataccttta agacaaacaa acaaacacac acacaaacaa gctctaagct | 2300 |
| gctgtagcct gaagaagaca agatttctgg acaagctcag cccaggaaac | 2350 |
| aaagggtaaa caaaaaacta aacttatac aagataccat ttacactgaa | 2400 |
| catagaattc cctagtggaa tgtcatctat agttcactcg gaacatctcc | 2450 |
| cgtggactta tctgaagtat gacaagatta taatgctttt ggcttaggtg | 2500 |
| cagggttgca aagggatcag aaaaaaaaaa tcataataaa gctttagttc | 2550 |
| atgaggg | 2557 |

<210> SEQ ID NO 128
<211> LENGTH: 529
<212> TYPE: PRT
<213> ORGANISM: Homo Sapien

<400> SEQUENCE: 128

```
Met Ala Arg Phe Pro Lys Ala Asp Leu Ala Ala Gly Val Met
 1               5                  10                  15
Leu Leu Cys His Phe Thr Asp Gln Phe Gln Phe Ala Asp Gly
                20                  25                  30
Lys Pro Gly Asp Gln Ile Leu Asp Trp Gln Tyr Gly Val Thr Gln
                35                  40                  45
Ala Phe Pro His Thr Glu Glu Val Glu Val Asp Ser His Ala
                50                  55                  60
Tyr Ser His Arg Trp Lys Arg Asn Leu Asp Phe Leu Lys Ala Val
                65                  70                  75
Asp Thr Asn Arg Ala Ser Val Gly Gln Asp Ser Pro Glu Pro Arg
                80                  85                  90
Ser Phe Thr Asp Leu Leu Asp Asp Gly Gln Asp Asn Asn Thr
                95                  100                 105
Gln Ile Glu Glu Asp Thr Asp His Asn Tyr Tyr Ile Ser Arg Ile
                110                 115                 120
Tyr Gly Pro Ser Asp Ser Ala Ser Arg Asp Leu Trp Val Asn Ile
                125                 130                 135
Asp Gln Met Glu Lys Asp Lys Val Lys Ile His Gly Ile Leu Ser
                140                 145                 150
Asn Thr His Arg Gln Ala Ala Arg Val Asn Leu Ser Phe Asp Phe
                155                 160                 165
Pro Phe Tyr Gly His Phe Leu Arg Glu Ile Thr Val Ala Thr Gly
                170                 175                 180
Gly Phe Ile Tyr Thr Gly Glu Val Val His Arg Met Leu Thr Ala
                185                 190                 195
Thr Gln Tyr Ile Ala Pro Leu Met Ala Asn Phe Asp Pro Ser Val
                200                 205                 210
Ser Arg Asn Ser Thr Val Arg Tyr Phe Asp Asn Gly Thr Ala Leu
                215                 220                 225
Val Val Gln Trp Asp His Val His Leu Gln Asp Asn Tyr Asn Leu
                230                 235                 240
Gly Ser Phe Thr Phe Gln Ala Thr Leu Leu Met Asp Gly Arg Ile
                245                 250                 255
Ile Phe Gly Tyr Lys Glu Ile Pro Val Leu Val Thr Gln Ile Ser
                260                 265                 270
```

| | | | | | | | | | | |
|---|---|---|---|---|---|---|---|---|---|---|
|Ser|Thr|Asn|His|Pro|Val|Lys|Val|Gly|Leu|Ser|Asp|Ala|Phe|Val|
| | |  |275| | | |280| | | |  |  | |285|
|Val|Val|His|Arg|Ile|Gln|Gln|Ile|Pro|Asn|Val|Arg|Arg|Arg|Thr|
| | |  |290| | | |295| | | |  |  | |300|
|Ile|Tyr|Glu|Tyr|His|Arg|Val|Glu|Leu|Gln|Met|Ser|Lys|Ile|Thr|
| | |  |305| | | |310| | | |  |  | |315|
|Asn|Ile|Ser|Ala|Val|Glu|Met|Thr|Pro|Leu|Pro|Thr|Cys|Leu|Gln|
| | |  |320| | | |325| | | |  |  | |330|
|Phe|Asn|Arg|Cys|Gly|Pro|Cys|Val|Ser|Ser|Gln|Ile|Gly|Phe|Asn|
| | |  |335| | | |340| | | |  |  | |345|
|Cys|Ser|Trp|Cys|Ser|Lys|Leu|Gln|Arg|Cys|Ser|Ser|Gly|Phe|Asp|
| | |  |350| | | |355| | | |  |  | |360|
|Arg|His|Arg|Gln|Asp|Trp|Val|Asp|Ser|Gly|Cys|Pro|Glu|Glu|Ser|
| | |  |365| | | |370| | | |  |  | |375|
|Lys|Glu|Lys|Met|Cys|Glu|Asn|Thr|Glu|Pro|Val|Glu|Thr|Ser|Ser|
| | |  |380| | | |385| | | |  |  | |390|
|Arg|Thr|Thr|Thr|Thr|Val|Gly|Ala|Thr|Thr|Gln|Phe|Arg|Val|
| | |  |395| | | |400| | | |  |  | |405|
|Leu|Thr|Thr|Thr|Arg|Arg|Ala|Val|Thr|Ser|Gln|Phe|Pro|Thr|Ser|
| | |  |410| | | |415| | | |  |  | |420|
|Leu|Pro|Thr|Glu|Asp|Asp|Thr|Lys|Ile|Ala|Leu|His|Leu|Lys|Asp|
| | |  |425| | | |430| | | |  |  | |435|
|Asn|Gly|Ala|Ser|Thr|Asp|Asp|Ser|Ala|Ala|Glu|Lys|Lys|Gly|Gly|
| | |  |440| | | |445| | | |  |  | |450|
|Thr|Leu|His|Ala|Gly|Leu|Ile|Ile|Gly|Ile|Leu|Ile|Leu|Val|Leu|
| | |  |455| | | |460| | | |  |  | |465|
|Ile|Val|Ala|Thr|Ala|Ile|Leu|Val|Thr|Val|Tyr|Met|Tyr|His|His|
| | |  |470| | | |475| | | |  |  | |480|
|Pro|Thr|Ser|Ala|Ala|Ser|Ile|Phe|Phe|Ile|Glu|Arg|Arg|Pro|Ser|
| | |  |485| | | |490| | | |  |  | |495|
|Arg|Trp|Pro|Ala|Met|Lys|Phe|Arg|Arg|Gly|Ser|Gly|His|Pro|Ala|
| | |  |500| | | |505| | | |  |  | |510|
|Tyr|Ala|Glu|Val|Glu|Pro|Val|Gly|Glu|Lys|Glu|Gly|Phe|Ile|Val|
| | |  |515| | | |520| | | |  |  | |525|
|Ser|Glu|Gln|Cys| | | | | | | | | | | |

<210> SEQ ID NO 129
<211> LENGTH: 4834
<212> TYPE: DNA
<213> ORGANISM: Homo Sapien
<220> FEATURE:
<221> NAME/KEY: unsure
<222> LOCATION: 3784
<223> OTHER INFORMATION: unknown base

<400> SEQUENCE: 129

```
gcagccctag cagggatgga catgatgctg ttggtgcagg gtgcttgttg        50
ctcgaaccag tggctggcgg cggtgctcct cagcctgtgc tgcctgctac       100
cctcctgcct cccggctgga cagagtgtgg acttcccctg gcggccgtg        150
gacaacatga tggtcagaaa agggacacg gcggtgctta gtgttatt          200
ggaagatgga gcttcaaagg gtgcctggct gaaccggtca agtattattt       250
ttgcgggagg tgataagtgg tcagtggatc ctcgagtttc aatttcaaca       300
ttgaataaaa gggactacag cctccagata cagaatgtag atgtgacaga       350
```

-continued

```
tgatggccca tacacgtgtt ctgttcagac tcaacataca cccagaacaa      400
tgcaggtgca tctaactgtg caagttcctc ctaagatata tgacatctca      450
aatgatatga ccgtcaatga aggaaccaac gtcactctta cttgtttggc      500
cactgggaaa ccagagcctt ccatttcttg gcgacacatc tccccatcag      550
caaaaccatt tgaaaatgga caatatttgg acatttatgg aattacaagg      600
gaccaggctg gggaatatga atgcagtgcg gaaaatgatg tgtcattccc      650
agatgtgagg aaagtaaaag ttgttgtcaa ctttgctcct actattcagg      700
aaattaaatc tggcaccgtg accccggac gcagtggcct gataagatgt       750
gaaggtgcag gtgtgccgcc tccagccttt gaatggtaca aggagagaa       800 gaagctcttc aatggccaac aaggaattat tattcaaaat tttagcacaa      850
gatccattct cactgttacc aacgtgacac aggagcactt cggcaattat      900
acttgtgtgg ctgccaacaa gctaggcaca accaatgcga gcctgcctct      950
taaccctcca gtacagccc agtatggaat taccgggagc gctgatgttc       1000
ttttctcctg ctggtacctt tgtgttgacac tgtcctcttt caccagcata     1050
ttctacctga agaatgccat tctacaataa attcaaagac ccataaaagg      1100
cttttaagga ttctctgaaa gtgctgatgg ctggatccaa tctggtacag      1150
tttgttaaaa gcagcgtggg atataatcag cagtgcttac atggggatga      1200
tcgccttctg tagaattgct cattatgtaa atactttaat tctactcttt      1250
tttgattagc tacattacct tgtgaagcag tacacattgt cctttttta       1300 agacgtgaaa gctctgaaat tacttttaga ggatattaat tgtgatttca      1350
tgtttgtaat ctacaacttt tcaaaagcat tcagtcatgg tctgctaggt      1400
tgcaggctgt agtttacaaa aacgaatatt gcagtgaata tgtgattctt      1450
taaggctgca atacaagcat tcagttccct gtttcaataa gagtcaatcc      1500
acatttacaa agatgcattt ttttcttttt tgataaaaaa gcaaataata      1550
ttgccttcag attatttctt caaaatataa cacatatcta gattttctg       1600 ctcgcatgat attcaggttt caggaatgag ccttgtaata taactggctg      1650
tgcagctctg cttctctttc ctgtaagttc agcatgggtg tgccttcata      1700
caataatatt tttctctttg tctccaacta atataaaatg ttttgctaaa      1750
tcttacaatt tgaaagtaaa aataaaccag agtgatcaag ttaaaccata      1800
cactatctct aagtaacgaa ggagctattg gactgtaaaa atctcttcct      1850
gcactgacaa tggggtttga gaattttgcc ccacactaac tcagttcttg      1900
tgatgagaga caatttaata acagtatagt aaatatacca tatgatttct      1950
ttagttgtag ctaaatgtta gatccaccgt gggaaatcat tccctttaaa      2000
atgcacgcac agtccactca aaggattgcc tagcaataca gcatcttttc      2050 cttttcactag tccaagccaa aaattttaag atgatttgtc agaaagggca     2100
caaagtccta tcacctaata ttacaagagt tggtaagcgc tcatcattaa      2150 ttttatttg tggcagctaa gttagtatga cagaggcagt gctcctgtgg       2200
acaggagcat tttgcatatt ttccatctga agtatcact cagttgatag       2250 tctggaatgc atgttatata ttttaaaact tccaaaatat attataacaa      2300
```

```
acattctata tcggtatgta gcagaccaat ctctaaaata gctaattctt      2350
caataaaatc tttctatata gccatttcag tgcaaacaag taaaatcaaa      2400
aaagaccatc ctttattttt ccttacatga tatatgtaag atgcgatcaa      2450
ataaagacaa acaccagtg atgagaatat cttaagataa gtaattatca       2500
aattattgtg aatgttaaat tatttctact ataaagaagc aaaactacat      2550
ttttgaagga aaatgctgtt actctaacat taatttacag gaatagtttg      2600
atggtttcac tctttactaa agaaaggcca tcaccttgaa agccatttta      2650
caggtttgat gaagttacca atttcagtac acctaaattt ctacaaatag      2700
tccccttta caagttgtaa caacaaagac cctataataa aattagatac        2750
aagaaatttt gcagtggtta tacatatttg agatatctag tatgttgccc      2800
tagcagggat ggcttaaaaa ctgtgatttt ttttcttcaa gtaaaactta      2850
gtcccaaagt acatcataaa tcaattttaa ttagaaaaat gaatcttaaa      2900
tgagggaca taagtatact ctttccacaa aatggcaata ataaggcata       2950
aagctagtaa atctactaac tgtaataaat gtatgacatt attttgattg      3000
atacattaaa aaagagttttt tagaacaaat atggcattta actttattat     3050
ttatttgctt ttaagaaata ttctttgtgg aattgttgaa taaactataa      3100
aatattattt tgtattgcag ctttaaagtg gcacactcca taataatcta      3150
cttactagaa atagtggtgc taccacaaaa aatgttaacc atcagtacca      3200
ttgtttggga gaaagaaaca gatcaagaat gcatattatt cagtgaccgc      3250
tttcctagag ttaaaatacc tcctctttgt aaggtttgta ggtaaattga      3300
ggtataaact atggatgaac caaataatta gttcaaagtg ttgtcatgat      3350
tccaaatttg tggagtctgg tgttttacc atagaatgtg acagaagtac       3400
agtcatagct cagtagctat atgtatttgc ctttatgtta gaagagactt      3450
tcttgagtga catttttaaa tagaggaggt attcactatg tttttctgta      3500
tcacagcagc attcctagtc cttaggccct cggacagagt gaaatcatga      3550
gtatttatga gttcaatatt gtcaaataag gctacagtat ttgcttttt      3600
gtgtgaatgt attgcatata atgttcaagt agatgatttt acatttatgg     3650
acatataaaa tgtctgatta ccccatttta tcagtcctga ctgtacaaga     3700
ttgttgcaat ttcagaatag cagttttata aattgattta tcttttaatc     3750
tataacaatt tgtgttagct gttcatttca ggantatatt ttctacaagt      3800
tccacttgtg ggactccttt tgttgcccct atttttttt aaagaaggaa       3850
gaaagaaaaa taagtagcag tttaaaaatg agaatggaga gaaagaaaa       3900
agaatgaaaa ggaaaggcag taagaggga aaaaaagga aggatggaag        3950
gaatgaagga aggaagggag gaaggggaga aggtaggaag aaagaaagga      4000
tgagagggaca ggaagaatca gagtattagg gtagttaact tacacatttg    4050
cattcttagt ttaactgcaa gtggtgtaac tatgttttc aatgatcgca       4100
tttgaaacat aagtcctatt ataccattaa gttcctatta tgcagcaatt     4150
atataataaa aagtactgcc caagttatag taatgtgggt gttttgaga      4200
cactaaaaga tttgagaggg agaatttcaa acttaaagcc acttttgggg     4250
ggtttataac ttaactgaaa aattaatgct tcatcataac atttaagcta     4300
```

-continued

```
tatctagaaa gtagactgga gaactgagaa aattacccag gtaattcagg         4350
gaaaaaaaaa aatatatata tatataaata cccctacatt tgaagtcaga         4400
aaactctgaa aaactgaatt atcaaagtca atcatctata atgatcaaat         4450
ttactgaaca attgttaatt tatccattgt gcttagcttt gtgacacagc         4500
caaaagttac ctatttaatc ttttcaataa aaattgtttt ttgaaatcca         4550
gaaatgattt aaaaagaggt caggtttttta actatttatt gaagtatgtg        4600
gatgtacagt atttcaatag atatgaatat gaataaatgg tatgccttaa         4650
gattctttga atatgtattt actttaaaga ctggaaaaag ctcttcctgt         4700
cttttagtaa aacatccata tttcataacc tgatgtaaaa tatgttgtac         4750
tgtttccaat aggtgaatat aaactcagtt tatcaattaa aaaaaaaaa          4800 aaaaaaaaaa aaaaaaaaaa aaaaaaaaaa aaaa                          4834
```

<210> SEQ ID NO 130
<211> LENGTH: 354
<212> TYPE: PRT
<213> ORGANISM: Homo Sapien

<400> SEQUENCE: 130

```
Met Asp Met Met Leu Leu Val Gln Gly Ala Cys Cys Ser Asn Gln
 1               5                  10                  15

Trp Leu Ala Ala Val Leu Leu Ser Leu Cys Cys Leu Leu Pro Ser
                20                  25                  30

Cys Leu Pro Ala Gly Gln Ser Val Asp Phe Pro Trp Ala Ala Val
                35                  40                  45

Asp Asn Met Met Val Arg Lys Gly Asp Thr Ala Val Leu Arg Cys
                50                  55                  60

Tyr Leu Glu Asp Gly Ala Ser Lys Gly Ala Trp Leu Asn Arg Ser
                65                  70                  75

Ser Ile Ile Phe Ala Gly Gly Asp Lys Trp Ser Val Asp Pro Arg
                80                  85                  90

Val Ser Ile Ser Thr Leu Asn Lys Arg Asp Tyr Ser Leu Gln Ile
                95                 100                 105

Gln Asn Val Asp Val Thr Asp Asp Gly Pro Tyr Thr Cys Ser Val
               110                 115                 120

Gln Thr Gln His Thr Pro Arg Thr Met Gln Val His Leu Thr Val
               125                 130                 135

Gln Val Pro Pro Lys Ile Tyr Asp Ile Ser Asn Asp Met Thr Val
               140                 145                 150

Asn Glu Gly Thr Asn Val Thr Leu Thr Cys Leu Ala Thr Gly Lys
               155                 160                 165

Pro Glu Pro Ser Ile Ser Trp Arg His Ile Ser Pro Ser Ala Lys
               170                 175                 180

Pro Phe Glu Asn Gly Gln Tyr Leu Asp Ile Tyr Gly Ile Thr Arg
               185                 190                 195

Asp Gln Ala Gly Glu Tyr Glu Cys Ser Ala Glu Asn Asp Val Ser
               200                 205                 210

Phe Pro Asp Val Arg Lys Val Lys Val Val Asn Phe Ala Pro
               215                 220                 225

Thr Ile Gln Glu Ile Lys Ser Gly Thr Val Thr Pro Gly Arg Ser
               230                 235                 240
```

```
Gly Leu Ile Arg Cys Glu Gly Ala Gly Val Pro Pro Pro Ala Phe
                245                 250                 255

Glu Trp Tyr Lys Gly Glu Lys Lys Leu Phe Asn Gly Gln Gln Gly
                260                 265                 270

Ile Ile Ile Gln Asn Phe Ser Thr Arg Ser Ile Leu Thr Val Thr
                275                 280                 285

Asn Val Thr Gln Glu His Phe Gly Asn Tyr Thr Cys Val Ala Ala
                290                 295                 300

Asn Lys Leu Gly Thr Thr Asn Ala Ser Leu Pro Leu Asn Pro Pro
                305                 310                 315

Ser Thr Ala Gln Tyr Gly Ile Thr Gly Ser Ala Asp Val Leu Phe
                320                 325                 330

Ser Cys Trp Tyr Leu Val Leu Thr Leu Ser Ser Phe Thr Ser Ile
                335                 340                 345

Phe Tyr Leu Lys Asn Ala Ile Leu Gln
                350

<210> SEQ ID NO 131
<211> LENGTH: 823
<212> TYPE: DNA
<213> ORGANISM: Homo Sapien

<400> SEQUENCE: 131
atagtagaag aatgtctctg aaattactgg atgagtttca gtcatacttt           50
cacatgggca caatttcaca ttcaagctcc ttatcctagg ctaattttat          100
attatgttaa atcacttgtt tttgttctca cggcttcctg cctgctatag          150
gcataattac gaggaagcag aacttctcca gaagcaagcg cacatgcgtt          200
ccaaaataag agcaaattcg ctctaaacac aggaaaagac ctgaagcttt          250
aattaagggg ttacatccaa ccccagagcg cttttgtggg cactgattgc          300
tccagcttct gcgtcactgc gcgagggaag agggaagagg atccaggcgt          350
tagacatgta tagacacaaa aacagctgga gattgggctt aaaatacccca         400 ccaagctcca agaagagac ccaagtcccc aaaacattga tttcagggct           450
gccaggaagg aagagcagca gcagggtggg agagaagctc cagtcagccc          500
acaagatgcc attgtccccc ggcctcctgc tgctgctgct ctccggggcc          550
acggccaccg ctgccctgcc cctggagggt ggccccaccg ccgagacag           600 cgagcatatg caggaagcgg caggaataag gaaaagcagc ctcctgactt          650
tcctcgcttg gtggtttgag tggacctccc aggccagtgc cgggcccctc          700
ataggagagg aagctcggga ggtggccagg cggcaggaag gcgcaccccc          750
ccagcaatcc gcgcgccggg acagaatgcc ctgcaggaac ttcttctgga          800
agaccttctc ctcctgcaaa tag                                       823

<210> SEQ ID NO 132
<211> LENGTH: 155
<212> TYPE: PRT
<213> ORGANISM: Homo Sapien

<400> SEQUENCE: 132

Met Tyr Arg His Lys Asn Ser Trp Arg Leu Gly Leu Lys Tyr Pro
  1               5                  10                  15

Pro Ser Ser Lys Glu Glu Thr Gln Val Pro Lys Thr Leu Ile Ser
                 20                  25                  30
```

```
Gly Leu Pro Gly Arg Lys Ser Ser Arg Val Gly Glu Lys Leu
             35                  40                  45

Gln Ser Ala His Lys Met Pro Leu Ser Pro Gly Leu Leu Leu
         50                  55                  60

Leu Leu Ser Gly Ala Thr Ala Thr Ala Ala Leu Pro Leu Glu Gly
 65                  70                  75

Gly Pro Thr Gly Arg Asp Ser Glu His Met Gln Glu Ala Ala Gly
             80                  85                  90

Ile Arg Lys Ser Ser Leu Leu Thr Phe Leu Ala Trp Trp Phe Glu
             95                 100                 105

Trp Thr Ser Gln Ala Ser Ala Gly Pro Leu Ile Gly Glu Glu Ala
            110                 115                 120

Arg Glu Val Ala Arg Arg Gln Glu Gly Ala Pro Pro Gln Gln Ser
            125                 130                 135

Ala Arg Arg Asp Arg Met Pro Cys Arg Asn Phe Phe Trp Lys Thr
            140                 145                 150

Phe Ser Ser Cys Lys
            155
```

```
<210> SEQ ID NO 133
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 133
tcagggctgc caggaaggaa gagc                                    24

<210> SEQ ID NO 134
<211> LENGTH: 28
<212> TYPE: DNA
<213> ORGANISM: Artificial Sequence
<220> FEATURE:
<223> OTHER INFORMATION: Synthetic oligonucleotide probe

<400> SEQUENCE: 134
gcaggaggag aaggtcttcc agaagaag                                28

<210> SEQ ID NO 135
<211> LENGTH: 45
<212> TYPE: DNA
<213> ORGANISM: Artificial Sequence
<220> FEATURE:
<223> OTHER INFORMATION: Synthetic oligonucleotide probe

<400> SEQUENCE: 135
agaagttcca gtcagcccac aagatgccat tgtcccccgg cctcc             45

<210> SEQ ID NO 136
<211> LENGTH: 1875
<212> TYPE: DNA
<213> ORGANISM: Homo Sapien

<400> SEQUENCE: 136
gtcgtgtgct tggaggaagc cgcggaaccc ccagcgtccg tccatggcgt         50
ggagccttgg gagctggctg ggtggctgcc tgctggtgtc agcattggga        100
atggtaccac ctcccgaaaa tgtcagaatg aattctgtta atttcaagaa        150
cattctacag tgggagtcac ctgcttttgc caaagggaac ctgactttca        200
```

-continued

```
cagctcagta cctaagttat aggatattcc aagataaatg catgaatact        250
accttgacgg aatgtgattt ctcaagtctt tccaagtatg gtgaccacac        300
cttgagagtc agggctgaat tgcagatga gcattcagac tgggtaaaca        350
tcaccttctg tcctgtggat gacaccatta ttggacccc tggaatgcaa         400 gtagaagtac ttgctgattc tttacatatg cgtttcttag cccctaaaat        450
tgagaatgaa tacgaaactt ggactatgaa gaatgtgtat aactcatgga        500
cttataatgt gcaatactgg aaaaacggta ctgatgaaaa gtttcaaatt        550
actccccagt atgactttga ggtcctcaga aacctggagc catggacaac        600
ttattgtgtt caagttcgag ggtttcttcc tgatcggaac aaagctgggg        650
aatggagtga gcctgtctgt gagcaaacaa cccatgacga aacggtcccc        700
tcctggatgg tggccgtcat cctcatggcc tcggtcttca tggtctgcct        750
ggcactcctc ggctgcttct ccttgctgtg gtgcgtttac aagaagacaa        800
agtacgcctt ctcccctagg aattctcttc cacagcacct gaaagagttt        850
ttgggccatc ctcatcataa cacacttctg tttttctcct ttccattgtc        900
ggatgagaat gatgttttg acaagctaag tgtcattgca gaagactctg         950
agagcggcaa gcagaatcct ggtgacagct gcagcctcgg gaccccgcct       1000
gggcaggggc cccaaagcta ggctctgaga aggaaacaca ctcggctggg       1050
cacagtgacg tactccatct cacatctgcc tcagtgaggg atcagggcag       1100
caaacaaggg ccaagaccat ctgagccagc cccacatcta gaactccaga       1150
cctggactta gccaccagag agctacattt taaaggctgt cttggcaaaa       1200
atactccatt tgggaactca ctgccttata aaggctttca tgatgttttc       1250
agaagttggc cactgagagt gtaattttca gccttttata tcactaaaat       1300
aagatcatgt tttaattgtg agaaacaggg ccgagcacag tggctcacgc       1350
ctgtaatacc agcaccttag aggtcgaggc aggcggatca cttgaggtca       1400
ggagttcaag accagcctgg ccaatatggt gaaacccagt ctctactaaa       1450
aatacaaaaa ttagctaggc atgatggcgc atgcctataa tcccagctac       1500
tcgagtgcct gaggcaggag aattgcatga acccgggagg aggaggagga       1550
ggttgcagtg agccgagata gcggcactgc actccagcct gggtgacaaa       1600
gtgagactcc atctcaaaaa aaaaaaaaa aaattgtgag aaacagaaat        1650
acttaaaatg aggaataaga atggagatgt tacatctggt agatgtaaca       1700
ttctaccaga ttatggatgg actgatctga aaatcgacct caactcaagg       1750
gtggtcagct caatgctaca cagagcacgg acttttggat tctttgcagt       1800
actttgaatt tatttttcta cctatatatg tttatatgc tgctggtgct         1850 ccattaaagt tttactctgt gttgc                                   1875
```

<210> SEQ ID NO 137
<211> LENGTH: 325
<212> TYPE: PRT
<213> ORGANISM: Homo Sapien

<400> SEQUENCE: 137

```
Met Ala Trp Ser Leu Gly Ser Trp Leu Gly Gly Cys Leu Leu Val
 1               5                  10                  15
```

```
Ser Ala Leu Gly Met Val Pro Pro Glu Asn Val Arg Met Asn
             20                  25                  30

Ser Val Asn Phe Lys Asn Ile Leu Gln Trp Glu Ser Pro Ala Phe
             35                  40                  45

Ala Lys Gly Asn Leu Thr Phe Thr Ala Gln Tyr Leu Ser Tyr Arg
             50                  55                  60

Ile Phe Gln Asp Lys Cys Met Asn Thr Thr Leu Thr Glu Cys Asp
             65                  70                  75

Phe Ser Ser Leu Ser Lys Tyr Gly Asp His Thr Leu Arg Val Arg
             80                  85                  90

Ala Glu Phe Ala Asp Glu His Ser Asp Trp Val Asn Ile Thr Phe
             95                 100                 105

Cys Pro Val Asp Asp Thr Ile Ile Gly Pro Pro Gly Met Gln Val
            110                 115                 120

Glu Val Leu Ala Asp Ser Leu His Met Arg Phe Leu Ala Pro Lys
            125                 130                 135

Ile Glu Asn Glu Tyr Glu Thr Trp Thr Met Lys Asn Val Tyr Asn
            140                 145                 150

Ser Trp Thr Tyr Asn Val Gln Tyr Trp Lys Asn Gly Thr Asp Glu
            155                 160                 165

Lys Phe Gln Ile Thr Pro Gln Tyr Asp Phe Glu Val Leu Arg Asn
            170                 175                 180

Leu Glu Pro Trp Thr Thr Tyr Cys Val Gln Val Arg Gly Phe Leu
            185                 190                 195

Pro Asp Arg Asn Lys Ala Gly Glu Trp Ser Glu Pro Val Cys Glu
            200                 205                 210

Gln Thr Thr His Asp Glu Thr Val Pro Ser Trp Met Val Ala Val
            215                 220                 225

Ile Leu Met Ala Ser Val Phe Met Val Cys Leu Ala Leu Leu Gly
            230                 235                 240

Cys Phe Ser Leu Leu Trp Cys Val Tyr Lys Lys Thr Lys Tyr Ala
            245                 250                 255

Phe Ser Pro Arg Asn Ser Leu Pro Gln His Leu Lys Glu Phe Leu
            260                 265                 270

Gly His Pro His His Asn Thr Leu Leu Phe Phe Ser Phe Pro Leu
            275                 280                 285

Ser Asp Glu Asn Asp Val Phe Asp Lys Leu Ser Val Ile Ala Glu
            290                 295                 300

Asp Ser Glu Ser Gly Lys Gln Asn Pro Gly Asp Ser Cys Ser Leu
            305                 310                 315

Gly Thr Pro Pro Gly Gln Gly Pro Gln Ser
            320                 325

<210> SEQ ID NO 138
<211> LENGTH: 2570
<212> TYPE: DNA
<213> ORGANISM: Homo Sapien

<400> SEQUENCE: 138
cgagcgccaa cccgctagcg cctgaatccg gcgtgctgcc cgctcgccgc         50
ccgccatggc ccgcgcagcc ccgctgctcg ccgcgttgac cgcgctcctc         100
gccgccgccg ctgctggcgg agatgccccg ccgggcaaaa tcgcggtggt         150
tggggctggg attgggggct ctgctgtggc ccatttttctc cagcagcact        200
```

-continued

| | |
|---|---|
| ttggacctcg ggtgcagatc gacgtgtacg agaagggaac cgtgggtggc | 250 |
| cgcttggcca ccatctcagt caacaagcag cactatgaga gcggggctgc | 300 |
| ctccttccac tccctgagcc tgcacatgca ggacttcgtc aagctgctgg | 350 |
| ggctgaggca ccggcgcgag gtggtgggca ggagcgccat cttcggcggg | 400 |
| gagcacttca tgctggagga gactgactgg tacctgctga acctcttccg | 450 |
| cctctggtgg cactatggca tcagcttcct gaggctgcag atgtgggtgg | 500 |
| aggaggtcat ggagaagttc atgaggatct ataagtacca ggcccacggc | 550 |
| tatgccttct cgggtgtgga ggagctgctc tactcactgg gggagtccac | 600 |
| ctttgttaac atgacccagc actctgtggc tgagtccctg ctgcaggtgg | 650 |
| gcgtcacgca gcgctttatt gatgatgtcg tttctgctgt cctgcgggcc | 700 |
| agctatggcc agtcagcagc gatgcccgcc tttgcaggag ccatgtcact | 750 |
| agccggggcc caaggcagcc tgtggtctgt ggaaggaggc aataagctgg | 800 |
| tttgttccgg tttgctgaag ctcaccaagg ccaatgtgat ccatgccaca | 850 |
| gtgacctctg tgaccctgca cagcacagag gggaaagccc tgtaccaggt | 900 |
| ggcgtatgag aatgaggtag caacagctc tgacttctat gacatcgtgg | 950 |
| tcatcgccac ccccctgcac ctggacaaca gcagcagcaa cttaaccttt | 1000 |
| gcaggcttcc acccgcccat tgatgacgtg cagggctctt ccagcccac | 1050 |
| cgtcgtctcc ttggtccacg gctacctcaa ctcgtcctac ttcggtttcc | 1100 |
| cagaccctaa gcttttcccc tttgccaaca tccttaccac agatttcccc | 1150 |
| agcttcttct gcactctgga caacatctgc cctgtcaaca tctctgccag | 1200 |
| cttccggcga aagcagcccc aggaggcagc tgtttggcga gtccagtccc | 1250 |
| ccaagcccct ctttcggacc cagctaaaga ccctgttccg ttcctattac | 1300 |
| tcagtgcaga cagctgagtg gcaggccat cccctctatg ctcccgccc | 1350 |
| cacgctcccg aggtttgcac tccatgacca gctcttctac ctcaatgccc | 1400 |
| tggagtgggc ggccagctcc gtggaggtga tggccgtggc tgccaagaat | 1450 |
| gtggccttgc tggcttacaa ccgctggtac caggacctag acaagattga | 1500 |
| tcaaaaagat ttgatgcaca aggtcaagac tgaactgtga gggctctagg | 1550 |
| gagagcctgg gaactttcat cccccactga agatggatca tcccacagca | 1600 |
| gcccaggact gaataagcca tgctcgccca ccaggcttct ttctgacccc | 1650 |
| tcatgtatca agcatctcca ggtgacctac tgtctgccta tattaagggt | 1700 |
| ccacacggcg gctgctgctt ttttttaagg gggaaagtaa gaaaagagaa | 1750 |
| ggaaatccaa gccagtatat ttgttttatt tatttttttt aagaagaaaa | 1800 |
| aagttcatct tcacaaggtg cttcagactt ggtttcttag ctagaaacca | 1850 |
| gaagactacg ggaggaata taaggcagag aactatgagt cttattttat | 1900 |
| tactgttttt cactacctac tcccacaatg acaatcaat tgaggcaacc | 1950 |
| tacaagaaaa catttacaac cagatggtta caaataaagt agaagggaag | 2000 |
| atcagaaaac ctaagaaatg atcatagctc ctggttactg tggacttgat | 2050 |
| ggatttgaag tacctagttc agaactccct agtcaccatc tccaagcctg | 2100 |
| tcaacatcac tgcatattgg aggagatgac tgtggtagga cccaaggaag | 2150 |

-continued

```
agatgtgtgc ctgaatagtc gtcaccatat ctccaagctt cctggcaacc         2200
agtgggaaaa gaaacatgcg aggctgtagg aagagggaag ctcttccttg         2250
gcacctagag gaattagcca ttctcttcct tatgcaaaga ttgaggaatg         2300
caacaatata agaagagaa gtccccagat ggtagagagc agtcatatct          2350
tacccctaga tgttcatccc agcagaagaa agaagaaggt gttggggtag         2400
gattcttcag aggttagcct ggtacttict catcagacac tagcttgaag         2450
taagaggaga attatgcttt tctttgcttt ttctacaaac ccttaaaaat         2500
cacttgtttt aaaagaaag taaaagcсcct tttcattcaa aaaaaaaaa          2550 aaaaaaaaaa aaaaaaaaa                                           2570
```

<210> SEQ ID NO 139
<211> LENGTH: 494
<212> TYPE: PRT
<213> ORGANISM: Homo Sapien

<400> SEQUENCE: 139

```
Met Ala Arg Ala Ala Pro Leu Ala Ala Leu Thr Ala Leu Leu
 1               5                  10                  15

Ala Ala Ala Ala Gly Gly Asp Ala Pro Pro Gly Lys Ile Ala
                20                  25                  30

Val Val Gly Ala Gly Ile Gly Ser Ala Val Ala His Phe Leu
                35                  40                  45

Gln Gln His Phe Gly Pro Arg Val Gln Ile Asp Val Tyr Glu Lys
            50                  55                  60

Gly Thr Val Gly Gly Arg Leu Ala Thr Ile Ser Val Asn Lys Gln
            65                  70                  75

His Tyr Glu Ser Gly Ala Ala Ser Phe His Ser Leu Ser Leu His
            80                  85                  90

Met Gln Asp Phe Val Lys Leu Leu Gly Leu Arg His Arg Glu
                95                  100                 105

Val Val Gly Arg Ser Ala Ile Phe Gly Gly Glu His Phe Met Leu
            110                 115                 120

Glu Glu Thr Asp Trp Tyr Leu Leu Asn Leu Phe Arg Leu Trp Trp
            125                 130                 135

His Tyr Gly Ile Ser Phe Leu Arg Leu Gln Met Trp Val Glu Glu
            140                 145                 150

Val Met Glu Lys Phe Met Arg Ile Tyr Lys Tyr Gln Ala His Gly
            155                 160                 165

Tyr Ala Phe Ser Gly Val Glu Glu Leu Leu Tyr Ser Leu Gly Glu
            170                 175                 180

Ser Thr Phe Val Asn Met Thr Gln His Ser Val Ala Glu Ser Leu
            185                 190                 195

Leu Gln Val Gly Val Thr Gln Arg Phe Ile Asp Asp Val Val Ser
            200                 205                 210

Ala Val Leu Arg Ala Ser Tyr Gly Gln Ser Ala Ala Met Pro Ala
            215                 220                 225

Phe Ala Gly Ala Met Ser Leu Ala Gly Ala Gln Gly Ser Leu Trp
            230                 235                 240

Ser Val Glu Gly Gly Asn Lys Leu Val Cys Ser Gly Leu Leu Lys
            245                 250                 255

Leu Thr Lys Ala Asn Val Ile His Ala Thr Val Thr Ser Val Thr
            260                 265                 270
```

```
Leu His Ser Thr Glu Gly Lys Ala Leu Tyr Gln Val Ala Tyr Glu
            275                 280                 285

Asn Glu Val Gly Asn Ser Ser Asp Phe Tyr Asp Ile Val Val Ile
            290                 295                 300

Ala Thr Pro Leu His Leu Asp Asn Ser Ser Ser Asn Leu Thr Phe
            305                 310                 315

Ala Gly Phe His Pro Pro Ile Asp Asp Val Gln Gly Ser Phe Gln
            320                 325                 330

Pro Thr Val Val Ser Leu Val His Gly Tyr Leu Asn Ser Ser Tyr
            335                 340                 345

Phe Gly Phe Pro Asp Pro Lys Leu Phe Pro Phe Ala Asn Ile Leu
            350                 355                 360

Thr Thr Asp Phe Pro Ser Phe Phe Cys Thr Leu Asp Asn Ile Cys
            365                 370                 375

Pro Val Asn Ile Ser Ala Ser Phe Arg Arg Lys Gln Pro Gln Glu
            380                 385                 390

Ala Ala Val Trp Arg Val Gln Ser Pro Lys Pro Leu Phe Arg Thr
            395                 400                 405

Gln Leu Lys Thr Leu Phe Arg Ser Tyr Tyr Ser Val Gln Thr Ala
            410                 415                 420

Glu Trp Gln Ala His Pro Leu Tyr Gly Ser Arg Pro Thr Leu Pro
            425                 430                 435

Arg Phe Ala Leu His Asp Gln Leu Phe Tyr Leu Asn Ala Leu Glu
            440                 445                 450

Trp Ala Ala Ser Ser Val Glu Val Met Ala Val Ala Ala Lys Asn
            455                 460                 465

Val Ala Leu Leu Ala Tyr Asn Arg Trp Tyr Gln Asp Leu Asp Lys
            470                 475                 480

Ile Asp Gln Lys Asp Leu Met His Lys Val Lys Thr Glu Leu
            485                 490

<210> SEQ ID NO 140
<211> LENGTH: 23
<212> TYPE: DNA
<213> ORGANISM: Artificial Sequence
<220> FEATURE:
<223> OTHER INFORMATION: Synthetic oligonucleotide probe

<400> SEQUENCE: 140
gggacgtgct tctacaagaa cag                                              23

<210> SEQ ID NO 141
<211> LENGTH: 26
<212> TYPE: DNA
<213> ORGANISM: Artificial Sequence
<220> FEATURE:
<223> OTHER INFORMATION: Synthetic oligonucleotide probe

<400> SEQUENCE: 141
caggcttaca atgttatgat cagaca                                           26

<210> SEQ ID NO 142
<211> LENGTH: 31
<212> TYPE: DNA
<213> ORGANISM: Artificial Sequence
<220> FEATURE:
<223> OTHER INFORMATION: Synthetic oligonucleotide probe

<400> SEQUENCE: 142
```

```
tattcagagt tttccattgg cagtgccagt t                                      31

<210> SEQ ID NO 143
<211> LENGTH: 18
<212> TYPE: DNA
<213> ORGANISM: Artificial Sequence
<220> FEATURE:
<223> OTHER INFORMATION: Synthetic oligonucleotide probe

<400> SEQUENCE: 143
ggccttgcag acaaccgt                                                     18

<210> SEQ ID NO 144
<211> LENGTH: 21
<212> TYPE: DNA
<213> ORGANISM: Artificial Sequence
<220> FEATURE:
<223> OTHER INFORMATION: Synthetic oligonucleotide probe

<400> SEQUENCE: 144
cagactgagg gagatccgag a                                                 21

<210> SEQ ID NO 145
<211> LENGTH: 26
<212> TYPE: DNA
<213> ORGANISM: Artificial Sequence
<220> FEATURE:
<223> OTHER INFORMATION: Synthetic oligonucleotide probe

<400> SEQUENCE: 145
gcagattttg aggacagcca cctcca                                            26

<210> SEQ ID NO 146
<211> LENGTH: 18
<212> TYPE: DNA
<213> ORGANISM: Artificial Sequence
<220> FEATURE:
<223> OTHER INFORMATION: Synthetic oligonucleotide probe

<400> SEQUENCE: 146
catcaagcgc ctctacca                                                     18

<210> SEQ ID NO 147
<211> LENGTH: 21
<212> TYPE: DNA
<213> ORGANISM: Artificial Sequence
<220> FEATURE:
<223> OTHER INFORMATION: Synthetic oligonucleotide probe

<400> SEQUENCE: 147
cacaaactcg aactgcttct g                                                 21

<210> SEQ ID NO 148
<211> LENGTH: 20
<212> TYPE: DNA
<213> ORGANISM: Artificial Sequence
<220> FEATURE:
<223> OTHER INFORMATION: Synthetic oligonucleotide probe

<400> SEQUENCE: 148
cagctgccct tccccaacca                                                   20

<210> SEQ ID NO 149
<211> LENGTH: 22
<212> TYPE: DNA
```

```
<213> ORGANISM: Artificial Sequence
<220> FEATURE:
<223> OTHER INFORMATION: Synthetic oligonucleotide probe

<400> SEQUENCE: 149
ggcagagact tccagtcact ga                                              22

<210> SEQ ID NO 150
<211> LENGTH: 22
<212> TYPE: DNA
<213> ORGANISM: Artificial Sequence
<220> FEATURE:
<223> OTHER INFORMATION: Synthetic oligonucleotide probe

<400> SEQUENCE: 150
gccaagggtg gtgttagata gg                                              22

<210> SEQ ID NO 151
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 151 caggcccct tgatctgtac ccca                                             24
```

SECRETED AND TRANSMEMBRANE POLYPEPTIDES AND NUCLEIC ACIDS ENCODING THE SAME

RELATED APPLICATIONS

This application is a continuation of, and claims priority under 35 USC §120 to, U.S. application Ser. No. 10/002796 filed Nov. 15, 2001, now abandoned which is a continuation of, and claims priority under 35 USC §120 to, PCT Application PCT/US00/14042 filed May 22, 2000, which is a continuation-in-part of, and claims priority under 35 USC §120 to, PCT/US00/04342 filed Feb. 2, 2000, which is a continuation-in-part of, and claims priority under 35 USC §120 to, U.S. Application 09/403297 filed Oct. 18, 1999, now abandoned, which is a continuation-in-part of, and claims priority under 35 USC §120 to, PCT Application PCT/US99/20111 filed Sep. 1, 1999, which claims priority under 35 USC 119 to U.S. Provisional Application No. 60/106032 filed Oct. 28, 1998.

FIELD OF THE INVENTION

The present invention relates generally to the identification and isolation of novel DNA and to the recombinant production of novel polypeptides.

BACKGROUND OF THE INVENTION

Extracellular proteins play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. These secreted polypeptides or signaling molecules normally pass through the cellular secretory pathway to reach their site of action in the extracellular environment.

Secreted proteins have various industrial applications, including as pharmaceuticals, diagnostics, biosensors and bioreactors. Most protein drugs available at present, such as thrombolytic agents, interferons, interleukins, erythropoietins, colony stimulating factors, and various other cytokines, are secretory proteins. Their receptors, which are membrane proteins, also have potential as therapeutic or diagnostic agents. Efforts are being undertaken by both industry and academia to identify new, native secreted proteins. Many efforts are focused on the screening of mammalian recombinant DNA libraries to identify the coding sequences for novel secreted proteins. Examples of screening methods and techniques are described in the literature [see, for example, Klein et al., *Proc. Natl. Acad. Sci.* 93:7108-7113 (1996); U.S. Pat. No. 5,536,637)].

Membrane-bound proteins and receptors can play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. Such membrane-bound proteins and cell receptors include, but are not limited to, cytokine receptors, receptor kinases, receptor phosphatases, receptors involved in cell-cell interactions, and cellular adhesin molecules like selectins and integrins. For instance, transduction of signals that regulate cell growth and differentiation is regulated in part by phosphorylation of various cellular proteins. Protein tyrosine kinases, enzymes that catalyze that process, can also act as growth factor receptors. Examples include fibroblast growth factor receptor and nerve growth factor receptor.

Membrane-bound proteins and receptor molecules have various industrial applications, including as pharmaceutical and diagnostic agents. Receptor immunoadhesins, for instance, can be employed as therapeutic agents to block receptor-ligand interactions. The membrane-bound proteins can also be employed for screening of potential peptide or small molecule inhibitors of the relevant receptor/ligand interaction.

Efforts are being undertaken by both industry and academia to identify new, native receptor or membrane-bound proteins. Many efforts are focused on the screening of mammalian recombinant DNA libraries to identify the coding sequences for novel receptor or membrane-bound proteins.

1. PRO196

The abbreviations "TIE" or "tie" are acronyms, which stand for "tyrosine kinase containing Ig and EGF homology domains" and were coined to designate a new family of receptor tyrosine kinases which are almost exclusively expressed in vascular endothelial cells and early hemopoietic cells, and are characterized by the presence of an EGF-like domain, and extracellular folding units stabilized by intra-chain disulfide bonds, generally referred to as "immunoglobulin (IG)-like" folds. A tyrosine kinase homologous cDNA fragment from human leukemia cells (tie) was described by Partanen et al., *Proc. Natl. Acad. Sci. USA* 87, 8913-8917 (1990). The mRNA of this human "tie" receptor has been detected in all human fetal and mouse embryonic tissues, and has been reported to be localized in the cardiac and vascular endothelial cells. Korhonen et al., *Blood* 80, 2548-2555 (1992); PCT Application Publication No. WO 93/14124 (published 22 Jul. 1993). The rat homolog of humantie, referred to as "tie", was identified by Maisonpierre et al., *Oncogene* 8, 1631-1637 (1993)). Another tie receptor, designated "tie-2" was originally identified in rats (Dumont et al., *Oncogene* 8, 1293-1301 (1993)), while the human homolog of tie-2, referred to as "ork" was described in U.S. Pat. No. 5,447,860 (Ziegler). The murine homolog of tie-2 was originally termed "tek." The cloning of a mouse tie-2 receptor from a brain capillary cDNA library is disclosed in PCT Application Publication No. WO 95/13387 (published May 18, 1995). The TIE receptors are believed to be actively involved in angiogenesis, and may play a role in hemopoiesis as well.

The expression cloning of human TIE-2 ligands has been described in PCT Application Publication No. WO 96/11269 (published Apr. 18, 1996) and in U.S. Pat. No. 5,521,073 (published May 28, 1996). A vector designated as λgt10 encoding a TIE-2 ligand named "htie-2 ligand 1" or "hTL1" has been deposited under ATCC Accession No. 75928. A plasmid encoding another TIE-2 ligand designated "htie-22" or "hTL2" is available under ATCC Accession No. 75928.

This second ligand has been described as an antagonist of the TAI-2 receptor. The identification of secreted human and mouse ligands for the TIE-2 receptor has been reported by Davis et al., Cell 87, 1161-1169 (1996). The human ligand designated "Angiopoietin-1", to reflect its role in angiogenesis and potential action during hemopoiesis, is the same ligand as the ligand variously designated as "htie-21" or "hTL-1" in WO 96/11269. Angiopoietin-1 has been described to play an angiogenic role later and distinct from that of VEGF (Suri et al., Cell 87, 1171-1180 (1996)). Since TIE-2 is apparently upregulated during the pathologic angiogenesis requisite for tumor growth (Kaipainen et al., Cancer Res. 54, 6571-6577 (1994)) angiopoietin-1 has been suggested to be additionally useful for specifically targeting tumor vasculature (Davis et al., supra).

2. PRO444

Efforts are being undertaken by both industry and academia to identify new, native secreted proteins. Many efforts are focused on the screening of mammalian recombinant DNA libraries to identify the coding sequences for novel secreted proteins. We herein describe the identification and isolation of cDNA molecules encoding novel secreted polypeptides, designated herein as PRO444 polypeptides.

3. PRO183

Efforts are being undertaken by both industry and academia to identify new, native secreted proteins. Many efforts are focused on the screening of mammalian recombinant DNA libraries to identify the coding sequences for novel secreted proteins. We herein describe the identification and isolation of cDNA molecules encoding novel polypeptides, designated herein as PRO183 polypeptides.

4. PRO185

Efforts are being undertaken by both industry and academia to identify new, native secreted proteins. Many efforts are focused on the screening of mammalian recombinant DNA libraries to identify the coding sequences for novel secreted proteins. We herein describe the identification and isolation of cDNA molecules encoding novel polypeptides, designated herein as PRO185 polypeptides.

5. PRO210 and PRO217

Epidermal growth factor (EGF) is a conventional mitogenic factor that stimulates the proliferation of various types of cells including epithelial cells and fibroblasts. EGF binds to and activates the EGF receptor (EGFR), which initiates intracellular signaling and subsequent effects. The EGFR is expressed in neurons of the cerebral cortex, cerebellum, and hippocampus in addition to other regions of the central nervous system (CNS). In addition, EGF is also expressed in various regions of the CNS. Therefore, EGF acts not only on mitotic cells, but also on postmitotic neurons. In fact, many studies have indicated that EGF has neurotrophic or neuromodulatory effects on various types of neurons in the CNS. For example, EGF acts directly on cultured cerebral cortical and cerebellar neurons, enhancing neurite outgrowth and survival. On the other hand, EGF also acts on other cell types, including septal cholinergic and mesencephalic dopaminergic neurons, indirectly through glial cells. Evidence of the effects of EGF on neurons in the CNS is accumulating, but the mechanisms of action remain essentially unknown. EGF-induced signaling in mitotic cells is better understood than in postmitotic neurons. Studies of cloned pheochromocytoma PC 12 cells and cultured cerebral cortical neurons have suggested that the EGF-induced neurotrophic actions are mediated by sustained activation of the EGFR and mitogen-activated protein kinase (MAPK) in response to EGF. The sustained intracellular signaling correlates with the decreased rate of EGFR down-regulation, which might determine the response of neuronal cells to EGF. It is likely that EGF is a multi-potent growth factor that acts upon various types of cells including mitotic cells and postmitotic neurons.

EGF is produced by the salivary and Brunner's glands of the gastrointestinal system, kidney, pancreas, thyroid gland, pituitary gland, and the nervous system, and is found in body fluids such as saliva, blood, cerebrospinal fluid (CSF), urine, amniotic fluid, prostatic fluid, pancreatic juice, and breast milk, Plata-Salaman, CR Peptides 12: 653-663 (1991).

EGF is mediated by its membrane specific receptor, which contains an intrinsic tyrosine kinase. Stoscheck C M et al., J. Cell Biochem. 31: 135-152 (1986). EGF is believed to function by binding to the extracellular portion of its receptor which induces a transmembrane signal that activates the intrinsic tyrosine kinase.

Purification and sequence analysis of the EGF-like domain has revealed the presence of six conserved cysteine residues which cross-bind to create three peptide loops, Savage C R et al., J. Biol. Chem. 248: 7669-7672 (1979). It is now generally known that several other peptides can react with the EGF receptor which share the same generalized motif $XnCX7CX4/5CX10CXCX5GX2CXn$, where X represents any non-cysteine amino acid, and n is a variable repeat number. Non isolated peptides having this motif include TGF-a, amphiregulin, schwannoma-derived growth factor (SDGF), heparin-binding EGF-like growth factors and certain virally encoded peptides (e.g., Vaccinia virus, Reisner A H, Nature 313: 801-803 (1985), Shope fibroma virus, Chang W., et al., Mol Cell Biol. 7: 535-540 (1987), Molluscum contagiosum, Porter CD & Archard L C, J. Gen. Virol. 68: 673-682 (1987), and Myxoma virus, Upton C et al., J. Virol. 61: 1271-1275 (1987). Prigent S A & Lemoine N. R., Prog. Growth Factor Res. 4: 1-24 (1992).

EGF-like domains are not confined to growth factors but have been observed in a variety of cell-surface and extracellular proteins which have interesting properties in cell adhesion, protein-protein interaction and development, Laurence D J R & Gusterson B A, Tumor Biol. 11: 229-261 (1990). These proteins include blood coagulation factors (factors VI, IX, X, XII, protein C, protein S, protein Z, tissue plasminogen activator, urokinase), extracellular matrix components (laminin, cytotactin, entactin), cell surface receptors (LDL receptor, thrombomodulin receptor) and immunity-related proteins (complement Clr, uromodulin).

Even more interesting, the general structure pattern of EGF-like precursors is preserved through lower organisms as well as in mammalian cells. A number of genes with developmental significance have been identified in invertebrates with EGF-like repeats. For example, the notch gene of *Drosophila* encodes 36 tandemly arranged 40 amino acid repeats which show homology to EGF, Wharton W et al., Cell 43: 557-581 (1985). Hydropathy plots indicate a putative membrane spanning domain, with the EGF-related sequences being located on the extracellular side of the membrane. Other homeotic genes with EGF-like repeats include Delta, 95F and 5ZD which were identified using probes based on Notch, and the nematode gene Lin-12 which encodes a putative receptor for a developmental signal transmitted between two specified cells.

Specifically, EGF has been shown to have potential in the preservation and maintenance of gastrointestinal mucosa and the repair of acute and chronic mucosal lesions, Konturek, P C et al., Eur. J. Gastroenterol Hepatol. 7 (10), 933-37 (1995), including the treatment of necrotizing enterocolitis, Zollinger-Ellison syndrome, gastrointestinal ulceration gastrointestinal ulcerations and congenital microvillus atrophy, A. Guglietta & P B Sullivan, Eur. J. Gastroenterol Hepatol, 7(10), 945-50 (1995). Additionally, EGF has been implicated in hair follicle differentiation; C. L. du Cros, J. Invest. Dermatol. 101 (1 Suppl.), 106S-113S (1993), S G Hillier, Clin. Endocrinol. 33(4), 427-28 (1990); kidney function, L. L. Hamm et al., Semin. Nephrol. 13 (1): 109-15 (1993), R C Harris, Am. J. Kidney Dis. 17(6): 627-30 (1991); tear fluid, G B van Setten et al., Int. Ophthalmol 15(6); 359-62 (1991); vitamin K mediated blood coagulation, J. Stenflo et al., Blood 78(7): 1637-51 (1991). EGF is also implicated various skin disease characterized by abnormal keratinocyte differentiation, e.g., psoriasis, epithelial cancers such as squamousi cell carcinomas of the lung, epidermoid carcinoma of the vulva and gliomas. King, L E et al., Am. J. Med. Sci. 296: 154-158 (1988).

Of great interest is mounting evidence that genetic alterations in growth factors signaling pathways are closely linked to developmental abnormalities and to chronic diseases including cancer. Aaronson S A, Science 254: 1146-1153 (1991). For example, c-erb-2 (also known as HER-2), a proto-oncogene with close structural similarity to EGF receptor protein, is overexpressed in human breast cancer. King et al., Science 229: 974-976 (1985); Gullick, W J, Hormones and their actions, Cooke B A et al., eds, Amsterdam, Elsevier, pp 349-360 (1986).

6. PRO215

Protein-protein interactions include receptor and antigen complexes and signaling mechanisms. As more is known about the structural and functional mechanisms underlying protein-protein interactions, protein-protein interactions can be more easily manipulated to regulate the particular result of the protein-protein interaction. Thus, the underlying mechanisms of protein-protein interactions are of interest to the scientific and medical community.

All proteins containing leucine-rich repeats are thought to be involved in protein-protein interactions. Leucine-rich repeats are short sequence motifs present in a number of proteins with diverse functions and cellular locations. The crystal structure of ribonuclease inhibitor protein has revealed that leucine-rich repeats correspond to beta-alpha structural units. These units are arranged so that they form a parallel beta-sheet with one surface exposed to solvent, so that the protein acquires an unusual, nonglubular shape. These two features have been indicated as responsible for the protein-binding functions of proteins containing leucine-rich repeats. See, Kobe and Deisenhofer, *Trends Biochem. Sci.,* 19(10):415-421 (Oct. 1994).

A study has been reported on leucine-rich proteoglycans which serve as tissue organizers, orienting and ordering collagen fibrils during ontogeny and are involved in pathological processes such as wound healing, tissue repair. and tumor stroma formation. Iozzo, R. V., *Crit. Rev. Biochem. Mol. Biol.,* 32(2): 141-174 (1997). Others studies implicating leucine rich proteins in wound healing and tissue repair are De La Salle, C., et al., *Vouv. Rev. Fr. Hematol.* (Germany), 37(4):215-222 (1995), reporting mutations in the leucine rich motif in a complex associated with the bleeding disorder Bernard-Soulier syndrome and Chlemetson, K. J., *Thromb. Haemost.* (Germany), 74(1):111-116 (July 1995), reporting that platelets have leucine rich repeats. Another protein of particular interest which has been reported to have leucine-rich repeats is the SLIT protein which has been reported to be useful in treating neuro-degenerative diseases such as Alzheimer's disease, nerve damage such as in Parkinson's disease, and for diagnosis of cancer, see, Artavanistsakonas, S. and Rothberg, J. M., WO9210518-A1 by Yale University. Other studies reporting on the biological functions of proteins having leucine-rich repeats include: Tayar, N., et al., *Mol. Cell Endocrinol.,* (Ireland), 125(1-2): 65-70 (Dec. 1996) (gonadotropin receptor involvement); Miura, Y., et al., *Nippon Rinsho* (Japan), 54(7):1784-1789 (July 1996) (apoptosis involvement); Harris, P. C., et al., *J. Am. Soc. Nephrol.,* 6(4):1125-1133 (Oct. 1995) (kidney disease involvement); and Ruoslahti, E. I., et al., WO9110727-A by La Jolla Cancer Research Foundation (decorin binding to transforming growth factors involvement for treatment for cancer, wound healing and scarring).

7. PRO242, PRO1318 and PRO1600

Leukocytes include monocytes, macrophages, basophils, and eosinophils and play an important role in the immune response. These cells are important in the mechanisms initiated by T and/or B lymphocytes and secrete a range of cytokines which recruit and activate other inflammatory cells and contribute to tissue destruction.

Thus, investigation of the regulatory processes by which leukocytes move to their appropriate destination and interact with other cells is critical. Currently, leukocytes are thought to move from the blood to injured or inflamed tissues by rolling along the endothelial cells of the blood vessel wall. This movement is mediated by transient interactions between selectins and their ligands. Next, the leukocyte must move through the vessel wall and into the tissues. This diapedesis and extravasation step involves cell activation which promotes a more stable leukocyte-endothelial cell interaction, again mediated by integrins and their ligands.

Chemokines are a large family of structurally related polypeptide cytokines. These molecules stimulate leukocyte movement and may explain leukocyte trafficking in different inflammatory situations. Chemokines mediate the expression of particular adhesion molecules on endothelial cells, and they produce chemoattractants which activate specific cell types. In addition, the chemokines stimulate proliferation and regulate activation of specific cell types. In both of these activities, chemokines demonstrate a high degree of target cell specificity.

The chemokine family is divided into two subfamilies based on whether two amino terminal cysteine residues are immediately adjacent (C-C) or separated by one amino acid (C-X-C). Chemokines of the C-X-C family generally activate neutrophils and fibroblasts while the C-C chemokines act on a more diverse group of target cells including monocytes/macrophages, basophils, eosinophils and T lymphocytes. The known chemokines of both subfamilies are synthesized by many diverse cell types as reviewed in Thomson A. (1994) The Cytokine Handbook, 2 d Ed. Academic Press, N.Y.

Known chemokines include macrophage inflammatory proteins alpha and beta (MIP-1 alpha and beta), I-309, RANTES, and monocyte chemotactic protein (MCP-1).

MIP-1 alpha and MIP-1 beta were first purified from a stimulated mouse macrophage cell line and elicited an inflammatory response when injected into normal tissues. MIP-1 alpha and MIP-1 beta consist of 68-69 amino acids and share approximately 70% identity in their mature secreted forms. Both are expressed in T cells, B cells and monocytes which are stimulated by mitogens, anti-CD3 and endotoxin, and both polypeptides bind heparin and stimulate monocytes. MIP-1 alpha acts as a chemoattractant for the CD-8 subset of T lymphocytes and eosinophils, while MIP-1 beta chemoattracts the CD-4 subset of T lymphocytes. In addition, these proteins are known to stimulate myelopoiesis in mice.

RANTES is regulated by interleukins-1 and -4, transforming nerve factor and interferon-gamma and is expressed in T cells, platelets, stimulated rheumatoid synovial fibroblasts, and in some tumor cell lines. RANTES affects lymphocytes, monocytes, basophils and eosinophils. RANTES expression is substantially reduced upon T cell stimulation.

Monocyte chemotactic protein (MCP-1) is a 76 amino acid protein which appears to be expressed in almost all cells and tissues upon stimulation by a variety of agents. However, the targets of MCP-1 are limited monocytes and basophils. In these cells, MCP-1 induces a MCP-1 receptor. Two related proteins, MCP-2 and MCP-3, have 62% and 73% identity, respectively, with MCP-1 and share its chemoattractant specificity or monocytes.

Current techniques for diagnosis of abnormalities in inflamed or diseased issues mainly rely on observation of clinical symptoms or serological analyses of body tissues or fluids for hormones, polypeptides or various metabolites. Problems exist with these diagnostic techniques. First, patients may not manifest clinical symptoms at early stages of disease. Second, serological tests do not always differentiate between invasive diseases and genetic syndromes. Thus, the identification of expressed chemokines is important to the development of new diagnostic techniques, effective therapies, and to aid in the understanding of molecular pathogenesis.

The chemokine molecules were reviewed in Schall T J (1994) Chemotactic Cytokines: Targets for Therapeutic Development. International Business Communications, Southborough Mass. pp 180-270; and in Paul W E (1993) Fundamental Immunology, 3rd Ed. Raven Press, N.Y. pp 822-826.

8. PRO288

Control of cell numbers in mammals is believed to be determined, in part, by a balance between cell proliferation and cell death. One form of cell death, sometimes referred to as necrotic cell death, is typically characterized as a pathologic form of cell death resulting from some trauma or cellular injury. In contrast, there is another, "physiologic" form of cell death which usually proceeds in an orderly or controlled manner. This orderly or controlled form of cell death is often referred to as "apoptosis" [see, e.g., Barr et al., Bio/Technology, 12:487-493 (1994); Steller et al., Science, 267:1445-1449 (1995)]. Apoptotic cell death naturally occurs in many physiological processes, including embryonic development and clonal selection in the immune system [Itoh et al., Cell, 66:233-243 (1991)]. Decreased levels of apoptotic cell death have been associated with a variety of pathological conditions, including cancer, lupus, and herpes virus infection [Thompson, Science, 267:1456-1462 (1995)]. Increased levels of apoptotic cell death may be associated with a variety of other pathological conditions, including AIDS, Alzheimer's disease, Parkinson's disease, amyotrophic lateral sclerosis, multiple sclerosis, retinitis pigmentosa, cerebellar degeneration, aplastic anemia, myocardial infarction, stroke, reperfusion injury, and toxin-induced liver disease [see, Thompson, supra].

Apoptotic cell death is typically accompanied by one or more characteristic morphological and biochemical changes in cells, such as condensation of cytoplasm, loss of plasma membrane microvilli, segmentation of the nucleus, degradation of chromosomal DNA or loss of mitochondrial function. A variety of extrinsic and intrinsic signals are believed to trigger or induce such morphological and biochemical cellular changes [Raff, Nature, 356:397-400 (1992); Steller, supra; Sachs et al., Blood, 82:15 (1993)]. For instance, they can be triggered by hormonal stimuli, such as glucocorticoid hormones for immature thymocytes, as well as withdrawal of certain growth factors [Watanabe-Fukunaga et al., Nature, 356:314-317 (1992)]. Also, some identified oncogenes such as myc, rel, and ElA, and tumor suppressors, like p53, have been reported to have a role in inducing apoptosis. Certain chemotherapy drugs and some forms of radiation have likewise been observed to have apoptosis-inducing activity [Thompson, supra].

Various molecules, such as tumor necrosis factor-α ("TNF-α"), tumor necrosis factory ("TNF-β" or "lymphotoxin"), CD30 ligand, CD27 ligand, CD40 ligand, OX-40 ligand, 4-1BB ligand, Apo-1 ligand (also referred to as Fas ligand or CD95 ligand), and Apo-2 ligand (also referred to as TRAIL) have been identified as members of the tumor necrosis factor ("TNF") family of cytokines [See, e.g., Gruss and Dower, Blood, 85:3378-3404 (1995); Wiley et al., Immunity, 3:673-682 (1995); Pitti et al., J. Biol. Chem., 271:12687-12690 (1996)]. Among these molecules, TNF-α, TNF-β, CD30 ligand, 4-1BB ligand, Apo-1 ligand, and Apo-2 ligand (TRAIL) have been reported to be involved in apoptotic cell death. Both TNF-α and TNF-β have been reported to induce apoptotic death in susceptible tumor cells [Schmid et al., Proc. Natl. Acad. Sci., 83:1881 (1986); Dealtry et al., Eur. J. Immunol., 17:689 (1987)]. Zheng et al. have reported that TNF-α is involved in post-stimulation apoptosis of CD8-positive T cells [Zheng et al., Nature, 377:348-351 (1995)]. Other investigators have reported that CD30 ligand may be involved in deletion of self-reactive T cells in the thymus [Amakawa et al., Cold Spring Harbor Laboratory Symposium on Programmed Cell Death, Abstr. No. 10, (1995)].

Mutations in the mouse Fas/Apo-1 receptor or ligand genes (called lpr and gld, respectively) have been associated with some autoimmune disorders, indicating that Apo-1 ligand may play a role in regulating the clonal deletion of self-reactive lymphocytes in the periphery [Krammer et al., Curr. Op. Immunol., 6:279-289 (1994); Nagata et al., Science, 267:1449-1456 (1995)]. Apo-1 ligand is also reported to induce post-stimulation apoptosis in CD4-positive T lymphocytes and in B lymphocytes, and may be involved in the elimination of activated lymphocytes when their function is no longer needed [Krammer et al., supra; Nagata et al., supra]. Agonist mouse monoclonal antibodies specifically binding to the Apo-1 receptor have been reported to exhibit cell killing activity that is comparable to or similar to that of TNF-α [Yonehara et al., J. Exp. Med., 169:1747-1756 (1989)].

Induction of various cellular responses mediated by such TNF family cytokines is believed to be initiated by their binding to specific cell receptors. Two distinct TNF receptors of approximately 55-kDa (TNFR1) and 75-kDa (TNFR2) have been identified [Hohman et al., J. Biol. Chem., 264:14927-14934(1989); Brockhaus et al., Proc. Natl. Acad. Sci., 87:3127-3131 (1990); EP 417,563, published Mar. 20, 1991] and human and mouse cDNAs corresponding to both receptor types have been isolated and characterized [Loetscher et al., Cell, 61:351 (1990); Schall et al., Cell, 61:361 (1990); Smith et al., Science, 248:1019-1023 (1990); Lewis et al., Proc. Natl. Acad. Sci., 88:2830-2834 (1991); Goodwin et al., Mol. Cell. Biol., 11:3020-3026 (1991)]. Extensive polymorphisms have been associated with both TNF receptor genes [see, e.g., Takao et al., Immunogenetics, 37:199-203 (1993)]. Both TNFRs share the typical structure of cell surface receptors including extracellular, transmembrane and intracellular regions. The extracellular portions of both receptors are found naturally also as soluble TNF-binding proteins [Nophar, Y. et al., *EMBO J.*, 9:3269 (1990); and Kohno, T. et al., *Proc. Natl. Acad. Sci. U.S.A.*, 87:8331 (1990)]. More recently, the cloning of recombinant soluble TNF receptors was reported by Hale et al. [*J. Cell. Biochem. Supplement* 15F, 1991, p. 113 (P424)].

The extracellular portion of type 1 and type 2 TNFRs (TNFR1 and TNFR2) contains a repetitive amino acid sequence pattern of four cysteine-rich domains (CRDs) designated 1 through 4, starting from the $NH_2$-terminus. Each CRD is about 40 amino acids long and contains 4 to 6 cysteine residues at positions which are well conserved [Schall et al., supra; Loetscher et al., supra; Smith et al., supra; Nophar et al., supra; Kohno et al., supra]. In TNFR1, the approximate boundaries of the four CRDs are as follows: CRD1-amino acids 14 to about 53; CRD2-amino acids from about 54 to about 97; CRD3-amino acids from about 98 to about 138; CRD4-amino acids from about 139 to about 167. In TNFR2, CRD1 includes amino acids 17 to about 54; CRD2-amino acids from about 55 to about 97; CRD3-amino acids from about 98 to about 140; and CRD4-amino acids from about 141 to about 179 [Banner et al., *Cell*, 73:431-435 (1993)]. The potential role of the CRDs in ligand binding is also described by Banner et al., supra.

A similar repetitive pattern of CRDs exists in several other cell-surface proteins, including the p75 nerve growth factor receptor (NGFR) [Johnson et al., *Cell*, 47:545 (1986); Radeke et al., *Nature*, 325:593 (1987)], the B cell antigen CD40 [Stamenkovic et al., *EMBO J.*, 8:1403 (1989)], the T cell antigen OX40 [Mallet et al., *EMBO J.*, 9:1063 (1990)] and the Fas antigen [Yonehara et al., supra and Itoh et al., supra]. CRDs are also found in the soluble TNFR (sTNFR)-like T2 proteins of the Shope and myxoma poxviruses [Upton et al., *Virology*, 160:20-29 (1987); Smith et al., *Biochem. Biophys. Res. Commun.*, 176:335 (1991); Upton et al., *Virology*, 184:370 (1991)]. Optimal alignment of these sequences indicates that the positions of the cysteine residues are well conserved. These receptors are sometimes collectively referred to as members of the TNF/NGF receptor superfamily. Recent studies on p75NGFR showed that the deletion of CRD1 [Welcher, A. A. et al., *Proc. Natl. Acad. Sci. USA*, 88:159-163 (1991)] or a 5-amino acid insertion in this domain [Yan, H. and Chao, M. V., *J. Biol. Chem.*, 266:12099-12104 (1991)] had little or no effect on NGF binding [Yan, H. and Chao, M. V. supra]. p75 NGFR contains a proline-rich stretch of about 60 amino acids, between its CRD4 and transmembrane region, which is not involved in NGF binding [Peetre, C. et al., *Eur. J. Hematol.*, 41:414-419 (1988); Seckinger, P. et al., *J. Biol. Chem.*, 264:11966-11973 (1989); Yan, H. and Chao, M. V., supra]. A similar proline-rich region is found in TNFR2 but not in TNFR1.

Itoh et al. disclose that the Apo-1 receptor can signal an apoptotic cell death similar to that signaled by the 55-kDa TNFR1 [Itoh et al., supra]. Expression of the Apo-1 antigen has also been reported to be down-regulated along with that of TNFR1 when cells are treated with either TNF-α or anti-Apo-1 mouse monoclonal antibody [Krammer et al., supra; Nagata et al., supra]. Accordingly, some investigators have hypothesized that cell lines that co-express both Apo-1 and TNFR1 receptors may mediate cell killing through common signaling pathways [Id.].

The TNF family ligands identified to date, with the exception of lymphotoxin-α, are type II transmembrane proteins, whose C-terminus is extracellular. In contrast, the receptors in the TNF receptor (TNFR) family identified to date are type I transmembrane proteins. In both the TNF ligand and receptor families, however, homology identified between family members has been found mainly in the extracellular domain ("ECD"). Several of the TNF family cytokines, including TNF-α, Apo-1 ligand and CD40 ligand, are cleaved proteolytically at the cell surface; the resulting protein in each case typically forms a homotrimeric molecule that functions as a soluble cytokine. TNF receptor family proteins are also usually cleaved proteolytically to release soluble receptor ECDs that can function as inhibitors of the cognate cytokines.

Recently, other members of the TNFR family have been identified. In Marsters et al., *Curr. Biol.*, 6:750 (1996), investigators describe a full length native sequence human polypeptide, called Apo-3, which exhibits similarity to the TNFR family in its extracellular cysteine-rich repeats and resembles TNFR1 and CD95 in that it contains a cytoplasmic death domain sequence [see also Marsters et al., *Curr. Biol.*, 6:1669 (1996)]. Apo-3 has also been referred to by other investigators as DR3, wsl-1 and TRAMP [Chinnaiyan et al., *Science*, 274:990 (1996); Kitson et al., *Nature*, 384: 372 (1996); Bodmer et al., *Immunity*, 6:79 (1997)].

Pan et al. have disclosed another TNF receptor family member referred to as "DR4" [Pan et al., *Science*, 276:111-113 (1997)]. The DR4 was reported to contain a cytoplasmic death domain capable of engaging the cell suicide apparatus. Pan et al. disclose that DR4 is believed to be a receptor for the ligand known as Apo-2 ligand or TRAIL.

In Sheridan et al., *Science*, 277:818-821 (1997) and Pan et al., *Science*, 277:815-818 (1997), another molecule believed to be a receptor for the Apo-2 ligand (TRAIL) is described. That molecule is referred to as DR5 (it has also been alternatively referred to as Apo-2). Like DR4, DR5 is reported to contain a cytoplasmic death domain and be capable of signaling apoptosis.

In Sheridan et al., supra, a receptor called DcR1 (or alternatively, Apo-2DcR) is disclosed as being a potential decoy receptor for Apo-2 ligand (TRAIL). Sheridan et al. report that DcR1 can inhibit Apo-2 ligand function in vitro. See also, Pan et al., supra, for disclosure on the decoy receptor referred to as TRID.

As presently understood, the cell death program contains at least three important elements—activators, inhibitors, and effectors; in *C. elegans*, these elements are encoded respectively by three genes, Ced-4, Ced-9 and Ced-3 [Steller, *Science*, 267:1445 (1995); Chinnaiyan et al., *Science*, 275: 1122-1126 (1997); Wang et al., *Cell*, 90:1-20 (1997)]. Two of the TNFR family members, TNFR1 and Fas/Apo1 (CD95), can activate apoptotic cell death [Chinnaiyan and Dixit, *Current Biology*, 6:555-562(1996); Fraser and Evan, *Cell;* 85:781-784 (1996)]. TNFR1 is also known to mediate activation of the transcription factor, NF-κB [Tartaglia et al., *Cell*, 74:845-853 (1993); Hsu et al., *Cell*, 84:299-308 (1996)]. In addition to some ECD homology, these two receptors share homology in their intracellular domain (ICD) in an oligomerization interface known as the death domain [Tartaglia et al., supra; Nagata, *Cell*, 88:355 (1997)]. Death domains are also found in several metazoan proteins that regulate apoptosis, namely, the Drosophila protein, Reaper, and the mammalian proteins referred to as FADD/ MORT1, TRADD, and RIP [Cleaveland and Ihle, *Cell*, 81:479-482 (1995)]. Using the yeast-two hybrid system, Raven et al. report the identification of protein, wsl-1, which binds to the TNFR1 death domain [Raven et al., Programmed Cell Death Meeting, Sep. 20-24, 1995, Abstract at page 127; Raven et al., *European Cytokine Network,* 7: Abstr. 82 at page 210 (April-June 1996); see also, Kitson et al., *Nature,* 384:372-375 (1996)]. The wsl-1 protein is described as being homologous to TNFR1 (48% identity) and having a restricted tissue distribution. According to Raven et al., the tissue distribution of wsl-1 is significantly different from the TNFR 1 binding protein, TRADD.

Upon ligand binding and receptor clustering, TNFR1 and CD95 are believed to recruit FADD into a death-inducing signalling complex. CD95 purportedly binds FADD directly, while TNFR1 binds FADD indirectly via TRADD [Chinnaiyan et al., *Cell,* 81:505-512 (1995); Boldin et al., *J. Biol. Chem.,* 270:387-391 (1995); Hsu et al., supra; Chinnaiyan et al., *J. Biol. Chem.,* 271:4961-4965 (1996)]. It has been reported that FADD serves as an adaptor protein which recruits the Ced-3-related protease, MACHα/FLICE (caspase 8), into the death signalling complex [Boldin et al., *Cell,* 85:803-815 (1996); Muzio et al., *Cell,* 85:817-827 (1996)]. MACHα/FLICE appears to be the trigger that sets off a cascade of apoptotic proteases, including the interleukin-1β converting enzyme (ICE) and CPP32/Yama, which may execute some critical aspects of the cell death programme [Fraser and Evan, supra].

It was recently disclosed that programmed cell death involves the activity of members of a family of cysteine proteases related to the *C. elegans* cell death gene, ced-3, and to the mammalian IL-1-converting enzyme, ICE. The activity of the ICE and CPP32/Yama proteases can be inhibited by the product of the cowpox virus gene, crmA [Ray et al., *Cell,* 69:597-604 (1992); Tewari et al., *Cell,* 81:801-809 (1995)]. Recent studies show that CrmA can inhibit TNFR1- and CD95-induced cell death [Enari et al., *Nature,* 375:78-81 (1995); Tewari et al., *J. Biol. Chem.,* 270:3255-3260 (1995)].

As reviewed recently by Tewari et al., TNFR1, TNFR2 and CD40 modulate the expression of proinflammatory and costimulatory cytokines, cytokine receptors, and cell adhesion molecules through activation of the transcription factor, NF-ΚB [Tewari et al., *Curr. Op. Genet. Develop.,* 6:39-44 (1996)]. NF-κB is the prototype of a family of dimeric transcription factors whose subunits contain conserved Rel regions [Verma et al., *Genes Develop.,* 2:2723-2735 (1996); Baldwin, *Ann. Rev. Immunol.,* 14:649-681 (1996)]. In its latent form, NF-κB is complexed with members of the IκB inhibitor family; upon inactivation of the IκB in response to certain stimuli, released NF-κB translocates to the nucleus where it binds to specific DNA sequences and activates gene transcription.

For a review of the TNF family of cytokines and their receptors, see Gruss and Dower, supra.

9. PRO365

Polypeptides such as human 2-19 protein may function as cytokines. Cytokines are low molecular weight proteins which function to stimulate or inhibit the differentiation, proliferation or function of immune cells. Cytokines often act as intercellular messengers and have multiple physiological effects. Given the physiological importance of immune mechanisms in vivo, efforts are currently being under taken to identify new, native proteins which are involved in effecting the immune system. We describe herein the identification of a novel polypeptide which has homology to the human 2-19 protein.

10. PRO1361

Efforts are being undertaken by both industry and academia to identify new, native transmembrane receptor proteins. Many efforts are focused on the screening of mammalian recombinant DNA libraries to identify the coding sequences for novel receptor proteins. We herein describe the identification and characterization of novel transmembrane polypeptides, designated herein as PRO1361 polypeptides.

11. PRO1308

Follistatin is a secreted protein that regulates secretion of pituitary follicle-stimulating hormone (FSH). It functions by binding to, and thereby inhibiting, proteins such as activin and other members of the transforming growth factor beta (TGFβ) family, that stimulate the production and secretion of FSH from the anterior pituitary. Follistatin is also involved in mechanisms that control basic development, including the induction of neural development. Follistatin also exhibits angiogenic properties, particularly in combination with basic fibroblast growth factor (bFGF). As such, there is strong interest in identifying new members of the follistatin family of proteins. The identification and characterization of follistatins is the topic of the following references which are incorporated hereinby reference: Sugino et al. *J. Med Invest* (1997) 44: (1-2): 1-14; Mather et al., *Proc. Soc. Exp.* biol. Med. (1997) 215(3):209-222; Thomsen, G. H., *Trends Genet* (1997) 13(6): 209-211; DePaolo, L. V., *Proc. Soc. Exp. Biol. Med.* (1997) 214(4):328-339; Peng et al., *Biol. Signals* (1996) 5(2):81-89, and Halvorson et al. *Fertil Steril* (1996) 65(3):459-469.

12. PRO1183

Protoporphyrinogen oxidase catalyzes the penultimate step in the heme biosynthetic pathway. Deficiency in activity of this enzyme results in the human genetic disease variegate porphyria. Thus, protoporphyrinogen oxidases and molecules which either modulate or are related to these oxidases are of interest. Moreover, oxidases, and related molecules in general are also of interest. Oxidases are further described in at least Birchfield, et al., *Biochemistry,* 37(19):6905-6910 (1998); Fingar, et al., *Cancer Res.,* 57(20):4551-4556 (1997); Arnould, et al., *Biochemistry,* 36(33): 10178-10184 (1997); and Dailey and Dailey, *Cell Mol. Biol.,* 43(1):67-73 (1997).

13. PRO1272

The cement gland is an ectodermal organ in the head of frog embryos, lying anterior to any neural tissue. The cement gland, like neural tissue, has been shown to be induced by the dorsal mesoderm. XAG-1 is a cement gland specific protein that is useful as a marker of cement gland induction during development. See, Sive, et al., *Cell,* 58(1):171-180 (1989); Itoh, et al., *Development,* 121(12):3979-3988 (1995). XAG-2 and other proteins related to the XAG family are further described in Aberger, et al., Mech. Dev., 72(1-2):115-130 (1998) and Gammill and Sive, *Development,* 124(2):471-481 (1997). Thus, novel polypeptides having sequence identity with XAG proteins are of interest.

14. PRO1419

Efforts are being undertaken by both industry and academia to identify new, native secreted proteins. Many efforts are focused on the screening of mammalian recombinant DNA libraries to identify the coding sequences for novel secreted proteins. We herein describe the identification and characterization of novel secreted polypeptides, designated herein as PRO1419 polypeptides.

15. PRO4999

Uromodulin is synthesized in the kidney and is the most abundant protein in normal human urine. The amino acid sequence encoded by one of the exons of the uromodulin gene has homology to the low-density-lipoprotein receptor and the epidermal growth factor precursor. Pennica et al., *Science* 236:83-88 (1987). The function of uromodulin is not known; however, it may function as a unique renal regulatory glycoprotein that specifically binds to and regulates the circulating activity of a number of potent cytokines, as it binds to IL-1, IL-2 and TNF with high affinity. See Hession et al., Science 237:1479-1484 (1987). Su et al. suggest that uromodulin plays a significant role in the innate immunity of the urinary system and that the immunostimulatory activity of uromodulin is potentially useful for immunotherapy. Su et al., J. Immunology, 158:3449-3456 (1997).

We herein describe the identification and characterization of novel polypeptides having sequence similarity to uromodulin, designated herein as PRO4999 polypeptides.

16. PRO7170

Efforts are being undertaken by both industry and academia to identify new, native secreted proteins. Many efforts are focused on the screening of mammalian recombinant DNA libraries to identify the coding sequences for novel secreted proteins. We herein describe the identification and characterization of novel secreted polypeptides, designated herein as PRO7170 polypeptides.

17. PRO248

Cytokines have been implicated in the pathogenesis of a number of brain diseases in which neurological dysfuntion has been attributed to a change in amino acid neurotransmitter metabolism. In particular, members of the transforming growth factorβs (TGFB) have been implicated. Transforming growth peptides are small polypeptides that were first identified by their ability to induce proliferation and transformation in noncancerous cells in culture. Although initially defined as a growth factor, TGFB also inhibits proliferation of epithelial, endothelial, lymphoid, and hematopoietic cells. This cytokine is thought to play an important role in regulating the duration of the inflammatory response, allowing the healing process to proceed. It is also a potent immunomodulator, which has many pleiotrophic effects, including regulating many other cytokines.

The TGFβ family includes basic myelin proteins (BMP-2, BMP-4, BMP-5, BMP-6, BMP-7), activins A & B, decapentaplegic (dpp), 60A, OP-2, dorsalin, growth differentiation factors (GDFs) 1, 3, and 9, nodal, MIS, Inhibin α, transforming growth factors betas (TGF-β1, TGF-β2, TGF-β3, TGF-β5), and glial-derived neurotrophic factor (GDNF), Atrisano, et al., *J. Biochemica et Biophysica Acta.* 1222:71-80 (1994). Of particuar interest are the growth differentiation factors, for as their name implies, these factors are implicated in the differentiation of cells.

Thus, identifying proteins having homology to the TGFβ family members, particularly growth differentiation factor (GDF) 3, is of importance to the medical and industrial community. Generally, proteins having homology to each other have similar function. It is also of interest when proteins having homology do not have similar functions, indicating that certain structural motifs identify information other than function, such as locality of function.

18. PRO353

The complement proteins comprise a large group of serum proteins some of which act in an enzymatic cascade, producing effector molecules involved in inflammation. The complement proteins are of particular importance in regulating movement and function of cells involved in inflammation. Given the physiological importance of inflammation and related mechanisms in vivo, efforts are currently being under taken to identify new, native proteins which are involved in inflamation. We describe herein the identification and characterization of novel polypeptides which have homology to complement proteins, designated herein as PRO353 polypeptides.

19. PRO533

Growth factors are molecular signals or mediators that enhance cell growth or proliferation, alone or in concert, by binding to specific cell surface receptors. however, there are other cellular reactions than only growth upon expression to growth factors. As a result, growth factors are better characterized as multifunctional and potent cellular regulators. Their biological effects include proliferation, chemotaxis and stimulation of extracellular matrix production. Growth factors can have both stimulatory and inhibitory effects. For example, transforming growth factors (TGF-β) is highly pleiotropic and can stimulate proliferation in some cells, especially connective tissues, while being a potent inhibitor of proliferation in others, such as lymphocytes and epithelial cells.

The physiological effect of growth stimulation or inhibition by growth factors depends upon the state of development and differentiation of the target tissue. The mechanism of local cellular regulation by classical endocrine molecules comprehends autocrine (same cell), juxtacrine (neighbor cell), and paracrine (adjacent cell) pathways. Peptide growth factors are elements of a complex biological language, providing the basis for intercellular communication. They permit cells to convey information between each other, mediate interaction between cells and change gene expression. the effect of these multifunctional and pluripotent factors is dependent on the presence or absence of other peptides.

Fibroblast growth factors (FGFs) are a family of heparin-binding, potent mitogens for both normal diploid fibroblasts and established cell lines, Godpodarowicz, D. et al. (1984), Proc. Natl. Acad. Sci. USA 81: 6983. the FGF family comprises acidic FGF (FGF-1), basic FGF (FGF-2), INT-2 (FGF-3), K-FGF/HST (FGF-4), FGF-5, FGF-6, KGF (FGF-7), AIGF (FGF-8) among others. All FGFs have two conserved cysteine residues and share 30-50% sequence homology at the amino acid level. These factors are mitogenic for a wide variety of normal diploid mesoderm-derived and neural crest-derived cells, inducing granulosa cells, adrenal cortical cells, chrondocytes, myoblasts, corneal and vascular endothelial cells (bovine or human), vascular smooth muscle cells, lens, retina and prostatic epithelial cells, oligodendrocytes, astrocytes, chrondocytes, myoblasts and osteoblasts.

Fibroblast growth factors can also stimulate a large number of cell types in a non-mitogenic manner. These activities include promotion of cell migration into a wound area (chemotaxis), initiation of new blood vessel formulation (angiogenesis), modulation of nerve regeneration and survival (neurotrophism), modulation of endocrine functions, and stimulation or suppression of specific cellular protein expression, extracellular matrix production and cell survival. Baird, A. & Bohlen, P., *Handbook of Exp. Phrmacol.* 95(1): 369-418 (1990). These properties provide a basis for using fibroblast growth factors in therapeutic approaches to accelerate wound healing, nerve repair, collateral blood vessel formation, and the like. For example, fibroblast growth factors, have been suggested to minimize myocardium damage in heart disease and surgery (U.S. Pat. No. 4,378,437).

We herein describe the identification and characterization of novel polypeptides having homology to FGF, herein designated PRO533 polypeptides.

20. PRO301

The widespread occurrence of cancer has prompted the devotion of considerable resources and discovering new treatments of treatment. One particular method involves the creation of tumor or cancer specific monoclonal antibodies (mAbs) which are specific to tumor antigens. Such mAbs, which can distinguish between normal and cancerous cells are useful in the diagnosis, prognosis and treatment of the disease. Particular antigens are known to be associated with neoplastic diseases, such as colorectal cancer.

One particular antigen, the A33 antigen is expressed in more than 90% of primary or metastatic colon cancers as well as normal colon epithelium. Since colon cancer is a widespread disease, early diagnosis and treatment is an important medical goal. Diagnosis and treatment of colon cancer can be implemented using monoclonal antibodies (mAbs) specific therefore having fluorescent. nuclear magnetic or radioactive tags. Radioactive gene, toxins and/or drug tagged mAbs can be used for treatment in situ with minimal patient description. mAbs can also be used to diagnose during the diagnosis and treatment of colon cancers. For example, when the serum levels of the A33 antigen are elevated in a patient, a drop of the levels after surgery would indicate the tumor resection was successful. On the other hand, a subsequent rise in serum A33 antigen levels after surgery would indicate that metastases of the original tumor may have formed or that new primary tumors may have appeared. Such monoclonal antibodies can be used in lieu of, or in conjunction with surgery and/or other chemotherapies. For example, U.S. Pat. No. 4,579,827 and U.S. Ser. No. 424,991 (E.P. 199,141) are directed to therapeutic administration of monoclonal antibodies, the latter of which relates to the application of anti-A33 mAb.

Many cancers of epithelial origin have adenovirus receptors. In fact, adenovirus-derived vectors have been proposed as a means of inserting antisense nucleic acids into tumors (U.S. Pat. No. 5,518,885). Thus, the association of viral receptors with neoplastic tumors is not unexpected.

We herein describe the identification and characterization of novel polypeptides having homology to certain cancer-associated antigens, designated herein as PRO301 polypeptides.

21. PRO187

Growth factors are molecular signals or mediators that enhance cell growth or proliferation, alone or in concert, by binding to specific cell surface receptors. However, there are other cellular reactions than only growth upon expression to growth factors. As a result, growth factors are better characterized as multifunctional and potent cellular regulators. Their biological effects include proliferation, chemotaxis and stimulation of extracellular matrix production. Growth factors can have both stimulatory and inhibitory effects. For example, transforming growth factor (TGF-β) is highly pleiotropic and can stimulate proliferation in some cells, especially connective tissue, while being a potent inhibitor of proliferation in others, such as lymphocytes and epithelial cells.

The physiological effect of growth stimulation or inhibition by growth factors depends upon the state of development and differentiation of the target tissue. The mechanism of local cellular regulation by classical endocrine molecules involves comprehends autocrine (same cell), juxtacrine (neighbor cell), and paracrine (adjacent cells) pathways. Peptide growth factors are elements of a complex biological language, providing the basis for intercellular communication. They permit cells to convey information between each other, mediate interaction between cells and change gene expression. The effect of these multifunctional and pluripotent factors is dependent on the presence or absence of other peptides.

FGF-8 is a member of the fibroblast growth factors (FGFs) which are a family of heparin-binding, potent mitogens for both normal diploid fibroblasts and established cell lines, Gospodarowicz et al. (1984), *Proc. Natl. Acad. Sci. USA* 81:6963. The FGF family comprises acidic FGF (FGF-1), basic FGF (FGF-2), INT-2 (FGF-3), K-FGF/HST (FGF-4), FGF-5, FGF-6, KGF (FGF-7), AIGF (FGF-8) among others. All FGFs have two conserved cysteine residues and share 30-50% sequence homology at the amino acid level. These factors are mitogenic for a wide variety of normal diploid mesoderm-derived and neural crest-derived cells, including granulosa cells, adrenal cortical cells, chondrocytes, myoblasts, corneal and vascular endothelial cells (bovine or human), vascular smooth muscle cells, lens, retina and prostatic epithelial cells, oligodendrocytes, astrocytes, chrondocytes, myoblasts and osteoblasts.

Fibroblast growth factors can also stimulate a large number of cell types in a non-mitogenic manner. These activities include promotion of cell migration into wound area (chemotaxis), initiation of new blood vessel formulation (angiogenesis), modulation of nerve regeneration and survival (neurotrophism), modulation of endocrine functions, and stimulation or suppression of specific cellular protein expression, extracellular matrix production and cell survival. Baird & Bohlen, Handbook of Exp. Pharmacol. 95(1): 369-418, Springer, (1990). These properties provide a basis for using fibroblast growth factors in therapeutic approaches to accelerate wound healing, nerve repair, collateral blood vessel formation, and the like. For example, fibroblast growth factors have been suggested to minimize myocardium damage in heart disease and surgery (U.S. Pat. No. 4,378,347).

FGF-8, also known as androgen-induced growth factor (AIGF), is a 215 amino acid protein which shares 3040% sequence homology with the other members of the FGF family. FGF-8 has been proposed to be under androgenic regulation and induction in the mouse mammary carcinoma cell line SC3. Tanaka et al., *Proc. Natl. Acad. Sci. USA* 89: 8928-8932 (1992); Sato et al., *J. Steroid Biochem. Molec. Biol.* 47: 91-98 (1993). As a result, FGF-8 may have a local role in the prostate, which is known to be an androgen-responsive organ. FGF-8 can also be oncogenic, as it displays transforming activity when transfected into NIH-3T3 fibroblasts. Kouhara et al., *Oncogene* 9455-462 (1994). While FGF-8 has been detected in heart, brain, lung, kidney, testis, prostate and ovary, expression was also detected in the absence of exogenous androgens. Schmitt et al., *J. Steroid Biochem. Mol. Biol.* 57 (3-4): 173-78 (1996).

FGF-8 shares the property with several other FGFs of being expressed at a variety of stages of murine embryogenesis, which supports the theory that the various FGFs have multiple and perhaps coordinated roles in differentiation and embryogenesis. Moreover, FGF-8 has also been identified as a protooncogene that cooperates with Wnt-1 in the process of mammary tumorigenesis (Shackleford et al., *Proc. Natl. Acad. Sci. USA* 90, 740-744 (1993); Heikinheimo et al., Mech. Dev. 48: 129-138 (1994)).

In contrast to the other FGFs, FGF-8 exists as three protein isoforms, as a result of alternative splicing of the primary transcript. Tanaka et al., supra. Normal adult expression of FGF-8 is weak and confined to gonadal tissue, however northern blot analysis has indicated that FGF-8 mRNA is present from day 10 through day 12 or murine gestation, which suggests that FGF-8 is important to normal development. Heikinheimo et al., Mech Dev. 48(2): 129-38 (1994). Further in situ hybridization assays between day 8 and 16 of gestation indicated initial expression in the surface ectoderm of the first bronchial arches, the frontonasal process, the forebrain and the midbrain-hindbrain junction. At days 10-12, FGF-8 was expressed in the surface ectoderm of the forelimb and hindlimb buds, the nasal its and nasopharynx, the infundibulum and in the telencephalon, diencephalon and metencephalon. Expression continues in the developing hindlimbs through day 13 of gestation, but is undetectable thereafter. The results suggest that FGF-8 has a unique temporal and spatial pattern in embryogenesis and suggests a role for this growth factor in multiple regions of ectodermal differentiation in the post-gastrulation embryo.

We herein describe the identification of novel poypeptides having homology to FGF-8, wherein those polypeptides are heein designated PRO187 polypeptides.

22. PRO337

Neuronal development in higher vertebrates is characterized by processes that must successfully navigate distinct cellular environment en route to their synaptic targets. The result is a functionally precise-formation of neural circuits. The precision is believed to result form mechanisms that regulate growth cone pathfinding and target recognition, followed by latter refinement and remodeling of such projections by events that require neuronal activity, Goodman and Shatz, Cell/Neuron [Suppl.] 72(10): 77-98 (1993). It is further evident that different neurons extend nerve fibers that are biochemically distinct and rely on specific guidance cues provided by cell-cell, cell-matrix, and chemotrophic interactions to reach their appropriate synaptic targets, Goodman et al., supra.

One particular means by which diversity of the neuronal cell surface may be generated is through differential expression of cell surface proteins referred to as cell adhesion molecules (CAMs). Neuronally expressed CAMs have been implicated in diverse developmental processes, including migration of neurons along radial glial cells, providing permissive or repulsive substrates for neurite extension, and in promoting the selective fasciculation of axons in projectional pathways. Jessel, Neuron 1: 3-13 (1988); Edelman and Crossin, Annu. Rev. Biochem. 60: 155-190 (1991). Interactions between CAMs present on the growth cone membrane and molecules on opposing cell membranes or in the extracellular matrix are thought to provide the specific guidance cues that direct nerve fiber outgrowth along appropriate projectional pathways. Such interactions are likely to result in the activation of various second messenger systems within the growth cone that regulate neurite outgrowth. Doherty and Walsh, Curr. Opin Neurobiol. 2: 595-601 (1992).

In higher vertebrates, most neural CAMs have been found to be members of three major structural families of proteins: the integrins, the cadherins, and the immunoglobulin gene superfamily (IgSF). Jessel, supra.; Takeichi, Annu. Rev. Biochem. 59: 237-252 (1990); Reichardt and Tomaselli, Annu. Rev. Neurosci. 14: 531-570(1991). Cell adhesion molecules of the IgSF (or Ig-CAMs), inparticular, constitutea large family of proteins frequently implicated in neural cell interactions and nerve fiber outgrowth during development, Salzer and Colman, Dev. Neurosci. 11: 377-390 (1989); Brümmendorf and Rathjen, J. Neurochem. 61: 1207-1219 (1993). However, the majority of mammalian Ig-CAMs appear to be too widely expressed to specify navigational pathways or synaptic targets suggesting that other CAMs, yet to be identified, have role in these more selective interactions of neurons.

Many of the known neural Ig-CAMs have been found to be attached to the plasma membrane via a glycosylphosphatidylinositol (GPI) anchor. Additionally, many studies have implicated GPI-anchored proteins in providing specific guidance cues during the outgrowth on neurons in specific pathways. In studies of the grasshopper nervous system, treatment of embryos with phosphatidylinositol-specific phopholipase C (PIPLC), which selectively removes GPI-anchored proteins from the surfaces of cells, resulted in misdirection and faulty navigation among subsets of pioneering growth cones, as well as inhibited migratory patterns of a subset of early neurons, Chang et al., Devel. 114: 507-519 (1992). The projection of retinal fibers to the optic tectum appears to depend, in part, on a 33 kDa GPI-anchored protein, however, the precise nature of this protein is unknown. Stahl et al., Neuron 5: 735-743 (1990).

The expression of various GPI-anchored proteins has been characterized amongst the different populations of primary rat neurons amongst dorsal root ganglion, sympathetic neurons of the cervical ganglion, sympathetic neurons of the superior cervical ganglion, and cerebellar granule neurons. Rosen et al., J. Cell Biol. 117: 617-627 (1992). In contrast to the similar pattern of total membrane protein expression by these different types of neurons, striking differences were observed in the expression of GPI-anchored proteins between these neurons. Recently, a 65 kDa protein band known as neurotrimin was discovered and found to be differentially expressed by primary neurons (Rosen et al., supra), and restricted to the nervous system and found to be the most abundant and earliest expressed of the GPI-anchored species in the CNS. Struyk et al., J. Neuroscience 15(3): 2141-2156 (1995). The discovery of neurotrimin has further lead to the identification of a family of IgSF members, each containing three Ig-like domains that share significant amino acid identity, now termed IgLON. Struyk et al., supra; Pimenta et al., Gene 170(2): 189-95 (1996).

Additional members of the IgLON subfamily include opiate binding cell adhesion molecule (OBCAM), Schofield et al., EMBO J. 8: 489495 (1989); limbic associated membrane protein (LAMP), Pimenta et al., supra; CEPU-1; GP55, Wilson et al., J. Cell Sci. 109: 3129-3138 (1996); Eur. J. Neurosci. 9(2): 334-41 (1997); and AvGp50, Hancox et al., Brain Res. Mol. Brain Res. 44(2): 273-85 (1997).

While the expression of neurotrimin appears to be widespread, it does appear to correlated with the development of several neural circuits. For example, between E18 and P10, neurotimin mRNA expression within the forebrain is maintained at high levels in neurons of the developing thalamus, cortical subplate, and cortex, particularly laminae V and VI (with less intense expression in II, II, and IV, and minimal expression in lamina I). Cortical subplate neurons may provide an early, temporary scaffold for the ingrowing thalamic afferents en route to their final synaptic targets in the cortex. Allendoerfer and Shatz, Annu. Rev. Neurosci. 17: 185-218 (1994). Conversely, subplate neurons have been suggested to be required for cortical neurons from layer V to select VI to grow into the thalamus, and neurons from layer V to select their targets in the colliculus, pons, and spinal cord (McConnell et al., J. Neurosci. 14: 1892-1907 (1994).

The high level expression of neurotrimin in many of these projections suggests that it could be involved in their development.

In the hindbrain, high levels of neurotrimin message expression were observed within the pontine nucleus and by the internal granule cells and Purkinje cells of the cerebellum. The pontine nucleus received afferent input from a variety of sources including corticopontine fibers of layer V, and is a major source of afferent input, via mossy fibers, to the granule cells which, in turn, are a major source of afferent input via parallel fibers to Purkinje cells. [Palay and Chan-Palay, The cerebellar cortex: cytology and organization. New York: Springer (1974]. High level expression of neurotrimin these neurons again suggests potential involvement in the establishment of these circuits.

Neurotrimin also exhibits a graded expression pattern in the early postnatal striatum. Increased neurotrimin expression is found overlying the dorsolateral striatum of the rat, while lesser hybridization intensity is seen overlying the ventromedial striatum. Struyk et al., supra. This region of higher neurotrimin hybridization intensity does not correspond to a cytoarchitecturally differentiable region, rather it corresponds to the primary area of afferent input from layer VI of the contralateral sensorimotor cortex (Gerfen, Nature 311: 461-464 (1984); Donoghue and Herkenham, Brain Res. 365: 397403 (1986)). The ventromedial striatum, by contrast, receives the majority of its afferent input from the perirhinal and association cortex. It is noteworthy that a complementary graded pattern of LAMP expression, has been observed within the striatium, with highest expression in ventromedial regions, and lowest expression dorsolaterally. Levitt, Science 223: 299-301 (1985); Chesselet et al., Neuroscience 40: 725-733 (1991).

23. PRO1411

Efforts are being undertaken by both industry and academia to identify new, native secreted proteins. Many efforts are focused on the screening of mammalian recombinant DNA libraries to identify the coding sequences for novel secreted proteins. We herein describe the identification and characterization of a novel secreted protein designated herein as PRO1411.

24. PRO4356

Glycosylphosphatidylinositol (GPI) anchored proteoglycans are generally localized to the cell surface and are thus known to be involved in the regulation of responses of cells to numerous growth factors, cell adhesion molecules and extracellular matrix components. The metastasis-associated GPI-anchored protein (MAGPIAP) is one of these cell surface proteins which appears to be involved in metastasis. Metastasis is the form of cancer wherein the transformed or malignant cells are traveling and spreading the cancer from one site to another. Therefore, identifying the polypeptides related to metastasis and MAGPIAP is of interest.

25. PRO246

The cell surface protein HCAR is a membrane-bound protein that acts as a receptor for subgroup C of the adenoviruses and subgroup B of the coxsackieviruses. Thus, HCAR may provide a means for mediating viral infection of cells in that the presence of the HCAR receptor on the cellular surface provides a binding site for viral particles, thereby facilitating viral infection.

In light of the physiological importance of membrane-bound proteins and specficially those which serve a cell surface receptor for viruses, efforts are currently being undertaken by both industry and academia to identify new, native membrane-bound receptor proteins. Many of these efforts are focused on the screening of mammalian recombinant DNA libraries to identify the coding sequences for novel receptor proteins. We herein describe a novel membrane-bound polypeptide (designated herein as PRO246) having homology to the cell surface protein HCAR and to various tumor antigens including A33 and carcinoembryonic antigen, wherein this polypeptide may be a novel cell surface virus receptor or tumor antigen.

26. PRO265

Protein-protein interactions include receptor and antigen complexes and signaling mechanisms. As more is known about the structural and functional mechanisms underlying protein-protein interactions, protein-protein interactions can be more easily manipulated to regulate the particular result of the protein-protein interaction. Thus, the underlying mechanisms of protein-protein interactions are of interest to the scientific and medical community.

All proteins containing leucine-rich repeats are thought to be involved in protein-protein interactions. Leucine-rich repeats are short sequence motifs present in a number of proteins with diverse functions and cellular locations. The crystal structure of ribonuclease inhibitor protein has revealed that leucine-rich repeats correspond to beta-alpha structural units. These units are arranged so that they form a parallel beta-sheet with one surface exposed to solvent, so that the protein acquires an unusual, nonglubular shape. These two features have been indicated as responsible for the protein-binding functions of proteins containing leucine-rich repeats. See, Kobe and Deisenhofer, *Trends Biochem. Sci.*, 19(10):415-421 (Oct. 1994).

A study has been reported on leucine-rich proteoglycans which serve as tissue organizers, orienting and ordering collagen fibrils during ontogeny and are involved in pathological processes such as wound healing, tissue repair, and tumor stroma formation. Iozzo, R. V., *Crit. Rev. Biochem. Mol. Biol.*, 32(2): 141-174 (1997). Others studies implicating leucine rich proteins in wound healing and tissue repair are De La Salle, C., et al., *Vouv. Rev. Fr. Hematol.* (Germany), 37(4):215-222 (1995), reporting mutations in the leucine rich motif in a complex associated with the bleeding disorder Bernard-Soulier syndrome and Chlemetson, K. J., *Thromb. Haemost.* (Germany), 74(1): 111-116 (July 1995), reporting that platelets have leucine rich repeats. Another protein of particular interest which has been reported to have leucine-rich repeats is the SLIT protein which has been reported to be useful in treating neuro-degenerative diseases such as Alzheimer's disease, nerve damage such as in Parkinson's disease, and for diagnosis of cancer, see, Artavanistsakonas, S. and Rothberg, J. M., WO9210518-A1 by Yale University. Other studies reporting on the biological functions of proteins having leucine-rich repeats include: Tayar, N., et al., *Mol. Cell Endocrinol.*, (Ireland), 125(1-2): 65-70 (Dec. 1996) (gonadotropin receptor involvement); Miura, Y., et al., *Nippon Rinsho* (Japan), 54(7):1784-1789 (July 1996) (apoptosis involvement); Harris, P. C., et al., *J. Am. Soc. Nephrol.*, 6(4):1125-1133 (Oct. 1995) (kidney disease involvement); and Ruoslahti, E. I., et al., WO9110727-A by La Jolla Cancer Research Foundation (decorin binding to transforming growth factor-β involvement for treatment for cancer, wound healing and scarring). Also of particular interest is fibromodulin and its use to prevent or reduce dermal scarring. A study of fibromodulin is found in U.S. Pat. No. 5,654,270 to Ruoslahti, et al.

Efforts are therefore being undertaken by both industry and academia to identify new proteins having leucine rich repeats to better understand protein-protein interactions. Of particular interest are those proteins having leucine rich repeats and homology to known proteins having leucine rich repeats such as fibromodulin, the SLIT protein and platelet glycoprotein V. Many efforts are focused on the screening of mammalian recombinant DNA libraries to identify the coding sequences for novel secreted and membrane-bound proteins having leucine rich repeats. We herein describe the identification and characterization of novel polypeptides having homology to fibromodulin, herein designated as PRO265 polypeptides.

27. PRO941

Cadherins are a large family of transmembrane proteins. Cadherins comprise a family of calcium-dependent glycoproteins that function in mediating cell-cell adhesion in virtually all solid tissues of multicellular organisms. At least cadherins 1-13 as well as types B, E, EP, M, N, P and R have been identified and characterized. Among the functions cadherins are known for, with some exceptions, are that cadherins participate in cell aggregation and are associated with cell-cell adhesion sites. Recently, it has been reported that while all cadherins share multiple repeats of a cadherin specific motif believed to correspond to folding of extracellular domains, members of the cadherin superfamily have divergent structures and, possibly, functions. In particular it has been reported that members of the cadherin superfamily are involved in signal transduction. See, Suzuki, *J. Cell Biochem.*, 61(4):531-542 (1996). Cadherins are further described in Tanihara et al., *J. Cell Sci.*, 107(6): 1697-1704 (1994), Aberle et al., *J. Cell Biochem.*, 61(4):514-523 (1996) and Tanihara et al., *Cell Adhes. Commun.*, 2(1):15-26 (1994). We herein describe the identification and characterization of a novel polypeptide having homology to a cadherin protein, designated herein as PRO941.

28. PRO10096

Interleukin-10 (IL-10) is a pleiotropic immunosuppressive cytokine that has been implicated as an important regulator of the functions of myeloid and lymphoid cells. It has been demonstrated that IL-10 functions as a potent inhibitor of the activation of the synthesis of various inflammatory cytokines including, for example, IL-1, IL-6, IFN-γ and TNF-γ (Gesser et al., *Proc. Natl. Acad. Sci. USA* 94:14620-14625 (1997)). Moreover, IL-10 has been demonstrated to strongly inhibit several of the accessory activities of macrophages, thereby functioning as a potent suppressor of the effector functions of macrophages, T-cells and NK cells (Kuhn et al., *Cell* 75:263-274 (1993)). Furthermore, IL-10 has been strongly implicated in the regulation of B-cell, mast cell and thymocyte differentiation.

IL-10was independently identified in two separate lines of experiments. First, cDNA clones encoding murine IL-10 were identified based upon the expression of cytokine synthesis inhibitory factor (Moore et al., *Science* 248:1230-1234 (1990)), wherein the human IL-10 counterpart cDNAs were subsequently identified by cross-hybridization with the murine IL-10 cDNA (Viera et al., *Proc. Natl. Acad. Sci. USA* 88:1172-1176 (1991)). Additionally, IL-10 was independently identified as a B-cell-derived mediator which functioned to co-stimulate active thymocytes (Suda et al., *Cell Immunol.* 129:228 (1990)).

We herein describe the identification and characterization of novel polypeptides having sequence similarity to IL-10, designated herein as PRO10096 polypeptides.

29. PRO6003

Efforts are being undertaken by both industry and academia to identify new, native receptor or membrane-bound proteins. Many efforts are focused on the screening of mammalian recombinant DNA libraries to identify the coding sequences for novel receptor or membrane-bound proteins. We herein describe the identification and characterization of novel polypeptides designated herein as PRO6003 polypeptides.

SUMMARY OF THE INVENTION

In one embodiments of the present invention, the invention provides vectors comprising DNA encoding any of the herein described polypeptides. Host cell comprising any such vector are also provided. By way of example, the host cells may be CHO cells, *E. coli*, or yeast. A process for producing any of the herein described polypeptides is further provided and comprises culturing host cells under conditions suitable for expression of the desired polypeptide and recovering the desired polypeptide from the cell culture.

In other embodiments, the invention provides chimeric molecules comprising any of the herein described polypeptides fused to a heterologous polypeptide or amino acid sequence. Example of such chimeric molecules comprise any of the herein described polypeptides fused to an epitope tag sequence or a Fc region of an immunoglobulin.

In another embodiment, the invention provides an antibody which specifically binds to any of the above or below described polypeptides. Optionally, the antibody is a monoclonal antibody, humanized antibody, antibody fragment or single-chain antibody.

In yet other embodiments, the invention provides oligonucleotide probes useful for isolating genomic and cDNA nucleotide sequences or as antisense probes, wherein those probes may be derived from any of the above or below described nucleotide sequences.

In other embodiments, the invention provides an isolated nucleic acid molecule comprising a nucleotide sequence that encodes a PRO polypeptide.

In one aspect, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule encoding a PRO polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein, or (b) the complement of the DNA molecule of (a).

In other aspects, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule comprising the coding sequence of a full-length PRO polypeptide cDNA as disclosed herein, the coding sequence of a PRO polypeptide lacking the signal peptide as disclosed herein, the coding sequence of an extracellular domain of a transmembrane PRO polypeptide, with or without the signal peptide, as disclosed herein or the coding sequence of any other specifically defined fragment of the full-length amino acid sequence as disclosed herein, or (b) the complement of the DNA molecule of (a).

In a further aspect, the invention concerns an isolated nucleic acid molecule comprising a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule that encodes the same mature polypeptide encoded by any of the human protein cDNAs deposited with the ATCC as disclosed herein, or (b) the complement of the DNA molecule of (a).

Another aspect the invention provides an isolated nucleic acid molecule comprising a nucleotide sequence encoding a PRO polypeptide which is either transmembrane domain-deleted or transmembrane domain-inactivated, or is complementary to such encoding nucleotide sequence, wherein the transmembrane domain(s) of such polypeptide are disclosed herein. Therefore, soluble extracellular domains of the herein described PRO polypeptides are contemplated.

Another embodiment is directed to fragments of a PRO polypeptide coding sequence, or the complement thereof, that may find use as, for example, hybridization probes, for encoding fragments of a PRO polypeptide that may optionally encode a polypeptide comprising a binding site for an anti-PRO antibody or as antisense oligonucleotide probes. Such nucleic acid fragments are usually at least about 20 nucleotides in length, alternatively at least about 30 nucleotides in length, alternatively at least about 40 nucleotides in length, alternatively at least about 50 nucleotides in length, alternatively at least about 60 nucleotides in length, alternatively at least about 70 nucleotides in length, alternatively at least about 80 nucleotides in length, alternatively at least about 90 nucleotides in length, alternatively at least about 100 nucleotides in length, alternatively at least about 110 nucleotides in length, alternatively at least about 120 nucleotides in length, alternatively at least about 130 nucleotides in length, alternatively at least about 140 nucleotides in length, alternatively at least about 150 nucleotides in length, alternatively at least about 160 nucleotides in length, alternatively at least about 170 nucleotides in length, alternatively at least about 180 nucleotides in length, alternatively at least about 190 nucleotides in length, alternatively at least about 200 nucleotides in length, alternatively at least about 250 nucleotides in length, alternatively at least about 300 nucleotides in length, alternatively at least about 350 nucleotides in length, alternatively at least about 400 nucleotides in length, alternatively at least about 450 nucleotides in length, alternatively at least about 500 nucleotides in length, alternatively at least about 600 nucleotides in length, alternatively at least about 700 nucleotides in length, alternatively at least about 800 nucleotides in length, alternatively at least about 900 nucleotides in length and alternatively at least about 1000 nucleotides in length, wherein in this context the term "about" means the referenced nucleotide sequence length plus or minus 10% of that referenced length. It is noted that novel fragments of a PRO polypeptide-encoding nucleotide sequence may be determined in a routine manner by aligning the PRO polypeptide-encoding nucleotide sequence with other known nucleotide sequences using any of a number of well known sequence alignment programs and determining which PRO polypeptide-encoding nucleotide sequence fragment(s) are novel. All of such PRO polypeptide-encoding nucleotide sequences are contemplated herein. Also contemplated are the PRO polypeptide fragments encoded by these nucleotide molecule fragments, preferably those PRO polypeptide fragments that comprise a binding site for an anti-PRO antibody.

In another embodiment, the invention provides isolated PRO polypeptide encoded by any of the isolated nucleic acid sequences hereinabove identified.

In a certain aspect, the invention concerns an isolated PRO polypeptide, comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a PRO polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein.

In a further aspect, the invention concerns an isolated PRO polypeptide comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to an amino acid sequence encoded by any of the human protein cDNAs deposited with the ATCC as disclosed herein.

In a further aspect, the invention concerns an isolated PRO polypeptide comprising an amino acid sequence scoring at least about 80% positives, alternatively at least about 81% positives, alternatively at least about 82% positives, alternatively at least about 83% positives, alternatively at least about 84% positives, alternatively at least about 85% positives, alternatively at least about 86% positives, alternatively at least about 87% positives, alternatively at least about 88% positives, alternatively at least about 89% positives, alternatively at least about 90% positives, alternatively at least about 91% positives, alternatively at least about 92% positives, alternatively at least about 93% positives, alternatively at least about 94% positives, alternatively at least about 95% positives, alternatively at least about 96% positives, alternatively at least about 97% positives, alternatively at least about 98% positives and alternatively at least about 99% positives when compared with the amino acid sequence of a PRO polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein.

In a specific aspect, the invention provides an isolated PRO polypeptide without the N-terminal signal sequence and/or the initiating methionine and is encoded by a nucleotide sequence that encodes such an amino acid sequence as hereinbefore described. Processes for producing the same are also herein described, wherein those processes comprise culturing a host cell comprising a vector which comprises the appropriate encoding nucleic acid molecule under conditions suitable for expression of the PRO polypeptide and recovering the PRO polypeptide from the cell culture.

Another aspect the invention provides an isolated PRO polypeptide which is either transmembrane domain-deleted or transmembrane domain-inactivated. Processes for producing the same are also herein described, wherein those processes comprise culturing a host cell comprising a vector which comprises the appropriate encoding nucleic acid molecule under conditions suitable for expression of the PRO polypeptide and recovering the PRO polypeptide from the cell culture.

In yet another embodiment, the invention concerns agonists and antagonists of a native PRO polypeptide as defined herein. In a particular embodiment, the agonist or antagonist is an anti-PRO antibody or a small molecule.

In a further embodiment, the invention concerns a method of identifying agonists or antagonists to a PRO polypeptide which comprise contacting the PRO polypeptide with a candidate molecule and monitoring a biological activity mediated by said PRO polypeptide. Preferably, the PRO polypeptide is a native PRO polypeptide.

In a still further embodiment, the invention concerns a composition of matter comprising a PRO polypeptide, or an agonist or antagonist of a PRO polypeptide as herein described, or an anti-PRO antibody, in combination with a carrier. Optionally, the carrier is a pharmaceutically acceptable carrier.

Another embodiment of the present invention is directed to the use of a PRO polypeptide, or an agonist or antagonist thereof as hereinbefore described, or an anti-PRO antibody, for the preparation of a medicament useful in the treatment of a condition which is responsive to the PRO polypeptide, an agonist or antagonist thereof or an anti-PRO antibody.

BRIEF DESCRIPTION OF THE DRAWINGS

FIG. 1 shows a nucleotide sequence (SEQ ID NO:3) of a native sequence PRO196 cDNA, wherein SEQ ID NO:3 is a clone designated herein as "DNA22779-1130".

FIG. 2 shows the amino acid sequence (SEQ ID NO:4) derived from the coding sequence of SEQ ID NO:3 shown in FIG. 1.

FIG. 3 shows a nucleotide sequence (SEQ ID NO:8) of a native sequence PRO444 cDNA, wherein SEQ ID NO:8 is a clone designated herein as "DNA26846-1397".

FIG. 4 shows the amino acid sequence (SEQ ID NO:9) derived from the coding sequence of SEQ ID NO:8 shown in FIG. 3.

FIG. 5 shows a nucleotide sequence (SEQ ID NO:10) of a native sequence PRO183 cDNA, wherein SEQ ID NO:10 is a clone designated herein as "DNA28498".

FIG. 6 shows the amino acid sequence (SEQ ID NO:11) derived from the coding sequence of SEQ ID NO:10 shown in FIG. 5.

FIG. 7 shows a nucleotide sequence (SEQ ID NO:12) of a native sequence PRO185 cDNA, wherein SEQ ID NO:12 is a clone designated herein as "DNA28503".

FIG. 8 shows the amino acid sequence (SEQ ID NO:13) derived from the coding sequence of SEQ ID NO:12 shown in FIG. 7.

FIG. 9 shows a nucleotide sequence (SEQ ID NO:14) of a native sequence PRO210 cDNA, wherein SEQ ID NO:14 is a clone designated herein as "DNA32279-1131".

FIG. 10 shows the amino acid sequence (SEQ ID NO:15) derived from the coding sequence of SEQ ID NO:14 shown in FIG. 9.

FIG. 11 shows a nucleotide sequence (SEQ ID NO:16) of a native sequence PRO215 cDNA, wherein SEQ ID NO:16 is a clone designated herein as "DNA32288-1132".

FIG. 12 shows the amino acid sequence (SEQ ID NO:17) derived from the coding sequence of SEQ ID NO:16 shown in FIG. 11.

FIG. 13 shows a nucleotide sequence (SEQ ID NO:21) of a native sequence PRO217 cDNA, wherein SEQ ID NO:21 is a clone designated herein as "DNA33094-1131".

FIG. 14 shows the amino acid sequence (SEQ ID NO:22) derived from the coding sequence of SEQ ID NO:21 shown in FIG. 13.

FIG. 15 shows a nucleotide sequence (SEQ ID NO:23) of a native sequence PRO242 cDNA, wherein SEQ ID NO:23 is a clone designated herein as "DNA33785-1143".

FIG. 16 shows the amino acid sequence (SEQ ID NO:24) derived from the coding sequence of SEQ ID NO:23 shown in FIG. 15.

FIG. 17 shows a nucleotide sequence (SEQ ID NO:28) of a native sequence PRO288 cDNA, wherein SEQ ID NO:28 is a clone designated herein as "DNA35663-1129".

FIG. 18 shows the amino acid sequence (SEQ ID NO:29) derived from the coding sequence of SEQ ID NO:28 shown in FIG. 17.

FIG. 19 shows a nucleotide sequence (SEQ ID NO:31) of a native sequence PRO365 cDNA, wherein SEQ ID NO:31 is a clone designated herein as "DNA46777-1253".

FIG. 20 shows the amino acid sequence (SEQ ID NO:32) derived from the coding sequence of SEQ ID NO:31 shown in FIG. 19.

FIG. 21 shows a nucleotide sequence (SEQ ID NO:38) of a native sequence PRO1361 cDNA, wherein SEQ ID NO:38 is a clone designated herein as "DNA60783-1611".

FIG. 22 shows the amino acid sequence (SEQ ID NO:39) derived from the coding sequence of SEQ ID NO:38 shown in FIG. 21.

FIG. 23 shows a nucleotide sequence (SEQ ID NO:40) of a native sequence PRO1308 cDNA,. wherein SEQ ID NO:40 is a clone designated herein as "DNA62306-1570".

FIG. 24 shows the amino acid sequence (SEQ ID NO:41) derived from the coding sequence of SEQ ID NO:40 shown in FIG. 23.

FIG. 25 shows a nucleotide sequence (SEQ ID NO:51) of a native sequence PRO1183 cDNA, wherein SEQ ID NO:51 is a clone designated herein as "DNA62880-1513".

FIG. 26 shows the amino acid sequence (SEQ ID NO:52) derived from the coding sequence of SEQ ID NO:51 shown in FIG. 25.

FIG. 27 shows a nucleotide sequence (SEQ ID NO:53) of a native sequence PRO1272 cDNA, wherein SEQ ID NO:53 is a clone designated herein as "DNA64896-1539".

FIG. 28 shows the amino acid sequence (SEQ ID NO:54) derived from the coding sequence of SEQ ID NO:53 shown in FIG. 27.

FIG. 29 shows a nucleotide sequence (SEQ ID NO:55) of a native sequence PRO1419 cDNA, wherein SEQ ID NO:55 is a clone designated herein as "DNA71290-1630".

FIG. 30 shows the amino acid sequence (SEQ ID NO:56) derived from the coding sequence of SEQ ID NO:55 shown in FIG. 29.

FIG. 31 shows a nucleotide sequence (SEQ ID NO:57) of a native sequence PRO4999 cDNA, wherein SEQ ID NO:57 is a clone designated herein as "DNA96031-2664".

FIG. 32 shows the amino acid sequence (SEQ ID NO:58) derived from the coding sequence of SEQ ID NO:57 shown in FIG. 31.

FIG. 33 shows a nucleotide sequence (SEQ ID NO:62) of a native sequence PRO7170 cDNA, wherein SEQ ID NO:62 is a clone designated herein as "DNA108722-2743".

FIG. 34 shows the amino acid sequence (SEQ ID NO:63) derived from the coding sequence of SEQ ID NO:62 shown in FIG. 33.

FIG. 35 shows a nucleotide sequence (SEQ ID NO:64) of a native sequence PRO248 cDNA, wherein SEQ ID NO:64 is a clone designated herein as "DNA35674-1142".

FIG. 36 shows the amino acid sequence (SEQ ID NO:65) derived from the coding sequence of SEQ ID NO:64 shown in FIG. 35.

FIG. 37 shows a nucleotide sequence (SEQ ID NO:72) of a native sequence PRO353 cDNA, wherein SEQ ID NO:72 is a clone designated herein as "DNA41234".

FIG. 38 shows the amino acid sequence (SEQ ID NO:73) derived from the coding sequence of SEQ ID NO:72 shown in FIG. 37.

FIG. 39 shows a nucleotide sequence (SEQ ID NO:77) of a native sequence PRO1318 cDNA, wherein SEQ ID NO:77 is a clone designated herein as "DNA73838-1674".

FIG. 40 shows the amino acid sequence (SEQ ID NO:78) derived from the coding sequence of SEQ ID NO:77 shown in FIG. 39.

FIG. 41 shows a nucleotide sequence (SEQ ID NO:79) of a native sequence PRO1600 cDNA, wherein SEQ ID NO:79 is a clone designated herein as "DNA77503-1686".

FIG. 42 shows the amino acid sequence (SEQ ID NO:80) derived from the coding sequence of SEQ ID NO:79 shown in FIG. 41.

FIG. 43 shows a nucleotide sequence (SEQ ID NO:83) of a native sequence PRO9940 cDNA, wherein SEQ ID NO:83 is a clone designated herein as "DNA92282".

FIG. 44 shows the amino acid sequence (SEQ ID NO:84) derived from the coding sequence of SEQ ID NO:83 shown in FIG. 43.

FIG. 45 shows a nucleotide sequence (SEQ ID NO:85) of a native sequence PRO533 cDNA, wherein SEQ ID NO:85 is a clone designated herein as "DNA49435-1219".

FIG. 46 shows the amino acid sequence (SEQ ID NO:86) derived from the coding sequence of SEQ ID NO:85 shown in FIG. 45.

FIG. 47 shows a nucleotide sequence (SEQ ID NO:90) of a native sequence PRO301 cDNA, wherein SEQ ID NO:90 is a clone designated herein as "DNA40628-1216".

FIG. 48 shows the amino acid sequence (SEQ ID NO:91) derived from the coding sequence of SEQ ID NO:90 shown in FIG. 47.

FIG. 49 shows a nucleotide sequence (SEQ ID NO:98) of a native sequence PRO187 cDNA, wherein SEQ ID NO:98 is a clone designated herein as "DNA27864-1155".

FIG. 50 shows the amino acid sequence (SEQ ID NO:99) derived from the coding sequence of SEQ ID NO:98 shown in FIG. 49.

FIG. 51 shows a nucleotide sequence (SEQ ID NO:103) of a native sequence PRO337 cDNA, wherein SEQ ID NO:103 is a clone designated herein as "DNA43316-1237".

FIG. 52 shows the amino acid sequence (SEQ ID NO:104) derived from the coding sequence of SEQ ID NO:103 shown in FIG. 51.

FIG. 53 shows a nucleotide sequence (SEQ ID NO:105) of a native sequence PRO1411 cDNA, wherein SEQ ID NO:105 is a clone designated herein as "DNA59212-1627".

FIG. 54 shows the amino acid sequence (SEQ ID NO:106) derived from the coding sequence of SEQ ID NO:105 shown in FIG. 53.

FIG. 55 shows a nucleotide sequence (SEQ ID NO:107) of a native sequence PRO4356 cDNA, wherein SEQ ID NO:107 is a clone designated herein as "DNA86576-2595".

FIG. 56 shows the amino acid sequence (SEQ ID NO:108) derived from the coding sequence of SEQ ID NO:107 shown in FIG. 55.

FIG. 57 shows a nucleotide sequence (SEQ ID NO:109) of a native sequence PRO246 cDNA, wherein SEQ ID NO:109 is a clone designated herein as "DNA35639-1172".

FIG. 58 shows the amino acid sequence (SEQ ID NO:110) derived from the coding sequence of SEQ ID NO:109 shown in FIG. 57.

FIG. 59 shows a nucleotide sequence (SEQ ID NO:114) of a native sequence PRO265 cDNA, wherein SEQ ID NO:114 is a clone designated herein as "DNA36350-1158".

FIG. 60 shows the amino acid sequence (SEQ ID NO:115) derived from the coding sequence of SEQ ID NO:114 shown in FIG. 59.

FIG. 61 shows a nucleotide sequence (SEQ ID NO:120) of a native sequence PRO941 cDNA, wherein SEQ ID NO:120 is a clone designated herein as "DNA53906-1368".

FIG. 62 shows the amino acid sequence (SEQ ID NO:121) derived from the coding sequence of SEQ ID NO:120 shown in FIG. 61.

FIG. 63 shows a nucleotide sequence (SEQ ID NO:125) of a native sequence PRO10096 cDNA, wherein SEQ ID NO:125 is a clone designated herein as "DNA125185-2806".

FIG. 64 shows the amino acid sequence (SEQ ID NO:126) derived from the coding sequence of SEQ ID NO:125 shown in FIG. 63.

FIG. 65 shows a nucleotide sequence (SEQ ID NO:127) of a native sequence PRO6003 cDNA, wherein SEQ ID NO:127 is a clone designated herein as "DNA83568-2692".

FIG. 66 shows the amino acid sequence (SEQ ID NO:128) derived from the coding sequence of SEQ ID NO:127 shown in FIG. 65.

FIGS. 67A-B show a nucleotide sequence (SEQ ID NO:129) of a native sequence PRO6004 cDNA, wherein SEQ ID NO:129 is a clone designated herein as "DNA92259" FIG. 68 shows the amino acid sequence (SEQ ID NO:130) derived from the coding sequence of SEQ ID NO:129 shown in FIGS. 67A-B.

FIG. 69 shows a nucleotide sequence (SEQ ID NO:131) of a native sequence PRO350 cDNA, wherein SEQ ID NO:131 is a clone designated herein as "DNA44175-1314".

FIG. 70 shows the amino acid sequence (SEQ ID NO:132) derived from the coding sequence of SEQ ID NO:131 shown in FIG. 69.

FIG. 71 shows a nucleotide sequence (SEQ ID NO:136) of a native sequence PRO2630 cDNA, wherein SEQ ID NO:136 is a clone designated herein as "DNA83551".

FIG. 72 shows the amino acid sequence (SEQ ID NO:137) derived from the coding sequence of SEQ ID NO:136 shown in FIG. 71.

FIG. 73 shows a nucleotide sequence (SEQ ID NO:138) of a native sequence PRO6309 cDNA, wherein SEQ ID NO:138 is a clone designated herein as "DNA116510".

FIG. 74 shows the amino acid sequence (SEQ ID NO:139) derived from the coding sequence of SEQ ID NO:138 shown in FIG. 73.

DETAILED DESCRIPTION OF THE PREFERRED EMBODIMENTS

I. Definitions

The terms "PRO polypeptide" and "PRO" as used herein and when immediately followed by a numerical designation refer to various polypeptides, wherein the complete designation (i.e., PRO/number) refers to specific polypeptide sequences as described herein. The terms "PRO/number polypeptide" and "PRO/number" wherein the term "number" is provided as an actual numerical designation as used herein encompass native sequence polypeptides and polypeptide variants (which are further defined herein). The PRO polypeptides described herein may be isolated from a variety of sources, such as from human tissue types or from another source, or prepared by recombinant or synthetic methods. The term "PRO polypeptide" refers to each individual PRO/number polypeptide disclosed herein. All disclosures in this specification which refer to the "PRO polypeptide" refer to each of the polypeptides individually as well as jointly. For example, descriptions of the preparation of, purification of, derivation of, formation of antibodies to or against, administration of, compositions containing, treatment of a disease with, etc., pertain to each polypeptide of the invention individually. The term "PRO polypeptide" also includes variants of the PRO/number polypeptides disclosed herein.

A "native sequence PRO polypeptide" comprises a polypeptide having the same amino acid sequence as the corresponding PRO polypeptide derived from nature. Such native sequence PRO polypeptides can be isolated from nature or can be produced by recombinant or synthetic means. The term "native sequence PRO polypeptide" specifically encompasses naturally-occurring truncated or secreted forms of the specific PRO polypeptide (e.g., an extracellular domain sequence), naturally-occurring variant forms (e.g., alternatively spliced forms) and naturally-occurring allelic variants of the polypeptide. In various embodiments of the invention, the native sequence PRO polypeptides disclosed herein are mature or full-length native sequence polypeptides comprising the full-length amino acids sequences shown in the accompanying figures. Start and stop codons are shown in bold font and underlined in the figures. However, while the PRO polypeptide disclosed in the accompanying figures are shown to begin with methionine residues designated herein as amino acid position 1 in the figures, it is conceivable and possible that other methionine residues located either upstream or downstream from the amino acid position 1 in the figures may be employed as the starting amino acid residue for the PRO polypeptides.

The PRO polypeptide "extracellular domain" or "ECD" refers to a form of the PRO polypeptide which is essentially free of the transmembrane and cytoplasmic domains. Ordinarily, a PRO polypeptide ECD will have less than 1% of such transmembrane and/or cytoplasmic domains and preferably, will have less than 0.5% of such domains. It will be understood that any transmembrane domains identified for the PRO polypeptides of the present invention are identified pursuant to criteria routinely employed in the art for identifying that type of hydrophobic domain. The exact boundaries of a transmembrane domain may vary but most likely by no more than about 5 amino acids at either end of the domain as initially identified herein. Optionally, therefore, an extracellular domain of a PRO polypeptide may contain from about 5 or fewer amino acids on either side of the transmembrane domain/extracellular domain boundary as identified in the Examples or specification and such polypeptides, with or without the associated signal peptide, and nucleic acid encoding them, are comtemplated by the present invention.

The approximate location of the "signal peptides" of the various PRO polypeptides disclosed herein are shown in the present specification and/or the accompanying figures. It is noted, however, that the C-terminal boundary of a signal peptide may vary, but most likely by no more than about 5 amino acids on either side of the signal peptide C-terminal boundary as initially identified herein, wherein the C-terminal boundary of the signal peptide may be identified pursuant to criteria routinely employed in the art for identifying that type of amino acid sequence element (e.g., Nielsen et al., *Prot. Eng.* 10:1-6 (1997) and von Heinje et al., *Nucl. Acids. Res.* 14:4683-4690 (1986)). Moreover, it is also recognized that, in some cases, cleavage of a signal sequence from a secreted polypeptide is not entirely uniform, resulting in more than one secreted species.

These mature polypeptides, where the signal peptide is cleaved within no more than about 5 amino acids on either side of the C-terminal boundary of the signal peptide as identified herein, and the polynucleotides encoding them, are contemplated by the present invention.

"PRO polypeptide variant" means an active PRO polypeptide as defined above or below having at least about 80% amino acid sequence identity with a full-length native sequence PRO polypeptide sequence as disclosed herein, a PRO polypeptide sequence lacking the signal peptide as disclosed herein, an extracellular domain of a PRO polypeptide, with or without the signal peptide, as disclosed herein or any other fragment of a full-length PRO polypeptide sequence as disclosed herein. Such PRO polypeptide variants include, for instance, PRO polypeptides wherein one or more amino acid residues are added, or deleted, at the N- or C-terminus of the full-length native amino acid sequence. Ordinarily, a PRO polypeptide variant will have at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a full-length native sequence PRO polypeptide sequence as disclosed herein, a PRO polypeptide sequence lacking the signal peptide as disclosed herein, an extracellular domain of a PRO polypeptide, with or without the signal peptide, as disclosed herein or any other specifically defined fragment of a full-length PRO polypeptide sequence as disclosed herein. Ordinarily, PRO variant polypeptides are at least about 10 amino acids in length, alternatively at least about 20 amino acids in length, alternatively at least about 30 amino acids in length, alternatively at least about 40 amino acids in length, alternatively at least about 50 amino acids in length, alternatively at least about 60 amino acids in length, alternatively at least about 70 amino acids in length, alternatively at least about 80 amino acids in length, alternatively at least about 90 amino acids in length, alternatively at least about 100 amino acids in length, alternatively at least about 150 amino acids in length, alternatively at least about 200 amino acids in length, alternatively at least about 300 amino acids in length, or more. "Percent (%) amino acid sequence identity" with respect to the PRO polypeptide sequences identified herein is defined as the percentage of amino acid residues in a candidate sequence that are identical with the amino acid residues in the specific PRO polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations using this method, Tables 2 and 3 demonstrate how to calculate the % amino acid sequence identity of the amino acid sequence designated "Comparison Protein" to the amino acid sequence designated "PRO", wherein "PRO" represents the amino acid sequence of a hypothetical PRO polypeptide of interest, "Comparison Protein" represents the amino acid sequence of a polypeptide against which the "PRO" polypeptide of interest is being compared, and "X, "Y" and "Z" each represent different hypothetical amino acid residues.

Unless specifically stated otherwise, all % amino acid sequence identity values used herein are obtained as described in the immediately preceding paragraph using the ALIGN-2 computer program. However, % amino acid sequence identity values may also be obtained as described below by using the WU-BLAST-2 computer program (Altschul et al., *Methods in Enzymology* 266:460-480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % amino acid sequence identity value is determined by dividing (a) the number of matching identical amino acid residues between the amino acid sequence of the PRO polypeptide of interest having a sequence derived from the native PRO polypeptide and the comparison amino acid sequence of interest (i.e., the sequence against which the PRO polypeptide of interest is being compared which may be a PRO variant polypeptide) as determined by WU-BLAST-2 by (b) the total number of amino acid residues of the PRO polypeptide of interest. For example, in the statement "a polypeptide comprising an the amino acid sequence A which has or having at least 80% amino acid sequence identity to the amino acid sequence B", the amino acid sequence A is the comparison amino acid sequence of interest and the amino acid sequence B is the amino acid sequence of the PRO polypeptide of interest.

Percent amino acid sequence identity may also be determined using the sequence comparison program NCBI-BLAST2 (Altschul et al., *Nucleic Acids Res.* 25:3389-3402 (1997)). The NCBI-BLAST2 sequence comparison program may be downloaded from http://www.ncbi.nlm.nih.gov or otherwise obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-passe-value=0.01, constant for multi-pass=25, dropoff for final gapped alignment=25 and scoring matrix=BLOSUM62.

In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

"PRO variant polynucleotide" or "PRO variant nucleic acid sequence" means a nucleic acid molecule which encodes an active PRO polypeptide as defined below and which has at least about 80% nucleic acid sequence identity with a nucleotide acid sequence encoding a full-length native sequence PRO polypeptide sequence as disclosed herein, a full-length native sequence PRO polypeptide sequence lacking the signal peptide as disclosed herein, an extracellular domain of a PRO polypeptide, with or without the signal peptide, as disclosed herein or any other fragment of a full-length PRO polypeptide sequence as disclosed herein. Ordinarily, a PRO variant polynucleotide will have at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity with a nucleic acid sequence encoding a full-length native sequence PRO polypeptide sequence as disclosed herein, a full-length native sequence PRO polypeptide sequence lacking the signal peptide as disclosed herein, an extracellular domain of a PRO polypeptide, with or without the signal sequence, as disclosed herein or any other fragment of a full-length PRO polypeptide sequence as disclosed herein. Variants do not encompass the native nucleotide sequence.

Ordinarily, PRO variant polynucleotides are at least about 30 nucleotides in length, alternatively at least about 60 nucleotides in length, alternatively at least about 90 nucleotides in length, alternatively at least about 120 nucleotides in length, alternatively at least about 150 nucleotides in length, alternatively at least about 180 nucleotides in length, alternatively at least about 210 nucleotides in length, alternatively at least about 240 nucleotides in length, alternatively at least about 270 nucleotides in length, alternatively at least about 300 nucleotides in length, alternatively at least about 450 nucleotides in length, alternatively at least about 600 nucleotides in length, alternatively at least about 900 nucleotides in length, or more.

"Percent (%) nucleic acid sequence identity" with respect to PRO-encoding nucleic acid sequences identified herein is defined as the percentage of nucleotides in a candidate sequence that are identical with the nucleotides in the PRO nucleic acid sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. For purposes herein, however, % nucleic acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for nucleic acid sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Tables 4 and 5, demonstrate how to calculate the % nucleic acid sequence identity of the nucleic acid sequence designated "Comparison DNA" to the nucleic acid sequence designated "PRO-DNA", wherein "PRO-DNA " represents a hypothetical PRO-encoding nucleic acid sequence of interest, "Comparison DNA" represents the nucleotide sequence of a nucleic acid molecule against which the "PRO-DNA" nucleic acid molecule of interest is being compared, and "N", "L" and "V" each represent different hypothetical nucleotides.

Unless specifically stated otherwise, all % nucleic acid sequence identity values used herein are obtained as described in the immediately preceding paragraph using the ALIGN-2 computer program. However, % nucleic acid sequence identity values may also be obtained as described below by using the WU-BLAST-2 computer program (Altschul et al., *Methods in Enzymology* 266:460-480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % nucleic acid sequence identity value is determined by dividing (a) the number of matching identical nucleotides between the nucleic acid sequence of the PRO polypeptide-encoding nucleic acid molecule of interest having a sequence derived from the native sequence PRO polypeptide-encoding nucleic acid and the comparison nucleic acid molecule of interest (i.e., the sequence against which the PRO polypeptide-encoding nucleic acid molecule of interest is being compared which may be a variant PRO polynucleotide) as determined by WU-BLAST-2 by (b) the total number of nucleotides of the PRO polypeptide-encoding nucleic acid molecule of interest. For example, in the statement "an isolated nucleic acid molecule comprising a nucleic acid sequence A which has or having at least 80% nucleic acid sequence identity to the nucleic acid sequence B", the nucleic acid sequence A is the comparison nucleic acid molecule of interest and the nucleic acid sequence B is the nucleic acid sequence of the PRO polypeptide-encoding nucleic acid molecule of interest.

Percent nucleic acid sequence identity may also be determined using the sequence comparison program NCBI-BLAST2 (Altschul et al., *Nucleic Acids Res.* 25:3389-3402 (1997)). The NCBI-BLAST2 sequence comparison program may be downloaded from http://www.ncbi.nlm.nih.gov or otherwise obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program NCBI-BLAST2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

In other embodiments, PRO variant polynucleotides are nucleic acid molecules that encode an active PRO polypeptide and which are capable of hybridizing, preferably under stringent hybridization and wash conditions, to nucleotide sequences encoding a full-length PRO polypeptide as disclosed herein. PRO variant polypeptides may be those that are encoded by a PRO variant polynucleotide.

The term "positives", in the context of sequence comparison performed as described above, includes residues in the sequences compared that are not identical but have similar properties (e.g. as a result of conservative substitutions, see Table 6 below). For purposes herein, the % value of positives is determined by dividing (a) the number of amino acid residues scoring a positive value between the PRO polypeptide amino acid sequence of interest having a sequence derived from the native PRO polypeptide sequence and the comparison amino acid sequence of interest (i.e., the amino acid sequence against which the PRO polypeptide sequence is being compared) as determined in the BLOSUM62 matrix of WU-BLAST-2 by (b) the total number of amino acid residues of the PRO polypeptide of interest.

Unless specifically stated otherwise, the % value of positives is calculated as described in the immediately preceding paragraph. However, in the context of the amino acid sequence identity comparisons performed as described for ALIGN-2 and NCBI-BLAST-2 above, includes amino acid residues in the sequences compared that are not only identical, but also those that have similar properties. Amino acid residues that score a positive value to an amino acid residue of interest are those that are either identical to the amino acid residue of interest or are a preferred substitution (as defined in Table 6 below) of the amino acid residue of interest.

For amino acid sequence comparisons using ALIGN-2 or NCBI-BLAST2, the % value of positives of a given amino acid sequence A to, with, or against a given amino acid sequence B (which can alternatively be phrased as a given amino acid sequence A that has or comprises a certain % positives to, with, or against a given amino acid sequence B) is calculated as follows:

100 times the fraction X/Y where X is the number of amino acid residues scoring a positive value as defined above by the sequence alignment program ALIGN-2 or NCBI-BLAST2 in that program's alignment of A and B, and where Y is the total number of amino acid residues in B. It will be appreciated that where the length of amino acid sequence A is not equal to the length of amino acid sequence B, the % positives of A to B will not equal the % positives of B to A.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the PRO polypeptide natural environment will not be present. Ordinarily, however, isolated polypeptide will be prepared by at least one purification step.

An "isolated" PRO polypeptide-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers, for example, single anti-PRO monoclonal antibodies (including agonist, antagonist, and neutralizing antibodies), anti-PRO antibody compositions with polyepitopic specificity, single chain anti-PRO antibodies, and fragments of anti-PRO antibodies (see below). The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in all environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Labo-*

*ratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising a PRO polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

"Active" or "activity" for the purposes herein refers to form(s) of a PRO polypeptide which retain a biological and/or an immunological activity of native or naturally-occurring PRO, wherein "biological" activity refers to a biological function (either inhibitory or stimulatory) caused by a native or naturally-occurring PRO other than the ability to induce the production of an antibody against an antigenic epitope possessed by a native or naturally-occurring PRO and an "immunological" activity refers to the ability to induce the production of an antibody against an antigenic epitope possessed by a native or naturally-occurring PRO.

The term "antagonist" is used in the broadest sense, and includes any molecule that partially or fully blocks, inhibits, or neutralizes a biological activity of a native PRO polypeptide disclosed herein. In a similar manner, the term "agonist" is used in the broadest sense and includes any molecule that mimics a biological activity of a native PRO polypeptide disclosed herein. Suitable agonist or antagonist molecules specifically include agonist or antagonist antibodies or antibody fragments, fragments or amino acid sequence variants of native PRO polypeptides, peptides, antisense oligonucleotides, small organic molecules, etc. Methods for identifying agonists or antagonists of a PRO polypeptide may comprise contacting a PRO polypeptide with a candidate agonist or antagonist molecule and measuring a detectable change in one or more biological activities normally associated with the PRO polypeptide.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al., Protein Eng. 8(10): 1057-1062 [1995]); single-chain antibody molecules; and multi-specific antibodies formed from antibody fragments.

Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')2 fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG 1, IgG2, IgG3, IgG4, IgA, and IgA2.

"Single-chain Fv" or "sFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The word "label" when used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as a PRO polypeptide or antibody thereto) to a mammal. The components of the liposome are commonly arranged in a bilayer formation, similar to the lipid arrangement of biological membranes.

A "small molecule" is defined herein to have a molecular weight below about 500 Daltons.

"FGFR-1", "FGFR-2", "FGFR-3" and FGFR-4" refer to the fibroblast growth factor receptors 1, 2, 3 and 4, respectively, as disclosed by Isacchi et al., *Nuc. Acids Res.* 18(7): 1906 (1990), Dionne et al., *EMBO J.* 9(9):2685-2692 (1990), Keegan et al., *Proc. Natl. Acad. Sci. USA* 88:1095-1099 (1991) and Partanen et al., *EMBO J.* 10(6): 1347-1354 (1991), respectively.

Table 1

```
/*
 *
 * C-C increased from 12 to 15
 * Z is average of EQ
 * B is average of ND
 * match with stop is _M; stop-stop = 0; J (joker) match = 0
 */
define  _M       -8      /* value of a match with a stop */ int     _day[26][26] = {
/*      A  B  C  D  E  F  G  H  I  J  K  L  M  N  O  P  Q  R  S  T  U  V  W  X  Y  Z */
/* A */ { 2, 0,-2, 0, 0,-4, 1,-1,-1, 0,-1,-2,-1, 0,_M, 1, 0,-2, 1, 1, 0, 0,-6, 0,-3, 0},
/* B */ { 0, 3,-4, 3, 2,-5, 0, 1,-2, 0, 0,-3,-2, 2,_M,-1, 1, 0, 0, 0, 0,-2,-5, 0,-3, 1},
/* C */ {-2,-4,15,-5,-5,-4,-3,-3,-2, 0,-5,-6,-5,-4,_M,-3,-5,-4, 0,-2, 0,-2,-8, 0, 0,-5},
/* D */ { 0, 3,-5, 4, 3,-6, 1, 1,-2, 0, 0,-4,-3, 2,_M,-1, 2,-1, 0, 0, 0,-2,-7, 0,-4, 2},
/* E */ { 0, 2,-5, 3, 4,-5, 0, 1,-2, 0, 0,-3,-2, 1,_M,-1, 2,-1, 0, 0, 0,-2,-7, 0,-4, 3},
/* F */ {-4,-5,-4,-6,-5, 9,-5,-2, 1, 0,-5, 2, 0,-4,_M,-5,-5,-4,-3,-3, 0,-1, 0, 0, 7,-5},
/* G */ { 1, 0,-3, 1, 0,-5, 5,-2,-3, 0,-2,-4,-3, 0,_M,-1,-1,-3, 1, 0, 0,-1,-7, 0,-5, 0},
/* H */ {-1, 1,-3, 1, 1,-2,-2, 6,-2, 0, 0,-2,-2, 2,_M, 0, 3, 2,-1,-1, 0,-2,-3, 0, 0, 2},
/* I */ {-1,-2,-2,-2,-2, 1,-3,-2, 5, 0,-2, 2, 2,-2,_M,-2,-2,-2,-1, 0, 0, 4,-5, 0,-1,-2},
/* J */ { 0, 0, 0, 0, 0, 0, 0, 0, 0, 0, 0, 0, 0, 0,_M, 0, 0, 0, 0, 0, 0, 0, 0, 0, 0, 0},
/* K */ {-1, 0,-5, 0, 0,-5,-2, 0,-2, 0, 5,-3, 0, 1,_M,-1, 1, 3, 0, 0, 0,-2,-3, 0,-4, 0},
/* L */ {-2,-3,-6,-4,-3, 2,-4,-2, 2, 0,-3, 6, 4,-3,_M,-3,-2,-3,-3,-1, 0, 2,-2, 0,-1,-2},
/* M */ {-1,-2,-5,-3,-2, 0,-3,-2, 2, 0, 0, 4, 6,-2,_M,-2,-1, 0,-2,-1, 0, 2,-4, 0,-2,-1},
/* N */ { 0, 2,-4, 2, 1,-4, 0, 2,-2, 0, 1,-3,-2, 2,_M,-1, 1, 0, 1, 0, 0,-2,-4, 0,-2, 1},
/* O */ {_M,_M,_M,_M,_M,_M,_M,_M,_M,_M,_M,_M,_M,_M, 0,_M,_M,_M,_M,_M,_M,_M,_M,_M,_M,_M},
/* P */ { 1,-1,-3,-1,-1,-5,-1, 0,-2, 0,-1,-3,-2,-1,_M, 6, 0, 0, 1, 0, 0,-1,-6, 0,-5, 0},
/* Q */ { 0, 1,-5, 2, 2,-5,-1, 3,-2, 0, 1,-2,-1, 1,_M, 0, 4, 1,-1,-1, 0,-2,-5, 0,-4, 3},
/* R */ {-2, 0,-4,-1,-1,-4,-3, 2,-2, 0, 3,-3, 0, 0,_M, 0, 1, 6, 0,-1, 0,-2, 2, 0,-4, 0},
/* S */ { 1, 0, 0, 0, 0,-3, 1,-1,-1, 0, 0,-3,-2, 1,_M, 1,-1, 0, 2, 1, 0,-1,-2, 0,-3, 0},
/* T */ { 1, 0,-2, 0, 0,-3, 0,-1, 0, 0, 0,-1,-1, 0,_M, 0,-1,-1, 1, 3, 0, 0,-5, 0,-3, 0},
/* U */ { 0, 0, 0, 0, 0, 0, 0, 0, 0, 0, 0, 0, 0, 0,_M, 0, 0, 0, 0, 0, 0, 0, 0, 0, 0, 0},
/* V */ { 0,-2,-2,-2,-2,-1,-1,-2, 4, 0,-2, 2, 2,-2,_M,-1,-2,-2,-1, 0, 0, 4,-6, 0,-2,-2},
/* W */ {-6,-5,-8,-7,-7, 0,-7,-3,-5, 0,-3,-2,-4,-4,_M,-6,-5, 2,-2,-5, 0,-6,17, 0, 0,-6},
/* X */ { 0, 0, 0, 0, 0, 0, 0, 0, 0, 0, 0, 0, 0, 0,_M, 0, 0, 0, 0, 0, 0, 0, 0, 0, 0, 0},
/* Y */ {-3,-3, 0,-4,-4, 7,-5, 0,-1, 0,-4,-1,-2,-2,_M,-5,-4,-4,-3,-3, 0,-2, 0, 0,10,-4},
/* Z */ { 0, 1,-5, 2, 3,-5, 0, 2,-2, 0, 0,-2,-1, 1,_M, 0, 3, 0, 0, 0, 0,-2,-6, 0,-4, 4}
};
```

Table 1 (cont')

```
/*
*/
#include <stdio.h>
include <ctype.h> define   MAXJMP    16      /* max jumps in a diag */
define   MAXGAP    24      /* don't continue to penalize gaps larger than this */
#define   JMPS      1024    /* max jmps in an path */
define   MX        4       /* save if there's at least MX-1 bases since last jmp */ define   DMAT      3       /* value of matching bases */
define   DMIS      0       /* penalty for mismatched bases */
#define   DINS0     8       /* penalty for a gap */
#define   DINS1     1       /* penalty per base */
#define   PINS0     8       /* penalty for a gap */
define   PINS1     4       /* penalty per residue */ struct jmp {
          short         n[MAXJMP];       /* size of jmp (neg for dely) */
          unsigned short x[MAXJMP];      /* base no. of jmp in seq x */
};                                       /* limits seq to 2^16 -1 */ struct diag {
          int           score;           /* score at last jmp */
          long          offset;          /* offset of prev block */
          short         ijmp;            /* current jmp index */
          struct jmp    jp;              /* list of jmps */
};

struct path {
          int           spc;             /* number of leading spaces */
          short         n[JMPS];         /* size of jmp (gap) */
          int           x[JMPS];         /* loc of jmp (last elem before gap) */
};

char          *ofile;         /* output file name */
char          *namex[2];      /* seq names: getseqs() */
char          *prog;          /* prog name for err msgs */
char          *seqx[2];       /* seqs: getseqs() */
int           dmax;           /* best diag: nw() */
int           dmax0;          /* final diag */
int           dna;            /* set if dna: main() */
int           endgaps;        /* set if penalizing end gaps */
int           gapx, gapy;     /* total gaps in seqs */
int           len0, len1;     /* seq lens */
int           ngapx, ngapy;   /* total size of gaps */
int           smax;           /* max score: nw() */
int           *xbm;           /* bitmap for matching */
long          offset;         /* current offset in jmp file */
struct diag   *dx;            /* holds diagonals */
struct path   pp[2];          /* holds path for seqs */ char          *calloc(), *malloc(), *index(), *strcpy();
char          *getseq(), *g_calloc();
```

Table 1 (cont')

```
/* Needleman-Wunsch alignment program
 *
 * usage: progs file1 file2
 * where file1 and file2 are two dna or two protein sequences.
 * The sequences can be in upper- or lower-case an may contain ambiguity
 * Any lines beginning with ';', '>' or '<' are ignored
 * Max file length is 65535 (limited by unsigned short x in the jmp struct)
 * A sequence with 1/3 or more of its elements ACGTU is assumed to be DNA
 * Output is in the file "align.out"
 *
 * The program may create a tmp file in /tmp to hold info about traceback.
 * Original version developed under BSD 4.3 on a vax 8650
 */
include "nw.h"
#include "day.h"

static  _dbval[26] = {
        1,14,2,13,0,0,4,11,0,0,12,0,3,15,0,0,0,5,6,8,8,7,9,0,10,0
};

static  _pbval[26] = {
        1, 2|(1<<('D'-'A'))|(1<<('N'-'A')), 4, 8, 16, 32, 64,
        128, 256, 0xFFFFFFFF, 1<<10, 1<<11, 1<<12, 1<<13, 1<<14,
        1<<15, 1<<16, 1<<17, 1<<18, 1<<19, 1<<20, 1<<21, 1<<22,
        1<<23, 1<<24, 1<<25|(1<<('E'-'A'))|(1<<('Q'-'A'))
};

main(ac, av)                                                                    main
        int     ac;
        char    *av[];
{
        prog = av[0];
        if (ac != 3) {
                fprintf(stderr,"usage: %s file1 file2\n", prog);
                fprintf(stderr,"where file1 and file2 are two dna or two protein sequences.\n");
                fprintf(stderr,"The sequences can be in upper- or lower-case\n");
                fprintf(stderr,"Any lines beginning with ';' or '<' are ignored\n");
                fprintf(stderr,"Output is in the file \"align.out\"\n");
                exit(1);
        }
        namex[0] = av[1];
        namex[1] = av[2];
        seqx[0] = getseq(namex[0], &len0);
        seqx[1] = getseq(namex[1], &len1);
        xbm = (dna)? _dbval : _pbval;

endgaps = 0;            /* 1 to penalize endgaps */
        ofile = "align.out";    /* output file */ nw();                   /* fill in the matrix, get the possible jmps */
        readjmps();             /* get the actual jmps */
        print();                /* print stats, alignment */ cleanup(0);             /* unlink any tmp files */
}
```

Table 1 (cont')

```
/* do the alignment, return best score: main()
 * dna: values in Fitch and Smith, PNAS, 80, 1382-1386, 1983
 * pro: PAM 250 values
 * When scores are equal, we prefer mismatches to any gap, prefer
 * a new gap to extending an ongoing gap, and prefer a gap in seqx
 * to a gap in seq y.
 */
nw()                                                                            nw
{
        char        *px, *py;              /* seqs and ptrs */
        int         *ndely, *dely;         /* keep track of dely */
        int         ndelx, delx;           /* keep track of delx */
        int         *tmp;                  /* for swapping row0, row1 */
        int         mis;                   /* score for each type */
        int         ins0, ins1;            /* insertion penalties */
        register    id;                    /* diagonal index */
        register    ij;                    /* jmp index */
        register    *col0, *col1;          /* score for curr, last row */
        register    xx, yy;                /* index into seqs */ dx = (struct diag *)g_calloc("to get diags", len0+len1+1, sizeof(struct diag));

ndely = (int *)g_calloc("to get ndely", len1+1, sizeof(int));
        dely  = (int *)g_calloc("to get dely", len1+1, sizeof(int));
        col0  = (int *)g_calloc("to get col0", len1+1, sizeof(int));
        col1  = (int *)g_calloc("to get col1", len1+1, sizeof(int));
        ins0  = (dna)? DINS0 : PINS0;
        ins1  = (dna)? DINS1 : PINS1;

smax = -10000;
        if (endgaps) {
                for (col0[0] = dely[0] = -ins0, yy = 1; yy <= len1; yy++) {
                        col0[yy] = dely[yy] = col0[yy-1] - ins1;
                        ndely[yy] = yy;
                }
                col0[0] = 0;       /* Waterman Bull Math Biol 84 */
        }
        else
                for (yy = 1; yy <= len1; yy++)
                        dely[yy] = -ins0;

/* fill in match matrix
        */
        for (px = seqx[0], xx = 1; xx <= len0; px++, xx++) {
                /* initialize first entry in col
                */
                if (endgaps) {
                        if (xx == 1)
                                col1[0] = delx = -(ins0+ins1);
                        else
                                col1[0] = delx = col0[0] - ins1;
                        ndelx = xx;
                }
                else {
                        col1[0] = 0;
                        delx = -ins0;
                        ndelx = 0;
                }
```

Table 1 (cont')

...nw

```
for (py = seqx[1], yy = 1; yy <= len1; py++, yy++) {
    mis = col0[yy-1];
    if (dna)
            mis += (xbm[*px-'A']&xbm[*py-'A'])? DMAT : DMIS;
    else
            mis += _day[*px-'A'][*py-'A'];

/* update penalty for del in x seq;
     * favor new del over ongong del
     * ignore MAXGAP if weighting endgaps
     */
    if (endgaps || ndely[yy] < MAXGAP) {
            if (col0[yy] - ins0 >= dely[yy]) {
                    dely[yy] = col0[yy] - (ins0+ins1);
                    ndely[yy] = 1;
            } else {
                    dely[yy] -= ins1;
                    ndely[yy]++;
            }
    } else {
            if (col0[yy] - (ins0+ins1) >= dely[yy]) {
                    dely[yy] = col0[yy] - (ins0+ins1);
                    ndely[yy] = 1;
            } else
                    ndely[yy]++;
    }

/* update penalty for del in y seq;
     * favor new del over ongong del
     */
    if (endgaps || ndelx < MAXGAP) {
            if (col1[yy-1] - ins0 >= delx) {
                    delx = col1[yy-1] - (ins0+ins1);
                    ndelx = 1;
            } else {
                    delx -= ins1;
                    ndelx++;
            }
    } else {
            if (col1[yy-1] - (ins0+ins1) >= delx) {
                    delx = col1[yy-1] - (ins0+ins1);
                    ndelx = 1;
            } else
                    ndelx++;
    }

/* pick the maximum score; we're favoring
     * mis over any del and delx over dely
     */
```

Table 1 (cont')

...nw

```
                        id = xx - yy + lenl - 1;
                        if (mis > = delx && mis > = dely[yy])
                                coll[yy] = mis;
                        else if (delx > = dely[yy]) {
                                coll[yy] = delx;
                                ij = dx[id].ijmp;
                                if (dx[id].jp.n[0] && (!dna || (ndelx > = MAXJMP
                                && xx > dx[id].jp.x[ij]+MX) || mis > dx[id].score+DINS0)) {
                                        dx[id].ijmp++;
                                        if (++ij > = MAXJMP) {
                                                writejmps(id);
                                                ij = dx[id].ijmp = 0;
                                                dx[id].offset = offset;
                                                offset += sizeof(struct jmp) + sizeof(offset);
                                        }
                                }
                                dx[id].jp.n[ij] = ndelx;
                                dx[id].jp.x[ij] = xx;
                                dx[id].score = delx;
                        }
                        else {
                                coll[yy] = dely[yy];
                                ij = dx[id].ijmp;
if (dx[id].jp.n[0] && (!dna || (ndely[yy] > = MAXJMP
                                && xx > dx[id].jp.x[ij]+MX) || mis > dx[id].score+DINS0)) {
                                        dx[id].ijmp++;
                                        if (++ij > = MAXJMP) {
                                                writejmps(id);
                                                ij = dx[id].ijmp = 0;
                                                dx[id].offset = offset;
                                                offset += sizeof(struct jmp) + sizeof(offset);
                                        }
                                }
                                dx[id].jp.n[ij] = -ndely[yy];
                                dx[id].jp.x[ij] = xx;
                                dx[id].score = dely[yy];
                        }
                        if (xx == len0 && yy < lenl) {
                                /* last col
                                */
                                if (endgaps)
                                        coll[yy] -= ins0+ins1*(lenl-yy);
                                if (coll[yy] > smax) {
                                        smax = coll[yy];
                                        dmax = id;
                                }
                        }
                }
                if (endgaps && xx < len0)
                        coll[yy-1] -= ins0+ins1*(len0-xx);
                if (coll[yy-1] > smax) {
                        smax = coll[yy-1];
                        dmax = id;
                }
                tmp = col0; col0 = coll; coll = tmp;
        }
        (void) free((char *)ndely);
        (void) free((char *)dely);
        (void) free((char *)col0);
        (void) free((char *)coll);                              }
```

Table 1 (cont')

```
/*
 *
 * print() -- only routine visible outside this module
 *
 * static:
 * getmat() -- trace back best path, count matches: print()
 * pr_align() -- print alignment of described in array p[]: print()
 * dumpblock() -- dump a block of lines with numbers, stars: pr_align()
 * nums() -- put out a number line: dumpblock()
 * putline() -- put out a line (name, [num], seq, [num]): dumpblock()
 * stars() - -put a line of stars: dumpblock()
 * stripname() -- strip any path and prefix from a seqname
 */ include "nw.h"

define SPC      3
#define P_LINE   256      /* maximum output line */
define P_SPC    3        /* space between name or num and seq */ extern  _day[26][26];
int     olen;             /* set output line length */
FILE    *fx;              /* output file */ print()
{
        int     lx, ly, firstgap, lastgap;    /* overlap */ if ((fx = fopen(ofile, "w")) == 0) {
                fprintf(stderr,"%s: can't write %s\n", prog, ofile);
                cleanup(1);
        }
        fprintf(fx, " <first sequence: %s (length = %d)\n", namex[0], len0);
        fprintf(fx, " <second sequence: %s (length = %d)\n", namex[1], len1);
        olen = 60;
        lx = len0;
        ly = len1;
        firstgap = lastgap = 0;
        if (dmax < len1 - 1) {           /* leading gap in x */
                pp[0].spc = firstgap = len1 - dmax - 1;
                ly -= pp[0].spc;
        }
        else if (dmax > len1 - 1) {      /* leading gap in y */
                pp[1].spc = firstgap = dmax - (len1 - 1);
                lx -= pp[1].spc;
        }
        if (dmax0 < len0 - 1) {          /* trailing gap in x */
                lastgap = len0 - dmax0 -1;
                lx -= lastgap;
        }
        else if (dmax0 > len0 - 1) {     /* trailing gap in y */
                lastgap = dmax0 - (len0 - 1);
                ly -= lastgap;
        }
        getmat(lx, ly, firstgap, lastgap);
        pr_align();
}
``` print

Table 1 (cont')

```
/*
 * trace back the best path, count matches
 */
static
getmat(lx, ly, firstgap, lastgap)                              getmat
        int     lx, ly;                 /* "core" (minus endgaps) */
        int     firstgap, lastgap;      /* leading trailing overlap */
{
        int             nm, i0, i1, siz0, siz1;
        char            outx[32];
        double          pct;
        register        n0, n1;
        register char   *p0, *p1;

/* get total matches, score
         */
        i0 = i1 = siz0 = siz1 = 0;
        p0 = seqx[0] + pp[1].spc;
        p1 = seqx[1] + pp[0].spc;
        n0 = pp[1].spc + 1;
        n1 = pp[0].spc + 1;

nm = 0;
        while ( *p0 && *p1 ) {
                if (siz0) {
                        p1++;
                        n1++;
                        siz0--;
                }
                else if (siz1) {
                        p0++;
                        n0++;
                        siz1--;
                }
                else {
                        if (xbm[*p0-'A']&xbm[*p1-'A'])
                                nm++;
                        if (n0++ == pp[0].x[i0])
                                siz0 = pp[0].n[i0++];
                        if (n1++ == pp[1].x[i1])
                                siz1 = pp[1].n[i1++];
                        p0++;
                        p1++;
                }
        }

/* pct homology:
         * if penalizing endgaps, base is the shorter seq
         * else, knock off overhangs and take shorter core
         */
        if (endgaps)
                lx = (len0 < len1)? len0 : len1;
        else
                lx = (lx < ly)? lx : ly;
        pct = 100.*(double)nm/(double)lx;
        fprintf(fx, "\n");
        fprintf(fx, " <%d match%s in an overlap of %d: %.2f percent similarity\n",
                nm, (nm == 1)? "" : "es", lx, pct);
```

Table 1 (cont')

```
fprintf(fx, "<gaps in first sequence: %d", gapx);                               ...getmat
if (gapx) {
        (void) sprintf(outx, " (%d %s%s)",
                ngapx, (dna)? "base":"residue", (ngapx == 1)? "":"s");
        fprintf(fx,"%s", outx);

fprintf(fx, ", gaps in second sequence: %d", gapy);
if (gapy) {
        (void) sprintf(outx, " (%d %s%s)",
                ngapy, (dna)? "base":"residue", (ngapy == 1)? "":"s");
        fprintf(fx,"%s", outx);
}
if (dna)
        fprintf(fx,
        "\n<score: %d (match = %d, mismatch = %d, gap penalty = %d + %d per base)\n",
        smax, DMAT, DMIS, DINS0, DINS1);
else
        fprintf(fx,
        "\n<score: %d (Dayhoff PAM 250 matrix, gap penalty = %d + %d per residue)\n",
        smax, PINS0, PINS1);
if (endgaps)
        fprintf(fx,
        "<endgaps penalized. left endgap: %d %s%s, right endgap: %d %s%s\n",
        firstgap, (dna)? "base" : "residue", (firstgap == 1)? "" : "s",
        lastgap, (dna)? "base" : "residue", (lastgap == 1)? "" : "s");
else
        fprintf(fx, " <endgaps not penalized\n");
} static          nm;             /* matches in core -- for checking */
static          lmax;           /* lengths of stripped file names */
static          ij[2];          /* jmp index for a path */
static          nc[2];          /* number at start of current line */
static          ni[2];          /* current elem number -- for gapping */
static          siz[2];
static char     *ps[2];         /* ptr to current element */
static char     *po[2];         /* ptr to next output char slot */
static char     out[2][P_LINE]; /* output line */
static char     star[P_LINE];   /* set by stars() */

/*
* print alignment of described in struct path pp[]
*/
static
pr_align()                                                                      pr_align
{
        int       nn;     /* char count */
        int       more;
        register  i;

for (i = 0, lmax = 0; i < 2; i++) {
                nn = stripname(namex[i]);
                if (nn > lmax)
                        lmax = nn;

nc[i] = 1;
                ni[i] = 1;
                siz[i] = ij[i] = 0;
                ps[i] = seqx[i];
                po[i] = out[i];                                 }
```

Table 1 (cont')

```
        for (nn = nm = 0, more = 1; more; ) {                              ...pr_align
                for (i = more = 0; i < 2; i++) {
                        /*
                         * do we have more of this sequence?
                         */
                        if (!*ps[i])
                                continue;

more++;

if (pp[i].spc) {        /* leading space */
                                *po[i]++ = ' ';
                                pp[i].spc--;
                        }
                        else if (siz[i]) {      /* in a gap */
                                *po[i]++ = '-';
                                siz[i]--;
                        }
                        else {                  /* we're putting a seq element
                                                 */
                                *po[i] = *ps[i];
                                if (islower(*ps[i]))
                                        *ps[i] = toupper(*ps[i]);
                                po[i]++;
                                ps[i]++;

/*
                                 * are we at next gap for this seq?
                                 */
                                if (ni[i] == pp[i].x[ij[i]]) {
                                        /*
                                         * we need to merge all gaps
                                         * at this location
                                         */
                                        siz[i] = pp[i].n[ij[i]++];
                                        while (ni[i] == pp[i].x[ij[i]])
                                                siz[i] += pp[i].n[ij[i]++];
                                }
                                ni[i]++;
                        }
                }
                if (++nn == olen || !more && nn) {
                        dumpblock();
                        for (i = 0; i < 2; i++)
                                po[i] = out[i];
                        nn = 0;
                }
        }
}
/*
 * dump a block of lines, including numbers, stars: pr_align()
 */
static
dumpblock()                                                                dumpblock
{
        register i;

for (i = 0; i < 2; i++)
                *po[i]-- = '\0';
```

Table 1 (cont')

...dumpblock

```
            (void) putc('\n', fx);
            for (i = 0; i < 2; i++) {
                    if (*out[i] && (*out[i] != ' ' || *(po[i]) != ' ')) {
                            if (i == 0)
                                    nums(i);
                            if (i == 0 && *out[1])
                                    stars();
                            putline(i);
                            if (i == 0 && *out[1])
                                    fprintf(fx, star);
                            if (i == 1)
                                    nums(i);
                    }
            }
    }
    /*
     * put out a number line: dumpblock()
     */
    static
    nums(ix)                                                            nums
            int     ix;     /* index in out[] holding seq line */
    {
            char            nline[P_LINE];
            register        i, j;
            register char   *pn, *px, *py;

for (pn = nline, i = 0; i < lmax+P_SPC; i++, pn++)
                    *pn = ' ';
            for (i = nc[ix], py = out[ix]; *py; py++, pn++) {
                    if (*py == ' ' || *py == '-')
                            *pn = ' ';
                    else {
                            if (i%10 == 0 || (i == 1 && nc[ix] != 1)) {
                                    j = (i < 0)? -i : i;
                                    for (px = pn; j; j /= 10, px--)
                                            *px = j%10 + '0';
                                    if (i < 0)
                                            *px = '-';
                            }
                            else
                                    *pn = ' ';
                            i++;
                    }
            }
            *pn = '\0';
            nc[ix] = i;
            for (pn = nline; *pn; pn++)
                    (void) putc(*pn, fx);
            (void) putc('\n', fx);
    }
    /*
     * put out a line (name, [num], seq, [num]): dumpblock()
     */
    static
    putline(ix)                                                         putline
            int     ix;                     {
```

Table 1 (cont')

...putline

```
        int             i;
        register char   *px;

for (px = namex[ix], i = 0; *px && *px != ':'; px++, i++)
                (void) putc(*px, fx);
        for (; i < lmax+P_SPC; i++)
                (void) putc(' ', fx);

/* these count from 1:
         * ni[] is current element (from 1)
         * nc[] is number at start of current line
         */
        for (px = out[ix]; *px; px++)
                (void) putc(*px&0x7F, fx);
        (void) putc('\n', fx);
}

/*
 * put a line of stars (seqs always in out[0], out[1]): dumpblock()
 */
static
stars()
{
        int             i;
        register char   *p0, *p1, cx, *px;

if (!*out[0] || (*out[0] == ' ' && *(po[0]) == ' ') ||
            !*out[1] || (*out[1] == ' ' && *(po[1]) == ' '))
                return;
        px = star;
        for (i = lmax+P_SPC; i; i--)
                *px++ = ' ';

for (p0 = out[0], p1 = out[1]; *p0 && *p1; p0++, p1++) {
                if (isalpha(*p0) && isalpha(*p1)) {
                        if (xbm[*p0-'A']&xbm[*p1-'A']) {
                                cx = '*';
                                nm++;
                        }
                        else if (!dna && _day[*p0-'A'][*p1-'A'] > 0)
                                cx = '.';
                        else
                                cx = ' ';
                }
                else
                        cx = ' ';
                *px++ = cx;
        }
        *px++ = '\n';
        *px = '\0';
}
``` stars

Table 1 (cont')

```
/*
 * strip path or prefix from pn, return len: pr_align()
 */
static
stripname(pn)                                                              stripname
        char      *pn;      /* file name (may be path) */
{
        register char    *px, *py;

py = 0;
        for (px = pn; *px; px++)
                if (*px == '/')
                        py = px + 1;
        if (py)
                (void) strcpy(pn, py);
        return(strlen(pn));

}
```

Table 1 (cont')

```
/*
 * cleanup() -- cleanup any tmp file
 * getseq() -- read in seq, set dna, len, maxlen
 * g_calloc() -- calloc() with error checkin
 * readjmps() -- get the good jmps, from tmp file if necessary
 * writejmps() -- write a filled array of jmps to a tmp file: nw()
 */
include "nw.h"
include <sys/file.h> char    *jname = "/tmp/homgXXXXXX";     /* tmp file for jmps */
FILE    *fj;

int     cleanup();                      /* cleanup tmp file */
long    lseek();

/*
 * remove any tmp file if we blow
 */
cleanup(i)                                                              cleanup
        int     i;
{
        if (fj)
                (void) unlink(jname);
        exit(i);
}

/*
 * read, return ptr to seq, set dna, len, maxlen
 * skip lines starting with ';', '<', or '>'.
 * seq in upper or lower case
 */
char    *
getseq(file, len)                                                       getseq
        char    *file;  /* file name */
        int     *len;   /* seq len */
{
        char            line[1024], *pseq;
        register char   *px, *py;
        int             natgc, tlen;
        FILE            *fp;

if ((fp = fopen(file,"r")) == 0) {
                fprintf(stderr,"%s: can't read %s\n", prog, file);
                exit(1);
        }
        tlen = natgc = 0;
        while (fgets(line, 1024, fp)) {
                if (*line == ';' || *line == '<' || *line == '>')
                        continue;
                for (px = line; *px != '\n'; px++)
                        if (isupper(*px) || islower(*px))
                                tlen++;
        }
        if ((pseq = malloc((unsigned)(tlen+6))) == 0) {
                fprintf(stderr,"%s: malloc() failed to get %d bytes for %s\n", prog, tlen+6, file);
                exit(1);
        }
        pseq[0] = pseq[1] = pseq[2] = pseq[3] = '\0';
```

Table 1 (cont')

...getseq

```
            py = pseq + 4;
            *len = tlen;
            rewind(fp);

while (fgets(line, 1024, fp)) {
                    if (*line == ';' || *line == '<' || *line == '>')
                            continue;
                    for (px = line; *px != '\n'; px++) {
                            if (isupper(*px))
                                    *py++ = *px;
                            else if (islower(*px))
                                    *py++ = toupper(*px);
                            if (index("ATGCU",*(py-1)))
                                    natgc++;
                    }
            }
            *py++ = '\0';
            *py = '\0';
            (void) fclose(fp);
            dna = natgc > (tlen/3);
            return(pseq+4);
} char     *
g_calloc(msg, nx, sz)                                                              g_calloc
            char     *msg;          /* program, calling routine */
            int      nx, sz;        /* number and size of elements */
{
            char     *px, *calloc();

if ((px = calloc((unsigned)nx, (unsigned)sz)) == 0) {
                    if (*msg) {
                            fprintf(stderr, "%s: g_calloc() failed %s (n=%d, sz=%d)\n", prog, msg, nx, sz);
                            exit(1);
                    }
            }
            return(px);
}

/*
 * get final jmps from dx[] or tmp file, set pp[], reset dmax: main()
 */
readjmps()                                                                         readjmps
{
            int      fd = -1;
            int      siz, i0, i1;
            register i, j, xx;

if (fj) {
                    (void) fclose(fj);
                    if ((fd = open(jname, O_RDONLY, 0)) < 0) {
                            fprintf(stderr, "%s: can't open() %s\n", prog, jname);
                            cleanup(1);
                    }
            }
            for (i = i0 = i1 = 0, dmax0 = dmax, xx = len0; ; i++) {
                    while (1) {
                            for (j = dx[dmax].ijmp; j >= 0 && dx[dmax].jp.x[j] >= xx; j--)
                                    ;
```

Table 1 (cont')

...readjmps

```
                    if (j < 0 && dx[dmax].offset && fj) {
                            (void) lseek(fd, dx[dmax].offset, 0);
                            (void) read(fd, (char *)&dx[dmax].jp, sizeof(struct jmp));
                            (void) read(fd, (char *)&dx[dmax].offset, sizeof(dx[dmax].offset));
                            dx[dmax].ijmp = MAXJMP-1;
                    }
                    else
                            break;
            }
            if (i >= JMPS) {
                    fprintf(stdcrr, "%s: too many gaps in alignment\n", prog);
                    cleanup(1);
            }
            if (j >= 0) {
                    siz = dx[dmax].jp.n[j];
                    xx = dx[dmax].jp.x[j];
                    dmax += siz;
                    if (siz < 0) {              /* gap in second seq */
                            pp[1].n[i1] = -siz;
                            xx += siz;
                            /* id = xx - yy + len1 - 1
                            */
                            pp[1].x[i1] = xx - dmax + len1 - 1;
                            gapy++;
                            ngapy -= siz;
/* ignore MAXGAP when doing endgaps */
                            siz = (-siz < MAXGAP || endgaps)? -siz : MAXGAP;
                            i1++;
                    }
                    else if (siz > 0) {         /* gap in first seq */
                            pp[0].n[i0] = siz;
                            pp[0].x[i0] = xx;
                            gapx++;
                            ngapx += siz;
/* ignore MAXGAP when doing endgaps */
                            siz = (siz < MAXGAP || endgaps)? siz : MAXGAP;
                            i0++;
                    }
            }
            else
                    break;
    }

/* reverse the order of jmps
    */
    for (j = 0, i0--; j < i0; j++, i0--) {
            i = pp[0].n[j]; pp[0].n[j] = pp[0].n[i0]; pp[0].n[i0] = i;
            i = pp[0].x[j]; pp[0].x[j] = pp[0].x[i0]; pp[0].x[i0] = i;
    }
    for (j = 0, i1--; j < i1; j++, i1--) {
            i = pp[1].n[j]; pp[1].n[j] = pp[1].n[i1]; pp[1].n[i1] = i;
            i = pp[1].x[j]; pp[1].x[j] = pp[1].x[i1]; pp[1].x[i1] = i;
    }
    if (fd >= 0)
            (void) close(fd);
    if (fj) {
            (void) unlink(jname);
            fj = 0;
            offset = 0;
    }
}
```

Table 1 (cont')

```
/*
 * write a filled jmp struct offset of the prev one (if any): nw()
 */
writejmps(ix)                                                                    writejmps
        int     ix;
{
        char    *mktemp();

if (!fj) {
                if (mktemp(jname) < 0) {
                        fprintf(stderr, "%s: can't mktemp() %s\n", prog, jname);
                        cleanup(1);
                }
                if ((fj = fopen(jname, "w")) == 0) {
                        fprintf(stderr, "%s: can't write %s\n", prog, jname);
                        exit(1);
                }
        }
        (void) fwrite((char *)&dx[ix].jp, sizeof(struct jmp), 1, fj);
        (void) fwrite((char *)&dx[ix].offset, sizeof(dx[ix].offset), 1, fj);
}
```

TABLE 2

| | | |
|---|---|---|
| PRO | XXXXXXXXXXXXXXX | (Length = 15 amino acids) |
| Comparison Protein | XXXXXYYYYYYY | (Length = 12 amino acids) |

% amino acid sequence identity = (the number of identically matching amino acid residues between the two polypeptide sequences as determined by ALIGN-2) divided by (the total number of amino acid residues of the PRO polypeptide) = 5 divided by 15 = 33.3%

TABLE 3

| | | |
|---|---|---|
| PRO | XXXXXXXXXX | (Length = 10 amino acids) |
| Comparison Protein | XXXXXYYYYYYZZYZ | (Length = 15 amino acids) |

% amino acid sequence identity = (the number of identically matching amino acid residues between the two polypeptide sequences as determined by ALIGN-2) divided by (the total number of amino acid residues of the PRO polypeptide) = 5 divided by 10 = 50%

TABLE 4

| | | |
|---|---|---|
| PRO-DNA | NNNNNNNNNNNNNN | (Length = 14 nucleotides) |
| Comparison DNA | NNNNNNLLLLLLLLLL | (Length = 16 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 6 divided by 14 = 42.9%

TABLE 5

| | | |
|---|---|---|
| PRO-DNA | NNNNNNNNNNNN | (Length = 12 nucleotides) |
| Comparison DNA | NNNNLLLVV | (Length = 9 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 4 divided by 12 = 33.3%

II. Compositions and Methods of the Invention

A. Full-length PRO Polypeptides

The present invention provides newly identified and isolated nucleotide sequences encoding polypeptides referred to in the present application as PRO polypeptides. In particular, cDNAs encoding various PRO polypeptides have been identified and isolated, as disclosed in further detail in the Examples below. It is noted that proteins produced in separate expression rounds may be given different PRO numbers but the UNQ number is unique for any given DNA and the encoded protein, and will not be changed. However, for sake of simplicity, in the present specification the protein encoded by the full length native nucleic acid molecules disclosed herein as well as all further native homologues and variants included in the foregoing definition of PRO, will be referred to as "PRO/number", regardless of their origin or mode of preparation.

As disclosed in the Examples below, various cDNA clones have been deposited with the ATCC. The actual nucleotide sequences of those clones can readily be determined by the skilled artisan by sequencing of the deposited clone using routine methods in the art. The predicted amino acid sequence can be determined from the nucleotide sequence using routine skill. For the PRO polypeptides and encoding nucleic acids described herein, Applicants have identified what is believed to be the reading frame best identifiable with the sequence information available at the time.

1. Full-length PRO196 Polypeptides

The present invention provides newly identified and isolated nucleotide sequences encoding polypeptides referred to in the present application as PRO196. In particular, Applicants have identified and isolated cDNAs encoding a PRO196 polypeptide, as disclosed in further detail in the Examples below. Using BLAST and FastA sequence alignment computer programs, Applicants found that a cDNA sequence encoding full-length native sequence PRO196 encodes for a polypeptide having an amino acid sequence which has identity with the amino acid sequence of various TIE ligand polypeptides.

2. Full-length PRO444 Polypeptides

The DNA26846-1397 clone was isolated from a human fetal lung library using a trapping technique which selects for nucleotide sequences encoding secreted proteins. Thus, the DNA26846-1397 clone encodes a secreted factor. As far as is known, the DNA26846-1397 sequence encodes a novel factor designated herein as PRO444. Although, using WU-BLAST2 sequence alignment computer programs, some sequence identities with known proteins were revealed.

3. Full-length PRO183 Polypeptides

The DNA28498 clone was isolated from a human tissue library. As far as is known, the DNA28498 sequence encodes a novel factor designated herein as PRO183. Although. using WU-BLAST2 sequence alignment computer programs, some sequence identities with known proteins were revealed.

4. Full-length PRO185 Polypeptides

The DNA28503 clone was isolated from a human tissue library. As far as is known, the DNA28503 sequence encodes a novel factor designated herein as PRO185. Although, using WU-BLAST2 sequence alignment computer programs, some sequence identities with known proteins were revealed.

5. Full-length PRO210 and PRO217 Polypeptides

The present invention provides newly identified and isolated nucleotide sequences encoding polypeptides referred to in the present application as PRO210 and PRO217. In particular, Applicants have identified and isolated cDNAs encoding a PRO210 and PRO217 polypeptide, as disclosed in further detail in the Examples below. Using BLAST (FastA format) sequence alignment computer programs, Applicants found that cDNAs sequence encoding full-length native sequence PRO210 and PRO217 have homologies to known proteins having EGF-like domains. Accordingly, it is presently believed that the PRO210 and PRO217 polypeptides disclosed in the present application is a newly identified member of the EGF-like family and possesses properties typical of the EGF-like protein family.

6. Full-length PRO215 Polypeptides

The present invention provides newly identified and isolated nucleotide sequences encoding polypeptides referred to in the present application as PRO215. In particular, Applicants have identified and isolated cDNAs encoding a PRO215 polypeptide, as disclosed in further detail in the Examples below. Using BLAST and FastA sequence alignment computer programs, Applicants found that a cDNA sequence encoding full-length native sequence PRO215 (shown in FIG. 11 and SEQ ID NO:16) encodes for a polypeptide having an amino acid sequence which has identity with the amino acid sequence of the SLIT protein precursor. PRO215 also has identity with a leucine rich repeat protein.

7. Full-length PRO242 Polypeptides

The present invention provides newly identified and isolated nucleotide sequences encoding polypeptides referred to in the present application as PRO242. In particular, Applicants have identified and isolated cDNA encoding a PRO242 polypeptide, as disclosed in further detail in the Examples below. Using BLAST and FastA sequence alignment computer programs, Applicants found that a cDNA sequence encoding full-length native sequence PRO242 (shown in FIG. 15 and SEQ ID NO:23) has amino acid sequence identity with human macrophage inflammatory protein 1-alpha, rabbit macrophage inflammatory protein 1-beta, human LD78 and rabbit immune activation gene 2. Accordingly, it is presently believed that PRO242 polypeptide disclosed in the present application is a newly identified member of the chemokine family and possesses activity typical of the chemokine family.

8. Full-length PRO288 Polypeptides

The present invention provides newly identified and isolated PRO288 polypeptides. In particular, Applicants have identified and isolated various human PRO288 polypeptides. The properties and characteristics of some of these PRO288 polypeptides are described in further detail in the Examples below. Based upon the properties and characteristics of the PRO288 polypeptides disclosed herein, it is Applicants' present belief that PRO288 is a member of the TNFR family, and particularly, is a receptor for Apo-2 ligand.

9. Full-length PRO365 Polypeptides

The present invention provides newly identified and isolated nucleotide sequences encoding polypeptides referred to in the present application as PRO365. In particular, Applicants have identified and isolated cDNA encoding a PRO365 polypeptide, as disclosed in further detail in the Examples below. Using BLAST and FastA sequence alignment computer programs, Applicants found that various portions of the PRO365 polypeptide have significant homology with the human 2-19 protein. Accordingly, it is presently believed that PRO365 polypeptide disclosed in the present application is a newly identified member of the human 2-19 protein family.

10. Full-length PRO1361 Polypeptides The DNA60783-1611 clone was isolated from a human B cell library. As far as is known, the DNA60783-1611 sequence encodes a novel factor designated herein as PRO1361; using the WU-BLAST2 sequence alignment computer program, no sequence identities to any known proteins were revealed.

11. Full-length PRO1308 Polypeptides Using WU-BLAST2 sequence alignment computer programs, it has been found that PRO1308 shares certain amino acid sequence identity with the amino acid sequence of the follistatin protein designated "S55369" in the Dayhoff database. Accordingly, it is presently believed that PRO1308 disclosed in the present application is a newly identified member of the follistatin protein family and may possess activity or properties typical of that family of proteins.

12. Full-Length PRO1183 Polypeptides

Using WU-BLAST2 sequence alignment computer programs, it has been found that a full-length native sequence PRO1183 (shown in FIG. 26 and SEQ ID NO:52) has certain amino acid sequence identity with protoporphyrinogen oxidase. Accordingly, it is presently believed that PRO1183 disclosed in the present application is a newly identified member of the oxidase family and may possess enzymatic activity typical of oxidases.

13. Full-length PRO1272 Polypeptides

Using WU-BLAST2 sequence alignment computer programs, it has been found that a full-length native sequence PRO1272 (shown in FIG. 28 and SEQ ID NO:54) has certain amino acid sequence identity with cement gland-specific protein from *Xenopus laevis*. Accordingly, it is presently believed that PRO1272 disclosed in the present application is a newly identified member of the XAG family and may share at least one mechanism with the XAG proteins.

14. Full-length PRO1419 Polypeptides

As far as is known, the DNA71290-1630 sequence encodes a novel factor designated herein as PRO1419. Using WU-BLAST2 sequence alignment computer programs, minimal sequence identities to known proteins were revealed.

15. Full-length PRO4999 Polypeptides

Using the ALIGN-2 sequence alignment computer program referenced above, it has been found that the full-length native sequence PRO4999 (shown in FIG. 32 and SEQ ID NO:58) has certain amino acid sequence identity with UROM_HUMAN. Accordingly, it is presently believed that the PRO4999 polypeptide disclosed in the present application is a newly identified member of the uromodulin protein family and may possess one or more biological and/or immunological activities or properties typical of that protein family.

16. Full-length PRO7170 Polypeptides

The DNA108722-2743 clone was isolated from a human library as described in the Examples below. As far as is known, the DNA108722-2743 nucleotide sequence encodes a novel factor designated herein as PRO7170; using the ALIGN-2 sequence alignment computer program, no significant sequence identities to any known proteins were revealed.

17. Full-length PRO248 Polypeptides

The present invention provides newly identified and isolated nucleotide sequences encoding polypeptides referred to in the present application as PRO248. In particular, Applicants have identified and isolated cDNA encoding a PRO248 polypeptide, as disclosed in further detail in the Examples below. Using known programs such as BLAST and FastA sequence alignment computer programs, Applicants found that a cDNA sequence encoding full-length native sequence PRO248 (amino acid sequence shown in FIG. 36 and SEQ ID NO:65) has certain amino acid sequence identity with growth differentiation factor 3, from mouse and from homo sapiens. Accordingly, it is presently believed that PRO248 polypeptide disclosed in the present application is a newly identified member of the transforming growth factor β family and possesses growth and differentiation capabilities typical of the this family.

18. Full-length PRO353 Polypeptides

The present invention provides newly identified and isolated nucleotide sequences encoding polypeptides referred to in the present application as PRO353. In particular, Applicants have identified and isolated cDNA encoding PRO353 polypeptides, as disclosed in further detail in the Examples below. Using BLAST and, FastA sequence alignment computer programs, Applicants found that various portions of the PRO353 polypeptides have certain homology with the human and mouse complement proteins. Accordingly, it is presently believed that the PRO353 polypeptides disclosed in the present application are newly identified members of the complement protein family and possesses the ability to effect the inflammation process as is typical of the complement family of proteins.

19. Full-length PRO1318 and PRO1600 Polypeptides

The present invention provides newly identified and isolated nucleotide sequences encoding polypeptides referred to in the present application as PRO1318 and PRO1600. In particular, Applicants have identified and isolated cDNAs encoding PRO1318 and PRO1600 polypeptides, as disclosed in further detail in the Examples below. Using BLAST and FastA sequence alignment computer programs, Applicants found that cDNA sequence encoding full-length native sequence PRO1318 and PRO1600 (shown in FIG. 40 and SEQ ID NO:78 and FIG. 42 and SEQ ID NO:80, respectively) have amino acid sequence identity with one or more chemokines. Accordingly, it is presently believed that the PRO1318 and PRO1600 polypeptides disclosed in the present application are newly identified members of the chemokine family and possesses activity typical of the chemokine family.

20. Full-length PRO533 Polypeptides

The present invention provides newly identified and isolated nucleotide sequences encoding polypeptides referred to in the present application as PRO533. In particular, Applicants have identified and isolated cDNA encoding a PRO533 polypeptide, as disclosed in further detail in the Examples below. Using BLAST-2 and FastA sequence alignment computer programs, Applicants found that a full-length native sequence PRO533 (shown in FIG. 46 and SEQ ID NO:86) has a Blast score of 509 and 53% amino acid sequence identity with fibroblast growth factor (FGF). Accordingly, it is presently believed that PRO533 disclosed in the present application is a newly identified member of the fibroblast growth factor family and may possess activity typical of such polypeptides.

21. Full-length PRO301 Polypeptides

The present invention provides newly identified and isolated nucleotide sequences encoding polypeptides referred to in the present application as PRO301. In particular, Applicants have identified and isolated cDNA encoding a PRO301 polypeptide, as disclosed in further detail in the Examples below. Using BLAST and FastA sequence alignment computer programs, Applicants found that a full-length native sequence PRO301 (shown in FIG. 48 and SEQ ID NO:91) has a Blast score of 246 corresponding to 30% amino acid sequence identity with human A33 antigen precursor. Accordingly, it is presently believed that PRO301 disclosed in the present application is a newly identified member of the A33 antigen protein family and may be expressed in human neoplastic diseases such as colorectal cancer.

22. Full-length PRO187 Polypeptides

The present invention provides newly identified and isolated nucleotide sequences encoding polypeptides referred to in the present application as PRO187. In particular, Applicants have identified and isolated cDNA encoding a PRO187 polypeptide, as disclosed in further detail in the Examples below. Using BLAST and FastA sequence alignment computer programs, Applicants found that a full-length native sequence PRO187 (shown in FIG. 50) has 74% amino acid sequence identity and BLAST score of 310 with various androgen-induced growth factors and FGF-8. Accordingly, it is presently believed that PRO187 polypeptide disclosed in the present application is a newly identified member of the FGF-8 protein family and may possess identify activity or property typical of the FGF-8-like protein family.

23. Full-length PRO337 Polypeptides

The present invention provides newly identified and isolated nucleotide sequences encoding polypeptides referred to in the present application as PRO337. In particular, Applicants have identified and isolated cDNA encoding a PRO337 polypeptide, as disclosed in further detail in the Examples below. Using BLAST, BLAST-2 and FastA sequence alignment computer programs, Applicants found that a full-length native sequence PRO337 has 97% amino acid sequence identity with rat neurotrimin, 85% sequence identity with chicken CEPU, 73% sequence identity with chicken G55, 59% homology with human LAMP and 84% homology with human OPCAM. Accordingly, it is presently believed that PRO337 disclosed in the present application is a newly identified member of the IgLON sub family of the immunoglobulin superfamily and may possess neurite growth and differentiation potentiating properties.

24. Full-length PRO1411 Polypeptides

As far as is known, the DNA59212-1627 sequence encodes a novel factor designated herein as PRO1411. However, using WU-BLAST2 sequence alignment computer programs, some sequence identities to known proteins were revealed.

25. Full-length PRO4356 Polypeptides

Using WU-BLAST2 sequence alignment computer programs, it has been found that a full-length native sequence PRO4356 (shown in FIG. 56 and SEQ ID NO:108) has certain amino acid sequence identity with metastasis associated GPI-anchored protein. Accordingly, it is presently believed that PRO4356 disclosed in the present application is a newly identified member of this family and shares similar mechanisms.

26. Full-length PRO246 Polypeptides

The present invention provides newly identified and isolated nucleotide sequences encoding polypeptides referred to in the present application as PRO246. In particular, Applicants have identified and isolated cDNA encoding a PRO246 polypeptide, as disclosed in further detail in the Examples below. Using BLAST and FastA sequence alignment computer programs, Applicants found that a portion of the PRO246 polypeptide has significant homology with the human cell surface protein HCAR. Accordingly, it is presently believed that PRO246 polypeptide disclosed in the present application may be a newly identified membrane-bound virus receptor or tumor cell-specific antigen.

27. Full-length PRO265 Polypeptides

The present invention provides newly identified and isolated nucleotide sequences encoding polypeptides referred to in the present application as PRO265. In particular, Applicants have identified and isolated cDNA encoding a PRO265 polypeptide, as disclosed in further detail in the Examples below. Using programs such as BLAST and FastA sequence alignment computer programs, Applicants found that various portions of the PRO265 polypeptide have significant homology with the fibromodulin protein and fibromodulin precursor protein. Applicants have also found that the DNA encoding the PRO265 polypeptide has significant homology with platelet glycoprotein V, a member of the leucine rich related protein family involved in skin and wound repair. Accordingly, it is presently believed that PRO265 polypeptide disclosed in the present application is a newly identified member of the leucine rich repeat family and possesses protein protein binding capabilities, as well as be involved in skin and wound repair as typical of this family.

28. Full-length PRO941 Polypeptides

The present invention provides newly identified and isolated nucleotide sequences encoding polypeptides referred to in the present application as PRO941. In particular, Applicants have identified and isolated cDNA encoding a PRO941 polypeptide, as disclosed in further detail in the Examples below. Using BLAST and FastA sequence alignment computer programs, Applicants found that the PRO941 polypeptide has significant similarity to one or more cadherin proteins. Accordingly, it is presently believed that PRO941 polypeptide disclosed in the present application is a newly identified cadherin homolog.

29. Full-length PRO10096 Polypeptides

Using the ALIGN-2 sequence alignment computer program referenced above, it has been found that the full-length native sequence PRO10096 (shown in FIG. 64 and SEQ ID NO:126) has certain amino acid sequence identity with various interleukin-10-related molecules. Accordingly, it is presently believed that the PRO10096 polypeptide disclosed in the present application is a newly identified IL-10 homolog and may possess one or more biological and/or immunological activities or properties typical of that protein. 30. Full-length PRO6003 Polypeptides The DNA83568-2692 clone was isolated from a human fetal kidney library as described in the Examples below. As far as is known, the DNA83568-2692 nucleotide sequence encodes a novel factor designated herein as PRO6003; using the ALIGN-2 sequence alignment computer program, no significant sequence identities to any known proteins were revealed.

B. PRO Polypeptide Variants

In addition to the full-length native sequence PRO polypeptides described herein, it is contemplated that PRO variants can be prepared. PRO variants can be prepared by introducing appropriate nucleotide changes into the PRO DNA, and/or by synthesis of the desired PRO polypeptide. Those skilled in the art will appreciate that amino acid changes may alter post-translational processes of the PRO, such as changing the number or position of glycosylation sites or altering the membrane anchoring characteristics.

Variations in the native full-length sequence PRO or in various domains of the PRO described herein, can be made, for example, using any of the techniques and guidelines for conservative and non-conservative mutations set forth, for instance, in U.S. Pat. No. 5,364,934. Variations may be a substitution, deletion or insertion of one or more codons encoding the PRO that results in a change in the amino acid sequence of the PRO as compared with the native sequence PRO. Optionally the variation is by substitution of at least one amino acid with any other amino acid in one or more of the domains of the PRO. Guidance in determining which amino acid residue may be inserted, substituted or deleted without adversely affecting the desired activity may be found by comparing the sequence of the PRO with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

PRO polypeptide fragments are provided herein. Such fragments may be truncated at the N-terminus or C-terminus, or may lack internal residues, for example, when compared with a full length native protein. Certain fragments lack amino acid residues that are not essential for a desired biological activity of the PRO polypeptide.

PRO fragments may be prepared by any of a number of conventional techniques. Desired peptide fragments may be chemically synthesized. An alternative approach involves generating PRO fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, PRO polypeptide fragments share at least one biological and/or immunological activity with the native PRO polypeptide disclosed herein.

In particular embodiments, conservative substitutions of interest are shown in Table 6 under the heading of preferred substitutions. If such substitutions result in a change in biological activity, then more substantial changes, denominated exemplary substitutions in Table 6, or as further described below in reference to amino acid classes, are introduced and the products screened.

TABLE 6

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the PRO polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene*, 34:315 (1985)], restriction selection mutagenesis [Wells et al., *Philos. Trans. R. Soc. London SerA*, 317:415 (1986)] or other known techniques can be performed on the cloned DNA to produce the PRO variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science*, 244: 1081-1085 (1989)]. Alanine is also typically preferred because it is the most common amino acid. Further, it is frequently found in both buried and exposed positions [Creighton, *The Proteins*, (W.H. Freeman & Co., N.Y.); Chothia, *J. Mol. Biol.*, 150:1 (1976)]. If alanine substitution does not yield adequate amounts of variant, an isoteric amino acid can be used.

C. Modifications of PRO

Covalent modifications of PRO are included within the scope of this invention. One type of covalent modification includes reacting targeted amino acid residues of a PRO polypeptide with an organic derivatizing agent that is capable of reacting with selected side chains or the N- or C-terminal residues of the PRO. Derivatization with bifunctional agents is useful, for instance, for crosslinking PRO to a water-insoluble support matrix or surface for use in the method for purifying anti-PRO antibodies, and vice-versa. Commonly used crosslinking agents include, e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the a-amino groups of lysine, arginine, and histidine side chains [T. E. Creighton, *Proteins: Structure and Molecular Properties*, W.H. Freeman & Co., San Francisco, pp. 79-86 (1983)], acetylation of the N-terminal amine, and amidation of any C-terminal carboxyl group.

Another type of covalent modification of the PRO polypeptide included within the scope of this invention comprises altering the native glycosylation pattern of the polypeptide. "Altering the native glycosylation pattern" is intended for purposes herein to mean deleting one or more carbohydrate moieties found in native sequence PRO (either by removing the underlying glycosylation site or by deleting the glycosylation by chemical and/or enzymatic means), and/or adding one or more glycosylation sites that are not present in the native sequence PRO. In addition, the phrase includes qualitative changes in the glycosylation of the native proteins, involving a change in the nature and proportions of the various carbohydrate moieties present.

Addition of glycosylation sites to the PRO polypeptide may be accomplished by altering the amino acid sequence. The alteration may be made, for example, by the addition of, or substitution by, one or more serine or threonine residues to the native sequence PRO (for O-linked glycosylation sites). The PRO amino acid sequence may optionally be altered through changes at the DNA level, particularly by mutating the DNA encoding the PRO polypeptide at preselected bases such that codons are generated that will translate into the desired amino acids.

Another means of increasing the number of carbohydrate moieties on the PRO polypeptide is by chemical or enzymatic coupling of glycosides to the polypeptide. Such methods are described in the art, e.g., in WO 87/05330 published Sep. 11, 1987, and in Aplin and Wriston, *CRC Crit. Rev. Biochem.*, pp. 259-306 (1981).

Removal of carbohydrate moieties present on the PRO polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of PRO comprises linking the PRO polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The PRO of the present invention may also be modified in a way to form a chimeric molecule comprising PRO fused to another, heterologous polypeptide or amino acid sequence.

In one embodiment, such a chimeric molecule comprises a fusion of the PRO with a tag polypeptide which provides an epitope to which an anti-tag antibody can selectively bind. The epitope tag is generally placed at the amino- or carboxyl-terminus of the PRO. The presence of such epitope-tagged forms of the PRO can be detected using an antibody against the tag polypeptide. Also, provision of the epitope tag enables the PRO to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159-2165 (1988)]; the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology*, 6:1204-1210 (1988)]; the KT3 epitope peptide [Martin et al., *Science*, 255: 192-194 (1992)]; an α-tubulin epitope peptide [Skinner et al., *J. Biol. Chem.*, 266:15163-15166 (1991)]; and the T7 gene 10 protein peptide tag [Lutz-Freyermuth et al., *Proc. Natl. Acad. Sci. USA*, 87:6393-6397 (1990)].

In an alternative embodiment, the chimeric molecule may comprise a fusion of the PRO with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a PRO polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

D. Preparation of PRO

The description below relates primarily to production of PRO by culturing cells transformed or transfected with a vector containing PRO nucleic acid. It is, of course, contemplated that alternative methods, which are well known in the art, may be employed to prepare PRO. For instance, the PRO sequence, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.*, 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the PRO may be chemically synthesized separately and combined using chemical or enzymatic methods to produce the full-length PRO.

1. Isolation of DNA Encoding PRO

DNA encoding PRO may be obtained from a cDNA library prepared from tissue believed to possess the PRO mRNA and to express it at a detectable level. Accordingly, human PRO DNA can be conveniently obtained from a cDNA library prepared from human tissue, such as described in the Examples. The PRO-encoding gene may also be obtained from a genomic library or by known synthetic procedures (e.g., automated nucleic acid synthesis).

Libraries can be screened with probes (such as antibodies to the PRO or oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding PRO is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GEN-BANK database or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for PRO production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., *Gene*, 23:315 (1983) and WO 89/05859 published June 29, 1989. For mammalian cells without such cell walls, the calcium phosphate precipitation method of Graham and van der Eb, *Virology*, 52:456-457 (1978) can be employed. General aspects of mammalian cell host system transfections have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci.* (USA), 76:3829 (1979). However, other methods for introducing DNA into cells, such as by nuclear microinjection, electroporation, bacterial protoplast fusion with intact cells, or polycations, e.g., polybrene, polyomithine, may also be used. For various techniques for transforming mammalian cells, see Keown et al., *Methods in Enzymology*, 185:527-537 (1990) and Mansour et al., *Nature*, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5772 (ATCC 53,635). Other suitable prokaryotic host cells include Enterobacteriaceae such as *Escherichia*, e.g., *E. coli*, *Enterobacter*, *Erwinia*, *Klebsiella*, *Proteus*, *Salnonella*, e.g., *Salmonella typhimurium*, *Serratia*, e.g., *Serratia marcescans*, and *Shigella*, as well as *Bacilli* such as *B. subtilis* and *B. licheniformis* (e.g., *B. licheniformis* 41P disclosed in DD 266,710 published Apr. 12, 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including E. coli W3110 strain 1A2, which has the complete genotype tonA ; E. coli W3110 strain 9E4, which has the complete genotype tonA ptr3; E. coli W3110 strain 27C7 (ATCC 55,244), which has the complete genotype ton ptr3 phoA E15 (argF-lac)169 degP ompT kanr; E. coli W3110 strain 37D6, which has the complete genotype tonA ptr3 phoA E15 (argf-lac)169 degp ompT rbs7 ilvG kan$^r$; E. coli W3110 strain 40B4, which is strain 37D6 with a non-kanamycin resistant degp deletion mutation; and an E. coli strain having mutant periplasmic protease disclosed in U.S. Pat. No. 4,946,783 issued Aug. 7, 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for PRO-encoding vectors. Saccharomyces cerevisiae is a commonly used lower eukaryotic host microorganism. Others include Schizosaccharomyces pombe (Beach and Nurse, Nature, 290: 140 [1981]; EP 139,383 published May 2, 1985); Kluyveromyces hosts (U.S. Pat. No. 4,943,529; Fleer et al., Bio/Technology, 9:968-975(1991)) such as, e.g., K. lactis(MW98-8C, CBS683, CBS4574; Louvencourt et al., J. Bacteriol., 154(2):737-742 [1983]), K. fragilis (ATCC 12,424), K. bulgaricus (ATCC 16,045), K. wickeramii (ATCC 24,178), K. waltii (ATCC 56,500), K. drosophilarum (ATCC 36,906; Van den Berg et al., Bio/Technology, 8:135 (1990)), K. thermotolerans, and K. maxianus; yarrowia (EP 402,226); Pichia pastoris (EP 183,070; Sreekrishna et al., J. Basic Microbiol., 28:265-278 [1988]); Candida; Trichodenna reesia (EP 244,234); Neurospora crassa (Case et al., Proc. Natl. Acad. Sci. USA, 76:5259-5263 [1979]); Schwanniomyces such as Schwanniomyces occidentalis (EP 394,538 published 31 Oct. 1990); and filamentous fungi such as, e.g., Neurospora, Penicillium, Tolypocladium (WO 91/00357 published 10 Jan. 1991), and Aspergillus hosts such as A. nidulans (Ballance et al., Biochem. Biophys. Res. Commun., 112:284-289 [1983]; Tilburn et al., Gene, 26:205-221 [1983]; Yelton et al., Proc. Natl. Acad. Sci. USA, 81: 1470-1474 [1984]) and A. niger (Kelly and Hynes, EMBO J., 4:475-479 [1985]). Methylotropic yeasts are suitable herein and include, but are not limited to, yeast capable of growth on methanol selected from the genera consisting of Hansenula, Candida, Kloeckera, Pichia, Saccharomyces, Torulopsis, and Rhodotorula. A list of specific species that are exemplary of this class of yeasts may be found in C. Anthony, The Biochemistry of Methylotrophs, 269 (1982).

Suitable host cells for the expression of glycosylated PRO are derived from multicellular organisms. Examples of invertebrate cells include insect cells such as Drosophila S2 and Spodoptera Sf9, as well as plant cells. Examples of useful mammalian host cell lines include Chinese hamster ovary (CHO) and COS cells. More specific examples include monkey kidney CVI line transformed by SV40 (COS-7, ATCC CRL 1651); human embryonic kidney line (293 or 293 cells subcloned for growth in suspension culture, Graham et al., J. Gen Virol., 36:59 (1977)); Chinese hamster ovary cells/-DHFR (CHO, Urlaub and Chasin, Proc. Natl. Acad. Sci. USA, 77:4216 (1980)); mouse sertoli cells (TM4, Mather, Biol. Reprod., 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding PRO may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The PRO may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the PRO-encoding DNA that is inserted into the vector. The signal sequence may be a prokaryotic signal sequence selected, for example, from the group of the alkaline phosphatase, penicillinase, 1pp, or heat-stable enterotoxin II leaders. For yeast secretion the signal sequence may be, e.g., the yeast invertase leader, alpha factor leader (including Saccharomyces and Kluyveromyces α-factor leaders, the latter described in U.S. Pat. No. 5,010, 182), or acid phosphatase leader, the C. albicans glucoamylase leader (EP 362,179 published 4 Apr. 4, 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2 µ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the PRO-encoding nucleic acid, such as DHFR or thymidine kinase. An appropriate host cell when wild-type DHFR is employed is the CHO cell line deficient in DHFR activity, prepared and propagated as described by Urlaub et al., Proc. Natl. Acad. Sci. USA, 77:4216 (1980). A suitable selection gene for use in yeast is the trp1 gene present in the yeast plasmid YRp7 [Stinchcomb et al., Nature, 282:39 (1979); Kingsman et al., Gene, 7:141 (1979); Tschemper et al., Gene, 10:157 (1980)]. The trp1 gene provides a selection marker for a mutant strain of yeast lacking the ability to grow in tryptophan, for example, ATCC No. 44076 or PEP4-1 [Jones, *Genetics,* 85:12 (1977)].

Expression and cloning vectors usually contain a promoter operably linked to the PRO-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature,* 275:615 (1978); Goeddel et al., *Nature,* 281:544 (1979)], alkaline phosphatase, a tryptophan (trp) promoter system [Goeddel, *Nucleic Acids Res.,* 8:4057 (1980); EP 36,776], and hybrid promoters such as the tac promoter [deBoer et al., *Proc. Natl. Acad. Sci. USA,* 80:21-25 (1983)]. Promoters for use in bacterial systems also will contain a Shine-Dalgarno (S.D.) sequence operably linked to the DNA encoding PRO.

Examples of suitable promoting sequences for use with yeast hosts include the promoters for 3-phosphoglycerate kinase [Hitzemanet al., *J. Biol. Chem.,* 255:2073 (1980)] or other glycolytic enzymes [Hess et al., *J. Adv. Enzyme Reg.,* 7:149 (1968); Holland, *Biochemistry,* 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

PRO transcription from vectors in mammalian host cells is controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the PRO by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the PRO coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding PRO.

Still other methods, vectors, and host cells suitable for adaptation to the synthesis of PRO in recombinant vertebrate cell culture are described in Gething et al., *Nature,* 293:620-625 (1981); Mantei et al., *Nature,* 281:40-46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA,* 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence PRO polypeptide or against a synthetic peptide based on the DNA sequences provided herein or against exogenous sequence fused to PRO DNA and encoding a specific antibody epitope.

5. Purification of Polypeptide

Forms of PRO may be recovered from culture medium or from host cell lysates. If membrane-bound, it can be released from the membrane using a suitable detergent solution (e.g. Triton-X 100) or by enzymatic cleavage. Cells employed in expression of PRO can be disrupted by various physical or chemical means, such as freeze-thaw cycling, sonication, mechanical disruption, or cell lysing agents.

It may be desired to purify PRO from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the PRO. Various methods of protein purification may be employed and such methods are known in the art and described for example in Deutscher, *Methods in Enzymology,* 182 (1990); Scopes, *Protein Purification: Principles and Practice,* Springer-Verlag, New York (1982). The purification step(s) selected will depend, for example, on the nature of the production process used and the particular PRO produced.

E. Uses for PRO

Nucleotide sequences (or their complement) encoding PRO have various applications in the art of molecular biology, including uses as hybridization probes, in chromosome and gene mapping and in the generation of anti-sense RNA and DNA. PRO nucleic acid will also be useful for the preparation of PRO polypeptides by the recombinant techniques described herein.

The full-length native sequence PRO gene, or portions thereof, may be used as hybridization probes for a cDNA library to isolate the full-length PRO cDNA or to isolate still other cDNAs (for instance, those encoding naturally-occurring variants of PRO or PRO from other species) which have a desired sequence identity to the native PRO sequence disclosed herein. Optionally, the length of the probes will be about 20 to about 50 bases. The hybridization probes may be derived from at least partially novel regions of the full length native nucleotide sequence wherein those regions may be determined without undue experimentation or from genomic sequences including promoters, enhancer elements and introns of native sequence PRO. By way of example, a screening method will comprise isolating the coding region of the PRO gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the PRO gene of the present invention can be used to screen libraries of human cDNA, genomic DNA or mRNA to determine which members of such libraries the probe hybridizes to. Hybridization techniques are described in further detail in the Examples below.

Any EST sequences disclosed in the present application may similarly be employed as probes, using the methods disclosed herein.

Other useful fragments of the PRO nucleic acids include antisense or sense oligonucleotides comprising a singe-stranded nucleic acid sequence (either RNA or DNA) capable of binding to target PRO mRNA (sense) or PRO DNA (antisense) sequences. Antisense or sense oligonucleotides, according to the present invention, comprise a fragment of the coding region of PRO DNA. Such a fragment generally comprises at least about 14 nucleotides, preferably from about 14 to 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. The antisense oligonucleotides thus may be used to block expression of PRO proteins. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10048, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Antisense or sense RNA or DNA molecules are generally at least about 5 bases in length, about 10 bases in length, about 15 bases in length, about 20 bases in length, about 25 bases in length, about 30 bases in length, about 35 bases in length, about 40 bases in length, about 45 bases in length, about 50 bases in length, about 55 bases in length, about 60 bases in length, about 65 bases in length, about 70 bases in length, about 75 bases in length, about 80 bases in length, about 85 bases in length, about 90 bases in length, about 95 bases in length, about 100 bases in length, or more.

The probes may also be employed in PCR techniques to generate a pool of sequences for identification of closely related PRO coding sequences.

Nucleotide sequences encoding a PRO can also be used to construct hybridization probes for mapping the gene which encodes that PRO and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

When the coding sequences for PRO encode a protein which binds to another protein (example, where the PRO is a receptor), the PRO can be used in assays to identify the other proteins or molecules involved in the binding interaction. By such methods, inhibitors of the receptor/ligand binding interaction can be identified. Proteins involved in such binding interactions can also be used to screen for peptide or small molecule inhibitors or agonists of the binding interaction. Also, the receptor PRO can be used to isolate correlative ligand(s). Screening assays can be designed to find lead compounds that mimic the biological activity of a native PRO or a receptor for PRO. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode PRO or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding PRO can be used to clone genomic DNA encoding PRO in accordance with established techniques and the genomic sequences used to generate transgenic animals that contain cells which express DNA encoding PRO. Methods for generating transgenic animals, particularly animals such as mice or rats, have become conventional in the art and are described, for example, in U.S. Pat. Nos. 4,736,866 and 4,870,009. Typically, particular cells would be targeted for PRO transgene incorporation with tissue-specific enhancers. Transgenic animals that include a copy of a transgene encoding PRO introduced into the germ line of the animal at an embryonic stage can be used to examine the effect of increased expression of DNA encoding PRO. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of PRO can be used to construct a PRO "knock out" animal which has a defective or altered gene encoding PRO as a result of homologous recombination between the endogenous gene encoding PRO and altered genomic DNA encoding PRO introduced into an embryonic stem cell of the animal. For example, cDNA encoding PRO can be used to clone genomic DNA encoding PRO in accordance with established techniques. A portion of the genomic DNA encoding PRO can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell*, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell*, 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knock-out animals can be characterized for instance, for their ability to defend against certain pathological conditions and for their development of pathological conditions due to absence of the PRO polypeptide.

Nucleic acid encoding the PRO polypeptides may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA* 83:4143-4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11, 205-210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262, 4429-4432 (1987); and Wagner et al., *Proc. Natl. Acad. Sci. USA* 87, 3410-3414 (1990). For review of gene marking and gene therapy protocols see Anderson et al., *Science* 256, 808-813 (1992).

The PRO polypeptides described herein may also be employed as molecular weight markers for protein electrophoresis purposes and the isolated nucleic acid sequences may be used for recombinantly expressing those markers.

The nucleic acid molecules encoding the PRO polypeptides or fragments thereof described herein are useful for chromosome identification. In this regard, there exists an ongoing need to identify new chromosome markers, since relatively few chromosome marking reagents, based upon actual sequence data are presently available. Each PRO nucleic acid molecule of the present invention can be used as a chromosome marker.

The PRO polypeptides and nucleic acid molecules of the present invention may also be used for tissue typing, wherein the PRO polypeptides of the present invention may be differentially expressed in one tissue as compared to another. PRO nucleic acid molecules will find use for generating probes for PCR, Northern analysis, Southern analysis and Western analysis.

The PRO polypeptides described herein may also be employed as therapeutic agents. The PRO polypeptides of the present invention can be formulated according to known methods to prepare pharmaceutically useful compositions, whereby the PRO product hereof is combined in admixture with a pharmaceutically acceptable carrier vehicle. Therapeutic formulations are prepared for storage by mixing the active ingredient having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™ or PEG.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96.

When in vivo administration of a PRO polypeptide or agonist or antagonist thereof is employed, normal dosage amounts may vary from about 10 ng/kg to up to 100 mg/kg of mammal body weight or more per day, preferably about 1 µg/kg/day to 10 mg/kg/day, depending upon the route of administration. Guidance as to particular dosages and methods of delivery is provided in the literature; see, for example, U.S. Pat. Nos. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue.

Where sustained-release administration of a PRO polypeptide is desired in a formulation with release characteristics suitable for the treatment of any disease or disorder requiring administration of the PRO polypeptide, microencapsulation of the PRO polypeptide is contemplated. Microencapsulation of recombinant proteins for sustained release has been successfully performed with human growth hormone (rhGH), interferon-(rhIFN-), interleukin-2, and MN rgp120. Johnson et al., *Nat. Med.*, 2:795-799 (1996); Yasuda, *Biomed. Ther.*, 27:1221-1223 (1993); Hora et al., *Bio/Technology.* 8:755-758 (1990); Cleland, "Design and Production of Single Immunization Vaccines Using Polylactide Polyglycolide Microsphere Systems," in *Vaccine Design: The Subunit and Adjuvant Approach*, Powell and Newman, eds, (Plenum Press: New York, 1995), pp. 439-462; WO 97/03692, WO 96/40072, WO 96/07399; and U.S. Pat. No. 5,654,010.

The sustained-release formulations of these proteins were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasin and R. Langer (Eds.). *Biodegradable Polymers as Drug Delivery Systems* (Marcel Dekker: New York, 1990), pp. 1-41.

This invention encompasses methods of screening compounds to identify those that mimic the PRO polypeptide (agonists) or prevent the effect of the PRO polypeptide (antagonists). Screening assays for antagonist drug candidates are designed to identify compounds that bind or complex with the PRO polypeptides encoded by the genes identified herein, or otherwise interfere with the interaction of the encoded polypeptides with other cellular proteins. Such screening assays will include assays amenable to high-throughput screening of chemical libraries. making them particularly suitable for identifying small molecule drug candidates.

The assays can be performed in a variety of formats, including protein-protein binding assays, biochemical screening assays, immunoassays, and cell-based assays, which are well characterized in the art.

All assays for antagonists are common in that they call for contacting the drug candidate with a PRO polypeptide encoded by a nucleic acid identified herein under conditions and for a time sufficient to allow these two components to interact.

In binding assays, the interaction is binding and the complex formed can be isolated or detected in the reaction mixture. In a particular embodiment, the PRO polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the PRO polypeptide and drying. Alternatively, an immobilized antibody, e.g., a monoclonal antibody, specific for the PRO polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular PRO polypeptide encoded by a gene identified herein, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, *Nature (London)*, 340:245-246 (1989); Chien et al., *Proc. Natl. Acad. Sci. USA*, 88:9578-9582 (1991)) as disclosed by Chevray and Nathans, *Proc. Natl. Acad. Sci. USA*, 89: 5789-5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL 1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a gene encoding a PRO polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the PRO polypeptide may be added to a cell along with the compound to be screened for a particular activity and the ability of the compound to inhibit the activity of interest in the presence of the PRO polypeptide indicates that the compound is an antagonist to the PRO polypeptide. Alternatively, antagonists may be detected by combining the PRO polypeptide and a potential antagonist with membrane-bound PRO polypeptide receptors or recombinant receptors under appropriate conditions for a competitive inhibition assay. The PRO polypeptide can be labeled, such as by radioactivity, such that the number of PRO polypeptide molecules bound to the receptor can be used to determine the effectiveness of the potential antagonist. The gene encoding the receptor can be identified by numerous methods known to those of skill in the art, for example, ligand panning and FACS sorting. Coligan et al., *Current Protocols in Immun.*, 1(2): Chapter 5 (1991). Preferably, expression cloning is employed wherein polyadenylated RNA is prepared from a cell responsive to the PRO polypeptide and a cDNA library created from this RNA is divided into pools and used to transfect COS cells or other cells that are not responsive to the PRO polypeptide. Transfected cells that are grown on glass slides are exposed to labeled PRO polypeptide. The PRO polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach for receptor identification, labeled PRO polypeptide can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro- sequencing would be used to design a set of degenerate oligonucleotide probes to screen a cDNA library to identify the gene encoding the putative receptor.

In another assay for antagonists, mammalian cells or a membrane preparation expressing the receptor would be incubated with labeled PRO polypeptide in the presence of the candidate compound. The ability of the compound to enhance or block this interaction could then be measured.

More specific examples of potential antagonists include an oligonucleotide that binds to the fusions of immunoglobulin with PRO polypeptide, and, in particular, antibodies including, without limitation, poly-and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the PRO polypeptide that recognizes the receptor but imparts no effect, thereby competitively inhibiting the action of the PRO polypeptide.

Another potential PRO polypeptide antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature PRO polypeptides herein, is used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.*, 6:3073 (1979); Cooney et al., *Science*, 241: 456 (1988); Dervan et al., *Science*, 251:1360 (1991)), thereby preventing transcription and the production of the PRO polypeptide. The antisense RNA oligonucleotide hybridizes to the mRNA in vivo and blocks translation of the mRNA molecule into the PRO polypeptide (antisense—Okano, *Neurochem.*, 56:560 (1991); *Oligodeoxynucleotides as Antisense Inhibitors of Gene Expression* (CRC Press: Boca Raton, Fla., 1988). The oligonucleotides described above can also be delivered to cells such that the antisense RNA or DNA may be expressed in vivo to inhibit production of the PRO polypeptide. When antisense DNA is used, oligodeoxyribonucleotides derived from the translation-initiation site, e.g., between about −10 and +10 positions of the target gene nucleotide sequence, are preferred.

Potential antagonists include small molecules that bind to the active site, the receptor binding site, or growth factor or other relevant binding site of the PRO polypeptide, thereby blocking the normal biological activity of the PRO polypeptide. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology*, 4:469-471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed hereinabove and/or by any other screening techniques well known for those skilled in the art.

Uses of the herein disclosed molecules may also be based upon the positive functional assay hits disclosed and described below. Methods based upon those assay hits are also encompassed by the present invention.

F. Anti-PRO Antibodies

The present invention further provides anti-PRO antibodies. Exemplary antibodies include polyclonal, monoclonal, humanized, bispecific, and heteroconjugate antibodies.

1. Polyclonal Antibodies

The anti-PRO antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the PRO polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-PRO antibodies may, alternatively, be monoclonal antibodies. Monoclonal antibodies may be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the PRO polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51-63].

The culture medium in which the hybridoma cells are cultured can then be assayed for the presence of monoclonal antibodies directed against PRO. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Human and Humanized Antibodies

The anti-PRO antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522-525 (1986); Riechmann et al., *Nature*, 332:323-329 (1988); and Presta, *Curr. Op. Struct. Biol.*, 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522-525 (1986); Riechmann et al., *Nature*, 332:323-327 (1988); Verhoeyen et al., *Science*, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1991); Marks et al., *J. Mol. Biol.*, 222:581 (1991)]. The techniques of Cole et al. and Boemer et al. are also available for the preparation of human monoclonal antibodies (Cole et al., *Monoclonal Antibodies and Cancer Therapy*, Alan R. Liss, p. 77 (1985) and Boemer et al., *J. Immunol.*, 147(1):86-95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10, 779-783 (1992); Lonberg et al., *Nature* 368 856-859 (1994); Morrison, *Nature* 368, 812-13 (1994); Fishwild et al., *Nature Biotechnology* 14, 845-51 (1996); Neuberger, *Nature Biotechnology* 14, 826 (1996); Lonberg and Huszar, *Intern. Rev. Immunol.* 13 65-93 (1995).

The antibodies may also be affinity matured using known selection and/or mutagenesis methods as described above. Preferred affinity matured antibodies have an affinity which is five times, more preferably 10 times, even more preferably 20 or 30 times greater than the starting antibody (generally murine, humanized or human) from which the matured antibody is prepared.

4. Bispecific Antibodies

Bispecific antibodies are monoclonal, preferably human or humanized, antibodies that have binding specificities for at least two different antigens. In the present case, one of the binding specificities is for the PRO, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, *Nature,* 305:537-539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., *EMBO J.,* 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH 1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology,* 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby et al., *J. Exp. Med.* 175:217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various technique for making and isolating bispecific antibody fragments directly from recombinant cell culture have also been described. For example, bispecific antibodies have been produced using leucine zippers. Kostelny et al., *J. Immunol.* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See, Gruber et al., *J. Immunol* 152:5368 (1994). Antibodies with more than two valencies are contemplated. For example, trispecific antibodies can be prepared. Tutt et al., *J. Immunol.* 147:60 (1991).

Exemplary bispecific antibodies may bind to two different epitopes on a given PRO polypeptide herein. Alternatively, an anti-PRO polypeptide arm may be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular PRO polypeptide. Bispecific antibodies may also be used to localize cytotoxic agents to cells which express a particular PRO polypeptide. These antibodies possess a PRO-binding arm and an arm which binds a cytotoxic agent or a radionuclide chelator, such as EOTUBE, DPTA, DOTA, or TETA. Another bispecific antibody of interest binds the PRO polypeptide and further binds tissue factor (TF).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

6. Effector Function Engineering

It may be desirable to modify the antibody of the invention with respect to effector function, so as to enhance, e.g., the effectiveness of the antibody in treating cancer. For example, cysteine residue(s) may be introduced into the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.*, 176: 1191-1195 (1992) and Shopes, *J. Immunol.*, 148: 2918-2922 (1992). Homodimeric antibodies with enhanced anti-tumor activity may also be prepared using heterobifunctional cross-linkers as described in Wolff et al. *Cancer Research*, 53: 2560-2565 (1993). Alternatively, an antibody can be engineered that has dual Fc regions and may thereby have enhanced complement lysis and ADCC capabilities. See Stevenson et al., *Anti-Cancer Drug Design.* 3: 219-230 (1989).

7. Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-iazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science*, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

8. Immunoliposomes

The antibodies disclosed herein may also be formulated as immunoliposomes. Liposomes containing the antibody are prepared by methods known in the art, such as described in Epstein et al., *Proc. Natl. Acad. Sci. USA*, 82: 3688 (1985); Hwang et al., *Proc. Natl Acad. Sci. USA*, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al ., *J. Biol. Chem.*, 257: 286-288 (1982) via a disulfide-interchange reaction. A chemotherapeutic agent (such as Doxorubicin) is optionally contained within the liposome. See Gabizon et al., *J. National Cancer Inst.*, 81(19): 1484 (1989).

9. Pharmaceutical Compositions of Antibodies

Antibodies specifically binding a PRO polypeptide identified herein, as well as other molecules identified by the screening assays disclosed hereinbefore, can be administered for the treatment of various disorders in the form of pharmaceutical compositions.

If the PRO polypeptide is intracellular and whole antibodies are used as inhibitors, internalizing antibodies are preferred. However, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA*, 90: 7889-7893 (1993). The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacyliate) microcapsules, respectively, in colloidal drug delivery systems (for example, liposomes, albumin microspheres, microemulsions, nano-particles, and nanocapsules) or in macroemulsions. Such techniques are disclosed in Remington's Pharmaceutical Sciences, supra.

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S-S bond formation through thio-disulfide interchange, stabilization may be achieved by modifying sulfhydryl residues, lyophilizing from acidic solutions, controlling moisture content, using appropriate additives, and developing specific polymer matrix compositions.

G. Uses for anti-PRO Antibodies

The anti-PRO antibodies of the invention have various utilities. For example, anti-PRO antibodies may be used in diagnostic assays for PRO, e.g., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147-158]. The antibodies used in the diagnostic assays can be labeled with a detectable moiety. The detectable moiety should be capable of producing, either directly or indirectly, a detectable signal. For example, the detectable moiety may be a radioisotope, such as $^3H$, $_{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982).

Anti-PRO antibodies also are useful for the affinity purification of PRO from recombinant cell culture or natural sources. In this process, the antibodies against PRO are immobilized on a suitable support, such a Sephadex resin or filter paper, using methods well known in the art. The immobilized antibody then is contacted with a sample containing the PRO to be purified, and thereafter the support is washed with a suitable solvent that will remove substantially all the material in the sample except the PRO, which is bound to the immobilized antibody. Finally, the support is washed with another suitable solvent that will release the PRO from the antibody.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Extracellular Domain Homology Screening to Identify Novel Polypeptides and cDNA Encoding Therefor The extracellular domain (ECD) sequences (including the secretion signal sequence, if any) from about 950 known secreted proteins from the Swiss-Prot public database were used to search EST databases. The EST databases included public databases (e.g., DAYHOFF database, GENBANK database) and proprietary databases (e.g. LIFESEQ® database, Incyte Pharmaceuticals, Palo Alto, Calif.). The search was performed using the computer program BLAST or BLAST-2 (Altschul et al., Methods in Enzymology 266:460-480 (1996)) as a comparison of the ECD protein sequences to a 6 frame translation of the EST sequences. Those comparisons with a BLAST score of 70 (or in some cases 90) or greater that did not encode known proteins were clustered and assembled into consensus DNA sequences with the program "phrap" (Phil Green, University of Washington. Seattle. Wash.).

Using this extracellular domain homology screen. consensus DNA sequences were assembled relative to the other identified EST sequences using phrap. In addition, the consensus DNA sequences obtained were often (but not always) extended using repeated cycles of BLAST or BLAST-2 and phrap to extend the consensus sequence as far as possible using the sources of EST sequences discussed above.

Based upon the consensus sequences obtained as described above, oligonucleotides were then synthesized and used to identify by PCR a cDNA library that contained the sequence of interest and for use as probes to isolate a clone of the full-length coding sequence for a PRO polypeptide. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., Current Protocols in Molecular Biology, with the PCR primer pair. A positive library was then used to isolate clones encoding the gene of interest using the probe oligonucleotide and one of the primer pairs.

The cDNA libraries used to isolate the cDNA clones were constructed by standard methods using commercially available reagents such as those from Invitrogen, San Diego, CA. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science*, 253:1278-1280 (1991)) in the unique XhoI and NotI sites.

Example 2

Isolation of cDNA Clones by Amylase Screening

1. Preparation of Oligo dT Primed cDNA Library mRNA was isolated from a human tissue of interest using reagents and protocols from Invitrogen, San Diego, Calif. (Fast Track 2). This RNA was used to generate an oligo dT primed cDNA library in the vector pRK5D using reagents and protocols from Life Technologies, Gaithersburg, Md. (Super Script Plasmid System). In this procedure, the double stranded cDNA was sized to greater than 1000 bp and the SalI/NotI linkered cDNA was cloned into XhoI/NotI cleaved vector. pRK5D is a cloning vector that has an sp6 transcription initiation site followed by an SfiI restriction enzyme site preceding the XhoI/NotI cDNA cloning sites.

2. Preparation of Random Primed cDNA Library

A secondary cDNA library was generated in order to preferentially represent the 5' ends of the primary cDNA clones. Sp6 RNA was generated from the primary library (described above), and this RNA was used to generate a random primed cDNA library in the vector pSST-AMY.0 using reagents and protocols from Life Technologies (Super Script Plasmid System, referenced above). In this procedure the double stranded cDNA was sized to 500-1000 bp, Tinkered with blunt to NotI adaptors, cleaved with SfiI, and cloned into SfiI/NotI cleaved vector. pSST-AMY.0 is a cloning vector that has a yeast alcohol dehydrogenase promoter preceding the cDNA cloning sites and the mouse amylase sequence (the mature sequence without the secretion signal) followed by the yeast alcohol dehydrogenase terminator, after the cloning sites. Thus, cDNAs cloned into this vector that are fused in frame with amylase sequence will lead to the secretion of amylase from appropriately transfected yeast colonies.

3. Transformation and Detection

DNA from the library described in paragraph 2 above was chilled on ice to which was added electrocompetent DH10B bacteria (Life Technologies, 20 ml). The bacteria and vector mixture was then electroporated as recommended by the manufacturer. Subsequently, SOC media (Life Technologies, 1 ml) was added and the mixture was incubated at 37° C. for 30 minutes. The transformants were then plated onto 20 standard 150 mm LB plates containing ampicillin and incubated for 16 hours (37° C.). Positive colonies were scraped off the plates and the DNA was isolated from the bacterial pellet using standard protocols, e.g. CsCl-gradient. The purified DNA was then carried on to the yeast protocols below.

The yeast methods were divided into three categories: (1) Transformation of yeast with the plasmid/cDNA combined vector; (2) Detection and isolation of yeast clones secreting amylase; and (3) PCR amplification of the insert directly from the yeast colony and purification of the DNA for sequencing and further analysis.

The yeast strain used was HD56-5A (ATCC-90785). This strain has the following genotype: MAT alpha, ura3-52, leu2-3, leu2-112, his3-11, his3-15, MAL+, SUC+, GAL+. Preferably, yeast mutants can be employed that have deficient post-translational pathways. Such mutants may have translocation deficient alleles in sec71, sec72, sec62, with truncated sec71 being most preferred. Alternatively, antagonists (including antisense nucleotides and/or ligands) which interfere with the normal operation of these genes, other proteins implicated in this post translation pathway (e.g., SEC61p, SEC72p, SEC62p, SEC63p, TDJ1p or SSA1p-4p) or the complex formation of these proteins may also be preferably employed in combination with the amylase-expressing yeast.

Transformation was performed based on the protocol outlined by Gietz et al., *Nucl. Acid. Res.*, 20:1425 (1992). Transformed cells were then inoculated from agar into YEPD complex media broth (100 ml) and grown overnight at 30° C. The YEPD broth was prepared as described in Kaiser et al., *Methods in Yeast Genetics*, Cold Spring Harbor Press, Cold Spring Harbor, N.Y., p. 207 (1994). The overnight culture was then diluted to about $2 \times 10^6$ cells/ml (approx. $OD_{600}$ =0.1) into fresh YEPD broth (500 ml) and regrown to $1 \times 10^7$ cells/ml (approx. $OD_{600}$=0.4-0.5).

The cells were then harvested and prepared for transformation by transfer into GS3 rotor bottles in a Sorval GS3 rotor at 5,000 rpm for 5 minutes, the supernatant discarded, and then resuspended into sterile water, and centrifuged again in 50 ml falcon tubes at 3,500 rpm in a Beckman GS-6KR centrifuge. The supernatant was discarded and the cells were subsequently washed with LiAc/TE (10 ml, 10 mM Tris-HCl, 1 mM EDTA pH 7.5, 100 mM $Li_2OOCCH_3$), and resuspended into LiAc/TE (2.5 ml).

Transformation took place by mixing the prepared cells (100 μl) with freshly denatured single stranded salmon testes DNA (Lofstrand Labs, Gaithersburg, Md.) and transforming DNA (1 μg, vol.<10 μl) in microfuge tubes. The mixture was mixed briefly by vortexing, then 40% PEG/TE (600 μl, 40% polyethylene glycol-4000, 10 mM Tris-HCl, 1 mM EDTA, 100 mM $Li_2OOCCH_3$, pH 7.5) was added. This mixture was gently mixed and incubated at 30° C. while agitating for 30 minutes. The cells were then heat shocked at 42° C. for 15 minutes, and the reaction vessel centrifuged in a microfuge at 12,000 rpm for 5-10 seconds, decanted and resuspended into TE (500, μl, 10 mM Tris-HCl, 1 mM EDTA pH 7.5) followed by recentrifugation. The cells were then diluted into TE (1 ml) and aliquots (200 μl) were spread onto the selective media previously prepared in 150 mm growth plates (VWR).

Alternatively, instead of multiple small reactions, the transformation was performed using a single, large scale reaction, wherein reagent amounts were scaled up accordingly.

The selective media used was a synthetic complete dextrose agar lacking uracil (SCD-Ura) prepared as described in Kaiser et al., *Methods in Yeast Genetics*, Cold Spring Harbor Press, Cold Spring Harbor, N.Y., p. 208-210 (1994). Transformants were grown at 30° C. for 2-3 days.

The detection of colonies secreting amylase was performed by including red starch in the selective growth media. Starch was coupled to the red dye (Reactive Red-120, Sigma) as per the procedure described by Biely et al., *Anal. Biochem.*, 172:176-179 (1988). The coupled starch was incorporated into the SCD-Ura agar plates at a final concentration of 0.15% (w/v), and was buffered with potassium phosphate to a pH of 7.0 (50-100 mM final concentration).

The positive colonies were picked and streaked across fresh selective media (onto 150 mm plates) in order to obtain well isolated and identifiable single colonies. Well isolated single colonies positive for amylase secretion were detected by direct incorporation of red starch into buffered SCD-Ura agar. Positive colonies were determined by their ability to break down starch resulting in a clear halo around the positive colony visualized directly.

4. Isolation of DNA by PCR Amplification

When a positive colony was isolated, a portion of it was picked by a toothpick and diluted into sterile water (30 μl)

in a 96 well plate. At this time, the positive colonies were either frozen and stored for subsequent analysis or immediately amplified. An aliquot of cells (5 μl) was used as a template for the PCR reaction in a 25 μl volume containing: 0.5 μl Klentaq (Clontech, Palo Alto, Calif.); 4.0 μl 10 mM dNTP's (Perkin Elmer-Cetus); 2.5 μl Kentaq buffer (Clontech); 0.25 μl forward oligo 1; 0.25 μl reverse oligo 2; 12.5 μl distilled water. The sequence of the forward oligonucleotide 1 was:

5'-TGTAAAACGACGGCCAGTTAAATAGAC-CTGCAATTATTAATCT-3' (SEQ ID NO:1)

The sequence of reverse oligonucleotide 2 was:
5'-CAGGAAACAGCTATGACCACCTGCACAC-CTGCAAATCCATT-3' (SEQ ID NO:2)

PCR was then performed as follows:

| a. | | Denature | 92° C., | 5 minutes |
|---|---|---|---|---|
| b. | 3 cycles of: | Denature | 92° C., | 30 seconds |
| | | Anneal | 59° C., | 30 seconds |
| | | Extend | 72° C., | 60 seconds |
| c. | 3 cycles of: | Denature | 92° C., | 30 seconds |
| | | Anneal | 57° C., | 30 seconds |
| | | Extend | 72° C., | 60 seconds |
| d. | 25 cycles of: | Denature | 92° C., | 30 seconds |
| | | Anneal | 55° C., | 30 seconds |
| | | Extend | 72° C., | 60 seconds |
| e. | | Hold | 4° C. | |

The underlined regions of the oligonucleotides annealed to the ADH promoter region and the amylase region, respectively, and amplified a 307 bp region from vector pSST-AMY.0 when no insert was present. Typically, the first 18 nucleotides of the 5' end of these oligonucleotides contained annealing sites for the sequencing primers. Thus, the total product of the PCR reaction from an empty vector was 343 bp. However, signal sequence-fused cDNA resulted in considerably longer nucleotide sequences.

Following the PCR, an aliquot of the reaction (5 μl) was examined by agarose gel electrophoresis in a 1% agarose gel using a Tris-Borate-EDTA (TBE) buffering system as described by Sambrook et al., supra. Clones resulting in a single strong PCR product larger than 400 bp were further analyzed by DNA sequencing after purification with a 96 Qiaquick PCR clean-up column (Qiagen Inc., Chatsworth, Calif.).

Example 3

Isolation of cDNA Clones Using Signal Algorithm Analysis

Various polypeptide-encoding nucleic acid sequences were identified by applying a proprietary signal sequence finding algorithm developed by Genentech, Inc. (South San Francisco, Calif.) upon ESTs as well as clustered and assembled EST fragments from public (e.g., GENBANK database) and/or private (LIFESEQ® database, Incyte Pharmaceuticals, Inc., Palo Alto, Calif.) databases. The signal sequence algorithm computes a secretion signal score based on the character of the DNA nucleotides surrounding the first and optionally the second methionine codon(s) (ATG) at the 5'-end of the sequence or sequence fragment under consideration. The nucleotides following the first ATG must code for at least 35 unambiguous amino acids without any stop codons. If the first ATG has the required amino acids, the second is not examined. If neither meets the requirement, the candidate sequence is not scored. In order to determine whether the EST sequence contains an authentic signal sequence, the DNA and corresponding amino acid sequences surrounding the ATG codon are scored using a set of seven sensors (evaluation parameters) known to be associated with secretion signals. Use of this algorithm resulted in the identification of numerous polypeptide-encoding nucleic acid sequences.

Example 4

Isolation of cDNA clones Encoding Human PRO196

PRO196 was identified by screening the GENBANK database using the computer program BLAST (Altshul et al., Methods in Enzymology 266:460-480 (1996). The PRO196 sequence shows homology with known expressed sequence tag (EST) sequences T35448, T11442, and W77823. None of the known EST sequences have been identified as full length sequences, or described as ligands associated with the TIE receptors.

Following its identification, NL1 was cloned from a human fetal lung library prepared from mRNA purchased from Clontech, Inc. (Palo Alto, Calif. USA), catalog # 6528-1, following the manufacturer's instructions. The library was screened by hybridization with synthetic oligonucleotide probes:

(a)  5'-GCTGACGAACCAAGGCAACTACAAACTC-CTGGT-3' (SEQ ID NO:5);
(b)  5'-TGCGGCCGGACCAGTCCTCCATGGTCAC-CAGGAGTTTGTAG-3' (SEQ ID NO:6);
(c)  5'-GGTGGTGAACTGCTTGCCGTTGTGCCAT-GTAAA-3' (SEQ ID NO:7).

based on the ESTs found in the GENBANK database. cDNA sequences were sequenced in their entireties.

The nucleotide and amino acid sequences of PRO196 are shown in FIG. 1 (SEQ ID NO:3) and FIG. 2 (SEQ ID NO:4), respectively. PRO196 shows significant sequence identity with both the TIE1 and the TIE2 ligand.

A clone of PRO196 was deposited with the American Type Culture Collection, 10801 University Blvd., Manassas, Va. 20110-2209, USA (ATCC) on Sep. 18, 1997 under the terms of the Budapest Treaty, and has been assigned the deposit number 209280.

Example 5

Isolation of cDNA Clones Encoding Human PRO444

A cDNA sequence isolated in the amylase screen described in Example 2 above was designated DNA13121. Oligonucleotide probes were generated to this sequence and used to screen a human fetal lung library (LIB25) prepared as described in paragraph 1 of Example 2 above. The cloning vector was pRK5B (pRK5B is a precursor of pRK5D that does not contain the SfiI site; see, Holmes et al., *Science*, 253:1278-1280 (1991)), and the cDNA size cut was less than 2800 bp.

A full length clone was identified that contained a single open reading frame with an apparent translational initiation site at nucleotide positions 608-610 and ending at the stop codon found at nucleotide positions 959-961 (FIG. 3, SEQ ID NO:8). The predicted polypeptide precursor is 117 amino acids long, has a calculated molecular weight of approximately 12,692 daltons and an estimated pI of approximately 7.50. Analysis of the full-length PRO444 sequence shown in FIG. 4 (SEQ ID NO:9) evidences the presence of a signal peptide at amino acid 1 to about amino acid 16. An analysis of the Dayhoff database (version 35.45 SwissProt 35) evidenced homology between the PRO444 amino acid sequence and the following Dayhoff sequences: CEF44D12_8, P_R88452, YNE1_CAEEL, A47312, AF009957_1, and A06133_1.

Clone DNA26846-1397 was deposited with the ATCC on Oct. 27, 1998 and is assigned ATCC deposit no. 203406.

Example 6

Isolation of cDNA clones Encoding Human PRO183. PRO185, PRO9940. PRO2630 and PRO6309

DNA molecules encoding the PRO183, PRO185, PRO9940, PRO2630 and PRO6309 polypeptides shown in the accompanying figures were obtained through the GEN-BANK database.

Example 7

Isolation of cDNA Clones Encoding Human PRO210 and PRO217

A consensus DNA sequence was assembled using phrap as described in Example 1 above. In some cases, the consensus DNA sequence as extended using repeated cycles of blast and phrap to extend the consensus sequence as far as possible using the sources of EST sequences listed above. Based on this consensus sequence, oligonucleotides were synthesized: 1) to identify by PCR a cDNA library that contained the sequence of interest, and 2) for use as probes to isolate a clone of the full-length coding sequence. The library used to isolate DNA32279-1131 was fetal kidney.

cDNA clones were sequenced in their entirety. The entire nucleotide sequence of DNA32279-1131 is shown in FIG. 9 (SEQ ID NO:14) and amino acid sequence of PRO210 is shown in FIG. 10 (SEQ ID NO: 15). The entire nucleotide sequence of DNA33094-1131 is shown in FIG. 13 (SEQ ID NO:21) and amino acid sequence of PRO217 is shown in FIG. 14 (SEQ ID NO:22).

Example 8

Isolation of cDNA Clones Encoding Human PRO215

A consensus DNA sequence was assembled relative to the other identified EST sequences as described in Example 1 above, wherein the consensus sequence was designated herein as DNA28748. Based on the DNA28748 consensus sequence, oligonucleotides were synthesized to identify by PCR a cDNA library that contained the sequence of interest and for use as probes to isolate a clone of the full-length coding sequence for PRO215.

A pair of PCR primers (forward and reverse) were synthesized:
forward PCR primer 5'-GTGGCTGGCACACAAT-GAGATC-3' (SEQ ID NO:18)
reverse PCR primer 5'-CCAATGTGTGCAAGCGGT-TGTG-3' (SEQ ID NO:19)

Additionally, a synthetic oligonucleotide hybridization probe was constructed from the consensus DNA28748 sequence which had the following nucleotide sequence:

hybridization probe 5'-TCAAGAGCCTGGACCTCAGC-CACAATCTCATCTCTGACTTTGCCTGGAGC-3' (SEQ ID NO:20).

In order to screen several libraries for a source of a full-length clone, DNA from the libraries was screened by PCR amplification with the PCR primer pair identified above. A positive library was then used to isolate clones encoding the PRO215 gene using the probe oligonucleotide and one of the PCR primers.

RNA for construction of the cDNA libraries was isolated from human fetal lung tissue. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science,* 253:1278-1280 (1991)) in the unique XhoI and NotI sites.

DNA sequencing of the clones isolated as described above gave the full-length DNA sequence for PRO215 [herein designated as DNA32288-1132 and the derived protein sequence for PRO215.

The entire nucleotide sequence of DNA32288-1132 is shown in FIG. 11 (SEQ ID NO:16). Clone DNA32288-1132 contains a single open reading frame with an apparent translational initiation site at nucleotide positions 308-310 and ending at the stop codon at nucleotide positions 1591-1593 (FIG. 11, the initiation and stop codons are circled). The predicted polypeptide precursor is 428 amino acids long (FIG. 12). Clone DNA32288-1132 has been deposited with ATCC and is assigned ATCC deposit no. 209261.

Analysis of the amino acid sequence of the full-length PRO215 shows it has homology to member of the leucine rich repeat protein superfamily, including the leucine rich repeat protein and the SLIT protein.

Example 9

Isolation of cDNA Clones Encoding Human PRO242

An expressed sequence tag (EST) DNA database (LIFESEQ™, Incyte Pharmaceuticals, Palo Alto, Calif.) was searched and an EST was identified which showed homology to a chemokine. Based on this sequence, oligonucleotides were synthesized to identify by PCR a cDNA library that contained the sequence of interest and for use as probes to isolate a clone of the full-length coding sequence for PRO242.

A pair of PCR primer (forward and reverse) were synthesized:
forward PCR primer 5'-GGATCAGGCAGGAG-GAGTTTGGG-3' (SEQ ID NO:25)
reverse PCR primer 5'-GGATGGGTACAGACTTTCT-TGCC-3' (SEQ ID NO:26)

Additionaly, a synthetic oligonucleotide hybridization probe was constructed from the consensus DNA28709 sequence which had the following nucleotide sequence:
hybridization probe 5'-ATGATGGGCCTCTCCTTGGC-CTCTGCTGTGCTCCTGGCCTCCCTCCTGAG-3" (SEQ ID NO:27)

In order to screen several libraries for a source of a full-length clone, DNA from the libraries was screened by PCR amplification with the PCR primer pair identified above. A positive library was then used to isolate clones encoding the PRO242 gene using the probe oligonucleotide and one of the PCR primers.

RNA for construction of the cDNA libraries was isolated from human fetal lung tissue. A cDNA clone was sequenced in entirety. The entire nucleotide sequence of DNA33785-1143 is shown in FIG. 15 (SEQ ID NO:23). Clone DNA33785-1143 contains a single open reading frame with an apparent translational initiation site at nucleotide positions 333-335 and ending at the stop codon at nucleotide positions 615-617 (FIG. 16; SEQ ID NO:24). The predicted polypeptide precursor is 94 amino acids long (FIG. 16).

Based on a BLAST and FastA sequence alignment analysis (using the ALIGN computer program) of the fill-length sequence, PRO242 shows amino acid sequence identity to human macrophage inflammatory protein 1-alpha, rabbitt macrophage inflammatory protein 1-beta, human LD78 and rabbit immune activation gene 2.

Example 10

Isolation of cDNA Clones Encoding Human PRO288

A synthetic probe based on the sequence encoding the DcR 1 ECD [Sheridan et al., supra] and having the following sequence:
5'-CATAAAAGTTCCTGCACCATGACCA-GAGACACAGTGTGTCAGTGTAAAGA-3' (SEQ ID NO:30)
was used to screen a human fetal lung cDNA library. To prepare the cDNA library, mRNA was isolated from human fetal lung tissue using reagents and protocols from Invitrogen, San Diego, Calif. (Fast Track 2). This RNA was used to generate an oligo dT primed cDNA library in the vector pRK5D using reagents and protocols from Life Technologies, Gaithersburg, Md. (Super Script Plasmid System). In this procedure, the double stranded cDNA was sized to greater than 1000 bp and the SalI/NotI Tinkered cDNA was cloned into XhoI/NotI cleaved vector. pRK5D is a cloning vector that has an sp6 transcription initiation site followed by an SfiI restriction enzyme site preceding the XhoI/NotI cDNA cloning sites.

A full length clone was identified (DNA35663-1129) that contained a single open reading frame with an apparent translational initiation site at nucleotide positions 157-159 and ending at the stop codon found at nucleotide positions 1315-1317 (FIG. 17; SEQ ID NO:28). The clone is referred to as pRK5-35663 and is deposited as ATCC No. 209201.

The predicted polypeptide precursor is 386 amino acids long and has a calculated molecular weight of approximately 41.8 kDa. Sequence analysis indicated a N-terminal signal peptide (amino acids 1-55), followed by an ECD (amino acids 56-212), transmembrane domain (amino acids 213-232) and intracellular region (amino acids 233-386). (FIG. 18). The signal peptide cleavage site was confirmed by N-terminal protein sequencing of a PRO288 ECD immunoadhesin (not shown). This structure suggests that PRO288 is a type I transmembrane protein. PRO288 contains 3 potential N-linked glycosylation sites, at amino acid positions 127, 171 and 182. (FIG. 18)

TNF receptor family proteins are typically characterized by the presence of multiple (usually four) cysteine-rich domains in their extracellular regions—each cysteine-rich domain being approximately 45 amino acids long and containing approximately 6, regularly spaced, cysteine residues. Based on the crystal structure of the type 1 TNF receptor, the cysteines in each domain typically form three disulfide bonds in which usually cysteines 1 and 2, 3 and 5, and 4 and 6 are paired together. Like DR4, DR5, and DcR1, PRO288 contains two extracellular cysteine-rich pseudorepeats, whereas other identified mammalian TNFR family members contain three or more such domains [Smith et al., Cell, 76:959 (1994)].

Based on an alignment analysis of the PRO288 sequence shown in FIG. 18 (SEQ ID NO:29), PRO288 shows more sequence identity to the ECD of DR4, DR5, or DcR1 than to other apoptosis-linked receptors, such as TNFR1, Fas/Apo-1 or DR3. The predicted intracellular sequence of PRO288 also shows more homology to the corresponding region of DR4 or DR5 as compared to TNFR1, Fas or DR3. The intracellular region of PRO288 is about 50 residues shorter than the intracellular regions identified for DR4 or DR5. It is presently believed that PRO288 may contain an truncated death domain (amino acids 340-364), which corresponds to the carboxy-terminal portion of the death domain sequences of DR4 and DR5. Five out of six amino acids that are essential for signaling by TNFR1 [Tartaglia et al., sudra] and that are conserved or semi-conserved in DR4 and DR5, are absent in PRO288.

Example 11

Isolation of cDNA Clones Encoding Human PRO365

A consensus DNA sequence was assembled relative to other EST sequences using phrap as described in Example 1 above. This consensus sequence is herein designated DNA35613. Based on the DNA35613 consensus sequence, oligonucleotides were synthesized: 1) to identify by PCR a cDNA library that contained the sequence of interest, and 2) for use as probes to isolate a clone of the full-length coding sequence for PRO365.

Forward and reverse PCR primers were synthesized:
forward PCR primer 5'-GGCTGGCCTGCAGAGATC-3' (SEQ ID NO:33)
forward PCR primer 5'-AATGTGACCACTGGACTCCC-3' (SEQ ID NO:34)
forward PCR primer 5'-AGGCTTGGAACTCCCTTC-3' (SEQ ID NO:35)
reverse PCR primer 5'-AAGATTCTTGAGCGATTC-CAGCTG-3' (SEQ ID NO:36)

Additionally, a synthetic oligonucleotide hybridization probe was constructed from the consensus DNA35613 sequence which had the following nucleotide sequence
hybridization probe 5'-AATCCCTGCTCTTCATGGTGAC-CTATGACGACGGAAGCACAAGACTG-3' (SEQ ID NO:37)

In order to screen several libraries for a source of a full-length clone, DNA from the libraries was screened by PCR amplification with one of the PCR primer pairs identified above. A positive library was then used to isolate clones encoding the PRO365 gene using the probe oligonucleotide and one of the PCR primers.RNA for construction of the cDNA libraries was isolated from human fetal kidney tissue.

DNA sequencing of the clones isolated as described above gave the full-length DNA sequence for PRO365 [herein designated as DNA46777-1253] (SEQ ID NO:31) and the derived protein sequence for PRO365.

The entire nucleotide sequence of DNA46777-1253 is shown in FIG. 19 (SEQ ID NO:31). Clone DNA46777-1253 contains a single open reading frame with an apparent translational initiation site at nucleotide positions 15-17 and ending at the stop codon at nucleotide positions 720-722 (FIG. 19). The predicted polypeptide precursor is 235 amino acids long (FIG. 20). Important regions of the polypeptide sequence encoded by clone DNA46777-1253 have been identified and include the following: a signal peptide corresponding to amino acids 1-20 and multiple potential N-glycosylation sites. Clone DNA46777-1253 has been deposited with ATCC and is assigned ATCC deposit no. 209619.

Analysis of the amino acid sequence of the full-length PRO365 polypeptide suggests that portions of it possess significant homology to the human 2-19 protein, thereby indicating that PRO365 may be a novel human 2-19 protein homolog.

Example 12

Isolation of cDNA clones Encoding Human PRO1361

Use of the signal sequence algorithm described in Example 3 above allowed identification of an EST cluster sequence from the Incyte database, designated INCYTE CLUSTER SEQUENCE 10685. This EST cluster sequence was then compared to a variety of expressed sequence tag (EST) databases which included public EST databases (e.g., GENBANK database) and a proprietary EST DNA database (LIFESEQ database, Incyte Pharmaceuticals, Palo Alto, Calif.) to identify existing homologies. The homology search was performed using the computer program BLAST or BLAST2 (Altshul et al., Methods in Enzymology 266: 460-480 (1996)). Those comparisons resulting in a BLAST program score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA58839.

In light of an observed sequence homology between the DNA58839 sequence and an EST sequence contained within the Incyte EST clone no. 2967927, the Incyte EST clone no. 2967927 was purchased and the cDNA insert was obtained and sequenced. The sequence of this cDNA insert is shown in FIG. 21 and is herein designated as DNA60783-1611.

Clone DNA60783-1611 contains a single open reading frame with an apparent translational initiation site at nucleotide positions 142-144 and ending at the stop codon at nucleotide positions 1132-1134 (FIG. 21). The predicted polypeptide precursor is 330 amino acids long (FIG. 22). The full-length PRO1361 protein shown in FIG. 22 has an estimated molecular weight of about 36,840 daltons and a pI of about 4.84. Analysis of the full-length PRO1361 sequence shown in FIG. 22 (SEQ ID NO:39) evidences the presence of the following: a signal peptide from about amino acid 1 to about amino acid 23, a transmembrane domain from about amino acid 266 to about amino acid 284, a leucine zipper pattern sequence from about amino acid 155 to about amino acid 176 and potential N-glycosylation sites from about amino acid 46 to about amino acid 49, from about amino acid 64 to about amino acid 67, from about amino acid 166 to about amino acid 169 and from about amino acid 191 to about amino acid 194. Clone DNA60783-1611 has been deposited with ATCC on Aug. 18, 1998 and is assigned ATCC deposit no. 203130.

An analysis of the Dayhoff database (version 35.45 SwissProt 35), using a WU-BLAST2 sequence alignment analysis of the full-length sequence shown in FIG. 22 (SEQ ID NO:39), evidenced significant homology between the PRO1361 amino acid sequence and the following Dayhoff sequences: 150620, G64876, PMCMSG102B_2MSG104, HUMIGLVXY_1 and PH1370.

Example 13

Isolation of cDNA Clones Encoding Human PRO1308

A consensus DNA sequence was assembled relative to other EST sequences using phrap as described in Example 1 above. The consensus sequence was extended then using repeated cycles of BLAST and phrap to extend the consensus sequence as far as possible using the sources of EST sequences discussed above. The extended consensus sequence is designated herein as "DNA35726". Based on the DNA35726 consensus sequence, oligonucleotides were synthesized: 1) to identify by PCR a cDNA library that contained the sequence of interest, and 2) for use as probes to isolate a clone of the full-length coding sequence for PRO1308.

The following PCR primers (forward and reverse) were synthesized:
forward PCR primers 5'-TCCTGTGAGCACGTGGTGTG-3' (SEQ ID NO:42);
5'-GGGTGGGATAGACCTGCG-3' (SEQ ID NO:43);
5'-AAGGCCAAGAAGGCTGCC-3' (SEQ ID NO:44); and
5'-CCAGGCCTGCAGACCCAG-3' (SEQ ID NO:45).
reverse PCR primers 5'-CTTCCTCAGTCCTTCCAG-GATATC-3' (SEQ ID NO:46);
5'-AAGCTGGATATCCTCCGTGTTGTC-3' (SEQ ID NO:47);
5'-CCTGAAGAGGCATGACTGCTTTTCTCA-3' (SEQ ID NO:48); and
5'-GGGGATAAACCTATTAATTATTGCTAC-3' (SEQ ID NO:49).

Additionally, a synthetic oligonucleotide hybridization probe was constructed from the consensus DNA35726 sequence which had the following nucleotide sequence:

hybridization probe: 5'-AACGTCACCTACATCTCCTCGTGCCACATGCGCCAGGCCACCTG-3' (SEQ ID NO:50).

In order to screen several libraries for a source of a full-length clone, DNA from the libraries was screened by PCR amplification with the PCR primer pair identified above. A positive library was then used to isolate clones encoding the PRO1308 gene using the probe oligonucleotide and one of the PCR primers. RNA for construction of the cDNA libraries was isolated from a human SK-Lu-1 adenocarcinoma cell line.

DNA sequencing of the clones isolated as described above gave the full-length DNA sequence for PRO1308 (designated herein as DNA62306-1570 [FIG. 23, SEQ ID NO:40]; and the derived protein sequence for PRO1308.

The entire coding sequence of PRO1308 is shown in FIG. 23 (SEQ ID NO:40). Clone DNA62306-1570 contains a single open reading frame with an apparent translational initiation site at nucleotide positions 17-19 and an apparent stop codon at nucleotide positions 806-808. The predicted polypeptide precursor is 263 amino acids long. The full-length PRO1308 protein shown in FIG. 24 has an estimated molecular weight of about 27,663 daltons and a pI of about 6.77. Additional features include a signal peptide at about amino acids 1-20, potential N-glycosylation sites at about amino acids 73-76 and 215-218, and regions of homology with osteonectin domains at about amino acids 97-129 and 169-201.

An analysis of the Dayhoff database (version 35.45 SwissProt 35), using a WU-BLAST2 sequence alignment analysis of the full-length sequence shown in FIG. 24 (SEQ ID NO:41), revealed significant homology between the PRO1308 amino acid sequence and Dayhoff sequence S55369. Homology was also revealed between the PRO1308 amino acid sequence and the following Dayhoff sequences: FSA_HUMAN, P_R20063, CELT13C2_1, AGRI_RAT, p_W09406, G01639, SC1_RAT, S60062, S51362, and IOV7_CHICK.

Clone DNA62306-1570 has been deposited with ATCC and is assigned ATCC deposit no. 203254.

Example 14

Isolation of cDNA Clones Encoding Human PRO1183

Use of the signal sequence algorithm described in Example 3 above allowed identification of an EST cluster sequence from the Incyte database. This EST cluster sequence was then compared to a variety of expressed sequence tag (EST) databases which included public EST databases (e.g., GENBANK database) and a proprietary EST DNA database (LIFESEQ® database, Incyte Pharmaceuticals, Palo Alto, Calif.) to identify existing homologies. The homology search was performed using the computer program BLAST or BLAST2 (Altshul et al., Methods in Enzymology 266:460-480 (1996)). Those comparisons resulting in a BLAST program score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA56037.

In light of an observed sequence homology between the DNA56037 sequence and an EST sequence contained within the Incyte EST 1645856 (from a library constructed from prostate tumor tissue), the clone which includes EST 1645856 was purchased and the cDNA insert was obtained and sequenced. The sequence of this cDNA insert is shown in FIG. 25 and is herein designated as DNA62880-1513.

The full length clone shown in FIG. 25 contained a single open reading frame with an apparent translational initiation site at nucleotide positions 20-22 and ending at the stop codon found at nucleotide positions 1535-1537 (FIG. 25; SEQ ID NO:51). The predicted polypeptide precursor (FIG. 26, SEQ ID NO:52) is 505 amino acids long. The signal peptide is approximately at amino acids 1-23 of SEQ ID NO:52. PRO1183 has a calculated molecular weight of approximately 56,640 daltons and an estimated pI of approximately 6.1. Clone DNA62880-1513 was deposited with the ATCC on Aug. 4, 1998 and is assigned ATCC deposit no. 203097.

An analysis of the Dayhoff database (version 35.45 SwissProt 35), using a WU-BLAST2 sequence alignment analysis of the full-length sequence shown in FIG. 26 (SEQ ID NO:52), revealed sequence identity between the PRO1183 amino acid sequence and the following Dayhoff sequences: MTVO10_1, P_W41604, S54021, AOFB_HUMAN, NPAJ46831, S74689, GEN13608, ACHC_ACHFU, AB011173_1 and PUO_MICRU. It is believed that administration of PRO1183 or regulators thereof may treat certain oxidase disorders such as variegate porphyria.

Example 15

Isolation of cDNA Clones Encoding Human PRO1272

Use of the signal sequence algorithm described in Example 3 above allowed identification of an EST cluster sequence from the Incyte database. This EST cluster sequence was then compared to a variety of expressed sequence tag (EST) databases which included public EST databases (e.g., GENBANK database) and a proprietary EST DNA database (LIFESEQ® database, Incyte Pharmaceuticals, Palo Alto, Calif.) to identify existing homologies. The homology search was performed using the computer program BLAST or BLAST2 (Altshul et al., Methods in Enzymology 266:460-480 (1996)). Those comparisons resulting in a BLAST program score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA58753.

In light of an observed sequence homology between the DNA58753 sequence and an EST sequence contained witin the EST clone 3049165, the Incyte clone (from a lung library) including EST 3049165 was purchased and the cDNA insert was obtained and sequenced. The sequence of this cDNA insert is shown in FIG. 27 and is herein designated as DNA64896-1539.

The full length clone shown in FIG. 27 contained a single open reading frame with an apparent translational initiation site at nucleotide positions 58-60 and ending at the stop codon found at nucleotide positions 556-558 (FIG. 27; SEQ ID NO:53). The predicted polypeptide precursor (FIG. 28, SEQ ID NO:54) is 166 amino acids long. The signal peptide is at about amino acids 1-23 of SEQ ID NO:54. PRO1272 has a calculated molecular weight of approximately 19,171 daltons and an estimated pI of approximately 8.26. Clone DNA64896-1539 was deposited with the ATCC on Sep. 9, 1998 and is assigned ATCC deposit no. 203238.

An analysis of the Dayhoff database (version 35.45 SwissProt 35), using a WU-BLAST2 sequence alignment analysis of the full-length sequence shown in FIG. 28 (SEQ ID NO:54), revealed sequence identity between the PRO1272 amino acid sequence and the following Dayhoff sequences (information from database incorporated herein): AF025474_1, D69100, AE000757_10, H69466, CELC5OE3_12, XLRANBP1_1, YD67_SCHPO, B69459, H36856, and FRU40755_1.

Example 16

Isolation of cDNA clones Encoding Human PRO1419

Use of the signal sequence algorithm described in Example 3 above allowed identification of an EST cluster sequence from the Incyte database. This EST cluster sequence was then compared to a variety of expressed sequence tag (EST) databases which included public EST databases (e.g., GENBANK database) and a proprietary EST DNA database (LIFESEQ® database, Incyte Pharmaceuticals, Palo Alto, Calif.) to identify existing homologies. One or more of the ESTs was derived from a diseased tonsil tissue library. The homology search was performed using the computer program BLAST or BLAST2 (Altshul et al., Methods in Enzymology 266:460-480 (1996)). Those comparisons resulting in a BLAST program score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA59761.

In light of an observed sequence homology between the DNA59761 sequence and an EST sequence contained within the Incyte EST 3815008, the clone including this EST was purchased and the cDNA insert was obtained and sequenced. The sequence of this cDNA insert is shown in FIG. 29 and is herein designated as DNA71290-1630.

The full length clone shown in FIG. 29 contained a single open reading frame with an apparent translational initiation site at nucleotide positions 86-88 and ending at the stop codon found at nucleotide positions 341-343 (FIG. 29; SEQ ID NO:55). The predicted polypeptide precursor (FIG. 30, SEQ ID NO:56) is 85 amino acids long with the signal peptide at about amino acids 1-17 of SEQ ID NO:56. PRO1419 has a calculated molecular weight of approximately 9,700 daltons and an estimated pI of approximately 9.55. Clone DNA71290-1630 was deposited with the ATCC on Sep. 22, 1998 and is assigned ATCC deposit no. 203275.

An analysis of the Dayhoff database (version 35.45 SwissProt 35), using a WU-BLAST2 sequence alignment analysis of the full-length sequence shown in FIG. 30 (SEQ ID NO:56), revealed sequence identity between the PRO1419 amino acid sequence and the following Dayhoff sequences (data incorporated herein): S07975 (B3-hordein), C48232, HOR7 HORVU, GEN11764, S14970, AF0203121, STAJ3220_1, CER07E3_1, CEY37A1B_4, and ATAC00423810.

Example 17

Isolation of cDNA clones Encoding Human PRO4999

A consensus DNA sequence was assembled relative to other EST sequences using phrap as described in Example 1 above. This consensus sequence is herein designated DNA86634. Based on the DNA86634 consensus sequence, oligonucleotides were synthesized: 1) to identify by PCR a cDNA library that contained the sequence of interest, and 2) for use as probes to isolate a clone of the full-length coding sequence for PRO4999.

PCR primers (forward and reverse) were synthesized:
forward PCR primer 5'-CCACTTGCCATGAACATGC-CAC-3' (SEQ ID NO:59)
reverse PCR primer 5'-CCTCTTGACAGACATAGC-GAGCCAC-3' (SEQ ID NO:60)

Additionally, a synthetic oligonucleotide hybridization probe was constructed from the consensus DNA86634 sequence which had the following nucleotide sequence
hybridization probe 5'-CACTCTTGTCTGTGGGAACCA-CACATCTTGCCACAACTGTGGC-3' (SEQ ID NO :61)

RNA for construction of the cDNA libraries was isolated from human testis tissue. DNA sequencing of the clones isolated as described above gave the full-length DNA sequence for a full-length PRO4999 polypeptide (designated herein as DNA96031-2664 [FIG. 31, SEQ ID NO:57]) and the derived protein sequence for that PRO4999 polypeptide.

The full length clone identified above contained a single open reading frame with an apparent translational initiation site at nucleotide positions 4244 and a stop signal at nucleotide positions 2283-2285 (FIG. 31, SEQ ID NO:57). The predicted polypeptide precursor is 747 amino acids long, has a calculated molecular weight of approximately 82,710 daltons and an estimated pI of approximately 6.36. Analysis of the full-length PRO4999 sequence shown in FIG. 32 (SEQ ID NO:58) evidences the presence of a variety of important polypeptide domains as shown in FIG. 32, wherein the locations given for those important polypeptide domains are approximate as described above. Clone DNA96031-2664 has been deposited with ATCC on Jun. 15, 1999 and is assigned ATCC deposit no. 237-PTA.

An analysis of the Dayhoff database (version 35.45 SwissProt 35), using the ALIGN-2 sequence alignment analysis of the full-length sequence shown in FIG. 32 (SEQ ID NO:58), evidenced sequence identity between the PRO4999 amino acid sequence and the following Dayhoff sequences: UROM_HUMAN; FBN1_HUMAN; GGU88872_1; S52111; GEN12408; P_R79478; P_W48756; P_R53087; P_R14584; and S78549.

Example 18

Isolation of cDNA Clones Encoding Human PRO7170

Use of the signal sequence algorithm described in Example 3 above allowed identification of an EST cluster sequence from the LIFESEQ® database, Incyte Pharmaceuticals, Palo Alto, designated herein as CLU57836. This EST cluster sequence was then compared to a variety of expressed sequence tag (EST) databases which included public EST databases (e.g., GENBANK database) and a proprietary EST DNA database (LIFESEQ® database, Incyte Pharmaceuticals, Palo Alto, Calif.) to identify existing homologies. The homology search was performed using the computer program BLAST or BLAST2 (Altshul et al., Methods in Enzymology 266:460-480 (1996)). Those comparisons resulting in a BLAST program score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA58756.

In light of an observed sequence homology between the DNA58756 sequence and an EST sequence encompassed within clone no. 2251462 from the LIFESEQ® database, Incyte Pharmaceuticals, Palo Alto, Calif. clone no. 2251462 was purchased and the cDNA insert was obtained and sequenced. It was found herein that that cDNA insert encoded a full-length protein. The sequence of this cDNA insert is shown in FIG. 33 and is herein designated as DNA108722-2743.

Clone DNA108722-2743 contains a single open reading frame with an apparent translational initiation site at nucleotide positions 60-62 and ending at the stop codon at nucleotide positions 1506-1508 (FIG. 33). The predicted polypeptide precursor is 482 amino acids long (FIG. 34). The full-length PRO7170 protein shown in FIG. 34 has an estimated molecular weight of about 49,060 daltons and a pi of about 4.74. Analysis of the full-length PRO7170 sequence shown in FIG. 34 (SEQ ID NO:63) evidences the presence of a variety of important polypeptide domains as shown in FIG. 34, wherein the locations given for those important polypeptide domains are approximate as described above. Clone DNA108722-2743 has been deposited with ATCC on Aug. 17, 1999 and is assigned ATCC Deposit No. 552-PTA.

An analysis of the Dayhoff database (version 35.45 SwissProt 35), using the ALIGN-2 sequence alignment analysis of the full-length sequence shown in FIG. 34 (SEQ ID NO:63), evidenced sequence identity between the PRO7170 amino acid sequence and the following Dayhoff sequences: P_Y12291,147141, D88733__1, DMC56G7__1, P__11606, HWP1CANAL, HSMUC5BEX__1, HSU785501, HSU70136__1, and SGS3_DROME.

Example 19

Isolation of cDNA Clones Encoding Human PRO248

A consensus DNA sequence was assembled relative to the other identified EST sequences as described in Example 1 above, wherein the consensus sequence is designated herein as DNA33481. Based on the DNA33481 consensus sequence, oligonucleotides were synthesized to identify by PCR a cDNA library that contained the sequence of interest and for use as probes to isolate a clone of the full-length coding sequence for PRO248. Specifically, the following primers were used:
Forward primer 1 (SEQ ID NO:66): 5'-GTCTGACAGC-CACTCCAGAG-3'

```
Hybridization probe (SEQ ID NO:67):
5'-TCTCCAATTTCTGGGCTTAGATAAGGCGCCTTCACCCCAGAAGTTCC-3'
```

Reverse primer 1 (SEQ ID NO:68): 5'-GTCCCAGGTTAT-AGTAAGAATTGG-3'
Forward primer 2 (SEQ ID NO:69): 5'-GTGTTGCGGT-CAGTCCCATG-3'
Forward primer 3 (SEQ ID NO:70): 5'-GCTGTCTC-CCATTTCCATGC-3'
Reverse primer 2 (SEO ID NO:71): 5'-CGACTACCAT-GTCTTCATAATGTC-3'

In order to screen several libraries for a source of a full-length clone, DNA from the libraries was screened by PCR amplification with the PCR primer pair identified above. A positive library was then used to isolate clones encoding the PRO248 gene using the probe oligonucleotide and one of the PCR primers. RNA for construction of the cDNA libraries was isolated from human fetal kidney tissue.

DNA sequencing of the clones isolated as described above gave the full-length DNA sequence for PRO248 [herein designated as DNA35674-1142] and the derived protein sequence for PRO248.

The entire nucleotide sequence of DNA35674-1142 is shown in FIG. 35 (SEQ ID NO:64). Clone DNA35674-1142 contains a single open reading frame with an apparent translational initiation site at nucleotide positions 66-68 and ending at the stop codon at nucleotide positions 1217-1219 (FIG. 35; SEQ ID NO:64). The predicted polypeptide precursor is 364 amino acids long (FIG. 36). Clone DNA35674-1142 has been deposited on Oct. 28, 1997 with ATCC and is assigned ATCC deposit no. 209416.

Analysis of the amino acid sequence of the full-length PRO248 suggests that it has certain amino acid sequence identity with growth differentiation factor 3 from human and mouse.

Example 20

Isolation of cDNA Clones Encoding Human PRO353

A consensus DNA sequence was assembled relative to other EST sequences using phrap as described in Example 1 above. This consensus sequences is herein designated DNA36363. The consensus DNA sequence was extended using repeated cycles of BLAST and phrap to extend the consensus sequence as far as possible using the sources of EST sequences discussed above. Based on the DNA36363 consensus sequence, oligonucleotides were synthesized: 1) to identify by PCR a cDNA library that contained the sequence of interest, and 2) for use as probes to isolate a clone of the full-length coding sequence for PRO353.

Based on the DNA36363 consensus sequence, forward and reverse PCR primers were synthesized as follows:
forward PCR primer 5'-TACAGGCCCAGTCAGGAC-CAGGGG-3' (SEQ ID NO:74)
reverse PCR primer 5'-CTGAAGAAGTAGAGGC-CGGGCACG-3' (SEQ ID NO:75).

Additionally, a synthetic oligonucleotide hybridization probe was constructed from the DNA36363 consensus sequence which had the following nucleotide sequence:
hybridization probe 5'-CCCGGTGCTTGCGCTGCTGT-GACCCCGGTACCTCCATGTACCCGG-3' (SEQ ID NO:76)

In order to screen several libraries for a source of a full-length clone, DNA from the libraries was screened by PCR amplification with one of the PCR primer pairs identified above. A positive library was then used to isolate clones encoding the PRO353 gene using the probe oligonucleotide and one of the PCR primers. RNA for construction of the cDNA libraries was isolated from human fetal kidney tissue.

DNA sequencing of the clones isolated as described above gave the full-length DNA sequence for PRO353 [herein designated as DNA41234-1242] (SEQ ID NO:72) and the derived protein sequence for PRO353.

The entire nucleotide sequence of DNA41234-1242 is shown in FIG. 37 (SEQ ID NO:72). Clone DNA41234-1242 contains a single open reading frame with an apparent translational initiation site at nucleotide positions 305-307 and ending at the stop codon at nucleotide positions 1148-1150 (FIG. 37). The predicted polypeptide precursor is 281 amino acids long (FIG. 38). Important regions of the amino acid sequence encoded by PRO353 include the signal peptide, corresponding to amino acids 1-26, the start of the mature protein at amino acid position 27, a potential N-glycosylation site, corresponding to amino acids 93-98 and a region which has homology to a 30 kd adipocyte complement-related protein precursor, corresponding to amino acids 99-281. Clone DNA41234-1242 has been deposited with the ATCC and is assigned ATCC deposit no. 209618.

Analysis of the amino acid sequence of the full-length PRO353 polypeptides suggests that portions of them possess significant homology to portions of human and murine complement proteins, thereby indicating that PRO353 may be a novel complement protein.

Example 21

Isolation of cDNA Clones Encoding Human PRO1318

The cDNA molecule corresponding to DNA73838-1674 as shown in FIG. 39 (SEQ ID NO:77) was obtained from Curagen, Inc.

Example 22

Isolation of cDNA clones Encoding Human PRO1600

A consensus DNA sequence was assembled relative to other EST sequences using phrap as described in Example 1 above. This consensus sequences is herein designated DNA75516. The consensus DNA sequence was extended using repeated cycles of BLAST and phrap to extend the consensus sequence as far as possible using the sources of EST sequences discussed above. Based on the DNA75516 consensus sequence, oligonucleotides were synthesized: 1) to identify by PCR a cDNA library that contained the sequence of interest, and 2) for use as probes to isolate a clone of the full-length coding sequence for PRO1600.

Based on the DNA75516 consensus sequence, oligonucleotide probes were synthesized as follows:

5'-AGACATGGCTCAGTCACTGG-3' (SEQ ID NO:81)
5'-GACCCCTAAAGGGCCATAG-3' (SEQ ID NO:82).

In order to screen several libraries for a source of a full-length clone, DNA from the libraries was screened with the probes identified above. RNA for construction of the cDNA libraries was isolated from human fetal heart tissue.

DNA sequencing of the clones isolated as described above gave the full-length DNA sequence for PRO1600 [herein designated as DNA77503-1686] (SEQ ID NO:79) and the derived protein sequence for PRO1600.

The entire nucleotide sequence of DNA77503-1686 is shown in FIG. 41 (SEQ ID NO:79). Clone DNA77503-1686 contains a single open reading frame with an apparent translational initiation site at nucleotide positions 6-8 and ending at the stop codon at nucleotide positions 408-410 (FIG. 41). The predicted polypeptide precursor is 134 amino acids long (FIG. 42). Important regions of the amino acid sequence of PRO1600 are shown in FIG. 42. Clone DNA77503-1686 has been deposited with the ATCC and is assigned ATCC deposit no. 203362.

Example 23

Isolation of cDNA Clones Encoding Human PRO533

The EST sequence accession number AF007268, a murine fibroblast growth factor (FGF-15) was used to search various public EST databases (e.g., GENBANK database, DAYHOFF database, etc.). The search was performed using the computer program BLAST or BLAST2 [Altschul et al., Methods in Enzymology, 266:460-480 (1996)] as a comparison of the ECD protein sequences to a 6 frame translation of the EST sequences. The search resulted in a hit with EST AA220994 from the GENBANK database, which has been identified as stratagene NT2 neuronal precursor 937230.

Based on the GENBANK database EST AA220994 sequence, oligonucleotides were synthesized: 1) to identify by PCR a cDNA library that contained the sequence of interest, and 2) for use as probes to isolate a clone of the full-length coding sequence. Forward and reverse PCR primers may range from 20 to 30 nucleotides (typically about 24), and are designed to give a PCR product of 100-1000 bp in length. The probe sequences are typically 40-55 bp (typically about 50) in length. In order to screen several libraries for a source of a full-length clone, DNA from the libraries was screened by PCR amplification, as per Ausubel et al., Current Protocols in Molecular Biology, with the PCR primer pair. A positive library was then used to isolate clones encoding the gene of interest using the probe oligonucleotide and one of the PCR primers.

In order to screen several libraries for a source of a full-length clone, DNA from the libraries was screened by PCR amplification with the PCR primer pair identified below. A positive library was then used to isolate clones encoding the PRO533 gene using the probe oligonucleotide and one of the PCR primers.

RNA for construction of the cDNA libraries was isolated from human fetal retina. The cDNA libraries used to isolated the cDNA clones were constructed by standard methods using commercially available reagents (e.g., Invitrogen, San Diego, Calif.; Clontech, etc.) The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or PRKD; pRK5B is a precursor of pRK5D that does not contain the SfiI site; see, Holmes et al., *Science,* 253:1278-1280 (1991)) in the unique XhoI and NotI sites.

A cDNA clone was sequenced in its entirety. The full length nucleotide sequence of PRO533 is shown in FIG. 45 (SEQ ID NO:85). Clone DNA49435-1219 contains a single open reading frame with an apparent translational initiation site at nucleotide positions 459-461 (FIG. 45; SEQ ID NO:85). The predicted polypeptide precursor is 216 amino acids long. Clone DNA47412-1219 has been deposited with ATCC and is assigned ATCC deposit no. ATCC 209480.

Based on a BLAST-2 and FastA sequence alignment analysis of the full-length sequence, PRO533 shows amino acid sequence identity to fibroblast growth factor (53%). The oligonucleotide sequences used in the above procedure were the following:

FGF15. forward: 5'-ATCCGCCCAGATGGCTACAATGT-GTA-3' (SEQ ID NO:87);

FGF15. probe: 5'-GCCTCCCGGTCTCCCTGAGCAGT-GCCAAACAGCGGCAGTGTA-3' (SEQ ID NO:88);

FGF15. reverse: 5'-CCAGTCCGGTGACAAGCCCAAA-3' (SEQ ID NO:89).

Example 24

Isolation of cDNA Clones Encoding Human PRO301

A consensus DNA sequence designated herein as DNA35936 was assembled using phrap as described in Example 1 above. Based on this consensus sequence, oligonucleotides were synthesized: 1) to identify by PCR a cDNA library that contained the sequence of interest, and 2) for use as probes to isolate a clone of the full-length coding sequence.

In order to screen several libraries for a source of a full-length clone, DNA from the libraries was screened by PCR amplification with the PCR primer pair identified below. A positive library was then used to isolate clones encoding the PRO301 gene using the probe oligonucleotide and one of the PCR primers.

RNA for construction of the cDNA libraries was isolated from human fetal kidney.

A cDNA clone was sequenced in its entirety. The full length nucleotide sequence of native sequence PRO301 is shown in FIG. 47 (SEQ ID NO:90). Clone DNA40628-1216 contains a single open reading frame with an apparent translational initiation site at nucleotide positions 52-54 (FIG. 47; SEQ ID NO:90). The predicted polypeptide precursor is 299 amino acids long with a predicted molecular weight of 32,583 daltons and pI of 8.29. Clone DNA40628-1216 has been deposited with ATCC and is assigned ATCC deposit No. ATCC 209432.

Based on a BLAST and FastA sequence alignment analysis of the full-length sequence, PRO301 shows amino acid sequence identity to A33 antigen precursor (30%) and coxsackie and adenovirus receptor protein (29%).

The oligonucleotide sequences used in the above procedure were the following:
OLI2162 (35936.f1) 5'-TCGCGGAGCTGTGTTCT-GTTTCCC-3' (SEQ ID NO:92)
OLI2163 (35936.p1) 5'-TGATCGCGATGGGGACAAAG-GCGCAAGCTCGAGAGGAAACTGTTGTGCCT-3' (SEQ ID NO:93)
OLI2164 (35936.f2) 5'-ACACCTGGTTCAAAGATGGG-3' (SEQ ID NO:94)
OLI2165 (35936.r1) 5'-TAGGAAGAGTTGCTGAAG-GCACGG-3' (SEQ ID NO:95)
OLI2166 (35936.f3) 5'-TTGCCTTACTCAGGTGCTAC-3' (SEQ ID NO:96)
OLI2167 (35936. r2) 5'-ACTCAGCAGTGGTAGGAAAG-3' (SEQ ID NO:97)

Example 25

Isolation of cDNA Clones Encoding Human PRO187

A proprietary expressed sequence tag (EST) DNA database (LIFESEQ™, Incyte Pharmaceuticals, Palo Alto, Calif.) was searched and an EST (#843193) was identified which showed homology to fibroblast growth factor (FGF-8) also known as androgen-induced growth factor. mRNA was isolated from human fetal lung tissue using reagents and protocols from Invitrogen, San Diego, Calif. (Fast Track 2). The cDNA libraries used to isolate the cDNA clones were constructed by standard methods using commercially available reagents (e.g., Invitrogen, San Diego, Calif., Life Technologies, Gaithersburg, Md.). The cDNA was primed with oligo dT containing a NotI site, linked with blunt to SalI hemikinased adaptors, cleaved with NotI, sized appropriately by gel electrophoresis, and cloned in a defined orientation into the cloning vector pRK5D using reagents and protocols from Life Technologies, Gaithersburg, Md. (Super Script Plasmid System). The double-stranded cDNA was sized to greater than 1000 bp and the SalI/NotI linkered cDNA was cloned into XhoI/NotI cleaved vector. pRK5D is a cloning vector that has an sp6 transcription initiation site followed by an SfiI restriction enzyme site preceding the XhoI/NotI cDNA cloning sites.

Several libraries from various tissue sources were screened by PCR amplification with the following oligonucleotide probes:

```
IN843193.f(OLI315) (SEQ ID NO:100)
5'-CAGTACGTGAGGGACCAGGGCGCCATGA-3'

IN843193.r(OLI 317) (SEQ ID NO:101)
5'-CCGGTGACCTGCACGTGCTTGCCA-3'
```

A positive library was then used to isolate clones encoding the PRO187 gene using one of the above oligonucleotides and the following oligonucleotide probe:

```
IN843193.p (OLI 316) (SEO ID NO:102)
5'-GCGGATCTGCCGCCTGCTCANCTGGTCGGTCATGGCGCCCT-3'
```

A cDNA clone was sequenced in entirety. The entire nucleotide sequence of PRO187 (DNA27864-1155) is shown in FIG. 49 (SEQ ID NO:98). Clone DNA27864-1155 contains a single open reading frame with an apparent translational initiation site at nucleotide position 1 (FIG. 49; SEQ ID NO:98). The predicted polypeptide precursor is 205 amino acids long. Clone DNA27864-1155 has been deposited with the ATCC (designation: DNA27864-1155) and is assigned ATCC deposit no. ATCC 209375.

Based on a BLAST and FastA sequence alignment analysis (using the ALIGN computer program) of the full-length sequence, the PRO187 polypeptide shows 74% amino acid sequence identity (Blast score 310) to human fibroblast growth factor-8 (androgen-induced growth factor).

Example 26

Isolation of cDNA clones Encoding Human PRO337

A cDNA sequence identified in the amylase screen described in Example 2 above is herein designated DNA42301. The DNA42301 sequence was then compared to other EST sequences using phrap as described in Example 1 above and a consensus sequence designated herein as DNA28761 was identified. Based on this consensus sequence, oligonucleotides were synthesized: 1) to identify by PCR a cDNA library that contained the sequence of interest, and 2) for use as probes to isolate a clone of the full-length coding sequence. In order to screen several libraries for a source of a full-length clone, DNA from the libraries was screened by PCR amplification with the PCR primer pair identified above. A positive library was then used to isolate clones encoding the PRO337 gene using the probe oligonucleotide and one of the PCR primers. RNA for construction of the cDNA libraries was isolated from human fetal brain.

A cDNA clone was sequenced in its entirety. The full length nucleotide sequence of DNA43316-1237 is shown in FIG. 51 (SEQ ID NO:103). Clone DNA43316-1237 contains a single open reading frame with an apparent translational initiation site at nucleotide positions 134-136 (FIG. 51; SEQ ID NO:103). The predicted polypeptide precursor is 344 amino acids long. Clone DNA43316-1237 has been deposited with ATCC and is assigned ATCC deposit no. 209487 Based on a BLAST-2 and FastA sequence alignment analysis of the full-length sequence, PRO337 shows amino acid sequence identity to rat neurotrimin (97%).

Example 27

Isolation of cDNA clones Encoding Human PRO1411

Use of the signal sequence algorithm described in Example 3 above allowed identification of an EST cluster sequence from an Incyte database. This EST cluster sequence was then compared to a variety of expressed sequence tag (EST) databases which included public EST databases (e.g., GENBANK database) and a proprietary EST DNA database (LIFESEQ® database, Incyte Pharmaceuticals, Palo Alto, Calif.) to identify existing homologies. One or more of the ESTs were derived from a thryroid tissue library. The homology search was performed using the computer program BLAST or BLAST2 (Altshul et al., Methods in Enzymology 266:460-480 (1996)). Those comparisons resulting in a BLAST program score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA56013.

In light of the sequence homology between the DNA56013 sequence and an EST sequence contained within the Incyte EST 1444225, the clone including this EST was purchased and the cDNA insert was obtained and sequenced. The sequence of this cDNA insert is shown in FIG. 53 and is herein designated as DNA59212-1627.

The full length clone shown in FIG. 53 contained a single open reading frame with an apparent translational initiation site at nucleotide positions 184-186 and ending at the stop codon found at nucleotide positions 1504-1506 (FIG. 53; SEQ ID NO:105). The predicted polypeptide precursor (FIG. 54, SEQ ID NO: 106) is 440 amino acids long. The signal peptide is at about amino acids 1-21, and the cell attachment site is at about amino acids 301-303 of SEQ ID NO:106. PRO1411 has a calculated molecular weight of approximately 42,208 daltons and an estimated pI of approximately 6.36. Clone DNA59212-1627 was deposited with the ATCC on Sep. 9, 1998 and is assigned ATCC deposit no. 203245.

An analysis of the Dayhoff database (version 35.45 SwissProt 35), using a WU-BLAST2 sequence alignment analysis of the full-length sequence shown in FIG. 54 (SEQ ID NO:106), revealed sequence identity between the PRO1411 amino acid sequence and the following Dayhoff sequences (data from database incorporated herein): MTV023_19, P_R05307, P_W26348, P_P82962, AF000949_1, EBN1_EBV, P_R95107, GRP2_PHAVU, P_R81318, and S74439_1.

Example 28

Isolation of cDNA Clones Encoding Human PRO4356

A consensus DNA sequence was assembled relative to other EST sequences using phrap asdescribed in Example 1 above. This consensus sequence is designated herein "DNA80200". Based upon an observed homology between the DNA80200 consensus sequence and an EST sequence contained within Merck EST clone 248287, Merck EST clone 248287 was purchased and its insert obtained and sequenced, thereby providing DNA86576-2595.

The entire coding sequence of PRO4356 is shown in FIG. 55 (SEQ ID NO:107). Clone DNA86576-2595 contains a single open reading frame with an apparent translational initiation site at nucleotide positions 55-57, and an apparent stop codon at nucleotide positions 808-810. The predicted polypeptide precursor is 251 amino acids long. Clone DNA86576-2595 has been deposited with ATCC and is assigned ATCC deposit no. 203868. The full-length PRO4356 protein shown in FIG. 56 has an estimated molecular weight of about 26,935 daltons and a pI of about 7.42.

An analysis of the Dayhoff database (version 35.45 SwissProt 35), using a WU-BLAST2 sequence alignment analysis of the full-length sequence shown in FIG. 56 (SEQ ID NO:108), revealed homology between the PRO4356 amino acid sequence and the following Dayhoff sequences incorporated herein: RNMAGPIAN_1, UPAR_BOVIN, S42152, AF007789_1, UPAR_RAT, UPAR_MOUSE, P_W31165, P_W31168, P_R44423 and P_W26359.

Example 29

Isolation of cDNA Clones Encoding Human PRO246

A consensus DNA sequence was assembled relative to other EST sequences using phrap as described in Example 1 above. This consensus sequence is herein designated DNA30955. Based on the DNA30955 consensus sequence, oligonucleotides were synthesized: 1) to identify by PCR a cDNA library that contained the sequence of interest, and 2) for use as probes to isolate a clone of the full-length coding sequence for PRO246.

A pair of PCR primers (forward and reverse) were synthesized:
forward PCR primer 5'-AGGGTCTCCAGGAGAAA-GACTC-3' (SEQ ID NO:111)
reverse PCR primer 5'-ATTGTGGGCCTTGCAGACATA-GAC-3' (SEQ ID NO:112)

Additionally, a synthetic oligonucleotide hybridization probe was constructed from the consensus DNA30955 sequence which had the following nucleotide sequence
hybridization probe 5'-GGCCACAGCATCAAAACCTTA-GAACTCAATGTACTGGTTCCTCCAGCTCC-3' (SEQ ID NO:113)

In order to screen several libraries for a source of a full-length clone, DNA from the libraries was screened by PCR amplification with the PCR primer pair identified above. A positive library was then used to isolate clones encoding the PRO246 gene using the probe oligonucleotide and one of the PCR primers.

RNA for construction of the cDNA libraries was isolated from human fetal liver tissue. DNA sequencing of the clones isolated as described above gave the full-length DNA sequence for PRO246 [herein designated as DNA35639-1172] (SEQ ID NO:109) and the derived protein sequence for PRO246.

The entire nucleotide sequence of DNA35639-1172 is shown in FIG. 57 (SEQ ID NO:109). Clone DNA35639-1172 contains a single open reading frame with an apparent translational initiation site at nucleotide positions 126-128 and ending at the stop codon at nucleotide positions 1296-1298 (FIG. 57). The predicted polypeptide precursor is 390 amino acids long (FIG. 58). Clone DNA35639-1172 has been deposited with ATCC and is assigned ATCC deposit no. ATCC 209396.

Analysis of the amino acid sequence of the full-length PRO246 polypeptide suggests that it possess significant homology to the human cell surface protein HCAR, thereby indicating that PRO246 may be a novel cell surface virus receptor.

Example 30

Isolation of cDNA Clones Encoding Human PRO265

A consensus DNA sequence was assembled relative to other EST sequences as described in Example 1 above using phrap. This consensus sequence is herein designated DNA33679. Based on the DNA33679 consensus sequence, oligonucleotides were synthesized: 1) to identify by PCR a cDNA library that contained the sequence of interest, and 2) for use as probes to isolate a clone of the full-length coding sequence for PRO265.

PCR primers (two forward and one reverse) were synthesized:
forward PCR primer A: 5'-CGGTCTACCTGTATG-GCAACC-3' (SEQ ID NO:116);
forward PCR primer B: 5'-GCAGGACAACCAGATAAAC-CAC-3 (SEQ ID NO:117);
reverse PCR primer 5'-ACGCAGATTTGAGAAGGCT-GTC-3' (SEQ ID NO:118)

Additionally, a synthetic oligonucleotide hybridization probe was constructed from the consensus DNA33679 sequence which had the following nucleotide sequence hybridization probe

5'-TTCACGGGCTGCTCTTGCCCAGCTCT-TGAAGCTTGAAGAGCTGCAC-3' (SEQ ID NO:119)

In order to screen several libraries for a source of a full-length clone, DNA from the libraries was screened by PCR amplification with PCR primer pairs identified above. A positive library was then used to isolate clones encoding the PRO265 gene using the probe oligonucleotide and one of the PCR primers.

RNA for construction of the cDNA libraries was isolated from human a fetal brain library.

DNA sequencing of the clones isolated as described above gave the full-length DNA sequence for PRO265 [herein designated as DNA36350-1158] (SEQ ID NO:114) and the derived protein sequence for PRO265.

The entire nucleotide sequence of DNA36350-1158 is shown in FIG. 59 (SEQ ID NO:114). Clone DNA36350-1158 contains a single open reading frame with an apparent translational initiation site at nucleotide positions 352-354 and ending at the stop codon at positions 2332-2334 (FIG. 59). The predicted polypeptide precursor is 660 amino acids long (FIG. 60). Clone DNA36350-1158 has been deposited with ATCC and is assigned ATCC deposit no. ATCC 209378.

Analysis of the amino acid sequence of the full-length PRO265 polypeptide suggests that portions of it possess significant homology to the fibromodulin and the fibromodulin precursor, thereby indicating that PRO265 may be a novel member of the leucine rich repeat family, particularly related to fibromodulin.

Example 31

Isolation of cDNA Clones Encoding Human PRO941

A consensus sequence was obtained relative to a variety of EST sequences as described in Example 1 above, wherein the consensus sequence obtained is herein designated DNA35941. Based on the DNA35941 consensus sequence, oligonucleotides were synthesized: 1) to identify by PCR a cDNA library that contained the sequence of interest, and 2) for use as probes to isolate a clone of the full-length coding sequence for PRO941.

A pair of PCR primers (forward and reverse) were synthesized:
forward PCR primer 5'-CTTGACTGTCTCTGAATCTG-CACCC-3' (SEQ ID NO:122)
reverse PCR primer 5'-AAGTGGTGGAAGCCTCCAGT-GTGG-3' (SEQ ID NO:123)

Additionally, a synthetic oligonucleotide hybridization probe was constructed from the consensus DNA35941 sequence which had the following nucleotide sequence hybridization probe

5'-CCACTACGGTATTAGAGCAAAAGT-TAAAAACCATCATGGTTCCTGGAGCAGC-3' (SEQ ID NO: 124)

In order to screen several libraries for a source of a full-length clone, DNA from the libraries was screened by PCR amplification with the PCR primer pair identified above. A positive library was then used to isolate clones encoding the PRO941 gene using the probe oligonucleotide and one of the PCR primers. RNA for construction of the cDNA libraries was isolated from human fetal kidney tissue (LIB227).

DNA sequencing of the clones isolated as described above gave the full-length DNA sequence for PRO941 [herein designated as DNA53906-1368] (SEQ ID NO:120) and the derived protein sequence for PRO941.

The entire nucleotide sequence of DNA53906-1368 is shown in FIG. 61 (SEQ ID NO:120). Clone DNA53906-1368 contains a single open reading frame with an apparent translational initiation site at nucleotide positions 37-39 and ending at the stop codon at nucleotide positions 2353-2355 (FIG. 61). The predicted polypeptide precursor is 772 amino acids long (FIG. 62). The full-length PRO941 protein shown in FIG. 62 has an estimated molecular weight of about 87,002 daltons and a pI of about 4.64. Analysis of the full-length PRO941 sequence shown in FIG. 62 (SEQ ID NO:121) evidences the presence of the following: a signal peptide from about amino acid 1 to about amino acid 21, potential N-glycosylation sites from about amino acid 57 to about amino acid 60, from about amino acid 74 to about amino acid 77, from about amino acid 419 to about amino acid 422, from about amino acid 437 to about amino acid 440, from about amino acid 508 to about amino acid 511, from about amino acid 515 to about amino acid 518, from about amino acid 516 to about amino acid 519 and from about amino acid 534 to about amino acid 537, and cadherin extracellular repeated domain signature sequences from about amino acid 136 to about amino acid 146 and from about amino acid 244 to about amino acid 254. Clone DNA53906-1368 has been deposited with ATCC on Apr. 7, 1998 and is assigned ATCC deposit no. 209747.

Analysis of the amino acid sequence of the full-length PRO941 polypeptide suggests that it possesses significant sequence similarity to a cadherin protein, thereby indicating that PRO941 may be a novel cadherin protein family member. More specifically, an analysis of the Dayhoff database (version 35.45 SwissProt 35) evidenced significant homology between the PRO941 amino acid sequence and the following Dayhoff sequences, I50180, CADA_CHICK, I50178, GEN12782, CADC_HUMAN, P_W25637, A38992, P_R49731, D38992 and G02678.

Example 32

Isolation of cDNA Clones Encoding Human PRO10096

Use of the signal sequence algorithm described in Example 3 above allowed identification of an EST cluster sequence from the Incyte database, designated herein as 5086173H1. This EST cluster sequence was then compared to a variety of expressed sequence tag (EST) databases which included public EST databases (e.g., GENBANK database) and a proprietary EST DNA database (LIFESEQ® database, Incyte Pharmaceuticals, Palo Alto, Calif.) to identify existing homologies. The homology search was performed using the computer program BLAST or BLAST2 (Altshul et al., Methods in Enzymology 266:460-480 (1996)). Those comparisons resulting in a BLAST program score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA110880.

In light of an observed sequence homology between the DNA 110880 sequence and an EST sequence encompassed within clone no. 5088384 from the Incyte database, clone no. 5088384 was purchased and the cDNA insert was obtained and sequenced. It was found herein that that cDNA insert encoded a full-length protein. The sequence of this cDNA insert is shown in FIG. 63 and is herein designated as DNA125185-2506.

Clone DNA125185-2506 contains a single open reading frame with an apparent translational initiation site at nucleotide positions 58-60 and ending at the stop codon at nucleotide positions 595-597 (FIG. 63). The predicted polypeptide precursor is 179 amino acids long (FIG. 64). The full-length PRO10096 protein shown in FIG. 64 has an estimated molecular weight of about 20,011 daltons and a pI of about 8.10. Analysis of the full-length PRO10096 sequence shown in FIG. 64 (SEQ ID NO:126) evidences the presence of a variety of important polypeptide domains as shown in FIG. 64, wherein the locations given for those important polypeptide domains are approximate as described above. Clone DNA125185-2506 has been deposited with ATCC on Dec. 7, 1999 and is assigned ATCC deposit no. 1031-PTA.

Example 33

Isolation of cDNA Clones Encoding Human PRO6003

A cDNA clone (DNA83568-2692) encoding a native human PRO6003 polypeptide was identified using a yeast screen, in a human fetal kidney cDNA library that preferentially represents the 5' ends of the primary cDNA clones.

Clone DNA83568-2692 contains a single open reading frame with an apparent translational initiation site at nucleotide positions 638-640 and ending at the stop codon at nucleotide positions 2225-2227 (FIG. 65). The predicted polypeptide precursor is 529 amino acids long (FIG. 66). The full-length PRO6003 protein shown in FIG. 66 has an estimated molecular weight of about 59,583 daltons and a pI of about 6.36. Analysis of the full-length PRO6003 sequence shown in FIG. 66 (SEQ ID NO:128) evidences the presence of a variety of important polypeptide domains as shown in FIG. 66, wherein the locations given for those important polypeptide domains are approximate as described above. Clone DNA83568-2692 has been deposited with ATCC on Jul. 20, 1999 and is assigned ATCC Deposit No. 386-PTA.

An analysis of the Dayhoff database (version 35.45 SwissProt 35), using the ALIGN-2 sequence alignment analysis of the full-length sequence shown in FIG. 66 (SEQ ID NO:128), evidenced sequence identity between the PRO6003 amino acid sequence and the following Dayhoff sequences: P_W58986, PTND7_1, YKZ3_YEAST, CEK04B12_1, AB014464_1, PCU07059_1, S31213, CELF25E2_2, AF036408_1, and AB007932_1.

Example 34

Isolation of cDNA Clones Encoding Human PRO6004

A consensus sequence was obtained relative to a variety of EST sequences as described in Example 1 above, wherein the consensus sequence obtained is herein designated DNA85042. Based upon an observed homology between the DNA85402 consensus sequence and an EST sequence contained within Incyte EST clone no. 3078492, that clone was purchased and its insert obtained and sequenced. The sequence of that insert is herein designated as DNA92259 and is shown in FIGS. 67A-B (SEQ ID NO:129).

Clone DNA92259 contains a single open reading frame with an apparent translational initiation site at nucleotide positions 16-18 and ending at the stop codon at nucleotide positions 1078-1080 (FIGS. 67A-B). The predicted polypeptide precursor is 354 amino acids long (FIG. 68). The full-length PRO6004 protein shown in FIG. 68 has an estimated molecular weight of about 38,719 daltons and a pI of about 6.12. Analysis of the full-length PRO6004 sequence shown in FIG. 68 (SEQ ID NO:130) evidences the presence of a variety of important polypeptide domains as shown in FIG. 68, wherein the locations given for those important polypeptide domains are approximate as described above.

An analysis of the Dayhoff database (version 35.45 SwissProt 35), using the ALIGN-2 sequence alignment analysis of the full-length sequence shown in FIG. 68 (SEQ ID NO:130), evidenced sequence identity between the PRO6004 amino acid sequence and the following Dayhoff sequences: P_WO5152, LAMP_HUMAN, P_W05157, P_WO5155,156551, OPCM_RAT, AMAL_DROME, DMU78177_1,137246 and NCA1_HUMAN.

Example 35

Isolation of cDNA Clones Encoding Human PRO350

A consensus sequence was obtained relative to a variety of EST sequences as described in Example 1 above, wherein the consensus sequence obtained is herein designated DNA39493. Based on the DNA39493 consensus sequence, oligonucleotides were synthesized: 1) to identify by PCR a cDNA library that contained the sequence of interest, and 2) for use as probes to isolate a clone of the full-length coding sequence for PRO350.

A pair of PCR primers (forward and reverse) were synthesized:
forward PCR primer 5'-TCAGGGCTGCCAGGAAGGAA-GAGC-3' (SEQ ID NO:133)
reverse PCR primer 5'-GCAGGAGGAGAAGGTCTTCCA-GAAGAAG-3' (SEQ ID NO:134)
Additionally, a synthetic oligonucleotide hybridization probe was constructed from the consensus DNA39493 sequence which had the following nucleotide sequence
hybridization probe 5'-AGAAGTTCCAGTCAGCCCA-CAAGATGCCATTGTCCCCCGGCCTCC-3' (SEQ ID NO:135)

In order to screen several libraries for a source of a full-length clone, DNA from the libraries was screened by PCR amplification with the PCR primer pair identified above. A positive library was then used to isolate clones encoding the PRO350 gene using the probe oligonucleotide and one of the PCR primers. RNA for construction of the cDNA libraries was isolated from human fetal kidney tissue.

DNA sequencing of the clones isolated as described above gave the full-length DNA sequence for PRO350 [herein designated as DNA44175-1314] (SEQ ID NO:131) and the derived protein sequence for PRO350.

The entire nucleotide sequence of DNA44175-1314 is shown in FIG. 69 (SEQ ID NO:131). Clone DNA44175-1314 contains a single open reading frame with an apparent translational initiation site at nucleotide positions 356-358 and ending at the stop codon at nucleotide positions 821-823 (FIG. 69). The predicted polypeptide precursor is 155 amino acids long (FIG. 70). The full-length PRO350 protein shown in FIG. 70 has an estimated molecular weight of about 17,194 daltons and a pI of about 10.44. Analysis of the full-length PRO350 sequence shown in FIG. 70 (SEQ ID NO:132) evidences the presence of a variety of important polypeptide domains as shown in FIG. 70.

Example 36

Use of PRO as a hybridization Probe

The following method describes use of a nucleotide sequence encoding PRO as a hybridization probe.

DNA comprising the coding sequence of full-length or mature PRO as disclosed herein is employed as a probe to screen for homologous DNAs (such as those encoding naturally-occurring variants of PRO) in human tissue cDNA libraries or human tissue genomic libraries.

Hybridization and washing of filters containing either library DNAs is performed under the following high stringency conditions. Hybridization of radiolabeled PRO-derived probe to the filters is performed in a solution of 50% formamide, 5×SSC, 0.1% SDS, 0.1% sodium pyrophosphate, 50 mM sodium phosphate, pH 6.8, 2×Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence PRO can then be identified using standard techniques known in the art.

Example 37

Expression of PRO in E. Coli

This example illustrates preparation of an unglycosylated form of PRO by recombinant expression in E. coli.

The DNA sequence encoding PRO is initially amplified using selected PCR primers. The primers should contain restriction enzyme sites which correspond to the restriction enzyme sites on the selected expression vector. A variety of expression vectors may be employed. An example of a suitable vector is pBR322 (derived from E. coli; see Bolivar et al., Gene, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the PRO coding region, lambda transcriptional terminator, and an argU gene.

The ligation mixture is then used to transform a selected E. coli strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized PRO protein can then be purified using a metal chelating column under conditions that allow tight binding of the protein.

PRO may be expressed in E. coli in a poly-His tagged form, using the following procedure. The DNA encoding PRO is initially amplified using selected PCR primers. The primers will contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an E. coli host based on strain 52 (W3110 fuhA(tonA) lon galE rpoHts(htpRts) clpP(lacIq). Transformants are first grown in LB containing 50 mg/ml carbenicillin at 30° C. with shaking until an O.D.600 of 3-5 is reached. Cultures are then diluted 50-100 fold into CRAP media (prepared by mixing 3.57 g $(NH_4)_2SO_4$, 0.71 g sodium citrate•2H2O, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20-30 hours at 30° C. with shaking. Samples are removed to verify expression by SDS-PAGE analysis, and the bulk culture is centrifuged to pellet the cells. Cell pellets are frozen until purification and refolding.

E. coli paste from 0.5 to 1 L fermentations (6-10 g pellets) is resuspended in 10 volumes (w/v) in 7 M guanidine, 20 mM Tris, pH 8 buffer. Solid sodium sulfite and sodium tetrathionate is added to make final concentrations of 0.1 M and 0.02 M, respectively, and the solution is stirred overnight at 4° C. This step results in a denatured protein with all cysteine residues blocked by sulfitolization. The solution is centrifuged at 40,000 rpm in a Beckman Ultracentifuge for 30 min. The supernatant is diluted with 3-5 volumes of metal chelate column buffer (6 M guanidine, 20 mM Tris, pH 7.4) and filtered through 0.22 micron filters to clarify. The clarified extract is loaded onto a 5 ml Qiagen Ni-NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein are pooled and stored at 4° C. Protein concentration is estimated by its absorbance at 280 nm using the calculated extinction coefficient based on its amino acid sequence.

The proteins are refolded by diluting the sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes are chosen so that the final protein concentration is between 50 to 100 micrograms/ml. The refolding solution is stirred gently at 4° C. for 12-36 hours. The refolding reaction is quenched by the addition of TFA to a final concentration of 0.4% (pH of approximately 3). Before further purification of the protein, the solution is filtered through a 0.22 micron filter and acetonitrile is added to 2-10% final concentration. The refolded protein is chromatographed on a Poros R1/H reversed phase column using a mobile buffer of 0.1% TFA with elution with a gradient of acetonitrile from 10 to 80%. Aliquots of fractions with A280 absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded PRO polypeptide are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

Many of the PRO polypeptides disclosed herein were successfully expressed as described above.

Example 38

Expression of PRO in Mammalian Cells

This example illustrates preparation of a potentially glycosylated form of PRO by recombinant expression in mammalian cells.

The vector, pRK5 (see EP 307,247, published Mar. 15, 1989), is employed as the expression vector. Optionally, the PRO DNA is ligated into pRK5 with selected restriction enzymes to allow insertion of the PRO DNA using ligation methods such as described in Sambrook et al., supra. The resulting vector is called pRK5-PRO.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 µg pRK5-PRO DNA is mixed with about 1 µg DNA encoding the VA RNA gene [Thimmappaya et al., *Cell*, 31:543 (1982)] and dissolved in 500 µl of 1 mM Tris-HCl, 0.1 mM EDTA, 0.227 M $CaCl_2$. To this mixture is added, dropwise, 500 µl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 µCi/ml $^{35}$S-cysteine and 200 $^{Ci/ml}$ $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of PRO polypeptide. The cultures containing transfected cells may undergo further incubation (in serum free medium) and the medium is tested in selected bioassays.

In an alternative technique, PRO may be introduced into 293 cells transiently using the dextran sulfate method described by Somparyrac et al., *Proc. Natl. Acad. Sci.*, 12:7575 (1981). 293 cells are grown to maximal density in a spinner flask and 700 µg pRK5-PRO DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 µg/ml bovine insulin and 0.1 µg/ml bovine transferrin. After about four days, the conditioned media is centrifuged and filtered to remove cells and debris. The sample containing expressed PRO can then be concentrated and purified by any selected method, such as dialysis and/or column chromatography.

In another embodiment, PRO can be expressed in CHO cells. The pRK5-PRO can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of PRO polypeptide, the culture medium may be replaced with serum free medium. Preferably, the cultures are incubated for about 6 days, and then the conditioned medium is harvested. The medium containing the expressed PRO can then be concentrated and purified by any selected method.

Epitope-tagged PRO may also be expressed in host CHO cells. The PRO may be subcloned out of the pRK5 vector. The subclone insert can undergo PCR to fuse in frame with a selected epitope tag such as a poly-his tag into a Baculovirus expression vector. The poly-his tagged PRO insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged PRO can then be concentrated and purified by any selected method, such as by Ni$^{2+}$-chelate affinity chromatography.

PRO may also be expressed in CHO and/or COS cells by a transient expression procedure or in CHO cells by another stable expression procedure.

Stable expression in CHO cells is performed using the following procedure. The proteins are expressed as an IgG construct (immunoadhesin), in which the coding sequences for the soluble forms (e.g. extracellular domains) of the respective proteins are fused to an IgG1 constant region sequence containing the hinge, CH2 and CH2 domains and/or is a poly-His tagged form.

Following PCR amplification, the respective DNAs are subcloned in a CHO expression vector using standard techniques as described in Ausubel et al., *Current Protocols of Molecular Biology*, Unit 3.16, John Wiley and Sons (1997). CHO expression vectors are constructed to have compatible restriction sites 5' and 3' of the DNA of interest to allow the convenient shuttling of cDNA's. The vector used expression in CHO cells is as described in Lucas et al., *Nucl. Acids Res.* 24:9 (1774-1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available transfection reagents SUPERFECT. (Quiagen), DOSPER or FUGENE. (Boebringer Mannheim). The cells are grown as described in Lucas et al., supra. Approximately $3 \times 10^{-7}$ cells are frozen in an ampule for further growth and production as described below.

The ampules containing the plasmid DNA are thawed by placement into water bath and mixed by vortexing. The contents are pipetted into a centrifuge tube containing 10 mLs of media and centrifuged at 1000 rpm for 5 minutes. The supernatant is aspirated and the cells are resuspended in 10 mL of selective media (0.2 μm filtered PS20 with 5% 0.2 μm diafiltered fetal bovine serum). The cells are then aliquoted into a 100 mL spinner containing 90 mL of selective media After 1-2 days, the cells are transferred into a 250 mL spinner filled with 150 mL selective growth medium and incubated at 37° C. After another 2-3 days, 250 mL, 500 mL and 2000 mL spinners are seeded with $3 \times 10^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3L production spinner is seeded at $1.2 \times 10^6$ cells/mL. On day 0, the cell number pH ie determined. On day 1, the spinner is sampled and sparging with filtered air is commenced. On day 2, the spinner is sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion) taken. Throughout the production, the pH is adjusted as necessary to keep it at around 7.2. After 10 days, or until the viability dropped below 70%, the cell culture is harvested by centrifugation and filtering through a 0.22 μm filter. The filtrate was either stored at 4° C. or immediately loaded onto columns for purification.

For the poly-His tagged constructs, the proteins are purified using a Ni-NTA column (Qiagen). Before purification, imidazole is added to the conditioned media to a concentration of 5 mM. The conditioned media is pumped onto a 6 ml Ni-NTA column equilibrated in 20 mM Hepes, pH 7.4, buffer containing 0.3 M NaCl and 5 mM imidazole at a flow rate of 4-5 ml/min. at 4° C. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at -80° C.

Immunoadhesin (Fc-containing) constructs are purified from the conditioned media as follows. The conditioned medium is pumped onto a 5 ml Protein A column (Pharmacia) which had been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 L of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

Many of the PRO polypeptides disclosed herein were successfully expressed as described above.

Example 39

Expression of PRO in Yeast

The following method describes recombinant expression of PRO in yeast.

First, yeast expression vectors are constructed for intracellular production or secretion of PRO from the ADH2/GAPDH promoter. DNA encoding PRO and the promoter is inserted into suitable restriction enzyme sites in the selected plasmid to direct intracellular expression of PRO. For secretion, DNA encoding PRO can be cloned into the selected plasmid, together with DNA encoding the ADH2/GAPDH promoter, a native PRO signal peptide or other mammalian signal peptide, or, for example, a yeast alpha-factor or invertase secretory signal/leader sequence, and linker sequences (if needed) for expression of PRO.

Yeast cells, such as yeast strain AB 110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant PRO can subsequently be isolated and purified by removing the yeast cells from the fermentation medium by centrifugation and then concentrating the medium using selected cartridge filters. The concentrate containing PRO may further be purified using selected column chromatography resins.

Many of the PRO polypeptides disclosed herein were successfully expressed as described above.

Example 40

Expression of PRO in Baculovirus-Infected Insect Cells

The following method describes recombinant expression of PRO in Baculovirus-infected insect cells.

The sequence coding for PRO is fused upstream of an epitope tag contained within a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the sequence encoding PRO or the desired portion of the coding sequence of PRO such as the sequence encoding the extracellular domain of a transmembrane protein or the sequence encoding the mature protein if the protein is extracellular is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BACULOGOLD™ virus DNA (Pharmingen) into *Spodoptera frugiperda* ("Sf9") cells (ATCC CRL 1711) using lipofectin (commercially available from GIBCO-BRL). After 4-5 days of incubation at 28° C., the released viruses are harvested and used for further amplifications. Viral infection and protein expression are performed as described by O'Reilley et al., Baculovirus expression vectors: A Laboratory Manual, Oxford: Oxford University Press (1994).

Expressed poly-his tagged PRO can then be purified, for example, by $Ni^{2+}$-chelate affinity chromatography as follows. Extracts are prepared from recombinant virus-infected Sf9 cells as described by Rupert et al., Nature, 362:175-179 (1993). Briefly, Sf9 cells are washed, resuspended in sonication buffer (25 mL Hepes, pH 7.9; 12.5 mM $MgCl_2$; 0.1 MM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 μm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged PRO are pooled and dialyzed against loading buffer.

Alternatively, purification of the IgG tagged (or Fc tagged) PRO can be performed using known chromatography techniques, including for instance, Protein A or protein G column chromatography.

Many of the PRO polypeptides disclosed herein were successfully expressed as described above.

Example 41

Preparation of Antibodies that Bind PRO

This example illustrates preparation of monoclonal antibodies which can specifically bind PRO.

Techniques for producing the monoclonal antibodies are known in the art and are described, for instance, in Goding, supra. Immunogens that may be employed include purified PRO, fusion proteins containing PRO, and cells expressing recombinant PRO on the cell surface. Selection of the immunogen can be made by the skilled artisan without undue experimentation.

Mice, such as Balb/c, are immunized with the PRO immunogen emulsified in complete Freund's adjuvant and injected subcutaneously or intraperitoneally in an amount from 1-100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-PRO antibodies.

After a suitable antibody titer has been detected, the animals "positive" for antibodies can be injected with a final intravenous injection of PRO. Three to four days later, the mice are sacrificed and the spleen cells are harvested. The spleen cells are then fused (using 35% polyethylene glycol) to a selected murine myeloma cell line such as P3X63AgU. 1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against PRO. Determination of "positive" hybridoma cells secreting the desired monoclonal antibodies against PRO is within the skill in the art.

The positive hybridoma cells can be injected intraperitoneally into syngeneic Balb/c mice to produce ascites containing the anti-PRO monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 43

Purification of PRO Polyneptides Using Specific Antibodies

Native or recombinant PRO polypeptides may be purified by a variety of standard techniques in the art of protein purification. For example, pro-PRO polypeptide, mature PRO polypeptide, or pre-PRO polypeptide is purified by immunoaffinity chromatography using antibodies specific for the PRO polypeptide of interest. In general, an immunoaffinity column is constructed by covalently coupling the anti-PRO polypeptide antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SEPHAROSE™ (Pharmacia LKB Biotechnology). The antibody is coupled to the resin, the resin is blocked, and the derivative resin is washed according to the manufacturer's instructions.

Such an immunoaffinity column is utilized in the purification of PRO polypeptide by preparing a fraction from cells containing PRO polypeptide in a soluble form. This preparation is derived by solubilization of the whole cell or of a subcellular fraction obtained via differential centrifugation by the addition of detergent or by other methods well known in the art. Alternatively, soluble PRO polypeptide containing a signal sequence may be secreted in useful quantity into the medium in which the cells are grown.

A soluble PRO polypeptide-containing preparation is passed over the immunoaffinity column, and the column is washed under conditions that allow the preferential absorbance of PRO polypeptide (e.g., high ionic strength buffers in the presence of detergent). Then, the column is eluted under conditions that disrupt antibody/PRO polypeptide binding (e.g., a low pH buffer such as approximately pH 2-3, or a high concentration of a chaotrope such as urea or thiocyanate ion), and PRO polypeptide is collected.

Example 44

Drug Screening

This invention is particularly useful for screening compounds by using PRO polypeptides or binding fragment thereof in any of a variety of drug screening techniques. The PRO polypeptide or fragment employed in such a test may either be free in solution, affixed to a solid support, borne on a cell surface, or located intracellularly. One method of drug screening utilizes eukaryotic or prokaryotic host cells which are stably transformed with recombinant nucleic acids expressing the PRO polypeptide or fragment. Drugs are screened against such transformed cells in competitive binding assays. Such cells, either in viable or fixed form, can be used for standard binding assays. One may measure, for example, the formation of complexes between PRO polypeptide or a fragment and the agent being tested. Alternatively, one can examine the diminution in complex formation between the PRO polypeptide and its target cell or target receptors caused by the agent being tested.

Thus, the present invention provides methods of screening for drugs or any other agents which can affect a PRO polypeptide-associated disease or disorder. These methods comprise contacting such an agent with an PRO polypeptide or fragment thereof and assaying (I) for the presence of a complex between the agent and the PRO polypeptide or fragment, or (ii) for the presence of a complex between the PRO polypeptide or fragment and the cell, by methods well known in the art. In such competitive binding assays, the PRO polypeptide or fragment is typically labeled. After suitable incubation, free PRO polypeptide or fragment is separated from that present in bound form, and the amount of free or uncomplexed label is a measure of the ability of the particular agent to bind to PRO polypeptide or to interfere with the PRO polypeptide/cell complex.

Another technique for drug screening provides high throughput screening for compounds having suitable binding affinity to a polypeptide and is described in detail in WO 84/03564, published on Sep. 13, 1984. Briefly stated, large numbers of different small peptide test compounds are synthesized on a solid substrate, such as plastic pins or some other surface. As applied to a PRO polypeptide, the peptide test compounds are reacted with PRO polypeptide and washed. Bound PRO polypeptide is detected by methods well known in the art. Purified PRO polypeptide can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding PRO polypeptide specifically compete with a test compound for binding to PRO polypeptide or fragments thereof. In this manner, the antibodies can be used to detect the presence of any peptide which shares one or more antigenic determinants with PRO polypeptide.

Example 45

Rational Drug Design

The goal of rational drug design is to produce structural analogs of biologically active polypeptide of interest (i.e., a PRO polypeptide) or of small molecules with which they interact, e.g., agonists, antagonists, or inhibitors. Any of these examples can be used to fashion drugs which are more active or stable forms of the PRO polypeptide or which enhance or interfere with the function of the PRO polypeptide in vivo (cf., Hodgson, *Bio/Technology,* 9: 19-21 (1991)).

In one approach, the three-dimensional structure of the PRO polypeptide, or of an PRO polypeptide-inhibitor complex, is determined by x-ray crystallography, by computer modeling or, most typically, by a combination of the two approaches. Both the shape and charges of the PRO polypeptide must be ascertained to elucidate the structure and to determine active site(s) of the molecule. Less often, useful information regarding the structure of the PRO polypeptide may be gained by modeling based on the structure of homologous proteins. In both cases, relevant structural information is used to design analogous PRO polypeptide-like molecules or to identify efficient inhibitors. Useful examples of rational drug design may include molecules which have improved activity or stability as shown by Braxton and Wells, *Biochemistry.* 31:7796-7801 (1992) or which act as inhibitors, agonists, or antagonists of native peptides as shown by Athauda et al., *J. Biochem.,* 113:742-746 (1993).

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amounts of the PRO polypeptide may be made available to perform such

Example 46

Mouse Kidney Mesangial Cell Proliferation Assay
(Assay 92)

This assay shows that certain polypeptides of the invention act to induce proliferation of mammalian kidney mesangial cells and, therefore, are useful for treating kidney disorders associated with decreased mesangial cell function such as Berger disease or other nephropathies associated with Schonlein-Henoch purpura, celiac disease, dermatitis herpetiformis or Crohn disease. The assay is performed as follows. On day one, mouse kidney mesangial cells are plated on a 96 well plate in growth media (3:1 mixture of Dulbecco's modified Eagle's medium and Ham's F12 medium, 95% fetal bovine serum, 5% supplemented with 14 mM HEPES) and grown overnight. On day 2, PRO polypeptides are diluted at 2 concentrations(1% and 0.1%) in serum-free medium and added to the cells. Control samples are serum-free medium alone. On day 4, 20 µl of the Cell Titer 96 Aqueous one solution reagent (Progema) was added to each well and the colormetric reaction was allowed to proceed for 2 hours. The absorbance (OD) is then measured at 490 nm. A positive in the assay is anything that gives an absorbance reading which is at least 15% above the control reading.

The following polypeptides tested positive in this assay: PRO1272.

Example 47

Detection of PRO Polypeptides That Affect
Glucose or FFA Uptake by Primary Rat Adipocytes
(Assay 94)

This assay is designed to determine whether PRO polypeptides show the ability to affect glucose or FFA uptake by adipocyte cells. PRO polypeptides testing positive in this assay would be expected to be useful for the therapeutic treatment of disorders where either the stimulation or inhibition of glucose uptake by adipocytes would be beneficial including, for example, obesity, diabetes or hyper- or hypo-insulinemia.

In a 96 well format, PRO polypeptides to be assayed are added to primary rat adipocytes, and allowed to incubate overnight. Samples are taken at 4 and 16 hours and assayed for glycerol, glucose and FFA uptake. After the 16 hour incubation, insulin is added to the media and allowed to incubate for 4 hours. At this time, a sample is taken and glycerol, glucose and FFA uptake is measured. Media containing insulin without the PRO polypeptide is used as a positive reference control. As the PRO polypeptide being tested may either stimulate or inhibit glucose and FFA uptake, results are scored as positive in the assay if greater than 1.5 times or less than 0.5 times the insulin control.

The following PRO polypeptides tested positive as either stimulators or inhibitors of glucose and/or FFA uptake in this assay: PRO196, PRO185, PRO210, PRO215, PRO242, PRO288, PRO1183, PRO1419, PRO9940, PRO301, PRO337 and PRO265.

Example 48

Stimulation of Adult Heart Hypertrophy (Assay 2)

This assay is designed to measure the ability of various PRO polypeptides to stimulate hypertrophy of adult heart. PRO polypeptides testing positive in this assay would be expected to be useful for the therapeutic treatment of various cardiac insufficiency disorders.

Ventricular myocytes freshly isolated from adult (250 g) Sprague Dawley rats are plated at 2000 cell/well in 180 µl volume. Cells are isolated and plated on day 1, the PRO polypeptide-containing test samples or growth medium only (negative control) (20 µl volume) is added on day 2 and the cells are then fixed and stained on day 5. After staining, cell size is visualized wherein cells showing no growth enhancement as compared to control cells are given a value of 0.0, cells showing small to moderate growth enhancement as compared to control cells are given a value of 1.0 and cells showing large growth enhancement as compared to control cells are given a value of 2.0. Any degree of growth enhancement as compared to the negative control cells is considered positive for the assay.

The following PRO polypeptides tested positive in this assay: PRO301.

Example 49

Inhibition of Vascular Endothelial Growth Factor
(VEGF) Stimulated Proliferation of Endothelial
Cell Growth (Assay 9)

The ability of various PRO polypeptides to inhibit VEGF stimulated proliferation of endothelial cells was tested. Polypeptides testing positive in this assay are useful for inhibiting endothelial cell growth in mammals where such an effect would be beneficial, e.g., for inhibiting tumor growth.

Specifically, bovine adrenal cortical capillary endothelial cells (ACE) (from primary culture, maximum of 12-14 passages) were plated in 96-well plates at 500 cells/well per 100 microliter. Assay media included low glucose DMEM, 10% calf serum, 2 mM glutamine, and 1× penicillin/streptomycinlfungizone. Control wells included the following: (1) no ACE cells added; (2) ACE cells alone; (3) ACE cells plus 5 ng/ml FGF; (4) ACE cells plus 3 ng/ml VEGF; (5) ACE cells plus 3 ng/ml VEGF plus 1 ng/ml TGF-beta; and (6) ACE cells plus 3 ng/ml VEGF plus 5 ng/ml LIF. The test samples, poly-his tagged PRO polypeptides (in 100 microliter volumes), were then added to the wells (at dilutions of 1%, 0. 1% and 0.01%, respectively). The cell cultures were incubated for 6-7 days at 37° C./5% $CO_2$. After the incubation, the media in the wells was aspirated, and the cells were washed 1× with PBS. An acid phosphatase reaction mixture (100 microliter; 0.1 M sodium acetate, pH 5.5, 0. 1% Triton X-100, 10 mM p-nitrophenyl phosphate) was then added to each well. After a 2 hour incubation at 37° C., the reaction was stopped by addition of 10 microliters 1N NaOH. Optical density (OD) was measured on a microplate reader at 405 nm.

The activity of PRO polypeptides was calculated as the percent inhibition of VEGF (3 ng/ml) stimulated proliferation (as determined by measuring acid phosphatase activity at OD 405 nm) relative to the cells without stimulation. TGF-beta was employed as an activity reference at 1 ng/ml, since TGF-beta blocks 70-90% of VEGF-stimulated ACE cell proliferation. The results are indicative of the utility of the PRO polypeptides in cancer therapy and specifically in inhibiting tumor angiogenesis. Numerical values (relative inhibition) are determined by calculating the percent inhibition of VEGF stimulated proliferation by the PRO polypeptides relative to cells without stimulation and then dividing that percentage into the percent inhibition obtained by TGF-β at 1 ng/ml which is known to block 70-90% of VEGF stimulated cell proliferation. The results are considered positive if the PRO polypeptide exhibits 30% or greater inhibition of VEGF stimulation of endothelial cell growth (relative inhibition 30% or greater).

The following polypeptide tested positive in this assay: PRO301, PRO187 and PRO246.

Example 50

Stimulatory Activity in Mixed Lymphocyte Reaction (MLR) Assay (Assay 24)

This example shows that certain polypeptides of the invention are active as a stimulator of the proliferation of stimulated T-lymphocytes. Compounds which stimulate proliferation of lymphocytes are useful therapeutically where enhancement of an immune response is beneficial. A therapeutic agent may take the form of antagonists of the polypeptide of the invention, for example, murine-human chimeric, humanized or human antibodies against the polypeptide.

The basic protocol for this assay is described in Current Protocols in Immunology, unit 3.12; edited by J E Coligan, A M Kruisbeek, D H Marglies, E M Shevach, W Strober, National Insitutes of Health, Published by John Wiley & Sons, Inc.

More specifically, in one assay variant, peripheral blood mononuclear cells (PBMC) are isolated from mammalian individuals, for example a human volunteer, by leukopheresis (one donor will supply stimulator PBMCs, the other donor will supply responder PBMCs). If desired, the cells are frozen in fetal bovine serum and DMSO after isolation. Frozen cells may be thawed overnight in assay media (37° C., 5% $CO_2$) and then washed and resuspended to $3\times10^6$ cells/ml of assay media (RPMI; 10% fetal bovine serum, 1% penicillin/streptomycin, 1% glutamine, 1% HEPES, 1% non-essential amino acids, 1% pyruvate). The stimulator PBMCs are prepared by irradiating the cells (about 3000 Rads).

The assay is prepared by plating in triplicate wells a mixture of:
  100:1 of test sample diluted to 1% or to 0. 1%,
  50:1 of irradiated stimulator cells, and
  50:1 of responder PBMC cells.

100 microliters of cell culture media or 100 microliter of CD4-IgG is used as the control. The wells are then incubated at 37° C., 5% $CO_2$ for 4 days. On day 5, each well is pulsed with tritiated thymidine (1.0 mC/well; Amersham). After 6 hours the cells are washed 3 times and then the uptake of the label is evaluated.

In another variant of this assay, PBMCs are isolated from the spleens of Balb/c mice and C57B6 mice. The cells are teased from freshly harvested spleens in assay media (RPMI; 10% fetal bovine serum, 1% penicillin/streptomycin, 1% glutamine, 1% HEPES, 1% non-essential amino acids, 1% pyruvate) and the PBMCs are isolated by overlaying these cells over Lympholyte M (Organon Teknika), centrifuging at 2000 rpm for 20 minutes, collecting and washing the mononuclear cell layer in assay media and resuspending the cells to $1\times10^7$ cells/ml of assay media. The assay is then conducted as described above.

Positive increases over control are considered positive with increases of greater than or equal to 180% being preferred. However, any value greater than control indicates a stimulatory effect for the test protein.

The following PRO polypeptides tested positive in this assay: PRO533 and PRO301.

Example 51

PDB12 Cell Proliferation (Assay 29)

This example demonstrates that various PRO polypeptides have efficacy in inducing proliferation of PDB12 pancreatic ductal cells and are, therefore, useful in the therapeutic treatment of disorders which involve protein secretion by the pancreas, including diabetes, and the like.

PDB12 pancreatic ductal cells are plated on fibronectin coated 96 well plates at $1.5\times10^3$ cells per well in 100 μL/180 μL of growth media. 100 μL of growth media with the PRO polypeptide test sample or negative control lacking the PRO polypeptide is then added to well, for a final volume of 200 μL. Controls contain growth medium containing a protein shown to be inactive in this assay. Cells are incubated for 4 days at 37° C. 20 μL of Alamar Blue Dye (AB) is then added to each well and the flourescent reading is measured at 4 hours post addition of AB, on a microtiter plate reader at 530 rim excitation and 590 nm emission. The standard employed is cells without Bovine Pituitary Extract (BPE) and with various concentrations of BPE. Buffer or growth medium only controls from unknowns are run 2 times on each 96 well plate.

Percent increase in protein production is calculated by comparing the Alamar Blue Dye calculated protein concentration produced by the PRO polypeptide-treated cells with the Alamar Blue Dye calculated protein concentration produced by the negative control cells. A percent increase in protein production of greater than or equal to 25% as compared to the negative control cells is considered positive.

The following PRO polypeptides tested positive in this assay: PRO301.

Example 52

Guinea Pig Vascular Leak (Assay 32)

This assay is designed to determine whether PRO polypeptides of the present invention show the ability to induce vascular permeability. Polypeptides testing positive in this assay are expected to be useful for the therapeutic treatment of conditions which would benefit from enhanced vascular permeability including, for example, conditions which may benefit from enhanced local immune system cell infiltration.

Hairless guinea pigs weighing 350 grams or more were anesthetized with Ketamine (75-80 mg/kg) and 5 mg/kg Xylazine intramuscularly. Test samples containing the PRO polypeptide or a physiological buffer without the test polypeptide are injected into skin on the back of the test animals with 100 μl per injection site intradermally. There were approximately 16-24 injection sites per animal. One ml of Evans blue dye (1% in PBS) is then injected intracardially. Skin vascular permeability responses to the compounds (i.e., blemishes at the injection sites of injection) are visually scored by measuring the diameter (in mm) of blue-colored leaks from the site of injection at 1, 6 and 24 hours post administration of the test materials. The mm diameter of blueness at the site of injection is observed and recorded as well as the severity of the vascular leakage. Blemishes of at least 5 mm in diameter are considered positive for the assay when testing purified proteins, being indicative of the ability to induce vascular leakage or permeability. A response greater than 7 mm diameter is considered positive for conditioned media samples. Human VEGF at 0.1 µg/100 µl is used as a positive control, inducing a response of 4-8 mm diameter.

The following PRO polypeptides tested positive in this assay: PRO533.

Example 53

Retinal Neuron Survival (Assay 52)

This example demonstrates that certain PRO polypeptides have efficacy in enhancing the survival of retinal neuron cells and, therefore, are useful for the therapeutic treatment of retinal disorders or injuries including, for example, treating sight loss in mammals due to retinitis pigmentosum, AMD, etc.

Sprague Dawley rat pups at postnatal day 7 (mixed population: glia and retinal neuronal types) are killed by decapitation following $CO_2$ anesthesia and the eyes are removed under sterile conditions. The neural retina is dissected away from the pigment epithelium and other ocular tissue and then dissociated into a single cell suspension using 0.25% trypsin in $Ca^{2+}$, $Mg^{2+}$-free PBS. The retinas are incubated at 37° C. for 7-10 minutes after which the trypsin is inactivated by adding 1 ml soybean trypsin inhibitor. The cells are plated at 100,000 cells per well in 96 well plates in DMEM/F12 supplemented with N2 and with or without the specific test PRO polypeptide. Cells for all experiments are grown at 37° C. in a water saturated atmosphere of 5% $CO_2$. After 2-3 days in culture, cells are stained with calcein AM then fixed using 4% paraformaldehyde and stained with DAPI for determination of total cell count. The total cells (fluorescent) are quantified at 20× objective magnification using CCD camera and NIH image software for MacIntosh. Fields in the well are chosen at random.

The effect of various concentration of PRO polypeptides are reported herein where percent survival is calculated by dividing the total number of calcein AM positive cells at 2-3 days in culture by the total number of DAPI-labeled cells at 2-3 days in culture. Anything above 30% survival is considered positive.

The following PRO polypeptides tested positive in this assay using polypeptide concentrations within the range of 0.01% to 1.0% in the assay: PRO350.

Example 54

Proliferation of Rat Utricular Supporting Cells (Assay 54)

This assay shows that certain polypeptides of the invention act as potent mitogens for inner ear supporting cells which are auditory hair cell progenitors and, therefore, are useful for inducing the regeneration of auditory hair cells and treating hearing loss in mammals. The assay is performed as follows. Rat UEC-4 utricular epithelial cells are aliquoted into 96 well plates with a density of 3000 cells/well in 200 µl of serum-containing medium at 33° C. The cells are cultured overnight and are then switched to serum-free medium at 37° C. Various dilutions of PRO polypeptides (or nothing for a control) are then added to the cultures and the cells are incubated for 24 hours. After the 24 hour incubation, $^3$H-thymidine (1 µCi/well) is added and the cells are then cultured for an additional 24 hours. The cultures are then washed to remove unincorporated radiolabel, the cells harvested and Cpm per well determined. Cpm of at least 30% or greater in the PRO polypeptide treated cultures as compared to the control cultures is considered a positive in the assay.

The following polypeptides tested positive in this assay: PRO337.

Example 55

Rod Photoreceptor Cell Survival (Assay 56)

This assay shows that certain polypeptides of the invention act to enhance the survival/proliferation of rod photoreceptor cells and, therefore, are useful for the therapeutic treatment of retinal disorders or injuries including, for example, treating sight loss in mammals due to retinitis pigmentosum, AMD, etc.

Sprague Dawley rat pups at 7 day postnatal (mixed population: glia and retinal neuronal cell types) are killed by decapitation following $CO_2$ anesthesis and the eyes are removed under sterile conditions. The neural retina is dissected away form the pigment epithelium and other ocular tissue and then dissociated into a single cell suspension using 0.25% trypsin in $Ca^{2+}$, $Mg^{2+}$-free PBS. The retinas are incubated at 37° C. for 7-10 minutes after which the trypsin is inactivated by adding 1 ml soybean trypsin inhibitor. The cells are plated at 100,000 cells per well in 96 well plates in DMEM/F12 supplemented with $N_2$. Cells for all experiments are grown at 37° C. in a water saturated atmosphere of 5% $CO_2$. After 2-3 days in culture, cells are fixed using 4% paraformaldehyde, and then stained using CellTracker Green CMFDA. Rho 4D2 (ascites or IgG 1:100), a monoclonal antibody directed towards the visual pigment rhodopsin is used to detect rod photoreceptor cells by indirect immunofluorescence. The results are calculated as % survival: total number of calcein-rhodopsin positive cells at 2-3 days in culture, divided by the total number of rhodopsin positive cells at time 2-3 days in culture. The total cells (fluorescent) are quantified at 20× objective magnification using a CCD camera and NIH image software for MacIntosh. Fields in the well are chosen at random.

The following polypeptides tested positive in this assay: PRO350.

Example 56

Skin Vascular Permeability Assay (Assay 64)

This assay shows that certain polypeptides of the invention stimulate an immune response and induce inflammation by inducing mononuclear cell, eosinophil and PMN infiltration at the site of injection of the animal. Compounds which stimulate an immune response are useful therapeutically where stimulation of an immune response is beneficial. This skin vascular permeability assay is conducted as follows. Hairless guinea pigs weighing 350 grams or more are anesthetized with ketamine (75-80 mg/Kg) and 5 mg/Kg xylazine intramuscularly (IM). A sample of purified polypeptide of the invention or a conditioned media test sample is injected intradermally onto the backs of the test animals with 100 µl per injection site. It is possible to have about 10-30, preferably about 16-24, injection sites per animal. One µl of Evans blue dye (1% in physiologic buffered saline) is injected intracardially. Blemishes at the injection sites are then measured (mm diameter) at 1 hr and 6 hr post injection. Animals were sacrificed at 6 hrs after injection. Each skin injection site is biopsied and fixed in formalin. The skins are then prepared for histopathologic evaluation. Each site is evaluated for inflammatory cell infiltration into the skin. Sites with visible inflammatory cell inflammation are scored as positive. Inflammatory cells may be neutrophilic, eosinophilic, monocytic or lymphocytic. At least a minimal perivascular infiltrate at the injection site is scored as positve, no infiltrate at the site of injection is scored as negative.

The following polypeptide tested positive in this assay: PRO301.

Example 57

Induction of Endothelial Cell Apoptosis (Assay 73)

The ability of PRO polypeptides to induce apoptosis in endothelial cells was tested in human venous umbilical vein endothelial cells (HUVEC, Cell Systems). A positive test in the assay is indicative of the usefulness of the polypeptide in therapeutically treating tumors as well as vascular disorders where inducing apoptosis of endothelial cells would be beneficial.

The cells were plated on 96-well microtiter plates (Amersham Life Science, cytostar-T scintillating microplate, RPNQ160, sterile, tissue-culture treated, individually wrapped), in 10% serum (CSG-medium, Cell Systems), at a density of $2 \times 10^4$ cells per well in a total volume of 100 µl. On day 2, test samples containing the PRO polypeptide were added in triplicate at dilutions of 1%, 0.33% and 0.11%. Wells without cells were used as a blank and wells with cells only were used as a negative control. As a positive control 1:3 serial dilutions of 50 µl of a 3× stock of staurosporine were used. The ability of the PRO polypeptide to induce apoptosis was determined by processing of the 96 well plates for detection of Annexin V, a member of the calcium and phospholipid binding proteins, to detect apoptosis.

0.2 ml Annexin V-Biotin stock solution (100 µg/ml) was diluted in 4.6 ml $2 \times Ca^{2+}$binding buffer and 2.5% BSA (1:25 dilution). 50 µl of the diluted Annexin V-Biotin solution was added to each well (except controls) to a final concentration of 1.0 µg/ml. The samples were incubated for 10-15 minutes with Annexin-Biotin prior to direct addition of $^{35}$S-Streptavidin. $^{35}$S-Streptavidin was diluted in $2 \times Ca^2$ +Binding buffer, 2.5% BSA and was added to all wells at a final concentration of $3 \times 10^4$ cpm/well. The plates were then sealed, centrifuged at 1000 rpm for 15 minutes and placed on orbital shaker for 2 hours. The analysis was performed on a 1450 Microbeta Trilux (Wallac). Percent above background represents the percentage amount of counts per minute above the negative controls. Percents greater than or equal to 30% above background are considered positive.

The following PRO polypeptides tested positive in this assay: PRO301.

Example 58

Induction of c-fos in Cortical Neurons (Assay 83)

This assay is designed to determine whether PRO polypeptides show the ability to induce c-fos in cortical neurons. PRO polypeptides testing positive in this assay would be expected to be useful for the therapeutic treatment of nervous system disorders and injuries where neuronal proliferation would be beneficial.

Cortical neurons are dissociated and plated in growth medium at 10,000 cells per well in 96 well plates. After aproximately 2 cellular divisions, the cells are treated for 30 minutes with the PRO polypeptide or nothing (negative control). The cells are then fixed for 5 minutes with cold methanol and stained with an antibody directed against phosphorylated CREB. mRNA levels are then calculated using chemiluminescence. A positive in the assay is any factor that results in at least a 2-fold increase in c-fos message as compared to the negative controls.

The following PRO polypeptides tested positive in this assay: PRO288.

Example 59

Induction of Pancreatic β-Cell Precursor Differentiation (Assay 89)

This assay shows that certain polypeptides of the invention act to induce differentiation of pancreatic β-cell precursor cells into mature pancreatic β-cells and, therefore, are useful for treating various insulin deficient states in mammals, including diabetes mellitus. The assay is performed as follows. The assay uses a primary culture of mouse fetal pancreatic cells and the primary readout is an alteration in the expression of markers that represent either β-cell precursors or mature β-cells. Marker expression is measured by real time quantitative PCR (RTQ-PCR); wherein the marker being evaluated is insulin.

The pancreata are dissected from E14 embryos (CD1 mice). The pancreata are then digested with collagenase/dispase in F12/DMEM at 37° C. for 40 to 60 minutes (collagenase/dispase, 1.37 mg/ml, Boehringer Mannheim, #1097113). The digestion is then neutralized with an equal volume of 5% BSA and the cells are washed once with RPMI1640. At day 1, the cells are seeded into 12-well tissue culture plates (pre-coated with laminin, 20 µg/ml in PBS, Boehringer Mannheim, #124317). Cells from pancreata from 1-2 embryos are distributed per well. The culture medium for this primary cuture is 14F/1640. At day 2, the media is removed and the attached cells washed with RPMI/1640. Two mls of minimal media are added in addition to the protein to be tested. At day 4, the media is removed and RNA prepared from the cells and marker expression analyzed by real time quantitative RT-PCR. A protein is considered to be active in the assay if it increases the expression of the relevant β-cell marker as compared to untreated controls.

14F/1640 is RPMI1640 (Gibco) Plus the Following:
  group A 1:1000
  group B 1:1000
  recombinant human insulin 10 µg/ml
  Aprotinin (50 µg/ml) 1:2000 (Boehringer manheim #981532)
  Bovine pituitary extract (BPE) 60 µg/ml
  Gentamycin 100 ng/ml Group A: (in 10 ml PBS)
  Transferrin, 100 mg (Sigma T2252)
  Epidermal Growth Factor, 100 µg (BRL 100004)
  Triiodothyronine, 10 µl of $5 \times 10^{-6}$ M (Sigma T5516)
  Ethanolamine, 100 µl of $10^{-1}$ M (Sigma E0135)

Phosphoethalamine, 100 μl of $10^{-1}$ M (Sigma P0503)
Selenium, 4 μl of $10^{-1}$ M (Aesar #12574)

Group C: (in 10 ml 100% ethanol)
Hydrocortisone, 2 μl of $5 \times 10^{-3}$ M (Sigma #H0135)
Progesterone, 100 μl of $1 \times 10^{-3}$ M (Sigma #P6149)
Forskolin, 500 μl of 20 mM (Calbiochem #344270)

Minimal Media:
RPMI 1640 plus transferrin (10 μg/ml), insulin (1 μg/ml), gentamycin (100 ng/ml), aprotinin (50 μg/ml) and BPE (15 μg/ml).

Defined Media:
RPMI 1640 plus transferrin (10 μg/ml), insulin (1 μg/ml), gentamycin (100 ng/ml) and aprotinin (50 μg/ml).

The following polypeptides were positive in this assay: PRO1361, PRO1308, PRO1600 and PRO4356.

Example 60

Pericyte c-Fos Induction (Assay 93)

This assay shows that certain polypeptides of the invention act to induce the expression of c-fos in pericyte cells and, therefore, are useful not only as diagnostic markers for particular types of pericyte-associated tumors but also for giving rise to antagonists which would be expected to be useful for the therapeutic treatment of pericyte-associated tumors. Induction of c-fos expression in pericytes is also indicative of the induction of angiogenesis and, as such, PRO polypeptides capable of inducing the expression of c-fos would be expected to be useful for the treatment of conditions where induced angiogenesis would be beneficial including, for example, wound healing, and the like. Specifically, on day 1, pericytes are received from VEC Technologies and all but 5 ml of media is removed from flask. On day 2, the pericytes are trypsinized, washed, spun and then plated onto 96 well plates. On day 7, the media is removed and the pericytes are treated with 100 μl of PRO polypeptide test samples and controls (positive control=DME+5% serum +/− PDGF at 500 ng/ml; negative control=protein 32). Replicates are averaged and SD/CV are determined. Fold increase over Protein 32 (buffer control) value indicated by chemiluminescence units (RLU) luminometer reading verses frequency is plotted on a histogram. Two-fold above Protein 32 value is considered positive for the assay. ASY Matrix: Growth media=low glucose DMEM=20% FBS+1× pen strep+1×fungizone. Assay Media=low glucose DMEM+5% FBS.

The following polypeptides tested positive in this assay: PRO444 and PRO217.

Example 61

Detection of Polypeptides That Affect Glucose or FFA Uptake in Skeletal Muscle (Assay 106)

This assay is designed to determine whether PRO polypeptides show the ability to affect glucose or FFA uptake by skeletal muscle cells. PRO polypeptides testing positive in this assay would be expected to be useful for the therapeutic treatment of disorders where either the stimulation or inhibition of glucose uptake by skeletal muscle would be beneficial including, for example, diabetes or hyper- or hypo-insulinemia.

In a 96 well format, PRO polypeptides to be assayed are added to primary rat differentiated skeletal muscle, and allowed to incubate overnight. Then fresh media with the PRO polypeptide and +/− insulin are added to the wells. The sample media is then monitored to determine glucose and FFA uptake by the skeletal muscle cells. The insulin will stimulate glucose and FFA uptake by the skeletal muscle, and insulin in media without the PRO polypeptide is used as a positive control, and a limit for scoring. As the PRO polypeptide being tested may either stimulate or inhibit glucose and FFA uptake, results are scored as positive in the assay if greater than 1.5 times or less than 0.5 times the insulin control.

The following PRO polypeptides tested positive as either stimulators or inhibitors of glucose and/or FFA uptake in this assay: PRO196, PRO183, PRO185, PRO215, PRO288, PRO1361, PRO1600, PRO4999, PRO7170, PRO533 and PRO187.

Example 62

Fetal Hemoglobin Induction in an Erythroblastic Cell Line (Assay 107)

This assay is useful for screening PRO polypeptides for the ability to induce the switch from adult hemoglobin to fetal hemoglobin in an erythroblastic cell line. Molecules testing positive in this assay are expected to be useful for therapeutically treating various mammalian hemoglobin-associated disorders such as the various thalassemias. The assay is performed as follows. Erythroblastic cells are plated in standard growth medium at 1000 cells/well in a 96 well format. PRO polypeptides are added to the growth medium at a concentration of 0.2% or 2% and the cells are incubated for 5 days at 37° C. As a positive control, cells are treated with 100 μM hemin and as a negative control, the cells are untreated. After 5 days, cell lysates are prepared and analyzed for the expression of gamma globin (a fetal marker). A positive in the assay is a gamma globin level at least 2-fold above the negative control.

The following polypeptides tested positive in this assay: PRO1419.

Example 63

Chondrocyte Re-differentiation Assay (Assay 110)

This assay shows that certain polypeptides of the invention act to induce redifferentiation of chondrocytes, therefore, are expected to be useful for the treatment of various bone and/or cartilage disorders such as, for example, sports injuries and arthritis. The assay is performed as follows. Porcine chondrocytes are isolated by overnight collagenase digestion of articular cartilage of metacarpophalangeal joints of 4-6 month old female pigs. The isolated cells are then seeded at 25,000 cells/cm$^2$ in Ham F-12 containing 10% FBS and 4 μg/ml gentamycin. The culture media is changed every third day and the cells are then seeded in 96 well plates at 5,000 cells/well in 100 μl of the same media without serum and 100 μl of the test PRO polypeptide, 5 nM staurosporin (positive control) or medium alone (negative control) is added to give a final volume of 200 μl/well. After 5 days of incubation at 37° C., a picture of each well is taken and the differentiation state of the chondrocytes is determined. A positive result in the assay occurs when the redifferentiation of the chondrocytes is determined to be more similar to the positive control than the negative control.

The following polypeptide tested positive in this assay: PRO215, PRO353, PRO365, PRO1272, PRO301 and PRO337.

Example 64

Chondrocyte Proliferation Assay (Assay 111)

This assay is designed to determine whether PRO polypeptides of the present invention show the ability to induce the proliferation and/or redifferentiation of chondrocytes in culture. PRO polypeptides testing positive in this assay would be expected to be useful for the therapeutic treatment of various bone and/or cartilage disorders such as, for example, sports injuries and arthritis.

Porcine chondrocytes are isolated by overnight collagenase digestion of articular cartilage of the metacarpophalangeal joint of 4-6 month old female pigs. The isolated cells are then seeded at 25,000 cells/cm$^2$ in Ham F-12 containing 10% FBS and 4 µg/ml gentamycin. The culture media is changed every third day and the cells are reseeded to 25,000 cells/cm$^2$ every five days. On day 12, the cells are seeded in 96 well plates at 5,000 cells/well in 100 µl of the same media without serum and 100 µl of either serum-free medium (negative control), staurosporin (final concentration of 5 nM; positive control) or the test PRO polypeptide are added to give a final volume of 200 µl/well. After 5 days at 37° C., 20 µl of Alamar blue is added to each well and the plates are incubated for an additional 3 hours at 37° C. The fluorescence is then measured in each well (Ex:530 nm; Em: 590 nm). The fluorescence of a plate containing 200 µl of the serum-free medium is measured to obtain the background. A positive result in the assay is obtained when the fluorescence of the PRO polypeptide treated sample is more like that of the positive control than the negative control.

The following PRO polypeptides tested positive in this assay: PRO215, PRO217, PRO248, PRO1361, PRO1419, PRO533 and PRO265.

Example 65

Mouse Mesengial Cell Inhibition Assay (Assay 114)

This assay is designed to determine whether PRO polypeptides of the present invention show the ability to inhibit the proliferation of mouse mesengial cells in culture. PRO polypeptides testing positive in this assay would be expected to be useful for the therapeutic treatment of such diseases or conditions where inhibition of mesengial cell proliferation would be beneficial such as, for example, cystic renal dysplasia, polycystic kidney disease, or other kidney disease assoiciated with abnormal mesengial cell proliferation, renal tumors, and the like.

On day 1, mouse mesengial cells are plated on a 96 well plate in growth medium (a 3:1 mixture of Dulbecco's modified Eagle's medium and Ham's F12 medium, 95%; fetal bovine serum, 5%; supplemented with 14 mM HEPES) and then are allowed to grow overnight. On day 2, the PRO polypeptide is diluted at 2 different concentrations (1%, 0.1%) in serum-free medium and is added to the cells. The negative control is growth medium without added PRO polypeptide. After the cells are allowed to incubate for 48 hours, 20, al of the Cell Titer 96 Aqueous one solution reagent (Promega) is added to each well and the colormetric reaction is allowed to proceed for 2 hours. The absorbance (OD) is then measured at 490 nm. A positive in the assay is an absorbance reading which is at least 10% above the negative control.

The following PRO polypeptides tested positive in this assay: PRO1318.

Example 66

Induction of Pancreatic β-Cell Precursor Proliferation (Assay 117)

This assay shows that certain polypeptides of the invention act to induce an increase in the number of pancreatic P-cell precursor cells and, therefore, are useful for treating various insulin deficient states in mammals, including diabetes mellitus. The assay is performed as follows. The assay uses a primary culture of mouse fetal pancreatic cells and the primary readout is an alteration in the expression of markers that represent either β-cell precursors or mature β-cells. Marker expression is measured by real time quantitative PCR (RTQ-PCR); wherein the marker being evaluated is a transcription factor called Pdx1.

The pancreata are dissected from E14 embryos (CD1 mice). The pancreata are then digested with collagenase/ dispase in F12/DMEM at 37° C. for 40 to 60 minutes (collagenase/dispase, 1.37 mg/ml, Boehringer Mannheim, #1097113). The digestion is then neutralized with an equal volume of 5% BSA and the cells are washed once with RPMI1640. At day 1, the cells are seeded into 12-well tissue culture plates (pre-coated with laminin, 20 µg/ml in PBS, Boehringer Mannheim, #124317). Cells from pancreata from 1-2 embryos are distributed per well. The culture medium for this primary cuture is 14F/1640. At day 2, the media is removed and the attached cells washed with RPMI/1640. Two mls of minimal media are added in addition to the protein to be tested. At day 4, the media is removed and RNA prepared from the cells and marker expression analyzed by real time quantitative RT-PCR. A protein is considered to be active in the assay if it increases the expression of the relevant β-cell marker as compared to untreated controls.

14F/1640 is RPMI1640 (Gibco) plus the following:
    group A 1:1000
    group B 1:1000
    recombinant human insulin 10 µg/ml
    Aprotinin (50 µg/ml) 1:2000 (Boehringer manheim #981532)
    Bovine pituitary extract (BPE) 60 µg/ml
    Gentamycin 100 ng/ml Group A: (in 10 ml PBS)
    Transferrin, 100 mg (Sigma T2252)
    Epidermal Growth Factor, 100 µg (BRL 100004)
    Triiodothyronine, 10 µl of 5×10$^{-4}$ M (Sigma T5516)
    Ethanolamine, 100 µl of 10$^{-1}$ M (Sigma E0135)
    Phosphoethalamine, 100 µl of 10$^{-1}$ M (Sigma P0503)
    Selenium, 4 µl of 10$^{-1}$ M (Aesar #12574)

Group C: (in 10 ml 100% ethanol)
    Hydrocortisone, 2 µl of 5×10$^{-3}$ M (Sigma #H0135)
    Progesterone, 100 µl of 1×10$^{-3}$ M (Sigma #P6149)
    Forskolin, 500 µl of 20 mM (Calbiochem #344270)

Minimal Media:
    RPMI 1640 plus transferrin (10 µg/ml), insulin (1 µg/ml), gentamycin (100 ng/ml), aprotinin (50 µg/ml) and BPE (15 µg/ml).

Defined Media:

RPMI 1640 plus transferrin (10 μg/ml), insulin (100 ng/ml), gentamycin (100 ng/ml) and aprotinin (50 μg/ml).

The following polypeptides tested positive in this assay: PRO183, PRO185, PRO288.

Example 67

In Vitro Antitumor Assay (Assay 161)

The antiproliferative activity of various PRO polypeptides was determined in the investigational, disease-oriented in vitro anti-cancer drug discovery assay of the National Cancer Institute (NCI), using a sulforhodamine B (SRB) dye binding assay essentially as described by Skehan et al., *J. Natl. Cancer Inst.* 82:1107-1112 (1990). The 60 tumor cell lines employed in this study ("the NCI panel"), as well as conditions for their maintenance and culture in vitro have been described by Monks et al., *J. Natl. Cancer Inst.* 83:757-766 (1991). The purpose of this screen is to initially evaluate the cytotoxic and/or cytostatic activity of the test compounds against different types of tumors (Monks et al., supra; Boyd, *Cancer: Princ. Pract. Oncol. Update* 3(10):1-12 [1989]).

Cells from approximately 60 human tumor cell lines were harvested with trypsin/EDTA (Gibco), washed once, resuspended in IMEM and their viability was determined. The cell suspensions were added by pipet (100 μL volume) into separate 96-well microtiter plates. The cell density for the 6-day incubation was less than for the 2-day incubation to prevent overgrowth. Inoculates were allowed a preincubation period of 24 hours at 37° C. for stabilization. Dilutions at twice the intended test concentration were added at time zero in 100 μL aliquots to the microtiter plate wells (1:2 dilution). Test compounds were evaluated at five half-log dilutions (1000 to 100,000-fold). Incubations took place for two days and six days in a 5% $CO_2$ atmosphere and 100% humidity.

After incubation, the medium was removed and the cells were fixed in 0.1 ml of 10% trichloroacetic acid at 40° C. The plates were rinsed five times with deionized water, dried, stained for 30 minutes with 0.1 ml of 0.4% sulforhodamine B dye (Sigma) dissolved in 1% acetic acid, rinsed four times with 1% acetic acid to remove unbound dye, dried, and the stain was extracted for five minutes with 0.1 ml of 10 mM Tris base [tris(hydroxymethyl)aminomethane], pH 10.5. The absorbance (OD) of sulforhodamine B at 492 nm was measured using a computer-interfaced, 96-well microtiter plate reader.

A test sample is considered positive if it shows at least 50% growth inhibitory effect at one or more concentrations. The positive results are shown in the following Table 7.

TABLE 7

| Compound | Tumor Type | Designation |
| --- | --- | --- |
| PRO301 | NSCL | NCI-H322M |
| PRO301 | Leukemia | MOLT-4; SR |
| PRO301 | NSCL | A549/ATCC; EKVX; |
| PRO301 | NSCL | NCI-H23; NCI-460; NCI-H226 |
| PRO301 | Colon | COLO 205; HCC-2998; |
| PRO301 | Colon | HCT-15; KM12; HT29; |
| PRO301 | Colon | HCT-116 |
| PRO301 | CNS | SF-268; SF-295; SNB-19 |
| PRO301 | Melanoma | MALME-3M; SK-MEL-2; |
| PRO301 | Melanoma | SK-MEL-5; UACC-257 |
| PRO301 | Melanoma | UACC-62 |
| PRO301 | Ovarian | IGROV1; OVCAR-4 |

TABLE 7-continued

| Compound | Tumor Type | Designation |
| --- | --- | --- |
| PRO301 | Ovarian | OVCAR-5 |
| PRO301 | Ovarian | OVCAR-8; SK0OV-3 |
| PRO301 | Renal | ACHN; CAKI-1; TK-10; UO-31 |
| PRO301 | Prostate | PC-3; DU-145 |
| PRO301 | Breast | NCI/ADR-RES; HS 578T |
| PRO301 | Breast | MDA-MB-435; MDA-N; T-47D |
| PRO301 | Melanoma | M14 |
| PRO301 | Leukemia | CCRF-CEM; HL-60(TB); K-562 |
| PRO301 | Leukemia | RPMI-8226 |
| PRO301 | Melanoma | LOX IMVI |
| PRO301 | Renal | 786-0; SN12C |
| PRO301 | Breast | MCF7; MDA-MB-231/ATCC |
| PRO301 | Breast | BT-549 |
| PRO301 | NSCL | HOP-62 |
| PRO301 | CNS | SF-539 |
| PRO301 | Ovarian | OVCAR-3 |

The results of these assays demonstrate that the positive testing PRO polypeptides are useful for inhibiting neoplastic growth in a number of different tumor cell types and may be used therapeutically therefor. Antibodies against these PRO polypeptides are useful for affinity purification of these useful polypeptides. Nucleic acids encoding these PRO polypeptides are useful for the recombinant preparation of these polypeptides.

Example 68

Gene Amplification in Tumors

This example shows that certain PRO polypeptide-encoding genes are amplified in the genome of certain human lung, colon and/or breast cancers and/or cell lines. Amplification is associated with overexpression of the gene product, indicating that the polypeptides are useful targets for therapeutic intervention in certain cancers such as colon, lung, breast and other cancers and diagnostic determination of the presence of those cancers. Therapeutic agents may take the form of antagonists of the PRO polypeptide, for example, murine-human chimeric, humanized or human antibodies against a PRO polypeptide.

The starting material for the screen was genomic DNA isolated from a variety cancers. The DNA is quantitated precisely, e.g., fluorometrically. As a negative control, DNA was isolated from the cells of ten normal healthy individuals which was pooled and used as assay controls for the gene copy in healthy individuals (not shown). The 5' nuclease assay (for example, TAQMAN™ assay.) and real-time quantitative PCR (for example, ABI PRIZM 7700 SEQUENCE DETECTION SYSTEM™. (Perkin Elmer, Applied Biosystems Division, Foster City, Calif.)), were used to find genes potentially amplified in certain cancers. The results were used to determine whether the DNA encoding the PRO polypeptide is over-represented in any of the primary lung or colon cancers or cancer cell lines or breast cancer cell lines that were screened. The primary lung cancers were obtained from individuals with tumors of the type and stage as indicated in Table 8. An explanation of the abbreviations used for the designation of the primary tumors listed in Table 8 and the primary tumors and cell lines referred to throughout this example are given below.

The results of the TAQMAN™ assay are reported in delta (Δ) Ct units. One unit corresponds to 1 PCR cycle or approximately a 2-fold amplification relative to normal, two units corresponds to 4-fold, 3 units to 8-fold amplification and so on. Quantitation was obtained using primers and a TAQMAN™ fluorescent probe derived from the PRO polypeptide-encoding gene. Regions of the PRO polypeptide-encoding gene which are most likely to contain unique nucleic acid sequences and which are least likely to have spliced out introns are preferred for the primer and probe derivation, e.g., 3'-untranslated regions. The sequences for the primers and probes (forward, reverse and probe) used for the PRO polypeptide gene amplification analysis were as follows:

PRO533 (DNA49435-1219)
forward: 5'-GGGACGTGCTTCTACAAGAACAG-3' (SEQ ID NO:140)
reverse: 5'-CAGGCTTACAATGTTATGATCAGACA-3' (SEQ ID NO:141)
probe: 5'-TATTCAGAGTTTTCCATTGGCAGTGC-CAGTT-3' (SEQ ID NO:142)

PRO187 (DNA27864-1155)
forward: 5'-GGCCTTGCAGACAACCGT-3' (SEQ ID NO:143)
reverse: 5'-CAGACTGAGGGAGATCCGAGA-3' (SEQ ID NO:144)
probe: 5'-GCAGATTTTGAGGACAGCCACCTCCA-3' (SEQ ID NO:145)
forward2: 5'-CATCAAGCGCCTCTACCA-3' (SEQ ID NO:146)
reverse2: 5'-CACAAACTCGAACTGCTTCTG-3' (SEQ ID NO:147)
probe2: 5'-CAGCTGCCCTTCCCCAACCA-3' (SEQ ID NO:148)

PRO246 (DNA35639-1172)
forward: 5'-GGCAGAGACTTCCAGTCACTGA-3' (SEQ ID NO:149)
reverse: 5'-GCCAAGGGTGGTGTTAGATAGG-3' (SEQ ID NO:150)
probe: 5'-CAGGCCCCCTTGATCTGTACCCCA-3' (SEQ ID NO:151)

The 5' nuclease assay reaction is a fluorescent PCR-based technique which makes use of the 5' exonuclease activity of Taq DNA polymerase enzyme to monitor amplification in real time. Two oligonucleotide primers (forward [.f] and reverse [.r]) are used to generate an amplicon typical of a PCR reaction. A third oligonucleotide, or probe (.p), is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

The 5' nuclease procedure is run on a real-time quantitative PCR device such as the ABI PRIZM 7700 SEQUENCE DETECTION SYSTEM. The system consists of a thermocycler, laser, charge-coupled device (CCD) camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

5' Nuclease assay data are initially expressed as Ct, or the threshold cycle. This is defined as the cycle at which the reporter signal accumulates above the background level of fluorescence. The ΔCt values are used as quantitative measurement of the relative number of starting copies of a particular target sequence in a nucleic acid sample when comparing cancer DNA results to normal human DNA results.

Table 8 describes the stage, T stage and N stage of various primary tumors which were used to screen the PRO polypeptide compounds of the invention.

TABLE 8

Primary Lung and Colon Tumor Profiles

| Primary Tumor Stage | Stage | Other Stage | Dukes Stage | T Stage | N Stage |
| --- | --- | --- | --- | --- | --- |
| Human lung tumor AdenoCa (SRCC724) [LT1] | IIA | | | T1 | N1 |
| Human lung tumor SqCCa (SRCC725) [LT1a] | IIB | | | T3 | N0 |
| Human lung tumor AdenoCa (SRCC726) [LT2] | IB | | | T2 | N0 |
| Human lung tumor AdenoCa (SRCC727) [LT3] | IIIA | | | T1 | N2 |
| Human lung tumor AdenoCa (SRCC728) [LT4] | IB | | | T2 | N0 |
| Human lung tumor SqCCa (SRCC729) [LT6] | IB | | | T2 | N0 |
| Human lung tumor Aden/SqCCa (SRCC730) [LT7] | IA | | | T1 | N0 |
| Human lung tumor AdenoCa (SRCC731) [LT9] | IB | | | T2 | N0 |
| Human lung tumor SqCCa (SRCC732) [LT10] | IIB | | | T2 | N1 |
| Human lung tumor SqCCa (SRCC733) [LT11] | IIA | | | T1 | N1 |
| Human lung tumor AdenoCa (SRCC734) [LT12] | IV | | | T2 | N0 |
| Human lung tumor AdenoSqCCa (SRCC735)[LT13] | IB | | | T2 | N0 |
| Human lung tumor SqCCa (SRCC736) [LT15] | IB | | | T2 | N0 |
| Human lung tumor SqCCa (SRCC737) [LT16] | IB | | | T2 | N0 |
| Human lung tumor SqCCa (SRCC738) [LT17] | IIB | | | T2 | N1 |
| Human lung tumor SqCCa (SRCC739) [LT18] | IB | | | T2 | N0 |
| Human lung tumor SqCCa (SRCC740) [LT19] | IB | | | T2 | N0 |
| Human lung tumor LCCa (SRCC741) [LT21] | IIB | | | T3 | N1 |
| Human lung AdenoCa (SRCC811) [LT22] | 1A | | | T1 | N0 |
| Human colon AdenoCa (SRCC742) [CT2] | | M1 | D | pT4 | N0 |
| Human colon AdenoCa (SRCC743) [CT3] | | | B | pT3 | N0 |
| Human colon AdenoCa (SRCC744) [CT8] | | | B | T3 | N0 |
| Human colon AdenoCa (SRCC745) [CT10] | | | A | pT2 | N0 |

TABLE 8-continued

Primary Lung and Colon Tumor Profiles

| Primary Tumor Stage | Stage | Other Stage | Dukes Stage | T Stage | N Stage |
|---|---|---|---|---|---|
| Human colon AdenoCa (SRCC746) [CT12] | | MO, R1 | B | T3 | N0 |
| Human colon AdenoCa (SRCC747) [CT14] | | pMO, RO | B | pT3 | pN0 |
| Human colon AdenoCa (SRCC748) [CT15] | | M1, R2 | D | T4 | N2 |
| Human colon AdenoCa (SRCC749) [CT16] | | pMO | B | pT3 | pN0 |
| Human colon AdenoCa (SRCC750) [CT17] | | | C1 | pT3 | pN1 |
| Human colon AdenoCa (SRCC751) [CT1] | | MO, R1 | B | pT3 | N0 |
| Human colon AdenoCa (SRCC752) [CT4] | | | B | pT3 | M0 |
| Human colon AdenoCa (SRCC753) [CT5] | | G2 | C1 | pT3 | pN0 |
| Human colon AdenoCa (SRCC754) [CT6] | | pMO, RO | B | pT3 | pN0 |
| Human colon AdenoCa (SRCC755) [CT7] | | G1 | A | pT2 | pN0 |
| Human colon AdenoCa (SRCC756) [CT9] | | G3 | D | pT4 | pN2 |
| Human colon AdenoCa (SRCC757) [CT11] | | | B | T3 | N0 |
| Human colon AdenoCa (SRCC758) [CT18] | | MO, RO | B | pT3 | pN0 |

DNA Preparation:

DNA was prepared from cultured cell lines, primary tumors, normal human blood. The isolation was performed using purification kit, buffer set and protease and all from Quiagen, according to the manufacturer's instructions and the description below.

Cell Culture Lysis:

Cells were washed and trypsinized at a concentration of $7.5 \times 10^8$ per tip and pelleted by centrifuging at 1000 rpm for 5 minutes at 4° C., followed by washing again with 1/2 volume of PBS recentrifugation. The pellets were washed a third time, the suspended cells collected and washed 2× with PBS. The cells were then suspended into 10 ml PBS. Buffer C1 was equilibrated at 4° C. Qiagen protease #19155 was diluted into 6.25 ml cold ddH$_2$O to a final concentration of 20 mg/ml and equilibrated at 4° C. 10 ml of G2 Buffer was prepared by diluting Qiagen RNAse A stock (100 mg/ml) to a final concentration of 200 µg/ml.

Buffer C1 (10 ml, 4° C.) and ddH2O (40 ml, 4° C.) were then added to the 10 ml of cell suspension, mixed by inverting and incubated on ice for 10 minutes. The cell nuclei were pelleted by centrifuging in a Beckman swinging bucket rotor at 2500 rpm at 4° C. for 15 minutes. The supernatant was discarded and the nuclei were suspended with a vortex into 2 ml Buffer C1 (at 4° C.) and 6 ml ddH$_2$O, followed by a second 4° C. centrifugation at 2500 rpm for 15 minutes. The nuclei were then resuspended into the residual buffer using 200 µl per tip. G2 buffer (10 ml) was added to the suspended nuclei while gentle vortexing was applied. Upon completion of buffer addition, vigorous vortexing was applied for 30 seconds. Quiagen protease (200 µl, prepared as indicated above) was added and incubated at 50° C. for 60 minutes. The incubation and centrifugation was repeated until the lysates were clear (e.g., incubating additional 30-60 minutes, pelleting at 3000×g for 10 min., 4° C.).

Solid Human Tumor Sample Preparation and Lysis:

Tumor samples were weighed and placed into 50 ml conical tubes and held on ice. Processing was limited to no more than 250 mg tissue per preparation (1 tip/preparation). The protease solution was freshly prepared by diluting into 6.25 ml cold ddH$_2$O to a final concentration of 20 mg/ml and stored at 4° C. G2 buffer (20 ml) was prepared by diluting DNAse A to a final concentration of 200 mg/ml (from 100 mg/ml stock). The tumor tissue was homogenated in 19 ml G2 buffer for 60 seconds using the large tip of the polytron in a laminar-flow TC hood in order to avoid inhalation of aerosols, and held at room temperature. Between samples, the polytron was cleaned by spinning at 2×30 seconds each in 2L ddH$_2$O, followed by G2 buffer (50 ml). If tissue was still present on the generator tip, the apparatus was disassembled and cleaned.

Quiagen protease (prepared as indicated above, 1.0 ml) was added, followed by vortexing and incubation at 50° C. for 3 hours. The incubation and centrifugation was repeated until the lysates were clear (e.g., incubating additional 30-60 minutes, pelleting at 3000×g for 10 min., 4° C.).

Human blood preparation and lysis:

Blood was drawn from healthy volunteers using standard infectious agent protocols and citrated into 10 ml samples per tip. Quiagen protease was freshly prepared by dilution into 6.25 ml cold ddH$_2$O to a final concentration of 20 mg/ml and stored at 4° C. G2 buffer was prepared by diluting RNAse A to a final concentration of 200 µg/ml from 100 mg/ml stock. The blood (10 ml) was placed into a 50 ml conical tube and 10 ml C1 buffer and 30 ml ddH$_2$O (both previously equilibrated to 4° C.) were added, and the components mixed by inverting and held on ice for 10 minutes. The nuclei were pelleted with a Beckman swinging bucket rotor at 2500 rpm, 4° C. for 15 minutes and the supernatant discarded. With a vortex, the nuclei were suspended into 2 ml C1 buffer (4° C.) and 6 ml ddH$_2$O (4° C.). Vortexing was repeated until the pellet was white. The nuclei were then suspended into the residual buffer using a 200 µl tip. G2 buffer (10 ml) were added to the suspended nuclei while gently vortexing, followed by vigorous vortexing for 30 seconds. Quiagen protease was added (200 µl) and incubated at 50° C. for 60 minutes. The incubation and centrifugation was repeated until the lysates were clear (e.g., incubating additional 30-60 minutes, pelleting at 3000×g for 10 min., 4° C.).

Purification of Cleared Lysates:

(1) Isolation of genomic DNA:

Genomic DNA was equilibrated (1 sample per maxi tip preparation) with 10 ml QBT buffer. QF elution buffer was equilibrated at 50° C. The samples were vortexed for 30 seconds, then loaded onto equilibrated tips and drained by gravity. The tips were washed with 2×15 ml QC buffer. The DNA was eluted into 30 ml silanized, autoclaved 30 ml Corex tubes with 15 ml QF buffer (50° C.). Isopropanol (10.5 ml) was added to each sample, the tubes covered with parafin and mixed by repeated inversion until the DNA precipitated. Samples were pelleted by centrifugation in the SS-34 rotor at 15,000 rpm for 10 minutes at 4° C. The pellet location was marked, the supernatant discarded, and 10 ml 70% ethanol (4° C.) was added. Samples were pelleted again by centrifugation on the SS-34 rotor at 10,000 rpm for 10 minutes at 4° C. The pellet location was marked and the supernatant discarded. The tubes were then placed on their side in a drying rack and dried 10 minutes at 37° C., taking care not to overdry the samples.

After drying, the pellets were dissolved into 1.0 ml TE (pH 8.5) and placed at 50° C. for 1-2 hours. Samples were held overnight at 4° C. as dissolution continued. The DNA solution was then transferred to 1.5 ml tubes with a 26 gauge needle on a tuberculin syringe. The transfer was repeated 5×in order to shear the DNA. Samples were then placed at 50° C. for 1-2 hours.

(2) Quantitation of Genomic DNA and Preparation for Gene Amplification Assay:

The DNA levels in each tube were quantified by standard $A_2 60$, $A_{280}$ spectrophotometry on a 1:20 dilution (5 µl DNA+95 µl ddH$_2$O) using the 0.1 ml quartz cuvetts in the Beckman DU640 spectrophotometer. $A_{260}/A_{280}$ ratios were in the range of 1.8-1.9. Each DNA samples was then diluted further to approximately 200 ng/ml in TE (pH 8.5). If the original material was highly concentrated (about 700 ng/gl), the material was placed at 50° C. for several hours until resuspended.

Fluorometric DNA quantitation was then performed on the diluted material (20-600 ng/ml) using the manufacturer's guidelines as modified below. This was accomplished by allowing a Hoeffer DyNA Quant 200 fluorometer to warm-up for about 15 minutes. The Hoechst dye working solution (#H33258, 10 µl, prepared within 12 hours of use) was diluted into 100 ml 1×TNE buffer. A 2 ml cuvette was filled with the fluorometer solution, placed into the machine, and the machine was zeroed. pGEM 3Zf(+) (2 µl, lot #360851026) was added to 2 ml of fluorometer solution and calibrated at 200 units. An additional 2 µl of pGEM 3Zf(+) DNA was then tested and the reading confirmed at 400 +/− 10 units. Each sample was then read at least in triplicate. When 3 samples were found to be within 10% of each other, their average was taken and this value was used as the quantification value.

The fluorometricly determined concentration was then used to dilute each sample to 10 ng/gl in ddH$_2$O. This was done simultaneously on all template samples for a single TAQMAN™ plate assay, and with enough material to run 500-1000 assays. The samples were tested in triplicate with TAQMAN™ primers and probe both B-actin and GAPDH on a single plate with normal human DNA and no-template controls. The diluted samples were used provided that the CT value of normal human DNA subtracted from test DNA was +/−1 Ct. The diluted, lot-qualified genomic DNA was stored in 1.0 ml aliquots at −80° C. Aliquots which were subsequently to be used in the gene amplification assay were stored at 4° C. Each 1 ml aliquot is enough for 8-9 plates or 64 tests.

Gene Amplification Assay:

The PRO polypeptide compounds of the invention were screened in the following primary tumors and the resulting ΔCt values greater than or equal to 1.0 are reported in Table 9 below.

TABLE 9

ΔCt values in lung and colon primary tumors and cell line models

| Primary Tumors or Cell Lines | PRO187 | PRO533 | PRO246 |
|---|---|---|---|
| LT7 | | 1.04 | |
| LT13 | 2.74 | | 1.63 |
| | 2.98 | | 1.68 |
| | 2.44 | | |

TABLE 9-continued

ΔCt values in lung and colon primary tumors and cell line models

| Primary Tumors or Cell Lines | PRO187 | PRO533 | PRO246 |
|---|---|---|---|
| LT3 | | | 1.06 |
| LT12 | 2.70 | | 2.47 |
| | 2.90 | | 1.74 |
| | 2.27 | | |
| LT30 | 1.67 | | |
| LT21 | | | 1.50 |
| LT-1a | | 1.02 | |
| LT10 | | | 1.07 |
| LT11 | | 1.09 | 3.43 |
| | | | 1.41 |
| LT15 | 3.75 | | 2.11 |
| | 3.92 | | 1.56 |
| | 3.49 | | |
| LT16 | 2.10 | 1.66 | |
| LT17 | | 1.32 | 2.68 |
| | | | 1.69 |
| LT19 | 4.05 | 1.67 | 1.91 |
| | 3.99 | | 1.68 |
| | | | 1.16 |
| CT2 | 3.56 | | |
| CT8 | 1.01 | | |
| CT10 | 1.81 | | |
| CT14 | 1.82 | | |
| CT1 | 1.24 | | |
| | 1.34 | | |
| CT5 | 2.96 | | 1.33 |
| | 2.99 | | 2.39 |
| CT6 | 1.10 | | |
| CT7 | 1.40 | | |
| CT9 | 1.39 | | 1.09 |
| CT11 | 2.22 | | 1.48 |
| | 2.26 | | 1.12 |

Because amplification of the various DNAs described above occurs in various cancerous tumors and tumor cell lines derived from various human tissues, these molecules likely play a significant role in tumor formation and/or growth. As a result, amplification and/or enhanced expression of these molecules can serve as a diagnostic for detecting the presence of tumor in an individual and antagonists (e.g., antibodies) directed against the proteins encoded by the above described DNA molecules would be expected to have utility in cancer therapy.

Example 69

Gene Expression in Bovine Pericytes (Assay 105)

This assay is designed to identify gene expression patterns in pericytes induced by the hits in assay 93 described above. Bovine pericytes are plated on 60 mm culture dishes in growth media for 1 week. On day 1, various PRO polypeptides are diluted (1%) and incubated with the pericytes for 1, 4 and 24 hr. timepoints. The cells are harvested and the RNA isolated using Tm-Reagent following the included instructions. The RNA is then quantified by reading the 260/280 OD using a spectrophotometer. The gene expression analysis is done by TAQMAN™ reactions using Perkin Elmer reagents and specially designed bovine probes and primers. Expression of the following genes is analyzed: GAPDH, beta-integrin, connective tissue growth factor (CTGF), ICAM-1, monocyte chemoattractant protein-1 (MCP-1), osteopontin, transforming growth factor-beta (TGF-beta), TGF-beta receptor, tissue inhibitor of metalloproteinase (TIMP), tissue factor (TF), VEGF-.alpha., thrombospondin, VEGF-.beta., angiopoeitin-2, and collagenase. Replicates are then averaged and the SD determined. The gene expression levels are then normalized to GAPDH. These are then normalized to the expression levels obtained with a protein (PIN32) which does not significantly induce gene expression in bovine pericytes when compared to untreated controls. Any PRO polypeptide that gives a gene expression level 2-fold or higher over the PIN32 control is considered a positive hit.

The following PRO polypeptides tested positive in this assay: PRO217.

Example 70

Cytokine Release Assay (Assay 120)

This assay is designed to determine whether PRO polypeptides of the present invention are capable of inducing the release of cytokines from peripheral blood mononuclear cells (PBMCs). PRO polypeptides capable of inducing the release of cytokines from PBMCs are useful from the treatment of conditions which would benefit from enhanced cytokine release and will be readily evident to those of ordinary skill in the art. Specifically, $1 \times 10^6$ cells/ml of peripheral blood mononuclear cells (PBMC) are cultured with 1% of a PRO polypeptide for 3 days in complete RPMI media. The supernatant is then harvested and tested for increased concentrations of various cytokines by ELISA as compared to a human IgG treated control. A positive in the assay is a 10-fold or greater increase in cytokine concentration in the PRO polypeptide treated sample as compared to the human IgG treated control.

The following polypeptides tested positive in this assay: PRO9940.

Example 71

Identification of PRO Polypeptides That Activate Pericytes (Assay 125)

This assay shows that certain polypeptides of the invention act to activate proliferation of pericyte cells and, therefore, are useful not only as diagnostic markers for particular types of pericyte-associated tumors but also for giving rise to antagonists which would be expected to be useful for the therapeutic treatment of pericyte-associated tumors. Activation of pericyte proliferation also correlates with the induction of angiogenesis and, as such, PRO polypeptides capable of inducing pericyte proliferation would be expected to be useful for the treatment of conditions where induced angiogenesis would be beneficial including, for example, wound healing, and the like. Specifically, on day 1, pericytes are received from VEC Technologies, and all but 5 ml media is removed from the flask. On day 2, the pericytes are trypsinized, washed, spun and plated on 96 well plates. On day 7, the media is removed and the pericytes are treated with 100 µl of either the specific PRO polypeptide or control treatments (positive control=DME+5% +/− PDGF @ 50 ng/µl; negative control=PIN32, a polypeptide determined to have no significant effect on pericyte proliferation). C-fos and GAPDH gene expression levels are then determined and the replicates are averaged and the SD is determined. The c-fos values are normalized to GAPDH and the results are expressed as fold increase over PIN2. Anything providing at least a 2-fold or higher response as compared to the negative control is considered positive for the assay.

The following polypeptides tested positive in this assay: PRO217.

Example 72

Identification of Receptor/Ligand Interactions

In this assay, various PRO polypeptides are tested for ability to bind to a panel of potential receptor or ligand molecules for the purpose of identifying receptor/ligand interactions. The identification of a ligand for a known receptor, a receptor for a known ligand or a novel receptor/ligand pair is useful for a variety of indications including, for example, targeting bioactive molecules (linked to the ligand or receptor) to a cell known to express the receptor or ligand, use of the receptor or ligand as a reagent to detect the presence of the ligand or receptor in a composition suspected of containing the same, wherein the composition may comprise cells suspected of expressing the ligand or receptor, modulating the growth of or another biological or immunological activity of a cell known to express or respond to the receptor or ligand, modulating the immune response of cells or toward cells that express the receptor or ligand, allowing the preparaion of agonists, antagonists and/or antibodies directed against the receptor or ligand which will modulate the growth of or a biological or immunological activity of a cell expressing the receptor or ligand, and various other indications which will be readily apparent to the ordinarily skilled artisan.

The assay is performed as follows. A PRO polypeptide of the present invention suspected of being a ligand for a receptor is expressed as a fusion protein containing the Fc domain of human IgG (an immunoadhesin). Receptor-ligand binding is detected by allowing interaction of the immunoadhesin polypeptide with cells (e.g. Cos cells) expressing candidate PRO polypeptide receptors and visualization of bound immunoadhesin with fluorescent reagents directed toward the Fc fusion domain and examination by microscope. Cells expressing candidate receptors are produced by transient transfection, in parallel, of defined subsets of a library of cDNA expression vectors encoding PRO polypeptides that may function as receptor molecules. Cells are then incubated for 1 hour in the presence of the PRO polypeptide immunoadhesin being tested for possible receptor binding. The cells are then washed and fixed with paraformaldehyde. The cells are then incubated with fluorescent conjugated antibody directed against the Fc portion of the PRO polypeptide immunoadhesin (e.g. FITC conjugated goat anti-human-Fc antibody). The cells are then washed again and examined by microscope. A positive interaction is judged by the presence of fluorescent labeling of cells transfected with cDNA encoding a particular PRO polypeptide receptor or pool of receptors and an absence of similar fluorescent labeling of similarly prepared cells that have been transfected with other cDNA or pools of cDNA. If a defined pool of cDNA expression vectors is judged to be positive for interaction with a PRO polypeptide immunoadhesin, the individual cDNA species that comprise the pool are tested individually (the pool is "broken down") to determine the specific cDNA that encodes a receptor able to interact with the PRO polypeptide immunoadhesin.

In another embodiment of this assay, an epitope-tagged potential ligand PRO polypeptide (e.g. 8 histidine "His" tag) is allowed to interact with a panel of potential receptor PRO polypeptide molecules that have been expressed as fusions with the Fc domain of human IgG (immunoadhesins). Following a 1 hour co-incubation with the epitope tagged PRO polypeptide, the candidate receptors are each immunoprecipitated with protein A beads and the beads are washed. Potential ligand interaction is determined by western blot analysis of the immunoprecipitated complexes with antibody directed towards the epitope tag. An interaction is judged to occur if a band of the anticipated molecular weight of the epitope tagged protein is observed in the western blot analysis with a candidate receptor, but is not observed to occur with the other members of the panel of potential receptors.

Using these assays, the following receptor/ligand interactions have been herein identified:

(1) PRO533 binds to the fibroblast growth factor receptor-4 (FGFR-4; see Partanen et al., *EMBO J.* 10(6):1347-1354 (1991)).
(2) PRO301 binds to itself and, therefore, functions as an adhesion molecule.
(3) PRO187 binds to the fibroblast growth factor receptor-3 (FGFR-3; see Keegan et al., *Proc. Natl. Acad. Sci. USA* 88:1095-1099 (1991)) with high affinity and with lower affinity to to FGFR-1, 2 and 4 (see Isacchi et al., *Nuc. Acids Res.* 18(7):1906 (1990), Dionne et al., *EMBO J.* 9(9):2685-2692 (1990) and Partanen et al., *EMBO J.* 10(6):1347-1354 (1991), respectively).
(4) PRO337 binds to PRO6004.
(5) PRO1411 binds to PRO4356.
(6) PRO10096 binds to PRO2630.
(7) PRO246 binds to itself and, therefore, functions as an adhesion molecule.
(8) PRO6307 binds to PRO265.
(9) PRO6003 binds to PRO941.

Deposit of Material:

The following materials have been deposited with the American Type Culture Collection, 10801 University Blvd., Manassas, Va. 20110-2209, USA (ATCC):

TABLE 10

| Material | ATCC Dep. No. | Deposit Date |
| --- | --- | --- |
| DNA22779-1130 | 209280 | Sep. 18, 1997 |
| DNA26846-1397 | 203406 | Oct. 27, 1998 |
| DNA32279-1131 | 209259 | Sep. 16, 1997 |
| DNA32288-1132 | 209261 | Sep. 16, 1997 |
| DNA33094-1131 | 209256 | Sep. 16, 1997 |
| DNA33785-1143 | 209417 | Oct. 28, 1997 |
| DNA35663-1129 | 209201 | Jun. 18, 1997 |
| DNA46777-1253 | 209619 | Feb. 5, 1998 |
| DNA60783-1611 | 203130 | Aug. 18, 1998 |
| DNA62306-1570 | 203254 | Sep. 9, 1998 |
| DNA62880-1513 | 203097 | Aug. 4, 1998 |
| DNA64896-1539 | 203238 | Sep. 9, 1998 |
| DNA71290-1630 | 203275 | Sep. 22, 1998 |
| DNA96031-2664 | PTA-237 | Jun. 15, 1999 |
| DNA108722-2743 | PTA-552 | Aug. 17, 1999 |
| DNA35674-1142 | 209416 | Oct. 28, 1997 |
| DNA41234 | 209618 | Feb. 5, 1998 |
| DNA77503-1686 | 203362 | Oct. 20, 1998 |
| DNA49435-1219 | 209480 | Nov. 21, 1997 |

TABLE 10-continued

| Material | ATCC Dep. No. | Deposit Date |
| --- | --- | --- |
| DNA40628-1216 | 209432 | Nov. 7, 1997 |
| DNA27864-1155 | 209375 | Oct. 16, 1997 |
| DNA43316-1237 | 209487 | Nov. 21, 1997 |
| DNA59212-1627 | 203245 | Sep. 9, 1998 |
| DNA86576-2595 | 203868 | Mar. 23, 1999 |
| DNA35639-1172 | 209396 | Oct. 17, 1997 |
| DNA36350-1158 | 209378 | Oct. 16, 1997 |
| DNA53906-1368 | 209747 | Apr. 7, 1998 |
| DNA125185-2806 | PTA-1031 | Dec. 7, 1999 |
| DNA83568-2692 | PTA-386 | Jul. 20, 1999 |

These deposits were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposits will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC § 122 and the Commissioner's rules pursuant thereto (including 37 CFR §1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed. various modifications of the invention in addition to those shown and described herein will become apparent to those skilled in the art from the foregoing description and fall within the scope of the appended claims.

What is claimed is:

1. An isolated antibody that specifically binds to the polypeptide of SEQ ID NO:9.
2. The antibody of claim 1 which is a monoclonal antibody.
3. The antibody of claim 1 which is a humanized antibody.
4. The antibody of claim 1 which is an antibody fragment.
5. The antibody of claim 1 which is labeled.

* * * * *